United States Patent
Rees-Smith et al.

(10) Patent No.: US 10,428,153 B2
(45) Date of Patent: Oct. 1, 2019

(54) HUMAN ANTI TSHR ANTIBODIES

(71) Applicant: RSR Ltd., Cardiff (GB)

(72) Inventors: Bernard Rees-Smith, Cardiff (GB); Jane Sanders, Cardiff (GB); Jadwiga Furmaniak, Cardiff (GB)

(73) Assignee: RSR Ltd., Lancaster (GB)

( * ) Notice: Subject to any disclaimer, the term of this patent is extended or adjusted under 35 U.S.C. 154(b) by 0 days.

(21) Appl. No.: 14/790,489

(22) Filed: Jul. 2, 2015

(65) Prior Publication Data
US 2015/0344582 A1 Dec. 3, 2015

Related U.S. Application Data

(62) Division of application No. 13/142,217, filed as application No. PCT/GB2009/002946 on Dec. 23, 2009, now Pat. No. 9,073,992.

(30) Foreign Application Priority Data

Dec. 24, 2008 (GB) .................................... 0823562.4
May 22, 2009 (GB) .................................... 0908945.9

(51) Int. Cl.
*A61K 39/00* (2006.01)
*C07K 16/28* (2006.01)

(52) U.S. Cl.
CPC .......... *C07K 16/2869* (2013.01); *C07K 16/28* (2013.01); *A61K 2039/505* (2013.01); *C07K 2299/00* (2013.01); *C07K 2317/21* (2013.01); *C07K 2317/24* (2013.01); *C07K 2317/55* (2013.01); *C07K 2317/56* (2013.01); *C07K 2317/565* (2013.01); *C07K 2317/75* (2013.01); *C07K 2317/76* (2013.01); *C07K 2317/92* (2013.01)

(58) Field of Classification Search
CPC .............................................. A61K 2039/505
See application file for complete search history.

(56) References Cited

FOREIGN PATENT DOCUMENTS

| WO | WO 03/001863 | 1/2003 |
|----|--------------|--------|
| WO | WO 2004/050708 | 6/2004 |
| WO | WO 2006/016121 | 2/2006 |
| WO | WO 2008/025991 | 3/2008 |
| WO | WO 2008/091981 | 7/2008 |
| WO | WO 2008/099185 | 8/2008 |

OTHER PUBLICATIONS

Authorized Officer Dorothée Mülhausen, International Preliminary Report on Patentability, PCT/GB2009/002946 dated Jun. 29, 2011, 12 pages.

Authorized Officer Zoran Cilensek, International Search Report Written Opinion of the International Searching Authority, PCT/GB2009/002946 dated Jul. 1, 2010, 17 pages.
Ajjan and Weetman, "Techniques to quantify TSH receptor antibodies," Nat Clin Pract Endocrinol Metab. Aug. 2008;4(8):461-8.
Ando et al., "A monoclonal thyroid-stimulating antibody," J Clin Invest. Dec. 2002;110(11):1667-74.
Bolton et al., "Measurement of Thyroid-stimulating Hormone Receptor Autoantibodies by ELISA," *Clinical Chemistry*, 1999, 45:2285-2287.
Brünger, "Free R value: A novel statistical quantity for assessing the accuracy of crystal structures," *Nature*, 1992, 355:472-475.
Caldas et al., Mol. Immunol. May 2003; 39 (15): 941-952.
Carter, "Potent antibody therapeutics by design," *Nat Rev Immunol.*, 2006, 6:343-357.
Casset et al., Biochem. Biophys. Res. Commun. Jul. 18, 2003; 307 (1): 198-205.
Chen et al., "Suppression of thyrotropin receptor constitutive activity by a monoclonal antibody with inverse agonist activity," *Endocrinology*, 2007, 148:2375-2382.
Chien et al., Proc. Natl. Acad. Sci. USA. Jul. 1989; 86 (14): 5532-5536.
Collaborative computational project, No. 4, "The CCP4 Suite: Programs for Protein Crystallography," *Acta Cryst.*, 1994, D50:760-763.
De Pascalis et al., J. Immunol. 2002; 169 (6): 3076-3084.
Duntas and Cooper, "Review on the occasion of a decade of recombinant human TSH: prospects and novel uses," *Thyroid*, 2008, 18:509-516.
Evans et al., "Potent thyrotrophin receptor-blocking antibodies: a cause of transient congenital hypothyroidism and delayed thyroid development," *European Journal of Endocrinology*, 2004, 150:265-268.
Furmaniak et al., "Immunity to the thyroid-stimulating hormone receptor," *Springer Seminars in Immunopathology*, 1993, 14:309-321.
GenBank Accession No. P16473, May 16, 2012, 24 pages.
Giusti et al., Proc. Natl. Acad. Sci. USA. May 1987; 84 (9): 2926-2930.
Grossmann et al., "Novel insights into the molecular mechanisms of human thyrotropin action: structural, physiological, and therapeutic implications for the glycoprotein hormone family," *Endocrine Reviews*, 1997, 18:476-501.
Gussow et al., Methods in Enzymology. 1991; 203: 99-121.
Hoermann et al. (Thyroid. 1993 Winter; 3 (4): 273-8).
Holliger et al., ""Diabodies": small bivalent and bispecific antibody fragments," *Proc Natl Acad Sci USA*, 1993, 90:6444-6448.
Holm et al., Mol. Immunol. Feb. 2007; 44 (6): 1075-1084.
Jeffreys et al., "Characterization of the thyrotropin binding pocket," *Thyroid*, 2002, 12:1051-1061.

(Continued)

*Primary Examiner* — Stephen Rawlings
(74) *Attorney, Agent, or Firm* — Fish & Richardson P.C.

(57) ABSTRACT

According to one aspect there is provided An isolated human antibody molecule which binds to the TSHR and which reduces ligand-induced stimulation of the TSHR but has no effect on TSHR constitutive activity wherein the isolated human antibody molecule has the characteristic of patient serum TSHR autoantibodies of inhibiting TSH and M22 binding to the TSHR.

9 Claims, 268 Drawing Sheets
Specification includes a Sequence Listing.

(56) References Cited

OTHER PUBLICATIONS

Jiang et al., J. Biol. Chem. ,Feb. 11, 2005; 280 (6):4656-4662.
Kohn et al., "Characterization of monoclonal thyroid-stimulating and thyrotropin binding-inhibiting autoantibodies from a Hashimoto's patient whose children had intrauterine and neonatal thyroid disease," *J Clin Endocrinol Metab.*, Dec. 1997, 82(12):3998-4009.
Kraiem et al. (Clin Endocrinol (Oxf). Feb. 1992; 36 (2): 211-4).
MacCallum et al., J. Mol. Biol. Oct. 11, 1996; 262 (5): 732-745.
Mariuzza et al., Annu. Rev. Biophys. Biophys. Chem. 1987; 16: 139-159.
Matthews et al., "Antibodies to Acetylcholine Receptor in Parous Women with Myasthenia: Evidence for Immunization by Fetal Antigen," *Laboratory Investigation* 2002, 82:1407-1417.
Morgenthaler et al., "Stimulating and blocking thyroid-stimulating hormone (TSH) receptor autoantibodies from patients with Graves' disease and autoimmune hypothyroidism have very similar concentration, TSH receptor affinity, and binding sites," *J Clin Endocrinol Metab.*, Mar. 2007, 92(3):1058-1065, Dec. 19, 2006.
Neumann et al., Expert Rev. Endocrinol. Metab., Nov. 1, 2009, 4(6):669; pp. 1-20.
Nuñez et al., "Analysis of the thyrotropin receptor-thyrotropin interaction by comparative modeling," *Thyroid*, 2004, 14:991-1011.
Oda et al., "Binding Characteristics of antibodies to the TSH receptor," *Journal of Molecular Endocrinology*, 1998, 20:233-244.
Rees-Smith et al., "A new assay for thyrotropin receptor autoantibodies," *Thyroid*, 2004, 14:830-835.
Rees-Smith et al., "Autoantibodies to the thyrotropin receptor," *Endocrine Reviews*, 1988, 9:106-121.
Rees-Smith et al., "TSH receptor—autoantibody interactions," *Horm Metab Res.*, Jun. 2009, 41(6):448-455.
Rees-Smith et al., "TSH receptor antibodies," *Thyroid*, 2007, 17:923-938.
Rudikoff et al., Proc. Natl. Acad. Sci. USA. 1982; 79:1979-1983.
Sanders et al., "A human monoclonal autoantibody to the thyrotropin receptor with thyroid-stimulating blocking activity," *Thyroid*, Jul. 2008, 18(7):735-746.
Sanders et al., "Characteristics of a human monoclonal autoantibody to the thyrotropin receptor: sequence structure and function," *Thyroid*, 2004 14:560-570.
Sanders et al., "Characteristics of a monoclonal antibody to the thyrotropin receptor that acts as a powerful thyroid-stimulating autoantibody antagonist," *Thyroid*, Jul. 2005, 15(7):672-682.
Sanders et al., "Crystal structure of the TSH receptor in complex with a thyroid-stimulating autoantibody," *Thyroid*, 2007, 17:395-410.
Sanders et al., "The interaction of TSH receptor autoantibodies with $^{125}$I-labelled TSH receptor," *Journal of Clinical Endocrinology and Metabolism*, 1999, 84:3797-3802.
Sanders et al., Thyroid. Jul. 2005; 15 (7): 672-82.
Scatchard, "The Attractions of Proteins for. Small Molecules and Ions," *Annals of the New York Academy of Sciences*, 1949, 51:660-672.
Schott et al., "Thyrotropin receptor autoantibodies in Graves' disease," *Trends in Endocrinology and Metabolism*, 2005, 16:243-248.
Southgate et al., "A receptor assay for the measurement of TSH receptor antibodies in unextracted serum," *Clin Endocrinol.*, 1984, 20:539-548.
Szkudlinski et al., "Thyroid-Stimulating Hormone and Thyroid-Stimulating Hormone Receptor Structure-Function Relationships," *Physiological Reviews*, 2002, 82:473-502.
Vajdos et al., J. Mol. Biol. Jul. 5, 2002; 320 (2): 415-428.
Valente et al., "Monoclonal antibodies to the thyroptropin receptor: stimulating and blocking antibodies derived from the lymphocytes of patients with Graves disease," *Proc Natl Acad Sci USA*, Nov. 1982, 79(21):6680-6684.
Winkler et al., J. Immunol. Oct. 15, 2000; 165 (8): 4505-4514.
Wu et al., J. Mol. Biol. Nov. 19, 1999; 294 (1): 151-162.
Zóphel et al., "M22 based (manual) ELISA for TSH-receptor antibody (TRAb) measurement is more sensitive than 2nd generation TRAb assays," *Clinica Chimica Acta*, 2009, 1 page.

Figure 1A    Time course of binding of $^{125}$I-labelled K1-70 IgG and Fab to TSHR (full length) coated tubes
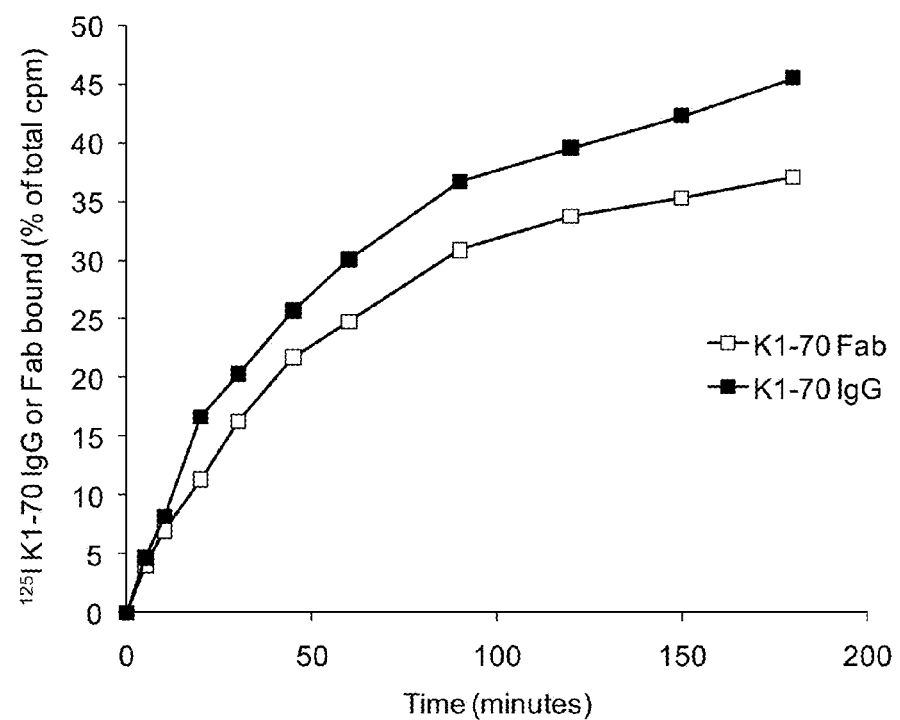
Non specific binding ie binding of labelled K1-70 IgG/Fab to tubes not coated with the TSHR was at below 2% of total cpm added and was not subtracted from the data shown in the Figure.

Figure 1B  Time course of binding of $^{125}$I-labelled K1-70 IgG to full length TSHR and TSHR260 coated tubes
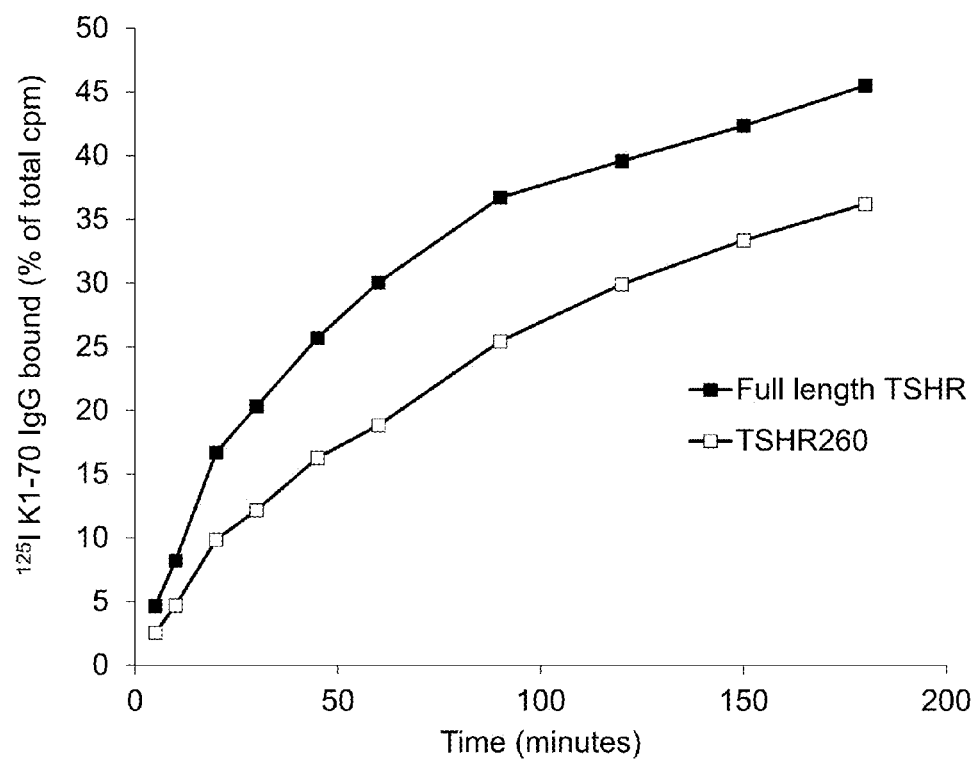
Non specific binding ie binding of labelled K1-70 IgG to tubes not coated with the TSHR was at below 2% of total cpm added and was not subtracted from the data shown in the Figure.

Figure 1C   Time course of binding of $^{125}$I-labelled K1-70 Fab to full length TSHR and TSHR260 coated tubes
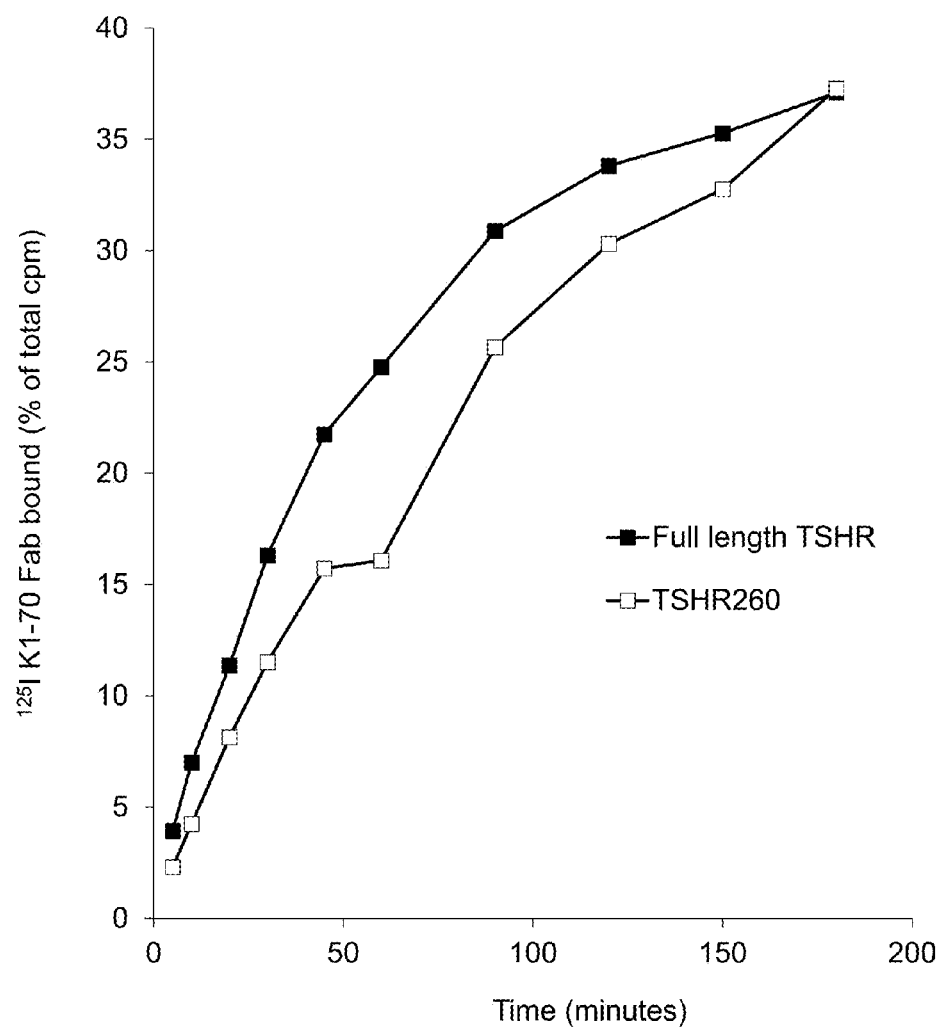
Non specific binding ie binding of labelled K1-70 IgG to tubes not coated with the TSHR was at below 2% of total cpm added and was not subtracted from the data shown in the Figure.

Figure 1D    Dissociation of $^{125}$I-K1-70 IgG from TSHR (full length) coated tubes in the presence of various unlabelled ligands
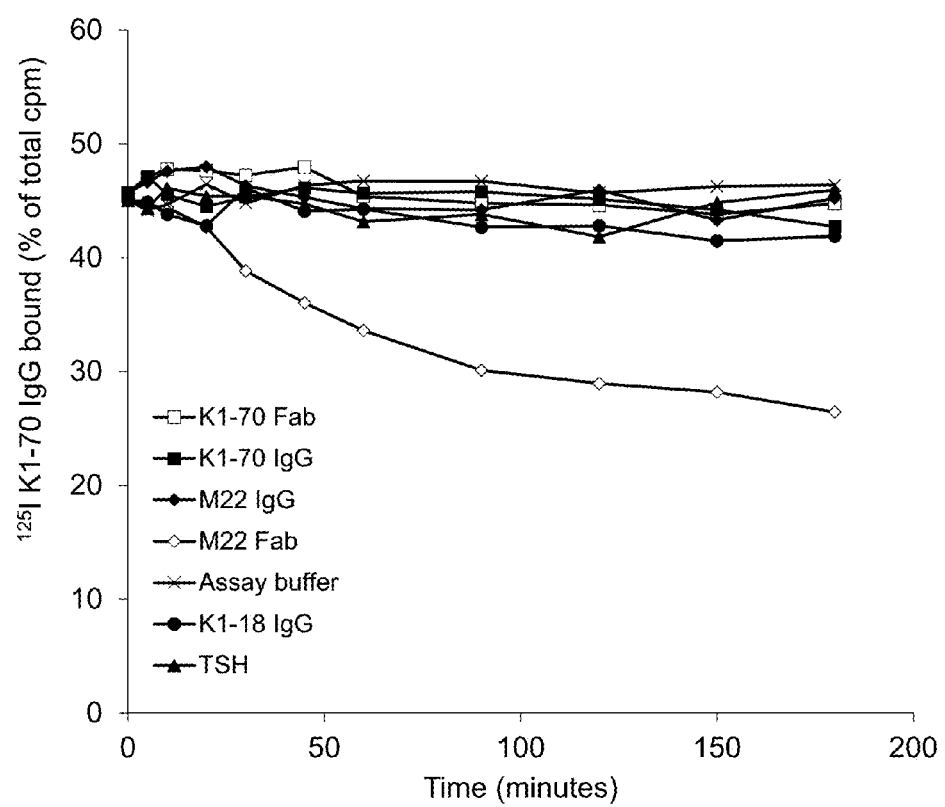

Figure 1E  Dissociation of $^{125}$I-K1-70 IgG from TSHR (full length) coated tubes in the presence of K1-18 Fab
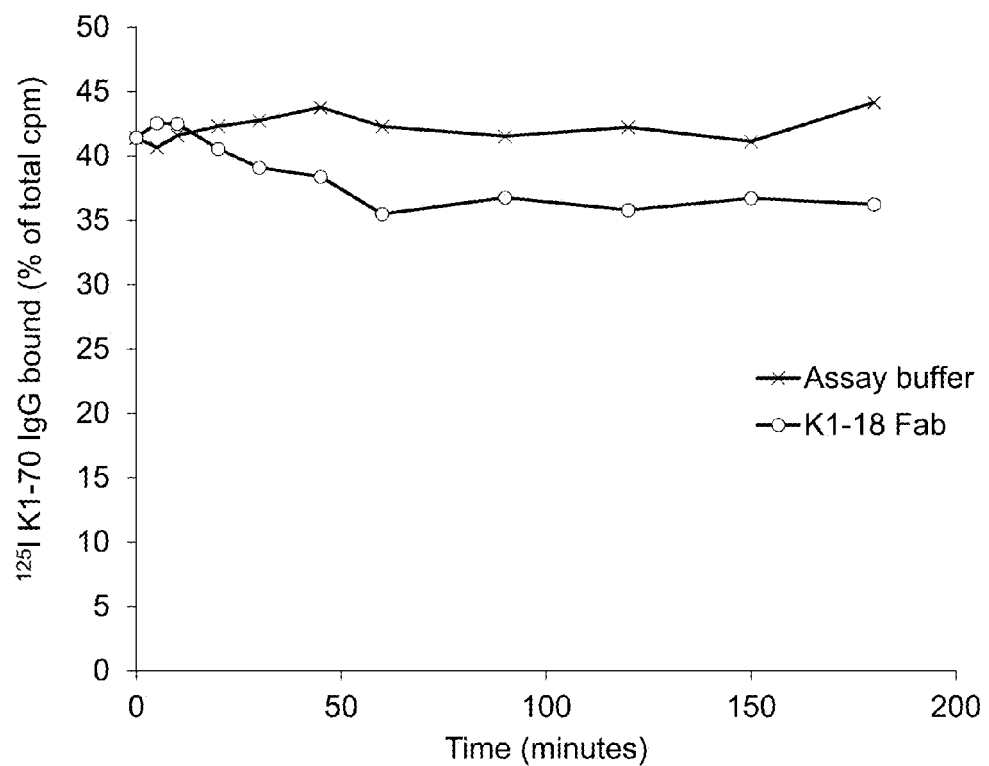

Figure 1F  Dissociation of $^{125}$I-K1-70 Fab from TSHR (full length) coated tubes in the presence of various unlabelled ligands
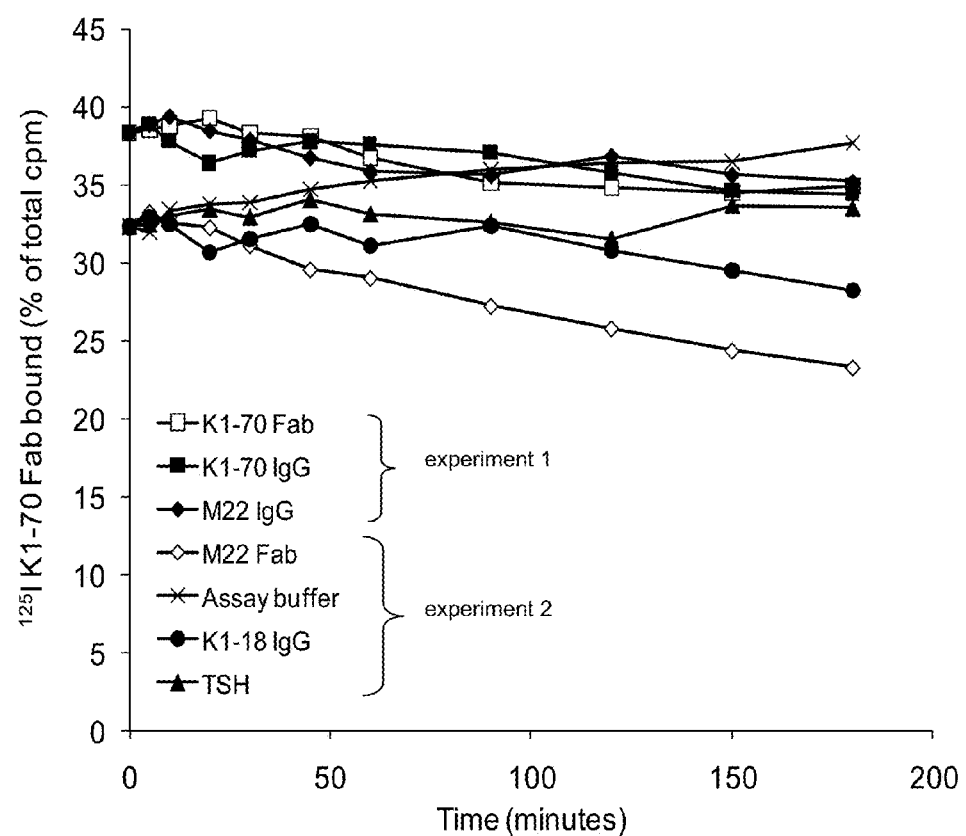
Experiments 1 and 2 were carried out on separate days, with different lots of TSHR coated tubes.

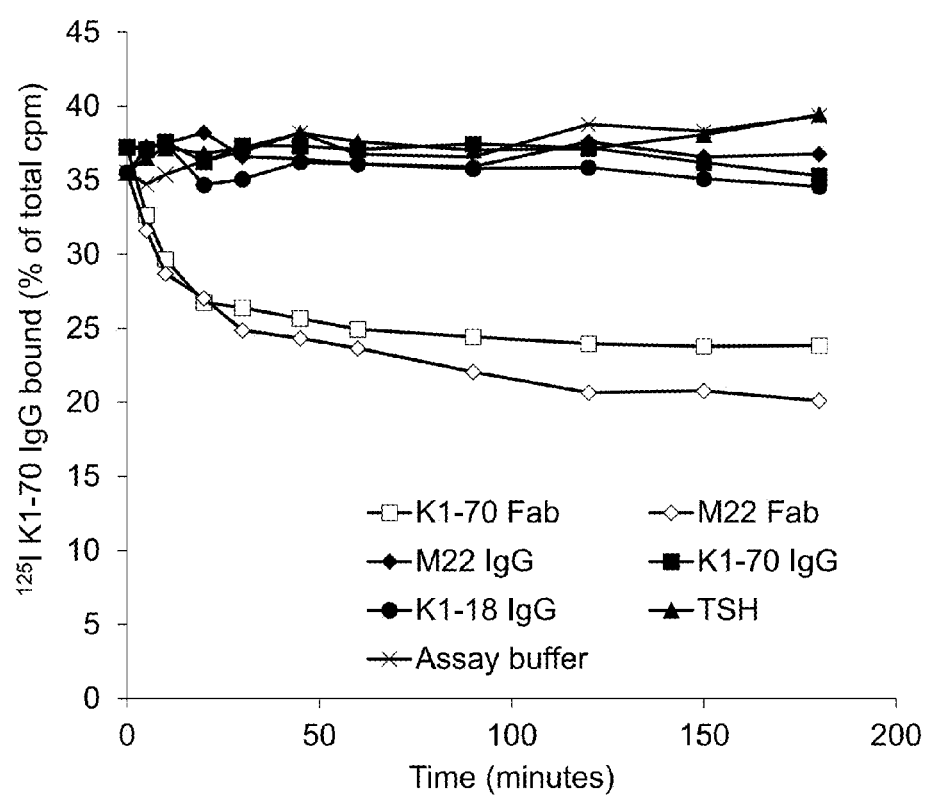
Figure 1G  Dissociation of $^{125}$I-K1-70 IgG from TSHR260 coated tubes in the presence of various unlabelled ligands

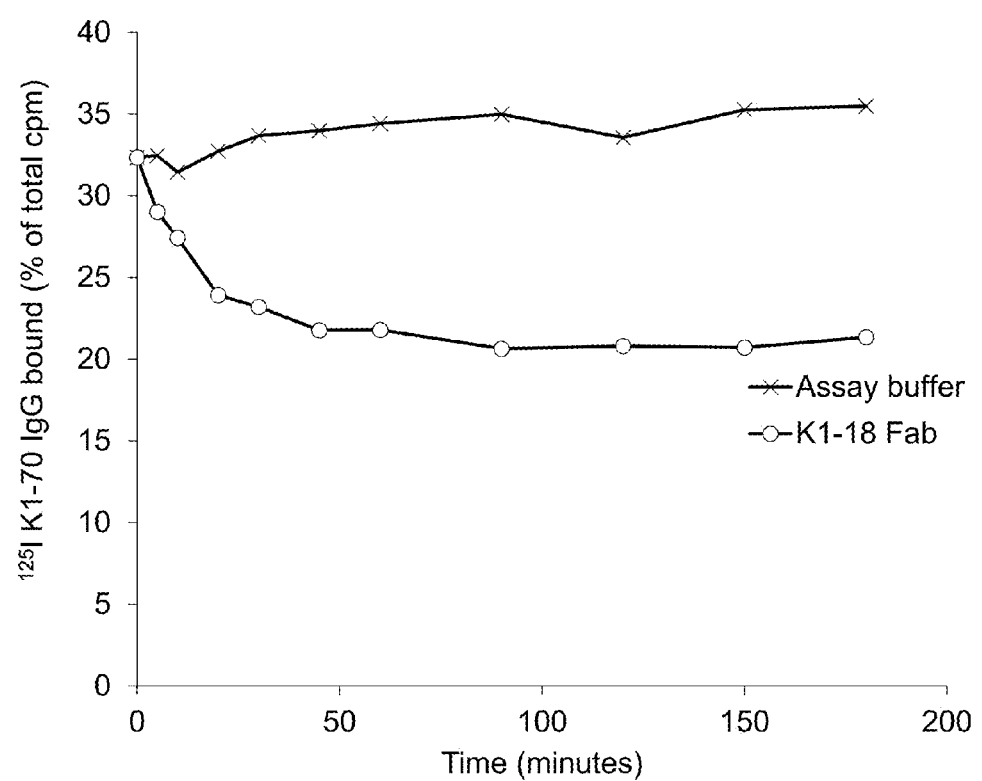
Figure 1H  Dissociation of $^{125}$I-K1-70 IgG from TSHR260 coated tubes in the presence of K1-18 Fab

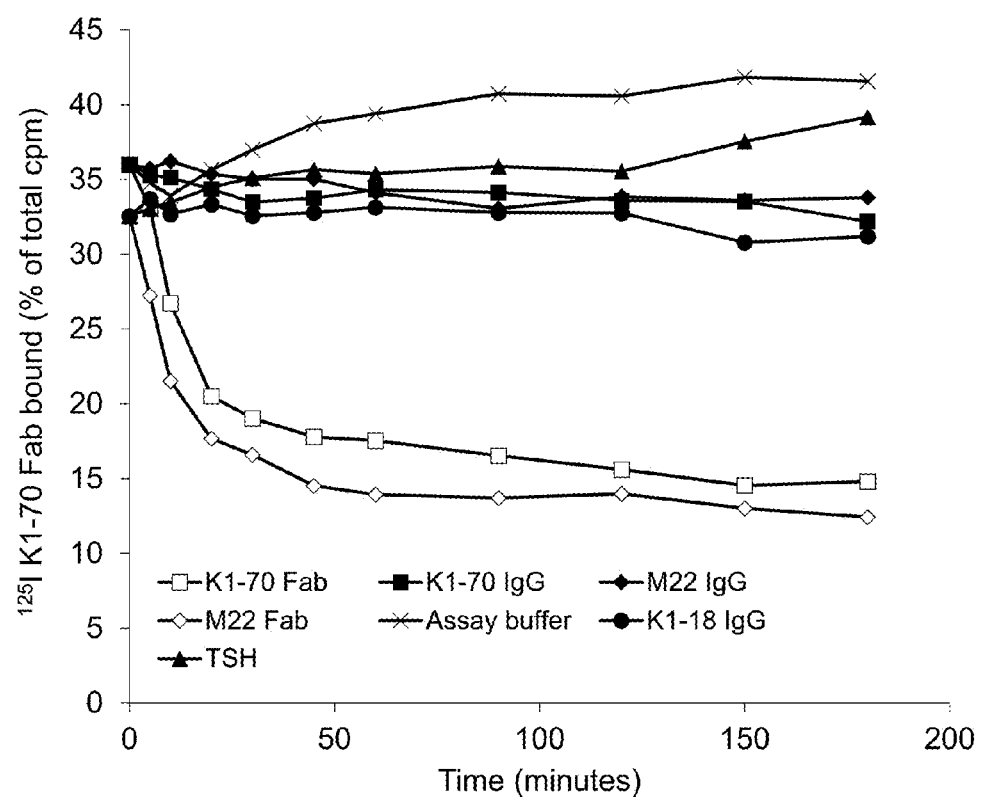
Figure 1I    Dissociation of $^{125}$I-K1-70 Fab from TSHR260 coated tubes in the presence of various unlabelled ligands

Figure 1J Time course of binding of $^{125}$I-labelled K1-18 IgG to full length TSHR and TSHR260 coated tubes
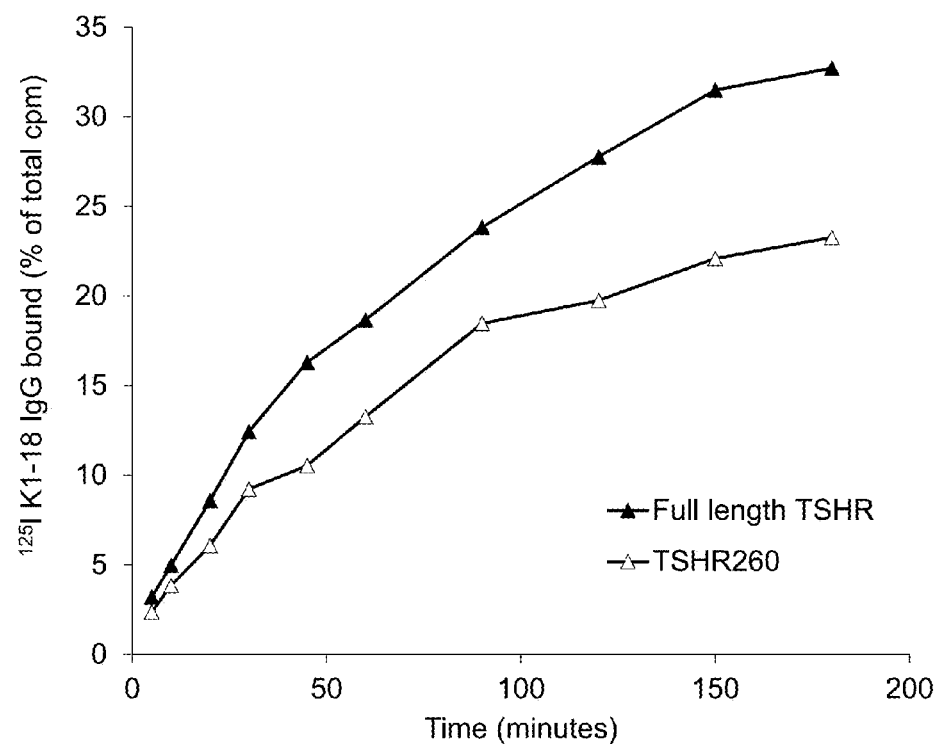

Figure 1K Dissociation of $^{125}$I-K1-18 IgG from TSHR (full length) coated tubes in the presence of various unlabelled ligands
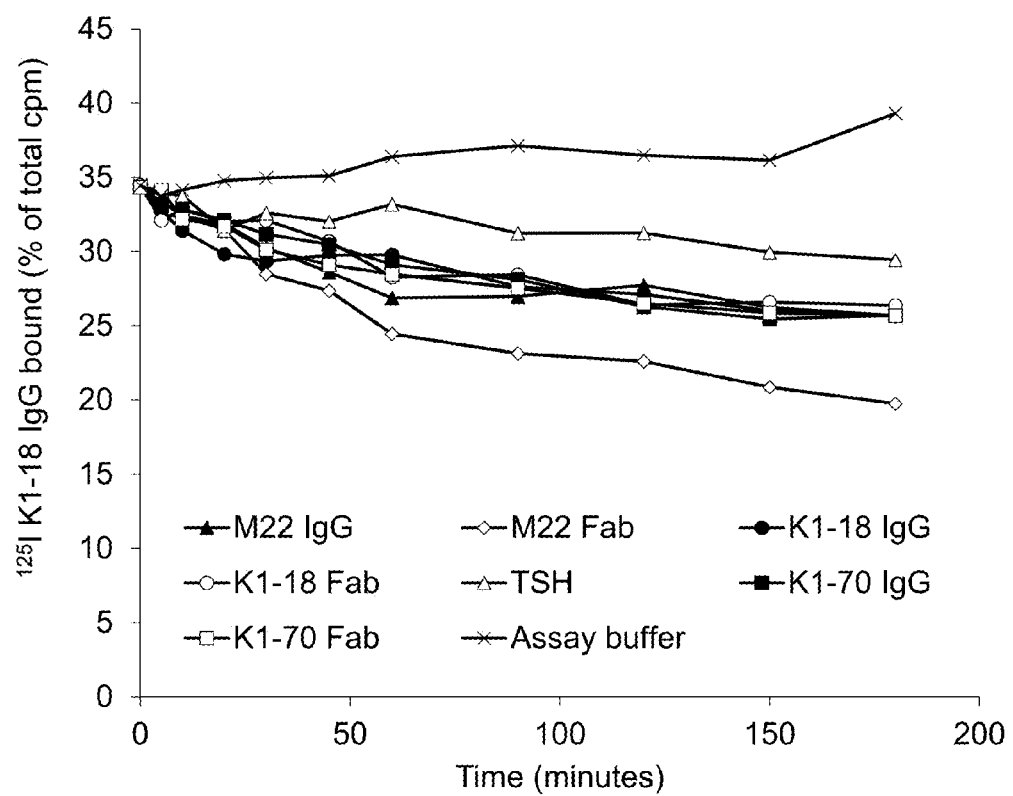

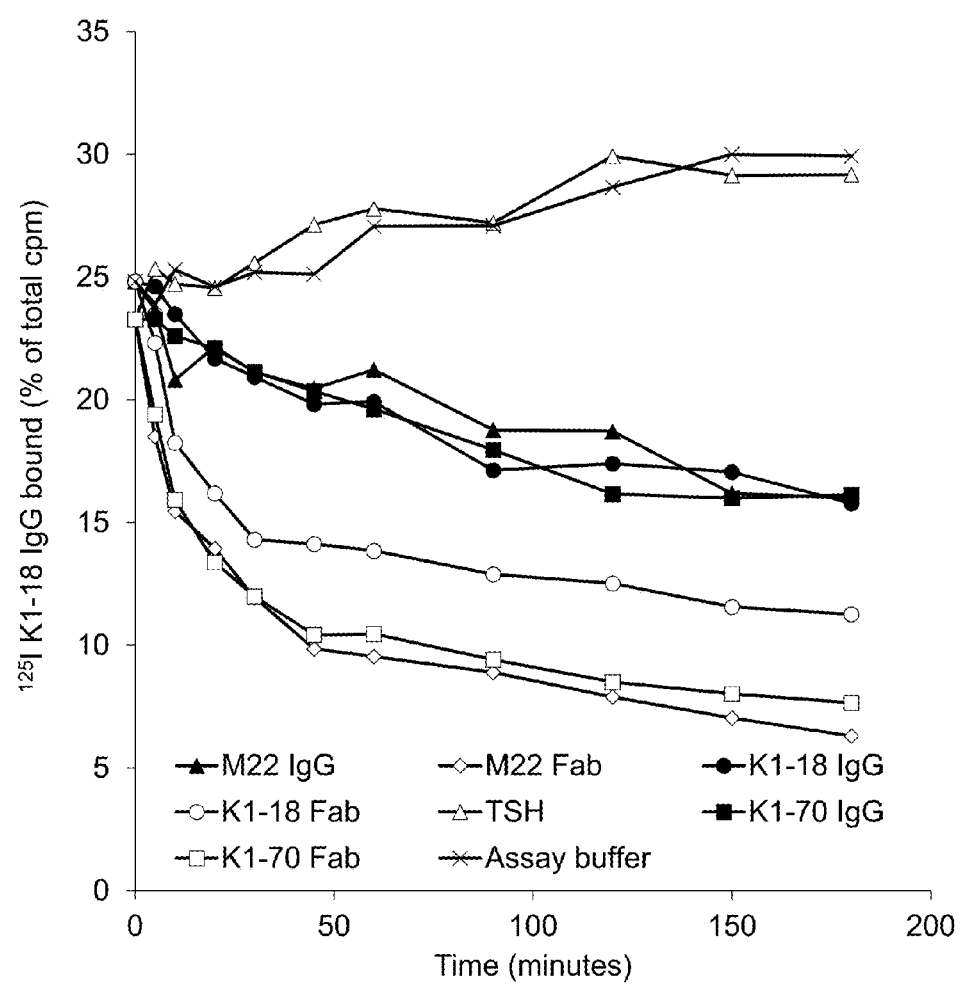
Figure 1L Dissociation of $^{125}$I-K1-18 IgG from tubes coated with TSHR260 in the presence of various unlabelled ligands

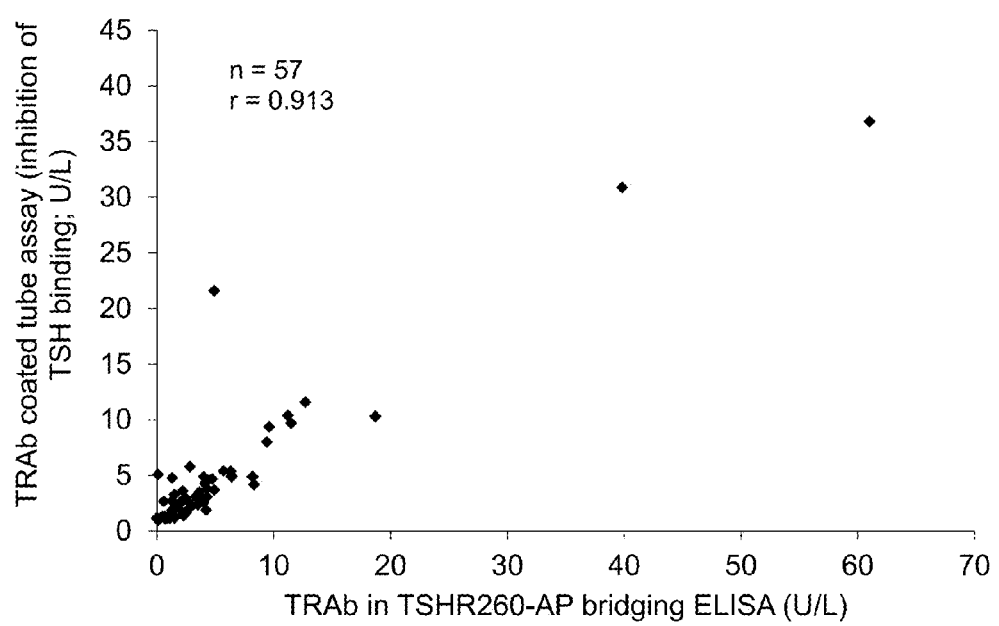
Figure 2A   Comparison of measurements of patient serum TRAbs in a TRAb coated tube assay (based on inhibition of TSH binding) and in a TSHR260-AP ELISA

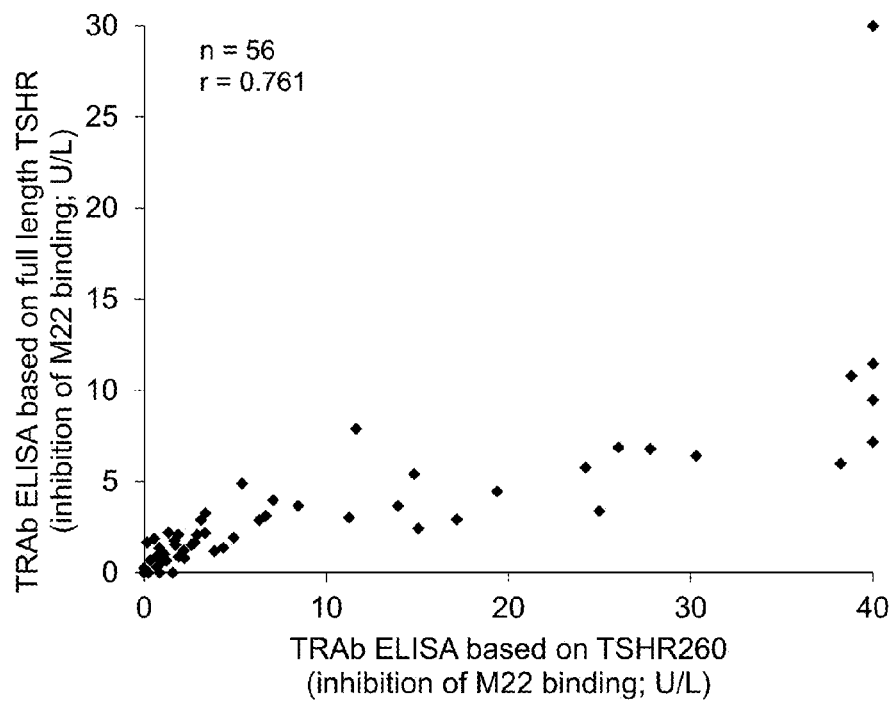
Figure 2B  Comparison of measurements by ELISAs based on inhibition of M22 Fab binding to full length TSHR and by inhibition of M22 Fab binding to TSHR260

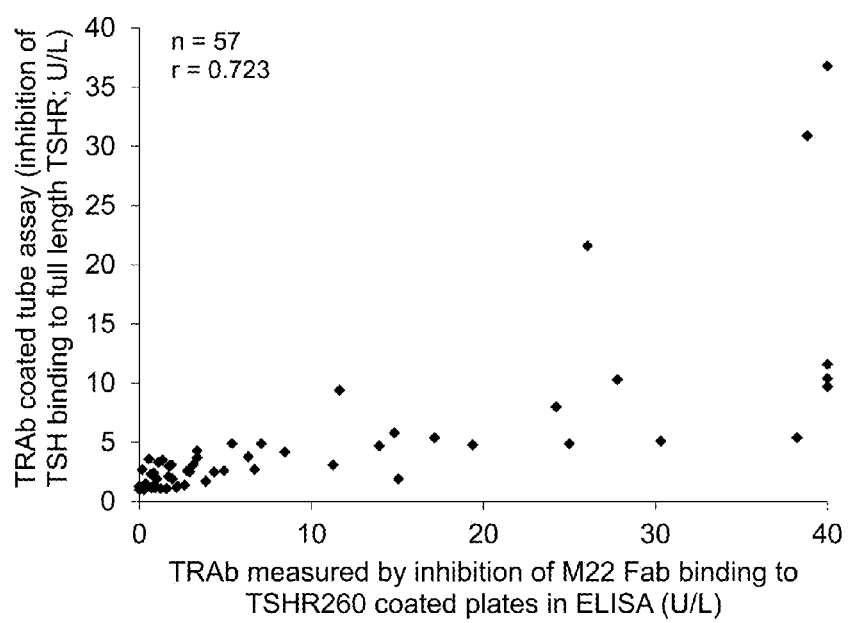
Figure 2C  Comparison of measurements of patient serum TRAbs in a TRAb coated tube assay (based on inhibition of TSH binding to full length TSHR) and by inhibition of M22 Fab binding to TSHR260 coated plates in an ELISA

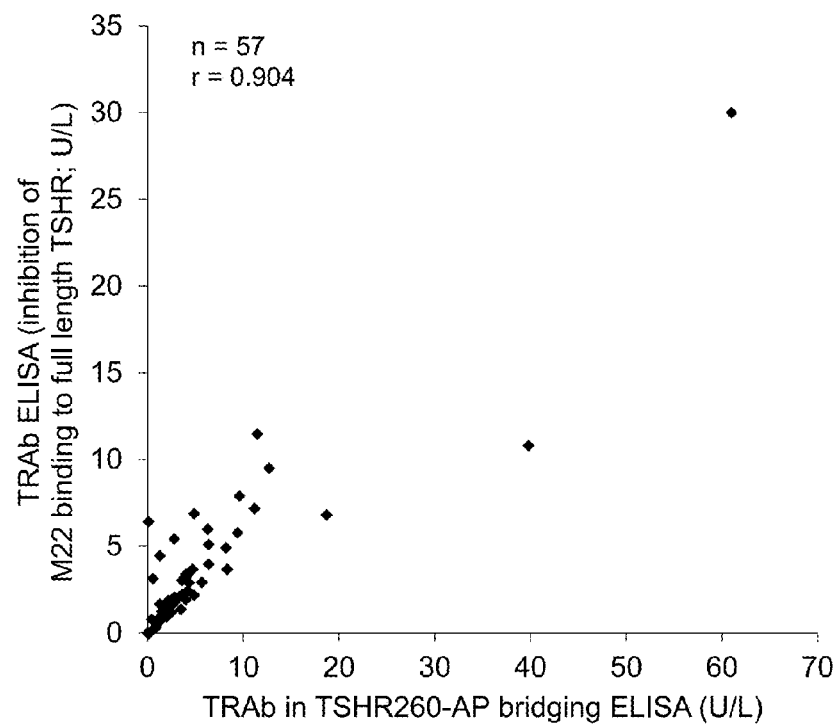
Figure 2D    Comparison of measurements of patient serum TRAbs in a TRAb ELISA (based on inhibition of M22 Fab binding to full length TSHR) and in a TSHR260-AP ELISA

Figure 3A  K1-18 heavy chain DNA

GAAGTGCAGCTGGTGGAGTCTGGAGCAGAGGTGAAAAAGCCCGGGGAGTC

TCTGAAGATCTCCTGCAAGGGTTCTGGATACAGCTTTACCAACTACTGGA

TCGGCTGGGTGCGCCAGATGCCCGGGAAAGGCCTGGAGTGGATGGGGATC

ATCTATCCTTATGACTCTGATACCAGATATAGCCCGTCCTTCGAAGGCCA

GGTCACCATCTCAGCCGACAAGTCCATCAGGACCGCCTACCTGCACTGGA

GCAGCCTGAAGGCCTCGGACACCGCCATGTATTACTGTGTGAGACCCCGC

GATGGGAGCTATCCTTATGATGCTTTTGATATCTGGGGCCAAGGGACAAT

GGTCACCGTCTCTTCAGCCTCCACCAAGGGCCCATCGGTCTTCCCCCTGG

CACCCTCCTCCAAGAGCACCTCTGGGGGCACAGCGGCCCTGGGCTGCCTG

GTCAAGGACTACTTCCCCGAACCGGTGACGGTGTCGTGGAACTCAGGCGC

CCTGACCAGCGGCGTGCACACCTTCCCGGCTGTCCTACAGTCCTCAGGAC

TCTACTCCCTCAGCAGCGTGGTGACCGTGCCCTCCAGCAGCTTGGGCACC

CAGACCTACATCTGCAACGTGAATCACAAGCCCAGCAACACCAAGGTGGA

CAAGAGAGTTGAGCCCAAATCTTGTGACAAAACTAGT

Figure 3A – CONT.

```
GAAGTGCAGCTGGTGGAGTCTGGAGCAGAGGTGAAAAAGCCCGGGGAGTC          50
pcr primer
TCTGAAGATCTCCTGCAAGGGTTCTGGATACAGCTTTACC AACTACTGGA         100
                                         CDR I
TCGGC TGGGTGCGCCAGATGCCCGGGAAAGGCCTGGAGTGGATGGGG ATC        150
                                                 CDR II
ATCTATCCTTATGACTCTGATACCAGATATAGCCCGTCCTTCGAAGGC CA         200

GGTCACCATCTCAGCCGACAAGTCCATCAGGACCGCCTACCTGCACTGGA         250

GCAGCCTGAAGGCCTCGGACACCGCCATGTATTACTGTGTGAGA CCCCGC        300
                                              CDR III
GATGGGAGCTATCCTTATGATGCTTTTGATATC TGGGGCCAAGGGACAAT        350

GGTCACCGTCTCTTCAGCCTCCACCAAGGGCCCATCGGTCTTCCCCCTGG         400
                 constant region
CACCCTCCTCCAAGAGCACCTCTGGGGGCACAGCGGCCCTGGGCTGCCTG         450

GTCAAGGACTACTTCCCCGAACCGGTGACGGTGTCGTGGAACTCAGGCGC         500

CCTGACCAGCGGCGTGCACACCTTCCCGGCTGTCCTACAGTCCTCAGGAC         550

TCTACTCCCTCAGCAGCGTGGTGACCGTGCCCTCCAGCAGCTTGGGCACC         600

CAGACCTACATCTGCAACGTGAATCACAAGCCCAGCAACACCAAGGTGGA         650

CAAGAGAGTTGAGCCCAAATCTTGTGACAAAACTAGT                      687
                PCR primer
```

Figure 3B     K1-18 heavy chain protein

EVQLVESGAEVKKPGESLKISCKGSGYSFTNYWIGWVRQMPGKGLEWMGI
IYPYDSDTRYSPSFEGQVTISADKSIRTAYLHWSSLKASDTAMYYCVRPR
DGSYPYDAFDIWGQGTMVTVSSASTKGPSVFPLAPSSKSTSGGTAALGCL
VKDYFPEPVTVSWNSGALTSGVHTFPAVLQSSGLYSLSSVVTVPSSSLGT
QTYICNVNHKPSNTKVDKRVEPKSCDKTS

EVQLVESGAEVKKPGESLKISCKGSGYSFT NYWIG WVRQMPGKGLEWMG I         50
PCR primer                     CDR I
IYPYDSDTRYSPSFEG QVTISADKSIRTAYLHWSSLKASDTAMYYCVR PR          100
CDR II
DGSYPYDAFDI WGQGTMVTVSSASTKGPSVFPLAPSSKSTSGGTAALGCL           150
CDR III                    constant region
VKDYFPEPVTVSWNSGALTSGVHTFPAVLQSSGLYSLSSVVTVPSSSLGT            200

QTYICNVNHKPSNTKVDKRVEPKSCDKTS                                 229
                     PCR primer

Figure 3C   K1-18 heavy chain DNA

```
ATGGGGTCAACCGCCATCCTCGCCCTCCTCCTGGGTGTTCTCCAAGGAGTCTGTGGCGAGGTGCAGCTGGTGCAGTC
TGGAGCAGAGGTGAAAAAGCCCGGGGAGTCTCTGAAGATCTCCTGCAAGGGTTCTGGATACAGCTTTACCAACTACT
GGATCGGCTGGGTGCGCCAGATGCCCGGGAAAGGCCTGGAGTGGATGGGGATCATCTATCCTTATGACTCTGATACC
AGATATAGCCCGTCCTTCGAAGGCCAGGTCACCATCTCAGCCGACAAGTCCATCAGGACCGCCTACCTGCACTGGAG
CAGCCTGAAGGCCTCGGACACCGCCATGTATTACTGTGTGAGACCCCGCGATGGGAGCTATCCTTATGATGCTTTTG
ATATCTGGGGCCAAGGGACAATGGTCACCGTCTCTTCAGCCTCCACCAAGGGCCCATCGGTCTTCCCCCTGGCACCC
TCCTCCAAGAGCACCTCTGGGGGCACAGCGGCCCTGGGCTGCCTGGTCAAGGACTACTTCCCCGAACCGGTGACGGT
GTCGTGGAACTCAGGCGCCCTGACCAGCGGCGTGCACACCTTCCCGGCTGTCCTACAGTCCTCAGGACTCTACTCCC
TCAGCAGCGTGGTGACCGTGCCCTCCAGCAGCTTGGGCACCCAGACCTACATCTGCAACGTGAATCACAAGCCCAGC
AACACCAAGGTGGACAAGACAGTTGAGCGCAAATCT
```

Figure 3D  K1-18 heavy chain protein

MGSTAILALLLGVLQGVCGEVQLVQSGAEVKKPGESLKISCKGSGYSFTNYWIGWVRQMPGKGLEWMGIIYPYDSDT
RYSPSFEGQVTISADKSIRTAYLHWSSLKASDTAMYYCVRPRDGSYPYDAFDIWGQGTMVTVSSASTKGPSVFPLAP
SSKSTSGGTAALGCLVKDYFPEPVTVSWNSGALTSGVHTFPAVLQSSGLYSLSSVVTVPSSSLGTQTYICNVNHKPS
NTKVDKTVERKS

```
mgstailallgvlqgvcgEVQLVQSGAEVKKPGESLKISCKGSGYSFT
PCR primer   leader                          CDR I
             sequence

YWIGWVRQMPGKGLEWMGIIYPYDSDTRYSPSFEGQVTISADKSIRTAYL
                      CDR II

HWSSLKASDTAMYYCVRPRDGSYPYDAFDIWGQGTMVTVSSASTKGPSVF
                 CDR III              constant region

PLAPSSKSTSGGTAALGCLVKDYFPEPVTVSWNSGALTSGVHTFPAVLQS

SGLYSLSSVVTVPSSSLGTQTYICNVNHKPSNTKVDKTVERKS
                                   PCR primer
```

Figure 4A     K1-18 light chain DNA

GAAATTGTGTTGACGCAGTCTCCAGGCACCCTGTCTTTGTCTCCAGGGGA

AAGAGCCACCCTCTCCTGCAGGGCCAGTCAGAGTGTTAGCAACAACTACT

TAGCCTGGTACCAGCAGAAGCCTGGCCAGGCTCCCAGGCTCCTCATCTAT

GGTGCATCCAGCAGGGCCACTGGCATCCCAGACAGGTTCAGTGGCAGTGG

GTCTGGGACAGACTTCACTCTCACCATCAGCAGACTGGAGCCTGAAGATT

TTGCAGTGTATTACTGTCAGCATTGTGGTAGCTCACTGAGGGCGTTCGGC

CAAGGGACCAAGGTGGAAATCAAACGAACTGTGGCTGCACCATCTGTCTT

CATCTTCCCGCCATCTGATGAGCAGTTGAAATCTGGAACTGCCTCTGTTG

TGTGCCTGCTGAATAACTTCTATCCCAGAGAGGCCAAAGTACAGTGGAAG

GTGGATAACGCCCTCCAATCGGGTAACTCCCAGGAGAGTGTCACAGAGCA

GGACAGCAAGGACAGCACCTACAGCCTCAGCAGCACCCTGACGCTGAGCA

AAGCAGACTACGAGAAACACAAACTCTACGCCTGCGAAGTCACCCATCAG

GGCCTGAGCTCGCCCGTC

Figure 4A – CONT.

| | |
|---|---|
| <u>GAAATTGTGTTGACGCAGT</u>CTCCAGGCACCCTGTCTTTGTCTCCAGGGGA | 50 |
| PCR primer | |
| AAGAGCCACCCTCTCCTGC`AGGGCCAGTCAGAGTGTTAGCAACAACTACT` | 100 |
| CDR I | |
| `TAGCC`TGGTACCAGCAGAAGCCTGGCCAGGCTCCCAGGCTCCTCATCTAT | 150 |
| `GGTGCATCCAGCAGGGCCACT`GGCATCCCAGACAGGTTCAGTGGCAGTGG | 200 |
| CDR II | |
| GTCTGGGACAGACTTCACTCTCACCATCAGCAGACTGGAGCCTGAAGATT | 250 |
| TTGCAGTGTATTACTGT`CAGCATTGTGGTAGCTCACTGAGGGCG`TTCGGC | 300 |
| CDR III | |
| CAAGGGACCAAGGTGGAAATCAAACGAACTGTGGCTGCACCATCTGTCTT | 350 |
| constant region | |
| CATCTTCCCGCCATCTGATGAGCAGTTGAAATCTGGAACTGCCTCTGTTG | 400 |
| TGTGCCTGCTGAATAACTTCTATCCCAGAGAGGCCAAAGTACAGTGGAAG | 450 |
| GTGGATAACGCCCTCCAATCGGGTAACTCCCAGGAGAGTGTCACAGAGCA | 500 |
| GGACAGCAAGGACAGCACCTACAGCCTCAGCAGCACCCTGACGCTGAGCA | 550 |
| AAGCAGACTACGAGAAACACAAACTCTACGCCTGCGAAGTCACCCATCAG | 600 |
| <u>GGCCTGAGCTCGCCCGTC</u> | 618 |
| PCR primer | |

Figure 4B  K1-18 light chain protein

EIVLTQSPGTLSLSPGERATLSCRASQSVSNNYLAWYQQKPGQAPRLLIY

GASSRATGIPDRFSGSGSGTDFTLTISRLEPEDFAVYYCQHCGSSLRAFG

QGTKVEIKRTVAAPSVFIFPPSDEQLKSGTASVVCLLNNFYPREAKVQWK

VDNALQSGNSQESVTEQDSKDSTYSLSSTLTLSKADYEKHKLYACEVTHQ

GLSSPV

EIVLTQSPGTLSLSPGERATLSCRASQSVSNNYLAWYQQKPGQAPRLLIY        50

PCR primer                CDR I

GASSRATGIPDRFSGSGSGTDFTLTISRLEPEDFAVYYCQHCGSSLRAFG        100

CDR II                                            CDR III

QGTKVEIKRTVAAPSVFIFPPSDEQLKSGTASVVCLLNNFYPREAKVQWK        150 constant region

VDNALQSGNSQESVTEQDSKDSTYSLSSTLTLSKADYEKHKLYACEVTHQ        200

GLSSPV                                                   206

PCR primer

Figure 4C    K1-18 light chain DNA

ATGGAAACCCCAGCGCAGCTTCTCTTCCTCCTGCTACTCTGGCTCCCAGATACCACCGGAGAAATTGTGTTGACGCA
GTCTCCAGGCACCCTGTCTTTGTCTCCAGGGGAAAGAGCCACCCTCTCCTGCAGGGCCAGTCAGAGTGTTAGCAACA
ACTACTTAGCCTGGTACCAGCAGAAGCCTGGCCAGGCTCCCAGGCTCCTCATCTATGGTGCATCCAGCAGGGCCACT
GGCATCCCAGACAGGTTCAGTGGCAGTGGGTCTGGGACAGACTTCACTCTCACCATCAGCAGACTGGAGCCTGAAGA
TTTTGCAGTGTATTACTGTCAGCATTGTGGTAGCTCACTGAGGGCGTTCGGCCAAGGGACCAAGGTGGAAATCAAAC
GAACTGTGGCTGCACCATCTGTCTTCATCTTCCCGCCATCTGATGAGCAGTTGAAATCTGGAACTGCCTCTGTTGTG
TGCCTGCTGAATAACTTCTATCCCAGAGAGGCCAAAGTACAGTGGAAGGTGGATAACGCCCTCCAATCGGGTAACTC
CCAGGAGAGTGTCACAGAGCAGGACAGCAAGGACAGCACCTACAGCCTCAGCAGCACCCTGACGCTGAGCAAAGCAG
ACTACGAGAAACACAAACTCTACGCCTGCGAAGTCACCCATCAGGGCCTGAGCTCGCCCGTCACA

Figure 4C – CONT.

atggaaaoccagogcagcttctcttcctcctgctactctggctcccaga
PCR primer          leader sequence taccaccggaGAAATTGTGTTGACGCAGTCTCCAGGCACCCTGTCTTTGT CTCCAGGGAAAGAGCCACCCTCTCCTGCAGGGCCAGTCAGAGTGTTAGC
                              CDR I

AACAACTACTTAGCCTGGTACCAGCAGAAGCCTGGCCAGGCTCCCAGGCT

CCTCATCTATGGTGCATCCAGCAGGGCCACTGGCATCCCAGACAGGTTCA
          CDR II

GTGGCAGTGGGTCTGGGACAGACTTCACTCTCACCATCAGCAGACTGGAG

CCTGAAGATTTTGCAGTGTATTACTGTCAGCATTGTGGTAGCTCACTGAG
                              CDR III

GGCGTTCGGCCAAGGGACCAAGGTGGAAATCAAACGAACTGTGGCTGCAC
                                    constant region

CATCTGTCTTCATCTTCCCGCCATCTGATGAGCAGTTGAAATCTGGAACT

GCCTCTGTTGTGTGCCTGCTGAATAACTTCTATCCCAGAGAGGCCAAAGT

ACAGTGGAAGGTGGATAACGCCCTCCAATCGGGTAACTCCCAGGAGAGTG

TCACAGAGCAGGACAGCAAGGACAGCACCTACAGCCTCAGCAGCACCCTG

ACGCTGAGCAAAGCAGACTACGAGAAACACAAACTCTACGCCTGCGAAGT

CACCCATCAGGGCCTGAGCTCGCCCGTCACA
            PCR primer

Figure 4D    K1-18 light chain protein

METPAQLLFLLLLWLPDTTGEIVLTQSPGTLSLSPGERATLSCRASQSVSNNYLAWYQQKPGQAPRLLIYGASSRAT
GIPDRFSGSGSGTDFTLTISRLEPEDFAVYYCQHCGSSLRAFGQGTKVEIKRTVAAPSVFIFPPSDEQLKSGTASVV
CLLNNFYPREAKVQWKVDNALQSGNSQESVTEQDSKDSTYSLSSTLTLSKADYEKHKLYACEVTHQGLSSPVT

```
metpaqllflllwlp-dttgEIVLTQSPGTLSLSPGERATLSC RASQSVS
PCR primer    leader                              CDR I
              sequence

SNYLAWYQQKPGQAPRLLIY GASSRAT GIPDRFSGSGSGTDFTLTISRLE
                     CDR II

PEDFAVYYC QHCGSSLRA FGQGTKVEIKR TVAAPSVFIFPPSDEQLKSGT
          CDR III               constant region
```

ASVVCLLNNFYPREAKVQWKVDNALQSGNSQESVTEQDSKDSTYSLSSTL

TLSKADYEKHKLYACEVTHQGLSSPVT
                     PCR primer

Figure 5A    K1-70 heavy chain DNA

CAGGTTCAGCTGGTGCAGTCTGGAGCAGAGGTGAAAAAGCCCGGGCAGTC

TCTGAAGATCTCCTGTAAGGCTTCTGGATACAGCTTAACCGACAACTGGA

TCGGCTGGGTGCGCCAGAAGCCCGGGAAAGGCCTGGAGTGGATGGGGATC

ATCTATCCTGGTGACTCTGACACCAGATACAGTCCGTCCTTCCAAGGCCA

GGTCACCATCTCAGCCGACAAGTCCATCAACACCGCCTACCTGCAGTGGA

GCAGCCTGAAGGCCTCGGACACCGCCATATATTACTGTGTGGGACTCGAT

TGGAACTACAACCCCCTGCGATACTGGGGCCCGGGAACCCTGGTCACCGT

CTCCTCAGCCTCCACCAAGGGCCCATCGGTCTTCCCCCTGGCACCCTCCT

CCAAGAGCACCTCTGGGGGCACAGCGGCCCTGGGCTGCCTGGTCAAGGAC

TACTTCCCCGAACCGGTGACGGTGTCGTGGAACTCAGGCGCCCTGACCAG

CGGCGTGCACACCTTCCCGGCTGTCCTACAGTCCTCAGGACTCTACTCCC

TCAGCAGCGTGGTGACCGTGCCCTCCAGCAGCTTGGGCACCCAGACCTAC

ATCTGCAACGTGAATCACAAGCCCAGCAACACCAAGGTGGACAAGAAAGT

TGAGCCCAAATCTTGTGACAAAACTAGTG

Figure 5A – CONT.

| | |
|---|---|
| CAGGTTCAGCTGGTGCAGTCTGGAGCAGAGGTGAAAAAGCCCGGGCAGTC | 50 |
| PCR primer | |
| TCTGAAGATCTCCTGTAAGGCTTCTGGATACAGCTTAACCGACAACTGGA | 100 |
| CDR I | |
| TCGGCTGGGTGCGCCAGAAGCCCGGGAAAGGCCTGGAGTGGATGGGGATC | 150 |
| CDR II | |
| ATCTATCCTGGTGACTCTGACACCAGATACAGTCCGTCCTTCCAAGGCCA | 200 |
| GGTCACCATCTCAGCCGACAAGTCCATCAACACCGCCTACCTGCAGTGGA | 250 |
| GCAGCCTGAAGGCCTCGGACACCGCCATATATTACTGTGTGGGACTCGAT | 300 |
| CDR III | |
| TGGAACTACAACCCCCTGCGATACTGGGGCCCGGGAACCCTGGTCACCGT | 350 |
| CTCCTCAGCCTCCACCAAGGGCCCATCGGTCTTCCCCCTGGCACCCTCCT | 400 |
| constant region | |
| CCAAGAGCACCTCTGGGGGCACAGCGGCCCTGGGCTGCCTGGTCAAGGAC | 450 |
| TACTTCCCCGAACCGGTGACGGTGTCGTGGAACTCAGGCGCCCTGACCAG | 500 |
| CGGCGTGCACACCTTCCCGGCTGTCCTACAGTCCTCAGGACTCTACTCCC | 550 |
| TCAGCAGCGTGGTGACCGTGCCCTCCAGCAGCTTGGGCACCCAGACCTAC | 600 |
| ATCTGCAACGTGAATCACAAGCCCAGCAACACCAAGGTGGACAAGAAAGT | 650 |
| TGAGCCCAAATCTTGTGACAAAACTAGTG | 679 |
| PCR primer | |

Figure 5B    K1-70 heavy chain protein

QVQLVQSGAEVKKPGQSLKISCKASGYSLTDNWIGWVRQKPGKGLEWMGI

IYPGDSDTRYSPSFQGQVTISADKSINTAYLQWSSLKASDTAIYYCVGLD

WNYNPLRYWGPGTLVTVSSASTKGPSVFPLAPSSKSTSGGTAALGCLVKD

YFPEPVTVSWNSGALTSGVHTFPAVLQSSGLYSLSSVVTVPSSSLGTQTY

ICNVNHKPSNTKVDKKVEPKSCDKTS

QVQLVQSGAEVKKPGQSLKISCKASGYSLTDNWIGWVRQKPGKGLEWMGI    50
PCR primer                    CDR I              CDR II

IYPGDSDTRYSPSFQGQVTISADKSINTAYLQWSSLKASDTAIYYCVGLD    100

CDR III
WNYNPLRYWGPGTLVTVSSASTKGPSVFPLAPSSKSTSGGTAALGCLVKD    150
                    constant region
YFPEPVTVSWNSGALTSGVHTFPAVLQSSGLYSLSSVVTVPSSSLGTQTY    200

ICNVNHKPSNTKVDKKVEPKSCDKTS                            226
                  PCR primer

Figure 5C     K1-70 heavy chain DNA

```
ATGGGGTCAACCGCCATCCTCGCCCTCCTCCTGGCTGTTCTCCAGGGAGTCTGTGCCGAGGTGCAGCTGGTGCAGTC
TGGAGCAGAGGTGAAAAAGCCCGGGCAGTCTCTGAAGATCTCCTGTAAGGCTTCTGGATACAGCTTAACCGACAACT
GGATCGGCTGGGTGCGCCAGAAGCCCGGGAAAGGCCTGGAGTGGATGGGGATCATCTATCCTGGTGACTCTGACACC
AGATACAGTCCGTCCTTCCAAGGCCAGGTCACCATCTCAGCCGACAAGTCCATCAACACCGCCTACCTGCAGTGGAG
CAGCCTGAAGGCCTCGGACACCGCCATATATTACTGTGTGGGACTCGATTGGAACTACAACCCCCTGCGATACTGGG
GCCCGGGAACCCTGGTCACCGTCTCCTCAGCCTCCACCAAGGGCCCATCGGTCTTCCCCCTGGCACCCTCCTCCAAG
AGCACCTCTGGGGGCACAGCGGCCCTGGGCTGCCTGGTCAAGGACTACTTCCCCGAACCGGTGACGGTGTCGTGGAA
CTCAGGCGCCCTGACCAGCGGCGTGCACACCTTCCCGGCTGTCCTACAGTCCTCAGGACTCTACTCCCTCAGCAGCG
TGGTGACCGTGCCCTCCAGCAGCTTGGGCACCCAGACCTACATCTGCAACGTGAATCACAAGCCCAGCAACACCAAG
GTGGACAAGACAGTTGAGCGCAAATCT
```

Figure 5C – CONT.

atggggtcaaccgccatcctcgccctcctggctgttctccaggagt
PCR primer          leader sequence ctgtgccGAGGTGCAGCTGGTGCAGTCTGGAGCAGAGGTGAAAAAGCCCG GGCAGTCTCTGAAGATCTCCTGTAAGGCTTCTGGATACAGCTTAACCGAC
                                                 CDR I

AACTGGATCGGCTGGGTGCGCCAGAAGCCCGGGAAAGGCCTGGAGTGGAT

GGGCATCATCTATCCTGGTGACTCTGACACCAGATACAGTCCGTCCTTCC
    CDR II

AAGGCCAGGTCACCATCTCAGCCGACAAGTCCATCAACACCGCCTACCTG

CAGTGGAGCAGCCTGAAGGCCTCGGACACCGCCATATATTACTGTGTGGG

ACTCGATTGGAACTACAACCCCCTGCGATACTGGGGCCCGGGAACCCTGG
    CDR III

TCACCGTCTCCTCAGCCTCCACCAAGGGCCCATCGGTCTTCCCCCTGGCA
                    constant region

CCCTCCTCCAAGAGCACCTCTGGGGGCACAGCGGCCCTGGGCTGCCTGGT

CAAGGACTACTTCCCCGAACCGGTGACGGTGTCGTGGAACTCAGGCGCCC

TGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCA

GACCTACATCTGCAACGTGAATCACAAGCCCAGCAACACCAAGGTGGACA

AGACAGTTGAGCGCAAATCT
PCR primer

Figure 5D  K1-70 heavy chain protein

MGSTAILALLLAVLQGVCAEVQLVQSGAEVKKPGQSLKISCKASGYSLTDNWIGWVRQKPGKGLEWMGIIYPGDSDT
RYSPSFQGQVTISADKSINTAYLQWSSLKASDTAIYYCVGLDWNYNPLRYWGPGTLVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTK
VDKTVERKS mgstailallavlqgvcaEVQLVQSGAEVKKPGQSLKISCKASGYSLTD
PCR primer    leader                                    CDR I
              sequence

NWIGWVRQKPGKGLEWMGIIYPGDSDTRYSPSFQGQVTISADKSINTAYL
              CDR II

QWSSLKASDTAIYYCVGLDWNYNPLRYWGPGTLVTVSSASTKGPSVFPLA
              CDR III                    constant region

PSSKSTSGGTAALGCLVKDYFPEPVTVSWNSGALTSGVHTFPAVLQSSGL

YSLSSVVTVPSSSLGTQTYICNVNHKPSNTKVDKTVERKS
                                        PCR primer

Figure 6A   K1-70 light chain DNA

CTGCCTGTGCTGACTCAGCCACCCTCAGTGTCCGTGTCCCAGGACAGAC

AGCCAGCATCACCTGCTCTGGAGATAAATTGGGGGATAAATATGCTTGCT

GGTATCAGCAGAAGCCAGGCCAGTCCCTGTGCTGGTCATCTATCAAGAT

AGCAAGCGGCCCTCAGGGATCCCTGAGCGATTCTCTGGCTCCAACTCTGG

GAACACAGCCACTCTGACCATCAGCGGGACCCAGGCTATGGATGAGGCTG

ACTATTACTGTCAGGCGTGGGACAGCAGCACTGCCGTGGTATTCGGCGGA

GGGACCAAGCTGACCGTCCTAGGTCAGCCCAAGGCTGCCCCTCGGTCAC

TCTGTTCCGCCCTCCTCTGAGGAGCTTCAAGCCAACAAGGCCACACTGG

TGTGTCTCATAAGTGACTTCTACCCGGGAGCCGTGACAGTGGCCTGGAAG

GCAGATAGCAGCCCCGTCAAGGCGGGAGTGGAGACCACCACACCCTCCAA

ACAAAGCAACAACAAGTACGCGGCCAGCAGCTATCTGAGCCTGACGCCTG

AGCAGTGGAAGTCCCACAGAAGCTACAGCTGCCAGGTCACGCATGAAGGG

AGCACCGTGGAGAAGACAGTGGCCCCTACAGAATGTTCA

Figure 6A – CONT.

```
CTGCCTGTGCTGACTCAGCCACCCTCAGTGTCCGTGTCCCCAGGACAGAC        50
```
PCR primer
```
AGCCAGCATCACCTGCTCTGGAGATAAATTGGGGGATAAATATGCTTGCT       100
                 CDR I
GGTATCAGCAGAAGCCAGGCCAGTCCCCTGTGCTGGTCATCTATCAAGAT       150
                                                CDR II
AGCAAGCGGCCCTCAGGGATCCCTGAGCGATTCTCTGGCTCCAACTCTGG       200

GAACACAGCCACTCTGACCATCAGCGGGACCCAGGCTATGGATGAGGCTG       250

ACTATTACTGTCAGGCGTGGGACAGCAGCACTGCCGTGGTATTCGGCGGA       300
            CDR III
```
constant region
```
GGGACCAAGCTGACCGTCCTAGGTCAGCCCAAGGCTGCCCCCTCGGTCAC       350

TCTGTTCCCGCCCTCCTCTGAGGAGCTTCAAGCCAACAAGGCCACACTGG       400

TGTGTCTCATAAGTGACTTCTACCCGGGAGCCGTGACAGTGGCCTGGAAG       450

GCAGATAGCAGCCCCGTCAAGGCGGGAGTGGAGACCACCACACCCTCCAA       500

ACAAAGCAACAACAAGTACGCGGCCAGCAGCTATCTGAGCCTGACGCCTG       550

AGCAGTGGAAGTCCCACAGAAGCTACAGCTGCCAGGTCACGCATGAAGGG       600

AGCACCGTGGAGAAGACAGTGGCCCCTACAGAATGTTCA                  639
```
PCR primer

Figure 6B    K1-70 light chain protein

LPVLTQPPSVSVSPGQTASITCSGDKLGDKYACWYQQKPGQSPVLVIYQD
SKRPSGIPERFSGSNSGNTATLTISGTQAMDEADYYCQAWDSSTAVVFGG
GTKLTVLGQPKAAPSVTLFPPSSEELQANKATLVCLISDFYPGAVTVAWK
ADSSPVKAGVETTTPSKQSNNKYAASSYLSLTPEQWKSHRSYSCQVTHEG
STVEKTVAPTECS

```
LPVLTQPPSVSVSPGQTASITC SGDKLGDKYAC WYQQKPGQSPVLVIY QD         50
PCR primer              CDR I
    CDR II
SKRPS GIPERFSGSNSGNTATLTISGTQAMDEADYYC QAWDSSTAVV FGG         100
                                        CDR III
GTKLTVLGQPKAAPSVTLFPPSSEELQANKATLVCLISDFYPGAVTVAWK            150
             constant region
ADSSPVKAGVETTTPSKQSNNKYAASSYLSLTPEQWKSHRSYSCQVTHEG            200

STVEKTVAPTECS                                                 213
      PCR primer
```

Figure 6C     K1-70 light chain DNA (preferred)

ATGGCCTGGTCTCCTCTCCTCCTCACCCTTCTCATTCACTGCACAGGGTCCTGGGCCCAGTCTGTGTTGACGCAGCC
GCCCTCAGTGTCTGCGGCCCCAGGACAGAAGGTCACCATTTCCTGCTCCGGAAGCAGCTCCGACATTGGGAGTAATT
ATGTATCCTGGTACCAGCAGTTCCCGGGAACAGCCCCCAAACTCCTCATTTATGACAATAATAAGCGACCCTCAGCG
ATTCCTGACCGATTCTCTGGCTCCAAGTCTGGCACGTCAGCCACCCTGGGCATCACCGGACTCCAGACTGGGGACGA
GGCCGATTATTACTGCGGAACATGGGATAGCAGACTGGGTATTGCTGTGTTCGGAGGAGGCACCCAGCTGACCGTCC
TCGGTCAGCCCAAGGCTGCCCCATCGGTCACTCTGTTCCCACCCTCCTCTGAGGAGCTTCAAGCCAACAAGGCCACA
CTGGTGTGTCTCGTAAGTGACTTCTACCCGGGAGCCGTGACAGTGGCCTGGAAGGCAGATGGCAGCCCCGTCAAGGT
GGGAGTGGAGACCACCAAACCCTCCAAACAAAGCAACAACAAGTATGCGGCCAGCAGCTACCTGAGCCTGACGCCCG
AGCAGTGGAAGTCCCACAGAAGCTACAGCTGCCGGGTCACGCATGAAGGGAGCACCGTGGAGAAGACAGTGGCCCCT
ACAGAATCTTCA

Figure 6C – CONT.

<u>atggcctggtctcctctcctcctcaccctcctcattcactgacaggqtc</u>
PCR primer          leader sequence ctgggccCAGTCTGTGTTGACGCAGCCGCCCTCAGTGTCTGCGGCCCCAG GACAGAAGGTCACCATTTCCTGC|TCCGGAAGCAGCTCCGACATTGGGAGT|
                        CDR I

|AATTATGTATCC|TGGTACCAGCAGTTCCCGGGAACAGCCCCCAAACTCCT

CATTTAT|GACAATAATAAGCGACCCTCA|GCGATTCCTGACCGATTCTCTG
        CDR II

GCTCCAAGTCTGGCACGTCAGCCACCCTGGGCATCACCGGACTCCAGACT

GGGGACGAGGCCGATTATTACTGC|GGAACATGGGATAGCAGACTGGGTAT|
                         CDR III

|TGCTGTC|TTCGGAGGAGGCACCCAGCTGACCGTCCTCGGTCAGCCCAAGG
                                          constant region

CTGCCCCATCGGTCACTCTGTTCCCACCCTCCTCTGAGGAGCTTCAAGCC

AACAAGGCCACACTGGTGTGTCTCGTAAGTGACTTCTACCCGGGAGCCGT

GACAGTGGCCTGGAAGGCAGATGGCAGCCCCGTCAAGGTGGGAGTGGAGA

CCACCAAACCCTCCAAACAAAGCAACAACAAGTATGCGGCCAGCAGCTAC

CTGAGCCTGACGCCCGAGCAGTGGAAGTCCCACAGAAGCTACAGCTGCCG

GGTCACGCATGAAGGGAGCACCGTGGAGAAGACAGTGGCCCCTACAGAAT
                                        PCR primer <u>GTTCA</u>

Figure 6D  K1-70 light chain protein (preferred)

MAWSPLLLTLLIHCTGSWAQSVLTQPPSVSAAPGQKVTISCSGSSSDIGSNYVSWYQQFPGTAPKLLIYDNNKRPSA
IPDRFSGSKSGTSATLGITGLQTGDEADYYCGTWDSRLGIAVFGGGTQLTVLGQPKAAPSVTLFPPSSEELQANKAT
LVCLVSDFYPGAVTVAWKADGSPVKVGVETTKPSKQSNNKYAASSYLSLTPEQWKSHRSYSCRVTHEGSTVEKTVAP
TECS mawsplllthlihctqswaQSVLTQPPSVSAAPGQKVTISC SGSSSDIGS
PCR primer    leader                      CDR I
              sequence

NYVS WYQQFPGTAPKLLIY DNNKRPS AIPDRFSGSKSGTSATLGITGLQT
                    CDR II

GDEADYYC GTWDSRLGIAV FGGGTQLTVLG QPKAAPSVTLFPPSSEELQA
         CDR III                 constant region

NKATLVCLVSDFYPGAVTVAWKADGSPVKVGVETTKPSKQSNNKYAASSY

LSLTPEQWKSHRSYSCRVTHEGSTVEKTVA PTECS
                                PCR primer

Figure 6E    K1-70 light chain N-terminal sequence (amino acids 2-21; the first N-terminal amino acid was removed by treatment with pyroglutamate aminopeptidase to enable the Edman reaction)

SVLTQPPSVSAAPGQKVTIS

Figure 7A   The consensus amino acid sequence of the human TSHR (accession no.P16473, http://www.ncbi.nlm.nih.gov/entrez/viewer.fcgi?db=protein&val=62298994). The leader sequence (amino acids 1-21) is shown in lowercase.

```
mrpadllqlv    llldlprdlg    gMGCSSPPCE    CHQEEDFRVT    CKDIQRIPSL    PPSTQTLKLI
ETHLRTIPSH    AFSNLPNISR    IYVSIDVTLQ    QLESHSFYNL    SKVTHIEIRN    TRNLTYIDPD
ALKELPLLKF    LGIFNTGLKM    FPDLTKVYST    DIFFILEITD    NPYMTSIPVN    AFQGLCNETL
TLKLYNNGFT    SVQGYAFNGT    KLDAVYLNKN    KYLTVIDKDA    FGGVYSGPSL    LDVSQTSVTA
LPSKGLEHLK    ELIARNTWTL    KKLPLSLSFL    HLTRADLSYP    SHCCAFKNQK    KIRGILESLM
CNESSMQSLR    QRKSVNALNS    PLHQEYEENL    GDSIVGYKEK    SKFQDTHNNA    HYYVFFEEQE
DEIIGFGQEL    KNPQEETLQA    FDSHYDYTIC    GDSEDMVCTP    KSDEFNPCED    IMGYKFLRIV
VWFVSLLALL    GNVFVLLILL    TSHYKLNVPR    FLMCNLAFAD    FCMGMYLLLI    ASVDLYTHSE
YYNHAIDWQT    GPGCNTAGFF    TVFASELSVY    TLTVITLERW    YAITFAMRLD    RKIRLRHACA
IMVGGWVCCF    LLALLPLVGI    SSYAKVSICL    PMDTETPLAL    AYIVFVLTLN    IVAFVIVCCC
YVKIYITVRN    PQYNPGDKDT    KIAKRMAVLI    FTDFICMAPI    SFYALSAILN    KPLITVSNSK
ILLVLFYPLN    SCANPFLYAI    FTKAFQRDVF    ILLSKFGICK    RQAQAYRGQR    VPPKNSTDIQ
VQKVTHDMRQ    GLHNMEDVYE    LIENSHLTPK    KQGQISEEYM    QTVL
```

Figure 7B The consensus amino acid sequence of the human TSHR (amino acids 1-260 including the leader sequence (amino acids 1-21) shown in lowercase). A 6 histidine sequence added at the C-terminus (following asparagines at position 260) is shown in bold

```
mrpadllqlv  lldlprdlg   gMGCSSPPCE  CHQEEDFRVT  CKDIQRIPSL  PPSTQTLKLI

ETHLRTIPSH  AFSNLPNISR  IYVSIDVTLQ  QLESHSFYNL  SKVTHIEIRN  TRNLTYIDPD

ALKELPLLKF  LGIFNTGLKM  FPDLTKVYST  DIFFILEITD  NPYMTSIPVN  AFQGLCNETL

TLKLYNNGFT  SVQGYAFNGT  KLDAVYLNKN  KYLTVIDKDA  FGGVYSGPSL  LDVSQTSVTA

LPSKGLEHLK  ELIARNIWTL  NHHHHHH
```

Figure 7C The amino acid sequence of the humanTSHR LRD C-CAP with C-terminal 6 histidine tag. The leader sequence (amino acids 1-21) are shown in lowercase

```
mrpadlqlv  llldlprdlg  gMGCSSPPCE  CHQEEDFRVT  CKDIQRIPSL  PPSTQTLKLI
ETHLRTIPSH  AFSNLPNISR  IYVSIDVTLQ  QLESHSFYNL  SKVTHIEIRN  TRNLTYIDPD
ALKELPLLKF  LGIFNTGLKM  FPDLTKVYST  DIFFILEITD  NPYMTSIPVN  AFQGLCNETL
TLKLYNNGFT  SVQGYAFNGT  KLDAVYLNKN  KYLTVIDKDA  FGGVYSGPSL  LDVSQTSVTA
LPSKGLEHLK  ELIARNTWTL  KKLPLSLSFL  HLTRADLSYP  SHCCAFKNQK  KIRGILESLM
CNESSYDYTI  CGDSEDMVCT  PKSDEFNPCE  HHHHHH
```

FIG 8 Coordinates of K1-70 Fab

```
HEADER      ----                                       XX-XXX-9-    xxxx
COMPND      ---
REMARK   3
REMARK   3 REFINEMENT.
REMARK   3   PROGRAM     : REFMAC 5.5.0072
REMARK   3   AUTHORS     : MURSHUDOV,VAGIN,DODSON
REMARK   3
REMARK   3    REFINEMENT TARGET : MAXIMUM LIKELIHOOD
REMARK   3
REMARK   3  DATA USED IN REFINEMENT.
REMARK   3   RESOLUTION RANGE HIGH (ANGSTROMS) :   2.22
REMARK   3   RESOLUTION RANGE LOW  (ANGSTROMS) :  44.86
REMARK   3   DATA CUTOFF            (SIGMA(F)) :  NONE
REMARK   3   COMPLETENESS FOR RANGE        (%) :  97.66
REMARK   3   NUMBER OF REFLECTIONS             :  51482
REMARK   3
REMARK   3  FIT TO DATA USED IN REFINEMENT.
REMARK   3   CROSS-VALIDATION METHOD           : THROUGHOUT
REMARK   3   FREE R VALUE TEST SET SELECTION   : RANDOM
REMARK   3   R VALUE     (WORKING + TEST SET) : 0.21907
REMARK   3   R VALUE            (WORKING SET) : 0.21667
REMARK   3   FREE R VALUE                     : 0.26396
REMARK   3   FREE R VALUE TEST SET SIZE   (%) : 5.1
REMARK   3   FREE R VALUE TEST SET COUNT      : 2775
REMARK   3
REMARK   3  FIT IN THE HIGHEST RESOLUTION BIN.
REMARK   3   TOTAL NUMBER OF BINS USED             :      20
REMARK   3   BIN RESOLUTION RANGE HIGH             :   2.220
REMARK   3   BIN RESOLUTION RANGE LOW              :   2.278
REMARK   3   REFLECTION IN BIN     (WORKING SET) :    3724
REMARK   3   BIN COMPLETENESS (WORKING+TEST) (%) :   96.83
REMARK   3   BIN R VALUE           (WORKING SET) :   0.307
REMARK   3   BIN FREE R VALUE SET COUNT            :     217
REMARK   3   BIN FREE R VALUE                      :   0.378
REMARK   3
REMARK   3  NUMBER OF NON-HYDROGEN ATOMS USED IN REFINEMENT.
REMARK   3   ALL ATOMS              :       6699
REMARK   3
REMARK   3  B VALUES.
REMARK   3   FROM WILSON PLOT           (A**2) : NULL
REMARK   3   MEAN B VALUE      (OVERALL, A**2) : 32.714
REMARK   3   OVERALL ANISOTROPIC B VALUE.
REMARK   3    B11 (A**2) :   -1.25
REMARK   3    B22 (A**2) :    2.71
REMARK   3    B33 (A**2) :   -1.25
REMARK   3    B12 (A**2) :    0.00
REMARK   3    B13 (A**2) :    0.75
REMARK   3    B23 (A**2) :    0.00
REMARK   3
REMARK   3  ESTIMATED OVERALL COORDINATE ERROR.
REMARK   3   ESU BASED ON R VALUE                        (A): 0.257
REMARK   3   ESU BASED ON FREE R VALUE                   (A): 0.217
REMARK   3   ESU BASED ON MAXIMUM LIKELIHOOD             (A): 0.158
REMARK   3   ESU FOR B VALUES BASED ON MAXIMUM LIKELIHOOD (A**2): 6.315
REMARK   3
REMARK   3 CORRELATION COEFFICIENTS.
REMARK   3   CORRELATION COEFFICIENT FO-FC      : 0.949
REMARK   3   CORRELATION COEFFICIENT FO-FC FREE : 0.927
REMARK   3
```

FIG 8 – CONT.

```
REMARK   3  RMS DEVIATIONS FROM IDEAL VALUES         COUNT     RMS    WEIGHT
REMARK   3   BOND LENGTHS REFINED ATOMS        (A):   6514 ; 0.014 ; 0.022
REMARK   3   BOND LENGTHS OTHERS               (A):   4237 ; 0.001 ; 0.020
REMARK   3   BOND ANGLES REFINED ATOMS   (DEGREES):   8927 ; 1.488 ; 1.955
REMARK   3   BOND ANGLES OTHERS          (DEGREES):  10432 ; 0.888 ; 3.003
REMARK   3   TORSION ANGLES, PERIOD 1    (DEGREES):    857 ; 6.849 ; 5.000
REMARK   3   TORSION ANGLES, PERIOD 2    (DEGREES):    216 ;36.386 ;24.861
REMARK   3   TORSION ANGLES, PERIOD 3    (DEGREES):    951 ;16.906 ;15.000
REMARK   3   TORSION ANGLES, PERIOD 4    (DEGREES):     11 ;18.673 ;15.000
REMARK   3   CHIRAL-CENTER RESTRAINTS       (A**3):   1017 ; 0.087 ; 0.200
REMARK   3   GENERAL PLANES REFINED ATOMS     (A):    7293 ; 0.007 ; 0.021
REMARK   3   GENERAL PLANES OTHERS            (A):    1216 ; 0.001 ; 0.020
REMARK   3
REMARK   3  ISOTROPIC THERMAL FACTOR RESTRAINTS.     COUNT    RMS    WEIGHT
REMARK   3   MAIN-CHAIN BOND REFINED ATOMS  (A**2):   4278 ; 0.743 ; 1.500
REMARK   3   MAIN-CHAIN BOND OTHER ATOMS    (A**2):   1731 ; 0.144 ; 1.500
REMARK   3   MAIN-CHAIN ANGLE REFINED ATOMS (A**2):   6916 ; 1.379 ; 2.000
REMARK   3   SIDE-CHAIN BOND REFINED ATOMS  (A**2):   2236 ; 1.903 ; 3.000
REMARK   3   SIDE-CHAIN ANGLE REFINED ATOMS (A**2):   2010 ; 3.036 ; 4.500
REMARK   3
REMARK   3  NCS RESTRAINTS STATISTICS
REMARK   3   NUMBER OF NCS GROUPS : NULL
REMARK   3
REMARK   3  TWIN DETAILS
REMARK   3   NUMBER OF TWIN DOMAINS  : NULL
REMARK   3
REMARK   3
REMARK   3  TLS DETAILS
REMARK   3   NUMBER OF TLS GROUPS   : NULL
REMARK   3
REMARK   3
REMARK   3  BULK SOLVENT MODELLING.
REMARK   3   METHOD USED : MASK
REMARK   3   PARAMETERS FOR MASK CALCULATION
REMARK   3   VDW PROBE RADIUS   :  1.40
REMARK   3   ION PROBE RADIUS   :  0.80
REMARK   3   SHRINKAGE RADIUS   :  0.80
REMARK   3
REMARK   3  OTHER REFINEMENT REMARKS:
REMARK   3  HYDROGENS HAVE BEEN ADDED IN THE RIDING POSITIONS
REMARK   3  U VALUES      : REFINED INDIVIDUALLY
REMARK   3
REMARK   [No title given]
SSBOND   1 CYS A    22    CYS A    92
SSBOND   2 CYS A   142    CYS A   208
SSBOND   3 CYS C    22    CYS C    92
SSBOND   4 CYS C   142    CYS C   208
SSBOND   5 CYS B    23    CYS B    88
SSBOND   6 CYS B   134    CYS B   194
SSBOND   7 CYS D    23    CYS D    88
SSBOND   8 CYS D   134    CYS D   194
CISPEP   1 PHE A   148    PRO A   149                       0.00
CISPEP   2 GLU A   150    PRO A   151                       0.00
CISPEP   3 TYR B   140    PRO B   141                       0.00
CISPEP   4 PHE C   148    PRO C   149                       0.00
CISPEP   5 GLU C   150    PRO C   151                       0.00
CISPEP   6 TYR D   140    PRO D   141                       0.00
CRYST1   70.180   62.140  131.030  90.00  98.29  90.00 P 1 21 1
SCALE1      0.014249  0.000000  0.002076        0.00000
SCALE2      0.000000  0.016093  0.000000        0.00000
SCALE3      0.000000  0.000000  0.007712        0.00000
```

FIG 8 – CONT.

| ATOM | 1 | N | GLN | A | 1 | 38.061 | -3.592 | 66.895 | 1.00 | 41.03 | A |
|---|---|---|---|---|---|---|---|---|---|---|---|
| ATOM | 2 | CA | GLN | A | 1 | 36.758 | -3.846 | 67.593 | 1.00 | 39.95 | A |
| ATOM | 4 | CB | GLN | A | 1 | 36.944 | -4.668 | 68.859 | 1.00 | 40.33 | A |
| ATOM | 11 | C | GLN | A | 1 | 36.080 | -2.516 | 67.908 | 1.00 | 39.20 | A |
| ATOM | 12 | O | GLN | A | 1 | 34.930 | -2.338 | 67.534 | 1.00 | 39.71 | A |
| ATOM | 16 | N | VAL | A | 2 | 36.777 | -1.598 | 68.586 | 1.00 | 38.20 | A |
| ATOM | 17 | CA | VAL | A | 2 | 36.258 | -0.226 | 68.806 | 1.00 | 37.19 | A |
| ATOM | 19 | CB | VAL | A | 2 | 36.917 | 0.479 | 70.008 | 1.00 | 37.15 | A |
| ATOM | 21 | CG1 | VAL | A | 2 | 36.330 | 1.908 | 70.212 | 1.00 | 34.81 | A |
| ATOM | 25 | CG2 | VAL | A | 2 | 36.773 | -0.372 | 71.272 | 1.00 | 36.30 | A |
| ATOM | 29 | C | VAL | A | 2 | 36.483 | 0.662 | 67.575 | 1.00 | 37.15 | A |
| ATOM | 30 | O | VAL | A | 2 | 37.612 | 0.841 | 67.128 | 1.00 | 37.22 | A |
| ATOM | 32 | N | GLN | A | 3 | 35.404 | 1.211 | 67.031 | 1.00 | 36.48 | A |
| ATOM | 33 | CA | GLN | A | 3 | 35.485 | 2.095 | 65.887 | 1.00 | 36.23 | A |
| ATOM | 35 | CB | GLN | A | 3 | 35.074 | 1.355 | 64.601 | 1.00 | 36.36 | A |
| ATOM | 38 | CG | GLN | A | 3 | 35.996 | 1.588 | 63.378 | 1.00 | 41.25 | A |
| ATOM | 41 | CD | GLN | A | 3 | 35.251 | 1.585 | 62.005 | 1.00 | 45.22 | A |
| ATOM | 42 | OE1 | GLN | A | 3 | 35.582 | 2.372 | 61.100 | 1.00 | 45.42 | A |
| ATOM | 43 | NE2 | GLN | A | 3 | 34.243 | 0.714 | 61.863 | 1.00 | 46.72 | A |
| ATOM | 46 | C | GLN | A | 3 | 34.537 | 3.266 | 66.148 | 1.00 | 34.98 | A |
| ATOM | 47 | O | GLN | A | 3 | 33.350 | 3.051 | 66.434 | 1.00 | 34.03 | A |
| ATOM | 49 | N | LEU | A | 4 | 35.060 | 4.485 | 66.068 | 1.00 | 33.47 | A |
| ATOM | 50 | CA | LEU | A | 4 | 34.230 | 5.674 | 66.077 | 1.00 | 32.90 | A |
| ATOM | 52 | CB | LEU | A | 4 | 34.876 | 6.789 | 66.887 | 1.00 | 32.86 | A |
| ATOM | 55 | CG | LEU | A | 4 | 34.993 | 6.528 | 68.385 | 1.00 | 33.36 | A |
| ATOM | 57 | CD1 | LEU | A | 4 | 35.732 | 7.660 | 69.092 | 1.00 | 32.38 | A |
| ATOM | 61 | CD2 | LEU | A | 4 | 33.607 | 6.282 | 69.018 | 1.00 | 32.62 | A |
| ATOM | 65 | C | LEU | A | 4 | 34.035 | 6.115 | 64.631 | 1.00 | 32.85 | A |
| ATOM | 66 | O | LEU | A | 4 | 35.002 | 6.357 | 63.918 | 1.00 | 34.56 | A |
| ATOM | 68 | N | VAL | A | 5 | 32.785 | 6.198 | 64.211 | 1.00 | 32.01 | A |
| ATOM | 69 | CA | VAL | A | 5 | 32.393 | 6.423 | 62.855 | 1.00 | 31.72 | A |

FIG 8 – CONT.

| | | | | | | | | | | | |
|---|---|---|---|---|---|---|---|---|---|---|---|
| ATOM | 71 | CB | VAL | A | 5 | 31.324 | 5.386 | 62.500 | 1.00 | 32.43 | A C |
| ATOM | 73 | CG1 | VAL | A | 5 | 30.791 | 5.589 | 61.074 | 1.00 | 32.92 | A C |
| ATOM | 77 | CG2 | VAL | A | 5 | 31.879 | 3.968 | 62.721 | 1.00 | 33.09 | A C |
| ATOM | 81 | C | VAL | A | 5 | 31.775 | 7.807 | 62.728 | 1.00 | 30.89 | A C |
| ATOM | 82 | O | VAL | A | 5 | 30.715 | 8.061 | 63.283 | 1.00 | 31.93 | A O |
| ATOM | 84 | N | GLN | A | 6 | 32.437 | 8.713 | 62.027 | 1.00 | 29.82 | A N |
| ATOM | 85 | CA | GLN | A | 6 | 31.972 | 10.097 | 61.912 | 1.00 | 28.45 | A C |
| ATOM | 87 | CB | GLN | A | 6 | 33.130 | 11.087 | 62.064 | 1.00 | 27.80 | A C |
| ATOM | 90 | CG | GLN | A | 6 | 33.716 | 11.042 | 63.462 | 1.00 | 26.92 | A C |
| ATOM | 93 | CD | GLN | A | 6 | 34.628 | 12.206 | 63.821 | 1.00 | 25.67 | A C |
| ATOM | 94 | OE1 | GLN | A | 6 | 35.734 | 11.990 | 64.257 | 1.00 | 27.99 | A O |
| ATOM | 95 | NE2 | GLN | A | 6 | 34.129 | 13.421 | 63.738 | 1.00 | 24.61 | A N |
| ATOM | 98 | C | GLN | A | 6 | 31.248 | 10.323 | 60.618 | 1.00 | 28.45 | A C |
| ATOM | 99 | O | GLN | A | 6 | 31.564 | 9.709 | 59.611 | 1.00 | 29.25 | A O |
| ATOM | 101 | N | SER | A | 7 | 30.288 | 11.237 | 60.637 | 1.00 | 28.18 | A N |
| ATOM | 102 | CA | SER | A | 7 | 29.512 | 11.565 | 59.456 | 1.00 | 27.75 | A C |
| ATOM | 104 | CB | SER | A | 7 | 28.270 | 12.395 | 59.846 | 1.00 | 28.05 | A C |
| ATOM | 107 | OG | SER | A | 7 | 28.647 | 13.553 | 60.597 | 1.00 | 29.10 | A O |
| ATOM | 109 | C | SER | A | 7 | 30.383 | 12.312 | 58.465 | 1.00 | 26.46 | A C |
| ATOM | 110 | O | SER | A | 7 | 31.472 | 12.766 | 58.795 | 1.00 | 26.06 | A O |
| ATOM | 112 | N | GLY | A | 8 | 29.911 | 12.420 | 57.235 | 1.00 | 26.33 | A N |
| ATOM | 113 | CA | GLY | A | 8 | 30.765 | 12.828 | 56.151 | 1.00 | 25.91 | A C |
| ATOM | 116 | C | GLY | A | 8 | 31.005 | 14.328 | 56.130 | 1.00 | 26.32 | A C |
| ATOM | 117 | O | GLY | A | 8 | 30.308 | 15.105 | 56.806 | 1.00 | 26.37 | A O |
| ATOM | 119 | N | ALA | A | 9 | 31.958 | 14.731 | 55.303 | 1.00 | 26.31 | A N |
| ATOM | 120 | CA | ALA | A | 9 | 32.346 | 16.144 | 55.150 | 1.00 | 26.77 | A C |
| ATOM | 122 | CB | ALA | A | 9 | 33.390 | 16.307 | 54.042 | 1.00 | 25.41 | A C |
| ATOM | 126 | C | ALA | A | 9 | 31.139 | 16.989 | 54.852 | 1.00 | 26.28 | A C |
| ATOM | 127 | O | ALA | A | 9 | 30.180 | 16.527 | 54.275 | 1.00 | 28.00 | A O |
| ATOM | 129 | N | GLU | A | 10 | 31.196 | 18.249 | 55.238 | 1.00 | 26.25 | A N |

FIG 8 – CONT.

| | | | | | | | | | | |
|---|---|---|---|---|---|---|---|---|---|---|
| ATOM | 130 | CA | GLU A | 10 | 30.062 | 19.110 | 55.111 | 1.00 | 25.55 | A |
| C | | | | | | | | | | |
| ATOM | 132 | CB | GLU A | 10 | 29.462 | 19.384 | 56.511 | 1.00 | 26.10 | A |
| C | | | | | | | | | | |
| ATOM | 135 | CG | GLU A | 10 | 28.805 | 18.148 | 57.192 | 1.00 | 27.86 | A |
| C | | | | | | | | | | |
| ATOM | 138 | CD | GLU A | 10 | 27.379 | 17.933 | 56.784 | 1.00 | 29.00 | A |
| C | | | | | | | | | | |
| ATOM | 139 | OE1 | GLU A | 10 | 26.859 | 18.679 | 55.926 | 1.00 | 29.68 | A |
| O | | | | | | | | | | |
| ATOM | 140 | OE2 | GLU A | 10 | 26.770 | 17.025 | 57.356 | 1.00 | 30.45 | A |
| O | | | | | | | | | | |
| ATOM | 141 | C | GLU A | 10 | 30.502 | 20.423 | 54.537 | 1.00 | 24.06 | A |
| C | | | | | | | | | | |
| ATOM | 142 | O | GLU A | 10 | 31.543 | 20.947 | 54.918 | 1.00 | 23.45 | A |
| O | | | | | | | | | | |
| ATOM | 144 | N | VAL A | 11 | 29.671 | 21.004 | 53.696 | 1.00 | 23.28 | A |
| N | | | | | | | | | | |
| ATOM | 145 | CA | VAL A | 11 | 30.011 | 22.300 | 53.111 | 1.00 | 23.88 | A |
| C | | | | | | | | | | |
| ATOM | 147 | CB | VAL A | 11 | 30.266 | 22.203 | 51.620 | 1.00 | 24.18 | A |
| C | | | | | | | | | | |
| ATOM | 149 | CG1 | VAL A | 11 | 30.668 | 23.620 | 51.067 | 1.00 | 21.94 | A |
| C | | | | | | | | | | |
| ATOM | 153 | CG2 | VAL A | 11 | 31.342 | 21.101 | 51.361 | 1.00 | 21.31 | A |
| C | | | | | | | | | | |
| ATOM | 157 | C | VAL A | 11 | 28.834 | 23.190 | 53.303 | 1.00 | 24.69 | A |
| C | | | | | | | | | | |
| ATOM | 158 | O | VAL A | 11 | 27.768 | 22.863 | 52.854 | 1.00 | 25.13 | A |
| O | | | | | | | | | | |
| ATOM | 160 | N | LYS A | 12 | 29.029 | 24.310 | 53.986 | 1.00 | 25.04 | A |
| N | | | | | | | | | | |
| ATOM | 161 | CA | LYS A | 12 | 27.914 | 25.103 | 54.459 | 1.00 | 26.04 | A |
| C | | | | | | | | | | |
| ATOM | 163 | CB | LYS A | 12 | 27.657 | 24.807 | 55.959 | 1.00 | 26.27 | A |
| C | | | | | | | | | | |
| ATOM | 166 | CG | LYS A | 12 | 27.128 | 23.391 | 56.246 | 1.00 | 28.22 | A |
| C | | | | | | | | | | |
| ATOM | 169 | CD | LYS A | 12 | 25.686 | 23.341 | 55.916 | 1.00 | 31.62 | A |
| C | | | | | | | | | | |
| ATOM | 172 | CE | LYS A | 12 | 25.064 | 22.070 | 56.293 | 1.00 | 33.33 | A |
| C | | | | | | | | | | |
| ATOM | 175 | NZ | LYS A | 12 | 23.648 | 22.167 | 56.008 | 1.00 | 33.77 | A |
| N | | | | | | | | | | |
| ATOM | 179 | C | LYS A | 12 | 28.197 | 26.577 | 54.277 | 1.00 | 26.04 | A |
| C | | | | | | | | | | |
| ATOM | 180 | O | LYS A | 12 | 29.335 | 26.991 | 54.144 | 1.00 | 25.17 | A |
| O | | | | | | | | | | |
| ATOM | 182 | N | LYS A | 13 | 27.131 | 27.357 | 54.265 | 1.00 | 27.42 | A |
| N | | | | | | | | | | |
| ATOM | 183 | CA | LYS A | 13 | 27.239 | 28.813 | 54.251 | 1.00 | 28.77 | A |
| C | | | | | | | | | | |
| ATOM | 185 | CB | LYS A | 13 | 26.158 | 29.390 | 53.367 | 1.00 | 30.06 | A |
| C | | | | | | | | | | |
| ATOM | 188 | CG | LYS A | 13 | 26.400 | 29.072 | 51.905 | 1.00 | 32.35 | A |
| C | | | | | | | | | | |
| ATOM | 191 | CD | LYS A | 13 | 25.417 | 29.806 | 51.032 | 1.00 | 36.42 | A |
| C | | | | | | | | | | |
| ATOM | 194 | CE | LYS A | 13 | 25.374 | 29.252 | 49.594 | 1.00 | 39.04 | A |
| C | | | | | | | | | | |
| ATOM | 197 | NZ | LYS A | 13 | 24.008 | 28.736 | 49.231 | 1.00 | 41.62 | A |

FIG 8 – CONT.

| ATOM | 201 | C | LYS | A | 13 | 27.094 | 29.348 | 55.663 | 1.00 | 28.55 | A |
|---|---|---|---|---|---|---|---|---|---|---|---|
| ATOM | 202 | O | LYS | A | 13 | 26.458 | 28.702 | 56.505 | 1.00 | 27.17 | A |
| ATOM | 204 | N | PRO | A | 14 | 27.674 | 30.532 | 55.925 | 1.00 | 28.34 | A |
| ATOM | 205 | CA | PRO | A | 14 | 27.589 | 31.129 | 57.258 | 1.00 | 27.11 | A |
| ATOM | 207 | CB | PRO | A | 14 | 28.312 | 32.468 | 57.099 | 1.00 | 27.85 | A |
| ATOM | 210 | CG | PRO | A | 14 | 29.224 | 32.251 | 55.877 | 1.00 | 28.50 | A |
| ATOM | 213 | CD | PRO | A | 14 | 28.338 | 31.443 | 54.965 | 1.00 | 28.38 | A |
| ATOM | 216 | C | PRO | A | 14 | 26.134 | 31.344 | 57.598 | 1.00 | 26.49 | A |
| ATOM | 217 | O | PRO | A | 14 | 25.347 | 31.635 | 56.718 | 1.00 | 23.98 | A |
| ATOM | 218 | N | GLY | A | 15 | 25.775 | 31.118 | 58.862 | 1.00 | 26.74 | A |
| ATOM | 219 | CA | GLY | A | 15 | 24.390 | 31.237 | 59.286 | 1.00 | 27.03 | A |
| ATOM | 222 | C | GLY | A | 15 | 23.597 | 29.961 | 59.262 | 1.00 | 28.01 | A |
| ATOM | 223 | O | GLY | A | 15 | 22.561 | 29.844 | 59.945 | 1.00 | 28.00 | A |
| ATOM | 225 | N | GLN | A | 16 | 24.071 | 28.974 | 58.513 | 1.00 | 27.70 | A |
| ATOM | 226 | CA | GLN | A | 16 | 23.319 | 27.750 | 58.431 | 1.00 | 28.22 | A |
| ATOM | 228 | CB | GLN | A | 16 | 23.713 | 26.915 | 57.207 | 1.00 | 28.21 | A |
| ATOM | 231 | CG | GLN | A | 16 | 23.205 | 27.536 | 55.895 | 1.00 | 28.83 | A |
| ATOM | 234 | CD | GLN | A | 16 | 23.486 | 26.658 | 54.713 | 1.00 | 30.43 | A |
| ATOM | 235 | OE1 | GLN | A | 16 | 24.624 | 26.277 | 54.482 | 1.00 | 30.66 | A |
| ATOM | 236 | NE2 | GLN | A | 16 | 22.438 | 26.278 | 53.992 | 1.00 | 32.45 | A |
| ATOM | 239 | C | GLN | A | 16 | 23.545 | 26.991 | 59.694 | 1.00 | 28.82 | A |
| ATOM | 240 | O | GLN | A | 16 | 24.550 | 27.173 | 60.369 | 1.00 | 29.45 | A |
| ATOM | 242 | N | SER | A | 17 | 22.580 | 26.152 | 60.013 | 1.00 | 29.04 | A |
| ATOM | 243 | CA | SER | A | 17 | 22.699 | 25.186 | 61.087 | 1.00 | 29.86 | A |
| ATOM | 245 | CB | SER | A | 17 | 21.297 | 24.786 | 61.568 | 1.00 | 29.97 | A |
| ATOM | 248 | OG | SER | A | 17 | 20.911 | 25.749 | 62.516 | 1.00 | 34.60 | A |
| ATOM | 250 | C | SER | A | 17 | 23.406 | 23.914 | 60.641 | 1.00 | 28.94 | A |
| ATOM | 251 | O | SER | A | 17 | 23.327 | 23.516 | 59.462 | 1.00 | 28.78 | A |
| ATOM | 253 | N | LEU | A | 18 | 24.038 | 23.248 | 61.597 | 1.00 | 28.07 | A |
| ATOM | 254 | CA | LEU | A | 18 | 24.675 | 21.975 | 61.334 | 1.00 | 27.68 | A |

FIG 8 – CONT.

| ATOM | 256 | CB  | LEU | A | 18 | 26.114 | 22.167 | 60.811 | 1.00 | 27.02 | A |
|------|-----|-----|-----|---|----|--------|--------|--------|------|-------|---|
| ATOM | 259 | CG  | LEU | A | 18 | 26.868 | 20.868 | 60.410 | 1.00 | 25.74 | A |
| ATOM | 261 | CD1 | LEU | A | 18 | 26.153 | 20.012 | 59.309 | 1.00 | 25.00 | A |
| ATOM | 265 | CD2 | LEU | A | 18 | 28.241 | 21.191 | 59.919 | 1.00 | 25.43 | A |
| ATOM | 269 | C   | LEU | A | 18 | 24.745 | 21.104 | 62.567 | 1.00 | 27.62 | A |
| ATOM | 270 | O   | LEU | A | 18 | 25.151 | 21.557 | 63.602 | 1.00 | 26.27 | A |
| ATOM | 272 | N   | LYS | A | 19 | 24.460 | 19.820 | 62.381 | 1.00 | 28.08 | A |
| ATOM | 273 | CA  | LYS | A | 19 | 24.627 | 18.821 | 63.396 | 1.00 | 28.78 | A |
| ATOM | 275 | CB  | LYS | A | 19 | 23.239 | 18.294 | 63.775 | 1.00 | 29.10 | A |
| ATOM | 278 | CG  | LYS | A | 19 | 23.204 | 17.335 | 64.935 | 1.00 | 31.63 | A |
| ATOM | 281 | CD  | LYS | A | 19 | 21.732 | 17.030 | 65.332 | 1.00 | 33.60 | A |
| ATOM | 284 | CE  | LYS | A | 19 | 21.623 | 16.747 | 66.827 | 1.00 | 34.80 | A |
| ATOM | 287 | NZ  | LYS | A | 19 | 20.219 | 16.487 | 67.341 | 1.00 | 32.71 | A |
| ATOM | 291 | C   | LYS | A | 19 | 25.470 | 17.700 | 62.807 | 1.00 | 28.19 | A |
| ATOM | 292 | O   | LYS | A | 19 | 25.046 | 17.062 | 61.850 | 1.00 | 28.77 | A |
| ATOM | 294 | N   | ILE | A | 20 | 26.643 | 17.450 | 63.356 | 1.00 | 27.75 | A |
| ATOM | 295 | CA  | ILE | A | 20 | 27.430 | 16.303 | 62.914 | 1.00 | 28.12 | A |
| ATOM | 297 | CB  | ILE | A | 20 | 28.859 | 16.705 | 62.450 | 1.00 | 27.37 | A |
| ATOM | 299 | CG1 | ILE | A | 20 | 29.725 | 17.116 | 63.618 | 1.00 | 28.36 | A |
| ATOM | 302 | CD1 | ILE | A | 20 | 31.137 | 17.549 | 63.210 | 1.00 | 28.24 | A |
| ATOM | 306 | CG2 | ILE | A | 20 | 28.757 | 17.817 | 61.410 | 1.00 | 27.20 | A |
| ATOM | 310 | C   | ILE | A | 20 | 27.470 | 15.211 | 63.984 | 1.00 | 28.35 | A |
| ATOM | 311 | O   | ILE | A | 20 | 27.205 | 15.458 | 65.178 | 1.00 | 28.28 | A |
| ATOM | 313 | N   | SER | A | 21 | 27.798 | 14.003 | 63.564 | 1.00 | 29.14 | A |
| ATOM | 314 | CA  | SER | A | 21 | 27.590 | 12.854 | 64.429 | 1.00 | 30.25 | A |
| ATOM | 316 | CB  | SER | A | 21 | 26.418 | 12.018 | 63.911 | 1.00 | 30.68 | A |
| ATOM | 319 | OG  | SER | A | 21 | 26.754 | 11.341 | 62.711 | 1.00 | 31.84 | A |
| ATOM | 321 | C   | SER | A | 21 | 28.777 | 11.976 | 64.564 | 1.00 | 30.78 | A |
| ATOM | 322 | O   | SER | A | 21 | 29.643 | 11.887 | 63.667 | 1.00 | 31.08 | A |
| ATOM | 324 | N   | CYS | A | 22 | 28.786 | 11.276 | 65.682 | 1.00 | 30.73 | A |
| ATOM | 325 | CA  | CYS | A | 22 | 29.808 | 10.317 | 65.975 | 1.00 | 31.75 | A |

FIG 8 – CONT.

| | | | | | | | | | | |
|---|---|---|---|---|---|---|---|---|---|---|
| ATOM | 327 | CB | CYS | A | 22 | 30.803 | 10.920 | 66.912 | 1.00 31.48 | A C |
| ATOM | 330 | SG | CYS | A | 22 | 31.894 | 9.691 | 67.511 | 1.00 33.53 | A S |
| ATOM | 332 | C | CYS | A | 22 | 29.202 | 9.061 | 66.624 | 1.00 33.03 | A C |
| ATOM | 333 | O | CYS | A | 22 | 28.734 | 9.112 | 67.762 | 1.00 32.76 | A O |
| ATOM | 335 | N | LYS | A | 23 | 29.237 | 7.947 | 65.900 | 1.00 33.70 | A N |
| ATOM | 336 | CA | LYS | A | 23 | 28.571 | 6.716 | 66.288 | 1.00 34.58 | A C |
| ATOM | 338 | CB | LYS | A | 23 | 27.655 | 6.289 | 65.126 | 1.00 35.41 | A C |
| ATOM | 341 | CG | LYS | A | 23 | 26.748 | 5.082 | 65.354 | 1.00 38.61 | A C |
| ATOM | 344 | CD | LYS | A | 23 | 26.202 | 4.638 | 64.029 | 1.00 44.88 | A C |
| ATOM | 347 | CE | LYS | A | 23 | 25.278 | 3.428 | 64.110 | 1.00 48.06 | A C |
| ATOM | 350 | NZ | LYS | A | 23 | 25.501 | 2.443 | 62.966 | 1.00 50.08 | A N |
| ATOM | 354 | C | LYS | A | 23 | 29.637 | 5.641 | 66.602 | 1.00 34.46 | A C |
| ATOM | 355 | O | LYS | A | 23 | 30.544 | 5.361 | 65.786 | 1.00 34.70 | A O |
| ATOM | 357 | N | ALA | A | 24 | 29.584 | 5.082 | 67.797 | 1.00 33.77 | A N |
| ATOM | 358 | CA | ALA | A | 24 | 30.580 | 4.095 | 68.170 | 1.00 34.00 | A C |
| ATOM | 360 | CB | ALA | A | 24 | 30.931 | 4.176 | 69.639 | 1.00 32.50 | A C |
| ATOM | 364 | C | ALA | A | 24 | 30.089 | 2.696 | 67.772 | 1.00 33.62 | A C |
| ATOM | 365 | O | ALA | A | 24 | 28.890 | 2.435 | 67.758 | 1.00 33.12 | A O |
| ATOM | 367 | N | SER | A | 25 | 31.045 | 1.850 | 67.382 | 1.00 33.88 | A N |
| ATOM | 368 | CA | SER | A | 25 | 30.834 | 0.430 | 67.099 | 1.00 33.69 | A C |
| ATOM | 370 | CB | SER | A | 25 | 31.206 | 0.118 | 65.641 | 1.00 34.01 | A C |
| ATOM | 373 | OG | SER | A | 25 | 30.056 | 0.230 | 64.825 | 1.00 37.14 | A O |
| ATOM | 375 | C | SER | A | 25 | 31.714 | -0.357 | 68.040 | 1.00 32.87 | A C |
| ATOM | 376 | O | SER | A | 25 | 32.825 | 0.055 | 68.335 | 1.00 33.66 | A O |
| ATOM | 378 | N | GLY | A | 26 | 31.241 | -1.504 | 68.503 | 1.00 32.68 | A N |
| ATOM | 379 | CA | GLY | A | 26 | 32.019 | -2.309 | 69.441 | 1.00 32.53 | A C |
| ATOM | 382 | C | GLY | A | 26 | 32.344 | -1.587 | 70.746 | 1.00 31.91 | A C |
| ATOM | 383 | O | GLY | A | 26 | 33.295 | -1.925 | 71.423 | 1.00 31.77 | A O |
| ATOM | 385 | N | TYR | A | 27 | 31.536 | -0.602 | 71.095 | 1.00 32.81 | A N |
| ATOM | 386 | CA | TYR | A | 27 | 31.833 | 0.368 | 72.184 | 1.00 33.89 | A C |

FIG 8 – CONT.

| | | | | | | | | | | |
|---|---|---|---|---|---|---|---|---|---|---|
| ATOM | 388 | CB | TYR A | 27 | 32.808 | 1.428 | 71.653 | 1.00 | 33.69 | A C |
| ATOM | 391 | CG | TYR A | 27 | 33.524 | 2.344 | 72.655 | 1.00 | 33.81 | A C |
| ATOM | 392 | CD1 | TYR A | 27 | 33.362 | 3.732 | 72.611 | 1.00 | 34.40 | A C |
| ATOM | 394 | CE1 | TYR A | 27 | 34.040 | 4.566 | 73.501 | 1.00 | 33.86 | A C |
| ATOM | 396 | CZ | TYR A | 27 | 34.897 | 4.035 | 74.401 | 1.00 | 35.93 | A C |
| ATOM | 397 | OH | TYR A | 27 | 35.597 | 4.839 | 75.292 | 1.00 | 40.96 | A O |
| ATOM | 399 | CE2 | TYR A | 27 | 35.079 | 2.660 | 74.455 | 1.00 | 36.03 | A C |
| ATOM | 401 | CD2 | TYR A | 27 | 34.393 | 1.840 | 73.581 | 1.00 | 34.01 | A C |
| ATOM | 403 | C | TYR A | 27 | 30.501 | 1.033 | 72.534 | 1.00 | 34.21 | A C |
| ATOM | 404 | O | TYR A | 27 | 29.891 | 1.633 | 71.665 | 1.00 | 34.34 | A O |
| ATOM | 406 | N | SER A | 28 | 30.020 | 0.885 | 73.767 | 1.00 | 35.63 | A N |
| ATOM | 407 | CA | SER A | 28 | 28.781 | 1.555 | 74.190 | 1.00 | 36.57 | A C |
| ATOM | 409 | CB | SER A | 28 | 27.918 | 0.699 | 75.138 | 1.00 | 37.09 | A C |
| ATOM | 412 | OG | SER A | 28 | 26.642 | 1.322 | 75.357 | 1.00 | 36.34 | A O |
| ATOM | 414 | C | SER A | 28 | 29.049 | 2.897 | 74.859 | 1.00 | 36.63 | A C |
| ATOM | 415 | O | SER A | 28 | 29.811 | 3.015 | 75.800 | 1.00 | 36.48 | A O |
| ATOM | 417 | N | LEU A | 29 | 28.330 | 3.896 | 74.395 | 1.00 | 37.55 | A N |
| ATOM | 418 | CA | LEU A | 29 | 28.407 | 5.220 | 74.996 | 1.00 | 37.99 | A C |
| ATOM | 420 | CB | LEU A | 29 | 27.957 | 6.278 | 73.983 | 1.00 | 37.33 | A C |
| ATOM | 423 | CG | LEU A | 29 | 28.830 | 6.539 | 72.756 | 1.00 | 38.98 | A C |
| ATOM | 425 | CD1 | LEU A | 29 | 28.543 | 7.956 | 72.208 | 1.00 | 38.20 | A C |
| ATOM | 429 | CD2 | LEU A | 29 | 30.297 | 6.386 | 73.064 | 1.00 | 38.44 | A C |
| ATOM | 433 | C | LEU A | 29 | 27.573 | 5.318 | 76.272 | 1.00 | 38.35 | A C |
| ATOM | 434 | O | LEU A | 29 | 27.523 | 6.384 | 76.898 | 1.00 | 37.68 | A O |
| ATOM | 436 | N | THR A | 30 | 26.928 | 4.227 | 76.689 | 1.00 | 39.71 | A N |
| ATOM | 437 | CA | THR A | 30 | 26.251 | 4.251 | 77.994 | 1.00 | 40.66 | A C |
| ATOM | 439 | CB | THR A | 30 | 25.051 | 3.234 | 78.127 | 1.00 | 40.53 | A C |
| ATOM | 441 | OG1 | THR A | 30 | 25.523 | 1.921 | 78.373 | 1.00 | 44.75 | A O |
| ATOM | 443 | CG2 | THR A | 30 | 24.189 | 3.218 | 76.894 | 1.00 | 37.82 | A C |
| ATOM | 447 | C | THR A | 30 | 27.275 | 4.158 | 79.134 | 1.00 | 40.96 | A C |
| ATOM | 448 | O | THR A | 30 | 27.033 | 4.669 | 80.209 | 1.00 | 41.65 | A |

FIG 8 – CONT.

| | | | | | | | | | | | |
|---|---|---|---|---|---|---|---|---|---|---|---|
| ATOM | 450 | N | ASP | A | 31 | 28.431 | 3.554 | 78.877 | 1.00 | 41.88 | A N |
| ATOM | 451 | CA | ASP | A | 31 | 29.476 | 3.386 | 79.897 | 1.00 | 42.66 | A C |
| ATOM | 453 | CB | ASP | A | 31 | 29.764 | 1.892 | 80.128 | 1.00 | 43.71 | A C |
| ATOM | 456 | CG | ASP | A | 31 | 28.497 | 1.066 | 80.379 | 1.00 | 47.27 | A C |
| ATOM | 457 | OD1 | ASP | A | 31 | 27.522 | 1.603 | 80.964 | 1.00 | 49.89 | A O |
| ATOM | 458 | OD2 | ASP | A | 31 | 28.495 | -0.137 | 79.998 | 1.00 | 51.66 | A O |
| ATOM | 459 | C | ASP | A | 31 | 30.803 | 4.065 | 79.519 | 1.00 | 42.08 | A C |
| ATOM | 460 | O | ASP | A | 31 | 31.847 | 3.746 | 80.105 | 1.00 | 42.10 | A O |
| ATOM | 462 | N | ASN | A | 32 | 30.782 | 4.954 | 78.518 | 1.00 | 40.76 | A N |
| ATOM | 463 | CA | ASN | A | 32 | 31.979 | 5.704 | 78.146 | 1.00 | 39.74 | A C |
| ATOM | 465 | CB | ASN | A | 32 | 32.679 | 5.052 | 76.946 | 1.00 | 39.76 | A C |
| ATOM | 468 | CG | ASN | A | 32 | 33.186 | 3.644 | 77.260 | 1.00 | 39.91 | A C |
| ATOM | 469 | OD1 | ASN | A | 32 | 34.193 | 3.484 | 77.937 | 1.00 | 40.69 | A O |
| ATOM | 470 | ND2 | ASN | A | 32 | 32.472 | 2.626 | 76.780 | 1.00 | 38.56 | A N |
| ATOM | 473 | C | ASN | A | 32 | 31.612 | 7.134 | 77.830 | 1.00 | 38.72 | A C |
| ATOM | 474 | O | ASN | A | 32 | 30.444 | 7.427 | 77.628 | 1.00 | 38.68 | A O |
| ATOM | 476 | N | TRP | A | 33 | 32.624 | 8.002 | 77.788 | 1.00 | 37.54 | A N |
| ATOM | 477 | CA | TRP | A | 33 | 32.464 | 9.419 | 77.513 | 1.00 | 36.78 | A C |
| ATOM | 479 | CB | TRP | A | 33 | 33.245 | 10.222 | 78.521 | 1.00 | 36.96 | A C |
| ATOM | 482 | CG | TRP | A | 33 | 32.726 | 10.175 | 79.920 | 1.00 | 39.80 | A C |
| ATOM | 483 | CD1 | TRP | A | 33 | 32.510 | 9.061 | 80.687 | 1.00 | 41.28 | A C |
| ATOM | 485 | NE1 | TRP | A | 33 | 32.064 | 9.434 | 81.937 | 1.00 | 42.35 | A N |
| ATOM | 487 | CE2 | TRP | A | 33 | 32.011 | 10.798 | 82.010 | 1.00 | 40.99 | A C |
| ATOM | 488 | CD2 | TRP | A | 33 | 32.414 | 11.303 | 80.749 | 1.00 | 39.55 | A C |
| ATOM | 489 | CE3 | TRP | A | 33 | 32.435 | 12.684 | 80.550 | 1.00 | 39.02 | A C |
| ATOM | 491 | CZ3 | TRP | A | 33 | 32.039 | 13.520 | 81.597 | 1.00 | 39.76 | A C |
| ATOM | 493 | CH2 | TRP | A | 33 | 31.629 | 12.983 | 82.837 | 1.00 | 40.90 | A C |
| ATOM | 495 | CZ2 | TRP | A | 33 | 31.607 | 11.626 | 83.057 | 1.00 | 40.06 | A C |
| ATOM | 497 | C | TRP | A | 33 | 33.010 | 9.795 | 76.133 | 1.00 | 35.78 | A C |
| ATOM | 498 | O | TRP | A | 33 | 33.983 | 9.192 | 75.642 | 1.00 | 35.20 | A O |

FIG 8 – CONT.

| ATOM | 500 | N   | ILE | A | 34 | 32.415 | 10.823 | 75.534 | 1.00 | 33.55 | A |
| --- | --- | --- | --- | --- | --- | --- | --- | --- | --- | --- | --- |
| N |
| ATOM | 501 | CA  | ILE | A | 34 | 32.837 | 11.284 | 74.221 | 1.00 | 32.00 | A |
| C |
| ATOM | 503 | CB  | ILE | A | 34 | 31.721 | 11.140 | 73.191 | 1.00 | 31.80 | A |
| C |
| ATOM | 505 | CG1 | ILE | A | 34 | 31.506 | 9.670  | 72.845 | 1.00 | 31.67 | A |
| C |
| ATOM | 508 | CD1 | ILE | A | 34 | 32.758 | 9.004  | 72.292 | 1.00 | 30.73 | A |
| C |
| ATOM | 512 | CG2 | ILE | A | 34 | 32.053 | 11.975 | 71.906 | 1.00 | 29.12 | A |
| C |
| ATOM | 516 | C   | ILE | A | 34 | 33.220 | 12.754 | 74.289 | 1.00 | 31.86 | A |
| C |
| ATOM | 517 | O   | ILE | A | 34 | 32.426 | 13.577 | 74.739 | 1.00 | 30.29 | A |
| O |
| ATOM | 519 | N   | GLY | A | 35 | 34.436 | 13.059 | 73.846 | 1.00 | 31.21 | A |
| N |
| ATOM | 520 | CA  | GLY | A | 35 | 34.873 | 14.439 | 73.658 | 1.00 | 31.94 | A |
| C |
| ATOM | 523 | C   | GLY | A | 35 | 34.943 | 14.887 | 72.192 | 1.00 | 31.44 | A |
| C |
| ATOM | 524 | O   | GLY | A | 35 | 34.911 | 14.064 | 71.256 | 1.00 | 30.69 | A |
| O |
| ATOM | 526 | N   | TRP | A | 36 | 35.090 | 16.192 | 72.009 | 1.00 | 31.05 | A |
| N |
| ATOM | 527 | CA  | TRP | A | 36 | 35.222 | 16.767 | 70.675 | 1.00 | 31.30 | A |
| C |
| ATOM | 529 | CB  | TRP | A | 36 | 33.982 | 17.552 | 70.305 | 1.00 | 30.75 | A |
| C |
| ATOM | 532 | CG  | TRP | A | 36 | 32.807 | 16.706 | 70.007 | 1.00 | 31.05 | A |
| C |
| ATOM | 533 | CD1 | TRP | A | 36 | 31.810 | 16.394 | 70.862 | 1.00 | 29.48 | A |
| C |
| ATOM | 535 | NE1 | TRP | A | 36 | 30.892 | 15.590 | 70.234 | 1.00 | 31.27 | A |
| N |
| ATOM | 537 | CE2 | TRP | A | 36 | 31.270 | 15.394 | 68.937 | 1.00 | 29.21 | A |
| C |
| ATOM | 538 | CD2 | TRP | A | 36 | 32.479 | 16.070 | 68.752 | 1.00 | 30.88 | A |
| C |
| ATOM | 539 | CE3 | TRP | A | 36 | 33.087 | 16.027 | 67.494 | 1.00 | 26.80 | A |
| C |
| ATOM | 541 | CZ3 | TRP | A | 36 | 32.476 | 15.337 | 66.495 | 1.00 | 27.08 | A |
| C |
| ATOM | 543 | CH2 | TRP | A | 36 | 31.275 | 14.655 | 66.699 | 1.00 | 26.62 | A |
| C |
| ATOM | 545 | CZ2 | TRP | A | 36 | 30.648 | 14.682 | 67.915 | 1.00 | 29.81 | A |
| C |
| ATOM | 547 | C   | TRP | A | 36 | 36.436 | 17.672 | 70.581 | 1.00 | 30.61 | A |
| C |
| ATOM | 548 | O   | TRP | A | 36 | 36.633 | 18.500 | 71.439 | 1.00 | 31.74 | A |
| O |
| ATOM | 550 | N   | VAL | A | 37 | 37.233 | 17.481 | 69.535 | 1.00 | 29.53 | A |
| N |
| ATOM | 551 | CA  | VAL | A | 37 | 38.476 | 18.216 | 69.311 | 1.00 | 29.28 | A |
| C |
| ATOM | 553 | CB  | VAL | A | 37 | 39.674 | 17.267 | 69.298 | 1.00 | 29.40 | A |
| C |
| ATOM | 555 | CG1 | VAL | A | 37 | 41.007 | 18.019 | 69.037 | 1.00 | 30.04 | A |
| C |
| ATOM | 559 | CG2 | VAL | A | 37 | 39.786 | 16.553 | 70.607 | 1.00 | 29.50 | A |

FIG 8 – CONT.

| | | | | | | | | | | |
|---|---|---|---|---|---|---|---|---|---|---|
| ATOM | 563 | C | VAL | A | 37 | 38.374 | 18.931 | 67.955 | 1.00 28.98 | A C |
| ATOM | 564 | O | VAL | A | 37 | 37.968 | 18.331 | 66.944 | 1.00 28.41 | A O |
| ATOM | 566 | N | ARG | A | 38 | 38.675 | 20.223 | 67.967 | 1.00 29.32 | A N |
| ATOM | 567 | CA | ARG | A | 38 | 38.788 | 21.009 | 66.747 | 1.00 29.81 | A C |
| ATOM | 569 | CB | ARG | A | 38 | 38.198 | 22.387 | 66.940 | 1.00 29.72 | A C |
| ATOM | 572 | CG | ARG | A | 38 | 38.161 | 23.221 | 65.658 | 1.00 30.20 | A C |
| ATOM | 575 | CD | ARG | A | 38 | 37.463 | 24.537 | 65.859 | 1.00 30.02 | A C |
| ATOM | 578 | NE | ARG | A | 38 | 38.304 | 25.547 | 66.498 | 1.00 33.82 | A N |
| ATOM | 580 | CZ | ARG | A | 38 | 37.895 | 26.793 | 66.733 | 1.00 36.47 | A C |
| ATOM | 581 | NH1 | ARG | A | 38 | 36.681 | 27.164 | 66.379 | 1.00 37.44 | A N |
| ATOM | 584 | NH2 | ARG | A | 38 | 38.704 | 27.678 | 67.291 | 1.00 38.80 | A N |
| ATOM | 587 | C | ARG | A | 38 | 40.252 | 21.127 | 66.302 | 1.00 30.14 | A C |
| ATOM | 588 | O | ARG | A | 38 | 41.162 | 21.273 | 67.129 | 1.00 30.80 | A O |
| ATOM | 590 | N | GLN | A | 39 | 40.475 | 21.024 | 64.995 | 1.00 29.78 | A N |
| ATOM | 591 | CA | GLN | A | 39 | 41.777 | 21.297 | 64.406 | 1.00 29.38 | A C |
| ATOM | 593 | CB | GLN | A | 39 | 42.523 | 20.016 | 64.062 | 1.00 29.55 | A C |
| ATOM | 596 | CG | GLN | A | 39 | 43.906 | 20.276 | 63.422 | 1.00 29.62 | A C |
| ATOM | 599 | CD | GLN | A | 39 | 44.778 | 19.050 | 63.417 | 1.00 30.20 | A C |
| ATOM | 600 | OE1 | GLN | A | 39 | 44.343 | 17.986 | 63.004 | 1.00 31.83 | A O |
| ATOM | 601 | NE2 | GLN | A | 39 | 46.020 | 19.194 | 63.861 | 1.00 31.03 | A N |
| ATOM | 604 | C | GLN | A | 39 | 41.527 | 22.114 | 63.164 | 1.00 30.19 | A C |
| ATOM | 605 | O | GLN | A | 39 | 41.010 | 21.592 | 62.184 | 1.00 28.48 | A O |
| ATOM | 607 | N | LYS | A | 40 | 41.795 | 23.419 | 63.257 | 1.00 31.74 | A N |
| ATOM | 608 | CA | LYS | A | 40 | 41.702 | 24.329 | 62.108 | 1.00 33.03 | A C |
| ATOM | 610 | CB | LYS | A | 40 | 41.774 | 25.795 | 62.557 | 1.00 33.43 | A C |
| ATOM | 613 | CG | LYS | A | 40 | 40.554 | 26.289 | 63.320 | 1.00 36.51 | A C |
| ATOM | 616 | CD | LYS | A | 40 | 40.273 | 27.822 | 63.150 | 1.00 40.28 | A C |
| ATOM | 619 | CE | LYS | A | 40 | 40.322 | 28.579 | 64.483 | 1.00 43.84 | A C |
| ATOM | 622 | NZ | LYS | A | 40 | 39.271 | 29.689 | 64.609 | 1.00 45.71 | A N |
| ATOM | 626 | C | LYS | A | 40 | 42.830 | 24.015 | 61.103 | 1.00 33.81 | A C |

FIG 8 – CONT.

| | | | | | | | | | | |
|---|---|---|---|---|---|---|---|---|---|---|
| ATOM | 627 | O | LYS | A | 40 | 43.832 | 23.362 | 61.448 | 1.00 33.52 | A |
| ATOM | 629 | N | PRO | A | 41 | 42.664 | 24.440 | 59.852 | 1.00 34.32 | A |
| ATOM | 630 | CA | PRO | A | 41 | 43.664 | 24.018 | 58.878 | 1.00 35.22 | A |
| ATOM | 632 | CB | PRO | A | 41 | 43.119 | 24.533 | 57.525 | 1.00 35.80 | A |
| ATOM | 635 | CG | PRO | A | 41 | 41.729 | 25.058 | 57.780 | 1.00 34.99 | A |
| ATOM | 638 | CD | PRO | A | 41 | 41.605 | 25.288 | 59.268 | 1.00 35.10 | A |
| ATOM | 641 | C | PRO | A | 41 | 45.050 | 24.596 | 59.169 | 1.00 35.61 | A |
| ATOM | 642 | O | PRO | A | 41 | 45.195 | 25.817 | 59.340 | 1.00 35.22 | A |
| ATOM | 643 | N | GLY | A | 42 | 46.030 | 23.692 | 59.254 | 1.00 36.25 | A |
| ATOM | 644 | CA | GLY | A | 42 | 47.424 | 24.017 | 59.550 | 1.00 37.18 | A |
| ATOM | 647 | C | GLY | A | 42 | 47.681 | 24.372 | 61.000 | 1.00 37.91 | A |
| ATOM | 648 | O | GLY | A | 42 | 48.728 | 24.931 | 61.320 | 1.00 38.86 | A |
| ATOM | 650 | N | LYS | A | 43 | 46.721 | 24.093 | 61.887 | 1.00 38.20 | A |
| ATOM | 651 | CA | LYS | A | 43 | 46.843 | 24.507 | 63.282 | 1.00 37.59 | A |
| ATOM | 653 | CB | LYS | A | 43 | 45.746 | 25.505 | 63.683 | 1.00 38.43 | A |
| ATOM | 656 | CG | LYS | A | 43 | 45.542 | 26.717 | 62.748 | 1.00 41.36 | A |
| ATOM | 659 | CD | LYS | A | 43 | 46.808 | 27.587 | 62.538 | 1.00 45.27 | A |
| ATOM | 662 | CE | LYS | A | 43 | 46.935 | 28.739 | 63.552 | 1.00 47.69 | A |
| ATOM | 665 | NZ | LYS | A | 43 | 48.136 | 29.621 | 63.266 | 1.00 50.39 | A |
| ATOM | 669 | C | LYS | A | 43 | 46.778 | 23.261 | 64.151 | 1.00 36.49 | A |
| ATOM | 670 | O | LYS | A | 43 | 46.718 | 22.138 | 63.647 | 1.00 34.96 | A |
| ATOM | 672 | N | GLY | A | 44 | 46.808 | 23.475 | 65.465 | 1.00 35.85 | A |
| ATOM | 673 | CA | GLY | A | 44 | 46.851 | 22.382 | 66.422 | 1.00 35.65 | A |
| ATOM | 676 | C | GLY | A | 44 | 45.484 | 21.909 | 66.864 | 1.00 35.17 | A |
| ATOM | 677 | O | GLY | A | 44 | 44.454 | 22.242 | 66.264 | 1.00 34.99 | A |
| ATOM | 679 | N | LEU | A | 45 | 45.486 | 21.120 | 67.926 | 1.00 35.75 | A |
| ATOM | 680 | CA | LEU | A | 45 | 44.262 | 20.521 | 68.480 | 1.00 35.33 | A |
| ATOM | 682 | CB | LEU | A | 45 | 44.577 | 19.150 | 69.073 | 1.00 35.55 | A |
| ATOM | 685 | CG | LEU | A | 45 | 45.366 | 18.223 | 68.157 | 1.00 35.03 | A |
| ATOM | 687 | CD1 | LEU | A | 45 | 45.697 | 16.905 | 68.844 | 1.00 32.57 | A |
| ATOM | 691 | CD2 | LEU | A | 45 | 44.566 | 18.001 | 66.857 | 1.00 34.27 | A |

FIG 8 – CONT.

| | | | | | | | | | | |
|---|---|---|---|---|---|---|---|---|---|---|
| C | | | | | | | | | | |
| ATOM | 695 | C | LEU | A | 45 | 43.717 | 21.447 | 69.549 | 1.00 35.66 | A |
| C | | | | | | | | | | |
| ATOM | 696 | O | LEU | A | 45 | 44.495 | 22.036 | 70.312 | 1.00 35.74 | A |
| O | | | | | | | | | | |
| ATOM | 698 | N | GLU | A | 46 | 42.388 | 21.592 | 69.585 | 1.00 35.51 | A |
| N | | | | | | | | | | |
| ATOM | 699 | CA | GLU | A | 46 | 41.701 | 22.338 | 70.625 | 1.00 35.35 | A |
| C | | | | | | | | | | |
| ATOM | 701 | CB | GLU | A | 46 | 41.088 | 23.603 | 70.062 | 1.00 35.03 | A |
| C | | | | | | | | | | |
| ATOM | 704 | CG | GLU | A | 46 | 42.032 | 24.534 | 69.368 | 1.00 35.81 | A |
| C | | | | | | | | | | |
| ATOM | 707 | CD | GLU | A | 46 | 41.259 | 25.511 | 68.523 | 1.00 37.54 | A |
| C | | | | | | | | | | |
| ATOM | 708 | OE1 | GLU | A | 46 | 41.034 | 25.201 | 67.328 | 1.00 36.49 | A |
| O | | | | | | | | | | |
| ATOM | 709 | OE2 | GLU | A | 46 | 40.801 | 26.534 | 69.074 | 1.00 35.91 | A |
| O | | | | | | | | | | |
| ATOM | 710 | C | GLU | A | 46 | 40.581 | 21.491 | 71.242 | 1.00 35.90 | A |
| C | | | | | | | | | | |
| ATOM | 711 | O | GLU | A | 46 | 39.798 | 20.879 | 70.507 | 1.00 36.50 | A |
| O | | | | | | | | | | |
| ATOM | 713 | N | TRP | A | 47 | 40.530 | 21.445 | 72.579 | 1.00 35.61 | A |
| N | | | | | | | | | | |
| ATOM | 714 | CA | TRP | A | 47 | 39.486 | 20.728 | 73.308 | 1.00 35.62 | A |
| C | | | | | | | | | | |
| ATOM | 716 | CB | TRP | A | 47 | 39.874 | 20.551 | 74.781 | 1.00 35.83 | A |
| C | | | | | | | | | | |
| ATOM | 719 | CG | TRP | A | 47 | 38.923 | 19.682 | 75.558 | 1.00 38.06 | A |
| C | | | | | | | | | | |
| ATOM | 720 | CD1 | TRP | A | 47 | 38.090 | 20.068 | 76.589 | 1.00 38.95 | A |
| C | | | | | | | | | | |
| ATOM | 722 | NE1 | TRP | A | 47 | 37.379 | 18.984 | 77.048 | 1.00 38.23 | A |
| N | | | | | | | | | | |
| ATOM | 724 | CE2 | TRP | A | 47 | 37.736 | 17.880 | 76.323 | 1.00 38.31 | A |
| C | | | | | | | | | | |
| ATOM | 725 | CD2 | TRP | A | 47 | 38.695 | 18.281 | 75.371 | 1.00 37.86 | A |
| C | | | | | | | | | | |
| ATOM | 726 | CE3 | TRP | A | 47 | 39.223 | 17.326 | 74.504 | 1.00 39.33 | A |
| C | | | | | | | | | | |
| ATOM | 728 | CZ3 | TRP | A | 47 | 38.777 | 16.019 | 74.594 | 1.00 39.47 | A |
| C | | | | | | | | | | |
| ATOM | 730 | CH2 | TRP | A | 47 | 37.818 | 15.644 | 75.552 | 1.00 40.29 | A |
| C | | | | | | | | | | |
| ATOM | 732 | CZ2 | TRP | A | 47 | 37.292 | 16.559 | 76.426 | 1.00 39.63 | A |
| C | | | | | | | | | | |
| ATOM | 734 | C | TRP | A | 47 | 38.235 | 21.537 | 73.263 | 1.00 34.55 | A |
| C | | | | | | | | | | |
| ATOM | 735 | O | TRP | A | 47 | 38.268 | 22.719 | 73.603 | 1.00 34.14 | A |
| O | | | | | | | | | | |
| ATOM | 737 | N | MET | A | 48 | 37.125 | 20.931 | 72.842 | 1.00 33.49 | A |
| N | | | | | | | | | | |
| ATOM | 738 | CA | MET | A | 48 | 35.862 | 21.673 | 72.822 | 1.00 32.83 | A |
| C | | | | | | | | | | |
| ATOM | 740 | CB | MET | A | 48 | 35.118 | 21.405 | 71.527 | 1.00 32.10 | A |
| C | | | | | | | | | | |
| ATOM | 743 | CG | MET | A | 48 | 35.941 | 21.688 | 70.274 | 1.00 31.48 | A |
| C | | | | | | | | | | |
| ATOM | 746 | SD | MET | A | 48 | 34.973 | 21.325 | 68.798 | 1.00 25.00 | A |
| S | | | | | | | | | | |

FIG 8 — CONT.

| | | | | | | | | | | | |
|---|---|---|---|---|---|---|---|---|---|---|---|
| ATOM | 747 | CE | MET | A | 48 | 33.732 | 22.617 | 68.878 | 1.00 | 24.93 | A |
| C | | | | | | | | | | | |
| ATOM | 751 | C | MET | A | 48 | 34.949 | 21.333 | 74.015 | 1.00 | 33.05 | A |
| C | | | | | | | | | | | |
| ATOM | 752 | O | MET | A | 48 | 34.203 | 22.179 | 74.516 | 1.00 | 32.70 | A |
| O | | | | | | | | | | | |
| ATOM | 754 | N | GLY | A | 49 | 34.975 | 20.082 | 74.439 | 1.00 | 32.45 | A |
| N | | | | | | | | | | | |
| ATOM | 755 | CA | GLY | A | 49 | 34.122 | 19.657 | 75.534 | 1.00 | 32.59 | A |
| C | | | | | | | | | | | |
| ATOM | 758 | C | GLY | A | 49 | 33.835 | 18.168 | 75.454 | 1.00 | 32.99 | A |
| C | | | | | | | | | | | |
| ATOM | 759 | O | GLY | A | 49 | 34.340 | 17.440 | 74.563 | 1.00 | 31.48 | A |
| O | | | | | | | | | | | |
| ATOM | 761 | N | ILE | A | 50 | 32.988 | 17.727 | 76.378 | 1.00 | 33.00 | A |
| N | | | | | | | | | | | |
| ATOM | 762 | CA | ILE | A | 50 | 32.812 | 16.315 | 76.627 | 1.00 | 32.98 | A |
| C | | | | | | | | | | | |
| ATOM | 764 | CB | ILE | A | 50 | 33.790 | 15.874 | 77.721 | 1.00 | 33.24 | A |
| C | | | | | | | | | | | |
| ATOM | 766 | CG1 | ILE | A | 50 | 34.053 | 14.367 | 77.652 | 1.00 | 33.21 | A |
| C | | | | | | | | | | | |
| ATOM | 769 | CD1 | ILE | A | 50 | 35.191 | 13.968 | 78.530 | 1.00 | 34.22 | A |
| C | | | | | | | | | | | |
| ATOM | 773 | CG2 | ILE | A | 50 | 33.274 | 16.289 | 79.106 | 1.00 | 32.52 | A |
| C | | | | | | | | | | | |
| ATOM | 777 | C | ILE | A | 50 | 31.389 | 16.073 | 77.066 | 1.00 | 33.14 | A |
| C | | | | | | | | | | | |
| ATOM | 778 | O | ILE | A | 50 | 30.738 | 16.982 | 77.577 | 1.00 | 33.05 | A |
| O | | | | | | | | | | | |
| ATOM | 780 | N | ILE | A | 51 | 30.910 | 14.854 | 76.853 | 1.00 | 33.23 | A |
| N | | | | | | | | | | | |
| ATOM | 781 | CA | ILE | A | 51 | 29.594 | 14.446 | 77.285 | 1.00 | 33.73 | A |
| C | | | | | | | | | | | |
| ATOM | 783 | CB | ILE | A | 51 | 28.544 | 14.585 | 76.144 | 1.00 | 33.08 | A |
| C | | | | | | | | | | | |
| ATOM | 785 | CG1 | ILE | A | 51 | 27.154 | 14.184 | 76.648 | 1.00 | 32.16 | A |
| C | | | | | | | | | | | |
| ATOM | 788 | CD1 | ILE | A | 51 | 25.978 | 14.743 | 75.875 | 1.00 | 28.16 | A |
| C | | | | | | | | | | | |
| ATOM | 792 | CG2 | ILE | A | 51 | 28.939 | 13.739 | 74.933 | 1.00 | 33.52 | A |
| C | | | | | | | | | | | |
| ATOM | 796 | C | ILE | A | 51 | 29.651 | 12.993 | 77.771 | 1.00 | 35.33 | A |
| C | | | | | | | | | | | |
| ATOM | 797 | O | ILE | A | 51 | 30.361 | 12.182 | 77.191 | 1.00 | 34.69 | A |
| O | | | | | | | | | | | |
| ATOM | 799 | N | TYR | A | 52 | 28.928 | 12.696 | 78.853 | 1.00 | 37.35 | A |
| N | | | | | | | | | | | |
| ATOM | 800 | CA | TYR | A | 52 | 28.657 | 11.328 | 79.275 | 1.00 | 38.70 | A |
| C | | | | | | | | | | | |
| ATOM | 802 | CB | TYR | A | 52 | 28.803 | 11.139 | 80.794 | 1.00 | 39.14 | A |
| C | | | | | | | | | | | |
| ATOM | 805 | CG | TYR | A | 52 | 28.552 | 9.699 | 81.273 | 1.00 | 41.31 | A |
| C | | | | | | | | | | | |
| ATOM | 806 | CD1 | TYR | A | 52 | 28.899 | 8.601 | 80.474 | 1.00 | 41.96 | A |
| C | | | | | | | | | | | |
| ATOM | 808 | CE1 | TYR | A | 52 | 28.672 | 7.298 | 80.890 | 1.00 | 44.89 | A |
| C | | | | | | | | | | | |
| ATOM | 810 | CZ | TYR | A | 52 | 28.105 | 7.045 | 82.143 | 1.00 | 45.29 | A |
| C | | | | | | | | | | | |
| ATOM | 811 | OH | TYR | A | 52 | 27.900 | 5.737 | 82.517 | 1.00 | 44.43 | A |

FIG 8 – CONT.

| | | | | | | | | | | |
|---|---|---|---|---|---|---|---|---|---|---|
| ATOM | 813 | CE2 | TYR A | 52 | 27.758 | 8.107 | 82.972 | 1.00 45.28 | A | O C |
| ATOM | 815 | CD2 | TYR A | 52 | 27.981 | 9.436 | 82.533 | 1.00 44.42 | A | C |
| ATOM | 817 | C | TYR A | 52 | 27.239 | 10.998 | 78.851 | 1.00 39.57 | A | C |
| ATOM | 818 | O | TYR A | 52 | 26.291 | 11.414 | 79.516 | 1.00 40.07 | A | O |
| ATOM | 820 | N | PRO A | 52A | 27.079 | 10.268 | 77.724 | 1.00 41.19 | A | N |
| ATOM | 821 | CA | PRO A | 52A | 25.753 | 9.980 | 77.151 | 1.00 41.70 | A | C |
| ATOM | 823 | CB | PRO A | 52A | 26.084 | 9.143 | 75.909 | 1.00 41.57 | A | C |
| ATOM | 826 | CG | PRO A | 52A | 27.480 | 9.406 | 75.620 | 1.00 41.16 | A | C |
| ATOM | 829 | CD | PRO A | 52A | 28.150 | 9.651 | 76.912 | 1.00 41.38 | A | C |
| ATOM | 832 | C | PRO A | 52A | 24.824 | 9.195 | 78.086 | 1.00 42.86 | A | C |
| ATOM | 833 | O | PRO A | 52A | 23.603 | 9.291 | 77.969 | 1.00 43.51 | A | O |
| ATOM | 834 | N | GLY A | 53 | 25.407 | 8.413 | 78.989 | 1.00 44.26 | A | N |
| ATOM | 835 | CA | GLY A | 53 | 24.648 | 7.645 | 79.970 | 1.00 45.66 | A | C |
| ATOM | 838 | C | GLY A | 53 | 23.625 | 8.471 | 80.729 | 1.00 46.42 | A | C |
| ATOM | 839 | O | GLY A | 53 | 22.466 | 8.047 | 80.876 | 1.00 46.33 | A | O |
| ATOM | 841 | N | ASP A | 54 | 24.058 | 9.651 | 81.180 | 1.00 47.22 | A | N |
| ATOM | 842 | CA | ASP A | 54 | 23.195 | 10.579 | 81.899 | 1.00 48.16 | A | C |
| ATOM | 844 | CB | ASP A | 54 | 23.577 | 10.558 | 83.389 | 1.00 48.65 | A | C |
| ATOM | 847 | CG | ASP A | 54 | 24.876 | 11.296 | 83.673 | 1.00 50.90 | A | C |
| ATOM | 848 | OD1 | ASP A | 54 | 25.282 | 11.397 | 84.855 | 1.00 52.26 | A | O |
| ATOM | 849 | OD2 | ASP A | 54 | 25.487 | 11.794 | 82.701 | 1.00 55.93 | A | O |
| ATOM | 850 | C | ASP A | 54 | 23.210 | 12.036 | 81.331 | 1.00 47.98 | A | C |
| ATOM | 851 | O | ASP A | 54 | 22.661 | 12.955 | 81.955 | 1.00 47.95 | A | O |
| ATOM | 853 | N | SER A | 55 | 23.834 | 12.237 | 80.162 | 1.00 47.67 | A | N |
| ATOM | 854 | CA | SER A | 55 | 23.839 | 13.550 | 79.458 | 1.00 46.90 | A | C |
| ATOM | 856 | CB | SER A | 55 | 22.423 | 14.030 | 79.155 | 1.00 46.83 | A | C |
| ATOM | 859 | OG | SER A | 55 | 21.640 | 12.966 | 78.659 | 1.00 48.59 | A | O |
| ATOM | 861 | C | SER A | 55 | 24.571 | 14.668 | 80.178 | 1.00 45.76 | A | C |
| ATOM | 862 | O | SER A | 55 | 24.314 | 15.845 | 79.922 | 1.00 46.32 | A | O |
| ATOM | 864 | N | ASP A | 56 | 25.480 | 14.312 | 81.063 | 1.00 44.12 | A | N |

FIG 8 – CONT.

| | | | | | | | | | | |
|---|---|---|---|---|---|---|---|---|---|---|
| ATOM | 865 | CA | ASP | A | 56 | 26.333 | 15.288 | 81.704 | 1.00 43.56 | A C |
| ATOM | 867 | CB | ASP | A | 56 | 27.068 | 14.579 | 82.850 | 1.00 43.39 | A C |
| ATOM | 870 | CG | ASP | A | 56 | 27.897 | 15.506 | 83.702 | 1.00 44.43 | A C |
| ATOM | 871 | OD1 | ASP | A | 56 | 27.864 | 16.737 | 83.517 | 1.00 44.77 | A O |
| ATOM | 872 | OD2 | ASP | A | 56 | 28.611 | 14.970 | 84.579 | 1.00 48.72 | A O |
| ATOM | 873 | C | ASP | A | 56 | 27.319 | 15.874 | 80.656 | 1.00 43.06 | A C |
| ATOM | 874 | O | ASP | A | 56 | 28.128 | 15.150 | 80.074 | 1.00 41.91 | A O |
| ATOM | 876 | N | THR | A | 57 | 27.237 | 17.182 | 80.432 | 1.00 42.55 | A N |
| ATOM | 877 | CA | THR | A | 57 | 28.011 | 17.861 | 79.400 | 1.00 42.74 | A C |
| ATOM | 879 | CB | THR | A | 57 | 27.057 | 18.540 | 78.386 | 1.00 42.72 | A C |
| ATOM | 881 | OG1 | THR | A | 57 | 26.157 | 17.560 | 77.841 | 1.00 43.16 | A O |
| ATOM | 883 | CG2 | THR | A | 57 | 27.827 | 19.153 | 77.249 | 1.00 42.99 | A C |
| ATOM | 887 | C | THR | A | 57 | 28.950 | 18.892 | 80.037 | 1.00 42.82 | A C |
| ATOM | 888 | O | THR | A | 57 | 28.561 | 19.584 | 80.970 | 1.00 43.34 | A O |
| ATOM | 890 | N | ARG | A | 58 | 30.193 | 18.978 | 79.578 | 1.00 42.64 | A N |
| ATOM | 891 | CA | ARG | A | 58 | 31.118 | 20.010 | 80.078 | 1.00 43.02 | A C |
| ATOM | 893 | CB | ARG | A | 58 | 32.043 | 19.457 | 81.186 | 1.00 42.65 | A C |
| ATOM | 902 | C | ARG | A | 58 | 31.947 | 20.617 | 78.937 | 1.00 43.10 | A C |
| ATOM | 903 | O | ARG | A | 58 | 32.693 | 19.914 | 78.269 | 1.00 44.44 | A O |
| ATOM | 905 | N | TYR | A | 59 | 31.827 | 21.930 | 78.755 | 1.00 43.46 | A N |
| ATOM | 906 | CA | TYR | A | 59 | 32.446 | 22.657 | 77.650 | 1.00 42.85 | A C |
| ATOM | 908 | CB | TYR | A | 59 | 31.495 | 23.708 | 77.101 | 1.00 42.17 | A C |
| ATOM | 911 | CG | TYR | A | 59 | 30.236 | 23.158 | 76.512 | 1.00 40.72 | A C |
| ATOM | 912 | CD1 | TYR | A | 59 | 29.075 | 23.027 | 77.278 | 1.00 39.43 | A C |
| ATOM | 914 | CE1 | TYR | A | 59 | 27.900 | 22.530 | 76.720 | 1.00 37.31 | A C |
| ATOM | 916 | CZ | TYR | A | 59 | 27.888 | 22.149 | 75.393 | 1.00 35.86 | A C |
| ATOM | 917 | OH | TYR | A | 59 | 26.738 | 21.651 | 74.821 | 1.00 33.81 | A O |
| ATOM | 919 | CE2 | TYR | A | 59 | 29.013 | 22.281 | 74.624 | 1.00 37.37 | A C |
| ATOM | 921 | CD2 | TYR | A | 59 | 30.179 | 22.785 | 75.171 | 1.00 38.00 | A C |
| ATOM | 923 | C | TYR | A | 59 | 33.678 | 23.395 | 78.090 | 1.00 43.80 | A C |
| ATOM | 924 | O | TYR | A | 59 | 33.738 | 23.936 | 79.206 | 1.00 44.75 | A |

FIG 8 – CONT.

| | | | | | | | | | | | |
|---|---|---|---|---|---|---|---|---|---|---|---|
| ATOM | 926 | N | SER | A | 60 | 34.644 | 23.459 | 77.190 | 1.00 | 43.96 | A |
| ATOM | 927 | CA | SER | A | 60 | 35.753 | 24.365 | 77.334 | 1.00 | 44.35 | A |
| ATOM | 929 | CB | SER | A | 60 | 36.759 | 24.114 | 76.215 | 1.00 | 44.47 | A |
| ATOM | 932 | OG | SER | A | 60 | 37.920 | 24.914 | 76.380 | 1.00 | 47.76 | A |
| ATOM | 934 | C | SER | A | 60 | 35.208 | 25.795 | 77.305 | 1.00 | 44.29 | A |
| ATOM | 935 | O | SER | A | 60 | 34.313 | 26.108 | 76.523 | 1.00 | 44.38 | A |
| ATOM | 937 | N | PRO | A | 61 | 35.705 | 26.667 | 78.195 | 1.00 | 44.88 | A |
| ATOM | 938 | CA | PRO | A | 61 | 35.208 | 28.065 | 78.238 | 1.00 | 45.02 | A |
| ATOM | 940 | CB | PRO | A | 61 | 36.176 | 28.779 | 79.199 | 1.00 | 44.99 | A |
| ATOM | 943 | CG | PRO | A | 61 | 36.865 | 27.697 | 79.961 | 1.00 | 45.76 | A |
| ATOM | 946 | CD | PRO | A | 61 | 36.739 | 26.397 | 79.210 | 1.00 | 44.78 | A |
| ATOM | 949 | C | PRO | A | 61 | 35.217 | 28.770 | 76.879 | 1.00 | 44.75 | A |
| ATOM | 950 | O | PRO | A | 61 | 34.276 | 29.477 | 76.550 | 1.00 | 44.94 | A |
| ATOM | 951 | N | SER | A | 62 | 36.267 | 28.566 | 76.095 | 1.00 | 44.64 | A |
| ATOM | 952 | CA | SER | A | 62 | 36.325 | 29.140 | 74.740 | 1.00 | 44.75 | A |
| ATOM | 954 | CB | SER | A | 62 | 37.718 | 28.952 | 74.149 | 1.00 | 45.07 | A |
| ATOM | 957 | OG | SER | A | 62 | 38.495 | 28.069 | 74.952 | 1.00 | 47.60 | A |
| ATOM | 959 | C | SER | A | 62 | 35.254 | 28.633 | 73.750 | 1.00 | 43.80 | A |
| ATOM | 960 | O | SER | A | 62 | 35.063 | 29.259 | 72.711 | 1.00 | 44.42 | A |
| ATOM | 962 | N | PHE | A | 63 | 34.580 | 27.515 | 74.062 | 1.00 | 42.13 | A |
| ATOM | 963 | CA | PHE | A | 63 | 33.474 | 26.976 | 73.240 | 1.00 | 40.78 | A |
| ATOM | 965 | CB | PHE | A | 63 | 33.808 | 25.554 | 72.774 | 1.00 | 40.41 | A |
| ATOM | 968 | CG | PHE | A | 63 | 34.963 | 25.505 | 71.830 | 1.00 | 39.48 | A |
| ATOM | 969 | CD1 | PHE | A | 63 | 34.763 | 25.673 | 70.463 | 1.00 | 37.74 | A |
| ATOM | 971 | CE1 | PHE | A | 63 | 35.810 | 25.670 | 69.595 | 1.00 | 36.52 | A |
| ATOM | 973 | CZ | PHE | A | 63 | 37.115 | 25.498 | 70.073 | 1.00 | 37.30 | A |
| ATOM | 975 | CE2 | PHE | A | 63 | 37.339 | 25.343 | 71.435 | 1.00 | 37.41 | A |
| ATOM | 977 | CD2 | PHE | A | 63 | 36.260 | 25.358 | 72.308 | 1.00 | 38.86 | A |
| ATOM | 979 | C | PHE | A | 63 | 32.113 | 26.992 | 73.935 | 1.00 | 40.59 | A |
| ATOM | 980 | O | PHE | A | 63 | 31.078 | 26.746 | 73.312 | 1.00 | 39.47 | A |

FIG 8 – CONT.

| ATOM | 982 | N | GLN | A | 64 | 32.111 | 27.284 | 75.230 | 1.00 | 40.77 | A |
|---|---|---|---|---|---|---|---|---|---|---|---|
| ATOM | 983 | CA | GLN | A | 64 | 30.870 | 27.442 | 75.956 | 1.00 | 40.99 | A |
| ATOM | 985 | CB | GLN | A | 64 | 31.164 | 27.941 | 77.381 | 1.00 | 41.38 | A |
| ATOM | 988 | CG | GLN | A | 64 | 29.911 | 28.176 | 78.238 | 1.00 | 43.82 | A |
| ATOM | 991 | CD | GLN | A | 64 | 29.182 | 26.886 | 78.583 | 1.00 | 45.77 | A |
| ATOM | 992 | OE1 | GLN | A | 64 | 28.001 | 26.705 | 78.243 | 1.00 | 48.79 | A |
| ATOM | 993 | NE2 | GLN | A | 64 | 29.874 | 25.987 | 79.269 | 1.00 | 45.19 | A |
| ATOM | 996 | C | GLN | A | 64 | 29.982 | 28.445 | 75.241 | 1.00 | 40.20 | A |
| ATOM | 997 | O | GLN | A | 64 | 30.407 | 29.555 | 74.980 | 1.00 | 40.26 | A |
| ATOM | 999 | N | GLY | A | 65 | 28.750 | 28.052 | 74.941 | 1.00 | 39.76 | A |
| ATOM | 1000 | CA | GLY | A | 65 | 27.814 | 28.903 | 74.237 | 1.00 | 39.82 | A |
| ATOM | 1003 | C | GLY | A | 65 | 27.935 | 29.008 | 72.718 | 1.00 | 39.99 | A |
| ATOM | 1004 | O | GLY | A | 65 | 27.037 | 29.549 | 72.078 | 1.00 | 40.05 | A |
| ATOM | 1006 | N | GLN | A | 66 | 29.015 | 28.494 | 72.139 | 1.00 | 39.72 | A |
| ATOM | 1007 | CA | GLN | A | 66 | 29.221 | 28.546 | 70.682 | 1.00 | 40.48 | A |
| ATOM | 1009 | CB | GLN | A | 66 | 30.715 | 28.672 | 70.358 | 1.00 | 40.75 | A |
| ATOM | 1012 | CG | GLN | A | 66 | 31.415 | 29.833 | 71.069 | 1.00 | 43.12 | A |
| ATOM | 1015 | CD | GLN | A | 66 | 30.705 | 31.162 | 70.846 | 1.00 | 45.98 | A |
| ATOM | 1016 | OE1 | GLN | A | 66 | 30.628 | 31.659 | 69.721 | 1.00 | 46.21 | A |
| ATOM | 1017 | NE2 | GLN | A | 66 | 30.154 | 31.728 | 71.924 | 1.00 | 49.51 | A |
| ATOM | 1020 | C | GLN | A | 66 | 28.657 | 27.296 | 69.989 | 1.00 | 39.72 | A |
| ATOM | 1021 | O | GLN | A | 66 | 28.154 | 27.365 | 68.881 | 1.00 | 40.22 | A |
| ATOM | 1023 | N | VAL | A | 67 | 28.680 | 26.177 | 70.693 | 1.00 | 38.73 | A |
| ATOM | 1024 | CA | VAL | A | 67 | 28.303 | 24.914 | 70.130 | 1.00 | 37.89 | A |
| ATOM | 1026 | CB | VAL | A | 67 | 29.581 | 24.233 | 69.645 | 1.00 | 37.43 | A |
| ATOM | 1028 | CG1 | VAL | A | 67 | 30.311 | 23.557 | 70.800 | 1.00 | 37.62 | A |
| ATOM | 1032 | CG2 | VAL | A | 67 | 29.276 | 23.325 | 68.545 | 1.00 | 38.96 | A |
| ATOM | 1036 | C | VAL | A | 67 | 27.533 | 24.082 | 71.157 | 1.00 | 37.27 | A |
| ATOM | 1037 | O | VAL | A | 67 | 27.625 | 24.339 | 72.342 | 1.00 | 37.74 | A |
| ATOM | 1039 | N | THR | A | 68 | 26.744 | 23.114 | 70.694 | 1.00 | 36.10 | A |
| ATOM | 1040 | CA | THR | A | 68 | 26.031 | 22.219 | 71.583 | 1.00 | 35.19 | A |

FIG 8 – CONT.

| | | | | | | | | | | | |
|---|---|---|---|---|---|---|---|---|---|---|---|
| ATOM | 1042 | CB | THR | A | 68 | 24.519 | 22.348 | 71.394 | 1.00 | 35.75 | A C |
| ATOM | 1044 | OG1 | THR | A | 68 | 24.131 | 23.712 | 71.632 | 1.00 | 35.81 | A O |
| ATOM | 1046 | CG2 | THR | A | 68 | 23.766 | 21.431 | 72.340 | 1.00 | 35.62 | A C |
| ATOM | 1050 | C | THR | A | 68 | 26.478 | 20.774 | 71.384 | 1.00 | 34.20 | A C |
| ATOM | 1051 | O | THR | A | 68 | 26.332 | 20.197 | 70.307 | 1.00 | 34.38 | A O |
| ATOM | 1053 | N | ILE | A | 69 | 27.053 | 20.205 | 72.436 | 1.00 | 32.55 | A N |
| ATOM | 1054 | CA | ILE | A | 69 | 27.362 | 18.795 | 72.493 | 1.00 | 31.48 | A C |
| ATOM | 1056 | CB | ILE | A | 69 | 28.624 | 18.564 | 73.318 | 1.00 | 31.20 | A C |
| ATOM | 1058 | CG1 | ILE | A | 69 | 29.795 | 19.239 | 72.602 | 1.00 | 30.37 | A C |
| ATOM | 1061 | CD1 | ILE | A | 69 | 31.020 | 19.384 | 73.459 | 1.00 | 28.68 | A C |
| ATOM | 1065 | CG2 | ILE | A | 69 | 28.865 | 17.069 | 73.564 | 1.00 | 28.27 | A C |
| ATOM | 1069 | C | ILE | A | 69 | 26.162 | 18.020 | 73.071 | 1.00 | 31.77 | A C |
| ATOM | 1070 | O | ILE | A | 69 | 25.626 | 18.379 | 74.128 | 1.00 | 31.83 | A O |
| ATOM | 1072 | N | SER | A | 70 | 25.729 | 16.981 | 72.361 | 1.00 | 30.60 | A N |
| ATOM | 1073 | CA | SER | A | 70 | 24.611 | 16.158 | 72.808 | 1.00 | 30.60 | A C |
| ATOM | 1075 | CB | SER | A | 70 | 23.280 | 16.622 | 72.196 | 1.00 | 30.96 | A C |
| ATOM | 1078 | OG | SER | A | 70 | 23.144 | 16.257 | 70.827 | 1.00 | 31.95 | A O |
| ATOM | 1080 | C | SER | A | 70 | 24.844 | 14.701 | 72.451 | 1.00 | 30.63 | A C |
| ATOM | 1081 | O | SER | A | 70 | 25.859 | 14.342 | 71.856 | 1.00 | 28.70 | A O |
| ATOM | 1083 | N | ALA | A | 71 | 23.890 | 13.863 | 72.818 | 1.00 | 31.11 | A N |
| ATOM | 1084 | CA | ALA | A | 71 | 24.050 | 12.434 | 72.632 | 1.00 | 31.93 | A C |
| ATOM | 1086 | CB | ALA | A | 71 | 25.048 | 11.865 | 73.640 | 1.00 | 31.57 | A C |
| ATOM | 1090 | C | ALA | A | 71 | 22.714 | 11.748 | 72.736 | 1.00 | 32.53 | A C |
| ATOM | 1091 | O | ALA | A | 71 | 21.806 | 12.228 | 73.425 | 1.00 | 33.20 | A O |
| ATOM | 1093 | N | ASP | A | 72 | 22.605 | 10.639 | 72.018 | 1.00 | 33.06 | A N |
| ATOM | 1094 | CA | ASP | A | 72 | 21.427 | 9.781 | 72.002 | 1.00 | 33.73 | A C |
| ATOM | 1096 | CB | ASP | A | 72 | 20.636 | 9.949 | 70.690 | 1.00 | 34.23 | A C |
| ATOM | 1099 | CG | ASP | A | 72 | 19.399 | 9.049 | 70.627 | 1.00 | 35.55 | A C |
| ATOM | 1100 | OD1 | ASP | A | 72 | 18.540 | 9.249 | 69.743 | 1.00 | 38.48 | A O |
| ATOM | 1101 | OD2 | ASP | A | 72 | 19.311 | 8.109 | 71.438 | 1.00 | 38.47 | A O |

FIG 8 – CONT.

| ATOM | 1102 | C | ASP | A | 72 | 21.956 | 8.360 | 72.210 | 1.00 | 33.45 | A C |
| ATOM | 1103 | O | ASP | A | 72 | 22.450 | 7.702 | 71.290 | 1.00 | 32.90 | A O |
| ATOM | 1105 | N | LYS | A | 73 | 21.910 | 7.922 | 73.461 | 1.00 | 33.46 | A N |
| ATOM | 1106 | CA | LYS | A | 73 | 22.490 | 6.641 | 73.846 | 1.00 | 33.23 | A C |
| ATOM | 1108 | CB | LYS | A | 73 | 22.572 | 6.493 | 75.357 | 1.00 | 33.80 | A C |
| ATOM | 1111 | CG | LYS | A | 73 | 21.257 | 6.363 | 76.067 | 1.00 | 35.47 | A C |
| ATOM | 1114 | CD | LYS | A | 73 | 21.493 | 6.499 | 77.585 | 1.00 | 39.67 | A C |
| ATOM | 1117 | CE | LYS | A | 73 | 20.223 | 6.117 | 78.377 | 1.00 | 42.22 | A C |
| ATOM | 1120 | NZ | LYS | A | 73 | 20.476 | 6.151 | 79.845 | 1.00 | 45.12 | A N |
| ATOM | 1124 | C | LYS | A | 73 | 21.773 | 5.460 | 73.259 | 1.00 | 32.52 | A C |
| ATOM | 1125 | O | LYS | A | 73 | 22.373 | 4.424 | 73.053 | 1.00 | 31.83 | A O |
| ATOM | 1127 | N | SER | A | 74 | 20.503 | 5.630 | 72.952 | 1.00 | 32.90 | A N |
| ATOM | 1128 | CA | SER | A | 74 | 19.722 | 4.559 | 72.368 | 1.00 | 33.19 | A C |
| ATOM | 1130 | CB | SER | A | 74 | 18.240 | 4.941 | 72.357 | 1.00 | 33.02 | A C |
| ATOM | 1133 | OG | SER | A | 74 | 17.910 | 5.706 | 71.204 | 1.00 | 33.57 | A O |
| ATOM | 1135 | C | SER | A | 74 | 20.203 | 4.145 | 70.947 | 1.00 | 33.34 | A C |
| ATOM | 1136 | O | SER | A | 74 | 19.959 | 3.012 | 70.514 | 1.00 | 33.75 | A O |
| ATOM | 1138 | N | ILE | A | 75 | 20.857 | 5.060 | 70.225 | 1.00 | 33.58 | A N |
| ATOM | 1139 | CA | ILE | A | 75 | 21.534 | 4.724 | 68.959 | 1.00 | 32.91 | A C |
| ATOM | 1141 | CB | ILE | A | 75 | 20.907 | 5.471 | 67.755 | 1.00 | 33.22 | A C |
| ATOM | 1143 | CG1 | ILE | A | 75 | 21.117 | 7.006 | 67.847 | 1.00 | 34.23 | A C |
| ATOM | 1146 | CD1 | ILE | A | 75 | 20.339 | 7.830 | 66.752 | 1.00 | 32.37 | A C |
| ATOM | 1150 | CG2 | ILE | A | 75 | 19.414 | 5.109 | 67.601 | 1.00 | 31.33 | A C |
| ATOM | 1154 | C | ILE | A | 75 | 23.057 | 4.933 | 69.035 | 1.00 | 33.28 | A C |
| ATOM | 1155 | O | ILE | A | 75 | 23.727 | 5.030 | 68.004 | 1.00 | 34.45 | A O |
| ATOM | 1157 | N | ASN | A | 76 | 23.598 | 5.017 | 70.252 | 1.00 | 33.03 | A N |
| ATOM | 1158 | CA | ASN | A | 76 | 25.031 | 5.091 | 70.508 | 1.00 | 32.93 | A C |
| ATOM | 1160 | CB | ASN | A | 76 | 25.679 | 3.732 | 70.190 | 1.00 | 33.54 | A C |
| ATOM | 1163 | CG | ASN | A | 76 | 26.860 | 3.419 | 71.089 | 1.00 | 32.89 | A C |
| ATOM | 1164 | OD1 | ASN | A | 76 | 26.758 | 3.548 | 72.307 | 1.00 | 32.46 | A O |
| ATOM | 1165 | ND2 | ASN | A | 76 | 28.014 | 3.032 | 70.490 | 1.00 | 30.43 | A |

FIG 8 – CONT.

| | | | | | | | | | | |
|---|---|---|---|---|---|---|---|---|---|---|
| ATOM | 1168 | C | ASN | A | 76 | 25.788 | 6.210 | 69.773 | 1.00 33.66 | A |
| ATOM | 1169 | O | ASN | A | 76 | 26.962 | 6.028 | 69.393 | 1.00 35.07 | A |
| ATOM | 1171 | N | THR | A | 77 | 25.156 | 7.373 | 69.630 | 1.00 32.33 | A |
| ATOM | 1172 | CA | THR | A | 77 | 25.660 | 8.455 | 68.792 | 1.00 31.88 | A |
| ATOM | 1174 | CB | THR | A | 77 | 24.724 | 8.645 | 67.571 | 1.00 32.12 | A |
| ATOM | 1176 | OG1 | THR | A | 77 | 24.682 | 7.416 | 66.808 | 1.00 31.80 | A |
| ATOM | 1178 | CG2 | THR | A | 77 | 25.171 | 9.814 | 66.675 | 1.00 31.37 | A |
| ATOM | 1182 | C | THR | A | 77 | 25.817 | 9.742 | 69.603 | 1.00 31.75 | A |
| ATOM | 1183 | O | THR | A | 77 | 24.911 | 10.109 | 70.363 | 1.00 31.65 | A |
| ATOM | 1185 | N | ALA | A | 78 | 26.987 | 10.386 | 69.508 | 1.00 30.61 | A |
| ATOM | 1186 | CA | ALA | A | 78 | 27.187 | 11.740 | 70.059 | 1.00 29.81 | A |
| ATOM | 1188 | CB | ALA | A | 78 | 28.482 | 11.850 | 70.844 | 1.00 29.41 | A |
| ATOM | 1192 | C | ALA | A | 78 | 27.177 | 12.760 | 68.939 | 1.00 29.38 | A |
| ATOM | 1193 | O | ALA | A | 78 | 27.474 | 12.425 | 67.789 | 1.00 29.65 | A |
| ATOM | 1195 | N | TYR | A | 79 | 26.823 | 14.011 | 69.268 | 1.00 28.24 | A |
| ATOM | 1196 | CA | TYR | A | 79 | 26.671 | 15.023 | 68.261 | 1.00 27.58 | A |
| ATOM | 1198 | CB | TYR | A | 79 | 25.220 | 15.306 | 67.953 | 1.00 27.23 | A |
| ATOM | 1201 | CG | TYR | A | 79 | 24.348 | 14.144 | 67.592 | 1.00 27.91 | A |
| ATOM | 1202 | CD1 | TYR | A | 79 | 24.233 | 13.705 | 66.268 | 1.00 27.66 | A |
| ATOM | 1204 | CE1 | TYR | A | 79 | 23.393 | 12.662 | 65.947 | 1.00 29.08 | A |
| ATOM | 1206 | CZ | TYR | A | 79 | 22.643 | 12.053 | 66.950 | 1.00 30.52 | A |
| ATOM | 1207 | OH | TYR | A | 79 | 21.781 | 11.015 | 66.675 | 1.00 30.38 | A |
| ATOM | 1209 | CE2 | TYR | A | 79 | 22.718 | 12.506 | 68.245 | 1.00 28.75 | A |
| ATOM | 1211 | CD2 | TYR | A | 79 | 23.554 | 13.537 | 68.556 | 1.00 27.70 | A |
| ATOM | 1213 | C | TYR | A | 79 | 27.334 | 16.360 | 68.633 | 1.00 27.75 | A |
| ATOM | 1214 | O | TYR | A | 79 | 27.553 | 16.661 | 69.803 | 1.00 27.38 | A |
| ATOM | 1216 | N | LEU | A | 80 | 27.646 | 17.144 | 67.598 | 1.00 27.53 | A |
| ATOM | 1217 | CA | LEU | A | 80 | 28.156 | 18.496 | 67.734 | 1.00 27.88 | A |
| ATOM | 1219 | CB | LEU | A | 80 | 29.608 | 18.552 | 67.311 | 1.00 28.35 | A |
| ATOM | 1222 | CG | LEU | A | 80 | 30.520 | 19.725 | 67.688 | 1.00 29.17 | A |

FIG 8 – CONT.

| | | | | | | | | | | |
|---|---|---|---|---|---|---|---|---|---|---|
| ATOM | 1224 | CD1 | LEU A | 80 | 30.583 | 19.933 | 69.203 | 1.00 | 27.30 | A |
| C | | | | | | | | | | |
| ATOM | 1228 | CD2 | LEU A | 80 | 31.902 | 19.420 | 67.122 | 1.00 | 26.46 | A |
| C | | | | | | | | | | |
| ATOM | 1232 | C | LEU A | 80 | 27.297 | 19.335 | 66.829 | 1.00 | 28.21 | A |
| C | | | | | | | | | | |
| ATOM | 1233 | O | LEU A | 80 | 27.001 | 18.938 | 65.684 | 1.00 | 27.75 | A |
| O | | | | | | | | | | |
| ATOM | 1235 | N | GLN A | 81 | 26.867 | 20.481 | 67.346 | 1.00 | 28.36 | A |
| N | | | | | | | | | | |
| ATOM | 1236 | CA | GLN A | 81 | 25.808 | 21.203 | 66.727 | 1.00 | 28.94 | A |
| C | | | | | | | | | | |
| ATOM | 1238 | CB | GLN A | 81 | 24.555 | 20.818 | 67.465 | 1.00 | 30.50 | A |
| C | | | | | | | | | | |
| ATOM | 1241 | CG | GLN A | 81 | 23.248 | 21.164 | 66.870 | 1.00 | 33.95 | A |
| C | | | | | | | | | | |
| ATOM | 1244 | CD | GLN A | 81 | 22.049 | 20.625 | 67.736 | 1.00 | 40.77 | A |
| C | | | | | | | | | | |
| ATOM | 1245 | OE1 | GLN A | 81 | 20.878 | 20.817 | 67.374 | 1.00 | 45.24 | A |
| O | | | | | | | | | | |
| ATOM | 1246 | NE2 | GLN A | 81 | 22.351 | 19.951 | 68.860 | 1.00 | 39.31 | A |
| N | | | | | | | | | | |
| ATOM | 1249 | C | GLN A | 81 | 26.026 | 22.709 | 66.805 | 1.00 | 27.75 | A |
| C | | | | | | | | | | |
| ATOM | 1250 | O | GLN A | 81 | 26.453 | 23.231 | 67.821 | 1.00 | 27.75 | A |
| O | | | | | | | | | | |
| ATOM | 1252 | N | TRP A | 82 | 25.679 | 23.390 | 65.730 | 1.00 | 26.47 | A |
| N | | | | | | | | | | |
| ATOM | 1253 | CA | TRP A | 82 | 25.816 | 24.818 | 65.632 | 1.00 | 26.71 | A |
| C | | | | | | | | | | |
| ATOM | 1255 | CB | TRP A | 82 | 26.853 | 25.167 | 64.575 | 1.00 | 26.51 | A |
| C | | | | | | | | | | |
| ATOM | 1258 | CG | TRP A | 82 | 28.266 | 24.933 | 64.949 | 1.00 | 24.55 | A |
| C | | | | | | | | | | |
| ATOM | 1259 | CD1 | TRP A | 82 | 29.099 | 25.817 | 65.549 | 1.00 | 22.00 | A |
| C | | | | | | | | | | |
| ATOM | 1261 | NE1 | TRP A | 82 | 30.325 | 25.266 | 65.698 | 1.00 | 22.96 | A |
| N | | | | | | | | | | |
| ATOM | 1263 | CE2 | TRP A | 82 | 30.311 | 23.989 | 65.201 | 1.00 | 22.28 | A |
| C | | | | | | | | | | |
| ATOM | 1264 | CD2 | TRP A | 82 | 29.035 | 23.756 | 64.697 | 1.00 | 22.62 | A |
| C | | | | | | | | | | |
| ATOM | 1265 | CE3 | TRP A | 82 | 28.761 | 22.532 | 64.083 | 1.00 | 23.71 | A |
| C | | | | | | | | | | |
| ATOM | 1267 | CZ3 | TRP A | 82 | 29.762 | 21.591 | 63.992 | 1.00 | 22.26 | A |
| C | | | | | | | | | | |
| ATOM | 1269 | CH2 | TRP A | 82 | 31.034 | 21.854 | 64.491 | 1.00 | 23.34 | A |
| C | | | | | | | | | | |
| ATOM | 1271 | CZ2 | TRP A | 82 | 31.332 | 23.054 | 65.104 | 1.00 | 23.33 | A |
| C | | | | | | | | | | |
| ATOM | 1273 | C | TRP A | 82 | 24.505 | 25.285 | 65.102 | 1.00 | 27.67 | A |
| C | | | | | | | | | | |
| ATOM | 1274 | O | TRP A | 82 | 23.977 | 24.676 | 64.176 | 1.00 | 27.76 | A |
| O | | | | | | | | | | |
| ATOM | 1276 | N | SER A | 82A | 23.983 | 26.376 | 65.633 | 1.00 | 28.10 | A |
| N | | | | | | | | | | |
| ATOM | 1277 | CA | SER A | 82A | 22.777 | 26.972 | 65.053 | 1.00 | 28.72 | A |
| C | | | | | | | | | | |
| ATOM | 1279 | CB | SER A | 82A | 21.898 | 27.548 | 66.160 | 1.00 | 28.87 | A |
| C | | | | | | | | | | |
| ATOM | 1282 | OG | SER A | 82A | 22.658 | 28.416 | 66.948 | 1.00 | 30.93 | A |

FIG 8 – CONT.

| | | | | | | | | | | |
|---|---|---|---|---|---|---|---|---|---|---|
| ATOM | 1284 | C | SER | A | 82A | 23.092 | 28.059 | 64.007 | 1.00 28.34 | A |
| O | | | | | | | | | | |
| ATOM | 1285 | O | SER | A | 82A | 22.262 | 28.382 | 63.165 | 1.00 29.96 | A |
| ATOM | 1287 | N | SER | A | 82B | 24.276 | 28.622 | 64.062 | 1.00 28.05 | A |
| N | | | | | | | | | | |
| ATOM | 1288 | CA | SER | A | 82B | 24.690 | 29.675 | 63.116 | 1.00 27.99 | A |
| C | | | | | | | | | | |
| ATOM | 1290 | CB | SER | A | 82B | 24.282 | 31.055 | 63.637 | 1.00 28.00 | A |
| C | | | | | | | | | | |
| ATOM | 1293 | OG | SER | A | 82B | 24.578 | 32.089 | 62.717 | 1.00 29.16 | A |
| O | | | | | | | | | | |
| ATOM | 1295 | C | SER | A | 82B | 26.203 | 29.615 | 62.899 | 1.00 26.85 | A |
| C | | | | | | | | | | |
| ATOM | 1296 | O | SER | A | 82B | 26.977 | 30.113 | 63.723 | 1.00 27.31 | A |
| O | | | | | | | | | | |
| ATOM | 1298 | N | LEU | A | 82C | 26.608 | 28.944 | 61.815 | 1.00 24.83 | A |
| N | | | | | | | | | | |
| ATOM | 1299 | CA | LEU | A | 82C | 28.004 | 28.717 | 61.525 | 1.00 23.64 | A |
| C | | | | | | | | | | |
| ATOM | 1301 | CB | LEU | A | 82C | 28.156 | 27.690 | 60.389 | 1.00 23.36 | A |
| C | | | | | | | | | | |
| ATOM | 1304 | CG | LEU | A | 82C | 27.802 | 26.213 | 60.676 | 1.00 19.96 | A |
| C | | | | | | | | | | |
| ATOM | 1306 | CD1 | LEU | A | 82C | 27.537 | 25.450 | 59.388 | 1.00 21.81 | A |
| C | | | | | | | | | | |
| ATOM | 1310 | CD2 | LEU | A | 82C | 28.908 | 25.531 | 61.446 | 1.00 16.23 | A |
| C | | | | | | | | | | |
| ATOM | 1314 | C | LEU | A | 82C | 28.689 | 29.999 | 61.106 | 1.00 23.79 | A |
| C | | | | | | | | | | |
| ATOM | 1315 | O | LEU | A | 82C | 28.095 | 30.840 | 60.437 | 1.00 21.28 | A |
| O | | | | | | | | | | |
| ATOM | 1317 | N | LYS | A | 83 | 29.968 | 30.083 | 61.451 | 1.00 24.55 | A |
| N | | | | | | | | | | |
| ATOM | 1318 | CA | LYS | A | 83 | 30.841 | 31.152 | 61.007 | 1.00 26.23 | A |
| C | | | | | | | | | | |
| ATOM | 1320 | CB | LYS | A | 83 | 31.591 | 31.783 | 62.196 | 1.00 27.12 | A |
| C | | | | | | | | | | |
| ATOM | 1323 | CG | LYS | A | 83 | 30.743 | 32.167 | 63.389 | 1.00 30.85 | A |
| C | | | | | | | | | | |
| ATOM | 1326 | CD | LYS | A | 83 | 31.635 | 32.621 | 64.588 | 1.00 33.74 | A |
| C | | | | | | | | | | |
| ATOM | 1329 | CE | LYS | A | 83 | 30.809 | 32.888 | 65.859 | 1.00 36.36 | A |
| C | | | | | | | | | | |
| ATOM | 1332 | NZ | LYS | A | 83 | 30.174 | 31.649 | 66.454 | 1.00 39.07 | A |
| N | | | | | | | | | | |
| ATOM | 1336 | C | LYS | A | 83 | 31.898 | 30.555 | 60.107 | 1.00 26.07 | A |
| C | | | | | | | | | | |
| ATOM | 1337 | O | LYS | A | 83 | 32.324 | 29.416 | 60.346 | 1.00 26.07 | A |
| O | | | | | | | | | | |
| ATOM | 1339 | N | ALA | A | 84 | 32.385 | 31.338 | 59.140 | 1.00 26.68 | A |
| N | | | | | | | | | | |
| ATOM | 1340 | CA | ALA | A | 84 | 33.484 | 30.897 | 58.233 | 1.00 27.36 | A |
| C | | | | | | | | | | |
| ATOM | 1342 | CB | ALA | A | 84 | 33.997 | 32.037 | 57.327 | 1.00 27.24 | A |
| C | | | | | | | | | | |
| ATOM | 1346 | C | ALA | A | 84 | 34.633 | 30.364 | 59.045 | 1.00 27.22 | A |
| C | | | | | | | | | | |
| ATOM | 1347 | O | ALA | A | 84 | 35.317 | 29.374 | 58.651 | 1.00 26.83 | A |
| O | | | | | | | | | | |

FIG 8 – CONT.

| ATOM | 1349 | N   | SER | A | 85 | 34.855 | 31.013 | 60.178 | 1.00 | 26.67 | A |
|------|------|-----|-----|---|----|--------|--------|--------|------|-------|---|
| ATOM | 1350 | CA  | SER | A | 85 | 35.935 | 30.594 | 61.066 | 1.00 | 27.57 | A |
| ATOM | 1352 | CB  | SER | A | 85 | 36.237 | 31.671 | 62.108 | 1.00 | 27.49 | A |
| ATOM | 1355 | OG  | SER | A | 85 | 35.172 | 31.727 | 63.029 | 1.00 | 29.15 | A |
| ATOM | 1357 | C   | SER | A | 85 | 35.661 | 29.239 | 61.764 | 1.00 | 27.13 | A |
| ATOM | 1358 | O   | SER | A | 85 | 36.564 | 28.671 | 62.353 | 1.00 | 28.51 | A |
| ATOM | 1360 | N   | ASP | A | 86 | 34.458 | 28.691 | 61.682 | 1.00 | 27.17 | A |
| ATOM | 1361 | CA  | ASP | A | 86 | 34.261 | 27.290 | 62.133 | 1.00 | 27.30 | A |
| ATOM | 1363 | CB  | ASP | A | 86 | 32.784 | 27.006 | 62.365 | 1.00 | 27.34 | A |
| ATOM | 1366 | CG  | ASP | A | 86 | 32.221 | 27.807 | 63.529 | 1.00 | 27.89 | A |
| ATOM | 1367 | OD1 | ASP | A | 86 | 32.934 | 27.889 | 64.567 | 1.00 | 25.26 | A |
| ATOM | 1368 | OD2 | ASP | A | 86 | 31.087 | 28.345 | 63.382 | 1.00 | 25.55 | A |
| ATOM | 1369 | C   | ASP | A | 86 | 34.837 | 26.233 | 61.179 | 1.00 | 27.15 | A |
| ATOM | 1370 | O   | ASP | A | 86 | 34.691 | 25.023 | 61.432 | 1.00 | 27.64 | A |
| ATOM | 1372 | N   | THR | A | 87 | 35.501 | 26.675 | 60.102 | 1.00 | 26.60 | A |
| ATOM | 1373 | CA  | THR | A | 87 | 36.060 | 25.764 | 59.083 | 1.00 | 25.29 | A |
| ATOM | 1375 | CB  | THR | A | 87 | 36.599 | 26.532 | 57.838 | 1.00 | 25.27 | A |
| ATOM | 1377 | OG1 | THR | A | 87 | 35.499 | 27.193 | 57.205 | 1.00 | 22.56 | A |
| ATOM | 1379 | CG2 | THR | A | 87 | 37.225 | 25.525 | 56.803 | 1.00 | 26.27 | A |
| ATOM | 1383 | C   | THR | A | 87 | 37.138 | 24.951 | 59.699 | 1.00 | 24.58 | A |
| ATOM | 1384 | O   | THR | A | 87 | 38.128 | 25.492 | 60.136 | 1.00 | 25.12 | A |
| ATOM | 1386 | N   | ALA | A | 88 | 36.971 | 23.635 | 59.762 | 1.00 | 24.07 | A |
| ATOM | 1387 | CA  | ALA | A | 88 | 37.949 | 22.845 | 60.496 | 1.00 | 23.53 | A |
| ATOM | 1389 | CB  | ALA | A | 88 | 37.940 | 23.237 | 62.026 | 1.00 | 23.75 | A |
| ATOM | 1393 | C   | ALA | A | 88 | 37.618 | 21.398 | 60.338 | 1.00 | 23.40 | A |
| ATOM | 1394 | O   | ALA | A | 88 | 36.570 | 21.068 | 59.813 | 1.00 | 22.83 | A |
| ATOM | 1396 | N   | ILE | A | 89 | 38.536 | 20.545 | 60.770 | 1.00 | 24.57 | A |
| ATOM | 1397 | CA  | ILE | A | 89 | 38.242 | 19.114 | 60.991 | 1.00 | 25.53 | A |
| ATOM | 1399 | CB  | ILE | A | 89 | 39.452 | 18.210 | 60.639 | 1.00 | 25.68 | A |
| ATOM | 1401 | CG1 | ILE | A | 89 | 39.775 | 18.349 | 59.150 | 1.00 | 28.20 | A |
| ATOM | 1404 | CD1 | ILE | A | 89 | 41.020 | 17.588 | 58.744 | 1.00 | 30.18 | A |

FIG 8 – CONT.

| | | | | | | | | | | |
|---|---|---|---|---|---|---|---|---|---|---|
| ATOM | 1408 | CG2 | ILE | A | 89 | 39.123 | 16.716 | 60.861 | 1.00 24.48 | A C |
| ATOM | 1412 | C | ILE | A | 89 | 37.846 | 18.959 | 62.446 | 1.00 25.04 | A C |
| ATOM | 1413 | O | ILE | A | 89 | 38.472 | 19.551 | 63.312 | 1.00 24.66 | A O |
| ATOM | 1415 | N | TYR | A | 90 | 36.780 | 18.203 | 62.696 | 1.00 26.11 | A N |
| ATOM | 1416 | CA | TYR | A | 90 | 36.273 | 17.932 | 64.058 | 1.00 26.13 | A C |
| ATOM | 1418 | CB | TYR | A | 90 | 34.826 | 18.392 | 64.202 | 1.00 25.90 | A C |
| ATOM | 1421 | CG | TYR | A | 90 | 34.698 | 19.895 | 64.141 | 1.00 25.39 | A C |
| ATOM | 1422 | CD1 | TYR | A | 90 | 34.491 | 20.543 | 62.928 | 1.00 23.85 | A C |
| ATOM | 1424 | CE1 | TYR | A | 90 | 34.407 | 21.925 | 62.850 | 1.00 24.38 | A C |
| ATOM | 1426 | CZ | TYR | A | 90 | 34.557 | 22.675 | 63.979 | 1.00 23.66 | A C |
| ATOM | 1427 | OH | TYR | A | 90 | 34.509 | 24.027 | 63.879 | 1.00 22.74 | A O |
| ATOM | 1429 | CE2 | TYR | A | 90 | 34.802 | 22.063 | 65.213 | 1.00 25.60 | A C |
| ATOM | 1431 | CD2 | TYR | A | 90 | 34.860 | 20.673 | 65.283 | 1.00 24.00 | A C |
| ATOM | 1433 | C | TYR | A | 90 | 36.402 | 16.439 | 64.331 | 1.00 26.99 | A C |
| ATOM | 1434 | O | TYR | A | 90 | 35.803 | 15.634 | 63.641 | 1.00 27.36 | A O |
| ATOM | 1436 | N | TYR | A | 91 | 37.225 | 16.091 | 65.309 | 1.00 27.77 | A N |
| ATOM | 1437 | CA | TYR | A | 91 | 37.429 | 14.720 | 65.709 | 1.00 28.43 | A C |
| ATOM | 1439 | CB | TYR | A | 91 | 38.881 | 14.461 | 66.074 | 1.00 27.77 | A C |
| ATOM | 1442 | CG | TYR | A | 91 | 39.868 | 14.759 | 64.971 | 1.00 28.69 | A C |
| ATOM | 1443 | CD1 | TYR | A | 91 | 40.061 | 13.867 | 63.922 | 1.00 28.54 | A C |
| ATOM | 1445 | CE1 | TYR | A | 91 | 40.957 | 14.151 | 62.895 | 1.00 28.98 | A C |
| ATOM | 1447 | CZ | TYR | A | 91 | 41.687 | 15.319 | 62.930 | 1.00 30.92 | A C |
| ATOM | 1448 | OH | TYR | A | 91 | 42.574 | 15.612 | 61.909 | 1.00 32.35 | A O |
| ATOM | 1450 | CE2 | TYR | A | 91 | 41.519 | 16.223 | 63.975 | 1.00 30.62 | A C |
| ATOM | 1452 | CD2 | TYR | A | 91 | 40.620 | 15.944 | 64.981 | 1.00 30.22 | A C |
| ATOM | 1454 | C | TYR | A | 91 | 36.562 | 14.379 | 66.922 | 1.00 30.62 | A C |
| ATOM | 1455 | O | TYR | A | 91 | 36.498 | 15.117 | 67.895 | 1.00 30.23 | A O |
| ATOM | 1457 | N | CYS | A | 92 | 35.901 | 13.237 | 66.791 | 1.00 32.19 | A N |
| ATOM | 1458 | CA | CYS | A | 92 | 35.229 | 12.505 | 67.835 | 1.00 34.04 | A C |
| ATOM | 1460 | CB | CYS | A | 92 | 34.272 | 11.481 | 67.139 | 1.00 34.17 | A C |

FIG 8 – CONT.

| ATOM | 1463 | SG | CYS | A | 92 | 33.400 | 10.741 | 68.304 | 1.00 | 43.42 | A |
|---|---|---|---|---|---|---|---|---|---|---|---|
| S | | | | | | | | | | | |
| ATOM | 1465 | C | CYS | A | 92 | 36.329 | 11.776 | 68.637 | 1.00 | 33.85 | A |
| C | | | | | | | | | | | |
| ATOM | 1466 | O | CYS | A | 92 | 37.218 | 11.166 | 68.058 | 1.00 | 33.88 | A |
| O | | | | | | | | | | | |
| ATOM | 1468 | N | VAL | A | 93 | 36.291 | 11.864 | 69.959 | 1.00 | 34.67 | A |
| N | | | | | | | | | | | |
| ATOM | 1469 | CA | VAL | A | 93 | 37.234 | 11.148 | 70.817 | 1.00 | 35.23 | A |
| C | | | | | | | | | | | |
| ATOM | 1471 | CB | VAL | A | 93 | 38.176 | 12.100 | 71.504 | 1.00 | 35.46 | A |
| C | | | | | | | | | | | |
| ATOM | 1473 | CG1 | VAL | A | 93 | 38.955 | 11.359 | 72.539 | 1.00 | 37.41 | A |
| C | | | | | | | | | | | |
| ATOM | 1477 | CG2 | VAL | A | 93 | 39.127 | 12.694 | 70.481 | 1.00 | 37.14 | A |
| C | | | | | | | | | | | |
| ATOM | 1481 | C | VAL | A | 93 | 36.517 | 10.298 | 71.900 | 1.00 | 35.34 | A |
| C | | | | | | | | | | | |
| ATOM | 1482 | O | VAL | A | 93 | 35.590 | 10.772 | 72.564 | 1.00 | 34.92 | A |
| O | | | | | | | | | | | |
| ATOM | 1484 | N | GLY | A | 94 | 36.948 | 9.048 | 72.046 | 1.00 | 34.89 | A |
| N | | | | | | | | | | | |
| ATOM | 1485 | CA | GLY | A | 94 | 36.369 | 8.114 | 73.006 | 1.00 | 35.14 | A |
| C | | | | | | | | | | | |
| ATOM | 1488 | C | GLY | A | 94 | 37.262 | 8.012 | 74.239 | 1.00 | 35.05 | A |
| C | | | | | | | | | | | |
| ATOM | 1489 | O | GLY | A | 94 | 38.458 | 7.744 | 74.113 | 1.00 | 35.02 | A |
| O | | | | | | | | | | | |
| ATOM | 1491 | N | LEU | A | 95 | 36.683 | 8.255 | 75.413 | 1.00 | 34.78 | A |
| N | | | | | | | | | | | |
| ATOM | 1492 | CA | LEU | A | 95 | 37.401 | 8.197 | 76.716 | 1.00 | 35.40 | A |
| C | | | | | | | | | | | |
| ATOM | 1494 | CB | LEU | A | 95 | 37.472 | 9.573 | 77.388 | 1.00 | 34.94 | A |
| C | | | | | | | | | | | |
| ATOM | 1497 | CG | LEU | A | 95 | 37.930 | 10.776 | 76.552 | 1.00 | 36.57 | A |
| C | | | | | | | | | | | |
| ATOM | 1499 | CD1 | LEU | A | 95 | 38.518 | 11.854 | 77.479 | 1.00 | 35.63 | A |
| C | | | | | | | | | | | |
| ATOM | 1503 | CD2 | LEU | A | 95 | 36.788 | 11.371 | 75.695 | 1.00 | 35.22 | A |
| C | | | | | | | | | | | |
| ATOM | 1507 | C | LEU | A | 95 | 36.683 | 7.229 | 77.667 | 1.00 | 35.40 | A |
| C | | | | | | | | | | | |
| ATOM | 1508 | O | LEU | A | 95 | 35.454 | 7.142 | 77.655 | 1.00 | 34.45 | A |
| O | | | | | | | | | | | |
| ATOM | 1510 | N | ASP | A | 96 | 37.458 | 6.517 | 78.494 | 1.00 | 36.80 | A |
| N | | | | | | | | | | | |
| ATOM | 1511 | CA | ASP | A | 96 | 36.908 | 5.516 | 79.435 | 1.00 | 37.42 | A |
| C | | | | | | | | | | | |
| ATOM | 1513 | CB | ASP | A | 96 | 38.034 | 4.734 | 80.092 | 1.00 | 37.47 | A |
| C | | | | | | | | | | | |
| ATOM | 1516 | CG | ASP | A | 96 | 38.862 | 3.928 | 79.097 | 1.00 | 38.55 | A |
| C | | | | | | | | | | | |
| ATOM | 1517 | OD1 | ASP | A | 96 | 40.102 | 3.913 | 79.251 | 1.00 | 39.27 | A |
| O | | | | | | | | | | | |
| ATOM | 1518 | OD2 | ASP | A | 96 | 38.296 | 3.323 | 78.174 | 1.00 | 39.34 | A |
| O | | | | | | | | | | | |
| ATOM | 1519 | C | ASP | A | 96 | 36.086 | 6.210 | 80.537 | 1.00 | 38.15 | A |
| C | | | | | | | | | | | |
| ATOM | 1520 | O | ASP | A | 96 | 35.105 | 5.659 | 81.067 | 1.00 | 37.85 | A |
| O | | | | | | | | | | | |
| ATOM | 1522 | N | TRP | A | 97 | 36.526 | 7.408 | 80.893 | 1.00 | 38.41 | A |

FIG 8 – CONT.

| | | | | | | | | | | |
|---|---|---|---|---|---|---|---|---|---|---|
| ATOM | 1523 | CA | TRP A | 97 | 35.811 | 8.245 | 81.812 | 1.00 | 39.41 | A |
| ATOM | 1525 | CB | TRP A | 97 | 35.975 | 7.752 | 83.255 | 1.00 | 39.03 | A |
| ATOM | 1528 | CG | TRP A | 97 | 34.869 | 8.226 | 84.167 | 1.00 | 38.59 | A |
| ATOM | 1529 | CD1 | TRP A | 97 | 34.938 | 9.251 | 85.064 | 1.00 | 38.82 | A |
| ATOM | 1531 | NE1 | TRP A | 97 | 33.731 | 9.396 | 85.691 | 1.00 | 39.23 | A |
| ATOM | 1533 | CE2 | TRP A | 97 | 32.849 | 8.470 | 85.199 | 1.00 | 37.11 | A |
| ATOM | 1534 | CD2 | TRP A | 97 | 33.529 | 7.714 | 84.242 | 1.00 | 35.85 | A |
| ATOM | 1535 | CE3 | TRP A | 97 | 32.845 | 6.689 | 83.586 | 1.00 | 39.57 | A |
| ATOM | 1537 | CZ3 | TRP A | 97 | 31.522 | 6.449 | 83.913 | 1.00 | 40.31 | A |
| ATOM | 1539 | CH2 | TRP A | 97 | 30.868 | 7.227 | 84.877 | 1.00 | 41.08 | A |
| ATOM | 1541 | CZ2 | TRP A | 97 | 31.513 | 8.244 | 85.523 | 1.00 | 38.87 | A |
| ATOM | 1543 | C | TRP A | 97 | 36.392 | 9.639 | 81.651 | 1.00 | 40.74 | A |
| ATOM | 1544 | O | TRP A | 97 | 37.346 | 9.811 | 80.922 | 1.00 | 41.00 | A |
| ATOM | 1546 | N | ASN A | 98 | 35.810 | 10.620 | 82.336 | 1.00 | 42.17 | A |
| ATOM | 1547 | CA | ASN A | 98 | 36.349 | 11.975 | 82.418 | 1.00 | 43.06 | A |
| ATOM | 1549 | CB | ASN A | 98 | 35.430 | 12.827 | 83.305 | 1.00 | 43.42 | A |
| ATOM | 1552 | CG | ASN A | 98 | 35.356 | 14.295 | 82.881 | 1.00 | 44.11 | A |
| ATOM | 1553 | OD1 | ASN A | 98 | 34.386 | 14.981 | 83.230 | 1.00 | 46.73 | A |
| ATOM | 1554 | ND2 | ASN A | 98 | 36.351 | 14.779 | 82.143 | 1.00 | 39.76 | A |
| ATOM | 1557 | C | ASN A | 98 | 37.752 | 11.962 | 82.999 | 1.00 | 44.18 | A |
| ATOM | 1558 | O | ASN A | 98 | 38.092 | 11.065 | 83.771 | 1.00 | 44.47 | A |
| ATOM | 1560 | N | TYR A | 99 | 38.566 | 12.949 | 82.613 | 1.00 | 45.47 | A |
| ATOM | 1561 | CA | TYR A | 99 | 39.956 | 13.088 | 83.076 | 1.00 | 46.38 | A |
| ATOM | 1563 | CB | TYR A | 99 | 39.964 | 13.380 | 84.581 | 1.00 | 47.16 | A |
| ATOM | 1566 | CG | TYR A | 99 | 39.007 | 14.490 | 84.942 | 1.00 | 49.54 | A |
| ATOM | 1567 | CD1 | TYR A | 99 | 39.167 | 15.760 | 84.394 | 1.00 | 53.72 | A |
| ATOM | 1569 | CE1 | TYR A | 99 | 38.285 | 16.799 | 84.694 | 1.00 | 55.48 | A |
| ATOM | 1571 | CZ | TYR A | 99 | 37.232 | 16.577 | 85.556 | 1.00 | 55.37 | A |
| ATOM | 1572 | OH | TYR A | 99 | 36.382 | 17.619 | 85.835 | 1.00 | 56.89 | A |
| ATOM | 1574 | CE2 | TYR A | 99 | 37.042 | 15.322 | 86.118 | 1.00 | 53.88 | A |

FIG 8 – CONT.

| ATOM | 1576 | CD2 | TYR | A | 99   | 37.930 | 14.276 | 85.796 | 1.00 | 51.82 | A | C |
|------|------|-----|-----|---|------|--------|--------|--------|------|-------|---|---|
| ATOM | 1578 | C   | TYR | A | 99   | 40.836 | 11.871 | 82.733 | 1.00 | 46.34 | A | C |
| ATOM | 1579 | O   | TYR | A | 99   | 41.816 | 11.584 | 83.445 | 1.00 | 47.97 | A | O |
| ATOM | 1581 | N   | ASN | A | 100  | 40.487 | 11.169 | 81.650 | 1.00 | 45.38 | A | N |
| ATOM | 1582 | CA  | ASN | A | 100  | 41.227 | 9.992  | 81.168 | 1.00 | 44.97 | A | C |
| ATOM | 1584 | CB  | ASN | A | 100  | 40.283 | 8.797  | 81.014 | 1.00 | 45.22 | A | C |
| ATOM | 1587 | CG  | ASN | A | 100  | 40.073 | 8.032  | 82.325 | 1.00 | 46.01 | A | C |
| ATOM | 1588 | OD1 | ASN | A | 100  | 39.792 | 8.629  | 83.375 | 1.00 | 46.33 | A | O |
| ATOM | 1589 | ND2 | ASN | A | 100  | 40.214 | 6.709  | 82.261 | 1.00 | 44.08 | A | N |
| ATOM | 1592 | C   | ASN | A | 100  | 41.914 | 10.292 | 79.831 | 1.00 | 44.70 | A | C |
| ATOM | 1593 | O   | ASN | A | 100  | 41.708 | 11.369 | 79.238 | 1.00 | 44.74 | A | O |
| ATOM | 1595 | N   | PRO | A | 100A | 42.755 | 9.365  | 79.358 | 1.00 | 44.02 | A | N |
| ATOM | 1596 | CA  | PRO | A | 100A | 43.421 | 9.681  | 78.103 | 1.00 | 43.60 | A | C |
| ATOM | 1598 | CB  | PRO | A | 100A | 44.513 | 8.598  | 77.990 | 1.00 | 43.55 | A | C |
| ATOM | 1601 | CG  | PRO | A | 100A | 44.156 | 7.542  | 78.930 | 1.00 | 43.58 | A | C |
| ATOM | 1604 | CD  | PRO | A | 100A | 43.261 | 8.120  | 79.970 | 1.00 | 44.17 | A | C |
| ATOM | 1607 | C   | PRO | A | 100A | 42.458 | 9.662  | 76.906 | 1.00 | 43.06 | A | C |
| ATOM | 1608 | O   | PRO | A | 100A | 41.457 | 8.922  | 76.914 | 1.00 | 42.88 | A | O |
| ATOM | 1609 | N   | LEU | A | 100B | 42.757 | 10.487 | 75.900 | 1.00 | 41.90 | A | N |
| ATOM | 1610 | CA  | LEU | A | 100B | 41.974 | 10.512 | 74.672 | 1.00 | 41.09 | A | C |
| ATOM | 1612 | CB  | LEU | A | 100B | 42.214 | 11.783 | 73.862 | 1.00 | 40.86 | A | C |
| ATOM | 1615 | CG  | LEU | A | 100B | 42.253 | 13.133 | 74.584 | 1.00 | 40.65 | A | C |
| ATOM | 1617 | CD1 | LEU | A | 100B | 41.662 | 14.192 | 73.686 | 1.00 | 40.25 | A | C |
| ATOM | 1621 | CD2 | LEU | A | 100B | 41.519 | 13.115 | 75.919 | 1.00 | 42.40 | A | C |
| ATOM | 1625 | C   | LEU | A | 100B | 42.398 | 9.293  | 73.892 | 1.00 | 41.02 | A | C |
| ATOM | 1626 | O   | LEU | A | 100B | 43.342 | 9.327  | 73.092 | 1.00 | 40.83 | A | O |
| ATOM | 1628 | N   | ARG | A | 101  | 41.669 | 8.212  | 74.130 | 1.00 | 40.24 | A | N |
| ATOM | 1629 | CA  | ARG | A | 101  | 42.102 | 6.892  | 73.769 | 1.00 | 39.70 | A | C |
| ATOM | 1631 | CB  | ARG | A | 101  | 41.511 | 5.910  | 74.780 | 1.00 | 40.24 | A | C |
| ATOM | 1634 | CG  | ARG | A | 101  | 41.855 | 4.475  | 74.547 | 1.00 | 42.55 | A | C |
| ATOM | 1637 | CD  | ARG | A | 101  | 41.881 | 3.691  | 75.867 | 1.00 | 45.19 | A |   |

FIG 8 – CONT.

| | | | | | | | | | |
|---|---|---|---|---|---|---|---|---|---|
| C | | | | | | | | | |
| ATOM | 1640 | NE | ARG | A | 101 | 41.495 | 2.316 | 75.624 | 1.00 46.70 | A |
| N | | | | | | | | | |
| ATOM | 1642 | CZ | ARG | A | 101 | 42.025 | 1.262 | 76.229 | 1.00 50.81 | A |
| C | | | | | | | | | |
| ATOM | 1643 | NH1 | ARG | A | 101 | 41.592 | 0.040 | 75.913 | 1.00 49.45 | A |
| N | | | | | | | | | |
| ATOM | 1646 | NH2 | ARG | A | 101 | 42.996 | 1.416 | 77.142 | 1.00 54.96 | A |
| N | | | | | | | | | |
| ATOM | 1649 | C | ARG | A | 101 | 41.696 | 6.502 | 72.368 | 1.00 38.55 | A |
| C | | | | | | | | | |
| ATOM | 1650 | O | ARG | A | 101 | 42.484 | 5.899 | 71.652 | 1.00 39.34 | A |
| O | | | | | | | | | |
| ATOM | 1652 | N | TYR | A | 102 | 40.464 | 6.809 | 71.983 | 1.00 37.16 | A |
| N | | | | | | | | | |
| ATOM | 1653 | CA | TYR | A | 102 | 39.934 | 6.413 | 70.685 | 1.00 35.86 | A |
| C | | | | | | | | | |
| ATOM | 1655 | CB | TYR | A | 102 | 38.706 | 5.507 | 70.826 | 1.00 35.34 | A |
| C | | | | | | | | | |
| ATOM | 1658 | CG | TYR | A | 102 | 38.918 | 4.195 | 71.590 | 1.00 37.22 | A |
| C | | | | | | | | | |
| ATOM | 1659 | CD1 | TYR | A | 102 | 39.592 | 3.129 | 71.024 | 1.00 37.21 | A |
| C | | | | | | | | | |
| ATOM | 1661 | CE1 | TYR | A | 102 | 39.770 | 1.917 | 71.728 | 1.00 37.64 | A |
| C | | | | | | | | | |
| ATOM | 1663 | CZ | TYR | A | 102 | 39.249 | 1.784 | 73.018 | 1.00 39.53 | A |
| C | | | | | | | | | |
| ATOM | 1664 | OH | TYR | A | 102 | 39.416 | 0.618 | 73.743 | 1.00 36.66 | A |
| O | | | | | | | | | |
| ATOM | 1666 | CE2 | TYR | A | 102 | 38.558 | 2.834 | 73.595 | 1.00 38.93 | A |
| C | | | | | | | | | |
| ATOM | 1668 | CD2 | TYR | A | 102 | 38.390 | 4.023 | 72.887 | 1.00 38.50 | A |
| C | | | | | | | | | |
| ATOM | 1670 | C | TYR | A | 102 | 39.583 | 7.676 | 69.866 | 1.00 34.62 | A |
| C | | | | | | | | | |
| ATOM | 1671 | O | TYR | A | 102 | 39.012 | 8.643 | 70.364 | 1.00 34.31 | A |
| O | | | | | | | | | |
| ATOM | 1673 | N | TRP | A | 103 | 39.915 | 7.656 | 68.592 | 1.00 33.17 | A |
| N | | | | | | | | | |
| ATOM | 1674 | CA | TRP | A | 103 | 39.738 | 8.831 | 67.755 | 1.00 31.66 | A |
| C | | | | | | | | | |
| ATOM | 1676 | CB | TRP | A | 103 | 41.096 | 9.317 | 67.302 | 1.00 32.00 | A |
| C | | | | | | | | | |
| ATOM | 1679 | CG | TRP | A | 103 | 41.858 | 9.899 | 68.403 | 1.00 30.14 | A |
| C | | | | | | | | | |
| ATOM | 1680 | CD1 | TRP | A | 103 | 42.482 | 9.235 | 69.395 | 1.00 31.06 | A |
| C | | | | | | | | | |
| ATOM | 1682 | NE1 | TRP | A | 103 | 43.089 | 10.128 | 70.248 | 1.00 28.68 | A |
| N | | | | | | | | | |
| ATOM | 1684 | CE2 | TRP | A | 103 | 42.834 | 11.394 | 69.814 | 1.00 25.92 | A |
| C | | | | | | | | | |
| ATOM | 1685 | CD2 | TRP | A | 103 | 42.073 | 11.287 | 68.644 | 1.00 27.28 | A |
| C | | | | | | | | | |
| ATOM | 1686 | CE3 | TRP | A | 103 | 41.715 | 12.448 | 67.968 | 1.00 27.73 | A |
| C | | | | | | | | | |
| ATOM | 1688 | CZ3 | TRP | A | 103 | 42.100 | 13.687 | 68.505 | 1.00 25.84 | A |
| C | | | | | | | | | |
| ATOM | 1690 | CH2 | TRP | A | 103 | 42.856 | 13.751 | 69.663 | 1.00 27.09 | A |
| C | | | | | | | | | |
| ATOM | 1692 | CZ2 | TRP | A | 103 | 43.241 | 12.619 | 70.333 | 1.00 27.26 | A |
| C | | | | | | | | | |

FIG 8 – CONT.

| ATOM | 1694 | C   | TRP | A | 103 | 38.907 | 8.453  | 66.561 | 1.00 | 30.98 | A | C |
| ATOM | 1695 | O   | TRP | A | 103 | 39.123 | 7.406  | 65.967 | 1.00 | 31.17 | A | O |
| ATOM | 1697 | N   | GLY | A | 104 | 37.919 | 9.272  | 66.239 | 1.00 | 29.29 | A | N |
| ATOM | 1698 | CA  | GLY | A | 104 | 37.275 | 9.164  | 64.958 | 1.00 | 29.48 | A | C |
| ATOM | 1701 | C   | GLY | A | 104 | 38.194 | 9.701  | 63.856 | 1.00 | 28.58 | A | C |
| ATOM | 1702 | O   | GLY | A | 104 | 39.226 | 10.270 | 64.147 | 1.00 | 28.16 | A | O |
| ATOM | 1704 | N   | PRO | A | 105 | 37.840 | 9.484  | 62.590 | 1.00 | 28.63 | A | N |
| ATOM | 1705 | CA  | PRO | A | 105 | 38.732 | 9.903  | 61.478 | 1.00 | 29.12 | A | C |
| ATOM | 1707 | CB  | PRO | A | 105 | 38.243 | 9.088  | 60.276 | 1.00 | 29.01 | A | C |
| ATOM | 1710 | CG  | PRO | A | 105 | 36.926 | 8.582  | 60.626 | 1.00 | 28.98 | A | C |
| ATOM | 1713 | CD  | PRO | A | 105 | 36.734 | 8.645  | 62.133 | 1.00 | 27.88 | A | C |
| ATOM | 1716 | C   | PRO | A | 105 | 38.611 | 11.374 | 61.152 | 1.00 | 29.49 | A | C |
| ATOM | 1717 | O   | PRO | A | 105 | 39.421 | 11.889 | 60.374 | 1.00 | 31.88 | A | O |
| ATOM | 1718 | N   | GLY | A | 106 | 37.594 | 12.036 | 61.693 | 1.00 | 28.76 | A | N |
| ATOM | 1719 | CA  | GLY | A | 106 | 37.430 | 13.449 | 61.505 | 1.00 | 27.46 | A | C |
| ATOM | 1722 | C   | GLY | A | 106 | 36.302 | 13.730 | 60.546 | 1.00 | 27.43 | A | C |
| ATOM | 1723 | O   | GLY | A | 106 | 36.019 | 12.940 | 59.643 | 1.00 | 27.18 | A | O |
| ATOM | 1725 | N   | THR | A | 107 | 35.609 | 14.842 | 60.791 | 1.00 | 27.31 | A | N |
| ATOM | 1726 | CA  | THR | A | 107 | 34.643 | 15.378 | 59.858 | 1.00 | 26.44 | A | C |
| ATOM | 1728 | CB  | THR | A | 107 | 33.261 | 15.465 | 60.504 | 1.00 | 26.68 | A | C |
| ATOM | 1730 | OG1 | THR | A | 107 | 32.768 | 14.142 | 60.756 | 1.00 | 25.37 | A | O |
| ATOM | 1732 | CG2 | THR | A | 107 | 32.318 | 16.216 | 59.609 | 1.00 | 28.54 | A | C |
| ATOM | 1736 | C   | THR | A | 107 | 35.097 | 16.770 | 59.456 | 1.00 | 25.74 | A | C |
| ATOM | 1737 | O   | THR | A | 107 | 35.194 | 17.675 | 60.319 | 1.00 | 25.40 | A | O |
| ATOM | 1739 | N   | LEU | A | 108 | 35.340 | 16.957 | 58.152 | 1.00 | 24.68 | A | N |
| ATOM | 1740 | CA  | LEU | A | 108 | 35.705 | 18.254 | 57.613 | 1.00 | 24.57 | A | C |
| ATOM | 1742 | CB  | LEU | A | 108 | 36.402 | 18.138 | 56.227 | 1.00 | 24.92 | A | C |
| ATOM | 1745 | CG  | LEU | A | 108 | 36.690 | 19.542 | 55.590 | 1.00 | 25.99 | A | C |
| ATOM | 1747 | CD1 | LEU | A | 108 | 37.297 | 19.429 | 54.159 | 1.00 | 29.31 | A | C |
| ATOM | 1751 | CD2 | LEU | A | 108 | 37.600 | 20.471 | 56.473 | 1.00 | 23.79 | A | C |
| ATOM | 1755 | C   | LEU | A | 108 | 34.453 | 19.074 | 57.471 | 1.00 | 23.74 | A |   |

FIG 8 – CONT.

| ATOM | | | | | | | | | | |
|---|---|---|---|---|---|---|---|---|---|---|
| ATOM | 1756 | O | LEU | A | 108 | 33.475 | 18.660 | 56.839 | 1.00 24.03 | A |
| ATOM | 1758 | N | VAL | A | 109 | 34.478 | 20.257 | 58.031 | 1.00 23.35 | A |
| ATOM | 1759 | CA | VAL | A | 109 | 33.363 | 21.176 | 57.901 | 1.00 22.89 | A |
| ATOM | 1761 | CB | VAL | A | 109 | 32.718 | 21.505 | 59.273 | 1.00 22.83 | A |
| ATOM | 1763 | CG1 | VAL | A | 109 | 31.712 | 22.625 | 59.140 | 1.00 23.49 | A |
| ATOM | 1767 | CG2 | VAL | A | 109 | 32.040 | 20.300 | 59.837 | 1.00 19.85 | A |
| ATOM | 1771 | C | VAL | A | 109 | 33.944 | 22.428 | 57.290 | 1.00 23.58 | A |
| ATOM | 1772 | O | VAL | A | 109 | 34.855 | 23.049 | 57.877 | 1.00 23.81 | A |
| ATOM | 1774 | N | THR | A | 110 | 33.440 | 22.768 | 56.101 | 1.00 23.92 | A |
| ATOM | 1775 | CA | THR | A | 110 | 33.872 | 23.939 | 55.367 | 1.00 23.03 | A |
| ATOM | 1777 | CB | THR | A | 110 | 34.177 | 23.634 | 53.849 | 1.00 24.19 | A |
| ATOM | 1779 | OG1 | THR | A | 110 | 35.261 | 22.692 | 53.722 | 1.00 24.94 | A |
| ATOM | 1781 | CG2 | THR | A | 110 | 34.471 | 24.949 | 53.078 | 1.00 21.39 | A |
| ATOM | 1785 | C | THR | A | 110 | 32.718 | 24.841 | 55.397 | 1.00 23.60 | A |
| ATOM | 1786 | O | THR | A | 110 | 31.640 | 24.447 | 54.972 | 1.00 24.16 | A |
| ATOM | 1788 | N | VAL | A | 111 | 32.945 | 26.069 | 55.857 | 1.00 24.07 | A |
| ATOM | 1789 | CA | VAL | A | 111 | 31.925 | 27.062 | 55.924 | 1.00 24.57 | A |
| ATOM | 1791 | CB | VAL | A | 111 | 31.699 | 27.545 | 57.376 | 1.00 24.61 | A |
| ATOM | 1793 | CG1 | VAL | A | 111 | 30.514 | 28.480 | 57.431 | 1.00 22.21 | A |
| ATOM | 1797 | CG2 | VAL | A | 111 | 31.545 | 26.330 | 58.338 | 1.00 23.01 | A |
| ATOM | 1801 | C | VAL | A | 111 | 32.419 | 28.217 | 55.113 | 1.00 25.98 | A |
| ATOM | 1802 | O | VAL | A | 111 | 33.446 | 28.775 | 55.426 | 1.00 26.08 | A |
| ATOM | 1804 | N | SER | A | 112 | 31.699 | 28.573 | 54.062 | 1.00 28.32 | A |
| ATOM | 1805 | CA | SER | A | 112 | 32.051 | 29.770 | 53.268 | 1.00 30.32 | A |
| ATOM | 1807 | CB | SER | A | 112 | 33.230 | 29.513 | 52.296 | 1.00 30.72 | A |
| ATOM | 1810 | OG | SER | A | 112 | 32.778 | 28.842 | 51.111 | 1.00 31.46 | A |
| ATOM | 1812 | C | SER | A | 112 | 30.868 | 30.187 | 52.479 | 1.00 31.00 | A |
| ATOM | 1813 | O | SER | A | 112 | 29.893 | 29.458 | 52.363 | 1.00 30.87 | A |
| ATOM | 1815 | N | SER | A | 113 | 30.980 | 31.365 | 51.893 | 1.00 33.92 | A |
| ATOM | 1816 | CA | SER | A | 113 | 29.929 | 31.902 | 51.025 | 1.00 34.78 | A |

FIG 8 – CONT.

| ATOM | 1818 | CB | SER A 113 | 30.209 | 33.369 | 50.748 | 1.00 | 35.72 | A |
|---|---|---|---|---|---|---|---|---|---|
| | | C | | | | | | | |
| ATOM | 1821 | OG | SER A 113 | 30.192 | 34.115 | 51.970 | 1.00 | 36.27 | A |
| | | O | | | | | | | |
| ATOM | 1823 | C | SER A 113 | 29.765 | 31.113 | 49.724 | 1.00 | 36.14 | A |
| | | C | | | | | | | |
| ATOM | 1824 | O | SER A 113 | 28.651 | 31.024 | 49.196 | 1.00 | 37.02 | A |
| | | O | | | | | | | |
| ATOM | 1826 | N | ALA A 114 | 30.819 | 30.466 | 49.233 | 1.00 | 37.15 | A |
| | | N | | | | | | | |
| ATOM | 1827 | CA | ALA A 114 | 30.698 | 29.714 | 47.967 | 1.00 | 37.89 | A |
| | | C | | | | | | | |
| ATOM | 1829 | CB | ALA A 114 | 32.049 | 29.654 | 47.251 | 1.00 | 37.91 | A |
| | | C | | | | | | | |
| ATOM | 1833 | C | ALA A 114 | 30.180 | 28.316 | 48.248 | 1.00 | 39.05 | A |
| | | C | | | | | | | |
| ATOM | 1834 | O | ALA A 114 | 30.503 | 27.732 | 49.286 | 1.00 | 40.56 | A |
| | | O | | | | | | | |
| ATOM | 1836 | N | SER A 115 | 29.353 | 27.749 | 47.375 | 1.00 | 39.67 | A |
| | | N | | | | | | | |
| ATOM | 1837 | CA | SER A 115 | 28.901 | 26.358 | 47.612 | 1.00 | 39.83 | A |
| | | C | | | | | | | |
| ATOM | 1839 | CB | SER A 115 | 27.409 | 26.155 | 47.312 | 1.00 | 40.04 | A |
| | | C | | | | | | | |
| ATOM | 1842 | OG | SER A 115 | 26.993 | 26.885 | 46.179 | 1.00 | 41.24 | A |
| | | O | | | | | | | |
| ATOM | 1844 | C | SER A 115 | 29.765 | 25.396 | 46.814 | 1.00 | 39.55 | A |
| | | C | | | | | | | |
| ATOM | 1845 | O | SER A 115 | 30.619 | 25.813 | 46.042 | 1.00 | 38.70 | A |
| | | O | | | | | | | |
| ATOM | 1847 | N | THR A 116 | 29.537 | 24.113 | 47.003 | 1.00 | 39.36 | A |
| | | N | | | | | | | |
| ATOM | 1848 | CA | THR A 116 | 30.349 | 23.129 | 46.334 | 1.00 | 40.65 | A |
| | | C | | | | | | | |
| ATOM | 1850 | CB | THR A 116 | 30.003 | 21.708 | 46.822 | 1.00 | 40.56 | A |
| | | C | | | | | | | |
| ATOM | 1852 | OG1 | THR A 116 | 30.660 | 21.537 | 48.079 | 1.00 | 44.01 | A |
| | | O | | | | | | | |
| ATOM | 1854 | CG2 | THR A 116 | 30.540 | 20.622 | 45.912 | 1.00 | 43.56 | A |
| | | C | | | | | | | |
| ATOM | 1858 | C | THR A 116 | 30.286 | 23.310 | 44.814 | 1.00 | 40.20 | A |
| | | C | | | | | | | |
| ATOM | 1859 | O | THR A 116 | 29.228 | 23.638 | 44.265 | 1.00 | 39.87 | A |
| | | O | | | | | | | |
| ATOM | 1861 | N | LYS A 117 | 31.458 | 23.168 | 44.180 | 1.00 | 39.61 | A |
| | | N | | | | | | | |
| ATOM | 1862 | CA | LYS A 117 | 31.609 | 23.147 | 42.732 | 1.00 | 39.11 | A |
| | | C | | | | | | | |
| ATOM | 1864 | CB | LYS A 117 | 32.273 | 24.438 | 42.215 | 1.00 | 39.92 | A |
| | | C | | | | | | | |
| ATOM | 1867 | CG | LYS A 117 | 32.261 | 24.516 | 40.672 | 1.00 | 40.13 | A |
| | | C | | | | | | | |
| ATOM | 1870 | CD | LYS A 117 | 33.175 | 25.589 | 40.089 | 1.00 | 40.87 | A |
| | | C | | | | | | | |
| ATOM | 1873 | CE | LYS A 117 | 33.307 | 25.416 | 38.542 | 1.00 | 39.90 | A |
| | | C | | | | | | | |
| ATOM | 1876 | NZ | LYS A 117 | 33.942 | 24.114 | 38.119 | 1.00 | 38.37 | A |
| | | N | | | | | | | |
| ATOM | 1880 | C | LYS A 117 | 32.454 | 21.938 | 42.305 | 1.00 | 38.16 | A |
| | | C | | | | | | | |
| ATOM | 1881 | O | LYS A 117 | 33.555 | 21.715 | 42.811 | 1.00 | 37.03 | A |

FIG 8 – CONT.

| | | | | | | | | | |
|---|---|---|---|---|---|---|---|---|---|
| O | | | | | | | | | |
| ATOM | 1883 | N | GLY | A 118 | 31.912 | 21.157 | 41.383 | 1.00 36.96 | A |
| N | | | | | | | | | |
| ATOM | 1884 | CA | GLY | A 118 | 32.651 | 20.104 | 40.746 | 1.00 36.67 | A |
| C | | | | | | | | | |
| ATOM | 1887 | C | GLY | A 118 | 33.724 | 20.627 | 39.795 | 1.00 36.02 | A |
| C | | | | | | | | | |
| ATOM | 1888 | O | GLY | A 118 | 33.675 | 21.777 | 39.341 | 1.00 36.53 | A |
| O | | | | | | | | | |
| ATOM | 1890 | N | PRO | A 119 | 34.718 | 19.783 | 39.497 | 1.00 34.91 | A |
| N | | | | | | | | | |
| ATOM | 1891 | CA | PRO | A 119 | 35.773 | 20.177 | 38.593 | 1.00 34.20 | A |
| C | | | | | | | | | |
| ATOM | 1893 | CB | PRO | A 119 | 36.891 | 19.218 | 38.960 | 1.00 34.04 | A |
| C | | | | | | | | | |
| ATOM | 1896 | CG | PRO | A 119 | 36.108 | 17.912 | 39.301 | 1.00 34.88 | A |
| C | | | | | | | | | |
| ATOM | 1899 | CD | PRO | A 119 | 34.737 | 18.331 | 39.753 | 1.00 34.74 | A |
| C | | | | | | | | | |
| ATOM | 1902 | C | PRO | A 119 | 35.370 | 19.942 | 37.146 | 1.00 33.37 | A |
| C | | | | | | | | | |
| ATOM | 1903 | O | PRO | A 119 | 34.514 | 19.104 | 36.864 | 1.00 33.09 | A |
| O | | | | | | | | | |
| ATOM | 1904 | N | SER | A 120 | 35.991 | 20.678 | 36.244 | 1.00 32.97 | A |
| N | | | | | | | | | |
| ATOM | 1905 | CA | SER | A 120 | 36.067 | 20.277 | 34.847 | 1.00 32.61 | A |
| C | | | | | | | | | |
| ATOM | 1907 | CB | SER | A 120 | 35.927 | 21.487 | 33.908 | 1.00 32.81 | A |
| C | | | | | | | | | |
| ATOM | 1910 | OG | SER | A 120 | 34.777 | 22.278 | 34.203 | 1.00 33.20 | A |
| O | | | | | | | | | |
| ATOM | 1912 | C | SER | A 120 | 37.444 | 19.650 | 34.678 | 1.00 32.07 | A |
| C | | | | | | | | | |
| ATOM | 1913 | O | SER | A 120 | 38.450 | 20.125 | 35.213 | 1.00 31.82 | A |
| O | | | | | | | | | |
| ATOM | 1915 | N | VAL | A 121 | 37.486 | 18.584 | 33.905 | 1.00 32.10 | A |
| N | | | | | | | | | |
| ATOM | 1916 | CA | VAL | A 121 | 38.688 | 17.814 | 33.767 | 1.00 32.04 | A |
| C | | | | | | | | | |
| ATOM | 1918 | CB | VAL | A 121 | 38.458 | 16.375 | 34.109 | 1.00 31.60 | A |
| C | | | | | | | | | |
| ATOM | 1920 | CG1 | VAL | A 121 | 39.802 | 15.631 | 34.023 | 1.00 32.48 | A |
| C | | | | | | | | | |
| ATOM | 1924 | CG2 | VAL | A 121 | 37.855 | 16.261 | 35.508 | 1.00 31.41 | A |
| C | | | | | | | | | |
| ATOM | 1928 | C | VAL | A 121 | 39.188 | 17.887 | 32.349 | 1.00 31.75 | A |
| C | | | | | | | | | |
| ATOM | 1929 | O | VAL | A 121 | 38.437 | 17.647 | 31.410 | 1.00 32.19 | A |
| O | | | | | | | | | |
| ATOM | 1931 | N | PHE | A 122 | 40.466 | 18.205 | 32.210 | 1.00 30.71 | A |
| N | | | | | | | | | |
| ATOM | 1932 | CA | PHE | A 122 | 41.055 | 18.404 | 30.898 | 1.00 30.31 | A |
| C | | | | | | | | | |
| ATOM | 1934 | CB | PHE | A 122 | 41.496 | 19.854 | 30.736 | 1.00 29.67 | A |
| C | | | | | | | | | |
| ATOM | 1937 | CG | PHE | A 122 | 40.388 | 20.845 | 30.813 | 1.00 29.85 | A |
| C | | | | | | | | | |
| ATOM | 1938 | CD1 | PHE | A 122 | 39.380 | 20.842 | 29.893 | 1.00 31.76 | A |
| C | | | | | | | | | |
| ATOM | 1940 | CE1 | PHE | A 122 | 38.364 | 21.794 | 29.951 | 1.00 32.41 | A |
| C | | | | | | | | | |

FIG 8 – CONT.

| | | | | | | | | | | |
|---|---|---|---|---|---|---|---|---|---|---|
| ATOM | 1942 | CZ | PHE A 122 | 38.385 | 22.775 | 30.947 | 1.00 | 32.84 | | A C |
| ATOM | 1944 | CE2 | PHE A 122 | 39.389 | 22.814 | 31.848 | 1.00 | 29.89 | | A C |
| ATOM | 1946 | CD2 | PHE A 122 | 40.384 | 21.836 | 31.798 | 1.00 | 33.68 | | A C |
| ATOM | 1948 | C | PHE A 122 | 42.239 | 17.454 | 30.727 | 1.00 | 30.21 | | A C |
| ATOM | 1949 | O | PHE A 122 | 42.971 | 17.216 | 31.665 | 1.00 | 30.03 | | A O |
| ATOM | 1951 | N | PRO A 123 | 42.415 | 16.890 | 29.524 | 1.00 | 30.69 | | A N |
| ATOM | 1952 | CA | PRO A 123 | 43.562 | 16.014 | 29.286 | 1.00 | 30.93 | | A C |
| ATOM | 1954 | CB | PRO A 123 | 43.202 | 15.364 | 27.952 | 1.00 | 31.10 | | A C |
| ATOM | 1957 | CG | PRO A 123 | 42.531 | 16.489 | 27.206 | 1.00 | 30.26 | | A C |
| ATOM | 1960 | CD | PRO A 123 | 41.739 | 17.245 | 28.264 | 1.00 | 30.62 | | A C |
| ATOM | 1963 | C | PRO A 123 | 44.906 | 16.789 | 29.186 | 1.00 | 31.03 | | A C |
| ATOM | 1964 | O | PRO A 123 | 44.941 | 17.917 | 28.710 | 1.00 | 30.52 | | A O |
| ATOM | 1965 | N | LEU A 124 | 45.973 | 16.211 | 29.726 | 1.00 | 31.47 | | A N |
| ATOM | 1966 | CA | LEU A 124 | 47.313 | 16.729 | 29.548 | 1.00 | 32.14 | | A C |
| ATOM | 1968 | CB | LEU A 124 | 48.045 | 16.885 | 30.879 | 1.00 | 31.69 | | A C |
| ATOM | 1971 | CG | LEU A 124 | 47.365 | 17.885 | 31.833 | 1.00 | 31.03 | | A C |
| ATOM | 1973 | CD1 | LEU A 124 | 48.056 | 17.917 | 33.148 | 1.00 | 28.70 | | A C |
| ATOM | 1977 | CD2 | LEU A 124 | 47.316 | 19.295 | 31.235 | 1.00 | 28.96 | | A C |
| ATOM | 1981 | C | LEU A 124 | 47.975 | 15.724 | 28.607 | 1.00 | 33.30 | | A C |
| ATOM | 1982 | O | LEU A 124 | 48.504 | 14.701 | 29.024 | 1.00 | 32.71 | | A O |
| ATOM | 1984 | N | ALA A 125 | 47.870 | 16.021 | 27.320 | 1.00 | 34.64 | | A N |
| ATOM | 1985 | CA | ALA A 125 | 48.202 | 15.059 | 26.280 | 1.00 | 36.33 | | A C |
| ATOM | 1987 | CB | ALA A 125 | 47.691 | 15.561 | 24.925 | 1.00 | 36.13 | | A C |
| ATOM | 1991 | C | ALA A 125 | 49.714 | 14.798 | 26.204 | 1.00 | 37.52 | | A C |
| ATOM | 1992 | O | ALA A 125 | 50.503 | 15.736 | 26.265 | 1.00 | 36.34 | | A O |
| ATOM | 1994 | N | PRO A 126 | 50.104 | 13.518 | 26.038 | 1.00 | 39.55 | | A N |
| ATOM | 1995 | CA | PRO A 126 | 51.488 | 13.146 | 25.754 | 1.00 | 40.70 | | A C |
| ATOM | 1997 | CB | PRO A 126 | 51.443 | 11.622 | 25.701 | 1.00 | 40.71 | | A C |
| ATOM | 2000 | CG | PRO A 126 | 50.063 | 11.281 | 25.316 | 1.00 | 40.57 | | A C |
| ATOM | 2003 | CD | PRO A 126 | 49.171 | 12.416 | 25.739 | 1.00 | 40.13 | | A C |
| ATOM | 2006 | C | PRO A 126 | 51.931 | 13.715 | 24.419 | 1.00 | 41.71 | | A |

FIG 8 – CONT.

| ATOM | 2007 | O | PRO A 126 | 51.118 | 13.860 | 23.513 | 1.00 | 41.57 | A |
|---|---|---|---|---|---|---|---|---|---|
| ATOM | 2008 | N | SER A 127 | 53.199 | 14.092 | 24.315 | 1.00 | 43.99 | A |
| ATOM | 2009 | CA | SER A 127 | 53.703 | 14.708 | 23.070 | 1.00 | 45.68 | A |
| ATOM | 2011 | CB | SER A 127 | 53.383 | 16.198 | 23.052 | 1.00 | 45.12 | A |
| ATOM | 2014 | OG | SER A 127 | 54.308 | 16.880 | 23.856 | 1.00 | 44.45 | A |
| ATOM | 2016 | C | SER A 127 | 55.200 | 14.512 | 22.952 | 1.00 | 47.25 | A |
| ATOM | 2017 | O | SER A 127 | 55.790 | 13.893 | 23.820 | 1.00 | 48.05 | A |
| ATOM | 2019 | N | SER A 128 | 55.821 | 15.039 | 21.895 | 1.00 | 49.42 | A |
| ATOM | 2020 | CA | SER A 128 | 57.289 | 14.944 | 21.769 | 1.00 | 51.18 | A |
| ATOM | 2022 | CB | SER A 128 | 57.788 | 15.264 | 20.344 | 1.00 | 51.30 | A |
| ATOM | 2025 | OG | SER A 128 | 57.308 | 16.504 | 19.863 | 1.00 | 51.68 | A |
| ATOM | 2027 | C | SER A 128 | 57.950 | 15.829 | 22.831 | 1.00 | 52.47 | A |
| ATOM | 2028 | O | SER A 128 | 58.908 | 15.405 | 23.476 | 1.00 | 52.84 | A |
| ATOM | 2030 | N | LYS A 129 | 57.394 | 17.025 | 23.060 | 1.00 | 53.97 | A |
| ATOM | 2031 | CA | LYS A 129 | 57.843 | 17.907 | 24.167 | 1.00 | 54.90 | A |
| ATOM | 2033 | CB | LYS A 129 | 57.132 | 19.286 | 24.114 | 1.00 | 55.14 | A |
| ATOM | 2036 | CG | LYS A 129 | 57.840 | 20.358 | 23.253 | 1.00 | 55.12 | A |
| ATOM | 2042 | C | LYS A 129 | 57.725 | 17.295 | 25.590 | 1.00 | 55.30 | A |
| ATOM | 2043 | O | LYS A 129 | 58.434 | 17.741 | 26.514 | 1.00 | 55.79 | A |
| ATOM | 2045 | N | SER A 130 | 56.872 | 16.282 | 25.771 | 1.00 | 55.74 | A |
| ATOM | 2046 | CA | SER A 130 | 56.732 | 15.599 | 27.083 | 1.00 | 56.20 | A |
| ATOM | 2048 | CB | SER A 130 | 55.242 | 15.552 | 27.509 | 1.00 | 56.35 | A |
| ATOM | 2051 | OG | SER A 130 | 54.536 | 14.445 | 26.952 | 1.00 | 54.91 | A |
| ATOM | 2053 | C | SER A 130 | 57.345 | 14.181 | 27.151 | 1.00 | 57.08 | A |
| ATOM | 2054 | O | SER A 130 | 57.095 | 13.431 | 28.114 | 1.00 | 56.53 | A |
| ATOM | 2056 | N | THR A 133 | 58.149 | 13.822 | 26.147 | 1.00 | 58.30 | A |
| ATOM | 2057 | CA | THR A 133 | 58.665 | 12.454 | 26.005 | 1.00 | 59.19 | A |
| ATOM | 2059 | CB | THR A 133 | 58.010 | 11.709 | 24.811 | 1.00 | 59.61 | A |
| ATOM | 2061 | OG1 | THR A 133 | 58.430 | 12.309 | 23.584 | 1.00 | 61.18 | A |
| ATOM | 2063 | CG2 | THR A 133 | 56.491 | 11.745 | 24.883 | 1.00 | 58.93 | A |

FIG 8 – CONT.

| ATOM | 2067 | C | THR A 133 | 60.181 | 12.429 | 25.780 | 1.00 | 59.77 | A |
|---|---|---|---|---|---|---|---|---|---|
| ATOM | 2068 | O | THR A 133 | 60.715 | 13.151 | 24.937 | 1.00 | 59.56 | A |
| ATOM | 2070 | N | SER A 134 | 60.867 | 11.569 | 26.525 | 1.00 | 60.10 | A |
| ATOM | 2071 | CA | SER A 134 | 62.303 | 11.473 | 26.418 | 1.00 | 60.32 | A |
| ATOM | 2073 | CB | SER A 134 | 62.959 | 12.608 | 27.207 | 1.00 | 60.91 | A |
| ATOM | 2076 | OG | SER A 134 | 62.522 | 13.879 | 26.750 | 1.00 | 61.32 | A |
| ATOM | 2078 | C | SER A 134 | 62.782 | 10.129 | 26.950 | 1.00 | 59.85 | A |
| ATOM | 2079 | O | SER A 134 | 62.249 | 9.616 | 27.943 | 1.00 | 59.63 | A |
| ATOM | 2081 | N | GLY A 135 | 63.784 | 9.566 | 26.274 | 1.00 | 58.96 | A |
| ATOM | 2082 | CA | GLY A 135 | 64.408 | 8.325 | 26.707 | 1.00 | 58.18 | A |
| ATOM | 2085 | C | GLY A 135 | 63.431 | 7.183 | 26.835 | 1.00 | 57.49 | A |
| ATOM | 2086 | O | GLY A 135 | 63.508 | 6.404 | 27.779 | 1.00 | 57.70 | A |
| ATOM | 2088 | N | GLY A 136 | 62.486 | 7.101 | 25.904 | 1.00 | 56.86 | A |
| ATOM | 2089 | CA | GLY A 136 | 61.599 | 5.942 | 25.815 | 1.00 | 56.44 | A |
| ATOM | 2092 | C | GLY A 136 | 60.357 | 5.924 | 26.699 | 1.00 | 55.76 | A |
| ATOM | 2093 | O | GLY A 136 | 59.509 | 5.038 | 26.541 | 1.00 | 56.25 | A |
| ATOM | 2095 | N | THR A 137 | 60.236 | 6.850 | 27.649 | 1.00 | 54.54 | A |
| ATOM | 2096 | CA | THR A 137 | 58.955 | 6.995 | 28.366 | 1.00 | 53.57 | A |
| ATOM | 2098 | CB | THR A 137 | 59.077 | 6.644 | 29.867 | 1.00 | 53.90 | A |
| ATOM | 2100 | OG1 | THR A 137 | 60.078 | 7.457 | 30.482 | 1.00 | 53.59 | A |
| ATOM | 2102 | CG2 | THR A 137 | 59.413 | 5.122 | 30.053 | 1.00 | 54.05 | A |
| ATOM | 2106 | C | THR A 137 | 58.308 | 8.377 | 28.144 | 1.00 | 51.96 | A |
| ATOM | 2107 | O | THR A 137 | 58.987 | 9.359 | 27.885 | 1.00 | 51.65 | A |
| ATOM | 2109 | N | ALA A 138 | 56.979 | 8.415 | 28.186 | 1.00 | 50.47 | A |
| ATOM | 2110 | CA | ALA A 138 | 56.211 | 9.652 | 27.962 | 1.00 | 48.82 | A |
| ATOM | 2112 | CB | ALA A 138 | 55.270 | 9.482 | 26.767 | 1.00 | 48.79 | A |
| ATOM | 2116 | C | ALA A 138 | 55.415 | 10.055 | 29.216 | 1.00 | 46.92 | A |
| ATOM | 2117 | O | ALA A 138 | 55.007 | 9.194 | 30.014 | 1.00 | 47.22 | A |
| ATOM | 2119 | N | ALA A 139 | 55.214 | 11.363 | 29.382 | 1.00 | 44.56 | A |
| ATOM | 2120 | CA | ALA A 139 | 54.370 | 11.919 | 30.454 | 1.00 | 42.81 | A |
| ATOM | 2122 | CB | ALA A 139 | 55.072 | 13.098 | 31.140 | 1.00 | 42.04 | A |

FIG 8 – CONT.

| | | | | | | | | | | |
|---|---|---|---|---|---|---|---|---|---|---|
| ATOM | 2126 | C | ALA | A | 139 | 53.011 | 12.359 | 29.887 | 1.00 41.02 | A C |
| ATOM | 2127 | O | ALA | A | 139 | 52.947 | 13.069 | 28.894 | 1.00 40.89 | A O |
| ATOM | 2129 | N | LEU | A | 140 | 51.933 | 11.908 | 30.518 | 1.00 39.64 | A N |
| ATOM | 2130 | CA | LEU | A | 140 | 50.577 | 12.431 | 30.266 | 1.00 37.80 | A C |
| ATOM | 2132 | CB | LEU | A | 140 | 49.761 | 11.485 | 29.394 | 1.00 37.45 | A C |
| ATOM | 2135 | CG | LEU | A | 140 | 49.658 | 10.102 | 30.017 | 1.00 37.70 | A C |
| ATOM | 2137 | CD1 | LEU | A | 140 | 48.291 | 9.506 | 29.868 | 1.00 38.85 | A C |
| ATOM | 2141 | CD2 | LEU | A | 140 | 50.695 | 9.207 | 29.405 | 1.00 40.18 | A C |
| ATOM | 2145 | C | LEU | A | 140 | 49.884 | 12.581 | 31.604 | 1.00 36.42 | A C |
| ATOM | 2146 | O | LEU | A | 140 | 50.363 | 12.083 | 32.601 | 1.00 36.09 | A O |
| ATOM | 2148 | N | GLY | A | 141 | 48.747 | 13.265 | 31.614 | 1.00 34.99 | A N |
| ATOM | 2149 | CA | GLY | A | 141 | 48.017 | 13.511 | 32.854 | 1.00 33.65 | A C |
| ATOM | 2152 | C | GLY | A | 141 | 46.651 | 14.183 | 32.659 | 1.00 32.45 | A C |
| ATOM | 2153 | O | GLY | A | 141 | 46.170 | 14.375 | 31.519 | 1.00 29.54 | A O |
| ATOM | 2155 | N | CYS | A | 142 | 46.011 | 14.500 | 33.786 | 1.00 31.15 | A N |
| ATOM | 2156 | CA | CYS | A | 142 | 44.724 | 15.178 | 33.751 | 1.00 30.33 | A C |
| ATOM | 2158 | CB | CYS | A | 142 | 43.628 | 14.284 | 34.275 | 1.00 30.26 | A C |
| ATOM | 2161 | SG | CYS | A | 142 | 43.166 | 12.996 | 33.064 | 1.00 35.05 | A S |
| ATOM | 2163 | C | CYS | A | 142 | 44.835 | 16.394 | 34.590 | 1.00 28.59 | A C |
| ATOM | 2164 | O | CYS | A | 142 | 45.453 | 16.369 | 35.647 | 1.00 28.39 | A O |
| ATOM | 2166 | N | LEU | A | 143 | 44.244 | 17.461 | 34.102 | 1.00 27.31 | A N |
| ATOM | 2167 | CA | LEU | A | 143 | 44.138 | 18.696 | 34.829 | 1.00 26.81 | A C |
| ATOM | 2169 | CB | LEU | A | 143 | 44.347 | 19.862 | 33.883 | 1.00 25.52 | A C |
| ATOM | 2172 | CG | LEU | A | 143 | 44.089 | 21.265 | 34.435 | 1.00 25.10 | A C |
| ATOM | 2174 | CD1 | LEU | A | 143 | 44.910 | 21.552 | 35.637 | 1.00 21.58 | A C |
| ATOM | 2178 | CD2 | LEU | A | 143 | 44.324 | 22.307 | 33.370 | 1.00 21.21 | A C |
| ATOM | 2182 | C | LEU | A | 143 | 42.704 | 18.721 | 35.399 | 1.00 27.61 | A C |
| ATOM | 2183 | O | LEU | A | 143 | 41.730 | 18.670 | 34.650 | 1.00 27.90 | A O |
| ATOM | 2185 | N | VAL | A | 144 | 42.613 | 18.793 | 36.721 | 1.00 28.25 | A N |
| ATOM | 2186 | CA | VAL | A | 144 | 41.366 | 18.883 | 37.442 | 1.00 28.70 | A C |

FIG 8 – CONT.

| | | | | | | | | | | |
|---|---|---|---|---|---|---|---|---|---|---|
| ATOM | 2188 | CB | VAL | A | 144 | 41.397 | 17.916 | 38.613 | 1.00 29.11 | A C |
| ATOM | 2190 | CG1 | VAL | A | 144 | 40.052 | 17.904 | 39.310 | 1.00 28.72 | A C |
| ATOM | 2194 | CG2 | VAL | A | 144 | 41.722 | 16.500 | 38.087 | 1.00 28.65 | A C |
| ATOM | 2198 | C | VAL | A | 144 | 41.178 | 20.314 | 37.901 | 1.00 28.97 | A C |
| ATOM | 2199 | O | VAL | A | 144 | 41.780 | 20.762 | 38.856 | 1.00 28.85 | A O |
| ATOM | 2201 | N | LYS | A | 145 | 40.335 | 21.040 | 37.184 | 1.00 30.50 | A N |
| ATOM | 2202 | CA | LYS | A | 145 | 40.277 | 22.489 | 37.275 | 1.00 31.55 | A C |
| ATOM | 2204 | CB | LYS | A | 145 | 40.287 | 23.053 | 35.860 | 1.00 32.31 | A C |
| ATOM | 2207 | CG | LYS | A | 145 | 40.551 | 24.520 | 35.786 | 1.00 35.59 | A C |
| ATOM | 2210 | CD | LYS | A | 145 | 42.044 | 24.796 | 35.726 | 1.00 39.98 | A C |
| ATOM | 2213 | CE | LYS | A | 145 | 42.350 | 26.288 | 35.893 | 1.00 42.00 | A C |
| ATOM | 2216 | NZ | LYS | A | 145 | 41.343 | 27.102 | 35.108 | 1.00 44.61 | A N |
| ATOM | 2220 | C | LYS | A | 145 | 39.014 | 23.008 | 38.003 | 1.00 31.76 | A C |
| ATOM | 2221 | O | LYS | A | 145 | 37.918 | 22.506 | 37.784 | 1.00 30.89 | A O |
| ATOM | 2223 | N | ASP | A | 146 | 39.219 | 24.032 | 38.828 | 1.00 32.28 | A N |
| ATOM | 2224 | CA | ASP | A | 146 | 38.157 | 24.823 | 39.486 | 1.00 34.30 | A C |
| ATOM | 2226 | CB | ASP | A | 146 | 37.449 | 25.715 | 38.449 | 1.00 34.78 | A C |
| ATOM | 2229 | CG | ASP | A | 146 | 38.368 | 26.766 | 37.863 | 1.00 35.72 | A C |
| ATOM | 2230 | OD1 | ASP | A | 146 | 39.365 | 27.112 | 38.529 | 1.00 36.33 | A O |
| ATOM | 2231 | OD2 | ASP | A | 146 | 38.102 | 27.233 | 36.726 | 1.00 43.62 | A O |
| ATOM | 2232 | C | ASP | A | 146 | 37.127 | 24.015 | 40.278 | 1.00 34.71 | A C |
| ATOM | 2233 | O | ASP | A | 146 | 35.957 | 23.980 | 39.921 | 1.00 35.87 | A O |
| ATOM | 2235 | N | TYR | A | 147 | 37.566 | 23.347 | 41.338 | 1.00 35.41 | A N |
| ATOM | 2236 | CA | TYR | A | 147 | 36.647 | 22.571 | 42.181 | 1.00 35.47 | A C |
| ATOM | 2238 | CB | TYR | A | 147 | 36.977 | 21.100 | 42.139 | 1.00 34.88 | A C |
| ATOM | 2241 | CG | TYR | A | 147 | 38.308 | 20.745 | 42.748 | 1.00 35.13 | A C |
| ATOM | 2242 | CD1 | TYR | A | 147 | 39.449 | 20.621 | 41.958 | 1.00 34.68 | A C |
| ATOM | 2244 | CE1 | TYR | A | 147 | 40.677 | 20.271 | 42.511 | 1.00 32.33 | A C |
| ATOM | 2246 | CZ | TYR | A | 147 | 40.763 | 20.042 | 43.863 | 1.00 33.42 | A C |
| ATOM | 2247 | OH | TYR | A | 147 | 41.970 | 19.690 | 44.417 | 1.00 34.96 | A O |
| ATOM | 2249 | CE2 | TYR | A | 147 | 39.634 | 20.143 | 44.675 | 1.00 34.52 | A |

FIG 8 – CONT.

| | | | | | | | | | | |
|---|---|---|---|---|---|---|---|---|---|---|
| ATOM | 2251 | CD2 | TYR | A | 147 | 38.420 | 20.480 | 44.112 | 1.00 34.98 | A |
| ATOM | 2253 | C | TYR | A | 147 | 36.702 | 23.057 | 43.625 | 1.00 35.96 | A |
| ATOM | 2254 | O | TYR | A | 147 | 37.668 | 23.710 | 44.024 | 1.00 35.60 | A |
| ATOM | 2256 | N | PHE | A | 148 | 35.665 | 22.711 | 44.399 | 1.00 36.71 | A |
| ATOM | 2257 | CA | PHE | A | 148 | 35.544 | 23.197 | 45.768 | 1.00 36.98 | A |
| ATOM | 2259 | CB | PHE | A | 148 | 35.059 | 24.636 | 45.779 | 1.00 36.82 | A |
| ATOM | 2262 | CG | PHE | A | 148 | 35.066 | 25.266 | 47.142 | 1.00 38.12 | A |
| ATOM | 2263 | CD1 | PHE | A | 148 | 36.248 | 25.742 | 47.697 | 1.00 38.90 | A |
| ATOM | 2265 | CE1 | PHE | A | 148 | 36.264 | 26.357 | 48.951 | 1.00 37.29 | A |
| ATOM | 2267 | CZ | PHE | A | 148 | 35.086 | 26.496 | 49.650 | 1.00 38.80 | A |
| ATOM | 2269 | CE2 | PHE | A | 148 | 33.896 | 26.016 | 49.106 | 1.00 38.78 | A |
| ATOM | 2271 | CD2 | PHE | A | 148 | 33.889 | 25.410 | 47.864 | 1.00 37.90 | A |
| ATOM | 2273 | C | PHE | A | 148 | 34.612 | 22.394 | 46.646 | 1.00 37.05 | A |
| ATOM | 2274 | O | PHE | A | 148 | 33.580 | 21.893 | 46.181 | 1.00 37.39 | A |
| ATOM | 2276 | N | PRO | A | 149 | 35.014 | 22.190 | 47.915 | 1.00 36.47 | A |
| ATOM | 2277 | CA | PRO | A | 149 | 36.365 | 22.382 | 48.468 | 1.00 35.88 | A |
| ATOM | 2279 | CB | PRO | A | 149 | 36.086 | 22.539 | 49.958 | 1.00 36.09 | A |
| ATOM | 2282 | CG | PRO | A | 149 | 34.941 | 21.557 | 50.187 | 1.00 36.34 | A |
| ATOM | 2285 | CD | PRO | A | 149 | 34.137 | 21.518 | 48.886 | 1.00 36.87 | A |
| ATOM | 2288 | C | PRO | A | 149 | 37.149 | 21.090 | 48.204 | 1.00 34.64 | A |
| ATOM | 2289 | O | PRO | A | 149 | 36.717 | 20.281 | 47.392 | 1.00 32.91 | A |
| ATOM | 2290 | N | GLU | A | 150 | 38.266 | 20.892 | 48.888 | 1.00 34.28 | A |
| ATOM | 2291 | CA | GLU | A | 150 | 38.988 | 19.625 | 48.840 | 1.00 34.72 | A |
| ATOM | 2293 | CB | GLU | A | 150 | 40.297 | 19.741 | 49.619 | 1.00 35.20 | A |
| ATOM | 2296 | CG | GLU | A | 150 | 41.300 | 20.700 | 48.984 | 1.00 36.93 | A |
| ATOM | 2299 | CD | GLU | A | 150 | 42.307 | 19.980 | 48.108 | 1.00 37.86 | A |
| ATOM | 2300 | OE1 | GLU | A | 150 | 41.897 | 19.126 | 47.266 | 1.00 33.67 | A |
| ATOM | 2301 | OE2 | GLU | A | 150 | 43.516 | 20.267 | 48.308 | 1.00 39.30 | A |
| ATOM | 2302 | C | GLU | A | 150 | 38.160 | 18.509 | 49.444 | 1.00 34.81 | A |
| ATOM | 2303 | O | GLU | A | 150 | 37.239 | 18.767 | 50.208 | 1.00 35.34 | A |

FIG 8 – CONT.

| ATOM | 2305 | N   | PRO A 151 | 38.481 | 17.255 | 49.124 | 1.00 | 34.17 | A | N |
|------|------|-----|-----------|--------|--------|--------|------|-------|---|---|
| ATOM | 2306 | CA  | PRO A 151 | 39.481 | 16.734 | 48.231 | 1.00 | 34.03 | A | C |
| ATOM | 2308 | CB  | PRO A 151 | 40.061 | 15.572 | 49.030 | 1.00 | 33.99 | A | C |
| ATOM | 2311 | CG  | PRO A 151 | 38.825 | 14.970 | 49.691 | 1.00 | 34.07 | A | C |
| ATOM | 2314 | CD  | PRO A 151 | 37.937 | 16.196 | 49.988 | 1.00 | 34.72 | A | C |
| ATOM | 2317 | C   | PRO A 151 | 38.956 | 16.140 | 46.927 | 1.00 | 34.11 | A | C |
| ATOM | 2318 | O   | PRO A 151 | 37.757 | 15.863 | 46.783 | 1.00 | 33.00 | A | O |
| ATOM | 2319 | N   | VAL A 152 | 39.915 | 15.867 | 46.036 | 1.00 | 33.93 | A | N |
| ATOM | 2320 | CA  | VAL A 152 | 39.700 | 15.119 | 44.842 | 1.00 | 34.62 | A | C |
| ATOM | 2322 | CB  | VAL A 152 | 39.997 | 15.993 | 43.594 | 1.00 | 34.98 | A | C |
| ATOM | 2324 | CG1 | VAL A 152 | 40.526 | 15.157 | 42.404 | 1.00 | 33.96 | A | C |
| ATOM | 2328 | CG2 | VAL A 152 | 38.779 | 16.768 | 43.211 | 1.00 | 34.31 | A | C |
| ATOM | 2332 | C   | VAL A 152 | 40.589 | 13.882 | 44.838 | 1.00 | 35.42 | A | C |
| ATOM | 2333 | O   | VAL A 152 | 41.704 | 13.918 | 45.283 | 1.00 | 36.57 | A | O |
| ATOM | 2335 | N   | THR A 153 | 40.083 | 12.814 | 44.267 | 1.00 | 36.25 | A | N |
| ATOM | 2336 | CA  | THR A 153 | 40.765 | 11.542 | 44.191 | 1.00 | 37.59 | A | C |
| ATOM | 2338 | CB  | THR A 153 | 39.832 | 10.452 | 44.818 | 1.00 | 37.54 | A | C |
| ATOM | 2340 | OG1 | THR A 153 | 40.297 | 10.161 | 46.141 | 1.00 | 42.31 | A | O |
| ATOM | 2342 | CG2 | THR A 153 | 39.788 |  9.177 | 44.018 | 1.00 | 38.59 | A | C |
| ATOM | 2346 | C   | THR A 153 | 41.017 | 11.276 | 42.710 | 1.00 | 37.26 | A | C |
| ATOM | 2347 | O   | THR A 153 | 40.096 | 11.453 | 41.915 | 1.00 | 37.23 | A | O |
| ATOM | 2349 | N   | VAL A 154 | 42.234 | 10.875 | 42.330 | 1.00 | 36.78 | A | N |
| ATOM | 2350 | CA  | VAL A 154 | 42.487 | 10.487 | 40.952 | 1.00 | 36.88 | A | C |
| ATOM | 2352 | CB  | VAL A 154 | 43.441 | 11.465 | 40.226 | 1.00 | 36.98 | A | C |
| ATOM | 2354 | CG1 | VAL A 154 | 43.552 | 11.118 | 38.731 | 1.00 | 34.44 | A | C |
| ATOM | 2358 | CG2 | VAL A 154 | 42.978 | 12.889 | 40.419 | 1.00 | 33.14 | A | C |
| ATOM | 2362 | C   | VAL A 154 | 43.051 |  9.086 | 40.915 | 1.00 | 38.30 | A | C |
| ATOM | 2363 | O   | VAL A 154 | 43.966 |  8.761 | 41.648 | 1.00 | 39.27 | A | O |
| ATOM | 2365 | N   | SER A 156 | 42.464 |  8.232 | 40.100 | 1.00 | 39.47 | A | N |
| ATOM | 2366 | CA  | SER A 156 | 43.099 |  6.986 | 39.769 | 1.00 | 40.52 | A | C |
| ATOM | 2368 | CB  | SER A 156 | 42.264 |  5.816 | 40.271 | 1.00 | 40.65 | A |   |

FIG 8 – CONT.

| ATOM | | | | | | | | | | |
|---|---|---|---|---|---|---|---|---|---|---|
| ATOM | 2371 | OG | SER | A | 156 | 40.958 | 5.848 | 39.723 | 1.00 42.45 | A |
| ATOM | 2373 | C | SER | A | 156 | 43.237 | 6.959 | 38.258 | 1.00 41.24 | A |
| ATOM | 2374 | O | SER | A | 156 | 42.651 | 7.798 | 37.561 | 1.00 41.08 | A |
| ATOM | 2376 | N | TRP | A | 157 | 44.022 | 6.004 | 37.766 | 1.00 42.11 | A |
| ATOM | 2377 | CA | TRP | A | 157 | 44.193 | 5.776 | 36.349 | 1.00 42.86 | A |
| ATOM | 2379 | CB | TRP | A | 157 | 45.638 | 6.012 | 35.995 | 1.00 41.95 | A |
| ATOM | 2382 | CG | TRP | A | 157 | 45.990 | 7.467 | 36.027 | 1.00 39.47 | A |
| ATOM | 2383 | CD1 | TRP | A | 157 | 46.431 | 8.188 | 37.096 | 1.00 36.37 | A |
| ATOM | 2385 | NE1 | TRP | A | 157 | 46.643 | 9.489 | 36.731 | 1.00 34.76 | A |
| ATOM | 2387 | CE2 | TRP | A | 157 | 46.342 | 9.632 | 35.406 | 1.00 34.24 | A |
| ATOM | 2388 | CD2 | TRP | A | 157 | 45.915 | 8.377 | 34.931 | 1.00 36.62 | A |
| ATOM | 2389 | CE3 | TRP | A | 157 | 45.560 | 8.243 | 33.575 | 1.00 35.48 | A |
| ATOM | 2391 | CZ3 | TRP | A | 157 | 45.629 | 9.374 | 32.753 | 1.00 36.47 | A |
| ATOM | 2393 | CH2 | TRP | A | 157 | 46.051 | 10.606 | 33.266 | 1.00 36.46 | A |
| ATOM | 2395 | CZ2 | TRP | A | 157 | 46.410 | 10.751 | 34.593 | 1.00 35.73 | A |
| ATOM | 2397 | C | TRP | A | 157 | 43.760 | 4.361 | 35.953 | 1.00 45.14 | A |
| ATOM | 2398 | O | TRP | A | 157 | 44.081 | 3.393 | 36.639 | 1.00 45.94 | A |
| ATOM | 2400 | N | ASN | A | 162 | 43.024 | 4.258 | 34.852 | 1.00 47.51 | A |
| ATOM | 2401 | CA | ASN | A | 162 | 42.470 | 2.993 | 34.389 | 1.00 49.57 | A |
| ATOM | 2403 | CB | ASN | A | 162 | 43.551 | 2.152 | 33.694 | 1.00 50.11 | A |
| ATOM | 2406 | CG | ASN | A | 162 | 44.105 | 2.818 | 32.449 | 1.00 51.69 | A |
| ATOM | 2407 | OD1 | ASN | A | 162 | 43.545 | 3.800 | 31.945 | 1.00 54.04 | A |
| ATOM | 2408 | ND2 | ASN | A | 162 | 45.204 | 2.274 | 31.929 | 1.00 52.87 | A |
| ATOM | 2411 | C | ASN | A | 162 | 41.827 | 2.214 | 35.536 | 1.00 50.79 | A |
| ATOM | 2412 | O | ASN | A | 162 | 42.047 | 1.007 | 35.693 | 1.00 51.11 | A |
| ATOM | 2414 | N | SER | A | 163 | 41.040 | 2.940 | 36.329 | 1.00 52.02 | A |
| ATOM | 2415 | CA | SER | A | 163 | 40.342 | 2.420 | 37.490 | 1.00 52.74 | A |
| ATOM | 2417 | CB | SER | A | 163 | 39.136 | 1.609 | 37.034 | 1.00 52.90 | A |
| ATOM | 2420 | OG | SER | A | 163 | 38.329 | 2.379 | 36.154 | 1.00 53.87 | A |
| ATOM | 2422 | C | SER | A | 163 | 41.202 | 1.593 | 38.446 | 1.00 53.22 | A |

FIG 8 – CONT.

| ATOM | 2423 | O | SER A 163 | 40.702 | 0.648 | 39.051 | 1.00 53.74 | A |
|---|---|---|---|---|---|---|---|---|
| ATOM | 2425 | N | GLY A 164 | 42.474 | 1.948 | 38.598 | 1.00 53.50 | A |
| ATOM | 2426 | CA | GLY A 164 | 43.360 | 1.250 | 39.545 | 1.00 53.85 | A |
| ATOM | 2429 | C | GLY A 164 | 44.380 | 0.310 | 38.917 | 1.00 53.92 | A |
| ATOM | 2430 | O | GLY A 164 | 45.428 | 0.050 | 39.500 | 1.00 54.12 | A |
| ATOM | 2432 | N | ALA A 165 | 44.080 | -0.190 | 37.723 | 1.00 54.40 | A |
| ATOM | 2433 | CA | ALA A 165 | 45.012 | -1.049 | 36.963 | 1.00 54.69 | A |
| ATOM | 2435 | CB | ALA A 165 | 44.398 | -1.431 | 35.600 | 1.00 54.50 | A |
| ATOM | 2439 | C | ALA A 165 | 46.410 | -0.444 | 36.755 | 1.00 54.81 | A |
| ATOM | 2440 | O | ALA A 165 | 47.398 | -1.179 | 36.652 | 1.00 54.89 | A |
| ATOM | 2442 | N | LEU A 166 | 46.488 | 0.886 | 36.690 | 1.00 54.73 | A |
| ATOM | 2443 | CA | LEU A 166 | 47.744 | 1.591 | 36.485 | 1.00 54.50 | A |
| ATOM | 2445 | CB | LEU A 166 | 47.620 | 2.516 | 35.268 | 1.00 54.33 | A |
| ATOM | 2448 | CG | LEU A 166 | 48.834 | 3.336 | 34.834 | 1.00 54.33 | A |
| ATOM | 2450 | CD1 | LEU A 166 | 50.050 | 2.441 | 34.597 | 1.00 54.69 | A |
| ATOM | 2454 | CD2 | LEU A 166 | 48.509 | 4.152 | 33.571 | 1.00 53.54 | A |
| ATOM | 2458 | C | LEU A 166 | 48.046 | 2.390 | 37.737 | 1.00 54.62 | A |
| ATOM | 2459 | O | LEU A 166 | 47.255 | 3.243 | 38.140 | 1.00 54.80 | A |
| ATOM | 2461 | N | THR A 167 | 49.170 | 2.093 | 38.375 | 1.00 54.71 | A |
| ATOM | 2462 | CA | THR A 167 | 49.584 | 2.810 | 39.587 | 1.00 54.59 | A |
| ATOM | 2464 | CB | THR A 167 | 49.391 | 1.930 | 40.817 | 1.00 54.90 | A |
| ATOM | 2466 | OG1 | THR A 167 | 50.154 | 0.731 | 40.642 | 1.00 55.75 | A |
| ATOM | 2468 | CG2 | THR A 167 | 47.910 | 1.587 | 41.022 | 1.00 54.45 | A |
| ATOM | 2472 | C | THR A 167 | 51.059 | 3.234 | 39.556 | 1.00 54.32 | A |
| ATOM | 2473 | O | THR A 167 | 51.454 | 4.185 | 40.237 | 1.00 54.11 | A |
| ATOM | 2475 | N | SER A 168 | 51.865 | 2.508 | 38.780 | 1.00 54.01 | A |
| ATOM | 2476 | CA | SER A 168 | 53.307 | 2.774 | 38.632 | 1.00 53.44 | A |
| ATOM | 2478 | CB | SER A 168 | 54.007 | 1.501 | 38.124 | 1.00 53.53 | A |
| ATOM | 2481 | OG | SER A 168 | 54.972 | 1.807 | 37.133 | 1.00 54.95 | A |
| ATOM | 2483 | C | SER A 168 | 53.604 | 3.958 | 37.693 | 1.00 52.26 | A |
| ATOM | 2484 | O | SER A 168 | 53.119 | 4.018 | 36.573 | 1.00 51.99 | A |

FIG 8 – CONT.

| | | | | | | | | | |
|---|---|---|---|---|---|---|---|---|---|
| ATOM | 2486 | N | GLY A 169 | 54.418 | 4.891 | 38.163 | 1.00 | 51.56 | A N |
| ATOM | 2487 | CA | GLY A 169 | 54.655 | 6.147 | 37.451 | 1.00 | 50.90 | A C |
| ATOM | 2490 | C | GLY A 169 | 53.600 | 7.220 | 37.687 | 1.00 | 49.91 | A C |
| ATOM | 2491 | O | GLY A 169 | 53.685 | 8.320 | 37.134 | 1.00 | 50.41 | A O |
| ATOM | 2493 | N | VAL A 171 | 52.606 | 6.918 | 38.506 | 1.00 | 48.81 | A N |
| ATOM | 2494 | CA | VAL A 171 | 51.508 | 7.837 | 38.726 | 1.00 | 48.16 | A C |
| ATOM | 2496 | CB | VAL A 171 | 50.244 | 7.124 | 39.190 | 1.00 | 47.77 | A C |
| ATOM | 2498 | CG1 | VAL A 171 | 49.172 | 8.153 | 39.535 | 1.00 | 49.03 | A C |
| ATOM | 2502 | CG2 | VAL A 171 | 49.765 | 6.188 | 38.115 | 1.00 | 48.21 | A C |
| ATOM | 2506 | C | VAL A 171 | 51.868 | 8.810 | 39.799 | 1.00 | 47.09 | A C |
| ATOM | 2507 | O | VAL A 171 | 52.269 | 8.422 | 40.877 | 1.00 | 47.04 | A O |
| ATOM | 2509 | N | HIS A 172 | 51.690 | 10.087 | 39.535 | 1.00 | 46.25 | A N |
| ATOM | 2510 | CA | HIS A 172 | 51.821 | 11.025 | 40.615 | 1.00 | 45.20 | A C |
| ATOM | 2512 | CB | HIS A 172 | 53.209 | 11.594 | 40.641 | 1.00 | 45.93 | A C |
| ATOM | 2515 | CG | HIS A 172 | 53.463 | 12.497 | 41.805 | 1.00 | 47.99 | A C |
| ATOM | 2516 | ND1 | HIS A 172 | 54.593 | 13.283 | 41.896 | 1.00 | 50.65 | A N |
| ATOM | 2518 | CE1 | HIS A 172 | 54.540 | 13.988 | 43.015 | 1.00 | 52.66 | A C |
| ATOM | 2520 | NE2 | HIS A 172 | 53.426 | 13.676 | 43.659 | 1.00 | 51.76 | A N |
| ATOM | 2522 | CD2 | HIS A 172 | 52.738 | 12.739 | 42.925 | 1.00 | 50.06 | A C |
| ATOM | 2524 | C | HIS A 172 | 50.769 | 12.113 | 40.540 | 1.00 | 43.87 | A C |
| ATOM | 2525 | O | HIS A 172 | 50.699 | 12.902 | 39.580 | 1.00 | 43.54 | A O |
| ATOM | 2527 | N | THR A 173 | 49.944 | 12.133 | 41.578 | 1.00 | 41.94 | A N |
| ATOM | 2528 | CA | THR A 173 | 48.924 | 13.136 | 41.744 | 1.00 | 40.21 | A C |
| ATOM | 2530 | CB | THR A 173 | 47.648 | 12.454 | 42.245 | 1.00 | 40.25 | A C |
| ATOM | 2532 | OG1 | THR A 173 | 47.157 | 11.627 | 41.171 | 1.00 | 39.93 | A O |
| ATOM | 2534 | CG2 | THR A 173 | 46.575 | 13.486 | 42.695 | 1.00 | 38.55 | A C |
| ATOM | 2538 | C | THR A 173 | 49.454 | 14.173 | 42.706 | 1.00 | 38.96 | A C |
| ATOM | 2539 | O | THR A 173 | 49.879 | 13.829 | 43.799 | 1.00 | 38.92 | A O |
| ATOM | 2541 | N | PHE A 174 | 49.420 | 15.433 | 42.290 | 1.00 | 37.48 | A N |
| ATOM | 2542 | CA | PHE A 174 | 50.044 | 16.520 | 43.015 | 1.00 | 37.25 | A C |

FIG 8 – CONT.

| | | | | | | | | | | |
|---|---|---|---|---|---|---|---|---|---|---|
| ATOM | 2544 | CB | PHE | A | 174 | 50.565 | 17.597 | 42.053 | 1.00 37.16 | A C |
| ATOM | 2547 | CG | PHE | A | 174 | 51.789 | 17.182 | 41.248 | 1.00 36.29 | A C |
| ATOM | 2548 | CD1 | PHE | A | 174 | 53.019 | 17.748 | 41.498 | 1.00 36.50 | A C |
| ATOM | 2550 | CE1 | PHE | A | 174 | 54.137 | 17.386 | 40.757 | 1.00 37.79 | A C |
| ATOM | 2552 | CZ | PHE | A | 174 | 54.030 | 16.420 | 39.743 | 1.00 37.21 | A C |
| ATOM | 2554 | CE2 | PHE | A | 174 | 52.821 | 15.861 | 39.480 | 1.00 37.15 | A C |
| ATOM | 2556 | CD2 | PHE | A | 174 | 51.690 | 16.250 | 40.223 | 1.00 36.42 | A C |
| ATOM | 2558 | C | PHE | A | 174 | 49.087 | 17.172 | 43.982 | 1.00 37.44 | A C |
| ATOM | 2559 | O | PHE | A | 174 | 47.900 | 17.097 | 43.805 | 1.00 38.42 | A O |
| ATOM | 2561 | N | PRO | A | 175 | 49.611 | 17.821 | 45.022 | 1.00 37.95 | A N |
| ATOM | 2562 | CA | PRO | A | 175 | 48.822 | 18.696 | 45.876 | 1.00 37.88 | A C |
| ATOM | 2564 | CB | PRO | A | 175 | 49.847 | 19.180 | 46.910 | 1.00 37.69 | A C |
| ATOM | 2567 | CG | PRO | A | 175 | 50.771 | 18.032 | 47.064 | 1.00 38.02 | A C |
| ATOM | 2570 | CD | PRO | A | 175 | 50.858 | 17.391 | 45.692 | 1.00 38.34 | A C |
| ATOM | 2573 | C | PRO | A | 175 | 48.204 | 19.884 | 45.145 | 1.00 37.76 | A C |
| ATOM | 2574 | O | PRO | A | 175 | 48.892 | 20.584 | 44.403 | 1.00 38.15 | A O |
| ATOM | 2575 | N | ALA | A | 176 | 46.922 | 20.131 | 45.407 | 1.00 37.52 | A N |
| ATOM | 2576 | CA | ALA | A | 176 | 46.159 | 21.163 | 44.726 | 1.00 37.53 | A C |
| ATOM | 2578 | CB | ALA | A | 176 | 44.706 | 21.094 | 45.167 | 1.00 37.86 | A C |
| ATOM | 2582 | C | ALA | A | 176 | 46.703 | 22.541 | 45.004 | 1.00 37.66 | A C |
| ATOM | 2583 | O | ALA | A | 176 | 47.319 | 22.733 | 46.050 | 1.00 38.23 | A O |
| ATOM | 2585 | N | VAL | A | 177 | 46.508 | 23.467 | 44.054 | 1.00 37.71 | A N |
| ATOM | 2586 | CA | VAL | A | 177 | 46.691 | 24.894 | 44.275 | 1.00 38.64 | A C |
| ATOM | 2588 | CB | VAL | A | 177 | 47.132 | 25.735 | 43.006 | 1.00 38.04 | A C |
| ATOM | 2590 | CG1 | VAL | A | 177 | 48.591 | 25.694 | 42.824 | 1.00 38.77 | A C |
| ATOM | 2594 | CG2 | VAL | A | 177 | 46.397 | 25.344 | 41.754 | 1.00 36.42 | A C |
| ATOM | 2598 | C | VAL | A | 177 | 45.361 | 25.511 | 44.648 | 1.00 39.96 | A C |
| ATOM | 2599 | O | VAL | A | 177 | 44.329 | 25.111 | 44.116 | 1.00 40.05 | A O |
| ATOM | 2601 | N | LEU | A | 178 | 45.394 | 26.487 | 45.539 | 1.00 41.64 | A N |
| ATOM | 2602 | CA | LEU | A | 178 | 44.225 | 27.291 | 45.825 | 1.00 43.53 | A C |
| ATOM | 2604 | CB | LEU | A | 178 | 44.070 | 27.544 | 47.323 | 1.00 43.53 | A |

FIG 8 – CONT.

| | | | | | | | | | | |
|---|---|---|---|---|---|---|---|---|---|---|
| ATOM | 2607 | CG | LEU | A | 178 | 43.081 | 28.651 | 47.732 | 1.00 43.75 | A C |
| ATOM | 2609 | CD1 | LEU | A | 178 | 41.694 | 28.474 | 47.116 | 1.00 39.85 | A C |
| ATOM | 2613 | CD2 | LEU | A | 178 | 43.001 | 28.713 | 49.273 | 1.00 42.90 | A C |
| ATOM | 2617 | C | LEU | A | 178 | 44.440 | 28.587 | 45.090 | 1.00 44.81 | A C |
| ATOM | 2618 | O | LEU | A | 178 | 45.360 | 29.337 | 45.414 | 1.00 44.76 | A O |
| ATOM | 2620 | N | GLN | A | 179 | 43.612 | 28.836 | 44.081 | 1.00 46.73 | A N |
| ATOM | 2621 | CA | GLN | A | 179 | 43.785 | 30.020 | 43.234 | 1.00 48.30 | A C |
| ATOM | 2623 | CB | GLN | A | 179 | 43.097 | 29.819 | 41.889 | 1.00 48.66 | A C |
| ATOM | 2626 | CG | GLN | A | 179 | 43.510 | 28.540 | 41.169 | 1.00 51.00 | A C |
| ATOM | 2629 | CD | GLN | A | 179 | 42.339 | 27.879 | 40.458 | 1.00 55.23 | A C |
| ATOM | 2630 | OE1 | GLN | A | 179 | 41.888 | 26.774 | 40.830 | 1.00 56.47 | A O |
| ATOM | 2631 | NE2 | GLN | A | 179 | 41.819 | 28.563 | 39.441 | 1.00 58.08 | A N |
| ATOM | 2634 | C | GLN | A | 179 | 43.195 | 31.221 | 43.958 | 1.00 48.85 | A C |
| ATOM | 2635 | O | GLN | A | 179 | 42.700 | 31.071 | 45.073 | 1.00 49.39 | A O |
| ATOM | 2637 | N | SER | A | 180 | 43.260 | 32.398 | 43.328 | 1.00 49.37 | A N |
| ATOM | 2638 | CA | SER | A | 180 | 42.668 | 33.644 | 43.863 | 1.00 49.75 | A C |
| ATOM | 2640 | CB | SER | A | 180 | 43.221 | 34.880 | 43.129 | 1.00 50.42 | A C |
| ATOM | 2643 | OG | SER | A | 180 | 44.645 | 34.947 | 43.206 | 1.00 52.63 | A O |
| ATOM | 2645 | C | SER | A | 180 | 41.145 | 33.666 | 43.736 | 1.00 48.97 | A C |
| ATOM | 2646 | O | SER | A | 180 | 40.490 | 34.491 | 44.376 | 1.00 49.47 | A O |
| ATOM | 2648 | N | SER | A | 182 | 40.588 | 32.787 | 42.901 | 1.00 47.54 | A N |
| ATOM | 2649 | CA | SER | A | 182 | 39.134 | 32.627 | 42.807 | 1.00 46.42 | A C |
| ATOM | 2651 | CB | SER | A | 182 | 38.758 | 31.766 | 41.593 | 1.00 46.51 | A C |
| ATOM | 2654 | OG | SER | A | 182 | 39.272 | 30.437 | 41.709 | 1.00 45.25 | A O |
| ATOM | 2656 | C | SER | A | 182 | 38.531 | 31.970 | 44.056 | 1.00 45.51 | A C |
| ATOM | 2657 | O | SER | A | 182 | 37.325 | 32.045 | 44.271 | 1.00 45.61 | A O |
| ATOM | 2659 | N | GLY | A | 183 | 39.361 | 31.301 | 44.859 | 1.00 44.71 | A N |
| ATOM | 2660 | CA | GLY | A | 183 | 38.864 | 30.428 | 45.946 | 1.00 43.34 | A C |
| ATOM | 2663 | C | GLY | A | 183 | 38.599 | 28.998 | 45.485 | 1.00 42.18 | A C |
| ATOM | 2664 | O | GLY | A | 183 | 38.154 | 28.141 | 46.268 | 1.00 42.45 | A O |

FIG 8 – CONT.

| | | | | | | | | | | |
|---|---|---|---|---|---|---|---|---|---|---|
| ATOM | 2666 | N | LEU | A | 184 | 38.848 | 28.723 | 44.206 | 1.00 40.25 | A N |
| ATOM | 2667 | CA | LEU | A | 184 | 38.690 | 27.367 | 43.717 | 1.00 37.85 | A C |
| ATOM | 2669 | CB | LEU | A | 184 | 38.110 | 27.332 | 42.322 | 1.00 38.11 | A C |
| ATOM | 2672 | CG | LEU | A | 184 | 36.645 | 27.633 | 42.022 | 1.00 38.11 | A C |
| ATOM | 2674 | CD1 | LEU | A | 184 | 35.735 | 27.738 | 43.270 | 1.00 37.05 | A C |
| ATOM | 2678 | CD2 | LEU | A | 184 | 36.570 | 28.860 | 41.150 | 1.00 38.91 | A C |
| ATOM | 2682 | C | LEU | A | 184 | 40.042 | 26.724 | 43.710 | 1.00 35.45 | A C |
| ATOM | 2683 | O | LEU | A | 184 | 41.055 | 27.402 | 43.658 | 1.00 33.45 | A O |
| ATOM | 2685 | N | TYR | A | 185 | 40.036 | 25.396 | 43.808 | 1.00 33.45 | A N |
| ATOM | 2686 | CA | TYR | A | 185 | 41.246 | 24.619 | 43.700 | 1.00 32.03 | A C |
| ATOM | 2688 | CB | TYR | A | 185 | 41.170 | 23.455 | 44.683 | 1.00 32.46 | A C |
| ATOM | 2691 | CG | TYR | A | 185 | 41.151 | 23.866 | 46.151 | 1.00 33.17 | A C |
| ATOM | 2692 | CD1 | TYR | A | 185 | 42.328 | 24.053 | 46.855 | 1.00 33.88 | A C |
| ATOM | 2694 | CE1 | TYR | A | 185 | 42.320 | 24.402 | 48.218 | 1.00 36.18 | A C |
| ATOM | 2696 | CZ | TYR | A | 185 | 41.106 | 24.558 | 48.880 | 1.00 36.80 | A C |
| ATOM | 2697 | OH | TYR | A | 185 | 41.084 | 24.926 | 50.202 | 1.00 40.44 | A O |
| ATOM | 2699 | CE2 | TYR | A | 185 | 39.913 | 24.392 | 48.194 | 1.00 37.28 | A C |
| ATOM | 2701 | CD2 | TYR | A | 185 | 39.941 | 24.031 | 46.836 | 1.00 36.55 | A C |
| ATOM | 2703 | C | TYR | A | 185 | 41.426 | 24.035 | 42.280 | 1.00 31.26 | A C |
| ATOM | 2704 | O | TYR | A | 185 | 40.449 | 23.833 | 41.550 | 1.00 29.05 | A O |
| ATOM | 2706 | N | SER | A | 186 | 42.677 | 23.713 | 41.935 | 1.00 30.50 | A N |
| ATOM | 2707 | CA | SER | A | 186 | 42.959 | 22.830 | 40.799 | 1.00 29.55 | A C |
| ATOM | 2709 | CB | SER | A | 186 | 43.330 | 23.643 | 39.551 | 1.00 29.57 | A C |
| ATOM | 2712 | OG | SER | A | 186 | 42.291 | 24.539 | 39.187 | 1.00 27.51 | A O |
| ATOM | 2714 | C | SER | A | 186 | 44.106 | 21.927 | 41.163 | 1.00 29.19 | A C |
| ATOM | 2715 | O | SER | A | 186 | 44.993 | 22.312 | 41.918 | 1.00 29.36 | A O |
| ATOM | 2717 | N | LEU | A | 187 | 44.088 | 20.711 | 40.648 | 1.00 27.91 | A N |
| ATOM | 2718 | CA | LEU | A | 187 | 45.257 | 19.900 | 40.753 | 1.00 28.25 | A C |
| ATOM | 2720 | CB | LEU | A | 187 | 45.159 | 18.923 | 41.947 | 1.00 27.44 | A C |
| ATOM | 2723 | CG | LEU | A | 187 | 44.172 | 17.784 | 41.956 | 1.00 27.26 | A C |
| ATOM | 2725 | CD1 | LEU | A | 187 | 44.539 | 16.753 | 40.892 | 1.00 26.78 | A |

FIG 8 – CONT.

| | | | | | | | | | |
|---|---|---|---|---|---|---|---|---|---|
| ATOM | 2729 | CD2 | LEU A 187 | 44.078 | 17.122 | 43.406 | 1.00 | 23.16 | A C |
| ATOM | 2733 | C | LEU A 187 | 45.530 | 19.179 | 39.449 | 1.00 | 28.11 | A C |
| ATOM | 2734 | O | LEU A 187 | 44.697 | 19.177 | 38.551 | 1.00 | 28.57 | A O |
| ATOM | 2736 | N | SER A 188 | 46.705 | 18.563 | 39.366 | 1.00 | 28.53 | A N |
| ATOM | 2737 | CA | SER A 188 | 47.044 | 17.695 | 38.244 | 1.00 | 28.65 | A C |
| ATOM | 2739 | CB | SER A 188 | 48.149 | 18.320 | 37.398 | 1.00 | 28.14 | A C |
| ATOM | 2742 | OG | SER A 188 | 47.832 | 19.654 | 37.037 | 1.00 | 28.40 | A O |
| ATOM | 2744 | C | SER A 188 | 47.489 | 16.336 | 38.745 | 1.00 | 30.08 | A C |
| ATOM | 2745 | O | SER A 188 | 48.057 | 16.222 | 39.847 | 1.00 | 29.82 | A O |
| ATOM | 2747 | N | SER A 189 | 47.198 | 15.316 | 37.937 | 1.00 | 31.52 | A N |
| ATOM | 2748 | CA | SER A 189 | 47.718 | 13.974 | 38.114 | 1.00 | 33.54 | A C |
| ATOM | 2750 | CB | SER A 189 | 46.596 | 12.985 | 38.328 | 1.00 | 33.55 | A C |
| ATOM | 2753 | OG | SER A 189 | 47.099 | 11.699 | 38.677 | 1.00 | 33.88 | A O |
| ATOM | 2755 | C | SER A 189 | 48.467 | 13.605 | 36.846 | 1.00 | 35.34 | A C |
| ATOM | 2756 | O | SER A 189 | 47.986 | 13.883 | 35.744 | 1.00 | 36.52 | A O |
| ATOM | 2758 | N | VAL A 190 | 49.654 | 13.030 | 36.978 | 1.00 | 37.19 | A N |
| ATOM | 2759 | CA | VAL A 190 | 50.441 | 12.640 | 35.795 | 1.00 | 38.24 | A C |
| ATOM | 2761 | CB | VAL A 190 | 51.653 | 13.508 | 35.636 | 1.00 | 38.65 | A C |
| ATOM | 2763 | CG1 | VAL A 190 | 51.244 | 14.944 | 35.367 | 1.00 | 38.57 | A C |
| ATOM | 2767 | CG2 | VAL A 190 | 52.530 | 13.385 | 36.880 | 1.00 | 39.36 | A C |
| ATOM | 2771 | C | VAL A 190 | 50.949 | 11.207 | 35.862 | 1.00 | 39.50 | A C |
| ATOM | 2772 | O | VAL A 190 | 51.289 | 10.683 | 36.921 | 1.00 | 39.12 | A O |
| ATOM | 2774 | N | VAL A 191 | 51.011 | 10.575 | 34.709 | 1.00 | 41.42 | A N |
| ATOM | 2775 | CA | VAL A 191 | 51.619 | 9.271 | 34.628 | 1.00 | 43.23 | A C |
| ATOM | 2777 | CB | VAL A 191 | 50.650 | 8.152 | 34.197 | 1.00 | 43.54 | A C |
| ATOM | 2779 | CG1 | VAL A 191 | 51.094 | 6.822 | 34.819 | 1.00 | 44.19 | A C |
| ATOM | 2783 | CG2 | VAL A 191 | 49.232 | 8.476 | 34.548 | 1.00 | 44.73 | A C |
| ATOM | 2787 | C | VAL A 191 | 52.708 | 9.278 | 33.589 | 1.00 | 43.92 | A C |
| ATOM | 2788 | O | VAL A 191 | 52.539 | 9.860 | 32.508 | 1.00 | 44.20 | A O |
| ATOM | 2790 | N | THR A 192 | 53.803 | 8.591 | 33.920 | 1.00 | 44.90 | A N |

FIG 8 – CONT.

| | | | | | | | | | | |
|---|---|---|---|---|---|---|---|---|---|---|
| ATOM | 2791 | CA | THR | A | 192 | 54.863 | 8.274 | 32.981 | 1.00 45.28 | A |
| C | | | | | | | | | | |
| ATOM | 2793 | CB | THR | A | 192 | 56.221 | 8.500 | 33.628 | 1.00 45.44 | A |
| C | | | | | | | | | | |
| ATOM | 2795 | OG1 | THR | A | 192 | 56.178 | 7.948 | 34.939 | 1.00 47.35 | A |
| O | | | | | | | | | | |
| ATOM | 2797 | CG2 | THR | A | 192 | 56.533 | 9.987 | 33.737 | 1.00 44.13 | A |
| C | | | | | | | | | | |
| ATOM | 2801 | C | THR | A | 192 | 54.690 | 6.811 | 32.532 | 1.00 45.78 | A |
| C | | | | | | | | | | |
| ATOM | 2802 | O | THR | A | 192 | 54.502 | 5.893 | 33.342 | 1.00 45.42 | A |
| O | | | | | | | | | | |
| ATOM | 2804 | N | VAL | A | 193 | 54.727 | 6.622 | 31.219 | 1.00 46.88 | A |
| N | | | | | | | | | | |
| ATOM | 2805 | CA | VAL | A | 193 | 54.436 | 5.338 | 30.590 | 1.00 47.53 | A |
| C | | | | | | | | | | |
| ATOM | 2807 | CB | VAL | A | 193 | 52.988 | 5.322 | 30.066 | 1.00 47.54 | A |
| C | | | | | | | | | | |
| ATOM | 2809 | CG1 | VAL | A | 193 | 52.028 | 5.683 | 31.188 | 1.00 45.97 | A |
| C | | | | | | | | | | |
| ATOM | 2813 | CG2 | VAL | A | 193 | 52.820 | 6.274 | 28.871 | 1.00 45.32 | A |
| C | | | | | | | | | | |
| ATOM | 2817 | C | VAL | A | 193 | 55.411 | 5.126 | 29.431 | 1.00 48.94 | A |
| C | | | | | | | | | | |
| ATOM | 2818 | O | VAL | A | 193 | 56.087 | 6.067 | 29.019 | 1.00 48.97 | A |
| O | | | | | | | | | | |
| ATOM | 2820 | N | PRO | A | 194 | 55.501 | 3.897 | 28.897 | 1.00 50.66 | A |
| N | | | | | | | | | | |
| ATOM | 2821 | CA | PRO | A | 194 | 56.483 | 3.761 | 27.822 | 1.00 51.51 | A |
| C | | | | | | | | | | |
| ATOM | 2823 | CB | PRO | A | 194 | 56.672 | 2.247 | 27.688 | 1.00 51.67 | A |
| C | | | | | | | | | | |
| ATOM | 2826 | CG | PRO | A | 194 | 56.054 | 1.648 | 28.934 | 1.00 51.74 | A |
| C | | | | | | | | | | |
| ATOM | 2829 | CD | PRO | A | 194 | 54.936 | 2.596 | 29.296 | 1.00 50.85 | A |
| C | | | | | | | | | | |
| ATOM | 2832 | C | PRO | A | 194 | 55.928 | 4.375 | 26.546 | 1.00 52.48 | A |
| C | | | | | | | | | | |
| ATOM | 2833 | O | PRO | A | 194 | 54.757 | 4.181 | 26.229 | 1.00 52.57 | A |
| O | | | | | | | | | | |
| ATOM | 2834 | N | SER | A | 195 | 56.765 | 5.117 | 25.833 | 1.00 53.46 | A |
| N | | | | | | | | | | |
| ATOM | 2835 | CA | SER | A | 195 | 56.350 | 5.804 | 24.624 | 1.00 54.43 | A |
| C | | | | | | | | | | |
| ATOM | 2837 | CB | SER | A | 195 | 57.506 | 6.657 | 24.067 | 1.00 54.68 | A |
| C | | | | | | | | | | |
| ATOM | 2840 | OG | SER | A | 195 | 58.618 | 5.861 | 23.636 | 1.00 55.03 | A |
| O | | | | | | | | | | |
| ATOM | 2842 | C | SER | A | 195 | 55.834 | 4.831 | 23.562 | 1.00 55.33 | A |
| C | | | | | | | | | | |
| ATOM | 2843 | O | SER | A | 195 | 55.063 | 5.221 | 22.684 | 1.00 55.67 | A |
| O | | | | | | | | | | |
| ATOM | 2845 | N | SER | A | 196 | 56.250 | 3.570 | 23.639 | 1.00 56.25 | A |
| N | | | | | | | | | | |
| ATOM | 2846 | CA | SER | A | 196 | 55.779 | 2.549 | 22.704 | 1.00 57.19 | A |
| C | | | | | | | | | | |
| ATOM | 2848 | CB | SER | A | 196 | 56.653 | 1.293 | 22.801 | 1.00 57.17 | A |
| C | | | | | | | | | | |
| ATOM | 2851 | OG | SER | A | 196 | 56.632 | 0.752 | 24.117 | 1.00 58.27 | A |
| O | | | | | | | | | | |
| ATOM | 2853 | C | SER | A | 196 | 54.308 | 2.179 | 22.932 | 1.00 57.70 | A |

FIG 8 – CONT.

| | | | | | | | | | | |
|---|---|---|---|---|---|---|---|---|---|---|
| ATOM | 2854 | O | SER | A | 196 | 53.650 | 1.701 | 22.018 | 1.00 58.48 | A |
| ATOM | 2856 | N | SER | A | 197 | 53.792 | 2.399 | 24.140 | 1.00 57.95 | A |
| ATOM | 2857 | CA | SER | A | 197 | 52.386 | 2.105 | 24.447 | 1.00 57.75 | A |
| ATOM | 2859 | CB | SER | A | 197 | 52.172 | 2.099 | 25.970 | 1.00 58.04 | A |
| ATOM | 2862 | OG | SER | A | 197 | 52.184 | 3.415 | 26.520 | 1.00 55.63 | A |
| ATOM | 2864 | C | SER | A | 197 | 51.364 | 3.073 | 23.808 | 1.00 58.21 | A |
| ATOM | 2865 | O | SER | A | 197 | 50.173 | 2.762 | 23.741 | 1.00 58.03 | A |
| ATOM | 2867 | N | LEU | A | 198 | 51.817 | 4.238 | 23.347 | 1.00 58.57 | A |
| ATOM | 2868 | CA | LEU | A | 198 | 50.905 | 5.359 | 23.126 | 1.00 58.78 | A |
| ATOM | 2870 | CB | LEU | A | 198 | 51.670 | 6.630 | 22.759 | 1.00 58.34 | A |
| ATOM | 2873 | CG | LEU | A | 198 | 52.376 | 7.299 | 23.940 | 1.00 58.43 | A |
| ATOM | 2875 | CD1 | LEU | A | 198 | 53.091 | 8.555 | 23.466 | 1.00 58.44 | A |
| ATOM | 2879 | CD2 | LEU | A | 198 | 51.405 | 7.636 | 25.085 | 1.00 58.02 | A |
| ATOM | 2883 | C | LEU | A | 198 | 49.797 | 5.100 | 22.112 | 1.00 59.28 | A |
| ATOM | 2884 | O | LEU | A | 198 | 48.676 | 5.564 | 22.299 | 1.00 59.87 | A |
| ATOM | 2886 | N | GLY | A | 199 | 50.098 | 4.374 | 21.045 | 1.00 59.86 | A |
| ATOM | 2887 | CA | GLY | A | 199 | 49.072 | 4.020 | 20.041 | 1.00 60.01 | A |
| ATOM | 2890 | C | GLY | A | 199 | 48.116 | 2.900 | 20.456 | 1.00 59.84 | A |
| ATOM | 2891 | O | GLY | A | 199 | 46.926 | 2.899 | 20.093 | 1.00 60.21 | A |
| ATOM | 2893 | N | THR | A | 200 | 48.629 | 1.954 | 21.233 | 1.00 59.41 | A |
| ATOM | 2894 | CA | THR | A | 200 | 47.864 | 0.759 | 21.572 | 1.00 59.01 | A |
| ATOM | 2896 | CB | THR | A | 200 | 48.835 | -0.455 | 21.619 | 1.00 59.18 | A |
| ATOM | 2898 | OG1 | THR | A | 200 | 49.855 | -0.234 | 22.600 | 1.00 58.53 | A |
| ATOM | 2900 | CG2 | THR | A | 200 | 49.493 | -0.653 | 20.244 | 1.00 59.07 | A |
| ATOM | 2904 | C | THR | A | 200 | 47.131 | 0.879 | 22.893 | 1.00 58.54 | A |
| ATOM | 2905 | O | THR | A | 200 | 45.987 | 0.441 | 22.996 | 1.00 58.94 | A |
| ATOM | 2907 | N | GLN | A | 203 | 47.764 | 1.483 | 23.895 | 1.00 57.60 | A |
| ATOM | 2908 | CA | GLN | A | 203 | 47.238 | 1.462 | 25.251 | 1.00 56.60 | A |
| ATOM | 2910 | CB | GLN | A | 203 | 48.388 | 1.432 | 26.255 | 1.00 57.20 | A |
| ATOM | 2913 | CG | GLN | A | 203 | 47.946 | 1.232 | 27.709 | 1.00 57.95 | A |

FIG 8 – CONT.

| | | | | | | | | | | |
|---|---|---|---|---|---|---|---|---|---|---|
| ATOM | 2916 | CD | GLN | A | 203 | 47.283 | -0.110 | 27.933 | 1.00 59.41 | A C |
| ATOM | 2917 | OE1 | GLN | A | 203 | 47.692 | -1.120 | 27.346 | 1.00 60.68 | A O |
| ATOM | 2918 | NE2 | GLN | A | 203 | 46.255 | -0.133 | 28.781 | 1.00 58.11 | A N |
| ATOM | 2921 | C | GLN | A | 203 | 46.333 | 2.656 | 25.532 | 1.00 55.31 | A C |
| ATOM | 2922 | O | GLN | A | 203 | 46.639 | 3.788 | 25.149 | 1.00 54.76 | A O |
| ATOM | 2924 | N | THR | A | 205 | 45.219 | 2.376 | 26.206 | 1.00 53.59 | A N |
| ATOM | 2925 | CA | THR | A | 205 | 44.258 | 3.390 | 26.608 | 1.00 52.37 | A C |
| ATOM | 2927 | CB | THR | A | 205 | 42.806 | 2.851 | 26.603 | 1.00 52.38 | A C |
| ATOM | 2929 | OG1 | THR | A | 205 | 42.426 | 2.514 | 25.264 | 1.00 53.77 | A O |
| ATOM | 2931 | CG2 | THR | A | 205 | 41.820 | 3.889 | 27.135 | 1.00 51.79 | A C |
| ATOM | 2935 | C | THR | A | 205 | 44.581 | 3.847 | 28.007 | 1.00 50.81 | A C |
| ATOM | 2936 | O | THR | A | 205 | 44.770 | 3.034 | 28.904 | 1.00 51.51 | A O |
| ATOM | 2938 | N | TYR | A | 206 | 44.608 | 5.160 | 28.192 | 1.00 49.17 | A N |
| ATOM | 2939 | CA | TYR | A | 206 | 44.823 | 5.779 | 29.506 | 1.00 47.52 | A C |
| ATOM | 2941 | CB | TYR | A | 206 | 46.149 | 6.542 | 29.494 | 1.00 47.49 | A C |
| ATOM | 2944 | CG | TYR | A | 206 | 47.352 | 5.651 | 29.269 | 1.00 47.87 | A C |
| ATOM | 2945 | CD1 | TYR | A | 206 | 47.869 | 4.880 | 30.310 | 1.00 49.10 | A C |
| ATOM | 2947 | CE1 | TYR | A | 206 | 48.977 | 4.038 | 30.123 | 1.00 49.38 | A C |
| ATOM | 2949 | CZ | TYR | A | 206 | 49.584 | 3.974 | 28.895 | 1.00 49.15 | A C |
| ATOM | 2950 | OH | TYR | A | 206 | 50.679 | 3.153 | 28.741 | 1.00 50.12 | A O |
| ATOM | 2952 | CE2 | TYR | A | 206 | 49.090 | 4.737 | 27.829 | 1.00 49.58 | A C |
| ATOM | 2954 | CD2 | TYR | A | 206 | 47.974 | 5.575 | 28.026 | 1.00 47.62 | A C |
| ATOM | 2956 | C | TYR | A | 206 | 43.650 | 6.710 | 29.874 | 1.00 45.57 | A C |
| ATOM | 2957 | O | TYR | A | 206 | 43.301 | 7.624 | 29.118 | 1.00 45.93 | A O |
| ATOM | 2959 | N | ILE | A | 207 | 43.040 | 6.454 | 31.028 | 1.00 43.19 | A N |
| ATOM | 2960 | CA | ILE | A | 207 | 41.858 | 7.176 | 31.480 | 1.00 41.35 | A C |
| ATOM | 2962 | CB | ILE | A | 207 | 40.570 | 6.297 | 31.384 | 1.00 41.54 | A C |
| ATOM | 2964 | CG1 | ILE | A | 207 | 40.376 | 5.740 | 29.966 | 1.00 42.09 | A C |
| ATOM | 2967 | CD1 | ILE | A | 207 | 39.115 | 4.871 | 29.800 | 1.00 42.38 | A C |
| ATOM | 2971 | CG2 | ILE | A | 207 | 39.333 | 7.091 | 31.795 | 1.00 40.33 | A C |
| ATOM | 2975 | C | ILE | A | 207 | 42.089 | 7.547 | 32.924 | 1.00 39.54 | A |

FIG 8 – CONT.

| | | | | | | | | | | |
|---|---|---|---|---|---|---|---|---|---|---|
| ATOM | 2976 | O | ILE | A | 207 | 42.430 | 6.689 | 33.730 | 1.00 38.87 | A |
| ATOM | 2978 | N | CYS | A | 208 | 41.948 | 8.822 | 33.251 | 1.00 37.90 | A |
| ATOM | 2979 | CA | CYS | A | 208 | 42.012 | 9.236 | 34.648 | 1.00 37.10 | A |
| ATOM | 2981 | CB | CYS | A | 208 | 42.637 | 10.607 | 34.811 | 1.00 36.36 | A |
| ATOM | 2984 | SG | CYS | A | 208 | 41.723 | 11.907 | 34.041 | 1.00 35.33 | A |
| ATOM | 2986 | C | CYS | A | 208 | 40.596 | 9.229 | 35.191 | 1.00 36.90 | A |
| ATOM | 2987 | O | CYS | A | 208 | 39.679 | 9.669 | 34.502 | 1.00 37.27 | A |
| ATOM | 2989 | N | ASN | A | 209 | 40.420 | 8.677 | 36.386 | 1.00 36.32 | A |
| ATOM | 2990 | CA | ASN | A | 209 | 39.114 | 8.621 | 37.041 | 1.00 36.32 | A |
| ATOM | 2992 | CB | ASN | A | 209 | 38.764 | 7.196 | 37.533 | 1.00 35.75 | A |
| ATOM | 2995 | CG | ASN | A | 209 | 39.364 | 6.096 | 36.681 | 1.00 37.43 | A |
| ATOM | 2996 | OD1 | ASN | A | 209 | 40.440 | 5.558 | 37.004 | 1.00 39.73 | A |
| ATOM | 2997 | ND2 | ASN | A | 209 | 38.690 | 5.758 | 35.575 | 1.00 38.53 | A |
| ATOM | 3000 | C | ASN | A | 209 | 39.190 | 9.608 | 38.218 | 1.00 36.02 | A |
| ATOM | 3001 | O | ASN | A | 209 | 39.915 | 9.365 | 39.199 | 1.00 36.41 | A |
| ATOM | 3003 | N | VAL | A | 210 | 38.471 | 10.725 | 38.094 | 1.00 35.83 | A |
| ATOM | 3004 | CA | VAL | A | 210 | 38.540 | 11.845 | 39.032 | 1.00 35.28 | A |
| ATOM | 3006 | CB | VAL | A | 210 | 38.663 | 13.181 | 38.268 | 1.00 35.64 | A |
| ATOM | 3008 | CG1 | VAL | A | 210 | 38.638 | 14.353 | 39.190 | 1.00 34.63 | A |
| ATOM | 3012 | CG2 | VAL | A | 210 | 39.943 | 13.224 | 37.459 | 1.00 34.39 | A |
| ATOM | 3016 | C | VAL | A | 210 | 37.253 | 11.837 | 39.859 | 1.00 36.73 | A |
| ATOM | 3017 | O | VAL | A | 210 | 36.143 | 11.806 | 39.299 | 1.00 36.58 | A |
| ATOM | 3019 | N | ASN | A | 211 | 37.395 | 11.824 | 41.184 | 1.00 36.90 | A |
| ATOM | 3020 | CA | ASN | A | 211 | 36.247 | 11.765 | 42.089 | 1.00 37.19 | A |
| ATOM | 3022 | CB | ASN | A | 211 | 36.229 | 10.424 | 42.871 | 1.00 38.09 | A |
| ATOM | 3025 | CG | ASN | A | 211 | 34.922 | 10.213 | 43.700 | 1.00 41.74 | A |
| ATOM | 3026 | OD1 | ASN | A | 211 | 33.867 | 10.793 | 43.406 | 1.00 45.98 | A |
| ATOM | 3027 | ND2 | ASN | A | 211 | 35.009 | 9.379 | 44.748 | 1.00 45.29 | A |
| ATOM | 3030 | C | ASN | A | 211 | 36.307 | 12.993 | 42.986 | 1.00 36.21 | A |
| ATOM | 3031 | O | ASN | A | 211 | 37.356 | 13.301 | 43.591 | 1.00 35.01 | A |

FIG 8 – CONT.

| ATOM | 3033 | N | HIS A 212 | 35.213 | 13.752 | 42.969 | 1.00 34.89 | A N |
| ATOM | 3034 | CA | HIS A 212 | 35.018 | 14.871 | 43.855 | 1.00 34.21 | A C |
| ATOM | 3036 | CB | HIS A 212 | 34.874 | 16.147 | 43.068 | 1.00 33.97 | A C |
| ATOM | 3039 | CG | HIS A 212 | 34.728 | 17.361 | 43.915 | 1.00 32.77 | A C |
| ATOM | 3040 | ND1 | HIS A 212 | 33.667 | 18.230 | 43.787 | 1.00 30.85 | A N |
| ATOM | 3042 | CE1 | HIS A 212 | 33.820 | 19.231 | 44.635 | 1.00 30.11 | A C |
| ATOM | 3044 | NE2 | HIS A 212 | 34.938 | 19.044 | 45.311 | 1.00 30.56 | A N |
| ATOM | 3046 | CD2 | HIS A 212 | 35.521 | 17.872 | 44.888 | 1.00 32.97 | A C |
| ATOM | 3048 | C | HIS A 212 | 33.759 | 14.638 | 44.674 | 1.00 35.00 | A C |
| ATOM | 3049 | O | HIS A 212 | 32.688 | 15.150 | 44.325 | 1.00 34.75 | A O |
| ATOM | 3051 | N | LYS A 213 | 33.911 | 13.884 | 45.775 | 1.00 35.75 | A N |
| ATOM | 3052 | CA | LYS A 213 | 32.805 | 13.533 | 46.687 | 1.00 36.62 | A C |
| ATOM | 3054 | CB | LYS A 213 | 33.301 | 12.824 | 47.974 | 1.00 37.38 | A C |
| ATOM | 3057 | CG | LYS A 213 | 33.755 | 11.354 | 47.801 | 1.00 38.37 | A C |
| ATOM | 3063 | C | LYS A 213 | 31.891 | 14.682 | 47.075 | 1.00 36.18 | A C |
| ATOM | 3064 | O | LYS A 213 | 30.685 | 14.533 | 46.954 | 1.00 36.26 | A O |
| ATOM | 3066 | N | PRO A 214 | 32.439 | 15.836 | 47.501 | 1.00 36.50 | A N |
| ATOM | 3067 | CA | PRO A 214 | 31.570 | 16.946 | 47.956 | 1.00 36.18 | A C |
| ATOM | 3069 | CB | PRO A 214 | 32.535 | 18.106 | 48.128 | 1.00 36.05 | A C |
| ATOM | 3072 | CG | PRO A 214 | 33.855 | 17.517 | 48.301 | 1.00 36.04 | A C |
| ATOM | 3075 | CD | PRO A 214 | 33.867 | 16.170 | 47.641 | 1.00 36.74 | A C |
| ATOM | 3078 | C | PRO A 214 | 30.456 | 17.359 | 46.978 | 1.00 37.17 | A C |
| ATOM | 3079 | O | PRO A 214 | 29.382 | 17.764 | 47.419 | 1.00 37.50 | A O |
| ATOM | 3080 | N | SER A 215 | 30.723 | 17.290 | 45.671 | 1.00 37.38 | A N |
| ATOM | 3081 | CA | SER A 215 | 29.761 | 17.682 | 44.626 | 1.00 36.92 | A C |
| ATOM | 3083 | CB | SER A 215 | 30.490 | 18.443 | 43.513 | 1.00 37.59 | A C |
| ATOM | 3086 | OG | SER A 215 | 31.327 | 17.564 | 42.757 | 1.00 32.55 | A O |
| ATOM | 3088 | C | SER A 215 | 29.130 | 16.441 | 43.994 | 1.00 37.81 | A C |
| ATOM | 3089 | O | SER A 215 | 28.434 | 16.538 | 43.002 | 1.00 38.49 | A O |
| ATOM | 3091 | N | ASN A 216 | 29.442 | 15.275 | 44.537 | 1.00 38.20 | A N |
| ATOM | 3092 | CA | ASN A 216 | 28.995 | 14.004 | 44.007 | 1.00 38.72 | A |

FIG 8 – CONT.

```
ATOM   3094  CB   ASN A 216      27.504  13.857  44.283  1.00 39.22      A
C
ATOM   3097  CG   ASN A 216      27.206  13.643  45.738  1.00 40.12      A
C
ATOM   3098  OD1  ASN A 216      27.595  12.624  46.337  1.00 40.63      A
O
ATOM   3099  ND2  ASN A 216      26.497  14.589  46.318  1.00 42.23      A
N
ATOM   3102  C    ASN A 216      29.307  13.793  42.524  1.00 38.81      A
C
ATOM   3103  O    ASN A 216      28.516  13.197  41.778  1.00 38.88      A
O
ATOM   3105  N    THR A 217      30.483  14.259  42.115  1.00 38.80      A
N
ATOM   3106  CA   THR A 217      30.899  14.228  40.728  1.00 37.87      A
C
ATOM   3108  CB   THR A 217      31.423  15.583  40.308  1.00 37.09      A
C
ATOM   3110  OG1  THR A 217      30.394  16.537  40.461  1.00 35.10      A
O
ATOM   3112  CG2  THR A 217      31.849  15.577  38.861  1.00 36.87      A
C
ATOM   3116  C    THR A 217      32.009  13.214  40.527  1.00 38.45      A
C
ATOM   3117  O    THR A 217      32.945  13.137  41.313  1.00 37.98      A
O
ATOM   3119  N    LYS A 218      31.908  12.448  39.458  1.00 38.91      A
N
ATOM   3120  CA   LYS A 218      32.979  11.548  39.085  1.00 40.05      A
C
ATOM   3122  CB   LYS A 218      32.606  10.113  39.421  1.00 40.89      A
C
ATOM   3125  CG   LYS A 218      33.752   9.259  39.913  1.00 44.54      A
C
ATOM   3128  CD   LYS A 218      33.300   7.867  40.424  1.00 47.50      A
C
ATOM   3131  CE   LYS A 218      32.157   7.974  41.469  1.00 50.32      A
C
ATOM   3134  NZ   LYS A 218      32.081   6.831  42.464  1.00 49.31      A
N
ATOM   3138  C    LYS A 218      33.159  11.754  37.597  1.00 40.02      A
C
ATOM   3139  O    LYS A 218      32.177  11.726  36.843  1.00 40.14      A
O
ATOM   3141  N    VAL A 219      34.389  12.034  37.177  1.00 39.58      A
N
ATOM   3142  CA   VAL A 219      34.676  12.264  35.768  1.00 38.80      A
C
ATOM   3144  CB   VAL A 219      35.149  13.679  35.522  1.00 38.41      A
C
ATOM   3146  CG1  VAL A 219      35.420  13.900  34.014  1.00 36.36      A
C
ATOM   3150  CG2  VAL A 219      34.138  14.654  36.046  1.00 37.51      A
C
ATOM   3154  C    VAL A 219      35.745  11.305  35.287  1.00 39.14      A
C
ATOM   3155  O    VAL A 219      36.779  11.201  35.915  1.00 39.93      A
O
ATOM   3157  N    ASP A 220      35.474  10.585  34.196  1.00 39.03      A
N
```

FIG 8 – CONT.

| ATOM | 3158 | CA  | ASP A 220 | 36.492 | 9.793  | 33.516 | 1.00 | 39.30 | A |
|------|------|-----|-----------|--------|--------|--------|------|-------|---|
| C    |      |     |           |        |        |        |      |       |   |
| ATOM | 3160 | CB  | ASP A 220 | 35.966 | 8.415  | 33.126 | 1.00 | 39.44 | A |
| C    |      |     |           |        |        |        |      |       |   |
| ATOM | 3163 | CG  | ASP A 220 | 35.668 | 7.524  | 34.326 | 1.00 | 40.84 | A |
| C    |      |     |           |        |        |        |      |       |   |
| ATOM | 3164 | OD1 | ASP A 220 | 34.724 | 6.710  | 34.211 | 1.00 | 43.99 | A |
| O    |      |     |           |        |        |        |      |       |   |
| ATOM | 3165 | OD2 | ASP A 220 | 36.362 | 7.622  | 35.366 | 1.00 | 41.76 | A |
| O    |      |     |           |        |        |        |      |       |   |
| ATOM | 3166 | C   | ASP A 220 | 36.914 | 10.519 | 32.231 | 1.00 | 39.45 | A |
| C    |      |     |           |        |        |        |      |       |   |
| ATOM | 3167 | O   | ASP A 220 | 36.065 | 10.939 | 31.441 | 1.00 | 39.26 | A |
| O    |      |     |           |        |        |        |      |       |   |
| ATOM | 3169 | N   | LYS A 221 | 38.223 | 10.621 | 32.013 | 1.00 | 39.11 | A |
| N    |      |     |           |        |        |        |      |       |   |
| ATOM | 3170 | CA  | LYS A 221 | 38.775 | 11.329 | 30.868 | 1.00 | 39.15 | A |
| C    |      |     |           |        |        |        |      |       |   |
| ATOM | 3172 | CB  | LYS A 221 | 39.438 | 12.622 | 31.318 | 1.00 | 39.33 | A |
| C    |      |     |           |        |        |        |      |       |   |
| ATOM | 3175 | CG  | LYS A 221 | 39.665 | 13.604 | 30.220 | 1.00 | 41.19 | A |
| C    |      |     |           |        |        |        |      |       |   |
| ATOM | 3178 | CD  | LYS A 221 | 38.336 | 14.233 | 29.812 | 1.00 | 43.37 | A |
| C    |      |     |           |        |        |        |      |       |   |
| ATOM | 3181 | CE  | LYS A 221 | 38.454 | 15.074 | 28.592 | 1.00 | 43.33 | A |
| C    |      |     |           |        |        |        |      |       |   |
| ATOM | 3184 | NZ  | LYS A 221 | 37.109 | 15.545 | 28.229 | 1.00 | 44.90 | A |
| N    |      |     |           |        |        |        |      |       |   |
| ATOM | 3188 | C   | LYS A 221 | 39.794 | 10.469 | 30.172 | 1.00 | 39.04 | A |
| C    |      |     |           |        |        |        |      |       |   |
| ATOM | 3189 | O   | LYS A 221 | 40.817 | 10.116 | 30.755 | 1.00 | 39.33 | A |
| O    |      |     |           |        |        |        |      |       |   |
| ATOM | 3191 | N   | LYS A 222 | 39.505 | 10.111 | 28.933 | 1.00 | 39.29 | A |
| N    |      |     |           |        |        |        |      |       |   |
| ATOM | 3192 | CA  | LYS A 222 | 40.488 | 9.451  | 28.087 | 1.00 | 40.11 | A |
| C    |      |     |           |        |        |        |      |       |   |
| ATOM | 3194 | CB  | LYS A 222 | 39.838 | 8.770  | 26.872 | 1.00 | 40.66 | A |
| C    |      |     |           |        |        |        |      |       |   |
| ATOM | 3197 | CG  | LYS A 222 | 40.741 | 7.758  | 26.169 | 1.00 | 42.54 | A |
| C    |      |     |           |        |        |        |      |       |   |
| ATOM | 3200 | CD  | LYS A 222 | 39.955 | 6.800  | 25.257 | 1.00 | 46.18 | A |
| C    |      |     |           |        |        |        |      |       |   |
| ATOM | 3203 | CE  | LYS A 222 | 40.887 | 6.033  | 24.286 | 1.00 | 47.18 | A |
| C    |      |     |           |        |        |        |      |       |   |
| ATOM | 3206 | NZ  | LYS A 222 | 41.507 | 6.944  | 23.271 | 1.00 | 47.46 | A |
| N    |      |     |           |        |        |        |      |       |   |
| ATOM | 3210 | C   | LYS A 222 | 41.527 | 10.491 | 27.665 | 1.00 | 39.30 | A |
| C    |      |     |           |        |        |        |      |       |   |
| ATOM | 3211 | O   | LYS A 222 | 41.189 | 11.604 | 27.250 | 1.00 | 39.34 | A |
| O    |      |     |           |        |        |        |      |       |   |
| ATOM | 3213 | N   | VAL A 225 | 42.790 | 10.146 | 27.860 | 1.00 | 38.84 | A |
| N    |      |     |           |        |        |        |      |       |   |
| ATOM | 3214 | CA  | VAL A 225 | 43.887 | 11.008 | 27.459 | 1.00 | 38.59 | A |
| C    |      |     |           |        |        |        |      |       |   |
| ATOM | 3216 | CB  | VAL A 225 | 44.891 | 11.208 | 28.587 | 1.00 | 37.98 | A |
| C    |      |     |           |        |        |        |      |       |   |
| ATOM | 3218 | CG1 | VAL A 225 | 45.930 | 12.195 | 28.127 | 1.00 | 36.73 | A |
| C    |      |     |           |        |        |        |      |       |   |
| ATOM | 3222 | CG2 | VAL A 225 | 44.194 | 11.671 | 29.875 | 1.00 | 36.08 | A |
| C    |      |     |           |        |        |        |      |       |   |
| ATOM | 3226 | C   | VAL A 225 | 44.593 | 10.344 | 26.278 | 1.00 | 39.53 | A |

FIG 8 – CONT.

```
C
ATOM   3227  O    VAL A 225      45.068    9.223   26.382  1.00 38.94       A
O
ATOM   3229  N    GLU A 226      44.639   11.033   25.151  1.00 41.52       A
N
ATOM   3230  CA   GLU A 226      45.255   10.492   23.947  1.00 42.73       A
C
ATOM   3232  CB   GLU A 226      44.175   10.023   22.962  1.00 43.03       A
C
ATOM   3235  CG   GLU A 226      43.249   11.101   22.399  1.00 45.15       A
C
ATOM   3238  CD   GLU A 226      41.977   10.513   21.759  1.00 48.86       A
C
ATOM   3239  OE1  GLU A 226      41.684    9.314   21.987  1.00 50.60       A
O
ATOM   3240  OE2  GLU A 226      41.251   11.255   21.052  1.00 51.16       A
O
ATOM   3241  C    GLU A 226      46.226   11.530   23.371  1.00 43.43       A
C
ATOM   3242  O    GLU A 226      46.174   12.688   23.754  1.00 42.89       A
O
ATOM   3244  N    PRO A 227      47.141   11.104   22.471  1.00 44.31       A
N
ATOM   3245  CA   PRO A 227      48.228   11.956   21.987  1.00 44.04       A
C
ATOM   3247  CB   PRO A 227      48.986   11.018   21.047  1.00 44.16       A
C
ATOM   3250  CG   PRO A 227      48.797    9.688   21.643  1.00 44.05       A
C
ATOM   3253  CD   PRO A 227      47.345    9.700   22.051  1.00 44.59       A
C
ATOM   3256  C    PRO A 227      47.794   13.215   21.265  1.00 43.96       A
C
ATOM   3257  O    PRO A 227      46.753   13.184   20.632  1.00 44.44       A
O
TER
ATOM   3258  N    LEU B   4      49.940   24.507   76.812  1.00 48.76       B
N  ATOM   3259  CA   LEU B   4      51.276   23.846   76.911  1.00 49.16       B
C  ATOM   3261  CB   LEU B   4      51.151   22.322   76.877  1.00 48.29
B   C
ATOM   3264  CG   LEU B   4      50.109   21.688   77.794  1.00 48.03       B
C
ATOM   3266  CD1  LEU B   4      50.118   20.137   77.692  1.00 44.08       B
C
ATOM   3270  CD2  LEU B   4      50.326   22.148   79.244  1.00 47.12       B
C
ATOM   3274  C    LEU B   4      52.207   24.302   75.792  1.00 49.87       B
C
ATOM   3275  O    LEU B   4      51.745   24.739   74.727  1.00 50.29       B
O
ATOM   3279  N    THR B   5      53.518   24.179   76.030  1.00 50.57       B
N
ATOM   3280  CA   THR B   5      54.536   24.703   75.093  1.00 51.11       B
C
ATOM   3282  CB   THR B   5      55.298   25.902   75.687  1.00 51.06       B
C
ATOM   3284  OG1  THR B   5      54.360   26.926   76.033  1.00 51.02       B
O
ATOM   3286  CG2  THR B   5      56.274   26.455   74.684  1.00 50.93       B
C
ATOM   3290  C    THR B   5      55.540   23.642   74.661  1.00 51.31       B
```

FIG 8 – CONT.

| | | | | | | | | | | |
|---|---|---|---|---|---|---|---|---|---|---|
| ATOM | 3291 | O | THR | B | 5 | 56.221 | 23.040 | 75.483 | 1.00 51.33 | B |
| ATOM | 3293 | N | GLN | B | 6 | 55.600 | 23.421 | 73.354 | 1.00 51.60 | B |
| ATOM | 3294 | CA | GLN | B | 6 | 56.542 | 22.512 | 72.760 | 1.00 51.71 | B |
| ATOM | 3296 | CB | GLN | B | 6 | 55.826 | 21.382 | 72.008 | 1.00 51.57 | B |
| ATOM | 3299 | CG | GLN | B | 6 | 54.779 | 20.607 | 72.796 | 1.00 51.12 | B |
| ATOM | 3302 | CD | GLN | B | 6 | 54.028 | 19.581 | 71.937 | 1.00 49.07 | B |
| ATOM | 3303 | OE1 | GLN | B | 6 | 52.792 | 19.601 | 71.863 | 1.00 48.04 | B |
| ATOM | 3304 | NE2 | GLN | B | 6 | 54.767 | 18.700 | 71.283 | 1.00 46.66 | B |
| ATOM | 3307 | C | GLN | B | 6 | 57.357 | 23.332 | 71.789 | 1.00 52.16 | B |
| ATOM | 3308 | O | GLN | B | 6 | 56.972 | 24.437 | 71.437 | 1.00 52.51 | B |
| ATOM | 3310 | N | PRO | B | 7 | 58.504 | 22.809 | 71.361 | 1.00 52.87 | B |
| ATOM | 3311 | CA | PRO | B | 7 | 59.194 | 23.458 | 70.250 | 1.00 53.41 | B |
| ATOM | 3313 | CB | PRO | B | 7 | 60.546 | 22.741 | 70.215 | 1.00 53.38 | B |
| ATOM | 3316 | CG | PRO | B | 7 | 60.294 | 21.413 | 70.868 | 1.00 52.89 | B |
| ATOM | 3319 | CD | PRO | B | 7 | 59.233 | 21.637 | 71.878 | 1.00 52.88 | B |
| ATOM | 3322 | C | PRO | B | 7 | 58.423 | 23.218 | 68.950 | 1.00 53.75 | B |
| ATOM | 3323 | O | PRO | B | 7 | 57.823 | 22.147 | 68.801 | 1.00 53.64 | B |
| ATOM | 3324 | N | PRO | B | 8 | 58.412 | 24.205 | 68.031 | 1.00 54.30 | B |
| ATOM | 3325 | CA | PRO | B | 8 | 57.741 | 23.986 | 66.744 | 1.00 54.41 | B |
| ATOM | 3327 | CB | PRO | B | 8 | 57.957 | 25.301 | 65.988 | 1.00 54.43 | B |
| ATOM | 3330 | CG | PRO | B | 8 | 58.249 | 26.329 | 67.050 | 1.00 54.93 | B |
| ATOM | 3333 | CD | PRO | B | 8 | 58.921 | 25.587 | 68.169 | 1.00 54.64 | B |
| ATOM | 3336 | C | PRO | B | 8 | 58.332 | 22.825 | 65.953 | 1.00 54.73 | B |
| ATOM | 3337 | O | PRO | B | 8 | 57.591 | 22.073 | 65.309 | 1.00 54.79 | B |
| ATOM | 3338 | N | SER | B | 9 | 59.653 | 22.677 | 66.012 | 1.00 55.05 | B |
| ATOM | 3339 | CA | SER | B | 9 | 60.348 | 21.728 | 65.163 | 1.00 55.23 | B |
| ATOM | 3341 | CB | SER | B | 9 | 60.908 | 22.445 | 63.943 | 1.00 55.58 | B |
| ATOM | 3344 | OG | SER | B | 9 | 62.253 | 22.822 | 64.185 | 1.00 56.74 | B |
| ATOM | 3346 | C | SER | B | 9 | 61.499 | 21.015 | 65.867 | 1.00 55.11 | B |
| ATOM | 3347 | O | SER | B | 9 | 62.083 | 21.532 | 66.801 | 1.00 54.24 | B |

FIG 8 – CONT.

| ATOM | 3349 | N   | VAL | B | 11 | 61.809 | 19.816 | 65.382 | 1.00 | 55.34 | B | N |
| --- | --- | --- | --- | --- | --- | --- | --- | --- | --- | --- | --- | --- |
| ATOM | 3350 | CA  | VAL | B | 11 | 62.950 | 19.056 | 65.833 | 1.00 | 55.75 | B | C |
| ATOM | 3352 | CB  | VAL | B | 11 | 62.606 | 18.236 | 67.085 | 1.00 | 55.81 | B | C |
| ATOM | 3354 | CG1 | VAL | B | 11 | 63.687 | 17.225 | 67.374 | 1.00 | 56.17 | B | C |
| ATOM | 3358 | CG2 | VAL | B | 11 | 62.430 | 19.161 | 68.282 | 1.00 | 56.72 | B | C |
| ATOM | 3362 | C   | VAL | B | 11 | 63.406 | 18.139 | 64.695 | 1.00 | 56.19 | B | C |
| ATOM | 3363 | O   | VAL | B | 11 | 62.579 | 17.587 | 63.959 | 1.00 | 56.26 | B | O |
| ATOM | 3365 | N   | SER | B | 12 | 64.721 | 17.980 | 64.562 | 1.00 | 56.88 | B | N |
| ATOM | 3366 | CA  | SER | B | 12 | 65.336 | 17.314 | 63.404 | 1.00 | 57.56 | B | C |
| ATOM | 3368 | CB  | SER | B | 12 | 65.946 | 18.364 | 62.470 | 1.00 | 57.29 | B | C |
| ATOM | 3371 | OG  | SER | B | 12 | 65.160 | 19.539 | 62.465 | 1.00 | 58.47 | B | O |
| ATOM | 3373 | C   | SER | B | 12 | 66.435 | 16.374 | 63.853 | 1.00 | 57.73 | B | C |
| ATOM | 3374 | O   | SER | B | 12 | 67.095 | 16.645 | 64.842 | 1.00 | 57.98 | B | O |
| ATOM | 3376 | N   | ALA | B | 13 | 66.631 | 15.274 | 63.135 | 1.00 | 58.21 | B | N |
| ATOM | 3377 | CA  | ALA | B | 13 | 67.784 | 14.391 | 63.377 | 1.00 | 58.73 | B | C |
| ATOM | 3379 | CB  | ALA | B | 13 | 67.716 | 13.749 | 64.780 | 1.00 | 58.14 | B | C |
| ATOM | 3383 | C   | ALA | B | 13 | 67.902 | 13.319 | 62.290 | 1.00 | 59.00 | B | C |
| ATOM | 3384 | O   | ALA | B | 13 | 66.940 | 13.052 | 61.583 | 1.00 | 59.16 | B | O |
| ATOM | 3386 | N   | ALA | B | 14 | 69.093 | 12.733 | 62.159 | 1.00 | 59.55 | B | N |
| ATOM | 3387 | CA  | ALA | B | 14 | 69.353 | 11.669 | 61.187 | 1.00 | 60.03 | B | C |
| ATOM | 3389 | CB  | ALA | B | 14 | 70.856 | 11.429 | 61.053 | 1.00 | 60.06 | B | C |
| ATOM | 3393 | C   | ALA | B | 14 | 68.691 | 10.374 | 61.612 | 1.00 | 60.49 | B | C |
| ATOM | 3394 | O   | ALA | B | 14 | 68.527 | 10.133 | 62.813 | 1.00 | 60.54 | B | O |
| ATOM | 3396 | N   | PRO | B | 15 | 68.343 | 9.517  | 60.639 | 1.00 | 60.99 | B | N |
| ATOM | 3397 | CA  | PRO | B | 15 | 67.902 | 8.167  | 60.996 | 1.00 | 61.63 | B | C |
| ATOM | 3399 | CB  | PRO | B | 15 | 67.873 | 7.420  | 59.657 | 1.00 | 61.49 | B | C |
| ATOM | 3402 | CG  | PRO | B | 15 | 67.762 | 8.488  | 58.614 | 1.00 | 61.60 | B | C |
| ATOM | 3405 | CD  | PRO | B | 15 | 68.388 | 9.731  | 59.182 | 1.00 | 60.99 | B | C |
| ATOM | 3408 | C   | PRO | B | 15 | 68.899 | 7.520  | 61.945 | 1.00 | 62.31 | B | C |
| ATOM | 3409 | O   | PRO | B | 15 | 70.097 | 7.773  | 61.835 | 1.00 | 62.55 | B | O |
| ATOM | 3410 | N   | GLY | B | 16 | 68.405 | 6.722  | 62.886 | 1.00 | 62.99 | B |   |

FIG 8 – CONT.

| | | | | | | | | | | |
|---|---|---|---|---|---|---|---|---|---|---|
| ATOM | 3411 | CA | GLY | B | 16 | 69.259 | 6.045 | 63.850 | 1.00 63.27 | B |
| ATOM | 3414 | C | GLY | B | 16 | 69.430 | 6.807 | 65.152 | 1.00 63.71 | B |
| ATOM | 3415 | O | GLY | B | 16 | 69.493 | 6.186 | 66.219 | 1.00 64.37 | B |
| ATOM | 3417 | N | GLN | B | 17 | 69.506 | 8.137 | 65.084 | 1.00 63.63 | B |
| ATOM | 3418 | CA | GLN | B | 17 | 69.690 | 8.957 | 66.286 | 1.00 63.84 | B |
| ATOM | 3420 | CB | GLN | B | 17 | 69.956 | 10.436 | 65.931 | 1.00 63.94 | B |
| ATOM | 3423 | CG | GLN | B | 17 | 71.359 | 10.721 | 65.412 | 1.00 65.42 | B |
| ATOM | 3426 | CD | GLN | B | 17 | 71.745 | 12.200 | 65.511 | 1.00 67.33 | B |
| ATOM | 3427 | OE1 | GLN | B | 17 | 70.974 | 13.087 | 65.129 | 1.00 68.04 | B |
| ATOM | 3428 | NE2 | GLN | B | 17 | 72.954 | 12.466 | 66.020 | 1.00 67.21 | B |
| ATOM | 3431 | C | GLN | B | 17 | 68.500 | 8.881 | 67.242 | 1.00 63.49 | B |
| ATOM | 3432 | O | GLN | B | 17 | 67.442 | 8.333 | 66.917 | 1.00 63.25 | B |
| ATOM | 3434 | N | LYS | B | 18 | 68.713 | 9.441 | 68.430 | 1.00 63.45 | B |
| ATOM | 3435 | CA | LYS | B | 18 | 67.699 | 9.562 | 69.459 | 1.00 63.18 | B |
| ATOM | 3437 | CB | LYS | B | 18 | 68.270 | 9.140 | 70.827 | 1.00 63.24 | B |
| ATOM | 3440 | CG | LYS | B | 18 | 67.478 | 9.625 | 72.045 | 1.00 63.34 | B |
| ATOM | 3446 | C | LYS | B | 18 | 67.231 | 11.023 | 69.458 | 1.00 62.83 | B |
| ATOM | 3447 | O | LYS | B | 18 | 68.046 | 11.935 | 69.292 | 1.00 62.68 | B |
| ATOM | 3449 | N | VAL | B | 19 | 65.921 | 11.234 | 69.626 | 1.00 62.05 | B |
| ATOM | 3450 | CA | VAL | B | 19 | 65.342 | 12.581 | 69.612 | 1.00 61.60 | B |
| ATOM | 3452 | CB | VAL | B | 19 | 64.407 | 12.805 | 68.389 | 1.00 61.71 | B |
| ATOM | 3454 | CG1 | VAL | B | 19 | 64.481 | 14.260 | 67.942 | 1.00 61.90 | B |
| ATOM | 3458 | CG2 | VAL | B | 19 | 64.769 | 11.873 | 67.242 | 1.00 61.49 | B |
| ATOM | 3462 | C | VAL | B | 19 | 64.528 | 12.841 | 70.877 | 1.00 60.79 | B |
| ATOM | 3463 | O | VAL | B | 19 | 64.019 | 11.905 | 71.490 | 1.00 61.09 | B |
| ATOM | 3465 | N | THR | B | 20 | 64.391 | 14.113 | 71.240 | 1.00 59.79 | B |
| ATOM | 3466 | CA | THR | B | 20 | 63.705 | 14.489 | 72.463 | 1.00 59.07 | B |
| ATOM | 3468 | CB | THR | B | 20 | 64.728 | 14.674 | 73.619 | 1.00 59.12 | B |
| ATOM | 3470 | OG1 | THR | B | 20 | 64.357 | 13.842 | 74.723 | 1.00 58.55 | B |
| ATOM | 3472 | CG2 | THR | B | 20 | 64.846 | 16.135 | 74.072 | 1.00 58.28 | B |

FIG 8 – CONT.

| ATOM | 3476 | C | THR | B | 20 | 62.844 | 15.750 | 72.273 | 1.00 | 58.86 | B C |
| --- | --- | --- | --- | --- | --- | --- | --- | --- | --- | --- | --- |
| ATOM | 3477 | O | THR | B | 20 | 63.315 | 16.772 | 71.758 | 1.00 | 58.67 | B O |
| ATOM | 3479 | N | ILE | B | 21 | 61.583 | 15.670 | 72.710 | 1.00 | 58.34 | B N |
| ATOM | 3480 | CA | ILE | B | 21 | 60.621 | 16.762 | 72.551 | 1.00 | 57.78 | B C |
| ATOM | 3482 | CB | ILE | B | 21 | 59.389 | 16.323 | 71.686 | 1.00 | 57.84 | B C |
| ATOM | 3484 | CG1 | ILE | B | 21 | 59.806 | 16.024 | 70.249 | 1.00 | 57.83 | B C |
| ATOM | 3487 | CD1 | ILE | B | 21 | 58.654 | 15.547 | 69.375 | 1.00 | 58.60 | B C |
| ATOM | 3491 | CG2 | ILE | B | 21 | 58.314 | 17.405 | 71.650 | 1.00 | 57.49 | B C |
| ATOM | 3495 | C | ILE | B | 21 | 60.137 | 17.185 | 73.922 | 1.00 | 57.44 | B C |
| ATOM | 3496 | O | ILE | B | 21 | 59.547 | 16.389 | 74.634 | 1.00 | 56.86 | B O |
| ATOM | 3498 | N | SER | B | 22 | 60.377 | 18.440 | 74.280 | 1.00 | 57.43 | B N |
| ATOM | 3499 | CA | SER | B | 22 | 59.965 | 18.943 | 75.574 | 1.00 | 57.52 | B C |
| ATOM | 3501 | CB | SER | B | 22 | 60.839 | 20.119 | 76.019 | 1.00 | 57.51 | B C |
| ATOM | 3504 | OG | SER | B | 22 | 60.305 | 21.346 | 75.533 | 1.00 | 58.29 | B O |
| ATOM | 3506 | C | SER | B | 22 | 58.519 | 19.399 | 75.500 | 1.00 | 57.60 | B C |
| ATOM | 3507 | O | SER | B | 22 | 58.041 | 19.807 | 74.442 | 1.00 | 57.66 | B O |
| ATOM | 3509 | N | CYS | B | 23 | 57.840 | 19.324 | 76.644 | 1.00 | 57.55 | B N |
| ATOM | 3510 | CA | CYS | B | 23 | 56.480 | 19.824 | 76.816 | 1.00 | 57.36 | B C |
| ATOM | 3512 | CB | CYS | B | 23 | 55.477 | 18.669 | 76.749 | 1.00 | 56.63 | B C |
| ATOM | 3515 | SG | CYS | B | 23 | 53.755 | 19.088 | 77.136 | 1.00 | 55.74 | B S |
| ATOM | 3517 | C | CYS | B | 23 | 56.451 | 20.462 | 78.190 | 1.00 | 58.01 | B C |
| ATOM | 3518 | O | CYS | B | 23 | 56.682 | 19.779 | 79.184 | 1.00 | 58.18 | B O |
| ATOM | 3520 | N | SER | B | 24 | 56.200 | 21.760 | 78.272 | 1.00 | 58.48 | B N |
| ATOM | 3521 | CA | SER | B | 24 | 56.177 | 22.399 | 79.580 | 1.00 | 59.09 | B C |
| ATOM | 3523 | CB | SER | B | 24 | 57.408 | 23.310 | 79.755 | 1.00 | 59.26 | B C |
| ATOM | 3526 | OG | SER | B | 24 | 57.203 | 24.608 | 79.227 | 1.00 | 58.27 | B O |
| ATOM | 3528 | C | SER | B | 24 | 54.858 | 23.148 | 79.807 | 1.00 | 59.66 | B C |
| ATOM | 3529 | O | SER | B | 24 | 54.408 | 23.924 | 78.960 | 1.00 | 59.89 | B O |
| ATOM | 3531 | N | GLY | B | 25 | 54.230 | 22.892 | 80.947 | 1.00 | 59.88 | B N |
| ATOM | 3532 | CA | GLY | B | 25 | 53.011 | 23.592 | 81.316 | 1.00 | 60.23 | B C |
| ATOM | 3535 | C | GLY | B | 25 | 53.185 | 24.268 | 82.656 | 1.00 | 60.58 | B |

FIG 8 – CONT.

| ATOM | 3536 | O | GLY | B | 25 | 54.224 | 24.874 | 82.919 | 1.00 | 60.52 | B |
|---|---|---|---|---|---|---|---|---|---|---|---|
| ATOM | 3538 | N | SER | B | 26 | 52.167 | 24.149 | 83.509 | 1.00 | 60.92 | B |
| ATOM | 3539 | CA | SER | B | 26 | 52.178 | 24.761 | 84.837 | 1.00 | 60.96 | B |
| ATOM | 3541 | CB | SER | B | 26 | 51.400 | 26.101 | 84.815 | 1.00 | 61.29 | B |
| ATOM | 3544 | OG | SER | B | 26 | 50.019 | 25.924 | 84.547 | 1.00 | 61.74 | B |
| ATOM | 3546 | C | SER | B | 26 | 51.657 | 23.773 | 85.898 | 1.00 | 60.90 | B |
| ATOM | 3547 | O | SER | B | 26 | 51.589 | 22.556 | 85.650 | 1.00 | 60.67 | B |
| ATOM | 3549 | N | SER | B | 27 | 51.324 | 24.287 | 87.080 | 1.00 | 60.80 | B |
| ATOM | 3550 | CA | SER | B | 27 | 50.940 | 23.455 | 88.227 | 1.00 | 60.81 | B |
| ATOM | 3552 | CB | SER | B | 27 | 51.184 | 24.241 | 89.526 | 1.00 | 61.06 | B |
| ATOM | 3555 | OG | SER | B | 27 | 52.396 | 24.991 | 89.442 | 1.00 | 61.72 | B |
| ATOM | 3557 | C | SER | B | 27 | 49.476 | 22.975 | 88.145 | 1.00 | 60.45 | B |
| ATOM | 3558 | O | SER | B | 27 | 49.145 | 21.856 | 88.566 | 1.00 | 60.53 | B |
| ATOM | 3560 | N | SER | B | 27A | 48.610 | 23.838 | 87.621 | 1.00 | 60.09 | B |
| ATOM | 3561 | CA | SER | B | 27A | 47.243 | 23.464 | 87.236 | 1.00 | 59.71 | B |
| ATOM | 3563 | CB | SER | B | 27A | 46.613 | 24.584 | 86.388 | 1.00 | 59.77 | B |
| ATOM | 3566 | OG | SER | B | 27A | 47.326 | 25.811 | 86.523 | 1.00 | 60.50 | B |
| ATOM | 3568 | C | SER | B | 27A | 47.219 | 22.159 | 86.421 | 1.00 | 59.16 | B |
| ATOM | 3569 | O | SER | B | 27A | 46.450 | 21.234 | 86.722 | 1.00 | 58.99 | B |
| ATOM | 3571 | N | ASP | B | 27B | 48.078 | 22.086 | 85.404 | 1.00 | 58.35 | B |
| ATOM | 3572 | CA | ASP | B | 27B | 47.986 | 21.022 | 84.403 | 1.00 | 57.77 | B |
| ATOM | 3574 | CB | ASP | B | 27B | 48.006 | 21.590 | 82.959 | 1.00 | 57.48 | B |
| ATOM | 3577 | CG | ASP | B | 27B | 49.077 | 22.636 | 82.731 | 1.00 | 56.25 | B |
| ATOM | 3578 | OD1 | ASP | B | 27B | 50.264 | 22.250 | 82.669 | 1.00 | 53.12 | B |
| ATOM | 3579 | OD2 | ASP | B | 27B | 48.732 | 23.838 | 82.592 | 1.00 | 54.99 | B |
| ATOM | 3580 | C | ASP | B | 27B | 48.964 | 19.852 | 84.597 | 1.00 | 57.67 | B |
| ATOM | 3581 | O | ASP | B | 27B | 48.613 | 18.867 | 85.243 | 1.00 | 58.22 | B |
| ATOM | 3583 | N | ILE | B | 28 | 50.170 | 19.936 | 84.049 | 1.00 | 57.85 | B |
| ATOM | 3584 | CA | ILE | B | 28 | 51.109 | 18.810 | 84.125 | 1.00 | 58.15 | B |
| ATOM | 3586 | CB | ILE | B | 28 | 52.361 | 19.034 | 83.239 | 1.00 | 58.20 | B |

FIG 8 – CONT.

| | | | | | | | | | | |
|---|---|---|---|---|---|---|---|---|---|---|
| ATOM | 3588 | CG1 | ILE | B | 28 | 51.953 | 19.187 | 81.770 | 1.00 57.74 | B C |
| ATOM | 3591 | CD1 | ILE | B | 28 | 53.120 | 19.391 | 80.839 | 1.00 56.74 | B C |
| ATOM | 3595 | CG2 | ILE | B | 28 | 53.356 | 17.875 | 83.389 | 1.00 57.23 | B C |
| ATOM | 3599 | C | ILE | B | 28 | 51.527 | 18.544 | 85.579 | 1.00 58.39 | B C |
| ATOM | 3600 | O | ILE | B | 28 | 51.721 | 17.400 | 85.975 | 1.00 58.15 | B O |
| ATOM | 3602 | N | GLY | B | 29 | 51.643 | 19.610 | 86.365 | 1.00 59.02 | B N |
| ATOM | 3603 | CA | GLY | B | 29 | 51.890 | 19.503 | 87.812 | 1.00 59.34 | B C |
| ATOM | 3606 | C | GLY | B | 29 | 50.935 | 18.577 | 88.550 | 1.00 59.49 | B C |
| ATOM | 3607 | O | GLY | B | 29 | 51.353 | 17.802 | 89.424 | 1.00 59.84 | B O |
| ATOM | 3609 | N | SER | B | 30 | 49.657 | 18.638 | 88.189 | 1.00 59.30 | B N |
| ATOM | 3610 | CA | SER | B | 30 | 48.633 | 17.892 | 88.900 | 1.00 59.08 | B C |
| ATOM | 3612 | CB | SER | B | 30 | 47.441 | 18.812 | 89.225 | 1.00 59.31 | B C |
| ATOM | 3615 | OG | SER | B | 30 | 47.851 | 20.112 | 89.634 | 1.00 59.69 | B O |
| ATOM | 3617 | C | SER | B | 30 | 48.108 | 16.662 | 88.155 | 1.00 58.83 | B C |
| ATOM | 3618 | O | SER | B | 30 | 47.270 | 15.948 | 88.708 | 1.00 58.84 | B O |
| ATOM | 3620 | N | ASN | B | 31 | 48.561 | 16.404 | 86.922 | 1.00 58.47 | B N |
| ATOM | 3621 | CA | ASN | B | 31 | 47.862 | 15.424 | 86.069 | 1.00 58.04 | B C |
| ATOM | 3623 | CB | ASN | B | 31 | 46.824 | 16.140 | 85.204 | 1.00 57.83 | B C |
| ATOM | 3626 | CG | ASN | B | 31 | 45.654 | 16.661 | 86.010 | 1.00 57.28 | B C |
| ATOM | 3627 | OD1 | ASN | B | 31 | 44.724 | 15.916 | 86.305 | 1.00 55.71 | B O |
| ATOM | 3628 | ND2 | ASN | B | 31 | 45.691 | 17.955 | 86.365 | 1.00 55.50 | B N |
| ATOM | 3631 | C | ASN | B | 31 | 48.747 | 14.567 | 85.183 | 1.00 57.84 | B C |
| ATOM | 3632 | O | ASN | B | 31 | 49.911 | 14.861 | 84.991 | 1.00 58.03 | B O |
| ATOM | 3634 | N | TYR | B | 32 | 48.163 | 13.498 | 84.658 | 1.00 57.74 | B N |
| ATOM | 3635 | CA | TYR | B | 32 | 48.848 | 12.579 | 83.753 | 1.00 57.76 | B C |
| ATOM | 3637 | CB | TYR | B | 32 | 48.085 | 11.262 | 83.621 | 1.00 58.49 | B C |
| ATOM | 3640 | CG | TYR | B | 32 | 48.193 | 10.328 | 84.808 | 1.00 61.38 | B C |
| ATOM | 3641 | CD1 | TYR | B | 32 | 49.439 | 9.910 | 85.286 | 1.00 64.01 | B C |
| ATOM | 3643 | CE1 | TYR | B | 32 | 49.546 | 9.035 | 86.377 | 1.00 64.65 | B C |
| ATOM | 3645 | CZ | TYR | B | 32 | 48.398 | 8.567 | 86.987 | 1.00 65.78 | B C |
| ATOM | 3646 | OH | TYR | B | 32 | 48.493 | 7.702 | 88.053 | 1.00 68.07 | |

FIG 8 – CONT.

| ATOM | 3648 | CE2 | TYR | B | 32 | 47.143 | 8.957 | 86.529 | 1.00 | 65.63 | B |
|---|---|---|---|---|---|---|---|---|---|---|---|
| ATOM | 3650 | CD2 | TYR | B | 32 | 47.046 | 9.832 | 85.437 | 1.00 | 64.18 | B |
| ATOM | 3652 | C | TYR | B | 32 | 48.973 | 13.186 | 82.363 | 1.00 | 56.46 | B |
| ATOM | 3653 | O | TYR | B | 32 | 48.049 | 13.828 | 81.866 | 1.00 | 56.58 | B |
| ATOM | 3655 | N | VAL | B | 33 | 50.121 | 12.966 | 81.741 | 1.00 | 54.59 | B |
| ATOM | 3656 | CA | VAL | B | 33 | 50.449 | 13.580 | 80.469 | 1.00 | 53.12 | B |
| ATOM | 3658 | CB | VAL | B | 33 | 51.889 | 14.162 | 80.480 | 1.00 | 53.13 | B |
| ATOM | 3660 | CG1 | VAL | B | 33 | 52.303 | 14.657 | 79.088 | 1.00 | 51.95 | B |
| ATOM | 3664 | CG2 | VAL | B | 33 | 51.985 | 15.292 | 81.500 | 1.00 | 53.01 | B |
| ATOM | 3668 | C | VAL | B | 33 | 50.311 | 12.506 | 79.402 | 1.00 | 51.66 | B |
| ATOM | 3669 | O | VAL | B | 33 | 50.797 | 11.382 | 79.589 | 1.00 | 51.20 | B |
| ATOM | 3671 | N | SER | B | 34 | 49.627 | 12.838 | 78.307 | 1.00 | 49.43 | B |
| ATOM | 3672 | CA | SER | B | 34 | 49.552 | 11.936 | 77.169 | 1.00 | 47.95 | B |
| ATOM | 3674 | CB | SER | B | 34 | 48.099 | 11.672 | 76.791 | 1.00 | 47.75 | B |
| ATOM | 3677 | OG | SER | B | 34 | 47.438 | 10.935 | 77.809 | 1.00 | 46.65 | B |
| ATOM | 3679 | C | SER | B | 34 | 50.309 | 12.552 | 75.992 | 1.00 | 47.07 | B |
| ATOM | 3680 | O | SER | B | 34 | 50.522 | 13.760 | 75.951 | 1.00 | 46.69 | B |
| ATOM | 3682 | N | TRP | B | 35 | 50.728 | 11.716 | 75.052 | 1.00 | 45.46 | B |
| ATOM | 3683 | CA | TRP | B | 35 | 51.282 | 12.189 | 73.793 | 1.00 | 44.74 | B |
| ATOM | 3685 | CB | TRP | B | 35 | 52.750 | 11.788 | 73.641 | 1.00 | 45.20 | B |
| ATOM | 3688 | CG | TRP | B | 35 | 53.648 | 12.488 | 74.613 | 1.00 | 47.71 | B |
| ATOM | 3689 | CD1 | TRP | B | 35 | 53.916 | 12.107 | 75.907 | 1.00 | 48.41 | B |
| ATOM | 3691 | NE1 | TRP | B | 35 | 54.764 | 13.017 | 76.499 | 1.00 | 48.74 | B |
| ATOM | 3693 | CE2 | TRP | B | 35 | 55.089 | 13.988 | 75.592 | 1.00 | 49.39 | B |
| ATOM | 3694 | CD2 | TRP | B | 35 | 54.401 | 13.694 | 74.389 | 1.00 | 49.22 | B |
| ATOM | 3695 | CE3 | TRP | B | 35 | 54.564 | 14.547 | 73.294 | 1.00 | 50.62 | B |
| ATOM | 3697 | CZ3 | TRP | B | 35 | 55.398 | 15.639 | 73.423 | 1.00 | 51.20 | B |
| ATOM | 3699 | CH2 | TRP | B | 35 | 56.071 | 15.903 | 74.630 | 1.00 | 51.80 | B |
| ATOM | 3701 | CZ2 | TRP | B | 35 | 55.926 | 15.090 | 75.724 | 1.00 | 50.18 | B |
| ATOM | 3703 | C | TRP | B | 35 | 50.466 | 11.643 | 72.619 | 1.00 | 43.03 | B |

FIG 8 – CONT.

| ATOM | 3704 | O | TRP | B | 35 | 49.948 | 10.504 | 72.660 | 1.00 | 41.97 | B |
|---|---|---|---|---|---|---|---|---|---|---|---|
| ATOM | 3706 | N | TYR | B | 36 | 50.367 | 12.467 | 71.576 | 1.00 | 41.07 | B |
| ATOM | 3707 | CA | TYR | B | 36 | 49.605 | 12.108 | 70.399 | 1.00 | 40.16 | C |
| ATOM | 3709 | CB | TYR | B | 36 | 48.308 | 12.920 | 70.355 | 1.00 | 40.12 | C |
| ATOM | 3712 | CG | TYR | B | 36 | 47.491 | 12.731 | 71.609 | 1.00 | 37.82 | C |
| ATOM | 3713 | CD1 | TYR | B | 36 | 46.596 | 11.686 | 71.737 | 1.00 | 38.29 | C |
| ATOM | 3715 | CE1 | TYR | B | 36 | 45.849 | 11.525 | 72.908 | 1.00 | 39.22 | C |
| ATOM | 3717 | CZ | TYR | B | 36 | 46.045 | 12.397 | 73.970 | 1.00 | 38.29 | C |
| ATOM | 3718 | OH | TYR | B | 36 | 45.375 | 12.278 | 75.167 | 1.00 | 37.82 | O |
| ATOM | 3720 | CE2 | TYR | B | 36 | 46.957 | 13.414 | 73.858 | 1.00 | 38.82 | C |
| ATOM | 3722 | CD2 | TYR | B | 36 | 47.678 | 13.563 | 72.691 | 1.00 | 39.32 | C |
| ATOM | 3724 | C | TYR | B | 36 | 50.445 | 12.279 | 69.153 | 1.00 | 39.83 | C |
| ATOM | 3725 | O | TYR | B | 36 | 51.206 | 13.228 | 69.024 | 1.00 | 39.63 | O |
| ATOM | 3727 | N | GLN | B | 37 | 50.349 | 11.301 | 68.272 | 1.00 | 40.00 | N |
| ATOM | 3728 | CA | GLN | B | 37 | 51.105 | 11.272 | 67.033 | 1.00 | 39.70 | C |
| ATOM | 3730 | CB | GLN | B | 37 | 51.794 | 9.909 | 66.873 | 1.00 | 39.86 | C |
| ATOM | 3733 | CG | GLN | B | 37 | 52.621 | 9.750 | 65.579 | 1.00 | 40.84 | C |
| ATOM | 3736 | CD | GLN | B | 37 | 53.140 | 8.340 | 65.359 | 1.00 | 42.75 | C |
| ATOM | 3737 | OE1 | GLN | B | 37 | 54.322 | 8.143 | 65.079 | 1.00 | 44.67 | O |
| ATOM | 3738 | NE2 | GLN | B | 37 | 52.272 | 7.363 | 65.483 | 1.00 | 41.83 | N |
| ATOM | 3741 | C | GLN | B | 37 | 50.138 | 11.461 | 65.874 | 1.00 | 38.96 | C |
| ATOM | 3742 | O | GLN | B | 37 | 49.207 | 10.680 | 65.730 | 1.00 | 38.03 | O |
| ATOM | 3744 | N | GLN | B | 38 | 50.372 | 12.484 | 65.058 | 1.00 | 38.58 | N |
| ATOM | 3745 | CA | GLN | B | 38 | 49.545 | 12.743 | 63.873 | 1.00 | 38.27 | C |
| ATOM | 3747 | CB | GLN | B | 38 | 48.765 | 14.032 | 64.031 | 1.00 | 38.07 | C |
| ATOM | 3750 | CG | GLN | B | 38 | 47.849 | 14.368 | 62.827 | 1.00 | 36.38 | C |
| ATOM | 3753 | CD | GLN | B | 38 | 46.985 | 15.556 | 63.125 | 1.00 | 33.79 | C |
| ATOM | 3754 | OE1 | GLN | B | 38 | 47.439 | 16.502 | 63.771 | 1.00 | 31.70 | O |
| ATOM | 3755 | NE2 | GLN | B | 38 | 45.730 | 15.514 | 62.696 | 1.00 | 28.19 | N |
| ATOM | 3758 | C | GLN | B | 38 | 50.350 | 12.815 | 62.583 | 1.00 | 38.46 | C |
| ATOM | 3759 | O | GLN | B | 38 | 51.049 | 13.785 | 62.323 | 1.00 | 37.78 | B |

FIG 8 – CONT.

| | | | | | | | | | | |
|---|---|---|---|---|---|---|---|---|---|---|
| ATOM | 3761 | N | PHE | B | 39 | 50.222 | 11.789 | 61.767 | 1.00 39.32 | B N |
| ATOM | 3762 | CA | PHE | B | 39 | 50.751 | 11.839 | 60.410 | 1.00 40.54 | B C |
| ATOM | 3764 | CB | PHE | B | 39 | 50.755 | 10.441 | 59.776 | 1.00 40.91 | B C |
| ATOM | 3767 | CG | PHE | B | 39 | 51.562 | 9.409 | 60.552 | 1.00 41.80 | B C |
| ATOM | 3768 | CD1 | PHE | B | 39 | 52.933 | 9.554 | 60.714 | 1.00 43.62 | B C |
| ATOM | 3770 | CE1 | PHE | B | 39 | 53.682 | 8.595 | 61.414 | 1.00 43.97 | B C |
| ATOM | 3772 | CZ | PHE | B | 39 | 53.061 | 7.490 | 61.958 | 1.00 43.71 | B C |
| ATOM | 3774 | CE2 | PHE | B | 39 | 51.683 | 7.326 | 61.799 | 1.00 44.57 | B C |
| ATOM | 3776 | CD2 | PHE | B | 39 | 50.947 | 8.285 | 61.097 | 1.00 44.12 | B C |
| ATOM | 3778 | C | PHE | B | 39 | 49.868 | 12.783 | 59.586 | 1.00 41.16 | B C |
| ATOM | 3779 | O | PHE | B | 39 | 48.683 | 12.970 | 59.918 | 1.00 40.98 | B O |
| ATOM | 3781 | N | PRO | B | 40 | 50.433 | 13.387 | 58.511 | 1.00 41.43 | B N |
| ATOM | 3782 | CA | PRO | B | 40 | 49.710 | 14.370 | 57.702 | 1.00 40.97 | B C |
| ATOM | 3784 | CB | PRO | B | 40 | 50.706 | 14.724 | 56.587 | 1.00 41.56 | B C |
| ATOM | 3787 | CG | PRO | B | 40 | 52.032 | 14.226 | 57.055 | 1.00 42.49 | B C |
| ATOM | 3790 | CD | PRO | B | 40 | 51.726 | 13.023 | 57.898 | 1.00 41.87 | B C |
| ATOM | 3793 | C | PRO | B | 40 | 48.470 | 13.752 | 57.099 | 1.00 40.47 | B C |
| ATOM | 3794 | O | PRO | B | 40 | 48.505 | 12.585 | 56.735 | 1.00 40.37 | B O |
| ATOM | 3795 | N | GLY | B | 41 | 47.379 | 14.509 | 57.039 | 1.00 39.72 | B N |
| ATOM | 3796 | CA | GLY | B | 41 | 46.112 | 13.994 | 56.550 | 1.00 39.43 | B C |
| ATOM | 3799 | C | GLY | B | 41 | 45.521 | 12.826 | 57.343 | 1.00 39.20 | B C |
| ATOM | 3800 | O | GLY | B | 41 | 44.635 | 12.136 | 56.844 | 1.00 40.35 | B O |
| ATOM | 3802 | N | THR | B | 42 | 45.978 | 12.589 | 58.568 | 1.00 37.54 | B N |
| ATOM | 3803 | CA | THR | B | 42 | 45.410 | 11.517 | 59.379 | 1.00 36.48 | B C |
| ATOM | 3805 | CB | THR | B | 42 | 46.437 | 10.402 | 59.594 | 1.00 36.71 | B C |
| ATOM | 3807 | OG1 | THR | B | 42 | 47.044 | 10.089 | 58.340 | 1.00 37.79 | B O |
| ATOM | 3809 | CG2 | THR | B | 42 | 45.786 | 9.145 | 60.154 | 1.00 37.99 | B C |
| ATOM | 3813 | C | THR | B | 42 | 44.994 | 12.043 | 60.739 | 1.00 35.02 | B C |
| ATOM | 3814 | O | THR | B | 42 | 45.474 | 13.088 | 61.189 | 1.00 32.97 | B O |
| ATOM | 3816 | N | ALA | B | 43 | 44.107 | 11.289 | 61.384 | 1.00 34.44 | B N |

FIG 8 – CONT.

| ATOM | 3817 | CA | ALA | B | 43 | 43.676 | 11.560 | 62.746 | 1.00 | 33.90 | B |
|---|---|---|---|---|---|---|---|---|---|---|---|
| C | | | | | | | | | | | |
| ATOM | 3819 | CB | ALA | B | 43 | 42.528 | 10.643 | 63.123 | 1.00 | 33.47 | B |
| C | | | | | | | | | | | |
| ATOM | 3823 | C | ALA | B | 43 | 44.841 | 11.337 | 63.707 | 1.00 | 33.90 | B |
| C | | | | | | | | | | | |
| ATOM | 3824 | O | ALA | B | 43 | 45.607 | 10.394 | 63.550 | 1.00 | 34.57 | B |
| O | | | | | | | | | | | |
| ATOM | 3826 | N | PRO | B | 44 | 44.975 | 12.199 | 64.708 | 1.00 | 33.41 | B |
| N | | | | | | | | | | | |
| ATOM | 3827 | CA | PRO | B | 44 | 45.865 | 11.912 | 65.820 | 1.00 | 34.37 | B |
| C | | | | | | | | | | | |
| ATOM | 3829 | CB | PRO | B | 44 | 45.507 | 12.996 | 66.853 | 1.00 | 34.55 | B |
| C | | | | | | | | | | | |
| ATOM | 3832 | CG | PRO | B | 44 | 44.974 | 14.128 | 66.029 | 1.00 | 33.46 | B |
| C | | | | | | | | | | | |
| ATOM | 3835 | CD | PRO | B | 44 | 44.221 | 13.434 | 64.910 | 1.00 | 33.51 | B |
| C | | | | | | | | | | | |
| ATOM | 3838 | C | PRO | B | 44 | 45.608 | 10.546 | 66.418 | 1.00 | 35.29 | B |
| C | | | | | | | | | | | |
| ATOM | 3839 | O | PRO | B | 44 | 44.518 | 9.976 | 66.278 | 1.00 | 34.84 | B |
| O | | | | | | | | | | | |
| ATOM | 3840 | N | LYS | B | 45 | 46.629 | 9.997 | 67.050 | 1.00 | 36.58 | B |
| N | | | | | | | | | | | |
| ATOM | 3841 | CA | LYS | B | 45 | 46.424 | 8.814 | 67.833 | 1.00 | 37.72 | B |
| C | | | | | | | | | | | |
| ATOM | 3843 | CB | LYS | B | 45 | 46.640 | 7.553 | 67.006 | 1.00 | 38.16 | B |
| C | | | | | | | | | | | |
| ATOM | 3846 | CG | LYS | B | 45 | 47.977 | 6.916 | 67.106 | 1.00 | 39.84 | B |
| C | | | | | | | | | | | |
| ATOM | 3849 | CD | LYS | B | 45 | 48.099 | 5.745 | 66.089 | 1.00 | 42.74 | B |
| C | | | | | | | | | | | |
| ATOM | 3852 | CE | LYS | B | 45 | 49.506 | 5.107 | 66.162 | 1.00 | 44.78 | B |
| C | | | | | | | | | | | |
| ATOM | 3855 | NZ | LYS | B | 45 | 49.841 | 4.228 | 64.996 | 1.00 | 46.23 | B |
| N | | | | | | | | | | | |
| ATOM | 3859 | C | LYS | B | 45 | 47.271 | 8.835 | 69.080 | 1.00 | 38.34 | B |
| C | | | | | | | | | | | |
| ATOM | 3860 | O | LYS | B | 45 | 48.347 | 9.452 | 69.119 | 1.00 | 37.97 | B |
| O | | | | | | | | | | | |
| ATOM | 3862 | N | LEU | B | 46 | 46.734 | 8.175 | 70.101 | 1.00 | 38.88 | B |
| N | | | | | | | | | | | |
| ATOM | 3863 | CA | LEU | B | 46 | 47.376 | 8.068 | 71.381 | 1.00 | 40.00 | B |
| C | | | | | | | | | | | |
| ATOM | 3865 | CB | LEU | B | 46 | 46.447 | 7.379 | 72.390 | 1.00 | 39.76 | B |
| C | | | | | | | | | | | |
| ATOM | 3868 | CG | LEU | B | 46 | 46.967 | 7.299 | 73.834 | 1.00 | 40.52 | B |
| C | | | | | | | | | | | |
| ATOM | 3870 | CD1 | LEU | B | 46 | 47.005 | 8.678 | 74.481 | 1.00 | 39.66 | B |
| C | | | | | | | | | | | |
| ATOM | 3874 | CD2 | LEU | B | 46 | 46.115 | 6.310 | 74.663 | 1.00 | 40.14 | B |
| C | | | | | | | | | | | |
| ATOM | 3878 | C | LEU | B | 46 | 48.644 | 7.250 | 71.217 | 1.00 | 40.95 | B |
| C | | | | | | | | | | | |
| ATOM | 3879 | O | LEU | B | 46 | 48.587 | 6.116 | 70.726 | 1.00 | 41.18 | B |
| O | | | | | | | | | | | |
| ATOM | 3881 | N | LEU | B | 47 | 49.756 | 7.839 | 71.658 | 1.00 | 42.16 | B |
| N | | | | | | | | | | | |
| ATOM | 3882 | CA | LEU | B | 47 | 51.098 | 7.284 | 71.569 | 1.00 | 43.48 | B |
| C | | | | | | | | | | | |
| ATOM | 3884 | CB | LEU | B | 47 | 52.024 | 8.332 | 70.927 | 1.00 | 43.27 | B |

FIG 8 – CONT.

```
ATOM   3887  CG   LEU B  47      53.443   7.919  70.551  1.00 42.09      B
ATOM   3889  CD1  LEU B  47      53.411   6.906  69.437  1.00 42.25      B
ATOM   3893  CD2  LEU B  47      54.276   9.134  70.164  1.00 41.20      B
ATOM   3897  C    LEU B  47      51.679   6.938  72.942  1.00 44.79      B
ATOM   3898  O    LEU B  47      52.339   5.914  73.093  1.00 45.56      B
ATOM   3900  N    ILE B  48      51.489   7.837  73.904  1.00 46.00      B
ATOM   3901  CA   ILE B  48      51.882   7.639  75.298  1.00 47.15      B
ATOM   3903  CB   ILE B  48      53.124   8.437  75.697  1.00 46.74      B
ATOM   3905  CG1  ILE B  48      54.379   7.919  74.990  1.00 48.03      B
ATOM   3908  CD1  ILE B  48      54.670   6.432  75.195  1.00 46.46      B
ATOM   3912  CG2  ILE B  48      53.336   8.344  77.199  1.00 47.97      B
ATOM   3916  C    ILE B  48      50.772   8.136  76.208  1.00 47.84      B
ATOM   3917  O    ILE B  48      50.213   9.192  75.973  1.00 47.29      B
ATOM   3919  N    TYR B  49      50.469   7.365  77.246  1.00 49.09      B
ATOM   3920  CA   TYR B  49      49.495   7.760  78.256  1.00 50.25      B
ATOM   3922  CB   TYR B  49      48.165   7.042  78.018  1.00 50.46      B
ATOM   3925  CG   TYR B  49      48.155   5.564  78.330  1.00 51.06      B
ATOM   3926  CD1  TYR B  49      47.598   5.088  79.517  1.00 50.91      B
ATOM   3928  CE1  TYR B  49      47.576   3.752  79.802  1.00 50.99      B
ATOM   3930  CZ   TYR B  49      48.118   2.862  78.915  1.00 50.67      B
ATOM   3931  OH   TYR B  49      48.096   1.527  79.204  1.00 50.01      B
ATOM   3933  CE2  TYR B  49      48.666   3.304  77.731  1.00 51.09      B
ATOM   3935  CD2  TYR B  49      48.692   4.648  77.452  1.00 51.06      B
ATOM   3937  C    TYR B  49      50.044   7.454  79.640  1.00 51.06      B
ATOM   3938  O    TYR B  49      50.967   6.639  79.778  1.00 51.15      B
ATOM   3940  N    ASP B  50      49.477   8.110  80.651  1.00 52.17      B
ATOM   3941  CA   ASP B  50      49.977   8.040  82.046  1.00 53.00      B
ATOM   3943  CB   ASP B  50      49.624   6.694  82.703  1.00 52.96      B
ATOM   3946  CG   ASP B  50      48.122   6.529  82.982  1.00 54.23      B
ATOM   3947  OD1  ASP B  50      47.321   7.434  82.651  1.00 55.45      B
```

FIG 8 – CONT.

| ATOM | 3948 | OD2 | ASP | B | 50 | 47.742 | 5.469 | 83.543 | 1.00 | 54.90 | B |
|------|------|-----|-----|---|----|--------|-------|--------|------|-------|---|
| ATOM | 3949 | C   | ASP | B | 50 | 51.493 | 8.302 | 82.127 | 1.00 | 53.34 | B |
| ATOM | 3950 | O   | ASP | B | 50 | 52.250 | 7.533 | 82.717 | 1.00 | 53.00 | B |
| ATOM | 3952 | N   | ASN | B | 51 | 51.928 | 9.387 | 81.505 | 1.00 | 53.69 | B |
| ATOM | 3953 | CA  | ASN | B | 51 | 53.328 | 9.793 | 81.515 | 1.00 | 54.47 | B |
| ATOM | 3955 | CB  | ASN | B | 51 | 53.870 | 9.881 | 82.942 | 1.00 | 54.75 | B |
| ATOM | 3958 | CG  | ASN | B | 51 | 52.953 | 10.645| 83.849 | 1.00 | 56.45 | B |
| ATOM | 3959 | OD1 | ASN | B | 51 | 52.650 | 10.214| 84.971 | 1.00 | 59.00 | B |
| ATOM | 3960 | ND2 | ASN | B | 51 | 52.478 | 11.786| 83.363 | 1.00 | 56.20 | B |
| ATOM | 3963 | C   | ASN | B | 51 | 54.246 | 8.919 | 80.688 | 1.00 | 54.42 | B |
| ATOM | 3964 | O   | ASN | B | 51 | 54.999 | 9.446 | 79.875 | 1.00 | 54.79 | B |
| ATOM | 3966 | N   | ASN | B | 52 | 54.183 | 7.601 | 80.881 | 1.00 | 54.44 | B |
| ATOM | 3967 | CA  | ASN | B | 52 | 55.189 | 6.702 | 80.315 | 1.00 | 54.54 | B |
| ATOM | 3969 | CB  | ASN | B | 52 | 56.296 | 6.503 | 81.356 | 1.00 | 54.83 | B |
| ATOM | 3972 | CG  | ASN | B | 52 | 55.780 | 5.884 | 82.644 | 1.00 | 55.37 | B |
| ATOM | 3973 | OD1 | ASN | B | 52 | 54.928 | 4.992 | 82.619 | 1.00 | 57.24 | B |
| ATOM | 3974 | ND2 | ASN | B | 52 | 56.270 | 6.379 | 83.779 | 1.00 | 56.23 | B |
| ATOM | 3977 | C   | ASN | B | 52 | 54.710 | 5.325 | 79.826 | 1.00 | 54.45 | B |
| ATOM | 3978 | O   | ASN | B | 52 | 55.537 | 4.496 | 79.455 | 1.00 | 54.41 | B |
| ATOM | 3980 | N   | LYS | B | 53 | 53.406 | 5.074 | 79.815 | 1.00 | 54.28 | B |
| ATOM | 3981 | CA  | LYS | B | 53 | 52.892 | 3.794 | 79.318 | 1.00 | 54.67 | B |
| ATOM | 3983 | CB  | LYS | B | 53 | 51.607 | 3.386 | 80.061 | 1.00 | 54.83 | B |
| ATOM | 3986 | CG  | LYS | B | 53 | 51.688 | 3.598 | 81.586 | 1.00 | 55.69 | B |
| ATOM | 3989 | CD  | LYS | B | 53 | 50.584 | 2.869 | 82.345 | 1.00 | 57.43 | B |
| ATOM | 3992 | CE  | LYS | B | 53 | 50.622 | 3.171 | 83.857 | 1.00 | 58.16 | B |
| ATOM | 3995 | NZ  | LYS | B | 53 | 49.368 | 2.699 | 84.547 | 1.00 | 57.62 | B |
| ATOM | 3999 | C   | LYS | B | 53 | 52.642 | 3.903 | 77.810 | 1.00 | 54.74 | B |
| ATOM | 4000 | O   | LYS | B | 53 | 52.401 | 5.002 | 77.290 | 1.00 | 54.52 | B |
| ATOM | 4002 | N   | ARG | B | 54 | 52.712 | 2.764 | 77.126 | 1.00 | 54.33 | B |
| ATOM | 4003 | CA  | ARG | B | 54 | 52.455 | 2.679 | 75.693 | 1.00 | 54.55 | B |
| ATOM | 4005 | CB  | ARG | B | 54 | 53.653 | 2.060 | 74.979 | 1.00 | 55.00 | B |

FIG 8 – CONT.

| | | | | | | | | | | |
|---|---|---|---|---|---|---|---|---|---|---|
| ATOM | 4008 | CG | ARG | B | 54 | 54.792 | 3.021 | 74.643 | 1.00 56.53 | B |
| ATOM | 4011 | CD | ARG | B | 54 | 55.874 | 2.267 | 73.926 | 1.00 58.36 | B |
| ATOM | 4014 | NE | ARG | B | 54 | 56.455 | 1.228 | 74.782 | 1.00 60.98 | B |
| ATOM | 4016 | CZ | ARG | B | 54 | 57.470 | 1.409 | 75.633 | 1.00 61.84 | B |
| ATOM | 4017 | NH1 | ARG | B | 54 | 58.058 | 2.604 | 75.772 | 1.00 60.97 | B |
| ATOM | 4020 | NH2 | ARG | B | 54 | 57.911 | 0.374 | 76.349 | 1.00 61.83 | B |
| ATOM | 4023 | C | ARG | B | 54 | 51.272 | 1.776 | 75.403 | 1.00 54.03 | B |
| ATOM | 4024 | O | ARG | B | 54 | 51.142 | 0.742 | 76.022 | 1.00 54.23 | B |
| ATOM | 4026 | N | PRO | B | 55 | 50.421 | 2.143 | 74.434 | 1.00 53.78 | B |
| ATOM | 4027 | CA | PRO | B | 55 | 49.473 | 1.160 | 73.948 | 1.00 54.07 | B |
| ATOM | 4029 | CB | PRO | B | 55 | 48.578 | 1.958 | 72.997 | 1.00 54.08 | B |
| ATOM | 4032 | CG | PRO | B | 55 | 48.803 | 3.379 | 73.360 | 1.00 53.60 | B |
| ATOM | 4035 | CD | PRO | B | 55 | 50.226 | 3.444 | 73.782 | 1.00 53.65 | B |
| ATOM | 4038 | C | PRO | B | 55 | 50.225 | 0.061 | 73.216 | 1.00 54.46 | B |
| ATOM | 4039 | O | PRO | B | 55 | 51.367 | 0.265 | 72.783 | 1.00 53.63 | B |
| ATOM | 4040 | N | SER | B | 56 | 49.596 | −1.101 | 73.100 | 1.00 55.41 | B |
| ATOM | 4041 | CA | SER | B | 56 | 50.327 | −2.318 | 72.733 | 1.00 56.32 | B |
| ATOM | 4043 | CB | SER | B | 56 | 49.516 | −3.562 | 73.092 | 1.00 56.58 | B |
| ATOM | 4046 | OG | SER | B | 56 | 48.366 | −3.671 | 72.281 | 1.00 55.99 | B |
| ATOM | 4048 | C | SER | B | 56 | 50.740 | −2.368 | 71.262 | 1.00 56.75 | B |
| ATOM | 4049 | O | SER | B | 56 | 51.609 | −3.158 | 70.901 | 1.00 57.11 | B |
| ATOM | 4051 | N | ALA | B | 57 | 50.109 | −1.539 | 70.428 | 1.00 57.18 | B |
| ATOM | 4052 | CA | ALA | B | 57 | 50.496 | −1.402 | 69.017 | 1.00 57.50 | B |
| ATOM | 4054 | CB | ALA | B | 57 | 49.318 | −0.897 | 68.193 | 1.00 57.47 | B |
| ATOM | 4058 | C | ALA | B | 57 | 51.709 | −0.476 | 68.825 | 1.00 57.60 | B |
| ATOM | 4059 | O | ALA | B | 57 | 52.304 | −0.459 | 67.756 | 1.00 57.82 | B |
| ATOM | 4061 | N | ILE | B | 58 | 52.066 | 0.291 | 69.852 | 1.00 57.79 | B |
| ATOM | 4062 | CA | ILE | B | 58 | 53.176 | 1.228 | 69.755 | 1.00 57.68 | B |
| ATOM | 4064 | CB | ILE | B | 58 | 52.984 | 2.435 | 70.710 | 1.00 57.26 | B |
| ATOM | 4066 | CG1 | ILE | B | 58 | 51.667 | 3.165 | 70.388 | 1.00 56.54 | B |

FIG 8 – CONT.

| ATOM | 4069 | CD1 | ILE | B | 58 | 51.424 | 3.462 | 68.897 | 1.00 | 54.02 | B |
|------|------|-----|-----|---|----|--------|-------|--------|------|-------|---|
| ATOM | 4073 | CG2 | ILE | B | 58 | 54.145 | 3.418 | 70.623 | 1.00 | 56.58 | B |
| ATOM | 4077 | C   | ILE | B | 58 | 54.477 | 0.497 | 70.053 | 1.00 | 58.63 | C |
| ATOM | 4078 | O   | ILE | B | 58 | 54.541 | -0.309 | 70.986 | 1.00 | 59.29 | O |
| ATOM | 4080 | N   | PRO | B | 59 | 55.522 | 0.756 | 69.250 | 1.00 | 59.14 | N |
| ATOM | 4081 | CA  | PRO | B | 59 | 56.801 | 0.108 | 69.511 | 1.00 | 59.40 | C |
| ATOM | 4083 | CB  | PRO | B | 59 | 57.551 | 0.286 | 68.193 | 1.00 | 59.74 | C |
| ATOM | 4086 | CG  | PRO | B | 59 | 57.038 | 1.589 | 67.683 | 1.00 | 60.08 | C |
| ATOM | 4089 | CD  | PRO | B | 59 | 55.576 | 1.613 | 68.053 | 1.00 | 59.16 | C |
| ATOM | 4092 | C   | PRO | B | 59 | 57.574 | 0.758 | 70.655 | 1.00 | 59.40 | C |
| ATOM | 4093 | O   | PRO | B | 59 | 57.453 | 1.965 | 70.899 | 1.00 | 59.43 | O |
| ATOM | 4094 | N   | ASP | B | 60 | 58.379 | -0.062 | 71.323 | 1.00 | 59.19 | N |
| ATOM | 4095 | CA  | ASP | B | 60 | 59.184 | 0.341 | 72.493 | 1.00 | 59.21 | C |
| ATOM | 4097 | CB  | ASP | B | 60 | 59.978 | -0.877 | 73.019 | 1.00 | 59.40 | C |
| ATOM | 4100 | CG  | ASP | B | 60 | 60.578 | -1.733 | 71.881 | 1.00 | 60.98 | C |
| ATOM | 4101 | OD1 | ASP | B | 60 | 61.622 | -1.325 | 71.312 | 1.00 | 63.05 | O |
| ATOM | 4102 | OD2 | ASP | B | 60 | 59.990 | -2.795 | 71.542 | 1.00 | 61.10 | O |
| ATOM | 4103 | C   | ASP | B | 60 | 60.132 | 1.527 | 72.251 | 1.00 | 58.56 | C |
| ATOM | 4104 | O   | ASP | B | 60 | 60.594 | 2.169 | 73.196 | 1.00 | 58.71 | O |
| ATOM | 4106 | N   | ARG | B | 61 | 60.418 | 1.815 | 70.990 | 1.00 | 58.09 | N |
| ATOM | 4107 | CA  | ARG | B | 61 | 61.279 | 2.940 | 70.624 | 1.00 | 57.52 | C |
| ATOM | 4109 | CB  | ARG | B | 61 | 61.384 | 3.043 | 69.094 | 1.00 | 57.80 | C |
| ATOM | 4112 | CG  | ARG | B | 61 | 61.912 | 1.796 | 68.414 | 1.00 | 57.40 | C |
| ATOM | 4115 | CD  | ARG | B | 61 | 62.309 | 2.052 | 66.965 | 1.00 | 56.92 | C |
| ATOM | 4118 | NE  | ARG | B | 61 | 61.169 | 2.251 | 66.056 | 1.00 | 54.72 | N |
| ATOM | 4120 | CZ  | ARG | B | 61 | 60.749 | 3.428 | 65.583 | 1.00 | 52.29 | C |
| ATOM | 4121 | NH1 | ARG | B | 61 | 61.343 | 4.577 | 65.940 | 1.00 | 51.21 | N |
| ATOM | 4124 | NH2 | ARG | B | 61 | 59.708 | 3.453 | 64.753 | 1.00 | 50.92 | N |
| ATOM | 4127 | C   | ARG | B | 61 | 60.794 | 4.283 | 71.180 | 1.00 | 56.95 | C |
| ATOM | 4128 | O   | ARG | B | 61 | 61.600 | 5.179 | 71.457 | 1.00 | 56.79 | O |
| ATOM | 4130 | N   | PHE | B | 62 | 59.476 | 4.428 | 71.316 | 1.00 | 56.30 | B |

FIG 8 – CONT.

| ATOM | 4131 | CA | PHE | B | 62 | 58.895 | 5.641 | 71.891 | 1.00 | 55.75 | B |
|---|---|---|---|---|---|---|---|---|---|---|---|
| ATOM | 4133 | CB | PHE | B | 62 | 57.483 | 5.900 | 71.354 | 1.00 | 55.49 | B |
| ATOM | 4136 | CG | PHE | B | 62 | 57.417 | 6.060 | 69.858 | 1.00 | 53.95 | B |
| ATOM | 4137 | CD1 | PHE | B | 62 | 57.587 | 7.307 | 69.274 | 1.00 | 52.57 | B |
| ATOM | 4139 | CE1 | PHE | B | 62 | 57.521 | 7.462 | 67.901 | 1.00 | 52.81 | B |
| ATOM | 4141 | CZ | PHE | B | 62 | 57.283 | 6.363 | 67.092 | 1.00 | 53.10 | B |
| ATOM | 4143 | CE2 | PHE | B | 62 | 57.111 | 5.099 | 67.664 | 1.00 | 53.27 | B |
| ATOM | 4145 | CD2 | PHE | B | 62 | 57.173 | 4.960 | 69.043 | 1.00 | 53.17 | B |
| ATOM | 4147 | C | PHE | B | 62 | 58.826 | 5.492 | 73.394 | 1.00 | 55.84 | B |
| ATOM | 4148 | O | PHE | B | 62 | 58.400 | 4.458 | 73.901 | 1.00 | 55.51 | B |
| ATOM | 4150 | N | SER | B | 63 | 59.241 | 6.540 | 74.093 | 1.00 | 55.95 | B |
| ATOM | 4151 | CA | SER | B | 63 | 59.196 | 6.573 | 75.541 | 1.00 | 56.11 | B |
| ATOM | 4153 | CB | SER | B | 63 | 60.595 | 6.314 | 76.125 | 1.00 | 56.18 | B |
| ATOM | 4156 | OG | SER | B | 63 | 61.461 | 7.432 | 75.955 | 1.00 | 55.61 | B |
| ATOM | 4158 | C | SER | B | 63 | 58.692 | 7.937 | 75.976 | 1.00 | 56.15 | B |
| ATOM | 4159 | O | SER | B | 63 | 58.807 | 8.911 | 75.236 | 1.00 | 56.18 | B |
| ATOM | 4161 | N | GLY | B | 64 | 58.130 | 7.999 | 77.173 | 1.00 | 56.48 | B |
| ATOM | 4162 | CA | GLY | B | 64 | 57.707 | 9.259 | 77.745 | 1.00 | 57.27 | B |
| ATOM | 4165 | C | GLY | B | 64 | 58.026 | 9.361 | 79.226 | 1.00 | 57.87 | B |
| ATOM | 4166 | O | GLY | B | 64 | 58.047 | 8.355 | 79.946 | 1.00 | 57.71 | B |
| ATOM | 4168 | N | SER | B | 65 | 58.261 | 10.580 | 79.686 | 1.00 | 58.39 | B |
| ATOM | 4169 | CA | SER | B | 65 | 58.447 | 10.810 | 81.099 | 1.00 | 59.25 | B |
| ATOM | 4171 | CB | SER | B | 65 | 59.924 | 10.745 | 81.435 | 1.00 | 59.14 | B |
| ATOM | 4174 | OG | SER | B | 65 | 60.611 | 11.750 | 80.722 | 1.00 | 59.39 | B |
| ATOM | 4176 | C | SER | B | 65 | 57.910 | 12.173 | 81.485 | 1.00 | 60.04 | B |
| ATOM | 4177 | O | SER | B | 65 | 57.940 | 13.113 | 80.685 | 1.00 | 60.20 | B |
| ATOM | 4179 | N | LYS | B | 66 | 57.432 | 12.255 | 82.726 | 1.00 | 60.91 | B |
| ATOM | 4180 | CA | LYS | B | 66 | 56.992 | 13.493 | 83.344 | 1.00 | 61.47 | B |
| ATOM | 4182 | CB | LYS | B | 66 | 55.549 | 13.326 | 83.843 | 1.00 | 61.72 | B |
| ATOM | 4185 | CG | LYS | B | 66 | 55.032 | 14.463 | 84.716 | 1.00 | 61.99 | B |

FIG 8 – CONT.

| ATOM | 4188 | CD | LYS | B | 66 | 53.676 | 14.138 | 85.337 | 1.00 | 62.27 | B |
|---|---|---|---|---|---|---|---|---|---|---|---|
| C | | | | | | | | | | | |
| ATOM | 4191 | CE | LYS | B | 66 | 53.436 | 14.953 | 86.591 | 1.00 | 61.98 | B |
| C | | | | | | | | | | | |
| ATOM | 4194 | NZ | LYS | B | 66 | 52.004 | 14.932 | 87.005 | 1.00 | 62.66 | B |
| N | | | | | | | | | | | |
| ATOM | 4198 | C | LYS | B | 66 | 57.934 | 13.816 | 84.513 | 1.00 | 61.89 | B |
| C | | | | | | | | | | | |
| ATOM | 4199 | O | LYS | B | 66 | 58.391 | 12.908 | 85.212 | 1.00 | 61.75 | B |
| O | | | | | | | | | | | |
| ATOM | 4201 | N | SER | B | 67 | 58.211 | 15.110 | 84.706 | 1.00 | 62.33 | B |
| N | | | | | | | | | | | |
| ATOM | 4202 | CA | SER | B | 67 | 58.997 | 15.622 | 85.838 | 1.00 | 62.36 | B |
| C | | | | | | | | | | | |
| ATOM | 4204 | CB | SER | B | 67 | 60.504 | 15.572 | 85.537 | 1.00 | 62.68 | B |
| C | | | | | | | | | | | |
| ATOM | 4207 | OG | SER | B | 67 | 60.973 | 14.239 | 85.379 | 1.00 | 63.67 | B |
| O | | | | | | | | | | | |
| ATOM | 4209 | C | SER | B | 67 | 58.615 | 17.073 | 86.161 | 1.00 | 62.21 | B |
| C | | | | | | | | | | | |
| ATOM | 4210 | O | SER | B | 67 | 58.954 | 18.003 | 85.415 | 1.00 | 61.91 | B |
| O | | | | | | | | | | | |
| ATOM | 4212 | N | GLY | B | 68 | 57.940 | 17.273 | 87.288 | 1.00 | 62.07 | B |
| N | | | | | | | | | | | |
| ATOM | 4213 | CA | GLY | B | 68 | 57.567 | 18.618 | 87.715 | 1.00 | 61.84 | B |
| C | | | | | | | | | | | |
| ATOM | 4216 | C | GLY | B | 68 | 56.503 | 19.154 | 86.777 | 1.00 | 61.48 | B |
| C | | | | | | | | | | | |
| ATOM | 4217 | O | GLY | B | 68 | 55.528 | 18.450 | 86.491 | 1.00 | 61.48 | B |
| O | | | | | | | | | | | |
| ATOM | 4219 | N | THR | B | 69 | 56.716 | 20.371 | 86.268 | 1.00 | 60.90 | B |
| N | | | | | | | | | | | |
| ATOM | 4220 | CA | THR | B | 69 | 55.764 | 21.034 | 85.375 | 1.00 | 60.25 | B |
| C | | | | | | | | | | | |
| ATOM | 4222 | CB | THR | B | 69 | 55.760 | 22.552 | 85.610 | 1.00 | 60.40 | B |
| C | | | | | | | | | | | |
| ATOM | 4224 | OG1 | THR | B | 69 | 57.028 | 23.096 | 85.226 | 1.00 | 60.13 | B |
| O | | | | | | | | | | | |
| ATOM | 4226 | CG2 | THR | B | 69 | 55.474 | 22.878 | 87.068 | 1.00 | 60.27 | B |
| C | | | | | | | | | | | |
| ATOM | 4230 | C | THR | B | 69 | 56.103 | 20.792 | 83.901 | 1.00 | 59.84 | B |
| C | | | | | | | | | | | |
| ATOM | 4231 | O | THR | B | 69 | 55.692 | 21.557 | 83.025 | 1.00 | 59.59 | B |
| O | | | | | | | | | | | |
| ATOM | 4233 | N | SER | B | 70 | 56.848 | 19.723 | 83.638 | 1.00 | 59.09 | B |
| N | | | | | | | | | | | |
| ATOM | 4234 | CA | SER | B | 70 | 57.364 | 19.441 | 82.317 | 1.00 | 58.46 | B |
| C | | | | | | | | | | | |
| ATOM | 4236 | CB | SER | B | 70 | 58.792 | 19.993 | 82.202 | 1.00 | 58.66 | B |
| C | | | | | | | | | | | |
| ATOM | 4239 | OG | SER | B | 70 | 59.722 | 18.986 | 81.821 | 1.00 | 59.26 | B |
| O | | | | | | | | | | | |
| ATOM | 4241 | C | SER | B | 70 | 57.302 | 17.941 | 82.008 | 1.00 | 57.79 | B |
| C | | | | | | | | | | | |
| ATOM | 4242 | O | SER | B | 70 | 57.195 | 17.107 | 82.913 | 1.00 | 57.46 | B |
| O | | | | | | | | | | | |
| ATOM | 4244 | N | ALA | B | 71 | 57.323 | 17.609 | 80.715 | 1.00 | 57.10 | B |
| N | | | | | | | | | | | |
| ATOM | 4245 | CA | ALA | B | 71 | 57.371 | 16.215 | 80.269 | 1.00 | 56.35 | B |
| C | | | | | | | | | | | |
| ATOM | 4247 | CB | ALA | B | 71 | 55.986 | 15.647 | 80.025 | 1.00 | 56.19 | B |

FIG 8 – CONT.

```
ATOM   4251  C    ALA B  71      58.186  16.153  79.017  1.00 55.83      B
ATOM   4252  O    ALA B  71      58.498  17.175  78.395  1.00 55.87      B
ATOM   4254  N    THR B  72      58.555  14.941  78.660  1.00 55.16      B
ATOM   4255  CA   THR B  72      59.428  14.745  77.538  1.00 54.76      B
ATOM   4257  CB   THR B  72      60.921  14.720  77.972  1.00 54.98      B
ATOM   4259  OG1  THR B  72      61.325  16.032  78.388  1.00 55.34      B
ATOM   4261  CG2  THR B  72      61.808  14.305  76.820  1.00 55.40      B
ATOM   4265  C    THR B  72      59.042  13.456  76.863  1.00 53.75      B
ATOM   4266  O    THR B  72      58.774  12.464  77.524  1.00 53.50      B
ATOM   4268  N    LEU B  73      58.972  13.520  75.542  1.00 52.92      B
ATOM   4269  CA   LEU B  73      58.847  12.361  74.694  1.00 52.39      B
ATOM   4271  CB   LEU B  73      57.820  12.615  73.572  1.00 52.00      B
ATOM   4274  CG   LEU B  73      57.642  11.531  72.504  1.00 51.26      B
ATOM   4276  CD1  LEU B  73      56.975  10.319  73.096  1.00 47.55      B
ATOM   4280  CD2  LEU B  73      56.833  12.064  71.320  1.00 49.84      B
ATOM   4284  C    LEU B  73      60.222  12.169  74.091  1.00 52.35      B
ATOM   4285  O    LEU B  73      60.887  13.146  73.743  1.00 51.85      B
ATOM   4287  N    GLY B  74      60.633  10.907  73.971  1.00 52.76      B
ATOM   4288  CA   GLY B  74      61.907  10.536  73.367  1.00 52.60      B
ATOM   4291  C    GLY B  74      61.672   9.425  72.378  1.00 52.96      B
ATOM   4292  O    GLY B  74      60.834   8.546  72.603  1.00 52.64      B
ATOM   4294  N    ILE B  75      62.395   9.487  71.265  1.00 53.79      B
ATOM   4295  CA   ILE B  75      62.270   8.514  70.186  1.00 54.34      B
ATOM   4297  CB   ILE B  75      61.645   9.138  68.898  1.00 54.68      B
ATOM   4299  CG1  ILE B  75      60.440  10.017  69.244  1.00 54.95      B
ATOM   4302  CD1  ILE B  75      60.168  11.069  68.214  1.00 56.22      B
ATOM   4306  CG2  ILE B  75      61.218   8.048  67.899  1.00 53.39      B
ATOM   4310  C    ILE B  75      63.676   8.033  69.880  1.00 55.20      B
ATOM   4311  O    ILE B  75      64.608   8.832  69.761  1.00 55.26      B
ATOM   4313  N    THR B  76      63.805   6.720  69.751  1.00 55.96      B
```

FIG 8 – CONT.

| ATOM | 4314 | CA  | THR | B | 76 | 65.073 | 6.048  | 69.582 | 1.00 | 56.56 | B | C |
|------|------|-----|-----|---|----|--------|--------|--------|------|-------|---|---|
| ATOM | 4316 | CB  | THR | B | 76 | 65.349 | 5.129  | 70.787 | 1.00 | 56.46 | B | C |
| ATOM | 4318 | OG1 | THR | B | 76 | 66.114 | 5.858  | 71.750 | 1.00 | 57.27 | B | O |
| ATOM | 4320 | CG2 | THR | B | 76 | 66.106 | 3.855  | 70.375 | 1.00 | 57.18 | B | C |
| ATOM | 4324 | C   | THR | B | 76 | 64.964 | 5.216  | 68.332 | 1.00 | 57.06 | B | C |
| ATOM | 4325 | O   | THR | B | 76 | 63.880 | 4.727  | 68.006 | 1.00 | 57.58 | B | O |
| ATOM | 4327 | N   | GLY | B | 77 | 66.082 | 5.036  | 67.639 | 1.00 | 57.19 | B | N |
| ATOM | 4328 | CA  | GLY | B | 77 | 66.082 | 4.275  | 66.396 | 1.00 | 57.31 | B | C |
| ATOM | 4331 | C   | GLY | B | 77 | 65.297 | 5.037  | 65.342 | 1.00 | 57.23 | B | C |
| ATOM | 4332 | O   | GLY | B | 77 | 64.597 | 4.443  | 64.515 | 1.00 | 56.64 | B | O |
| ATOM | 4334 | N   | LEU | B | 78 | 65.433 | 6.360  | 65.383 | 1.00 | 57.22 | B | N |
| ATOM | 4335 | CA  | LEU | B | 78 | 64.690 | 7.243  | 64.509 | 1.00 | 57.33 | B | C |
| ATOM | 4337 | CB  | LEU | B | 78 | 65.334 | 8.619  | 64.499 | 1.00 | 57.18 | B | C |
| ATOM | 4340 | CG  | LEU | B | 78 | 64.555 | 9.743  | 63.827 | 1.00 | 57.95 | B | C |
| ATOM | 4342 | CD1 | LEU | B | 78 | 65.191 | 11.072 | 64.157 | 1.00 | 58.02 | B | C |
| ATOM | 4346 | CD2 | LEU | B | 78 | 64.527 | 9.550  | 62.339 | 1.00 | 59.37 | B | C |
| ATOM | 4350 | C   | LEU | B | 78 | 64.615 | 6.667  | 63.101 | 1.00 | 57.55 | B | C |
| ATOM | 4351 | O   | LEU | B | 78 | 65.635 | 6.260  | 62.522 | 1.00 | 57.90 | B | O |
| ATOM | 4353 | N   | GLN | B | 79 | 63.389 | 6.604  | 62.582 | 1.00 | 57.55 | B | N |
| ATOM | 4354 | CA  | GLN | B | 79 | 63.102 | 6.110  | 61.242 | 1.00 | 57.47 | B | C |
| ATOM | 4356 | CB  | GLN | B | 79 | 62.206 | 4.872  | 61.303 | 1.00 | 57.65 | B | C |
| ATOM | 4359 | CG  | GLN | B | 79 | 62.820 | 3.681  | 62.022 | 1.00 | 58.68 | B | C |
| ATOM | 4362 | CD  | GLN | B | 79 | 61.911 | 2.458  | 62.022 | 1.00 | 60.02 | B | C |
| ATOM | 4363 | OE1 | GLN | B | 79 | 60.869 | 2.446  | 61.369 | 1.00 | 62.22 | B | O |
| ATOM | 4364 | NE2 | GLN | B | 79 | 62.305 | 1.427  | 62.757 | 1.00 | 58.95 | B | N |
| ATOM | 4367 | C   | GLN | B | 79 | 62.394 | 7.190  | 60.424 | 1.00 | 57.13 | B | C |
| ATOM | 4368 | O   | GLN | B | 79 | 61.836 | 8.151  | 60.968 | 1.00 | 56.93 | B | O |
| ATOM | 4370 | N   | THR | B | 80 | 62.409 | 7.008  | 59.109 | 1.00 | 56.55 | B | N |
| ATOM | 4371 | CA  | THR | B | 80 | 61.717 | 7.905  | 58.209 | 1.00 | 56.23 | B | C |
| ATOM | 4373 | CB  | THR | B | 80 | 61.987 | 7.534  | 56.737 | 1.00 | 56.29 | B | C |
| ATOM | 4375 | OG1 | THR | B | 80 | 61.626 | 8.647  | 55.913 | 1.00 | 57.61 | B |   |

FIG 8 – CONT.

| | | | | | | | | | | |
|---|---|---|---|---|---|---|---|---|---|---|
| ATOM | 4377 | CG2 | THR | B | 80 | 61.187 | 6.292 | 56.320 | 1.00 56.10 | B |
| ATOM | 4381 | C | THR | B | 80 | 60.203 | 7.893 | 58.501 | 1.00 55.29 | B |
| ATOM | 4382 | O | THR | B | 80 | 59.554 | 8.934 | 58.467 | 1.00 54.94 | B |
| ATOM | 4384 | N | GLY | B | 81 | 59.669 | 6.712 | 58.822 | 1.00 54.38 | B |
| ATOM | 4385 | CA | GLY | B | 81 | 58.264 | 6.541 | 59.174 | 1.00 53.37 | B |
| ATOM | 4388 | C | GLY | B | 81 | 57.784 | 7.275 | 60.425 | 1.00 52.48 | B |
| ATOM | 4389 | O | GLY | B | 81 | 56.575 | 7.296 | 60.678 | 1.00 51.95 | B |
| ATOM | 4391 | N | ASP | B | 82 | 58.717 | 7.861 | 61.193 | 1.00 51.40 | B |
| ATOM | 4392 | CA | ASP | B | 82 | 58.428 | 8.626 | 62.423 | 1.00 50.58 | B |
| ATOM | 4394 | CB | ASP | B | 82 | 59.618 | 8.548 | 63.390 | 1.00 50.53 | B |
| ATOM | 4397 | CG | ASP | B | 82 | 59.930 | 7.130 | 63.832 | 1.00 50.71 | B |
| ATOM | 4398 | OD1 | ASP | B | 82 | 59.067 | 6.234 | 63.681 | 1.00 50.21 | B |
| ATOM | 4399 | OD2 | ASP | B | 82 | 61.054 | 6.911 | 64.335 | 1.00 50.56 | B |
| ATOM | 4400 | C | ASP | B | 82 | 58.105 | 10.112 | 62.222 | 1.00 49.95 | B |
| ATOM | 4401 | O | ASP | B | 82 | 57.706 | 10.797 | 63.183 | 1.00 49.20 | B |
| ATOM | 4403 | N | GLU | B | 83 | 58.318 | 10.607 | 60.998 | 1.00 49.24 | B |
| ATOM | 4404 | CA | GLU | B | 83 | 57.978 | 11.983 | 60.600 | 1.00 48.67 | B |
| ATOM | 4406 | CB | GLU | B | 83 | 58.254 | 12.203 | 59.105 | 1.00 49.01 | B |
| ATOM | 4409 | CG | GLU | B | 83 | 59.723 | 12.332 | 58.727 | 1.00 51.56 | B |
| ATOM | 4412 | CD | GLU | B | 83 | 59.921 | 13.035 | 57.387 | 1.00 53.83 | B |
| ATOM | 4413 | OE1 | GLU | B | 83 | 59.249 | 12.656 | 56.392 | 1.00 55.88 | B |
| ATOM | 4414 | OE2 | GLU | B | 83 | 60.757 | 13.959 | 57.342 | 1.00 54.34 | B |
| ATOM | 4415 | C | GLU | B | 83 | 56.505 | 12.253 | 60.823 | 1.00 47.08 | B |
| ATOM | 4416 | O | GLU | B | 83 | 55.674 | 11.614 | 60.209 | 1.00 47.04 | B |
| ATOM | 4418 | N | ALA | B | 84 | 56.182 | 13.207 | 61.682 | 1.00 45.51 | B |
| ATOM | 4419 | CA | ALA | B | 84 | 54.788 | 13.458 | 62.057 | 1.00 44.26 | B |
| ATOM | 4421 | CB | ALA | B | 84 | 54.180 | 12.237 | 62.776 | 1.00 43.27 | B |
| ATOM | 4425 | C | ALA | B | 84 | 54.773 | 14.651 | 62.970 | 1.00 43.21 | B |
| ATOM | 4426 | O | ALA | B | 84 | 55.832 | 15.119 | 63.378 | 1.00 42.60 | B |
| ATOM | 4428 | N | ASP | B | 85 | 53.574 | 15.132 | 63.286 | 1.00 42.27 | B |

FIG 8 – CONT.

| ATOM | 4429 | CA | ASP | B | 85 | 53.388 | 16.107 | 64.349 | 1.00 | 41.75 | B |
|---|---|---|---|---|---|---|---|---|---|---|---|
| ATOM | 4431 | CB | ASP | B | 85 | 52.251 | 17.095 | 64.025 | 1.00 | 41.95 | B |
| ATOM | 4434 | CG | ASP | B | 85 | 52.567 | 18.003 | 62.820 | 1.00 | 43.36 | B |
| ATOM | 4435 | OD1 | ASP | B | 85 | 53.759 | 18.179 | 62.495 | 1.00 | 44.74 | B |
| ATOM | 4436 | OD2 | ASP | B | 85 | 51.621 | 18.555 | 62.207 | 1.00 | 44.21 | B |
| ATOM | 4437 | C | ASP | B | 85 | 53.104 | 15.332 | 65.652 | 1.00 | 40.69 | B |
| ATOM | 4438 | O | ASP | B | 85 | 52.291 | 14.406 | 65.680 | 1.00 | 40.02 | B |
| ATOM | 4440 | N | TYR | B | 86 | 53.799 | 15.722 | 66.712 | 1.00 | 39.70 | B |
| ATOM | 4441 | CA | TYR | B | 86 | 53.648 | 15.109 | 68.009 | 1.00 | 39.38 | B |
| ATOM | 4443 | CB | TYR | B | 86 | 54.992 | 14.580 | 68.534 | 1.00 | 38.66 | B |
| ATOM | 4446 | CG | TYR | B | 86 | 55.458 | 13.390 | 67.746 | 1.00 | 37.96 | B |
| ATOM | 4447 | CD1 | TYR | B | 86 | 55.150 | 12.117 | 68.152 | 1.00 | 37.28 | B |
| ATOM | 4449 | CE1 | TYR | B | 86 | 55.537 | 11.026 | 67.421 | 1.00 | 38.35 | B |
| ATOM | 4451 | CZ | TYR | B | 86 | 56.246 | 11.188 | 66.250 | 1.00 | 37.20 | B |
| ATOM | 4452 | OH | TYR | B | 86 | 56.618 | 10.074 | 65.534 | 1.00 | 36.51 | B |
| ATOM | 4454 | CE2 | TYR | B | 86 | 56.545 | 12.449 | 65.800 | 1.00 | 37.21 | B |
| ATOM | 4456 | CD2 | TYR | B | 86 | 56.158 | 13.547 | 66.553 | 1.00 | 37.83 | B |
| ATOM | 4458 | C | TYR | B | 86 | 53.070 | 16.157 | 68.929 | 1.00 | 39.68 | B |
| ATOM | 4459 | O | TYR | B | 86 | 53.600 | 17.268 | 69.012 | 1.00 | 39.45 | B |
| ATOM | 4461 | N | TYR | B | 87 | 51.969 | 15.804 | 69.596 | 1.00 | 40.17 | B |
| ATOM | 4462 | CA | TYR | B | 87 | 51.296 | 16.722 | 70.523 | 1.00 | 40.76 | B |
| ATOM | 4464 | CB | TYR | B | 87 | 49.832 | 16.952 | 70.135 | 1.00 | 40.20 | B |
| ATOM | 4467 | CG | TYR | B | 87 | 49.609 | 17.748 | 68.867 | 1.00 | 39.48 | B |
| ATOM | 4468 | CD1 | TYR | B | 87 | 49.506 | 19.127 | 68.905 | 1.00 | 39.12 | B |
| ATOM | 4470 | CE1 | TYR | B | 87 | 49.310 | 19.850 | 67.763 | 1.00 | 38.71 | B |
| ATOM | 4472 | CZ | TYR | B | 87 | 49.197 | 19.207 | 66.566 | 1.00 | 38.03 | B |
| ATOM | 4473 | OH | TYR | B | 87 | 48.990 | 19.954 | 65.428 | 1.00 | 38.62 | B |
| ATOM | 4475 | CE2 | TYR | B | 87 | 49.290 | 17.839 | 66.508 | 1.00 | 37.19 | B |
| ATOM | 4477 | CD2 | TYR | B | 87 | 49.490 | 17.124 | 67.638 | 1.00 | 36.20 | B |
| ATOM | 4479 | C | TYR | B | 87 | 51.329 | 16.147 | 71.940 | 1.00 | 42.30 | B |
| ATOM | 4480 | O | TYR | B | 87 | 51.026 | 14.950 | 72.164 | 1.00 | 42.11 | B |

FIG 8 – CONT.

| | | | | | | | | | | |
|---|---|---|---|---|---|---|---|---|---|---|
| ATOM | 4482 | N | CYS | B | 88 | 51.674 | 16.997 | 72.898 | 1.00 43.70 | B N |
| ATOM | 4483 | CA | CYS | B | 88 | 51.474 | 16.638 | 74.286 | 1.00 45.63 | B C |
| ATOM | 4485 | CB | CYS | B | 88 | 52.622 | 17.125 | 75.174 | 1.00 45.94 | B C |
| ATOM | 4488 | SG | CYS | B | 88 | 52.728 | 18.878 | 75.341 | 1.00 48.52 | B S |
| ATOM | 4490 | C | CYS | B | 88 | 50.139 | 17.185 | 74.752 | 1.00 46.04 | B C |
| ATOM | 4491 | O | CYS | B | 88 | 49.657 | 18.224 | 74.261 | 1.00 46.57 | B O |
| ATOM | 4493 | N | GLY | B | 89 | 49.549 | 16.477 | 75.707 | 1.00 46.75 | B N |
| ATOM | 4494 | CA | GLY | B | 89 | 48.287 | 16.878 | 76.291 | 1.00 47.25 | B C |
| ATOM | 4497 | C | GLY | B | 89 | 48.110 | 16.351 | 77.699 | 1.00 47.91 | B C |
| ATOM | 4498 | O | GLY | B | 89 | 48.752 | 15.384 | 78.107 | 1.00 47.22 | B O |
| ATOM | 4500 | N | THR | B | 90 | 47.219 | 17.012 | 78.423 | 1.00 48.96 | B N |
| ATOM | 4501 | CA | THR | B | 90 | 46.920 | 16.685 | 79.803 | 1.00 50.01 | B C |
| ATOM | 4503 | CB | THR | B | 90 | 48.033 | 17.196 | 80.806 | 1.00 50.37 | B C |
| ATOM | 4505 | OG1 | THR | B | 90 | 47.857 | 16.582 | 82.100 | 1.00 50.29 | B O |
| ATOM | 4507 | CG2 | THR | B | 90 | 48.013 | 18.701 | 80.954 | 1.00 49.15 | B C |
| ATOM | 4511 | C | THR | B | 90 | 45.578 | 17.304 | 80.143 | 1.00 50.80 | B C |
| ATOM | 4512 | O | THR | B | 90 | 44.831 | 17.722 | 79.251 | 1.00 50.76 | B O |
| ATOM | 4514 | N | TRP | B | 91 | 45.278 | 17.346 | 81.437 | 1.00 51.84 | B N |
| ATOM | 4515 | CA | TRP | B | 91 | 44.065 | 17.956 | 81.947 | 1.00 52.22 | B C |
| ATOM | 4517 | CB | TRP | B | 91 | 43.228 | 16.906 | 82.665 | 1.00 52.26 | B C |
| ATOM | 4520 | CG | TRP | B | 91 | 42.725 | 15.842 | 81.756 | 1.00 51.33 | B C |
| ATOM | 4521 | CD1 | TRP | B | 91 | 43.367 | 14.688 | 81.394 | 1.00 51.08 | B C |
| ATOM | 4523 | NE1 | TRP | B | 91 | 42.578 | 13.958 | 80.538 | 1.00 50.13 | B N |
| ATOM | 4525 | CE2 | TRP | B | 91 | 41.411 | 14.646 | 80.322 | 1.00 49.09 | B C |
| ATOM | 4526 | CD2 | TRP | B | 91 | 41.472 | 15.839 | 81.077 | 1.00 49.33 | B C |
| ATOM | 4527 | CE3 | TRP | B | 91 | 40.389 | 16.724 | 81.042 | 1.00 48.26 | B C |
| ATOM | 4529 | CZ3 | TRP | B | 91 | 39.298 | 16.404 | 80.278 | 1.00 47.68 | B C |
| ATOM | 4531 | CH2 | TRP | B | 91 | 39.257 | 15.203 | 79.541 | 1.00 48.60 | B C |
| ATOM | 4533 | CZ2 | TRP | B | 91 | 40.306 | 14.314 | 79.546 | 1.00 48.00 | B C |
| ATOM | 4535 | C | TRP | B | 91 | 44.438 | 19.050 | 82.911 | 1.00 53.00 | B C |

FIG 8 – CONT.

| ATOM | 4536 | O   | TRP | B | 91  | 45.499 | 18.996 | 83.522 | 1.00 | 53.26 | B |
| --- | --- | --- | --- | --- | --- | --- | --- | --- | --- | --- | --- |
| ATOM | 4538 | N   | ASP | B | 92  | 43.558 | 20.034 | 83.048 | 1.00 | 53.98 | B |
| ATOM | 4539 | CA  | ASP | B | 92  | 43.760 | 21.126 | 83.968 | 1.00 | 54.79 | C |
| ATOM | 4541 | CB  | ASP | B | 92  | 43.579 | 22.458 | 83.253 | 1.00 | 55.10 | C |
| ATOM | 4544 | CG  | ASP | B | 92  | 43.613 | 23.631 | 84.208 | 1.00 | 55.49 | C |
| ATOM | 4545 | OD1 | ASP | B | 92  | 44.528 | 24.472 | 84.104 | 1.00 | 55.40 | O |
| ATOM | 4546 | OD2 | ASP | B | 92  | 42.726 | 23.691 | 85.081 | 1.00 | 56.62 | O |
| ATOM | 4547 | C   | ASP | B | 92  | 42.764 | 20.986 | 85.107 | 1.00 | 55.44 | C |
| ATOM | 4548 | O   | ASP | B | 92  | 41.562 | 20.930 | 84.876 | 1.00 | 55.38 | O |
| ATOM | 4550 | N   | SER | B | 93  | 43.277 | 20.963 | 86.339 | 1.00 | 56.49 | N |
| ATOM | 4551 | CA  | SER | B | 93  | 42.463 | 20.674 | 87.538 | 1.00 | 56.84 | C |
| ATOM | 4553 | CB  | SER | B | 93  | 43.365 | 20.341 | 88.733 | 1.00 | 57.06 | C |
| ATOM | 4556 | OG  | SER | B | 93  | 44.285 | 19.304 | 88.410 | 1.00 | 58.31 | O |
| ATOM | 4558 | C   | SER | B | 93  | 41.480 | 21.786 | 87.934 | 1.00 | 56.81 | C |
| ATOM | 4559 | O   | SER | B | 93  | 40.403 | 21.485 | 88.466 | 1.00 | 57.15 | O |
| ATOM | 4561 | N   | ARG | B | 94  | 41.842 | 23.050 | 87.684 | 1.00 | 56.69 | N |
| ATOM | 4562 | CA  | ARG | B | 94  | 40.945 | 24.190 | 87.967 | 1.00 | 56.65 | C |
| ATOM | 4564 | CB  | ARG | B | 94  | 41.724 | 25.522 | 87.961 | 1.00 | 56.98 | C |
| ATOM | 4573 | C   | ARG | B | 94  | 39.731 | 24.282 | 87.003 | 1.00 | 56.53 | C |
| ATOM | 4574 | O   | ARG | B | 94  | 38.594 | 24.471 | 87.464 | 1.00 | 56.66 | O |
| ATOM | 4576 | N   | LEU | B | 95  | 39.977 | 24.161 | 85.686 | 1.00 | 55.95 | N |
| ATOM | 4577 | CA  | LEU | B | 95  | 38.917 | 24.241 | 84.640 | 1.00 | 55.24 | C |
| ATOM | 4579 | CB  | LEU | B | 95  | 39.466 | 24.838 | 83.352 | 1.00 | 55.37 | C |
| ATOM | 4582 | CG  | LEU | B | 95  | 40.018 | 26.256 | 83.405 | 1.00 | 55.89 | C |
| ATOM | 4584 | CD1 | LEU | B | 95  | 40.779 | 26.546 | 82.098 | 1.00 | 55.61 | C |
| ATOM | 4588 | CD2 | LEU | B | 95  | 38.887 | 27.244 | 83.653 | 1.00 | 54.91 | C |
| ATOM | 4592 | C   | LEU | B | 95  | 38.292 | 22.894 | 84.275 | 1.00 | 54.35 | C |
| ATOM | 4593 | O   | LEU | B | 95  | 37.221 | 22.852 | 83.668 | 1.00 | 54.33 | O |
| ATOM | 4595 | N   | GLY | B | 95A | 38.970 | 21.804 | 84.617 | 1.00 | 53.33 | N |
| ATOM | 4596 | CA  | GLY | B | 95A | 38.443 | 20.461 | 84.387 | 1.00 | 52.79 | C |
| ATOM | 4599 | C   | GLY | B | 95A | 38.312 | 20.128 | 82.908 | 1.00 | 52.14 | |

FIG 8 – CONT.

| | | | | | | | | | | |
|---|---|---|---|---|---|---|---|---|---|---|
| ATOM | 4600 | O | GLY | B | 95A | 37.469 | 19.306 | 82.515 | 1.00 51.68 | O B |
| ATOM | 4602 | N | ILE | B | 95B | 39.159 | 20.765 | 82.096 | 1.00 50.97 | N B |
| ATOM | 4603 | CA | ILE | B | 95B | 39.175 | 20.547 | 80.658 | 1.00 50.13 | C B |
| ATOM | 4605 | CB | ILE | B | 95B | 38.934 | 21.873 | 79.876 | 1.00 49.77 | C B |
| ATOM | 4607 | CG1 | ILE | B | 95B | 40.102 | 22.836 | 80.014 | 1.00 50.47 | C B |
| ATOM | 4610 | CD1 | ILE | B | 95B | 39.903 | 24.134 | 79.229 | 1.00 50.70 | C B |
| ATOM | 4614 | CG2 | ILE | B | 95B | 37.657 | 22.543 | 80.344 | 1.00 50.36 | C B |
| ATOM | 4618 | C | ILE | B | 95B | 40.485 | 19.890 | 80.221 | 1.00 48.98 | C B |
| ATOM | 4619 | O | ILE | B | 95B | 41.504 | 19.988 | 80.901 | 1.00 48.50 | O B |
| ATOM | 4621 | N | ALA | B | 96 | 40.454 | 19.200 | 79.085 | 1.00 47.98 | N B |
| ATOM | 4622 | CA | ALA | B | 96 | 41.688 | 18.678 | 78.508 | 1.00 46.70 | C B |
| ATOM | 4624 | CB | ALA | B | 96 | 41.414 | 17.566 | 77.538 | 1.00 46.36 | C B |
| ATOM | 4628 | C | ALA | B | 96 | 42.406 | 19.834 | 77.843 | 1.00 45.45 | C B |
| ATOM | 4629 | O | ALA | B | 96 | 41.816 | 20.857 | 77.557 | 1.00 45.26 | O B |
| ATOM | 4631 | N | VAL | B | 97 | 43.697 | 19.663 | 77.618 | 1.00 44.85 | N B |
| ATOM | 4632 | CA | VAL | B | 97 | 44.585 | 20.781 | 77.293 | 1.00 44.17 | C B |
| ATOM | 4634 | CB | VAL | B | 97 | 45.048 | 21.491 | 78.631 | 1.00 44.38 | C B |
| ATOM | 4636 | CG1 | VAL | B | 97 | 46.524 | 21.654 | 78.714 | 1.00 45.55 | C B |
| ATOM | 4640 | CG2 | VAL | B | 97 | 44.343 | 22.821 | 78.800 | 1.00 43.63 | C B |
| ATOM | 4644 | C | VAL | B | 97 | 45.718 | 20.236 | 76.431 | 1.00 43.15 | C B |
| ATOM | 4645 | O | VAL | B | 97 | 46.091 | 19.073 | 76.563 | 1.00 43.30 | O B |
| ATOM | 4647 | N | PHE | B | 98 | 46.220 | 21.048 | 75.513 | 1.00 42.40 | N B |
| ATOM | 4648 | CA | PHE | B | 98 | 47.217 | 20.590 | 74.544 | 1.00 41.72 | C B |
| ATOM | 4650 | CB | PHE | B | 98 | 46.594 | 20.404 | 73.156 | 1.00 41.26 | C B |
| ATOM | 4653 | CG | PHE | B | 98 | 45.600 | 19.276 | 73.041 | 1.00 39.62 | C B |
| ATOM | 4654 | CD1 | PHE | B | 98 | 46.017 | 17.958 | 73.026 | 1.00 37.45 | C B |
| ATOM | 4656 | CE1 | PHE | B | 98 | 45.106 | 16.927 | 72.865 | 1.00 37.73 | C B |
| ATOM | 4658 | CZ | PHE | B | 98 | 43.764 | 17.207 | 72.681 | 1.00 37.31 | C B |
| ATOM | 4660 | CE2 | PHE | B | 98 | 43.341 | 18.517 | 72.670 | 1.00 37.38 | C B |
| ATOM | 4662 | CD2 | PHE | B | 98 | 44.255 | 19.545 | 72.845 | 1.00 37.68 | C B |

FIG 8 – CONT.

| | | | | | | | | | | |
|---|---|---|---|---|---|---|---|---|---|---|
| ATOM | 4664 | C | PHE | B | 98 | 48.367 | 21.581 | 74.348 | 1.00 41.90 | B C |
| ATOM | 4665 | O | PHE | B | 98 | 48.208 | 22.802 | 74.525 | 1.00 41.10 | B O |
| ATOM | 4667 | N | GLY | B | 99 | 49.511 | 21.030 | 73.940 | 1.00 42.03 | B N |
| ATOM | 4668 | CA | GLY | B | 99 | 50.594 | 21.823 | 73.358 | 1.00 42.35 | B C |
| ATOM | 4671 | C | GLY | B | 99 | 50.375 | 22.144 | 71.894 | 1.00 42.41 | B C |
| ATOM | 4672 | O | GLY | B | 99 | 49.561 | 21.507 | 71.231 | 1.00 42.31 | B O |
| ATOM | 4674 | N | GLY | B | 100 | 51.102 | 23.146 | 71.393 | 1.00 42.83 | B N |
| ATOM | 4675 | CA | GLY | B | 100 | 50.977 | 23.596 | 70.005 | 1.00 42.69 | B C |
| ATOM | 4678 | C | GLY | B | 100 | 51.488 | 22.601 | 68.979 | 1.00 43.13 | B C |
| ATOM | 4679 | O | GLY | B | 100 | 51.326 | 22.808 | 67.777 | 1.00 43.24 | B O |
| ATOM | 4681 | N | GLY | B | 101 | 52.135 | 21.529 | 69.432 | 1.00 43.43 | B N |
| ATOM | 4682 | CA | GLY | B | 101 | 52.633 | 20.491 | 68.521 | 1.00 43.57 | B C |
| ATOM | 4685 | C | GLY | B | 101 | 54.047 | 20.753 | 68.044 | 1.00 43.65 | B C |
| ATOM | 4686 | O | GLY | B | 101 | 54.479 | 21.904 | 67.938 | 1.00 43.13 | B O |
| ATOM | 4688 | N | THR | B | 102 | 54.772 | 19.667 | 67.789 | 1.00 43.77 | B N |
| ATOM | 4689 | CA | THR | B | 102 | 56.134 | 19.732 | 67.310 | 1.00 44.12 | B C |
| ATOM | 4691 | CB | THR | B | 102 | 57.111 | 19.125 | 68.339 | 1.00 44.36 | B C |
| ATOM | 4693 | OG1 | THR | B | 102 | 56.974 | 19.799 | 69.599 | 1.00 43.89 | B O |
| ATOM | 4695 | CG2 | THR | B | 102 | 58.570 | 19.236 | 67.837 | 1.00 43.26 | B C |
| ATOM | 4699 | C | THR | B | 102 | 56.243 | 18.935 | 66.030 | 1.00 45.17 | B C |
| ATOM | 4700 | O | THR | B | 102 | 55.891 | 17.751 | 66.010 | 1.00 45.07 | B O |
| ATOM | 4702 | N | GLN | B | 103 | 56.708 | 19.569 | 64.957 | 1.00 46.36 | B N |
| ATOM | 4703 | CA | GLN | B | 103 | 56.944 | 18.829 | 63.718 | 1.00 47.64 | B C |
| ATOM | 4705 | CB | GLN | B | 103 | 56.899 | 19.731 | 62.480 | 1.00 47.96 | B C |
| ATOM | 4708 | CG | GLN | B | 103 | 57.203 | 18.939 | 61.197 | 1.00 49.71 | B C |
| ATOM | 4711 | CD | GLN | B | 103 | 56.951 | 19.719 | 59.914 | 1.00 53.71 | B C |
| ATOM | 4712 | OE1 | GLN | B | 103 | 56.555 | 20.892 | 59.949 | 1.00 55.64 | B O |
| ATOM | 4713 | NE2 | GLN | B | 103 | 57.182 | 19.065 | 58.764 | 1.00 53.38 | B N |
| ATOM | 4716 | C | GLN | B | 103 | 58.285 | 18.107 | 63.779 | 1.00 48.13 | B C |
| ATOM | 4717 | O | GLN | B | 103 | 59.328 | 18.733 | 64.020 | 1.00 48.13 | B O |
| ATOM | 4719 | N | LEU | B | 104 | 58.251 | 16.798 | 63.548 | 1.00 48.96 | B |

FIG 8 – CONT.

| | | | | | | | | | | |
|---|---|---|---|---|---|---|---|---|---|---|
| ATOM | 4720 | CA | LEU | B | 104 | 59.465 | 15.972 | 63.510 | 1.00 49.87 | B |
| ATOM | 4722 | CB | LEU | B | 104 | 59.293 | 14.667 | 64.298 | 1.00 49.84 | B |
| ATOM | 4725 | CG | LEU | B | 104 | 60.609 | 13.911 | 64.570 | 1.00 50.64 | B |
| ATOM | 4727 | CD1 | LEU | B | 104 | 61.133 | 14.293 | 65.957 | 1.00 52.09 | B |
| ATOM | 4731 | CD2 | LEU | B | 104 | 60.456 | 12.388 | 64.457 | 1.00 49.06 | B |
| ATOM | 4735 | C | LEU | B | 104 | 59.864 | 15.649 | 62.060 | 1.00 50.32 | B |
| ATOM | 4736 | O | LEU | B | 104 | 59.148 | 14.938 | 61.341 | 1.00 49.50 | B |
| ATOM | 4738 | N | THR | B | 105 | 61.021 | 16.182 | 61.666 | 1.00 51.45 | B |
| ATOM | 4739 | CA | THR | B | 105 | 61.653 | 15.893 | 60.373 | 1.00 52.35 | B |
| ATOM | 4741 | CB | THR | B | 105 | 62.121 | 17.205 | 59.741 | 1.00 52.53 | B |
| ATOM | 4743 | OG1 | THR | B | 105 | 60.963 | 17.995 | 59.433 | 1.00 52.54 | B |
| ATOM | 4745 | CG2 | THR | B | 105 | 62.949 | 16.955 | 58.465 | 1.00 53.23 | B |
| ATOM | 4749 | C | THR | B | 105 | 62.842 | 14.929 | 60.511 | 1.00 52.60 | B |
| ATOM | 4750 | O | THR | B | 105 | 63.708 | 15.128 | 61.356 | 1.00 53.10 | B |
| ATOM | 4752 | N | VAL | B | 106 | 62.870 | 13.888 | 59.682 | 1.00 53.08 | B |
| ATOM | 4753 | CA | VAL | B | 106 | 63.975 | 12.940 | 59.648 | 1.00 53.68 | B |
| ATOM | 4755 | CB | VAL | B | 106 | 63.478 | 11.495 | 59.374 | 1.00 53.86 | B |
| ATOM | 4757 | CG1 | VAL | B | 106 | 64.662 | 10.522 | 59.212 | 1.00 53.25 | B |
| ATOM | 4761 | CG2 | VAL | B | 106 | 62.524 | 11.029 | 60.476 | 1.00 53.40 | B |
| ATOM | 4765 | C | VAL | B | 106 | 64.932 | 13.365 | 58.521 | 1.00 54.57 | B |
| ATOM | 4766 | O | VAL | B | 106 | 64.580 | 13.237 | 57.350 | 1.00 55.08 | B |
| ATOM | 4768 | N | LEU | B | 106A | 66.128 | 13.850 | 58.876 | 1.00 54.88 | B |
| ATOM | 4769 | CA | LEU | B | 106A | 67.103 | 14.365 | 57.905 | 1.00 55.30 | B |
| ATOM | 4771 | CB | LEU | B | 106A | 68.085 | 15.319 | 58.609 | 1.00 55.07 | B |
| ATOM | 4774 | CG | LEU | B | 106A | 67.422 | 16.537 | 59.273 | 1.00 54.77 | B |
| ATOM | 4776 | CD1 | LEU | B | 106A | 68.386 | 17.250 | 60.216 | 1.00 54.17 | B |
| ATOM | 4780 | CD2 | LEU | B | 106A | 66.881 | 17.491 | 58.215 | 1.00 52.39 | B |
| ATOM | 4784 | C | LEU | B | 106A | 67.852 | 13.240 | 57.155 | 1.00 56.11 | B |
| ATOM | 4785 | O | LEU | B | 106A | 67.386 | 12.097 | 57.098 | 1.00 56.21 | B |
| ATOM | 4787 | N | GLY | B | 107 | 68.979 | 13.592 | 56.524 | 1.00 56.88 | B |

FIG 8 – CONT.

| | | | | | | | | | | |
|---|---|---|---|---|---|---|---|---|---|---|
| ATOM | 4788 | CA | GLY | B | 107 | 69.847 | 12.623 | 55.861 | 1.00 56.78 | C |
| ATOM | 4791 | C | GLY | B | 107 | 69.558 | 12.269 | 54.406 | 1.00 56.54 | C |
| ATOM | 4792 | O | GLY | B | 107 | 70.319 | 11.493 | 53.829 | 1.00 57.41 | O |
| ATOM | 4794 | N | GLN | B | 108 | 68.478 | 12.784 | 53.805 | 1.00 55.51 | N |
| ATOM | 4795 | CA | GLN | B | 108 | 68.172 | 12.476 | 52.380 | 1.00 54.74 | C |
| ATOM | 4797 | CB | GLN | B | 108 | 66.775 | 12.990 | 51.938 | 1.00 55.20 | C |
| ATOM | 4800 | CG | GLN | B | 108 | 65.656 | 11.919 | 51.833 | 1.00 57.23 | C |
| ATOM | 4803 | CD | GLN | B | 108 | 65.594 | 11.157 | 50.479 | 1.00 59.15 | C |
| ATOM | 4804 | OE1 | GLN | B | 108 | 65.992 | 11.666 | 49.417 | 1.00 58.61 | O |
| ATOM | 4805 | NE2 | GLN | B | 108 | 65.063 | 9.930 | 50.530 | 1.00 60.03 | N |
| ATOM | 4808 | C | GLN | B | 108 | 69.252 | 13.110 | 51.483 | 1.00 52.71 | C |
| ATOM | 4809 | O | GLN | B | 108 | 69.687 | 14.228 | 51.747 | 1.00 51.86 | O |
| ATOM | 4811 | N | PRO | B | 109 | 69.687 | 12.385 | 50.434 | 1.00 51.12 | N |
| ATOM | 4812 | CA | PRO | B | 109 | 70.643 | 12.960 | 49.493 | 1.00 50.49 | C |
| ATOM | 4814 | CB | PRO | B | 109 | 71.049 | 11.762 | 48.628 | 1.00 50.42 | C |
| ATOM | 4817 | CG | PRO | B | 109 | 69.885 | 10.809 | 48.721 | 1.00 50.78 | C |
| ATOM | 4820 | CD | PRO | B | 109 | 69.312 | 11.000 | 50.073 | 1.00 50.90 | C |
| ATOM | 4823 | C | PRO | B | 109 | 69.974 | 14.027 | 48.634 | 1.00 49.73 | C |
| ATOM | 4824 | O | PRO | B | 109 | 68.760 | 13.944 | 48.410 | 1.00 49.70 | O |
| ATOM | 4825 | N | LYS | B | 110 | 70.747 | 15.020 | 48.185 | 1.00 48.80 | N |
| ATOM | 4826 | CA | LYS | B | 110 | 70.258 | 15.994 | 47.211 | 1.00 48.13 | C |
| ATOM | 4828 | CB | LYS | B | 110 | 71.390 | 16.894 | 46.681 | 1.00 48.25 | C |
| ATOM | 4835 | C | LYS | B | 110 | 69.607 | 15.196 | 46.085 | 1.00 47.19 | C |
| ATOM | 4836 | O | LYS | B | 110 | 70.096 | 14.123 | 45.755 | 1.00 48.20 | O |
| ATOM | 4838 | N | ALA | B | 111 | 68.456 | 15.656 | 45.583 | 1.00 45.73 | N |
| ATOM | 4839 | CA | ALA | B | 111 | 67.861 | 15.134 | 44.349 | 1.00 44.50 | C |
| ATOM | 4841 | CB | ALA | B | 111 | 66.719 | 14.222 | 44.643 | 1.00 44.76 | C |
| ATOM | 4845 | C | ALA | B | 111 | 67.412 | 16.307 | 43.463 | 1.00 43.93 | C |
| ATOM | 4846 | O | ALA | B | 111 | 66.815 | 17.294 | 43.938 | 1.00 43.35 | O |
| ATOM | 4848 | N | ALA | B | 112 | 67.758 | 16.218 | 42.179 | 1.00 43.05 | N |
| ATOM | 4849 | CA | ALA | B | 112 | 67.404 | 17.238 | 41.201 | 1.00 41.97 | B |

FIG 8 – CONT.

| ATOM | 4851 | CB | ALA B 112 | 68.366 | 17.176 | 39.977 | 1.00 | 42.24 | B C |
| --- | --- | --- | --- | --- | --- | --- | --- | --- | --- |
| ATOM | 4855 | C | ALA B 112 | 65.950 | 17.010 | 40.769 | 1.00 | 40.69 | B C |
| ATOM | 4856 | O | ALA B 112 | 65.508 | 15.864 | 40.645 | 1.00 | 40.28 | B O |
| ATOM | 4858 | N | PRO B 113 | 65.202 | 18.097 | 40.549 | 1.00 | 39.39 | B N |
| ATOM | 4859 | CA | PRO B 113 | 63.789 | 17.967 | 40.180 | 1.00 | 38.89 | B C |
| ATOM | 4861 | CB | PRO B 113 | 63.261 | 19.399 | 40.343 | 1.00 | 39.18 | B C |
| ATOM | 4864 | CG | PRO B 113 | 64.449 | 20.258 | 40.210 | 1.00 | 38.97 | B C |
| ATOM | 4867 | CD | PRO B 113 | 65.573 | 19.500 | 40.803 | 1.00 | 39.07 | B C |
| ATOM | 4870 | C | PRO B 113 | 63.578 | 17.494 | 38.754 | 1.00 | 38.47 | B O |
| ATOM | 4871 | O | PRO B 113 | 64.376 | 17.814 | 37.900 | 1.00 | 38.19 | B N |
| ATOM | 4872 | N | SER B 114 | 62.543 | 16.680 | 38.537 | 1.00 | 38.22 | B C |
| ATOM | 4873 | CA | SER B 114 | 61.973 | 16.440 | 37.211 | 1.00 | 38.09 | B C |
| ATOM | 4875 | CB | SER B 114 | 61.188 | 15.129 | 37.154 | 1.00 | 38.42 | B O |
| ATOM | 4878 | OG | SER B 114 | 62.062 | 14.032 | 37.145 | 1.00 | 40.70 | B C |
| ATOM | 4880 | C | SER B 114 | 60.988 | 17.548 | 36.979 | 1.00 | 37.29 | B O |
| ATOM | 4881 | O | SER B 114 | 60.254 | 17.919 | 37.895 | 1.00 | 37.90 | B N |
| ATOM | 4883 | N | VAL B 115 | 60.970 | 18.080 | 35.774 | 1.00 | 36.03 | B C |
| ATOM | 4884 | CA | VAL B 115 | 60.092 | 19.186 | 35.426 | 1.00 | 35.03 | B C |
| ATOM | 4886 | CB | VAL B 115 | 60.883 | 20.466 | 35.193 | 1.00 | 35.13 | B C |
| ATOM | 4888 | CG1 | VAL B 115 | 59.973 | 21.576 | 34.730 | 1.00 | 35.86 | B C |
| ATOM | 4892 | CG2 | VAL B 115 | 61.621 | 20.889 | 36.463 | 1.00 | 34.21 | B C |
| ATOM | 4896 | C | VAL B 115 | 59.356 | 18.800 | 34.170 | 1.00 | 34.59 | B O |
| ATOM | 4897 | O | VAL B 115 | 59.985 | 18.417 | 33.166 | 1.00 | 34.77 | B N |
| ATOM | 4899 | N | THR B 116 | 58.025 | 18.822 | 34.242 | 1.00 | 33.58 | B C |
| ATOM | 4900 | CA | THR B 116 | 57.174 | 18.608 | 33.076 | 1.00 | 32.47 | B C |
| ATOM | 4902 | CB | THR B 116 | 56.311 | 17.371 | 33.251 | 1.00 | 33.27 | B O |
| ATOM | 4904 | OG1 | THR B 116 | 57.128 | 16.278 | 33.672 | 1.00 | 32.18 | B C |
| ATOM | 4906 | CG2 | THR B 116 | 55.618 | 16.999 | 31.939 | 1.00 | 33.41 | B C |
| ATOM | 4910 | C | THR B 116 | 56.277 | 19.830 | 32.906 | 1.00 | 31.65 | B O |
| ATOM | 4911 | O | THR B 116 | 55.634 | 20.285 | 33.858 | 1.00 | 31.63 | B |

FIG 8 – CONT.

| | | | | | | | | | | |
|---|---|---|---|---|---|---|---|---|---|---|
| ATOM | 4913 | N | LEU | B | 117 | 56.231 | 20.369 | 31.697 | 1.00 30.08 | B N |
| ATOM | 4914 | CA | LEU | B | 117 | 55.371 | 21.487 | 31.396 | 1.00 29.80 | B C |
| ATOM | 4916 | CB | LEU | B | 117 | 56.189 | 22.672 | 30.929 | 1.00 29.38 | B C |
| ATOM | 4919 | CG | LEU | B | 117 | 55.451 | 23.932 | 30.451 | 1.00 30.41 | B C |
| ATOM | 4921 | CD1 | LEU | B | 117 | 54.718 | 24.586 | 31.590 | 1.00 29.69 | B C |
| ATOM | 4925 | CD2 | LEU | B | 117 | 56.441 | 24.915 | 29.859 | 1.00 30.40 | B C |
| ATOM | 4929 | C | LEU | B | 117 | 54.370 | 21.070 | 30.331 | 1.00 29.32 | B C |
| ATOM | 4930 | O | LEU | B | 117 | 54.779 | 20.555 | 29.288 | 1.00 30.05 | B O |
| ATOM | 4932 | N | PHE | B | 118 | 53.077 | 21.303 | 30.590 | 1.00 28.64 | B N |
| ATOM | 4933 | CA | PHE | B | 118 | 52.013 | 21.120 | 29.597 | 1.00 28.88 | B C |
| ATOM | 4935 | CB | PHE | B | 118 | 50.902 | 20.220 | 30.118 | 1.00 28.77 | B C |
| ATOM | 4938 | CG | PHE | B | 118 | 51.351 | 18.792 | 30.383 | 1.00 29.52 | B C |
| ATOM | 4939 | CD1 | PHE | B | 118 | 51.410 | 17.870 | 29.341 | 1.00 29.74 | B C |
| ATOM | 4941 | CE1 | PHE | B | 118 | 51.792 | 16.559 | 29.565 | 1.00 30.24 | B C |
| ATOM | 4943 | CZ | PHE | B | 118 | 52.127 | 16.150 | 30.862 | 1.00 31.72 | B C |
| ATOM | 4945 | CE2 | PHE | B | 118 | 52.074 | 17.085 | 31.916 | 1.00 31.26 | B C |
| ATOM | 4947 | CD2 | PHE | B | 118 | 51.694 | 18.388 | 31.666 | 1.00 27.58 | B C |
| ATOM | 4949 | C | PHE | B | 118 | 51.404 | 22.439 | 29.164 | 1.00 29.07 | B C |
| ATOM | 4950 | O | PHE | B | 118 | 51.197 | 23.331 | 29.994 | 1.00 27.95 | B O |
| ATOM | 4952 | N | PRO | B | 119 | 51.110 | 22.563 | 27.846 | 1.00 28.85 | B N |
| ATOM | 4953 | CA | PRO | B | 119 | 50.370 | 23.689 | 27.357 | 1.00 29.08 | B C |
| ATOM | 4955 | CB | PRO | B | 119 | 50.581 | 23.610 | 25.828 | 1.00 29.47 | B C |
| ATOM | 4958 | CG | PRO | B | 119 | 50.825 | 22.173 | 25.551 | 1.00 27.59 | B C |
| ATOM | 4961 | CD | PRO | B | 119 | 51.535 | 21.655 | 26.748 | 1.00 28.76 | B C |
| ATOM | 4964 | C | PRO | B | 119 | 48.905 | 23.523 | 27.676 | 1.00 29.41 | B C |
| ATOM | 4965 | O | PRO | B | 119 | 48.489 | 22.445 | 28.012 | 1.00 28.81 | B O |
| ATOM | 4966 | N | PRO | B | 120 | 48.112 | 24.571 | 27.481 | 1.00 30.58 | B N |
| ATOM | 4967 | CA | PRO | B | 120 | 46.667 | 24.402 | 27.534 | 1.00 31.63 | B C |
| ATOM | 4969 | CB | PRO | B | 120 | 46.140 | 25.736 | 27.012 | 1.00 31.81 | B C |
| ATOM | 4972 | CG | PRO | B | 120 | 47.285 | 26.697 | 27.119 | 1.00 31.37 | B C |
| ATOM | 4975 | CD | PRO | B | 120 | 48.497 | 25.885 | 26.947 | 1.00 30.69 | B |

FIG 8 – CONT.

| | | | | | | | | | | |
|---|---|---|---|---|---|---|---|---|---|---|
| ATOM | 4978 | C | PRO | B | 120 | 46.177 | 23.297 | 26.609 | 1.00 32.75 | B C |
| ATOM | 4979 | O | PRO | B | 120 | 46.730 | 23.117 | 25.535 | 1.00 32.30 | B O |
| ATOM | 4980 | N | SER | B | 121 | 45.128 | 22.588 | 27.008 | 1.00 33.58 | B N |
| ATOM | 4981 | CA | SER | B | 121 | 44.468 | 21.639 | 26.116 | 1.00 34.68 | B C |
| ATOM | 4983 | CB | SER | B | 121 | 43.703 | 20.572 | 26.941 | 1.00 34.99 | B C |
| ATOM | 4986 | OG | SER | B | 121 | 42.631 | 21.129 | 27.682 | 1.00 33.73 | B O |
| ATOM | 4988 | C | SER | B | 121 | 43.524 | 22.392 | 25.166 | 1.00 35.61 | B C |
| ATOM | 4989 | O | SER | B | 121 | 43.052 | 23.508 | 25.469 | 1.00 34.23 | B O |
| ATOM | 4991 | N | SER | B | 122 | 43.255 | 21.795 | 24.002 | 1.00 37.23 | B N |
| ATOM | 4992 | CA | SER | B | 122 | 42.310 | 22.414 | 23.043 | 1.00 38.71 | B C |
| ATOM | 4994 | CB | SER | B | 122 | 42.265 | 21.648 | 21.714 | 1.00 39.38 | B C |
| ATOM | 4997 | OG | SER | B | 122 | 42.325 | 20.241 | 21.915 | 1.00 42.79 | B O |
| ATOM | 4999 | C | SER | B | 122 | 40.923 | 22.528 | 23.666 | 1.00 39.02 | B C |
| ATOM | 5000 | O | SER | B | 122 | 40.256 | 23.571 | 23.551 | 1.00 39.37 | B O |
| ATOM | 5002 | N | GLU | B | 123 | 40.514 | 21.471 | 24.366 | 1.00 39.29 | B N |
| ATOM | 5003 | CA | GLU | B | 123 | 39.284 | 21.479 | 25.159 | 1.00 39.64 | B C |
| ATOM | 5005 | CB | GLU | B | 123 | 39.170 | 20.215 | 26.024 | 1.00 40.21 | B C |
| ATOM | 5008 | CG | GLU | B | 123 | 38.434 | 19.081 | 25.404 | 1.00 42.36 | B C |
| ATOM | 5011 | CD | GLU | B | 123 | 38.516 | 17.826 | 26.248 | 1.00 47.11 | B C |
| ATOM | 5012 | OE1 | GLU | B | 123 | 37.957 | 17.844 | 27.384 | 1.00 45.43 | B O |
| ATOM | 5013 | OE2 | GLU | B | 123 | 39.137 | 16.831 | 25.771 | 1.00 49.13 | B O |
| ATOM | 5014 | C | GLU | B | 123 | 39.193 | 22.683 | 26.074 | 1.00 39.30 | B C |
| ATOM | 5015 | O | GLU | B | 123 | 38.186 | 23.380 | 26.062 | 1.00 39.84 | B O |
| ATOM | 5017 | N | GLU | B | 124 | 40.224 | 22.944 | 26.872 | 1.00 39.19 | B N |
| ATOM | 5018 | CA | GLU | B | 124 | 40.133 | 24.079 | 27.793 | 1.00 39.19 | B C |
| ATOM | 5020 | CB | GLU | B | 124 | 41.328 | 24.137 | 28.741 | 1.00 38.76 | B C |
| ATOM | 5023 | CG | GLU | B | 124 | 41.245 | 25.283 | 29.723 | 1.00 35.14 | B C |
| ATOM | 5026 | CD | GLU | B | 124 | 42.464 | 25.423 | 30.584 | 1.00 34.43 | B C |
| ATOM | 5027 | OE1 | GLU | B | 124 | 43.587 | 24.965 | 30.197 | 1.00 30.32 | B O |
| ATOM | 5028 | OE2 | GLU | B | 124 | 42.294 | 26.018 | 31.674 | 1.00 32.82 | B O |

FIG 8 – CONT.

| ATOM | 5029 | C   | GLU | B | 124 | 39.988 | 25.383 | 27.023 | 1.00 | 40.51 | B | C |
|------|------|-----|-----|---|-----|--------|--------|--------|------|-------|---|---|
| ATOM | 5030 | O   | GLU | B | 124 | 39.249 | 26.260 | 27.425 | 1.00 | 41.00 | B | O |
| ATOM | 5032 | N   | LEU | B | 125 | 40.705 | 25.527 | 25.917 | 1.00 | 43.02 | B | N |
| ATOM | 5033 | CA  | LEU | B | 125 | 40.477 | 26.688 | 25.022 | 1.00 | 44.42 | B | C |
| ATOM | 5035 | CB  | LEU | B | 125 | 41.364 | 26.604 | 23.783 | 1.00 | 44.01 | B | C |
| ATOM | 5038 | CG  | LEU | B | 125 | 42.843 | 26.492 | 24.111 | 1.00 | 43.03 | B | C |
| ATOM | 5040 | CD1 | LEU | B | 125 | 43.670 | 26.444 | 22.861 | 1.00 | 43.29 | B | C |
| ATOM | 5044 | CD2 | LEU | B | 125 | 43.278 | 27.621 | 25.012 | 1.00 | 40.88 | B | C |
| ATOM | 5048 | C   | LEU | B | 125 | 38.997 | 26.813 | 24.623 | 1.00 | 45.91 | B | C |
| ATOM | 5049 | O   | LEU | B | 125 | 38.411 | 27.893 | 24.748 | 1.00 | 46.71 | B | O |
| ATOM | 5051 | N   | GLN | B | 126 | 38.375 | 25.696 | 24.239 | 1.00 | 47.41 | B | N |
| ATOM | 5052 | CA  | GLN | B | 126 | 36.972 | 25.706 | 23.784 | 1.00 | 48.25 | B | C |
| ATOM | 5054 | CB  | GLN | B | 126 | 36.480 | 24.305 | 23.403 | 1.00 | 48.49 | B | C |
| ATOM | 5061 | C   | GLN | B | 126 | 36.084 | 26.265 | 24.860 | 1.00 | 49.05 | B | C |
| ATOM | 5062 | O   | GLN | B | 126 | 35.061 | 26.894 | 24.564 | 1.00 | 50.24 | B | O |
| ATOM | 5064 | N   | ALA | B | 127 | 36.482 | 26.034 | 26.113 | 1.00 | 49.04 | B | N |
| ATOM | 5065 | CA  | ALA | B | 127 | 35.796 | 26.571 | 27.277 | 1.00 | 48.64 | B | C |
| ATOM | 5067 | CB  | ALA | B | 127 | 35.953 | 25.605 | 28.465 | 1.00 | 49.33 | B | C |
| ATOM | 5071 | C   | ALA | B | 127 | 36.292 | 27.967 | 27.660 | 1.00 | 48.29 | B | C |
| ATOM | 5072 | O   | ALA | B | 127 | 35.993 | 28.457 | 28.770 | 1.00 | 48.47 | B | O |
| ATOM | 5074 | N   | ASN | B | 128 | 37.016 | 28.625 | 26.751 | 1.00 | 47.24 | B | N |
| ATOM | 5075 | CA  | ASN | B | 128 | 37.485 | 30.003 | 26.974 | 1.00 | 46.66 | B | C |
| ATOM | 5077 | CB  | ASN | B | 128 | 36.303 | 30.950 | 27.090 | 1.00 | 47.30 | B | C |
| ATOM | 5080 | CG  | ASN | B | 128 | 36.169 | 31.831 | 25.876 | 1.00 | 50.69 | B | C |
| ATOM | 5081 | OD1 | ASN | B | 128 | 36.862 | 32.865 | 25.766 | 1.00 | 50.19 | B | O |
| ATOM | 5082 | ND2 | ASN | B | 128 | 35.281 | 31.425 | 24.936 | 1.00 | 51.95 | B | N |
| ATOM | 5085 | C   | ASN | B | 128 | 38.437 | 30.243 | 28.131 | 1.00 | 44.76 | B | C |
| ATOM | 5086 | O   | ASN | B | 128 | 38.410 | 31.285 | 28.746 | 1.00 | 44.52 | B | O |
| ATOM | 5088 | N   | LYS | B | 129 | 39.311 | 29.279 | 28.383 | 1.00 | 43.77 | B | N |
| ATOM | 5089 | CA  | LYS | B | 129 | 40.338 | 29.396 | 29.414 | 1.00 | 42.68 | B | C |
| ATOM | 5091 | CB  | LYS | B | 129 | 39.928 | 28.633 | 30.677 | 1.00 | 43.16 | B | |

FIG 8 – CONT.

```
C
ATOM   5094  CG   LYS B 129      38.716  29.189  31.450  1.00 44.82      B
C
ATOM   5097  CD   LYS B 129      37.757  28.051  31.878  1.00 46.72      B
C
ATOM   5100  CE   LYS B 129      38.442  26.841  32.576  1.00 46.89      B
C
ATOM   5103  NZ   LYS B 129      37.569  25.616  32.504  1.00 45.62      B
N
ATOM   5107  C    LYS B 129      41.625  28.783  28.896  1.00 40.13      B
C
ATOM   5108  O    LYS B 129      41.605  28.000  27.961  1.00 38.90      B
O
ATOM   5110  N    ALA B 130      42.736  29.114  29.545  1.00 37.07      B
N
ATOM   5111  CA   ALA B 130      44.010  28.516  29.194  1.00 34.91      B
C
ATOM   5113  CB   ALA B 130      44.703  29.344  28.106  1.00 34.50      B
C
ATOM   5117  C    ALA B 130      44.882  28.434  30.422  1.00 32.48      B
C
ATOM   5118  O    ALA B 130      45.194  29.458  31.023  1.00 32.68      B
O
ATOM   5120  N    THR B 131      45.306  27.223  30.759  1.00 29.90      B
N
ATOM   5121  CA   THR B 131      46.216  27.004  31.854  1.00 28.77      B
C
ATOM   5123  CB   THR B 131      45.572  26.140  32.942  1.00 28.26      B
C
ATOM   5125  OG1  THR B 131      44.206  26.555  33.152  1.00 27.37      B
O
ATOM   5127  CG2  THR B 131      46.385  26.242  34.209  1.00 25.68      B
C
ATOM   5131  C    THR B 131      47.487  26.300  31.434  1.00 28.37      B
C
ATOM   5132  O    THR B 131      47.436  25.233  30.839  1.00 28.94      B
O
ATOM   5134  N    LEU B 132      48.627  26.876  31.775  1.00 28.03      B
N
ATOM   5135  CA   LEU B 132      49.893  26.201  31.610  1.00 28.70      B
C
ATOM   5137  CB   LEU B 132      50.988  27.180  31.197  1.00 28.66      B
C
ATOM   5140  CG   LEU B 132      50.944  27.714  29.765  1.00 29.66      B
C
ATOM   5142  CD1  LEU B 132      49.823  28.659  29.629  1.00 27.92      B
C
ATOM   5146  CD2  LEU B 132      52.277  28.384  29.378  1.00 29.05      B
C
ATOM   5150  C    LEU B 132      50.224  25.541  32.946  1.00 29.06      B
C
ATOM   5151  O    LEU B 132      50.110  26.178  34.014  1.00 29.78      B
O
ATOM   5153  N    VAL B 133      50.587  24.266  32.897  1.00 29.37      B
N
ATOM   5154  CA   VAL B 133      50.880  23.475  34.093  1.00 29.13      B
C
ATOM   5156  CB   VAL B 133      50.056  22.166  34.098  1.00 29.87      B
C
ATOM   5158  CG1  VAL B 133      50.393  21.309  35.325  1.00 28.21      B
C
```

FIG 8 – CONT.

| ATOM | 5162 | CG2 | VAL | B | 133 | 48.537 | 22.485 | 34.038 | 1.00 | 31.34 | B |
| --- | --- | --- | --- | --- | --- | --- | --- | --- | --- | --- | --- |
| C | | | | | | | | | | | |
| ATOM | 5166 | C | VAL | B | 133 | 52.340 | 23.095 | 34.088 | 1.00 | 29.42 | B |
| C | | | | | | | | | | | |
| ATOM | 5167 | O | VAL | B | 133 | 52.801 | 22.469 | 33.146 | 1.00 | 29.30 | B |
| O | | | | | | | | | | | |
| ATOM | 5169 | N | CYS | B | 134 | 53.064 | 23.483 | 35.132 | 1.00 | 29.29 | B |
| N | | | | | | | | | | | |
| ATOM | 5170 | CA | CYS | B | 134 | 54.452 | 23.145 | 35.296 | 1.00 | 29.34 | B |
| C | | | | | | | | | | | |
| ATOM | 5172 | CB | CYS | B | 134 | 55.289 | 24.409 | 35.336 | 1.00 | 29.13 | B |
| C | | | | | | | | | | | |
| ATOM | 5175 | SG | CYS | B | 134 | 57.098 | 24.151 | 35.333 | 1.00 | 29.97 | B |
| S | | | | | | | | | | | |
| ATOM | 5177 | C | CYS | B | 134 | 54.607 | 22.306 | 36.586 | 1.00 | 29.28 | B |
| C | | | | | | | | | | | |
| ATOM | 5178 | O | CYS | B | 134 | 54.474 | 22.834 | 37.677 | 1.00 | 28.99 | B |
| O | | | | | | | | | | | |
| ATOM | 5180 | N | LEU | B | 135 | 54.875 | 21.013 | 36.411 | 1.00 | 29.23 | B |
| N | | | | | | | | | | | |
| ATOM | 5181 | CA | LEU | B | 135 | 54.994 | 20.044 | 37.484 | 1.00 | 30.31 | B |
| C | | | | | | | | | | | |
| ATOM | 5183 | CB | LEU | B | 135 | 54.263 | 18.779 | 37.082 | 1.00 | 30.20 | B |
| C | | | | | | | | | | | |
| ATOM | 5186 | CG | LEU | B | 135 | 52.844 | 19.148 | 36.640 | 1.00 | 31.16 | B |
| C | | | | | | | | | | | |
| ATOM | 5188 | CD1 | LEU | B | 135 | 52.150 | 17.981 | 36.015 | 1.00 | 29.38 | B |
| C | | | | | | | | | | | |
| ATOM | 5192 | CD2 | LEU | B | 135 | 52.027 | 19.749 | 37.823 | 1.00 | 27.60 | B |
| C | | | | | | | | | | | |
| ATOM | 5196 | C | LEU | B | 135 | 56.454 | 19.711 | 37.809 | 1.00 | 31.16 | B |
| C | | | | | | | | | | | |
| ATOM | 5197 | O | LEU | B | 135 | 57.252 | 19.341 | 36.937 | 1.00 | 30.32 | B |
| O | | | | | | | | | | | |
| ATOM | 5199 | N | VAL | B | 136 | 56.791 | 19.863 | 39.089 | 1.00 | 31.55 | B |
| N | | | | | | | | | | | |
| ATOM | 5200 | CA | VAL | B | 136 | 58.120 | 19.650 | 39.584 | 1.00 | 31.27 | B |
| C | | | | | | | | | | | |
| ATOM | 5202 | CB | VAL | B | 136 | 58.613 | 20.933 | 40.182 | 1.00 | 31.12 | B |
| C | | | | | | | | | | | |
| ATOM | 5204 | CG1 | VAL | B | 136 | 60.137 | 20.867 | 40.439 | 1.00 | 29.99 | B |
| C | | | | | | | | | | | |
| ATOM | 5208 | CG2 | VAL | B | 136 | 58.219 | 22.087 | 39.268 | 1.00 | 29.83 | B |
| C | | | | | | | | | | | |
| ATOM | 5212 | C | VAL | B | 136 | 58.087 | 18.573 | 40.644 | 1.00 | 32.87 | B |
| C | | | | | | | | | | | |
| ATOM | 5213 | O | VAL | B | 136 | 57.399 | 18.712 | 41.658 | 1.00 | 32.71 | B |
| O | | | | | | | | | | | |
| ATOM | 5215 | N | SER | B | 137 | 58.824 | 17.494 | 40.435 | 1.00 | 34.81 | B |
| N | | | | | | | | | | | |
| ATOM | 5216 | CA | SER | B | 137 | 58.807 | 16.423 | 41.423 | 1.00 | 36.46 | B |
| C | | | | | | | | | | | |
| ATOM | 5218 | CB | SER | B | 137 | 57.894 | 15.318 | 40.913 | 1.00 | 37.08 | B |
| C | | | | | | | | | | | |
| ATOM | 5221 | OG | SER | B | 137 | 58.410 | 14.841 | 39.703 | 1.00 | 39.60 | B |
| O | | | | | | | | | | | |
| ATOM | 5223 | C | SER | B | 137 | 60.171 | 15.820 | 41.733 | 1.00 | 37.09 | B |
| C | | | | | | | | | | | |
| ATOM | 5224 | O | SER | B | 137 | 61.166 | 16.101 | 41.048 | 1.00 | 36.35 | B |
| O | | | | | | | | | | | |
| ATOM | 5226 | N | ASP | B | 138 | 60.172 | 14.980 | 42.775 | 1.00 | 38.38 | B |

FIG 8 – CONT.

| ATOM | 5227 | CA | ASP | B | 138 | 61.293 | 14.138 | 43.185 | 1.00 | 39.25 | B | N C |
|---|---|---|---|---|---|---|---|---|---|---|---|---|
| ATOM | 5229 | CB | ASP | B | 138 | 61.579 | 13.076 | 42.126 | 1.00 | 40.36 | B | C |
| ATOM | 5232 | CG | ASP | B | 138 | 60.402 | 12.124 | 41.942 | 1.00 | 43.81 | B | C |
| ATOM | 5233 | OD1 | ASP | B | 138 | 60.046 | 11.448 | 42.938 | 1.00 | 46.17 | B | O |
| ATOM | 5234 | OD2 | ASP | B | 138 | 59.832 | 12.052 | 40.819 | 1.00 | 48.58 | B | O |
| ATOM | 5235 | C | ASP | B | 138 | 62.517 | 14.968 | 43.469 | 1.00 | 39.42 | B | C |
| ATOM | 5236 | O | ASP | B | 138 | 63.614 | 14.654 | 43.024 | 1.00 | 39.90 | B | O |
| ATOM | 5238 | N | PHE | B | 139 | 62.329 | 16.047 | 44.221 | 1.00 | 39.40 | B | N |
| ATOM | 5239 | CA | PHE | B | 139 | 63.454 | 16.869 | 44.588 | 1.00 | 38.84 | B | C |
| ATOM | 5241 | CB | PHE | B | 139 | 63.360 | 18.221 | 43.887 | 1.00 | 38.73 | B | C |
| ATOM | 5244 | CG | PHE | B | 139 | 62.259 | 19.102 | 44.360 | 1.00 | 37.86 | B | C |
| ATOM | 5245 | CD1 | PHE | B | 139 | 62.479 | 20.009 | 45.386 | 1.00 | 37.21 | B | C |
| ATOM | 5247 | CE1 | PHE | B | 139 | 61.501 | 20.866 | 45.809 | 1.00 | 35.89 | B | C |
| ATOM | 5249 | CZ | PHE | B | 139 | 60.266 | 20.844 | 45.187 | 1.00 | 37.19 | B | C |
| ATOM | 5251 | CE2 | PHE | B | 139 | 60.028 | 19.946 | 44.144 | 1.00 | 35.88 | B | C |
| ATOM | 5253 | CD2 | PHE | B | 139 | 61.032 | 19.099 | 43.725 | 1.00 | 38.06 | B | C |
| ATOM | 5255 | C | PHE | B | 139 | 63.692 | 16.992 | 46.103 | 1.00 | 38.94 | B | C |
| ATOM | 5256 | O | PHE | B | 139 | 62.774 | 16.800 | 46.909 | 1.00 | 38.19 | B | O |
| ATOM | 5258 | N | TYR | B | 140 | 64.954 | 17.260 | 46.457 | 1.00 | 38.69 | B | N |
| ATOM | 5259 | CA | TYR | B | 140 | 65.400 | 17.416 | 47.849 | 1.00 | 38.87 | B | C |
| ATOM | 5261 | CB | TYR | B | 140 | 65.667 | 16.053 | 48.509 | 1.00 | 38.64 | B | C |
| ATOM | 5264 | CG | TYR | B | 140 | 65.840 | 16.259 | 49.975 | 1.00 | 39.71 | B | C |
| ATOM | 5265 | CD1 | TYR | B | 140 | 64.733 | 16.192 | 50.836 | 1.00 | 40.11 | B | C |
| ATOM | 5267 | CE1 | TYR | B | 140 | 64.861 | 16.417 | 52.192 | 1.00 | 41.41 | B | C |
| ATOM | 5269 | CZ | TYR | B | 140 | 66.111 | 16.754 | 52.728 | 1.00 | 42.56 | B | C |
| ATOM | 5270 | OH | TYR | B | 140 | 66.225 | 17.001 | 54.093 | 1.00 | 42.55 | B | O |
| ATOM | 5272 | CE2 | TYR | B | 140 | 67.224 | 16.854 | 51.881 | 1.00 | 41.65 | B | C |
| ATOM | 5274 | CD2 | TYR | B | 140 | 67.077 | 16.613 | 50.509 | 1.00 | 39.71 | B | C |
| ATOM | 5276 | C | TYR | B | 140 | 66.690 | 18.246 | 47.887 | 1.00 | 38.73 | B | C |
| ATOM | 5277 | O | TYR | B | 140 | 67.644 | 17.901 | 47.182 | 1.00 | 38.34 | B | O |

FIG 8 – CONT.

| ATOM | 5279 | N | PRO | B | 141 | 66.758 | 19.301 | 48.723 | 1.00 | 38.58 | B |
|------|------|-----|-----|---|-----|--------|--------|--------|------|-------|---|
| ATOM | 5280 | CA | PRO | B | 141 | 65.806 | 19.775 | 49.738 | 1.00 | 38.84 | B |
| ATOM | 5282 | CB | PRO | B | 141 | 66.551 | 20.911 | 50.469 | 1.00 | 38.35 | B |
| ATOM | 5285 | CG | PRO | B | 141 | 67.879 | 21.049 | 49.847 | 1.00 | 38.48 | B |
| ATOM | 5288 | CD | PRO | B | 141 | 67.977 | 20.125 | 48.662 | 1.00 | 38.82 | B |
| ATOM | 5291 | C | PRO | B | 141 | 64.491 | 20.297 | 49.154 | 1.00 | 39.02 | B |
| ATOM | 5292 | O | PRO | B | 141 | 64.356 | 20.404 | 47.922 | 1.00 | 38.51 | B |
| ATOM | 5293 | N | GLY | B | 142 | 63.544 | 20.617 | 50.036 | 1.00 | 38.81 | B |
| ATOM | 5294 | CA | GLY | B | 142 | 62.183 | 21.010 | 49.642 | 1.00 | 39.10 | B |
| ATOM | 5297 | C | GLY | B | 142 | 62.057 | 22.504 | 49.497 | 1.00 | 39.64 | B |
| ATOM | 5298 | O | GLY | B | 142 | 61.333 | 23.151 | 50.269 | 1.00 | 40.67 | B |
| ATOM | 5300 | N | ALA | B | 143 | 62.775 | 23.054 | 48.520 | 1.00 | 39.66 | B |
| ATOM | 5301 | CA | ALA | B | 143 | 62.779 | 24.481 | 48.217 | 1.00 | 39.56 | B |
| ATOM | 5303 | CB | ALA | B | 143 | 63.810 | 25.234 | 49.104 | 1.00 | 39.91 | B |
| ATOM | 5307 | C | ALA | B | 143 | 63.133 | 24.638 | 46.728 | 1.00 | 39.33 | B |
| ATOM | 5308 | O | ALA | B | 143 | 64.197 | 24.199 | 46.294 | 1.00 | 39.51 | B |
| ATOM | 5310 | N | VAL | B | 144 | 62.209 | 25.199 | 45.951 | 1.00 | 38.72 | B |
| ATOM | 5311 | CA | VAL | B | 144 | 62.446 | 25.521 | 44.562 | 1.00 | 38.17 | B |
| ATOM | 5313 | CB | VAL | B | 144 | 61.696 | 24.615 | 43.567 | 1.00 | 38.59 | B |
| ATOM | 5315 | CG1 | VAL | B | 144 | 62.308 | 23.209 | 43.482 | 1.00 | 39.08 | B |
| ATOM | 5319 | CG2 | VAL | B | 144 | 60.199 | 24.571 | 43.914 | 1.00 | 38.38 | B |
| ATOM | 5323 | C | VAL | B | 144 | 61.899 | 26.895 | 44.322 | 1.00 | 37.45 | B |
| ATOM | 5324 | O | VAL | B | 144 | 61.046 | 27.371 | 45.050 | 1.00 | 36.68 | B |
| ATOM | 5326 | N | THR | B | 145 | 62.395 | 27.519 | 43.274 | 1.00 | 37.61 | B |
| ATOM | 5327 | CA | THR | B | 145 | 61.813 | 28.732 | 42.754 | 1.00 | 38.07 | B |
| ATOM | 5329 | CB | THR | B | 145 | 62.852 | 29.820 | 42.669 | 1.00 | 38.08 | B |
| ATOM | 5331 | OG1 | THR | B | 145 | 63.285 | 30.130 | 44.002 | 1.00 | 40.40 | B |
| ATOM | 5333 | CG2 | THR | B | 145 | 62.260 | 31.082 | 41.988 | 1.00 | 39.07 | B |
| ATOM | 5337 | C | THR | B | 145 | 61.305 | 28.392 | 41.369 | 1.00 | 37.84 | B |
| ATOM | 5338 | O | THR | B | 145 | 61.972 | 27.672 | 40.628 | 1.00 | 37.63 | B |
| ATOM | 5340 | N | VAL | B | 146 | 60.118 | 28.891 | 41.031 | 1.00 | 37.94 | B |

FIG 8 – CONT.

| ATOM | 5341 | CA | VAL | B | 146 | 59.553 | 28.710 | 39.693 | 1.00 | 36.89 | B N C |
| --- | --- | --- | --- | --- | --- | --- | --- | --- | --- | --- | --- |
| ATOM | 5343 | CB | VAL | B | 146 | 58.250 | 27.942 | 39.778 | 1.00 | 36.61 | B C |
| ATOM | 5345 | CG1 | VAL | B | 146 | 57.671 | 27.717 | 38.395 | 1.00 | 36.06 | B C |
| ATOM | 5349 | CG2 | VAL | B | 146 | 58.473 | 26.634 | 40.507 | 1.00 | 35.72 | B C |
| ATOM | 5353 | C | VAL | B | 146 | 59.284 | 30.095 | 39.128 | 1.00 | 36.84 | B C |
| ATOM | 5354 | O | VAL | B | 146 | 58.672 | 30.898 | 39.810 | 1.00 | 35.92 | B O |
| ATOM | 5356 | N | ALA | B | 147 | 59.766 | 30.375 | 37.911 | 1.00 | 36.67 | B N |
| ATOM | 5357 | CA | ALA | B | 147 | 59.489 | 31.633 | 37.226 | 1.00 | 36.88 | B C |
| ATOM | 5359 | CB | ALA | B | 147 | 60.723 | 32.471 | 37.151 | 1.00 | 36.32 | B C |
| ATOM | 5363 | C | ALA | B | 147 | 58.952 | 31.335 | 35.825 | 1.00 | 37.33 | B C |
| ATOM | 5364 | O | ALA | B | 147 | 59.281 | 30.300 | 35.244 | 1.00 | 38.09 | B O |
| ATOM | 5366 | N | TRP | B | 148 | 58.111 | 32.225 | 35.292 | 1.00 | 37.60 | B N |
| ATOM | 5367 | CA | TRP | B | 148 | 57.531 | 32.044 | 33.965 | 1.00 | 37.08 | B C |
| ATOM | 5369 | CB | TRP | B | 148 | 56.002 | 32.059 | 34.004 | 1.00 | 36.67 | B C |
| ATOM | 5372 | CG | TRP | B | 148 | 55.391 | 30.916 | 34.702 | 1.00 | 34.79 | B C |
| ATOM | 5373 | CD1 | TRP | B | 148 | 55.182 | 30.811 | 36.039 | 1.00 | 31.59 | B C |
| ATOM | 5375 | NE1 | TRP | B | 148 | 54.592 | 29.618 | 36.330 | 1.00 | 32.26 | B N |
| ATOM | 5377 | CE2 | TRP | B | 148 | 54.391 | 28.913 | 35.174 | 1.00 | 32.20 | B C |
| ATOM | 5378 | CD2 | TRP | B | 148 | 54.867 | 29.713 | 34.114 | 1.00 | 32.25 | B C |
| ATOM | 5379 | CE3 | TRP | B | 148 | 54.781 | 29.229 | 32.812 | 1.00 | 32.19 | B C |
| ATOM | 5381 | CZ3 | TRP | B | 148 | 54.213 | 27.953 | 32.607 | 1.00 | 33.91 | B C |
| ATOM | 5383 | CH2 | TRP | B | 148 | 53.728 | 27.189 | 33.698 | 1.00 | 33.41 | B C |
| ATOM | 5385 | CZ2 | TRP | B | 148 | 53.819 | 27.651 | 34.979 | 1.00 | 31.18 | B C |
| ATOM | 5387 | C | TRP | B | 148 | 57.994 | 33.137 | 33.031 | 1.00 | 37.97 | B C |
| ATOM | 5388 | O | TRP | B | 148 | 58.302 | 34.244 | 33.455 | 1.00 | 38.59 | B O |
| ATOM | 5390 | N | LYS | B | 149 | 58.031 | 32.829 | 31.745 | 1.00 | 38.55 | B N |
| ATOM | 5391 | CA | LYS | B | 149 | 58.363 | 33.828 | 30.739 | 1.00 | 39.18 | B C |
| ATOM | 5393 | CB | LYS | B | 149 | 59.815 | 33.701 | 30.318 | 1.00 | 39.83 | B C |
| ATOM | 5396 | CG | LYS | B | 149 | 60.807 | 34.144 | 31.386 | 1.00 | 43.10 | B C |
| ATOM | 5399 | CD | LYS | B | 149 | 62.219 | 33.750 | 31.010 | 1.00 | 47.23 | B C |

FIG 8 – CONT.

| ATOM | 5402 | CE | LYS | B | 149 | 63.229 | 34.110 | 32.111 | 1.00 | 50.42 | B |
| --- | --- | --- | --- | --- | --- | --- | --- | --- | --- | --- | --- |
| ATOM | 5405 | NZ | LYS | B | 149 | 63.034 | 35.457 | 32.722 | 1.00 | 50.83 | B |
| ATOM | 5409 | C | LYS | B | 149 | 57.462 | 33.674 | 29.526 | 1.00 | 38.50 | B |
| ATOM | 5410 | O | LYS | B | 149 | 57.044 | 32.559 | 29.177 | 1.00 | 37.90 | B |
| ATOM | 5412 | N | ALA | B | 150 | 57.142 | 34.813 | 28.916 | 1.00 | 38.20 | B |
| ATOM | 5413 | CA | ALA | B | 150 | 56.412 | 34.866 | 27.663 | 1.00 | 38.10 | B |
| ATOM | 5415 | CB | ALA | B | 150 | 55.112 | 35.647 | 27.831 | 1.00 | 37.51 | B |
| ATOM | 5419 | C | ALA | B | 150 | 57.331 | 35.543 | 26.662 | 1.00 | 38.24 | B |
| ATOM | 5420 | O | ALA | B | 150 | 57.658 | 36.729 | 26.827 | 1.00 | 38.25 | B |
| ATOM | 5422 | N | ASP | B | 151 | 57.762 | 34.789 | 25.647 | 1.00 | 38.58 | B |
| ATOM | 5423 | CA | ASP | B | 151 | 58.694 | 35.291 | 24.634 | 1.00 | 39.34 | B |
| ATOM | 5425 | CB | ASP | B | 151 | 58.002 | 36.342 | 23.749 | 1.00 | 39.38 | B |
| ATOM | 5428 | CG | ASP | B | 151 | 56.932 | 35.748 | 22.856 | 1.00 | 38.28 | B |
| ATOM | 5429 | OD1 | ASP | B | 151 | 57.105 | 34.619 | 22.345 | 1.00 | 37.99 | B |
| ATOM | 5430 | OD2 | ASP | B | 151 | 55.907 | 36.422 | 22.654 | 1.00 | 40.49 | B |
| ATOM | 5431 | C | ASP | B | 151 | 59.941 | 35.897 | 25.263 | 1.00 | 40.78 | B |
| ATOM | 5432 | O | ASP | B | 151 | 60.359 | 36.997 | 24.884 | 1.00 | 41.31 | B |
| ATOM | 5434 | N | GLY | B | 152 | 60.513 | 35.197 | 26.244 | 1.00 | 42.22 | B |
| ATOM | 5435 | CA | GLY | B | 152 | 61.663 | 35.692 | 26.999 | 1.00 | 43.63 | B |
| ATOM | 5438 | C | GLY | B | 152 | 61.417 | 36.807 | 28.019 | 1.00 | 44.79 | B |
| ATOM | 5439 | O | GLY | B | 152 | 62.353 | 37.212 | 28.712 | 1.00 | 46.34 | B |
| ATOM | 5441 | N | SER | B | 153 | 60.196 | 37.324 | 28.128 | 1.00 | 44.97 | B |
| ATOM | 5442 | CA | SER | B | 153 | 59.892 | 38.335 | 29.146 | 1.00 | 45.44 | B |
| ATOM | 5444 | CB | SER | B | 153 | 58.984 | 39.412 | 28.577 | 1.00 | 45.53 | B |
| ATOM | 5447 | OG | SER | B | 153 | 59.726 | 40.243 | 27.711 | 1.00 | 47.92 | B |
| ATOM | 5449 | C | SER | B | 153 | 59.203 | 37.712 | 30.366 | 1.00 | 45.45 | B |
| ATOM | 5450 | O | SER | B | 153 | 58.322 | 36.877 | 30.200 | 1.00 | 44.92 | B |
| ATOM | 5452 | N | PRO | B | 154 | 59.590 | 38.133 | 31.591 | 1.00 | 45.21 | B |
| ATOM | 5453 | CA | PRO | B | 154 | 58.983 | 37.548 | 32.782 | 1.00 | 44.79 | B |
| ATOM | 5455 | CB | PRO | B | 154 | 59.753 | 38.214 | 33.930 | 1.00 | 45.09 | B |
| ATOM | 5458 | CG | PRO | B | 154 | 61.071 | 38.637 | 33.301 | 1.00 | 45.28 | B |

FIG 8 – CONT.

| | | | | | | | | | | |
|---|---|---|---|---|---|---|---|---|---|---|
| ATOM | 5461 | CD | PRO | B | 154 | 60.652 | 39.095 | 31.944 | 1.00 45.11 | B C |
| ATOM | 5464 | C | PRO | B | 154 | 57.490 | 37.838 | 32.908 | 1.00 44.72 | B C |
| ATOM | 5465 | O | PRO | B | 154 | 57.037 | 38.931 | 32.614 | 1.00 44.69 | B O |
| ATOM | 5466 | N | VAL | B | 155 | 56.734 | 36.847 | 33.351 | 1.00 44.39 | B N |
| ATOM | 5467 | CA | VAL | B | 155 | 55.303 | 36.980 | 33.523 | 1.00 44.14 | B C |
| ATOM | 5469 | CB | VAL | B | 155 | 54.560 | 35.939 | 32.663 | 1.00 44.34 | B C |
| ATOM | 5471 | CG1 | VAL | B | 155 | 53.080 | 36.251 | 32.611 | 1.00 43.73 | B C |
| ATOM | 5475 | CG2 | VAL | B | 155 | 55.157 | 35.886 | 31.252 | 1.00 43.97 | B C |
| ATOM | 5479 | C | VAL | B | 155 | 55.038 | 36.681 | 34.980 | 1.00 44.31 | B C |
| ATOM | 5480 | O | VAL | B | 155 | 55.504 | 35.659 | 35.462 | 1.00 43.71 | B O |
| ATOM | 5482 | N | LYS | B | 156 | 54.317 | 37.566 | 35.675 | 1.00 44.58 | B N |
| ATOM | 5483 | CA | LYS | B | 156 | 54.007 | 37.392 | 37.112 | 1.00 44.90 | B C |
| ATOM | 5485 | CB | LYS | B | 156 | 54.625 | 38.535 | 37.933 | 1.00 45.11 | B C |
| ATOM | 5488 | CG | LYS | B | 156 | 56.155 | 38.676 | 37.780 | 1.00 46.55 | B C |
| ATOM | 5491 | CD | LYS | B | 156 | 56.848 | 39.245 | 39.049 | 1.00 47.64 | B C |
| ATOM | 5496 | C | LYS | B | 156 | 52.490 | 37.316 | 37.360 | 1.00 44.50 | B C |
| ATOM | 5497 | O | LYS | B | 156 | 51.995 | 36.530 | 38.195 | 1.00 44.84 | B O |
| ATOM | 5499 | N | VAL | B | 157 | 51.763 | 38.148 | 36.629 | 1.00 43.41 | B N |
| ATOM | 5500 | CA | VAL | B | 157 | 50.314 | 38.140 | 36.635 | 1.00 42.53 | B C |
| ATOM | 5502 | CB | VAL | B | 157 | 49.793 | 39.249 | 35.678 | 1.00 42.60 | B C |
| ATOM | 5504 | CG1 | VAL | B | 157 | 48.348 | 38.998 | 35.298 | 1.00 42.53 | B C |
| ATOM | 5508 | CG2 | VAL | B | 157 | 50.026 | 40.661 | 36.305 | 1.00 41.89 | B C |
| ATOM | 5512 | C | VAL | B | 157 | 49.763 | 36.772 | 36.205 | 1.00 41.68 | B C |
| ATOM | 5513 | O | VAL | B | 157 | 50.118 | 36.264 | 35.155 | 1.00 42.12 | B O |
| ATOM | 5515 | N | GLY | B | 158 | 48.905 | 36.179 | 37.027 | 1.00 40.39 | B N |
| ATOM | 5516 | CA | GLY | B | 158 | 48.251 | 34.919 | 36.683 | 1.00 39.40 | B C |
| ATOM | 5519 | C | GLY | B | 158 | 48.990 | 33.667 | 37.118 | 1.00 38.51 | B C |
| ATOM | 5520 | O | GLY | B | 158 | 48.563 | 32.553 | 36.799 | 1.00 38.15 | B O |
| ATOM | 5522 | N | VAL | B | 159 | 50.087 | 33.842 | 37.854 | 1.00 37.92 | B N |
| ATOM | 5523 | CA | VAL | B | 159 | 50.917 | 32.719 | 38.334 | 1.00 36.78 | B C |

FIG 8 – CONT.

| | | | | | | | | | | |
|---|---|---|---|---|---|---|---|---|---|---|
| ATOM | 5525 | CB | VAL | B | 159 | 52.385 | 33.137 | 38.413 | 1.00 36.34 | B C |
| ATOM | 5527 | CG1 | VAL | B | 159 | 53.249 | 32.062 | 39.042 | 1.00 33.56 | B C |
| ATOM | 5531 | CG2 | VAL | B | 159 | 52.877 | 33.485 | 37.001 | 1.00 35.87 | B C |
| ATOM | 5535 | C | VAL | B | 159 | 50.466 | 32.279 | 39.705 | 1.00 36.78 | B C |
| ATOM | 5536 | O | VAL | B | 159 | 50.287 | 33.104 | 40.580 | 1.00 35.71 | B O |
| ATOM | 5538 | N | GLU | B | 160 | 50.275 | 30.971 | 39.885 | 1.00 37.09 | B N |
| ATOM | 5539 | CA | GLU | B | 160 | 49.961 | 30.414 | 41.196 | 1.00 37.61 | B C |
| ATOM | 5541 | CB | GLU | B | 160 | 48.479 | 30.077 | 41.334 | 1.00 38.24 | B C |
| ATOM | 5544 | CG | GLU | B | 160 | 47.508 | 31.177 | 40.949 | 1.00 41.95 | B C |
| ATOM | 5547 | CD | GLU | B | 160 | 46.950 | 31.985 | 42.141 | 1.00 48.01 | B C |
| ATOM | 5548 | OE1 | GLU | B | 160 | 47.725 | 32.317 | 43.098 | 1.00 47.23 | B O |
| ATOM | 5549 | OE2 | GLU | B | 160 | 45.720 | 32.303 | 42.071 | 1.00 49.63 | B O |
| ATOM | 5550 | C | GLU | B | 160 | 50.787 | 29.168 | 41.409 | 1.00 37.03 | B C |
| ATOM | 5551 | O | GLU | B | 160 | 50.680 | 28.201 | 40.656 | 1.00 36.74 | B O |
| ATOM | 5553 | N | THR | B | 161 | 51.618 | 29.199 | 42.442 | 1.00 36.75 | B N |
| ATOM | 5554 | CA | THR | B | 161 | 52.545 | 28.116 | 42.705 | 1.00 36.96 | B C |
| ATOM | 5556 | CB | THR | B | 161 | 53.985 | 28.620 | 42.599 | 1.00 37.07 | B C |
| ATOM | 5558 | OG1 | THR | B | 161 | 54.204 | 29.087 | 41.275 | 1.00 37.64 | B O |
| ATOM | 5560 | CG2 | THR | B | 161 | 54.985 | 27.513 | 42.926 | 1.00 37.00 | B C |
| ATOM | 5564 | C | THR | B | 161 | 52.304 | 27.547 | 44.089 | 1.00 36.23 | B C |
| ATOM | 5565 | O | THR | B | 161 | 52.199 | 28.300 | 45.036 | 1.00 36.28 | B O |
| ATOM | 5567 | N | THR | B | 162 | 52.219 | 26.225 | 44.182 | 1.00 36.70 | B N |
| ATOM | 5568 | CA | THR | B | 162 | 52.089 | 25.530 | 45.450 | 1.00 37.11 | B C |
| ATOM | 5570 | CB | THR | B | 162 | 51.730 | 24.035 | 45.295 | 1.00 37.26 | B C |
| ATOM | 5572 | OG1 | THR | B | 162 | 52.830 | 23.303 | 44.724 | 1.00 34.85 | B O |
| ATOM | 5574 | CG2 | THR | B | 162 | 50.471 | 23.863 | 44.473 | 1.00 35.96 | B C |
| ATOM | 5578 | C | THR | B | 162 | 53.396 | 25.578 | 46.226 | 1.00 38.42 | B C |
| ATOM | 5579 | O | THR | B | 162 | 54.473 | 25.707 | 45.641 | 1.00 37.97 | B O |
| ATOM | 5581 | N | LYS | B | 163 | 53.285 | 25.455 | 47.553 | 1.00 39.22 | B N |
| ATOM | 5582 | CA | LYS | B | 163 | 54.446 | 25.267 | 48.423 | 1.00 39.56 | B C |
| ATOM | 5584 | CB | LYS | B | 163 | 54.077 | 25.486 | 49.916 | 1.00 40.66 | B |

FIG 8 – CONT.

| | | | | | | | | | | |
|---|---|---|---|---|---|---|---|---|---|---|
| ATOM | 5587 | CG | LYS | B | 163 | 53.484 | 26.891 | 50.276 | 1.00 39.70 | B C |
| ATOM | 5593 | C | LYS | B | 163 | 54.902 | 23.835 | 48.192 | 1.00 39.65 | B C |
| ATOM | 5594 | O | LYS | B | 163 | 54.091 | 22.978 | 47.872 | 1.00 38.93 | B O |
| ATOM | 5596 | N | PRO | B | 164 | 56.202 | 23.559 | 48.357 | 1.00 40.07 | B N |
| ATOM | 5597 | CA | PRO | B | 164 | 56.575 | 22.169 | 48.168 | 1.00 40.62 | B C |
| ATOM | 5599 | CB | PRO | B | 164 | 58.095 | 22.168 | 48.377 | 1.00 40.78 | B C |
| ATOM | 5602 | CG | PRO | B | 164 | 58.522 | 23.659 | 48.259 | 1.00 40.86 | B C |
| ATOM | 5605 | CD | PRO | B | 164 | 57.325 | 24.387 | 48.824 | 1.00 39.70 | B C |
| ATOM | 5608 | C | PRO | B | 164 | 55.906 | 21.283 | 49.205 | 1.00 41.42 | B C |
| ATOM | 5609 | O | PRO | B | 164 | 55.646 | 21.727 | 50.319 | 1.00 41.50 | B O |
| ATOM | 5610 | N | SER | B | 165 | 55.656 | 20.039 | 48.841 | 1.00 42.24 | B N |
| ATOM | 5611 | CA | SER | B | 165 | 55.031 | 19.093 | 49.735 | 1.00 43.51 | B C |
| ATOM | 5613 | CB | SER | B | 165 | 53.538 | 19.008 | 49.408 | 1.00 43.76 | B C |
| ATOM | 5616 | OG | SER | B | 165 | 53.110 | 17.665 | 49.289 | 1.00 46.75 | B O |
| ATOM | 5618 | C | SER | B | 165 | 55.732 | 17.728 | 49.625 | 1.00 44.15 | B C |
| ATOM | 5619 | O | SER | B | 165 | 56.188 | 17.335 | 48.552 | 1.00 43.12 | B O |
| ATOM | 5621 | N | LYS | B | 166 | 55.842 | 17.029 | 50.751 | 1.00 45.13 | B N |
| ATOM | 5622 | CA | LYS | B | 166 | 56.591 | 15.783 | 50.822 | 1.00 46.50 | B C |
| ATOM | 5624 | CB | LYS | B | 166 | 56.911 | 15.414 | 52.287 | 1.00 46.47 | B C |
| ATOM | 5627 | CG | LYS | B | 166 | 57.761 | 14.144 | 52.454 | 1.00 47.06 | B C |
| ATOM | 5633 | C | LYS | B | 166 | 55.765 | 14.713 | 50.177 | 1.00 47.30 | B C |
| ATOM | 5634 | O | LYS | B | 166 | 54.626 | 14.523 | 50.541 | 1.00 48.32 | B O |
| ATOM | 5636 | N | GLN | B | 167 | 56.309 | 14.038 | 49.186 | 1.00 48.90 | B N |
| ATOM | 5637 | CA | GLN | B | 167 | 55.594 | 12.923 | 48.591 | 1.00 50.78 | B C |
| ATOM | 5639 | CB | GLN | B | 167 | 55.890 | 12.812 | 47.080 | 1.00 51.03 | B C |
| ATOM | 5642 | CG | GLN | B | 167 | 57.326 | 12.520 | 46.683 | 1.00 52.14 | B C |
| ATOM | 5645 | CD | GLN | B | 167 | 57.732 | 13.092 | 45.293 | 1.00 52.29 | B C |
| ATOM | 5646 | OE1 | GLN | B | 167 | 57.390 | 14.222 | 44.926 | 1.00 52.37 | B O |
| ATOM | 5647 | NE2 | GLN | B | 167 | 58.490 | 12.307 | 44.547 | 1.00 50.67 | B N |
| ATOM | 5650 | C | GLN | B | 167 | 55.908 | 11.642 | 49.394 | 1.00 52.15 | B C |

FIG 8 – CONT.

```
ATOM   5651  O    GLN B 167      56.601  11.692  50.421  1.00 51.99           B
O
ATOM   5653  N    SER B 168      55.376  10.509  48.948  1.00 53.70           B
N
ATOM   5654  CA   SER B 168      55.536   9.252  49.675  1.00 54.82           B
C
ATOM   5656  CB   SER B 168      54.660   8.147  49.057  1.00 54.87           B
C
ATOM   5659  OG   SER B 168      55.053   7.863  47.720  1.00 56.89           B
O
ATOM   5661  C    SER B 168      57.009   8.802  49.733  1.00 55.31           B
C
ATOM   5662  O    SER B 168      57.455   8.237  50.745  1.00 56.02           B
O
ATOM   5664  N    ASN B 170      57.776   9.055  48.671  1.00 55.04           B
N
ATOM   5665  CA   ASN B 170      59.156   8.582  48.637  1.00 54.59           B
C
ATOM   5667  CB   ASN B 170      59.598   8.252  47.196  1.00 54.95           B
C
ATOM   5670  CG   ASN B 170      59.884   9.495  46.343  1.00 55.81           B
C
ATOM   5671  OD1  ASN B 170      59.817  10.627  46.819  1.00 56.28           B
O
ATOM   5672  ND2  ASN B 170      60.233   9.270  45.073  1.00 56.82           B
N
ATOM   5675  C    ASN B 170      60.098   9.553  49.338  1.00 53.91           B
C
ATOM   5676  O    ASN B 170      61.303   9.478  49.166  1.00 54.00           B
O
ATOM   5678  N    ASN B 171      59.527  10.470  50.120  1.00 53.33           B
N
ATOM   5679  CA   ASN B 171      60.267  11.404  50.981  1.00 52.76           B
C
ATOM   5681  CB   ASN B 171      61.198  10.649  51.950  1.00 53.39           B
C
ATOM   5684  CG   ASN B 171      60.419   9.875  52.994  1.00 55.56           B
C
ATOM   5685  OD1  ASN B 171      59.451  10.391  53.571  1.00 57.85           B
O
ATOM   5686  ND2  ASN B 171      60.817   8.623  53.228  1.00 58.68           B
N
ATOM   5689  C    ASN B 171      61.008  12.527  50.276  1.00 51.09           B
C
ATOM   5690  O    ASN B 171      61.681  13.307  50.924  1.00 49.37           B
O
ATOM   5692  N    LYS B 172      60.852  12.614  48.952  1.00 50.53           B
N
ATOM   5693  CA   LYS B 172      61.253  13.806  48.177  1.00 49.50           B
C
ATOM   5695  CB   LYS B 172      61.724  13.406  46.774  1.00 49.90           B
C
ATOM   5698  CG   LYS B 172      62.912  12.447  46.784  1.00 51.54           B
C
ATOM   5701  CD   LYS B 172      63.163  11.827  45.417  1.00 52.55           B
C
ATOM   5704  CE   LYS B 172      64.266  10.780  45.475  1.00 53.48           B
C
ATOM   5707  NZ   LYS B 172      64.724  10.400  44.118  1.00 53.77           B
N
ATOM   5711  C    LYS B 172      60.068  14.771  48.103  1.00 47.67           B
```

FIG 8 – CONT.

```
C
ATOM   5712  O    LYS B 172      59.006  14.486  48.649  1.00 47.85      B
O
ATOM   5714  N    TYR B 173      60.269  15.916  47.458  1.00 45.35      B
N
ATOM   5715  CA   TYR B 173      59.280  16.963  47.405  1.00 43.81      B
C
ATOM   5717  CB   TYR B 173      59.888  18.272  47.885  1.00 43.88      B
C
ATOM   5720  CG   TYR B 173      60.085  18.278  49.379  1.00 46.42      B
C
ATOM   5721  CD1  TYR B 173      59.120  18.850  50.230  1.00 46.48      B
C
ATOM   5723  CE1  TYR B 173      59.285  18.840  51.595  1.00 48.53      B
C
ATOM   5725  CZ   TYR B 173      60.417  18.242  52.134  1.00 48.27      B
C
ATOM   5726  OH   TYR B 173      60.581  18.219  53.478  1.00 49.67      B
O
ATOM   5728  CE2  TYR B 173      61.377  17.664  51.325  1.00 47.26      B
C
ATOM   5730  CD2  TYR B 173      61.205  17.680  49.954  1.00 46.35      B
C
ATOM   5732  C    TYR B 173      58.704  17.156  46.014  1.00 42.25      B
C
ATOM   5733  O    TYR B 173      59.372  16.924  44.998  1.00 42.60      B
O
ATOM   5735  N    ALA B 174      57.462  17.613  45.986  1.00 40.04      B
N
ATOM   5736  CA   ALA B 174      56.792  17.988  44.756  1.00 38.72      B
C
ATOM   5738  CB   ALA B 174      55.662  17.005  44.415  1.00 38.56      B
C
ATOM   5742  C    ALA B 174      56.247  19.385  44.927  1.00 37.30      B
C
ATOM   5743  O    ALA B 174      56.001  19.846  46.043  1.00 36.61      B
O
ATOM   5745  N    ALA B 175      56.078  20.056  43.803  1.00 35.50      B
N
ATOM   5746  CA   ALA B 175      55.457  21.357  43.755  1.00 33.86      B
C
ATOM   5748  CB   ALA B 175      56.461  22.449  44.047  1.00 33.14      B
C
ATOM   5752  C    ALA B 175      54.854  21.511  42.364  1.00 33.20      B
C
ATOM   5753  O    ALA B 175      55.210  20.761  41.442  1.00 32.44      B
O
ATOM   5755  N    SER B 176      53.936  22.466  42.244  1.00 32.17      B
N
ATOM   5756  CA   SER B 176      53.152  22.721  41.045  1.00 31.72      B
C
ATOM   5758  CB   SER B 176      51.708  22.274  41.248  1.00 31.34      B
C
ATOM   5761  OG   SER B 176      51.592  20.900  41.064  1.00 34.38      B
O
ATOM   5763  C    SER B 176      53.118  24.233  40.845  1.00 31.33      B
C
ATOM   5764  O    SER B 176      53.034  24.973  41.837  1.00 31.20      B
O
ATOM   5766  N    SER B 177      53.189  24.683  39.589  1.00 30.08      B
N
```

FIG 8 – CONT.

| ATOM | 5767 | CA | SER | B | 177 | 52.874 | 26.065 | 39.235 | 1.00 | 29.65 | B |
|------|------|-----|-----|---|-----|--------|--------|--------|------|-------|---|
| | | | | | | | | | | | C |
| ATOM | 5769 | CB | SER | B | 177 | 54.113 | 26.879 | 38.922 | 1.00 | 29.22 | B |
| | | | | | | | | | | | C |
| ATOM | 5772 | OG | SER | B | 177 | 53.784 | 28.259 | 38.851 | 1.00 | 29.12 | B |
| | | | | | | | | | | | O |
| ATOM | 5774 | C | SER | B | 177 | 51.912 | 26.095 | 38.062 | 1.00 | 29.83 | B |
| | | | | | | | | | | | C |
| ATOM | 5775 | O | SER | B | 177 | 52.058 | 25.298 | 37.127 | 1.00 | 30.25 | B |
| | | | | | | | | | | | O |
| ATOM | 5777 | N | TYR | B | 178 | 50.934 | 27.002 | 38.142 | 1.00 | 29.13 | B |
| | | | | | | | | | | | N |
| ATOM | 5778 | CA | TYR | B | 178 | 49.906 | 27.175 | 37.139 | 1.00 | 28.97 | B |
| | | | | | | | | | | | C |
| ATOM | 5780 | CB | TYR | B | 178 | 48.518 | 26.948 | 37.738 | 1.00 | 28.43 | B |
| | | | | | | | | | | | C |
| ATOM | 5783 | CG | TYR | B | 178 | 48.301 | 25.510 | 38.112 | 1.00 | 28.69 | B |
| | | | | | | | | | | | C |
| ATOM | 5784 | CD1 | TYR | B | 178 | 47.701 | 24.636 | 37.233 | 1.00 | 29.90 | B |
| | | | | | | | | | | | C |
| ATOM | 5786 | CE1 | TYR | B | 178 | 47.525 | 23.275 | 37.561 | 1.00 | 30.52 | B |
| | | | | | | | | | | | C |
| ATOM | 5788 | CZ | TYR | B | 178 | 47.984 | 22.785 | 38.776 | 1.00 | 28.98 | B |
| | | | | | | | | | | | C |
| ATOM | 5789 | OH | TYR | B | 178 | 47.824 | 21.457 | 39.060 | 1.00 | 28.34 | B |
| | | | | | | | | | | | O |
| ATOM | 5791 | CE2 | TYR | B | 178 | 48.604 | 23.635 | 39.675 | 1.00 | 28.91 | B |
| | | | | | | | | | | | C |
| ATOM | 5793 | CD2 | TYR | B | 178 | 48.756 | 25.001 | 39.340 | 1.00 | 30.23 | B |
| | | | | | | | | | | | C |
| ATOM | 5795 | C | TYR | B | 178 | 50.017 | 28.582 | 36.613 | 1.00 | 29.76 | B |
| | | | | | | | | | | | C |
| ATOM | 5796 | O | TYR | B | 178 | 50.111 | 29.518 | 37.394 | 1.00 | 29.41 | B |
| | | | | | | | | | | | O |
| ATOM | 5798 | N | LEU | B | 179 | 50.068 | 28.727 | 35.290 | 1.00 | 30.41 | B |
| | | | | | | | | | | | N |
| ATOM | 5799 | CA | LEU | B | 179 | 49.954 | 30.037 | 34.664 | 1.00 | 31.13 | B |
| | | | | | | | | | | | C |
| ATOM | 5801 | CB | LEU | B | 179 | 51.123 | 30.332 | 33.700 | 1.00 | 30.39 | B |
| | | | | | | | | | | | C |
| ATOM | 5804 | CG | LEU | B | 179 | 51.066 | 31.662 | 32.920 | 1.00 | 30.45 | B |
| | | | | | | | | | | | C |
| ATOM | 5806 | CD1 | LEU | B | 179 | 50.772 | 32.823 | 33.840 | 1.00 | 29.09 | B |
| | | | | | | | | | | | C |
| ATOM | 5810 | CD2 | LEU | B | 179 | 52.376 | 31.962 | 32.128 | 1.00 | 28.46 | B |
| | | | | | | | | | | | C |
| ATOM | 5814 | C | LEU | B | 179 | 48.614 | 30.040 | 33.956 | 1.00 | 31.80 | B |
| | | | | | | | | | | | C |
| ATOM | 5815 | O | LEU | B | 179 | 48.389 | 29.260 | 33.010 | 1.00 | 32.23 | B |
| | | | | | | | | | | | O |
| ATOM | 5817 | N | SER | B | 180 | 47.730 | 30.903 | 34.436 | 1.00 | 32.55 | B |
| | | | | | | | | | | | N |
| ATOM | 5818 | CA | SER | B | 180 | 46.399 | 31.039 | 33.897 | 1.00 | 33.30 | B |
| | | | | | | | | | | | C |
| ATOM | 5820 | CB | SER | B | 180 | 45.420 | 31.208 | 35.047 | 1.00 | 33.56 | B |
| | | | | | | | | | | | C |
| ATOM | 5823 | OG | SER | B | 180 | 45.383 | 29.998 | 35.816 | 1.00 | 36.31 | B |
| | | | | | | | | | | | O |
| ATOM | 5825 | C | SER | B | 180 | 46.368 | 32.243 | 32.948 | 1.00 | 33.77 | B |
| | | | | | | | | | | | C |
| ATOM | 5826 | O | SER | B | 180 | 46.902 | 33.304 | 33.251 | 1.00 | 34.62 | B |

FIG 8 – CONT.

| | | | | | | | | | | |
|---|---|---|---|---|---|---|---|---|---|---|
| O | | | | | | | | | | |
| ATOM | 5828 | N | LEU | B | 181 | 45.781 | 32.061 | 31.782 | 1.00 33.76 | B |
| N | | | | | | | | | | |
| ATOM | 5829 | CA | LEU | B | 181 | 45.821 | 33.085 | 30.740 | 1.00 34.18 | B |
| C | | | | | | | | | | |
| ATOM | 5831 | CB | LEU | B | 181 | 46.951 | 32.786 | 29.739 | 1.00 34.13 | B |
| C | | | | | | | | | | |
| ATOM | 5834 | CG | LEU | B | 181 | 48.397 | 32.741 | 30.193 | 1.00 35.50 | B |
| C | | | | | | | | | | |
| ATOM | 5836 | CD1 | LEU | B | 181 | 49.265 | 32.022 | 29.111 | 1.00 35.57 | B |
| C | | | | | | | | | | |
| ATOM | 5840 | CD2 | LEU | B | 181 | 48.928 | 34.136 | 30.493 | 1.00 33.08 | B |
| C | | | | | | | | | | |
| ATOM | 5844 | C | LEU | B | 181 | 44.523 | 32.992 | 29.982 | 1.00 33.46 | B |
| C | | | | | | | | | | |
| ATOM | 5845 | O | LEU | B | 181 | 43.880 | 31.928 | 29.979 | 1.00 33.70 | B |
| O | | | | | | | | | | |
| ATOM | 5847 | N | THR | B | 182 | 44.154 | 34.076 | 29.310 | 1.00 33.04 | B |
| N | | | | | | | | | | |
| ATOM | 5848 | CA | THR | B | 182 | 43.058 | 34.009 | 28.305 | 1.00 33.22 | B |
| C | | | | | | | | | | |
| ATOM | 5850 | CB | THR | B | 182 | 42.600 | 35.394 | 27.802 | 1.00 33.17 | B |
| C | | | | | | | | | | |
| ATOM | 5852 | OG1 | THR | B | 182 | 43.702 | 36.027 | 27.128 | 1.00 32.74 | B |
| O | | | | | | | | | | |
| ATOM | 5854 | CG2 | THR | B | 182 | 42.107 | 36.320 | 28.978 | 1.00 34.24 | B |
| C | | | | | | | | | | |
| ATOM | 5858 | C | THR | B | 182 | 43.611 | 33.257 | 27.091 | 1.00 33.14 | B |
| C | | | | | | | | | | |
| ATOM | 5859 | O | THR | B | 182 | 44.851 | 33.263 | 26.862 | 1.00 31.32 | B |
| O | | | | | | | | | | |
| ATOM | 5861 | N | PRO | B | 183 | 42.711 | 32.592 | 26.320 | 1.00 34.14 | B |
| N | | | | | | | | | | |
| ATOM | 5862 | CA | PRO | B | 183 | 43.150 | 31.903 | 25.089 | 1.00 35.02 | B |
| C | | | | | | | | | | |
| ATOM | 5864 | CB | PRO | B | 183 | 41.848 | 31.355 | 24.513 | 1.00 35.21 | B |
| C | | | | | | | | | | |
| ATOM | 5867 | CG | PRO | B | 183 | 40.951 | 31.146 | 25.742 | 1.00 34.73 | B |
| C | | | | | | | | | | |
| ATOM | 5870 | CD | PRO | B | 183 | 41.307 | 32.261 | 26.675 | 1.00 33.86 | B |
| C | | | | | | | | | | |
| ATOM | 5873 | C | PRO | B | 183 | 43.862 | 32.869 | 24.114 | 1.00 35.90 | B |
| C | | | | | | | | | | |
| ATOM | 5874 | O | PRO | B | 183 | 44.804 | 32.475 | 23.420 | 1.00 35.75 | B |
| O | | | | | | | | | | |
| ATOM | 5875 | N | GLU | B | 184 | 43.449 | 34.135 | 24.155 | 1.00 36.58 | B |
| N | | | | | | | | | | |
| ATOM | 5876 | CA | GLU | B | 184 | 44.033 | 35.211 | 23.366 | 1.00 37.86 | B |
| C | | | | | | | | | | |
| ATOM | 5878 | CB | GLU | B | 184 | 43.224 | 36.525 | 23.522 | 1.00 38.24 | B |
| C | | | | | | | | | | |
| ATOM | 5881 | CG | GLU | B | 184 | 41.713 | 36.359 | 23.231 | 1.00 41.38 | B |
| C | | | | | | | | | | |
| ATOM | 5884 | CD | GLU | B | 184 | 40.892 | 36.073 | 24.511 | 1.00 43.97 | B |
| C | | | | | | | | | | |
| ATOM | 5885 | OE1 | GLU | B | 184 | 40.234 | 35.007 | 24.572 | 1.00 44.52 | B |
| O | | | | | | | | | | |
| ATOM | 5886 | OE2 | GLU | B | 184 | 40.934 | 36.922 | 25.445 | 1.00 46.83 | B |
| O | | | | | | | | | | |
| ATOM | 5887 | C | GLU | B | 184 | 45.482 | 35.465 | 23.754 | 1.00 38.25 | B |
| C | | | | | | | | | | |

FIG 8 – CONT.

| ATOM | 5888 | O | GLU | B | 184 | 46.357 | 35.499 | 22.867 | 1.00 | 38.71 | B O |
| --- | --- | --- | --- | --- | --- | --- | --- | --- | --- | --- | --- |
| ATOM | 5890 | N | GLN | B | 185 | 45.731 | 35.667 | 25.057 | 1.00 | 37.86 | B N |
| ATOM | 5891 | CA | GLN | B | 185 | 47.100 | 35.863 | 25.578 | 1.00 | 37.73 | B C |
| ATOM | 5893 | CB | GLN | B | 185 | 47.072 | 36.055 | 27.101 | 1.00 | 38.45 | B C |
| ATOM | 5896 | CG | GLN | B | 185 | 46.594 | 37.430 | 27.532 | 1.00 | 40.63 | B C |
| ATOM | 5899 | CD | GLN | B | 185 | 46.125 | 37.503 | 28.994 | 1.00 | 43.11 | B C |
| ATOM | 5900 | OE1 | GLN | B | 185 | 46.165 | 36.528 | 29.754 | 1.00 | 42.38 | B O |
| ATOM | 5901 | NE2 | GLN | B | 185 | 45.640 | 38.676 | 29.373 | 1.00 | 45.76 | B N |
| ATOM | 5904 | C | GLN | B | 185 | 48.006 | 34.673 | 25.252 | 1.00 | 36.56 | B C |
| ATOM | 5905 | O | GLN | B | 185 | 49.184 | 34.825 | 24.939 | 1.00 | 37.45 | B O |
| ATOM | 5907 | N | TRP | B | 186 | 47.451 | 33.481 | 25.320 | 1.00 | 34.93 | B N |
| ATOM | 5908 | CA | TRP | B | 186 | 48.206 | 32.274 | 24.993 | 1.00 | 34.36 | B C |
| ATOM | 5910 | CB | TRP | B | 186 | 47.342 | 31.028 | 25.313 | 1.00 | 33.41 | B C |
| ATOM | 5913 | CG | TRP | B | 186 | 47.794 | 29.730 | 24.651 | 1.00 | 31.33 | B C |
| ATOM | 5914 | CD1 | TRP | B | 186 | 47.081 | 28.961 | 23.771 | 1.00 | 28.85 | B C |
| ATOM | 5916 | NE1 | TRP | B | 186 | 47.814 | 27.838 | 23.412 | 1.00 | 28.77 | B N |
| ATOM | 5918 | CE2 | TRP | B | 186 | 49.017 | 27.879 | 24.070 | 1.00 | 30.64 | B C |
| ATOM | 5919 | CD2 | TRP | B | 186 | 49.041 | 29.066 | 24.845 | 1.00 | 28.60 | B C |
| ATOM | 5920 | CE3 | TRP | B | 186 | 50.168 | 29.334 | 25.630 | 1.00 | 30.65 | B C |
| ATOM | 5922 | CZ3 | TRP | B | 186 | 51.238 | 28.441 | 25.590 | 1.00 | 29.81 | B C |
| ATOM | 5924 | CH2 | TRP | B | 186 | 51.194 | 27.289 | 24.776 | 1.00 | 28.09 | B C |
| ATOM | 5926 | CZ2 | TRP | B | 186 | 50.102 | 26.991 | 24.022 | 1.00 | 27.61 | B C |
| ATOM | 5928 | C | TRP | B | 186 | 48.620 | 32.290 | 23.498 | 1.00 | 34.54 | B C |
| ATOM | 5929 | O | TRP | B | 186 | 49.764 | 31.999 | 23.167 | 1.00 | 33.63 | B O |
| ATOM | 5931 | N | LYS | B | 187 | 47.674 | 32.637 | 22.620 | 1.00 | 35.69 | B N |
| ATOM | 5932 | CA | LYS | B | 187 | 47.873 | 32.530 | 21.143 | 1.00 | 36.42 | B C |
| ATOM | 5934 | CB | LYS | B | 187 | 46.522 | 32.364 | 20.433 | 1.00 | 36.06 | B C |
| ATOM | 5937 | CG | LYS | B | 187 | 45.924 | 30.978 | 20.614 | 1.00 | 39.16 | B C |
| ATOM | 5940 | CD | LYS | B | 187 | 44.501 | 30.849 | 19.995 | 1.00 | 42.57 | B C |
| ATOM | 5943 | CE | LYS | B | 187 | 43.911 | 29.445 | 20.162 | 1.00 | 44.52 | B C |
| ATOM | 5946 | NZ | LYS | B | 187 | 42.493 | 29.338 | 19.621 | 1.00 | 44.29 | B N |

FIG 8 – CONT.

| | | | | | | | | | | |
|---|---|---|---|---|---|---|---|---|---|---|
| ATOM | 5950 | C | LYS | B | 187 | 48.666 | 33.692 | 20.550 | 1.00 35.99 | B C |
| ATOM | 5951 | O | LYS | B | 187 | 49.250 | 33.581 | 19.461 | 1.00 36.39 | B O |
| ATOM | 5953 | N | SER | B | 188 | 48.702 | 34.798 | 21.286 | 1.00 36.61 | B N |
| ATOM | 5954 | CA | SER | B | 188 | 49.411 | 36.014 | 20.860 | 1.00 36.32 | B C |
| ATOM | 5956 | CB | SER | B | 188 | 48.874 | 37.259 | 21.603 | 1.00 36.60 | B C |
| ATOM | 5959 | OG | SER | B | 188 | 47.503 | 37.484 | 21.296 | 1.00 35.90 | B O |
| ATOM | 5961 | C | SER | B | 188 | 50.908 | 35.942 | 21.067 | 1.00 36.33 | B C |
| ATOM | 5962 | O | SER | B | 188 | 51.614 | 36.811 | 20.589 | 1.00 36.91 | B O |
| ATOM | 5964 | N | HIS | B | 189 | 51.407 | 34.923 | 21.763 | 1.00 35.84 | B N |
| ATOM | 5965 | CA | HIS | B | 189 | 52.835 | 34.817 | 22.001 | 1.00 36.16 | B C |
| ATOM | 5967 | CB | HIS | B | 189 | 53.138 | 34.774 | 23.512 | 1.00 36.13 | B C |
| ATOM | 5970 | CG | HIS | B | 189 | 52.914 | 36.092 | 24.176 | 1.00 36.40 | B C |
| ATOM | 5971 | ND1 | HIS | B | 189 | 53.874 | 37.080 | 24.194 | 1.00 37.23 | B N |
| ATOM | 5973 | CE1 | HIS | B | 189 | 53.388 | 38.149 | 24.799 | 1.00 39.63 | B C |
| ATOM | 5975 | NE2 | HIS | B | 189 | 52.136 | 37.900 | 25.143 | 1.00 39.70 | B N |
| ATOM | 5977 | CD2 | HIS | B | 189 | 51.814 | 36.622 | 24.755 | 1.00 36.20 | B C |
| ATOM | 5979 | C | HIS | B | 189 | 53.352 | 33.605 | 21.292 | 1.00 36.78 | B C |
| ATOM | 5980 | O | HIS | B | 189 | 52.567 | 32.721 | 20.937 | 1.00 37.32 | B O |
| ATOM | 5982 | N | ARG | B | 190 | 54.660 | 33.546 | 21.071 | 1.00 36.82 | B N |
| ATOM | 5983 | CA | ARG | B | 190 | 55.211 | 32.394 | 20.357 | 1.00 37.28 | B C |
| ATOM | 5985 | CB | ARG | B | 190 | 56.061 | 32.858 | 19.169 | 1.00 37.96 | B C |
| ATOM | 5988 | CG | ARG | B | 190 | 55.065 | 33.269 | 18.052 | 1.00 39.08 | B C |
| ATOM | 5991 | CD | ARG | B | 190 | 55.634 | 33.508 | 16.769 | 1.00 38.39 | B C |
| ATOM | 5994 | NE | ARG | B | 190 | 56.079 | 32.320 | 16.047 | 1.00 38.45 | B N |
| ATOM | 5996 | CZ | ARG | B | 190 | 55.318 | 31.475 | 15.348 | 1.00 36.90 | B C |
| ATOM | 5997 | NH1 | ARG | B | 190 | 53.988 | 31.577 | 15.313 | 1.00 36.30 | B N |
| ATOM | 6000 | NH2 | ARG | B | 190 | 55.923 | 30.487 | 14.694 | 1.00 34.47 | B N |
| ATOM | 6003 | C | ARG | B | 190 | 55.881 | 31.341 | 21.206 | 1.00 37.06 | B C |
| ATOM | 6004 | O | ARG | B | 190 | 55.950 | 30.167 | 20.779 | 1.00 36.40 | B O |
| ATOM | 6006 | N | SER | B | 191 | 56.324 | 31.741 | 22.402 | 1.00 36.92 | B N |
| ATOM | 6007 | CA | SER | B | 191 | 56.817 | 30.792 | 23.422 | 1.00 37.50 | B |

FIG 8 – CONT.

| | | | | | | | | | | |
|---|---|---|---|---|---|---|---|---|---|---|
| ATOM | 6009 | CB | SER | B | 191 | 58.342 | 30.680 | 23.460 | 1.00 37.32 | B |
| ATOM | 6012 | OG | SER | B | 191 | 58.891 | 30.584 | 22.169 | 1.00 44.45 | B |
| ATOM | 6014 | C | SER | B | 191 | 56.422 | 31.225 | 24.816 | 1.00 35.89 | B |
| ATOM | 6015 | O | SER | B | 191 | 56.374 | 32.409 | 25.111 | 1.00 35.06 | B |
| ATOM | 6017 | N | TYR | B | 192 | 56.201 | 30.230 | 25.666 | 1.00 35.30 | B |
| ATOM | 6018 | CA | TYR | B | 192 | 56.140 | 30.420 | 27.112 | 1.00 34.75 | B |
| ATOM | 6020 | CB | TYR | B | 192 | 54.750 | 30.131 | 27.656 | 1.00 34.04 | B |
| ATOM | 6023 | CG | TYR | B | 192 | 53.771 | 31.243 | 27.465 | 1.00 33.21 | B |
| ATOM | 6024 | CD1 | TYR | B | 192 | 53.628 | 32.225 | 28.432 | 1.00 35.70 | B |
| ATOM | 6026 | CE1 | TYR | B | 192 | 52.728 | 33.247 | 28.282 | 1.00 35.74 | B |
| ATOM | 6028 | CZ | TYR | B | 192 | 51.930 | 33.306 | 27.149 | 1.00 36.52 | B |
| ATOM | 6029 | OH | TYR | B | 192 | 51.041 | 34.349 | 27.034 | 1.00 39.07 | B |
| ATOM | 6031 | CE2 | TYR | B | 192 | 52.034 | 32.342 | 26.171 | 1.00 35.10 | B |
| ATOM | 6033 | CD2 | TYR | B | 192 | 52.966 | 31.310 | 26.336 | 1.00 35.29 | B |
| ATOM | 6035 | C | TYR | B | 192 | 57.146 | 29.474 | 27.714 | 1.00 34.60 | B |
| ATOM | 6036 | O | TYR | B | 192 | 57.353 | 28.381 | 27.190 | 1.00 34.60 | B |
| ATOM | 6038 | N | SER | B | 193 | 57.780 | 29.902 | 28.804 | 1.00 34.49 | B |
| ATOM | 6039 | CA | SER | B | 193 | 58.704 | 29.039 | 29.513 | 1.00 34.69 | B |
| ATOM | 6041 | CB | SER | B | 193 | 60.134 | 29.515 | 29.305 | 1.00 34.58 | B |
| ATOM | 6044 | OG | SER | B | 193 | 60.392 | 29.575 | 27.911 | 1.00 37.42 | B |
| ATOM | 6046 | C | SER | B | 193 | 58.392 | 28.923 | 31.002 | 1.00 34.50 | B |
| ATOM | 6047 | O | SER | B | 193 | 57.982 | 29.882 | 31.648 | 1.00 33.08 | B |
| ATOM | 6049 | N | CYS | B | 194 | 58.558 | 27.710 | 31.504 | 1.00 34.35 | B |
| ATOM | 6050 | CA | CYS | B | 194 | 58.617 | 27.455 | 32.918 | 1.00 35.40 | B |
| ATOM | 6052 | CB | CYS | B | 194 | 57.848 | 26.176 | 33.285 | 1.00 34.79 | B |
| ATOM | 6055 | SG | CYS | B | 194 | 57.775 | 26.010 | 35.046 | 1.00 37.55 | B |
| ATOM | 6057 | C | CYS | B | 194 | 60.079 | 27.281 | 33.324 | 1.00 35.78 | B |
| ATOM | 6058 | O | CYS | B | 194 | 60.776 | 26.402 | 32.798 | 1.00 34.81 | B |
| ATOM | 6060 | N | ARG | B | 195 | 60.526 | 28.071 | 34.301 | 1.00 36.72 | B |
| ATOM | 6061 | CA | ARG | B | 195 | 61.925 | 28.017 | 34.763 | 1.00 37.48 | B |

FIG 8 – CONT.

| ATOM | 6063 | CB | ARG | B | 195 | 62.586 | 29.353 | 34.479 | 1.00 | 38.48 | B |
|------|------|-----|-----|---|-----|--------|--------|--------|------|-------|---|
| ATOM | 6066 | CG | ARG | B | 195 | 63.882 | 29.595 | 35.174 | 1.00 | 42.76 | B |
| ATOM | 6069 | CD | ARG | B | 195 | 64.449 | 30.984 | 34.802 | 1.00 | 47.68 | B |
| ATOM | 6072 | NE | ARG | B | 195 | 65.401 | 30.831 | 33.707 | 1.00 | 52.31 | B |
| ATOM | 6074 | CZ | ARG | B | 195 | 66.728 | 30.821 | 33.825 | 1.00 | 54.93 | B |
| ATOM | 6075 | NH1 | ARG | B | 195 | 67.342 | 31.044 | 34.986 | 1.00 | 55.43 | B |
| ATOM | 6078 | NH2 | ARG | B | 195 | 67.451 | 30.618 | 32.732 | 1.00 | 58.03 | B |
| ATOM | 6081 | C | ARG | B | 195 | 61.975 | 27.680 | 36.243 | 1.00 | 37.12 | B |
| ATOM | 6082 | O | ARG | B | 195 | 61.473 | 28.442 | 37.090 | 1.00 | 37.42 | B |
| ATOM | 6084 | N | VAL | B | 196 | 62.567 | 26.528 | 36.539 | 1.00 | 36.50 | B |
| ATOM | 6085 | CA | VAL | B | 196 | 62.633 | 25.979 | 37.869 | 1.00 | 36.09 | B |
| ATOM | 6087 | CB | VAL | B | 196 | 62.004 | 24.602 | 37.886 | 1.00 | 36.09 | B |
| ATOM | 6089 | CG1 | VAL | B | 196 | 62.115 | 23.975 | 39.265 | 1.00 | 32.48 | B |
| ATOM | 6093 | CG2 | VAL | B | 196 | 60.535 | 24.717 | 37.427 | 1.00 | 34.70 | B |
| ATOM | 6097 | C | VAL | B | 196 | 64.072 | 25.901 | 38.389 | 1.00 | 37.11 | B |
| ATOM | 6098 | O | VAL | B | 196 | 64.907 | 25.171 | 37.843 | 1.00 | 36.57 | B |
| ATOM | 6100 | N | THR | B | 197 | 64.340 | 26.659 | 39.451 | 1.00 | 37.65 | B |
| ATOM | 6101 | CA | THR | B | 197 | 65.652 | 26.694 | 40.063 | 1.00 | 38.90 | B |
| ATOM | 6103 | CB | THR | B | 197 | 66.087 | 28.124 | 40.354 | 1.00 | 38.78 | B |
| ATOM | 6105 | OG1 | THR | B | 197 | 66.017 | 28.872 | 39.137 | 1.00 | 41.53 | B |
| ATOM | 6107 | CG2 | THR | B | 197 | 67.543 | 28.173 | 40.888 | 1.00 | 38.69 | B |
| ATOM | 6111 | C | THR | B | 197 | 65.663 | 25.854 | 41.349 | 1.00 | 39.44 | B |
| ATOM | 6112 | O | THR | B | 197 | 64.822 | 26.036 | 42.238 | 1.00 | 39.56 | B |
| ATOM | 6114 | N | HIS | B | 198 | 66.598 | 24.917 | 41.411 | 1.00 | 39.91 | B |
| ATOM | 6115 | CA | HIS | B | 198 | 66.818 | 24.102 | 42.596 | 1.00 | 41.16 | B |
| ATOM | 6117 | CB | HIS | B | 198 | 66.277 | 22.700 | 42.363 | 1.00 | 40.74 | B |
| ATOM | 6120 | CG | HIS | B | 198 | 66.543 | 21.752 | 43.490 | 1.00 | 42.35 | B |
| ATOM | 6121 | ND1 | HIS | B | 198 | 65.785 | 21.726 | 44.644 | 1.00 | 44.35 | B |
| ATOM | 6123 | CE1 | HIS | B | 198 | 66.233 | 20.768 | 45.435 | 1.00 | 43.74 | B |
| ATOM | 6125 | NE2 | HIS | B | 198 | 67.242 | 20.166 | 44.835 | 1.00 | 42.92 | B |
| ATOM | 6127 | CD2 | HIS | B | 198 | 67.458 | 20.766 | 43.621 | 1.00 | 43.20 | B |

FIG 8 – CONT.

| | | | | | | | | | | |
|---|---|---|---|---|---|---|---|---|---|---|
| ATOM | 6129 | C | HIS | B | 198 | 68.314 | 24.040 | 42.907 | 1.00 41.81 | B C |
| ATOM | 6130 | O | HIS | B | 198 | 69.101 | 23.540 | 42.082 | 1.00 41.20 | B O |
| ATOM | 6132 | N | GLU | B | 199 | 68.690 | 24.563 | 44.073 | 1.00 42.98 | B N |
| ATOM | 6133 | CA | GLU | B | 199 | 70.065 | 24.472 | 44.591 | 1.00 44.62 | B C |
| ATOM | 6135 | CB | GLU | B | 199 | 70.441 | 23.009 | 44.959 | 1.00 45.16 | B C |
| ATOM | 6138 | CG | GLU | B | 199 | 69.746 | 22.459 | 46.238 | 1.00 47.65 | B C |
| ATOM | 6141 | CD | GLU | B | 199 | 69.904 | 23.398 | 47.429 | 1.00 50.51 | B C |
| ATOM | 6142 | OE1 | GLU | B | 199 | 71.068 | 23.717 | 47.776 | 1.00 51.48 | B O |
| ATOM | 6143 | OE2 | GLU | B | 199 | 68.869 | 23.857 | 47.988 | 1.00 52.74 | B O |
| ATOM | 6144 | C | GLU | B | 199 | 71.037 | 25.036 | 43.569 | 1.00 44.77 | B C |
| ATOM | 6145 | O | GLU | B | 199 | 71.950 | 24.334 | 43.112 | 1.00 45.16 | B O |
| ATOM | 6147 | N | GLY | B | 200 | 70.807 | 26.292 | 43.179 | 1.00 44.59 | B N |
| ATOM | 6148 | CA | GLY | B | 200 | 71.661 | 26.966 | 42.198 | 1.00 44.59 | B C |
| ATOM | 6151 | C | GLY | B | 200 | 71.662 | 26.403 | 40.782 | 1.00 44.38 | B C |
| ATOM | 6152 | O | GLY | B | 200 | 72.353 | 26.922 | 39.928 | 1.00 44.65 | B O |
| ATOM | 6154 | N | SER | B | 203 | 70.875 | 25.362 | 40.531 | 1.00 43.68 | B N |
| ATOM | 6155 | CA | SER | B | 203 | 70.771 | 24.742 | 39.218 | 1.00 43.73 | B C |
| ATOM | 6157 | CB | SER | B | 203 | 71.254 | 23.304 | 39.348 | 1.00 43.17 | B C |
| ATOM | 6160 | OG | SER | B | 203 | 70.400 | 22.478 | 38.625 | 1.00 46.02 | B O |
| ATOM | 6162 | C | SER | B | 203 | 69.329 | 24.872 | 38.578 | 1.00 43.07 | B C |
| ATOM | 6163 | O | SER | B | 203 | 68.313 | 24.776 | 39.274 | 1.00 43.36 | B O |
| ATOM | 6165 | N | THR | B | 204 | 69.244 | 25.118 | 37.267 | 1.00 42.24 | B N |
| ATOM | 6166 | CA | THR | B | 204 | 67.967 | 25.515 | 36.634 | 1.00 41.20 | B C |
| ATOM | 6168 | CB | THR | B | 204 | 67.986 | 26.993 | 36.234 | 1.00 41.12 | B C |
| ATOM | 6170 | OG1 | THR | B | 204 | 68.118 | 27.801 | 37.408 | 1.00 40.14 | B O |
| ATOM | 6172 | CG2 | THR | B | 204 | 66.699 | 27.374 | 35.474 | 1.00 40.09 | B C |
| ATOM | 6176 | C | THR | B | 204 | 67.593 | 24.747 | 35.383 | 1.00 41.34 | B C |
| ATOM | 6177 | O | THR | B | 204 | 68.393 | 24.641 | 34.461 | 1.00 41.39 | B O |
| ATOM | 6179 | N | VAL | B | 205 | 66.367 | 24.227 | 35.357 | 1.00 41.15 | B N |
| ATOM | 6180 | CA | VAL | B | 205 | 65.788 | 23.605 | 34.176 | 1.00 40.79 | B C |

FIG 8 – CONT.

| ATOM | 6182 | CB  | VAL B 205 | 65.084 | 22.266 | 34.473 | 1.00 | 41.37 | B C |
| ATOM | 6184 | CG1 | VAL B 205 | 64.595 | 21.641 | 33.162 | 1.00 | 41.56 | B C |
| ATOM | 6188 | CG2 | VAL B 205 | 65.991 | 21.297 | 35.227 | 1.00 | 41.71 | B C |
| ATOM | 6192 | C   | VAL B 205 | 64.709 | 24.515 | 33.638 | 1.00 | 40.79 | B C |
| ATOM | 6193 | O   | VAL B 205 | 63.903 | 25.060 | 34.391 | 1.00 | 40.71 | B O |
| ATOM | 6195 | N   | GLU B 206 | 64.644 | 24.632 | 32.327 | 1.00 | 40.35 | B N |
| ATOM | 6196 | CA  | GLU B 206 | 63.698 | 25.535 | 31.719 | 1.00 | 40.17 | B C |
| ATOM | 6198 | CB  | GLU B 206 | 64.462 | 26.756 | 31.259 | 1.00 | 40.52 | B C |
| ATOM | 6201 | CG  | GLU B 206 | 63.661 | 27.939 | 30.825 | 1.00 | 41.87 | B C |
| ATOM | 6204 | CD  | GLU B 206 | 64.515 | 29.213 | 30.763 | 1.00 | 43.69 | B C |
| ATOM | 6205 | OE1 | GLU B 206 | 65.577 | 29.287 | 31.451 | 1.00 | 44.40 | B O |
| ATOM | 6206 | OE2 | GLU B 206 | 64.102 | 30.163 | 30.060 | 1.00 | 46.22 | B O |
| ATOM | 6207 | C   | GLU B 206 | 63.028 | 24.792 | 30.573 | 1.00 | 39.62 | B C |
| ATOM | 6208 | O   | GLU B 206 | 63.702 | 24.335 | 29.641 | 1.00 | 39.38 | B O |
| ATOM | 6210 | N   | LYS B 207 | 61.712 | 24.588 | 30.670 | 1.00 | 38.20 | B N |
| ATOM | 6211 | CA  | LYS B 207 | 60.989 | 23.958 | 29.582 | 1.00 | 36.90 | B C |
| ATOM | 6213 | CB  | LYS B 207 | 60.129 | 22.798 | 30.063 | 1.00 | 36.28 | B C |
| ATOM | 6216 | CG  | LYS B 207 | 60.812 | 21.763 | 30.917 | 1.00 | 36.84 | B C |
| ATOM | 6219 | CD  | LYS B 207 | 61.744 | 20.894 | 30.135 | 1.00 | 37.68 | B C |
| ATOM | 6222 | CE  | LYS B 207 | 61.711 | 19.448 | 30.541 | 1.00 | 38.95 | B C |
| ATOM | 6225 | NZ  | LYS B 207 | 62.685 | 19.157 | 31.581 | 1.00 | 40.55 | B N |
| ATOM | 6229 | C   | LYS B 207 | 60.134 | 25.012 | 28.909 | 1.00 | 36.63 | B C |
| ATOM | 6230 | O   | LYS B 207 | 59.797 | 26.037 | 29.505 | 1.00 | 36.62 | B O |
| ATOM | 6232 | N   | THR B 208 | 59.742 | 24.722 | 27.682 | 1.00 | 36.28 | B N |
| ATOM | 6233 | CA  | THR B 208 | 59.089 | 25.683 | 26.827 | 1.00 | 36.93 | B C |
| ATOM | 6235 | CB  | THR B 208 | 60.131 | 26.233 | 25.828 | 1.00 | 38.08 | B C |
| ATOM | 6237 | OG1 | THR B 208 | 61.026 | 27.122 | 26.532 | 1.00 | 39.48 | B O |
| ATOM | 6239 | CG2 | THR B 208 | 59.448 | 26.988 | 24.697 | 1.00 | 38.01 | B C |
| ATOM | 6243 | C   | THR B 208 | 57.928 | 25.036 | 26.064 | 1.00 | 36.11 | B C |
| ATOM | 6244 | O   | THR B 208 | 57.965 | 23.838 | 25.777 | 1.00 | 35.70 | B O |
| ATOM | 6246 | N   | VAL B 209 | 56.910 | 25.829 | 25.731 | 1.00 | 35.31 | B |

FIG 8 – CONT.

| | | | | | | | | | | |
|---|---|---|---|---|---|---|---|---|---|---|
| ATOM | 6247 | CA | VAL | B | 209 | 55.811 | 25.351 | 24.892 | 1.00 34.99 | B |
| ATOM | 6249 | CB | VAL | B | 209 | 54.556 | 24.916 | 25.709 | 1.00 34.80 | B |
| ATOM | 6251 | CG1 | VAL | B | 209 | 54.832 | 23.594 | 26.417 | 1.00 34.26 | B |
| ATOM | 6255 | CG2 | VAL | B | 209 | 54.124 | 26.011 | 26.689 | 1.00 32.24 | B |
| ATOM | 6259 | C | VAL | B | 209 | 55.406 | 26.445 | 23.926 | 1.00 35.83 | B |
| ATOM | 6260 | O | VAL | B | 209 | 55.488 | 27.625 | 24.260 | 1.00 35.71 | B |
| ATOM | 6262 | N | ALA | B | 210 | 54.979 | 26.039 | 22.730 | 1.00 36.68 | B |
| ATOM | 6263 | CA | ALA | B | 210 | 54.562 | 26.979 | 21.671 | 1.00 37.51 | B |
| ATOM | 6265 | CB | ALA | B | 210 | 55.493 | 26.885 | 20.444 | 1.00 37.92 | B |
| ATOM | 6269 | C | ALA | B | 210 | 53.138 | 26.676 | 21.282 | 1.00 37.57 | B |
| ATOM | 6270 | O | ALA | B | 210 | 52.788 | 25.522 | 21.128 | 1.00 37.93 | B |
| ATOM | 6272 | N | PRO | B | 211 | 52.297 | 27.705 | 21.177 | 1.00 37.94 | B |
| ATOM | 6273 | CA | PRO | B | 211 | 50.956 | 27.567 | 20.626 | 1.00 39.01 | B |
| ATOM | 6275 | CB | PRO | B | 211 | 50.501 | 29.008 | 20.509 | 1.00 39.30 | B |
| ATOM | 6278 | CG | PRO | B | 211 | 51.197 | 29.657 | 21.644 | 1.00 39.75 | B |
| ATOM | 6281 | CD | PRO | B | 211 | 52.528 | 29.043 | 21.725 | 1.00 37.72 | B |
| ATOM | 6284 | C | PRO | B | 211 | 50.882 | 26.898 | 19.257 | 1.00 39.43 | B |
| ATOM | 6285 | O | PRO | B | 211 | 50.107 | 25.945 | 19.099 | 1.00 40.89 | B |
| TER | | | | | | | | | | |
| ATOM | 6286 | N | GLN | C | 1 | 22.240 | -8.732 | -0.994 | 1.00 40.01 | C |
| ATOM | 6287 | CA | GLN | C | 1 | 23.641 | -8.863 | -1.516 | 1.00 39.17 | C |
| ATOM | 6289 | CB | GLN | C | 1 | 23.692 | -9.908 | -2.629 | 1.00 39.27 | C |
| ATOM | 6296 | C | GLN | C | 1 | 24.253 | -7.509 | -1.986 | 1.00 37.68 | C |
| ATOM | 6297 | O | GLN | C | 1 | 25.443 | -7.272 | -1.758 | 1.00 38.53 | C |
| ATOM | 6301 | N | VAL | C | 2 | 23.484 | -6.627 | -2.622 | 1.00 35.82 | G |
| ATOM | 6302 | CA | VAL | C | 2 | 24.023 | -5.293 | -2.934 | 1.00 34.05 | G |
| ATOM | 6304 | CB | VAL | C | 2 | 23.261 | -4.535 | -4.026 | 1.00 34.18 | C |
| ATOM | 6306 | CG1 | VAL | C | 2 | 23.774 | -3.064 | -4.119 | 1.00 31.13 | C |
| ATOM | 6310 | CG2 | VAL | C | 2 | 23.374 | -5.249 | -5.394 | 1.00 32.74 | C |
| ATOM | 6314 | C | VAL | C | 2 | 24.011 | -4.452 | -1.670 | 1.00 34.23 | G |
| ATOM | 6315 | O | VAL | C | 2 | 22.959 | -4.258 | -1.070 | 1.00 33.78 | G |

FIG 8 – CONT.

| | | | | | | | | | | |
|---|---|---|---|---|---|---|---|---|---|---|
| ATOM | 6317 | N | GLN | C | 3 | 25.177 | -3.958 | -1.257 | 1.00 33.68 | G N |
| ATOM | 6318 | CA | GLN | C | 3 | 25.241 | -3.052 | -0.122 | 1.00 33.28 | G C |
| ATOM | 6320 | CB | GLN | C | 3 | 25.667 | -3.829 | 1.116 | 1.00 34.38 | G C |
| ATOM | 6323 | CG | GLN | C | 3 | 25.429 | -3.100 | 2.419 | 1.00 38.11 | G C |
| ATOM | 6326 | CD | GLN | C | 3 | 25.739 | -3.981 | 3.636 | 1.00 44.27 | G C |
| ATOM | 6327 | OE1 | GLN | C | 3 | 26.587 | -3.634 | 4.476 | 1.00 46.34 | G O |
| ATOM | 6328 | NE2 | GLN | C | 3 | 25.083 | -5.148 | 3.710 | 1.00 46.46 | G N |
| ATOM | 6331 | C | GLN | C | 3 | 26.192 | -1.888 | -0.341 | 1.00 32.44 | G C |
| ATOM | 6332 | O | GLN | C | 3 | 27.312 | -2.048 | -0.858 | 1.00 30.81 | G O |
| ATOM | 6334 | N | LEU | C | 4 | 25.751 | -0.714 | 0.101 | 1.00 32.01 | G N |
| ATOM | 6335 | CA | LEU | C | 4 | 26.562 | 0.481 | 0.055 | 1.00 31.02 | G C |
| ATOM | 6337 | CB | LEU | C | 4 | 25.788 | 1.573 | -0.671 | 1.00 31.11 | G C |
| ATOM | 6340 | CG | LEU | C | 4 | 25.392 | 1.244 | -2.125 | 1.00 31.06 | G C |
| ATOM | 6342 | CD1 | LEU | C | 4 | 24.632 | 2.409 | -2.699 | 1.00 30.40 | G C |
| ATOM | 6346 | CD2 | LEU | C | 4 | 26.598 | 0.926 | -2.991 | 1.00 28.03 | G C |
| ATOM | 6350 | C | LEU | C | 4 | 26.978 | 0.913 | 1.468 | 1.00 31.40 | G C |
| ATOM | 6351 | O | LEU | C | 4 | 26.153 | 1.250 | 2.308 | 1.00 32.57 | G O |
| ATOM | 6353 | N | VAL | C | 5 | 28.270 | 0.910 | 1.723 | 1.00 30.81 | G N |
| ATOM | 6354 | CA | VAL | C | 5 | 28.800 | 1.230 | 3.023 | 1.00 31.05 | G C |
| ATOM | 6356 | CB | VAL | C | 5 | 29.824 | 0.138 | 3.450 | 1.00 31.75 | C C |
| ATOM | 6358 | CG1 | VAL | C | 5 | 30.421 | 0.395 | 4.849 | 1.00 32.33 | C C |
| ATOM | 6362 | CG2 | VAL | C | 5 | 29.144 | -1.265 | 3.418 | 1.00 33.05 | C C |
| ATOM | 6366 | C | VAL | C | 5 | 29.412 | 2.644 | 2.959 | 1.00 30.04 | G C |
| ATOM | 6367 | O | VAL | C | 5 | 30.319 | 2.938 | 2.134 | 1.00 30.14 | G O |
| ATOM | 6369 | N | GLN | C | 6 | 28.868 | 3.522 | 3.794 | 1.00 28.57 | G N |
| ATOM | 6370 | CA | GLN | C | 6 | 29.280 | 4.912 | 3.876 | 1.00 27.64 | G C |
| ATOM | 6372 | CB | GLN | C | 6 | 28.069 | 5.830 | 3.786 | 1.00 27.21 | G C |
| ATOM | 6375 | CG | GLN | C | 6 | 27.380 | 5.786 | 2.443 | 1.00 23.97 | G C |
| ATOM | 6378 | CD | GLN | C | 6 | 26.408 | 6.888 | 2.218 | 1.00 21.40 | G C |
| ATOM | 6379 | OE1 | GLN | C | 6 | 25.224 | 6.642 | 2.011 | 1.00 21.28 | G O |

FIG 8 – CONT.

| ATOM | 6380 | NE2 | GLN | C | 6  | 26.900 | 8.138  | 2.197  | 1.00 | 23.05 | G | N |
| ATOM | 6383 | C   | GLN | C | 6  | 30.082 | 5.232  | 5.141  | 1.00 | 28.59 | G | C |
| ATOM | 6384 | O   | GLN | C | 6  | 29.841 | 4.697  | 6.228  | 1.00 | 29.46 | G | O |
| ATOM | 6386 | N   | SER | C | 7  | 31.026 | 6.152  | 4.998  | 1.00 | 28.75 | G | N |
| ATOM | 6387 | CA  | SER | C | 7  | 31.914 | 6.504  | 6.083  | 1.00 | 28.22 | G | C |
| ATOM | 6389 | CB  | SER | C | 7  | 33.066 | 7.391  | 5.578  | 1.00 | 27.87 | G | C |
| ATOM | 6392 | OG  | SER | C | 7  | 32.581 | 8.452  | 4.782  | 1.00 | 28.45 | G | O |
| ATOM | 6394 | C   | SER | C | 7  | 31.119 | 7.187  | 7.187  | 1.00 | 27.27 | G | C |
| ATOM | 6395 | O   | SER | C | 7  | 29.977 | 7.621  | 6.988  | 1.00 | 27.51 | G | O |
| ATOM | 6397 | N   | GLY | C | 8  | 31.732 | 7.279  | 8.352  | 1.00 | 26.52 | G | N |
| ATOM | 6398 | CA  | GLY | C | 8  | 31.019 | 7.703  | 9.552  | 1.00 | 26.68 | G | C |
| ATOM | 6401 | C   | GLY | C | 8  | 30.811 | 9.203  | 9.627  | 1.00 | 25.66 | G | C |
| ATOM | 6402 | O   | GLY | C | 8  | 31.327 | 9.972  | 8.801  | 1.00 | 25.82 | G | O |
| ATOM | 6404 | N   | ALA | C | 9  | 30.091 | 9.599  | 10.653 | 1.00 | 24.38 | G | N |
| ATOM | 6405 | CA  | ALA | C | 9  | 29.665 | 10.964 | 10.852 | 1.00 | 24.24 | G | C |
| ATOM | 6407 | CB  | ALA | C | 9  | 28.754 | 11.050 | 12.072 | 1.00 | 24.33 | G | C |
| ATOM | 6411 | C   | ALA | C | 9  | 30.848 | 11.901 | 11.000 | 1.00 | 23.93 | G | C |
| ATOM | 6412 | O   | ALA | C | 9  | 31.864 | 11.535 | 11.548 | 1.00 | 23.40 | G | O |
| ATOM | 6414 | N   | GLU | C | 10 | 30.704 | 13.117 | 10.485 | 1.00 | 23.72 | G | N |
| ATOM | 6415 | CA  | GLU | C | 10 | 31.801 | 14.048 | 10.460 | 1.00 | 23.73 | G | C |
| ATOM | 6417 | CB  | GLU | C | 10 | 32.243 | 14.342 | 9.007  | 1.00 | 23.72 | G | C |
| ATOM | 6420 | CG  | GLU | C | 10 | 32.788 | 13.153 | 8.237  | 1.00 | 25.88 | G | C |
| ATOM | 6423 | CD  | GLU | C | 10 | 34.219 | 12.871 | 8.573  | 1.00 | 27.28 | G | C |
| ATOM | 6424 | OE1 | GLU | C | 10 | 34.843 | 13.623 | 9.355  | 1.00 | 31.67 | G | O |
| ATOM | 6425 | OE2 | GLU | C | 10 | 34.721 | 11.883 | 8.071  | 1.00 | 28.36 | G | O |
| ATOM | 6426 | C   | GLU | C | 10 | 31.353 | 15.347 | 11.055 | 1.00 | 23.09 | G | C |
| ATOM | 6427 | O   | GLU | C | 10 | 30.248 | 15.816 | 10.769 | 1.00 | 22.39 | G | O |
| ATOM | 6429 | N   | VAL | C | 11 | 32.266 | 15.946 | 11.817 | 1.00 | 23.93 | G | N |
| ATOM | 6430 | CA  | VAL | C | 11 | 32.069 | 17.244 | 12.404 | 1.00 | 24.65 | G | C |
| ATOM | 6432 | CB  | VAL | C | 11 | 31.909 | 17.142 | 13.928 | 1.00 | 25.12 | G | C |
| ATOM | 6434 | CG1 | VAL | C | 11 | 31.491 | 18.499 | 14.512 | 1.00 | 23.58 | G |   |

FIG 8 – CONT.

| ATOM | 6438 | CG2 | VAL | C | 11 | 30.844 | 16.053 | 14.257 | 1.00 | 26.06 | G |
|---|---|---|---|---|---|---|---|---|---|---|---|
| ATOM | 6442 | C | VAL | C | 11 | 33.295 | 18.055 | 12.067 | 1.00 | 24.66 | C |
| ATOM | 6443 | O | VAL | C | 11 | 34.409 | 17.648 | 12.347 | 1.00 | 24.79 | O |
| ATOM | 6445 | N | LYS | C | 12 | 33.072 | 19.219 | 11.484 | 1.00 | 24.72 | N |
| ATOM | 6446 | CA | LYS | C | 12 | 34.153 | 20.047 | 10.968 | 1.00 | 25.75 | C |
| ATOM | 6448 | CB | LYS | C | 12 | 34.288 | 19.833 | 9.457 | 1.00 | 25.55 | C |
| ATOM | 6451 | CG | LYS | C | 12 | 34.600 | 18.428 | 9.049 | 1.00 | 26.14 | C |
| ATOM | 6454 | CD | LYS | C | 12 | 35.850 | 17.887 | 9.657 | 1.00 | 28.05 | C |
| ATOM | 6457 | CE | LYS | C | 12 | 36.932 | 17.602 | 8.663 | 1.00 | 32.41 | C |
| ATOM | 6460 | NZ | LYS | C | 12 | 38.107 | 16.922 | 9.357 | 1.00 | 32.11 | N |
| ATOM | 6464 | C | LYS | C | 12 | 33.811 | 21.494 | 11.168 | 1.00 | 25.25 | C |
| ATOM | 6465 | O | LYS | C | 12 | 32.657 | 21.821 | 11.313 | 1.00 | 24.35 | O |
| ATOM | 6467 | N | LYS | C | 13 | 34.819 | 22.353 | 11.082 | 1.00 | 26.49 | N |
| ATOM | 6468 | CA | LYS | C | 13 | 34.625 | 23.808 | 11.051 | 1.00 | 27.08 | C |
| ATOM | 6470 | CB | LYS | C | 13 | 35.777 | 24.496 | 11.778 | 1.00 | 28.06 | C |
| ATOM | 6473 | CG | LYS | C | 13 | 35.892 | 24.000 | 13.209 | 1.00 | 31.43 | C |
| ATOM | 6476 | CD | LYS | C | 13 | 36.977 | 24.639 | 14.033 | 1.00 | 34.60 | C |
| ATOM | 6479 | CE | LYS | C | 13 | 36.501 | 24.749 | 15.501 | 1.00 | 36.83 | C |
| ATOM | 6482 | NZ | LYS | C | 13 | 37.543 | 25.229 | 16.455 | 1.00 | 36.99 | N |
| ATOM | 6486 | C | LYS | C | 13 | 34.555 | 24.320 | 9.628 | 1.00 | 26.82 | C |
| ATOM | 6487 | O | LYS | C | 13 | 35.166 | 23.756 | 8.729 | 1.00 | 25.97 | O |
| ATOM | 6489 | N | PRO | C | 14 | 33.873 | 25.448 | 9.416 | 1.00 | 27.45 | N |
| ATOM | 6490 | CA | PRO | C | 14 | 33.893 | 26.026 | 8.074 | 1.00 | 27.10 | C |
| ATOM | 6492 | CB | PRO | C | 14 | 33.177 | 27.364 | 8.251 | 1.00 | 27.77 | C |
| ATOM | 6495 | CG | PRO | C | 14 | 32.267 | 27.163 | 9.468 | 1.00 | 27.33 | C |
| ATOM | 6498 | CD | PRO | C | 14 | 33.115 | 26.289 | 10.367 | 1.00 | 28.03 | C |
| ATOM | 6501 | C | PRO | C | 14 | 35.313 | 26.221 | 7.572 | 1.00 | 27.26 | C |
| ATOM | 6502 | O | PRO | C | 14 | 36.206 | 26.565 | 8.350 | 1.00 | 27.12 | O |
| ATOM | 6503 | N | GLY | C | 15 | 35.532 | 25.966 | 6.280 | 1.00 | 27.31 | N |
| ATOM | 6504 | CA | GLY | C | 15 | 36.866 | 26.118 | 5.679 | 1.00 | 27.14 | C |

FIG 8 – CONT.

| ATOM | 6507 | C | GLY | C | 15 | 37.723 | 24.857 | 5.705 | 1.00 | 27.35 | G |
|---|---|---|---|---|---|---|---|---|---|---|---|
| ATOM | 6508 | O | GLY | C | 15 | 38.726 | 24.773 | 4.978 | 1.00 | 27.95 | G |
| ATOM | 6510 | N | GLN | C | 16 | 37.349 | 23.854 | 6.497 | 1.00 | 26.51 | G |
| ATOM | 6511 | CA | GLN | C | 16 | 38.095 | 22.579 | 6.462 | 1.00 | 27.16 | G |
| ATOM | 6513 | CB | GLN | C | 16 | 37.847 | 21.729 | 7.703 | 1.00 | 27.13 | C |
| ATOM | 6516 | CG | GLN | C | 16 | 38.353 | 22.440 | 8.952 | 1.00 | 28.97 | C |
| ATOM | 6519 | CD | GLN | C | 16 | 38.337 | 21.570 | 10.190 | 1.00 | 29.54 | C |
| ATOM | 6520 | OE1 | GLN | C | 16 | 37.295 | 21.097 | 10.591 | 1.00 | 32.99 | C |
| ATOM | 6521 | NE2 | GLN | C | 16 | 39.491 | 21.366 | 10.795 | 1.00 | 29.88 | C |
| ATOM | 6524 | C | GLN | C | 16 | 37.733 | 21.802 | 5.226 | 1.00 | 26.85 | G |
| ATOM | 6525 | O | GLN | C | 16 | 36.637 | 21.944 | 4.704 | 1.00 | 26.64 | G |
| ATOM | 6527 | N | SER | C | 17 | 38.659 | 20.993 | 4.758 | 1.00 | 27.50 | G |
| ATOM | 6528 | CA | SER | C | 17 | 38.376 | 20.106 | 3.680 | 1.00 | 29.18 | G |
| ATOM | 6530 | CB | SER | C | 17 | 39.637 | 19.845 | 2.844 | 1.00 | 29.84 | G |
| ATOM | 6533 | OG | SER | C | 17 | 40.535 | 19.010 | 3.549 | 1.00 | 32.90 | G |
| ATOM | 6535 | C | SER | C | 17 | 37.854 | 18.817 | 4.274 | 1.00 | 28.72 | G |
| ATOM | 6536 | O | SER | C | 17 | 38.002 | 18.580 | 5.454 | 1.00 | 30.57 | G |
| ATOM | 6538 | N | LEU | C | 18 | 37.253 | 17.987 | 3.430 | 1.00 | 28.24 | G |
| ATOM | 6539 | CA | LEU | C | 18 | 36.592 | 16.781 | 3.833 | 1.00 | 26.79 | G |
| ATOM | 6541 | CB | LEU | C | 18 | 35.258 | 17.088 | 4.529 | 1.00 | 25.88 | G |
| ATOM | 6544 | CG | LEU | C | 18 | 34.325 | 15.916 | 4.861 | 1.00 | 26.64 | G |
| ATOM | 6546 | CD1 | LEU | C | 18 | 34.888 | 14.986 | 5.938 | 1.00 | 23.57 | G |
| ATOM | 6550 | CD2 | LEU | C | 18 | 32.901 | 16.445 | 5.236 | 1.00 | 23.70 | G |
| ATOM | 6554 | C | LEU | C | 18 | 36.312 | 15.945 | 2.608 | 1.00 | 27.03 | G |
| ATOM | 6555 | O | LEU | C | 18 | 35.787 | 16.444 | 1.600 | 1.00 | 26.32 | G |
| ATOM | 6557 | N | LYS | C | 19 | 36.580 | 14.656 | 2.766 | 1.00 | 26.59 | G |
| ATOM | 6558 | CA | LYS | C | 19 | 36.321 | 13.645 | 1.773 | 1.00 | 27.36 | G |
| ATOM | 6560 | CB | LYS | C | 19 | 37.671 | 13.135 | 1.228 | 1.00 | 27.68 | G |
| ATOM | 6563 | CG | LYS | C | 19 | 37.596 | 12.292 | -0.034 | 1.00 | 31.52 | G |
| ATOM | 6566 | CD | LYS | C | 19 | 39.034 | 12.170 | -0.679 | 1.00 | 35.65 | G |
| ATOM | 6569 | CE | LYS | C | 19 | 39.029 | 11.546 | -2.083 | 1.00 | 38.23 | G |

FIG 8 – CONT.

```
C
ATOM   6572  NZ   LYS C  19    40.432  11.331  -2.620  1.00 39.21           G
N
ATOM   6576  C    LYS C  19    35.575  12.492   2.462  1.00 26.45           G
C
ATOM   6577  O    LYS C  19    36.054  11.958   3.450  1.00 25.38           G
O
ATOM   6579  N    ILE C  20    34.381  12.179   1.982  1.00 26.27           G
N
ATOM   6580  CA   ILE C  20    33.612  11.069   2.496  1.00 26.97           G
C
ATOM   6582  CB   ILE C  20    32.223  11.482   3.028  1.00 26.60           G
C
ATOM   6584  CG1  ILE C  20    31.302  11.969   1.934  1.00 26.82           G
C
ATOM   6587  CD1  ILE C  20    29.932  12.467   2.485  1.00 27.19           G
C
ATOM   6591  CG2  ILE C  20    32.367  12.519   4.171  1.00 26.13           G
C
ATOM   6595  C    ILE C  20    33.509   9.992   1.411  1.00 27.34           G
C
ATOM   6596  O    ILE C  20    33.725  10.276   0.222  1.00 27.42           G
O
ATOM   6598  N    SER C  21    33.174   8.780   1.835  1.00 27.34           G
N
ATOM   6599  CA   SER C  21    33.315   7.599   0.998  1.00 27.71           G
C
ATOM   6601  CB   SER C  21    34.538   6.817   1.461  1.00 28.12           G
C
ATOM   6604  OG   SER C  21    34.254   6.061   2.628  1.00 31.21           G
O
ATOM   6606  C    SER C  21    32.082   6.719   0.982  1.00 26.65           G
C
ATOM   6607  O    SER C  21    31.331   6.639   1.963  1.00 27.47           G
O
ATOM   6609  N    CYS C  22    31.865   6.092  -0.156  1.00 25.90           G
N
ATOM   6610  CA   CYS C  22    30.827   5.121  -0.365  1.00 27.13           G
C
ATOM   6612  CB   CYS C  22    29.760   5.702  -1.220  1.00 27.40           G
C
ATOM   6615  SG   CYS C  22    28.448   4.622  -1.826  1.00 27.41           G
S
ATOM   6617  C    CYS C  22    31.447   3.942  -1.067  1.00 28.61           G
C
ATOM   6618  O    CYS C  22    31.966   4.086  -2.194  1.00 30.76           G
O
ATOM   6620  N    LYS C  23    31.458   2.797  -0.389  1.00 28.60           G
N
ATOM   6621  CA   LYS C  23    31.993   1.570  -0.926  1.00 28.82           G
C
ATOM   6623  CB   LYS C  23    32.981   0.994   0.075  1.00 30.17           C
C
ATOM   6626  CG   LYS C  23    33.546  -0.365  -0.360  1.00 32.06           C
C
ATOM   6629  CD   LYS C  23    34.945  -0.585   0.210  1.00 34.96           C
C
ATOM   6632  CE   LYS C  23    35.226  -2.061   0.478  1.00 38.70           C
C
ATOM   6635  NZ   LYS C  23    34.822  -2.494   1.849  1.00 42.70           C
N
```

FIG 8 – CONT.

| ATOM | 6639 | C | LYS | C | 23 | 30.900 | 0.536 | -1.183 | 1.00 | 28.02 | G |
| --- | --- | --- | --- | --- | --- | --- | --- | --- | --- | --- | --- |
| ATOM | 6639 | C | LYS | C | 23 | 30.900 | 0.536 | -1.183 | 1.00 | 28.02 | C |
| ATOM | 6640 | O | LYS | C | 23 | 30.109 | 0.256 | -0.303 | 1.00 | 27.61 | O |
| ATOM | 6642 | N | ALA | C | 24 | 30.829 | 0.009 | -2.401 | 1.00 | 26.56 | N |
| ATOM | 6643 | CA | ALA | C | 24 | 29.800 | -0.964 | -2.746 | 1.00 | 25.85 | C |
| ATOM | 6645 | CB | ALA | C | 24 | 29.268 | -0.759 | -4.192 | 1.00 | 24.27 | C |
| ATOM | 6649 | C | ALA | C | 24 | 30.347 | -2.377 | -2.570 | 1.00 | 25.33 | C |
| ATOM | 6650 | O | ALA | C | 24 | 31.530 | -2.607 | -2.793 | 1.00 | 25.25 | O |
| ATOM | 6652 | N | SER | C | 25 | 29.448 | -3.280 | -2.176 | 1.00 | 25.75 | N |
| ATOM | 6653 | CA | SER | C | 25 | 29.668 | -4.727 | -1.938 | 1.00 | 25.78 | C |
| ATOM | 6655 | CB | SER | C | 25 | 29.317 | -5.053 | -0.500 | 1.00 | 25.68 | C |
| ATOM | 6658 | OG | SER | C | 25 | 30.441 | -4.868 | 0.310 | 1.00 | 28.66 | O |
| ATOM | 6660 | C | SER | C | 25 | 28.665 | -5.465 | -2.752 | 1.00 | 25.43 | C |
| ATOM | 6661 | O | SER | C | 25 | 27.527 | -5.011 | -2.782 | 1.00 | 25.04 | O |
| ATOM | 6663 | N | GLY | C | 26 | 29.023 | -6.626 | -3.326 | 1.00 | 25.96 | N |
| ATOM | 6664 | CA | GLY | C | 26 | 28.144 | -7.367 | -4.264 | 1.00 | 25.86 | C |
| ATOM | 6667 | C | GLY | C | 26 | 27.633 | -6.506 | -5.429 | 1.00 | 26.29 | C |
| ATOM | 6668 | O | GLY | C | 26 | 26.497 | -6.640 | -5.884 | 1.00 | 26.27 | O |
| ATOM | 6670 | N | TYR | C | 27 | 28.472 | -5.604 | -5.903 | 1.00 | 26.67 | N |
| ATOM | 6671 | CA | TYR | C | 27 | 28.033 | -4.542 | -6.850 | 1.00 | 26.87 | C |
| ATOM | 6673 | CB | TYR | C | 27 | 27.124 | -3.529 | -6.115 | 1.00 | 26.11 | C |
| ATOM | 6676 | CG | TYR | C | 27 | 26.290 | -2.617 | -6.982 | 1.00 | 24.77 | C |
| ATOM | 6677 | CD1 | TYR | C | 27 | 25.321 | -3.123 | -7.828 | 1.00 | 25.78 | C |
| ATOM | 6679 | CE1 | TYR | C | 27 | 24.528 | -2.281 | -8.609 | 1.00 | 26.52 | C |
| ATOM | 6681 | CZ | TYR | C | 27 | 24.715 | -0.907 | -8.532 | 1.00 | 25.34 | C |
| ATOM | 6682 | OH | TYR | C | 27 | 23.931 | -0.072 | -9.302 | 1.00 | 30.88 | O |
| ATOM | 6684 | CE2 | TYR | C | 27 | 25.675 | -0.386 | -7.725 | 1.00 | 23.58 | C |
| ATOM | 6686 | CD2 | TYR | C | 27 | 26.453 | -1.233 | -6.933 | 1.00 | 24.38 | C |
| ATOM | 6688 | C | TYR | C | 27 | 29.272 | -3.847 | -7.333 | 1.00 | 26.46 | C |
| ATOM | 6689 | O | TYR | C | 27 | 29.926 | -3.175 | -6.548 | 1.00 | 28.38 | O |
| ATOM | 6691 | N | SER | C | 28 | 29.643 | -4.057 | -8.584 | 1.00 | 26.71 | N |
| ATOM | 6692 | CA | SER | C | 28 | 30.868 | -3.498 | -9.119 | 1.00 | 26.94 | G |

FIG 8 – CONT.

| ATOM | 6694 | CB | SER | C | 28 | 31.441 | -4.370 | -10.254 | 1.00 | 27.55 | G C |
| --- | --- | --- | --- | --- | --- | --- | --- | --- | --- | --- | --- |
| ATOM | 6697 | OG | SER | C | 28 | 32.737 | -3.884 | -10.597 | 1.00 | 27.28 | G O |
| ATOM | 6699 | C | SER | C | 28 | 30.607 | -2.139 | -9.694 | 1.00 | 27.30 | G C |
| ATOM | 6700 | O | SER | C | 28 | 29.732 | -1.971 | -10.556 | 1.00 | 27.23 | G O |
| ATOM | 6702 | N | LEU | C | 29 | 31.387 | -1.167 | -9.252 | 1.00 | 28.24 | G N |
| ATOM | 6703 | CA | LEU | C | 29 | 31.287 | 0.183 | -9.804 | 1.00 | 29.01 | G C |
| ATOM | 6705 | CB | LEU | C | 29 | 31.770 | 1.196 | -8.793 | 1.00 | 29.04 | C C |
| ATOM | 6708 | CG | LEU | C | 29 | 31.094 | 1.247 | -7.422 | 1.00 | 28.87 | C C |
| ATOM | 6710 | CD1 | LEU | C | 29 | 31.566 | 2.499 | -6.743 | 1.00 | 27.96 | C C |
| ATOM | 6714 | CD2 | LEU | C | 29 | 29.605 | 1.237 | -7.525 | 1.00 | 26.44 | C C |
| ATOM | 6718 | C | LEU | C | 29 | 32.078 | 0.336 | -11.104 | 1.00 | 29.90 | G C |
| ATOM | 6719 | O | LEU | C | 29 | 32.230 | 1.450 | -11.629 | 1.00 | 30.31 | G O |
| ATOM | 6721 | N | THR | C | 30 | 32.582 | -0.782 | -11.625 | 1.00 | 30.73 | G N |
| ATOM | 6722 | CA | THR | C | 30 | 33.092 | -0.831 | -12.988 | 1.00 | 31.31 | G C |
| ATOM | 6724 | CB | THR | C | 30 | 33.985 | -2.052 | -13.190 | 1.00 | 31.80 | C C |
| ATOM | 6726 | OG1 | THR | C | 30 | 35.059 | -1.990 | -12.241 | 1.00 | 33.18 | C O |
| ATOM | 6728 | CG2 | THR | C | 30 | 34.579 | -2.099 | -14.650 | 1.00 | 32.42 | C C |
| ATOM | 6732 | C | THR | C | 30 | 31.933 | -0.880 | -13.966 | 1.00 | 31.44 | G C |
| ATOM | 6733 | O | THR | C | 30 | 32.064 | -0.449 | -15.117 | 1.00 | 31.43 | G O |
| ATOM | 6735 | N | ASP | C | 31 | 30.795 | -1.407 | -13.513 | 1.00 | 31.07 | G N |
| ATOM | 6736 | CA | ASP | C | 31 | 29.631 | -1.597 | -14.366 | 1.00 | 31.16 | G C |
| ATOM | 6738 | CB | ASP | C | 31 | 29.201 | -3.056 | -14.296 | 1.00 | 31.79 | G C |
| ATOM | 6741 | CG | ASP | C | 31 | 30.292 | -4.006 | -14.735 | 1.00 | 32.33 | G C |
| ATOM | 6742 | OD1 | ASP | C | 31 | 31.173 | -3.584 | -15.503 | 1.00 | 35.84 | G O |
| ATOM | 6743 | OD2 | ASP | C | 31 | 30.256 | -5.174 | -14.318 | 1.00 | 33.39 | G O |
| ATOM | 6744 | C | ASP | C | 31 | 28.411 | -0.746 | -13.999 | 1.00 | 30.81 | G C |
| ATOM | 6745 | O | ASP | C | 31 | 27.397 | -0.844 | -14.667 | 1.00 | 30.99 | G O |
| ATOM | 6747 | N | ASN | C | 32 | 28.484 | 0.023 | -12.914 | 1.00 | 29.63 | G N |
| ATOM | 6748 | CA | ASN | C | 32 | 27.324 | 0.727 | -12.377 | 1.00 | 28.61 | G C |
| ATOM | 6750 | CB | ASN | C | 32 | 26.684 | -0.026 | -11.187 | 1.00 | 28.90 | C C |

FIG 8 – CONT.

| ATOM | 6753 | CG | ASN | C | 32 | 26.068 | -1.365 | -11.584 | 1.00 | 29.04 | C |
|------|------|-----|-----|---|----|--------|--------|---------|------|-------|---|
| ATOM | 6754 | OD1 | ASN | C | 32 | 24.997 | -1.419 | -12.171 | 1.00 | 33.06 | O |
| ATOM | 6755 | ND2 | ASN | C | 32 | 26.744 | -2.449 | -11.249 | 1.00 | 30.54 | N |
| ATOM | 6758 | C   | ASN | C | 32 | 27.746 | 2.125  | -11.955 | 1.00 | 27.62 | C |
| ATOM | 6759 | O   | ASN | C | 32 | 28.924 | 2.395  | -11.746 | 1.00 | 26.77 | O |
| ATOM | 6761 | N   | TRP | C | 33 | 26.771 | 3.012  | -11.841 | 1.00 | 27.02 | N |
| ATOM | 6762 | CA  | TRP | C | 33 | 27.037 | 4.384  | -11.482 | 1.00 | 27.33 | C |
| ATOM | 6764 | CB  | TRP | C | 33 | 26.232 | 5.293  | -12.409 | 1.00 | 27.55 | C |
| ATOM | 6767 | CG  | TRP | C | 33 | 26.654 | 5.200  | -13.835 | 1.00 | 30.35 | C |
| ATOM | 6768 | CD1 | TRP | C | 33 | 26.853 | 4.043  | -14.596 | 1.00 | 33.03 | C |
| ATOM | 6770 | NE1 | TRP | C | 33 | 27.228 | 4.384  | -15.875 | 1.00 | 31.47 | N |
| ATOM | 6772 | CE2 | TRP | C | 33 | 27.292 | 5.749  | -15.968 | 1.00 | 33.34 | C |
| ATOM | 6773 | CD2 | TRP | C | 33 | 26.938 | 6.293  | -14.696 | 1.00 | 31.27 | C |
| ATOM | 6774 | CE3 | TRP | C | 33 | 26.933 | 7.680  | -14.526 | 1.00 | 27.96 | C |
| ATOM | 6776 | CZ3 | TRP | C | 33 | 27.302 | 8.483  | -15.589 | 1.00 | 30.90 | C |
| ATOM | 6778 | CH2 | TRP | C | 33 | 27.648 | 7.925  | -16.855 | 1.00 | 31.98 | C |
| ATOM | 6780 | CZ2 | TRP | C | 33 | 27.649 | 6.563  | -17.058 | 1.00 | 33.09 | C |
| ATOM | 6782 | C   | TRP | C | 33 | 26.680 | 4.688  | -10.013 | 1.00 | 26.76 | C |
| ATOM | 6783 | O   | TRP | C | 33 | 25.830 | 4.068  | -9.436  | 1.00 | 25.95 | O |
| ATOM | 6785 | N   | ILE | C | 34 | 27.311 | 5.702  | -9.443  | 1.00 | 27.56 | N |
| ATOM | 6786 | CA  | ILE | C | 34 | 26.981 | 6.192  | -8.099  | 1.00 | 26.77 | C |
| ATOM | 6788 | CB  | ILE | C | 34 | 28.191 | 6.074  | -7.172  | 1.00 | 27.10 | C |
| ATOM | 6790 | CG1 | ILE | C | 34 | 28.501 | 4.581  | -6.934  | 1.00 | 27.00 | C |
| ATOM | 6793 | CD1 | ILE | C | 34 | 27.632 | 3.914  | -5.933  | 1.00 | 24.42 | C |
| ATOM | 6797 | CG2 | ILE | C | 34 | 27.983 | 6.876  | -5.843  | 1.00 | 24.82 | C |
| ATOM | 6801 | C   | ILE | C | 34 | 26.516 | 7.650  | -8.171  | 1.00 | 27.08 | C |
| ATOM | 6802 | O   | ILE | C | 34 | 27.212 | 8.506  | -8.720  | 1.00 | 26.82 | O |
| ATOM | 6804 | N   | GLY | C | 35 | 25.324 | 7.904  | -7.637  | 1.00 | 27.28 | N |
| ATOM | 6805 | CA  | GLY | C | 35 | 24.838 | 9.239  | -7.415  | 1.00 | 27.29 | C |
| ATOM | 6808 | C   | GLY | C | 35 | 25.000 | 9.653  | -5.941  | 1.00 | 27.40 | C |
| ATOM | 6809 | O   | GLY | C | 35 | 25.124 | 8.796  | -5.054  | 1.00 | 26.66 | O |

FIG 8 – CONT.

| | | | | | | | | | | |
|---|---|---|---|---|---|---|---|---|---|---|
| ATOM | 6811 | N | TRP | C | 36 | 24.981 | 10.973 | -5.718 | 1.00 27.05 | G N |
| ATOM | 6812 | CA | TRP | C | 36 | 24.976 | 11.583 | -4.414 | 1.00 27.40 | G C |
| ATOM | 6814 | CB | TRP | C | 36 | 26.262 | 12.358 | -4.178 | 1.00 27.07 | G C |
| ATOM | 6817 | CG | TRP | C | 36 | 27.496 | 11.488 | -4.028 | 1.00 28.27 | G C |
| ATOM | 6818 | CD1 | TRP | C | 36 | 28.372 | 11.123 | -5.011 | 1.00 26.37 | G C |
| ATOM | 6820 | NE1 | TRP | C | 36 | 29.361 | 10.321 | -4.497 | 1.00 26.22 | G N |
| ATOM | 6822 | CE2 | TRP | C | 36 | 29.151 | 10.148 | -3.157 | 1.00 26.64 | G C |
| ATOM | 6823 | CD2 | TRP | C | 36 | 27.979 | 10.858 | -2.820 | 1.00 29.45 | G C |
| ATOM | 6824 | CE3 | TRP | C | 36 | 27.554 | 10.845 | -1.503 | 1.00 25.66 | G C |
| ATOM | 6826 | CZ3 | TRP | C | 36 | 28.301 | 10.131 | -0.560 | 1.00 26.97 | G C |
| ATOM | 6828 | CH2 | TRP | C | 36 | 29.442 | 9.452 | -0.918 | 1.00 27.83 | G C |
| ATOM | 6830 | CZ2 | TRP | C | 36 | 29.902 | 9.470 | -2.213 | 1.00 29.02 | G C |
| ATOM | 6832 | C | TRP | C | 36 | 23.761 | 12.521 | -4.234 | 1.00 27.39 | G C |
| ATOM | 6833 | O | TRP | C | 36 | 23.467 | 13.364 | -5.080 | 1.00 27.06 | G O |
| ATOM | 6835 | N | VAL | C | 37 | 23.074 | 12.322 | -3.112 | 1.00 26.89 | G N |
| ATOM | 6836 | CA | VAL | C | 37 | 21.905 | 13.062 | -2.721 | 1.00 26.74 | G C |
| ATOM | 6838 | CB | VAL | C | 37 | 20.693 | 12.170 | -2.656 | 1.00 27.37 | G C |
| ATOM | 6840 | CG1 | VAL | C | 37 | 19.460 | 12.993 | -2.207 | 1.00 26.09 | G C |
| ATOM | 6844 | CG2 | VAL | C | 37 | 20.461 | 11.516 | -4.017 | 1.00 25.82 | G C |
| ATOM | 6848 | C | VAL | C | 37 | 22.114 | 13.695 | -1.348 | 1.00 27.03 | G C |
| ATOM | 6849 | O | VAL | C | 37 | 22.555 | 13.038 | -0.405 | 1.00 26.54 | G O |
| ATOM | 6851 | N | ARG | C | 38 | 21.843 | 14.999 | -1.286 | 1.00 27.29 | G N |
| ATOM | 6852 | CA | ARG | C | 38 | 21.965 | 15.775 | -0.070 | 1.00 28.10 | G C |
| ATOM | 6854 | CB | ARG | C | 38 | 22.577 | 17.151 | -0.380 | 1.00 27.96 | G C |
| ATOM | 6857 | CG | ARG | C | 38 | 22.672 | 18.081 | 0.834 | 1.00 28.38 | G C |
| ATOM | 6860 | CD | ARG | C | 38 | 23.424 | 19.373 | 0.527 | 1.00 28.65 | G C |
| ATOM | 6863 | NE | ARG | C | 38 | 22.587 | 20.419 | -0.061 | 1.00 30.40 | G N |
| ATOM | 6865 | CZ | ARG | C | 38 | 22.992 | 21.660 | -0.367 | 1.00 32.08 | G C |
| ATOM | 6866 | NH1 | ARG | C | 38 | 24.249 | 22.032 | -0.197 | 1.00 34.78 | G N |
| ATOM | 6869 | NH2 | ARG | C | 38 | 22.141 | 22.528 | -0.897 | 1.00 33.81 | G N |

FIG 8 – CONT.

| ATOM | 6872 | C | ARG | C | 38 | 20.581 | 15.913 | 0.549 | 1.00 | 28.54 | G |
|---|---|---|---|---|---|---|---|---|---|---|---|
| ATOM | 6873 | O | ARG | C | 38 | 19.582 | 16.012 | -0.178 | 1.00 | 28.27 | G |
| ATOM | 6875 | N | GLN | C | 39 | 20.533 | 15.870 | 1.884 | 1.00 | 28.37 | G |
| ATOM | 6876 | CA | GLN | C | 39 | 19.303 | 16.139 | 2.637 | 1.00 | 28.88 | G |
| ATOM | 6878 | CB | GLN | C | 39 | 18.567 | 14.858 | 3.011 | 1.00 | 28.96 | G |
| ATOM | 6881 | CG | GLN | C | 39 | 17.205 | 15.116 | 3.703 | 1.00 | 28.56 | G |
| ATOM | 6884 | CD | GLN | C | 39 | 16.390 | 13.870 | 3.900 | 1.00 | 27.18 | G |
| ATOM | 6885 | OE1 | GLN | C | 39 | 16.915 | 12.840 | 4.313 | 1.00 | 28.56 | G |
| ATOM | 6886 | NE2 | GLN | C | 39 | 15.099 | 13.943 | 3.588 | 1.00 | 26.26 | G |
| ATOM | 6889 | C | GLN | C | 39 | 19.632 | 16.939 | 3.896 | 1.00 | 29.38 | G |
| ATOM | 6890 | O | GLN | C | 39 | 20.141 | 16.412 | 4.885 | 1.00 | 28.48 | G |
| ATOM | 6892 | N | LYS | C | 40 | 19.384 | 18.230 | 3.831 | 1.00 | 30.59 | G |
| ATOM | 6893 | CA | LYS | C | 40 | 19.669 | 19.081 | 4.955 | 1.00 | 31.84 | G |
| ATOM | 6895 | CB | LYS | C | 40 | 19.718 | 20.538 | 4.498 | 1.00 | 31.85 | C |
| ATOM | 6898 | CG | LYS | C | 40 | 20.888 | 20.819 | 3.599 | 1.00 | 33.26 | C |
| ATOM | 6901 | CD | LYS | C | 40 | 20.681 | 22.008 | 2.684 | 1.00 | 36.81 | C |
| ATOM | 6904 | CE | LYS | C | 40 | 21.096 | 23.305 | 3.282 | 1.00 | 37.69 | C |
| ATOM | 6907 | NZ | LYS | C | 40 | 21.470 | 24.276 | 2.219 | 1.00 | 41.50 | C |
| ATOM | 6911 | C | LYS | C | 40 | 18.587 | 18.815 | 6.025 | 1.00 | 32.48 | G |
| ATOM | 6912 | O | LYS | C | 40 | 17.500 | 18.351 | 5.712 | 1.00 | 31.60 | G |
| ATOM | 6914 | N | PRO | C | 41 | 18.889 | 19.101 | 7.299 | 1.00 | 33.77 | G |
| ATOM | 6915 | CA | PRO | C | 41 | 17.987 | 18.654 | 8.365 | 1.00 | 34.04 | G |
| ATOM | 6917 | CB | PRO | C | 41 | 18.661 | 19.151 | 9.656 | 1.00 | 34.24 | G |
| ATOM | 6920 | CG | PRO | C | 41 | 19.985 | 19.620 | 9.256 | 1.00 | 35.15 | G |
| ATOM | 6923 | CD | PRO | C | 41 | 19.924 | 20.001 | 7.807 | 1.00 | 33.43 | G |
| ATOM | 6926 | C | PRO | C | 41 | 16.610 | 19.238 | 8.218 | 1.00 | 33.83 | G |
| ATOM | 6927 | O | PRO | C | 41 | 16.449 | 20.433 | 7.970 | 1.00 | 33.25 | G |
| ATOM | 6928 | N | GLY | C | 42 | 15.628 | 18.360 | 8.315 | 1.00 | 34.90 | G |
| ATOM | 6929 | CA | GLY | C | 42 | 14.234 | 18.717 | 8.095 | 1.00 | 35.20 | G |
| ATOM | 6932 | C | GLY | C | 42 | 13.822 | 19.029 | 6.670 | 1.00 | 35.99 | G |
| ATOM | 6933 | O | GLY | C | 42 | 12.672 | 19.448 | 6.460 | 1.00 | 36.92 | G |

FIG 8 – CONT.

| | | | | | | | | | |
|---|---|---|---|---|---|---|---|---|---|
| ATOM | 6935 | N | LYS | C | 43 | 14.703 | 18.847 | 5.674 | 1.00 35.09 | G |
| ATOM | 6936 | CA | LYS | C | 43 | 14.332 | 19.221 | 4.314 | 1.00 35.02 | G |
| ATOM | 6938 | CB | LYS | C | 43 | 15.334 | 20.224 | 3.745 | 1.00 36.06 | G |
| ATOM | 6941 | CG | LYS | C | 43 | 15.396 | 21.598 | 4.451 | 1.00 39.16 | G |
| ATOM | 6944 | CD | LYS | C | 43 | 14.036 | 22.302 | 4.611 | 1.00 44.48 | G |
| ATOM | 6947 | CE | LYS | C | 43 | 13.217 | 22.443 | 3.285 | 1.00 47.97 | G |
| ATOM | 6950 | NZ | LYS | C | 43 | 12.220 | 23.583 | 3.332 | 1.00 51.00 | G |
| ATOM | 6954 | C | LYS | C | 43 | 14.220 | 18.020 | 3.375 | 1.00 33.79 | G |
| ATOM | 6955 | O | LYS | C | 43 | 14.395 | 16.869 | 3.770 | 1.00 32.32 | G |
| ATOM | 6957 | N | GLY | C | 44 | 13.926 | 18.316 | 2.117 | 1.00 33.29 | G |
| ATOM | 6958 | CA | GLY | C | 44 | 13.862 | 17.308 | 1.078 | 1.00 33.13 | G |
| ATOM | 6961 | C | GLY | C | 44 | 15.193 | 16.806 | 0.502 | 1.00 32.15 | G |
| ATOM | 6962 | O | GLY | C | 44 | 16.277 | 17.227 | 0.892 | 1.00 31.49 | G |
| ATOM | 6964 | N | LEU | C | 45 | 15.071 | 15.913 | -0.476 | 1.00 31.99 | G |
| ATOM | 6965 | CA | LEU | C | 45 | 16.222 | 15.319 | -1.161 | 1.00 31.01 | G |
| ATOM | 6967 | CB | LEU | C | 45 | 15.842 | 13.958 | -1.712 | 1.00 31.18 | G |
| ATOM | 6970 | CG | LEU | C | 45 | 15.210 | 12.979 | -0.746 | 1.00 30.21 | G |
| ATOM | 6972 | CD1 | LEU | C | 45 | 14.672 | 11.756 | -1.528 | 1.00 29.57 | G |
| ATOM | 6976 | CD2 | LEU | C | 45 | 16.196 | 12.592 | 0.325 | 1.00 26.90 | G |
| ATOM | 6980 | C | LEU | C | 45 | 16.672 | 16.187 | -2.309 | 1.00 30.56 | G |
| ATOM | 6981 | O | LEU | C | 45 | 15.847 | 16.636 | -3.104 | 1.00 29.91 | G |
| ATOM | 6983 | N | GLU | C | 46 | 17.987 | 16.388 | -2.419 | 1.00 29.82 | G |
| ATOM | 6984 | CA | GLU | C | 46 | 18.528 | 17.115 | -3.520 | 1.00 29.71 | G |
| ATOM | 6986 | CB | GLU | C | 46 | 19.178 | 18.400 | -3.042 | 1.00 29.77 | G |
| ATOM | 6989 | CG | GLU | C | 46 | 18.317 | 19.338 | -2.252 | 1.00 30.60 | G |
| ATOM | 6992 | CD | GLU | C | 46 | 19.182 | 20.295 | -1.519 | 1.00 31.95 | G |
| ATOM | 6993 | OE1 | GLU | C | 46 | 19.588 | 19.953 | -0.379 | 1.00 28.00 | G |
| ATOM | 6994 | OE2 | GLU | C | 46 | 19.530 | 21.358 | -2.114 | 1.00 36.27 | G |
| ATOM | 6995 | C | GLU | C | 46 | 19.575 | 16.278 | -4.262 | 1.00 29.67 | G |
| ATOM | 6996 | O | GLU | C | 46 | 20.464 | 15.679 | -3.651 | 1.00 29.91 | G |

FIG 8 – CONT.

| ATOM | 6998 | N   | TRP | C | 47 | 19.487 | 16.267 | -5.585  | 1.00 | 29.61 | G | N |
|------|------|-----|-----|---|----|--------|--------|---------|------|-------|---|---|
| ATOM | 6999 | CA  | TRP | C | 47 | 20.426 | 15.525 | -6.419  | 1.00 | 29.06 | G | C |
| ATOM | 7001 | CB  | TRP | C | 47 | 19.815 | 15.284 | -7.785  | 1.00 | 29.66 | G | C |
| ATOM | 7004 | CG  | TRP | C | 47 | 20.670 | 14.502 | -8.740  | 1.00 | 28.84 | G | C |
| ATOM | 7005 | CD1 | TRP | C | 47 | 21.303 | 14.978 | -9.830  | 1.00 | 27.40 | G | C |
| ATOM | 7007 | NE1 | TRP | C | 47 | 21.963 | 13.953 | -10.488 | 1.00 | 26.99 | G | N |
| ATOM | 7009 | CE2 | TRP | C | 47 | 21.739 | 12.784 | -9.810  | 1.00 | 28.64 | G | C |
| ATOM | 7010 | CD2 | TRP | C | 47 | 20.932 | 13.093 | -8.697  | 1.00 | 27.66 | G | C |
| ATOM | 7011 | CE3 | TRP | C | 47 | 20.568 | 12.072 | -7.825  | 1.00 | 28.38 | G | C |
| ATOM | 7013 | CZ3 | TRP | C | 47 | 21.000 | 10.802 | -8.069  | 1.00 | 29.60 | G | C |
| ATOM | 7015 | CH2 | TRP | C | 47 | 21.808 | 10.508 | -9.195  | 1.00 | 29.42 | G | C |
| ATOM | 7017 | CZ2 | TRP | C | 47 | 22.198 | 11.485 | -10.065 | 1.00 | 28.00 | G | C |
| ATOM | 7019 | C   | TRP | C | 47 | 21.677 | 16.341 | -6.573  | 1.00 | 28.38 | G | C |
| ATOM | 7020 | O   | TRP | C | 47 | 21.613 | 17.514 | -6.935  | 1.00 | 27.70 | G | O |
| ATOM | 7022 | N   | MET | C | 48 | 22.824 | 15.747 | -6.267  | 1.00 | 28.02 | G | N |
| ATOM | 7023 | CA  | MET | C | 48 | 24.064 | 16.488 | -6.391  | 1.00 | 28.83 | G | C |
| ATOM | 7025 | CB  | MET | C | 48 | 25.022 | 16.148 | -5.258  | 1.00 | 28.89 | G | C |
| ATOM | 7028 | CG  | MET | C | 48 | 24.415 | 16.469 | -3.899  | 1.00 | 27.73 | G | C |
| ATOM | 7031 | SD  | MET | C | 48 | 25.480 | 16.059 | -2.594  | 1.00 | 24.08 | G | S |
| ATOM | 7032 | CE  | MET | C | 48 | 26.791 | 17.266 | -2.802  | 1.00 | 21.60 | G | C |
| ATOM | 7036 | C   | MET | C | 48 | 24.744 | 16.226 | -7.708  | 1.00 | 29.23 | G | C |
| ATOM | 7037 | O   | MET | C | 48 | 25.331 | 17.127 | -8.263  | 1.00 | 30.53 | G | O |
| ATOM | 7039 | N   | GLY | C | 49 | 24.690 | 14.986 | -8.173  | 1.00 | 29.12 | G | N |
| ATOM | 7040 | CA  | GLY | C | 49 | 25.426 | 14.576 | -9.339  | 1.00 | 29.37 | G | C |
| ATOM | 7043 | C   | GLY | C | 49 | 25.726 | 13.101 | -9.328  | 1.00 | 29.31 | G | C |
| ATOM | 7044 | O   | GLY | C | 49 | 25.259 | 12.372 | -8.444  | 1.00 | 29.58 | G | O |
| ATOM | 7046 | N   | ILE | C | 50 | 26.556 | 12.668 | -10.273 | 1.00 | 29.20 | G | N |
| ATOM | 7047 | CA  | ILE | C | 50 | 26.721 | 11.257 | -10.540 | 1.00 | 29.32 | G | C |
| ATOM | 7049 | CB  | ILE | C | 50 | 25.576 | 10.748 | -11.468 | 1.00 | 29.89 | G | C |
| ATOM | 7051 | CG1 | ILE | C | 50 | 25.351 | 9.251  | -11.288 | 1.00 | 29.01 | G | C |
| ATOM | 7054 | CD1 | ILE | C | 50 | 24.255 | 8.675  | -12.141 | 1.00 | 28.52 | G |   |

FIG 8 – CONT.

| | | | | | | | | | | |
|---|---|---|---|---|---|---|---|---|---|---|
| ATOM | 7058 | CG2 | ILE | C | 50 | 25.883 | 11.060 | -12.945 | 1.00 31.49 | C G |
| ATOM | 7062 | C | ILE | C | 50 | 28.091 | 10.979 | -11.148 | 1.00 29.88 | C G |
| ATOM | 7063 | O | ILE | C | 50 | 28.696 | 11.859 | -11.763 | 1.00 30.79 | O G |
| ATOM | 7065 | N | ILE | C | 51 | 28.591 | 9.755 | -10.956 | 1.00 28.88 | N G |
| ATOM | 7066 | CA | ILE | C | 51 | 29.908 | 9.358 | -11.433 | 1.00 27.64 | C G |
| ATOM | 7068 | CB | ILE | C | 51 | 31.064 | 9.580 | -10.392 | 1.00 27.42 | C C |
| ATOM | 7070 | CG1 | ILE | C | 51 | 32.443 | 9.379 | -11.069 | 1.00 26.87 | C C |
| ATOM | 7073 | CD1 | ILE | C | 51 | 33.635 | 9.940 | -10.361 | 1.00 23.47 | C C |
| ATOM | 7077 | CG2 | ILE | C | 51 | 30.908 | 8.636 | -9.160 | 1.00 25.39 | C C |
| ATOM | 7081 | C | ILE | C | 51 | 29.872 | 7.888 | -11.892 | 1.00 28.35 | C G |
| ATOM | 7082 | O | ILE | C | 51 | 29.209 | 7.015 | -11.276 | 1.00 27.27 | O G |
| ATOM | 7084 | N | TYR | C | 52 | 30.551 | 7.635 | -13.007 | 1.00 29.14 | N G |
| ATOM | 7085 | CA | TYR | C | 52 | 30.740 | 6.281 | -13.519 | 1.00 30.05 | C G |
| ATOM | 7087 | CB | TYR | C | 52 | 30.443 | 6.198 | -15.013 | 1.00 30.54 | C G |
| ATOM | 7090 | CG | TYR | C | 52 | 30.648 | 4.782 | -15.578 | 1.00 31.98 | C G |
| ATOM | 7091 | CD1 | TYR | C | 52 | 30.424 | 3.650 | -14.779 | 1.00 32.10 | C G |
| ATOM | 7093 | CE1 | TYR | C | 52 | 30.621 | 2.401 | -15.263 | 1.00 32.51 | C G |
| ATOM | 7095 | CZ | TYR | C | 52 | 31.061 | 2.229 | -16.551 | 1.00 34.48 | C G |
| ATOM | 7096 | OH | TYR | C | 52 | 31.251 | 0.955 | -16.999 | 1.00 34.52 | O G |
| ATOM | 7098 | CE2 | TYR | C | 52 | 31.292 | 3.311 | -17.383 | 1.00 32.26 | C G |
| ATOM | 7100 | CD2 | TYR | C | 52 | 31.089 | 4.584 | -16.888 | 1.00 32.98 | C G |
| ATOM | 7102 | C | TYR | C | 52 | 32.187 | 5.920 | -13.263 | 1.00 29.81 | C G |
| ATOM | 7103 | O | TYR | C | 52 | 33.055 | 6.439 | -13.941 | 1.00 29.22 | O G |
| ATOM | 7105 | N | PRO | C | 52A | 32.454 | 5.084 | -12.236 | 1.00 30.18 | N G |
| ATOM | 7106 | CA | PRO | C | 52A | 33.846 | 4.862 | -11.889 | 1.00 30.06 | C G |
| ATOM | 7108 | CB | PRO | C | 52A | 33.755 | 4.121 | -10.547 | 1.00 29.78 | C G |
| ATOM | 7111 | CG | PRO | C | 52A | 32.423 | 4.544 | -10.003 | 1.00 30.55 | C G |
| ATOM | 7114 | CD | PRO | C | 52A | 31.551 | 4.575 | -11.181 | 1.00 30.25 | C G |
| ATOM | 7117 | C | PRO | C | 52A | 34.600 | 4.047 | -12.944 | 1.00 30.81 | C G |
| ATOM | 7118 | O | PRO | C | 52A | 35.811 | 3.974 | -12.901 | 1.00 30.53 | O G |

FIG 8 – CONT.

```
ATOM   7119  N    GLY C  53      33.870   3.421 -13.856  1.00 32.00          G
N
ATOM   7120  CA   GLY C  53      34.469   2.681 -14.930  1.00 33.17          G
C
ATOM   7123  C    GLY C  53      35.319   3.588 -15.790  1.00 34.06          G
C
ATOM   7124  O    GLY C  53      36.364   3.182 -16.230  1.00 34.62          G
O
ATOM   7126  N    ASP C  54      34.874   4.810 -16.048  1.00 34.85          G
N
ATOM   7127  CA   ASP C  54      35.684   5.691 -16.875  1.00 35.89          G
C
ATOM   7129  CB   ASP C  54      35.167   5.643 -18.314  1.00 35.62          G
C
ATOM   7132  CG   ASP C  54      33.781   6.181 -18.440  1.00 37.04          G
C
ATOM   7133  OD1  ASP C  54      33.133   5.893 -19.465  1.00 40.07          G
O
ATOM   7134  OD2  ASP C  54      33.335   6.897 -17.511  1.00 36.97          G
O
ATOM   7135  C    ASP C  54      35.767   7.108 -16.333  1.00 36.67          G
C
ATOM   7136  O    ASP C  54      36.302   7.987 -16.997  1.00 36.83          G
O
ATOM   7138  N    SER C  55      35.265   7.314 -15.111  1.00 37.18          G
N
ATOM   7139  CA   SER C  55      35.390   8.586 -14.389  1.00 37.61          G
C
ATOM   7141  CB   SER C  55      36.838   9.089 -14.361  1.00 37.92          G
C
ATOM   7144  OG   SER C  55      37.681   8.161 -13.695  1.00 39.54          G
O
ATOM   7146  C    SER C  55      34.492   9.671 -14.923  1.00 37.43          G
C
ATOM   7147  O    SER C  55      34.662  10.840 -14.574  1.00 37.51          G
O
ATOM   7149  N    ASP C  56      33.515   9.290 -15.731  1.00 37.34          G
N  ATOM   7150  CA   ASP C  56      32.591  10.247 -16.317  1.00 37.85
G   C  ATOM   7152  CB   ASP C  56      31.782   9.524 -17.399  1.00 38.54
G   C
ATOM   7155  CG   ASP C  56      30.835  10.437 -18.189  1.00 41.30          G
C
ATOM   7156  OD1  ASP C  56      30.756  11.668 -17.958  1.00 47.25          G
O
ATOM   7157  OD2  ASP C  56      30.145   9.888 -19.067  1.00 43.59          G
O
ATOM   7158  C    ASP C  56      31.696  10.780 -15.184  1.00 38.24          G
C
ATOM   7159  O    ASP C  56      30.966  10.014 -14.515  1.00 37.62          G
O
ATOM   7161  N    THR C  57      31.781  12.075 -14.928  1.00 37.96          G
N
ATOM   7162  CA   THR C  57      30.997  12.668 -13.857  1.00 38.58          G
C
ATOM   7164  CB   THR C  57      31.871  13.120 -12.633  1.00 38.46          C
C
ATOM   7166  OG1  THR C  57      32.107  14.517 -12.706  1.00 41.37          C
O
ATOM   7168  CG2  THR C  57      33.205  12.405 -12.577  1.00 36.81          C
C
ATOM   7172  C    THR C  57      30.133  13.807 -14.415  1.00 38.21          G
```

FIG 8 – CONT.

```
C
ATOM   7173  O    THR C  57      30.597  14.580 -15.252  1.00 38.13        G
O
ATOM   7175  N    ARG C  58      28.864  13.864 -13.980  1.00 37.45        G
N
ATOM   7176  CA   ARG C  58      27.945  14.935 -14.374  1.00 36.90        G
C
ATOM   7178  CB   ARG C  58      26.839  14.416 -15.311  1.00 36.54        G
C
ATOM   7187  C    ARG C  58      27.324  15.539 -13.126  1.00 36.64        G
C
ATOM   7188  O    ARG C  58      26.609  14.869 -12.385  1.00 35.96        G
O
ATOM   7190  N    TYR C  59      27.564  16.826 -12.916  1.00 36.55        G
N
ATOM   7191  CA   TYR C  59      27.021  17.497 -11.740  1.00 36.20        G
C
ATOM   7193  CB   TYR C  59      27.973  18.576 -11.269  1.00 35.46        G
C
ATOM   7196  CG   TYR C  59      29.292  18.080 -10.790  1.00 33.49        G
C
ATOM   7197  CD1  TYR C  59      30.327  17.874 -11.673  1.00 32.28        G
C
ATOM   7199  CE1  TYR C  59      31.553  17.410 -11.230  1.00 31.99        G
C
ATOM   7201  CZ   TYR C  59      31.754  17.162  -9.888  1.00 30.16        G
C
ATOM   7202  OH   TYR C  59      32.994  16.743  -9.464  1.00 28.30        G
O
ATOM   7204  CE2  TYR C  59      30.732  17.359  -8.991  1.00 30.40        G
C
ATOM   7206  CD2  TYR C  59      29.513  17.815  -9.438  1.00 31.48        G
C
ATOM   7208  C    TYR C  59      25.693  18.133 -12.022  1.00 36.80        G
C
ATOM   7209  O    TYR C  59      25.437  18.578 -13.134  1.00 38.18        G
O
ATOM   7211  N    SER C  60      24.845  18.208 -11.008  1.00 37.42        G
N
ATOM   7212  CA   SER C  60      23.745  19.173 -11.039  1.00 38.28        G
C
ATOM   7214  CB   SER C  60      22.813  18.998  -9.854  1.00 38.33        G
C
ATOM   7217  OG   SER C  60      21.961  20.116  -9.752  1.00 40.21        G
O
ATOM   7219  C    SER C  60      24.351  20.575 -11.045  1.00 38.32        G
C
ATOM   7220  O    SER C  60      25.361  20.801 -10.410  1.00 38.00        G
O
ATOM   7222  N    PRO C  61      23.768  21.507 -11.809  1.00 39.82        G
N
ATOM   7223  CA   PRO C  61      24.273  22.886 -11.863  1.00 40.50        G
C
ATOM   7225  CB   PRO C  61      23.235  23.609 -12.726  1.00 40.79        G
C
ATOM   7228  CG   PRO C  61      22.580  22.521 -13.518  1.00 41.43        G
C
ATOM   7231  CD   PRO C  61      22.568  21.327 -12.645  1.00 39.88        G
C
ATOM   7234  C    PRO C  61      24.338  23.575 -10.507  1.00 40.88        G
C
```

FIG 8 – CONT.

| ATOM | 7235 | O   | PRO | C | 61 | 25.206 | 24.392 | -10.308 | 1.00 | 41.63 | G |
| ATOM | 7236 | N   | SER | C | 62 | 23.420 | 23.261 | -9.592  | 1.00 | 41.24 | G |
| ATOM | 7237 | CA  | SER | C | 62 | 23.451 | 23.841 | -8.240  | 1.00 | 41.47 | G |
| ATOM | 7239 | CB  | SER | C | 62 | 22.246 | 23.398 | -7.423  | 1.00 | 41.65 | G |
| ATOM | 7242 | OG  | SER | C | 62 | 21.123 | 23.159 | -8.250  | 1.00 | 43.12 | G |
| ATOM | 7244 | C   | SER | C | 62 | 24.695 | 23.435 | -7.459  | 1.00 | 41.42 | G |
| ATOM | 7245 | O   | SER | C | 62 | 25.058 | 24.110 | -6.485  | 1.00 | 41.56 | G |
| ATOM | 7247 | N   | PHE | C | 63 | 25.346 | 22.340 | -7.876  | 1.00 | 40.56 | G |
| ATOM | 7248 | CA  | PHE | C | 63 | 26.514 | 21.826 | -7.154  | 1.00 | 39.80 | G |
| ATOM | 7250 | CB  | PHE | C | 63 | 26.242 | 20.407 | -6.717  | 1.00 | 39.54 | G |
| ATOM | 7253 | CG  | PHE | C | 63 | 25.154 | 20.316 | -5.730  | 1.00 | 38.29 | G |
| ATOM | 7254 | CD1 | PHE | C | 63 | 25.423 | 20.451 | -4.376  | 1.00 | 36.44 | G |
| ATOM | 7256 | CE1 | PHE | C | 63 | 24.431 | 20.407 | -3.470  | 1.00 | 34.23 | G |
| ATOM | 7258 | CZ  | PHE | C | 63 | 23.125 | 20.233 | -3.876  | 1.00 | 35.17 | G |
| ATOM | 7260 | CE2 | PHE | C | 63 | 22.827 | 20.124 | -5.205  | 1.00 | 36.77 | G |
| ATOM | 7262 | CD2 | PHE | C | 63 | 23.848 | 20.179 | -6.139  | 1.00 | 37.83 | G |
| ATOM | 7264 | C   | PHE | C | 63 | 27.811 | 21.903 | -7.907  | 1.00 | 39.75 | G |
| ATOM | 7265 | O   | PHE | C | 63 | 28.869 | 21.690 | -7.330  | 1.00 | 38.80 | G |
| ATOM | 7267 | N   | GLN | C | 64 | 27.717 | 22.227 | -9.196  | 1.00 | 40.90 | G |
| ATOM | 7268 | CA  | GLN | C | 64 | 28.880 | 22.389 | -10.068 | 1.00 | 41.14 | G |
| ATOM | 7270 | CB  | GLN | C | 64 | 28.431 | 22.854 | -11.466 | 1.00 | 41.68 | C |
| ATOM | 7273 | CG  | GLN | C | 64 | 29.558 | 23.025 | -12.502 | 1.00 | 43.10 | C |
| ATOM | 7276 | CD  | GLN | C | 64 | 30.083 | 21.695 | -13.058 | 1.00 | 46.85 | C |
| ATOM | 7277 | OE1 | GLN | C | 64 | 31.261 | 21.330 | -12.843 | 1.00 | 50.46 | C |
| ATOM | 7278 | NE2 | GLN | C | 64 | 29.226 | 20.972 | -13.783 | 1.00 | 44.04 | C |
| ATOM | 7281 | C   | GLN | C | 64 | 29.804 | 23.404 | -9.430  | 1.00 | 40.75 | G |
| ATOM | 7282 | O   | GLN | C | 64 | 29.383 | 24.508 | -9.106  | 1.00 | 41.26 | G |
| ATOM | 7284 | N   | GLY | C | 65 | 31.048 | 23.005 | -9.202  | 1.00 | 40.26 | G |
| ATOM | 7285 | CA  | GLY | C | 65 | 32.016 | 23.855 | -8.569  | 1.00 | 39.83 | G |
| ATOM | 7288 | C   | GLY | C | 65 | 31.978 | 23.964 | -7.054  | 1.00 | 39.73 | G |
| ATOM | 7289 | O   | GLY | C | 65 | 32.894 | 24.525 | -6.473  | 1.00 | 39.98 | G |

FIG 8 – CONT.

| ATOM | 7291 | N   | GLN | C | 66 | 30.936 | 23.473 | -6.400 | 1.00 | 39.75 | G | N |
| --- | --- | --- | --- | --- | --- | --- | --- | --- | --- | --- | --- | --- |
| ATOM | 7292 | CA  | GLN | C | 66 | 30.863 | 23.528 | -4.926 | 1.00 | 40.23 | G | C |
| ATOM | 7294 | CB  | GLN | C | 66 | 29.418 | 23.722 | -4.463 | 1.00 | 40.68 | G | C |
| ATOM | 7297 | CG  | GLN | C | 66 | 28.743 | 24.971 | -5.026 | 1.00 | 45.02 | G | C |
| ATOM | 7300 | CD  | GLN | C | 66 | 29.417 | 26.224 | -4.517 | 1.00 | 48.81 | G | C |
| ATOM | 7301 | OE1 | GLN | C | 66 | 29.625 | 26.361 | -3.314 | 1.00 | 52.74 | G | O |
| ATOM | 7302 | NE2 | GLN | C | 66 | 29.809 | 27.118 | -5.424 | 1.00 | 50.81 | G | N |
| ATOM | 7305 | C   | GLN | C | 66 | 31.428 | 22.255 | -4.270 | 1.00 | 39.30 | G | C |
| ATOM | 7306 | O   | GLN | C | 66 | 31.732 | 22.245 | -3.083 | 1.00 | 41.28 | G | O |
| ATOM | 7308 | N   | VAL | C | 67 | 31.577 | 21.194 | -5.044 | 1.00 | 37.53 | G | N |
| ATOM | 7309 | CA  | VAL | C | 67 | 31.927 | 19.899 | -4.503 | 1.00 | 36.13 | G | C |
| ATOM | 7311 | CB  | VAL | C | 67 | 30.655 | 19.186 | -3.961 | 1.00 | 35.93 | G | C |
| ATOM | 7313 | CG1 | VAL | C | 67 | 29.765 | 18.720 | -5.103 | 1.00 | 34.00 | G | C |
| ATOM | 7317 | CG2 | VAL | C | 67 | 31.043 | 18.047 | -3.024 | 1.00 | 36.38 | G | C |
| ATOM | 7321 | C   | VAL | C | 67 | 32.577 | 19.096 | -5.610 | 1.00 | 35.08 | G | C |
| ATOM | 7322 | O   | VAL | C | 67 | 32.370 | 19.387 | -6.781 | 1.00 | 34.93 | G | O |
| ATOM | 7324 | N   | THR | C | 68 | 33.398 | 18.116 | -5.248 | 1.00 | 33.58 | G | N |
| ATOM | 7325 | CA  | THR | C | 68 | 33.989 | 17.240 | -6.239 | 1.00 | 31.97 | G | C |
| ATOM | 7327 | CB  | THR | C | 68 | 35.479 | 17.330 | -6.241 | 1.00 | 31.77 | G | C |
| ATOM | 7329 | OG1 | THR | C | 68 | 35.851 | 18.658 | -6.600 | 1.00 | 31.06 | G | O |
| ATOM | 7331 | CG2 | THR | C | 68 | 36.079 | 16.363 | -7.261 | 1.00 | 32.91 | G | C |
| ATOM | 7335 | C   | THR | C | 68 | 33.556 | 15.826 | -5.982 | 1.00 | 31.35 | G | C |
| ATOM | 7336 | O   | THR | C | 68 | 33.733 | 15.308 | -4.878 | 1.00 | 31.36 | G | O |
| ATOM | 7338 | N   | ILE | C | 69 | 32.932 | 15.223 | -6.983 | 1.00 | 30.28 | G | N |
| ATOM | 7339 | CA  | ILE | C | 69 | 32.627 | 13.808 | -6.937 | 1.00 | 29.58 | G | C |
| ATOM | 7341 | CB  | ILE | C | 69 | 31.344 | 13.516 | -7.639 | 1.00 | 28.99 | C | C |
| ATOM | 7343 | CG1 | ILE | C | 69 | 30.169 | 14.160 | -6.906 | 1.00 | 28.50 | C | C |
| ATOM | 7346 | CD1 | ILE | C | 69 | 28.957 | 14.308 | -7.808 | 1.00 | 28.18 | C | C |
| ATOM | 7350 | CG2 | ILE | C | 69 | 31.133 | 12.028 | -7.752 | 1.00 | 27.59 | C | C |
| ATOM | 7354 | C   | ILE | C | 69 | 33.764 | 13.022 | -7.592 | 1.00 | 29.96 | G | C |

FIG 8 – CONT.

| ATOM | 7355 | O | ILE | C | 69 | 34.265 | 13.410 | -8.648 | 1.00 | 29.95 | G |
|---|---|---|---|---|---|---|---|---|---|---|---|
| ATOM | 7357 | N | SER | C | 70 | 34.207 | 11.947 | -6.957 | 1.00 | 29.86 | G |
| ATOM | 7358 | CA | SER | C | 70 | 35.340 | 11.196 | -7.497 | 1.00 | 30.38 | G |
| ATOM | 7360 | CB | SER | C | 70 | 36.690 | 11.800 | -7.078 | 1.00 | 30.64 | G |
| ATOM | 7363 | OG | SER | C | 70 | 37.068 | 11.512 | -5.747 | 1.00 | 34.10 | G |
| ATOM | 7365 | C | SER | C | 70 | 35.188 | 9.718 | -7.165 | 1.00 | 30.39 | G |
| ATOM | 7366 | O | SER | C | 70 | 34.205 | 9.305 | -6.526 | 1.00 | 29.50 | G |
| ATOM | 7368 | N | ALA | C | 71 | 36.068 | 8.901 | -7.721 | 1.00 | 30.03 | G |
| ATOM | 7369 | CA | ALA | C | 71 | 35.960 | 7.455 | -7.508 | 1.00 | 30.17 | G |
| ATOM | 7371 | CB | ALA | C | 71 | 34.842 | 6.849 | -8.337 | 1.00 | 28.80 | G |
| ATOM | 7375 | C | ALA | C | 71 | 37.278 | 6.787 | -7.806 | 1.00 | 30.43 | G |
| ATOM | 7376 | O | ALA | C | 71 | 38.120 | 7.368 | -8.472 | 1.00 | 30.30 | G |
| ATOM | 7378 | N | ASP | C | 72 | 37.422 | 5.570 | -7.282 | 1.00 | 31.02 | G |
| ATOM | 7379 | CA | ASP | C | 72 | 38.566 | 4.720 | -7.499 | 1.00 | 31.53 | G |
| ATOM | 7381 | CB | ASP | C | 72 | 39.521 | 4.807 | -6.286 | 1.00 | 32.02 | G |
| ATOM | 7384 | CG | ASP | C | 72 | 40.684 | 3.799 | -6.341 | 1.00 | 33.55 | G |
| ATOM | 7385 | OD1 | ASP | C | 72 | 41.612 | 3.950 | -5.520 | 1.00 | 34.26 | G |
| ATOM | 7386 | OD2 | ASP | C | 72 | 40.665 | 2.841 | -7.149 | 1.00 | 34.06 | G |
| ATOM | 7387 | C | ASP | C | 72 | 38.018 | 3.311 | -7.700 | 1.00 | 31.67 | G |
| ATOM | 7388 | O | ASP | C | 72 | 37.773 | 2.615 | -6.733 | 1.00 | 31.91 | G |
| ATOM | 7390 | N | LYS | C | 73 | 37.796 | 2.941 | -8.965 | 1.00 | 31.45 | G |
| ATOM | 7391 | CA | LYS | C | 73 | 37.481 | 1.574 | -9.429 | 1.00 | 31.52 | G |
| ATOM | 7393 | CB | LYS | C | 73 | 38.103 | 1.333 | -10.805 | 1.00 | 33.18 | C |
| ATOM | 7396 | CG | LYS | C | 73 | 37.305 | 1.665 | -11.932 | 1.00 | 36.77 | C |
| ATOM | 7399 | CD | LYS | C | 73 | 37.897 | 1.022 | -13.171 | 1.00 | 39.36 | C |
| ATOM | 7402 | CE | LYS | C | 73 | 39.314 | 1.504 | -13.498 | 1.00 | 40.65 | C |
| ATOM | 7405 | NZ | LYS | C | 73 | 39.555 | 1.228 | -14.921 | 1.00 | 41.04 | C |
| ATOM | 7409 | C | LYS | C | 73 | 38.148 | 0.473 | -8.706 | 1.00 | 29.76 | G |
| ATOM | 7410 | O | LYS | C | 73 | 37.563 | -0.584 | -8.516 | 1.00 | 29.75 | G |
| ATOM | 7412 | N | SER | C | 74 | 39.435 | 0.655 | -8.452 | 1.00 | 28.45 | G |
| ATOM | 7413 | CA | SER | C | 74 | 40.242 | -0.472 | -7.969 | 1.00 | 28.32 | G |

FIG 8 – CONT.

| | | | | | | | | | | |
|---|---|---|---|---|---|---|---|---|---|---|
| ATOM | 7415 | CB | SER | C | 74 | 41.737 | -0.141 | -8.023 | 1.00 27.79 | G |
| ATOM | 7418 | OG | SER | C | 74 | 42.110 | 0.792 | -7.042 | 1.00 29.51 | G |
| ATOM | 7420 | C | SER | C | 74 | 39.786 | -0.990 | -6.585 | 1.00 28.16 | G |
| ATOM | 7421 | O | SER | C | 74 | 39.973 | -2.175 | -6.286 | 1.00 27.49 | G |
| ATOM | 7423 | N | ILE | C | 75 | 39.162 | -0.114 | -5.783 | 1.00 27.07 | G |
| ATOM | 7424 | CA | ILE | C | 75 | 38.647 | -0.466 | -4.441 | 1.00 26.79 | G |
| ATOM | 7426 | CB | ILE | C | 75 | 39.446 | 0.266 | -3.348 | 1.00 27.00 | C |
| ATOM | 7428 | CG1 | ILE | C | 75 | 39.265 | 1.815 | -3.443 | 1.00 27.33 | C |
| ATOM | 7431 | CD1 | ILE | C | 75 | 39.914 | 2.617 | -2.305 | 1.00 29.89 | C |
| ATOM | 7435 | CG2 | ILE | C | 75 | 40.894 | -0.071 | -3.543 | 1.00 26.93 | C |
| ATOM | 7439 | C | ILE | C | 75 | 37.148 | -0.206 | -4.329 | 1.00 26.35 | G |
| ATOM | 7440 | O | ILE | C | 75 | 36.617 | 0.001 | -3.226 | 1.00 27.72 | G |
| ATOM | 7442 | N | ASN | C | 76 | 36.475 | -0.190 | -5.491 | 1.00 25.84 | G |
| ATOM | 7443 | CA | ASN | C | 76 | 35.018 | -0.062 | -5.629 | 1.00 24.71 | G |
| ATOM | 7445 | CB | ASN | C | 76 | 34.355 | -1.425 | -5.442 | 1.00 24.53 | G |
| ATOM | 7448 | CG | ASN | C | 76 | 33.101 | -1.579 | -6.241 | 1.00 22.36 | G |
| ATOM | 7449 | OD1 | ASN | C | 76 | 33.144 | -1.488 | -7.455 | 1.00 22.64 | G |
| ATOM | 7450 | ND2 | ASN | C | 76 | 31.956 | -1.825 | -5.573 | 1.00 21.83 | G |
| ATOM | 7453 | C | ASN | C | 76 | 34.376 | 1.005 | -4.724 | 1.00 26.07 | G |
| ATOM | 7454 | O | ASN | C | 76 | 33.349 | 0.757 | -4.094 | 1.00 26.38 | G |
| ATOM | 7456 | N | THR | C | 77 | 34.990 | 2.198 | -4.717 | 1.00 26.43 | G |
| ATOM | 7457 | CA | THR | C | 77 | 34.641 | 3.284 | -3.813 | 1.00 26.51 | G |
| ATOM | 7459 | CB | THR | C | 77 | 35.737 | 3.430 | -2.721 | 1.00 26.37 | G |
| ATOM | 7461 | OG1 | THR | C | 77 | 35.923 | 2.161 | -2.086 | 1.00 26.05 | G |
| ATOM | 7463 | CG2 | THR | C | 77 | 35.371 | 4.479 | -1.656 | 1.00 25.39 | G |
| ATOM | 7467 | C | THR | C | 77 | 34.464 | 4.611 | -4.584 | 1.00 26.41 | G |
| ATOM | 7468 | O | THR | C | 77 | 35.264 | 4.936 | -5.441 | 1.00 26.59 | G |
| ATOM | 7470 | N | ALA | C | 78 | 33.366 | 5.313 | -4.308 | 1.00 26.47 | G |
| ATOM | 7471 | CA | ALA | C | 78 | 33.129 | 6.675 | -4.768 | 1.00 26.27 | G |
| ATOM | 7473 | CB | ALA | C | 78 | 31.744 | 6.806 | -5.408 | 1.00 25.34 | G |

FIG 8 – CONT.

| | | | | | | | | | | | |
|---|---|---|---|---|---|---|---|---|---|---|---|
| ATOM | 7477 | C | ALA | C | 78 | 33.264 | 7.640 | -3.589 | 1.00 | 26.70 | G |
| | | C | | | | | | | | | |
| ATOM | 7478 | O | ALA | C | 78 | 33.140 | 7.257 | -2.429 | 1.00 | 26.69 | G |
| | | O | | | | | | | | | |
| ATOM | 7480 | N | TYR | C | 79 | 33.528 | 8.903 | -3.897 | 1.00 | 27.43 | G |
| | | N | | | | | | | | | |
| ATOM | 7481 | CA | TYR | C | 79 | 33.786 | 9.897 | -2.894 | 1.00 | 26.97 | G |
| | | C | | | | | | | | | |
| ATOM | 7483 | CB | TYR | C | 79 | 35.267 | 10.223 | -2.818 | 1.00 | 27.10 | C |
| | | C | | | | | | | | | |
| ATOM | 7486 | CG | TYR | C | 79 | 36.178 | 9.046 | -2.585 | 1.00 | 28.15 | C |
| | | C | | | | | | | | | |
| ATOM | 7487 | CD1 | TYR | C | 79 | 36.463 | 8.587 | -1.296 | 1.00 | 28.56 | C |
| | | C | | | | | | | | | |
| ATOM | 7489 | CE1 | TYR | C | 79 | 37.356 | 7.483 | -1.096 | 1.00 | 29.16 | C |
| | | C | | | | | | | | | |
| ATOM | 7491 | CZ | TYR | C | 79 | 37.948 | 6.869 | -2.204 | 1.00 | 29.37 | C |
| | | C | | | | | | | | | |
| ATOM | 7492 | OH | TYR | C | 79 | 38.830 | 5.795 | -2.091 | 1.00 | 29.80 | C |
| | | O | | | | | | | | | |
| ATOM | 7494 | CE2 | TYR | C | 79 | 37.670 | 7.335 | -3.469 | 1.00 | 29.24 | C |
| | | C | | | | | | | | | |
| ATOM | 7496 | CD2 | TYR | C | 79 | 36.815 | 8.427 | -3.656 | 1.00 | 30.10 | C |
| | | C | | | | | | | | | |
| ATOM | 7498 | C | TYR | C | 79 | 33.058 | 11.186 | -3.207 | 1.00 | 27.48 | G |
| | | C | | | | | | | | | |
| ATOM | 7499 | O | TYR | C | 79 | 32.735 | 11.488 | -4.378 | 1.00 | 27.98 | G |
| | | O | | | | | | | | | |
| ATOM | 7501 | N | LEU | C | 80 | 32.826 | 11.948 | -2.146 | 1.00 | 26.06 | G |
| | | N | | | | | | | | | |
| ATOM | 7502 | CA | LEU | C | 80 | 32.368 | 13.291 | -2.244 | 1.00 | 26.26 | G |
| | | C | | | | | | | | | |
| ATOM | 7504 | CB | LEU | C | 80 | 30.995 | 13.369 | -1.597 | 1.00 | 26.73 | G |
| | | C | | | | | | | | | |
| ATOM | 7507 | CG | LEU | C | 80 | 30.001 | 14.406 | -2.010 | 1.00 | 26.61 | G |
| | | C | | | | | | | | | |
| ATOM | 7509 | CD1 | LEU | C | 80 | 29.730 | 14.283 | -3.524 | 1.00 | 29.48 | G |
| | | C | | | | | | | | | |
| ATOM | 7513 | CD2 | LEU | C | 80 | 28.743 | 14.203 | -1.161 | 1.00 | 21.40 | G |
| | | C | | | | | | | | | |
| ATOM | 7517 | C | LEU | C | 80 | 33.399 | 14.122 | -1.501 | 1.00 | 26.06 | G |
| | | C | | | | | | | | | |
| ATOM | 7518 | O | LEU | C | 80 | 33.868 | 13.715 | -0.431 | 1.00 | 26.00 | G |
| | | O | | | | | | | | | |
| ATOM | 7520 | N | GLN | C | 81 | 33.767 | 15.266 | -2.067 | 1.00 | 25.75 | G |
| | | N | | | | | | | | | |
| ATOM | 7521 | CA | GLN | C | 81 | 34.901 | 16.006 | -1.586 | 1.00 | 27.06 | G |
| | | C | | | | | | | | | |
| ATOM | 7523 | CB | GLN | C | 81 | 36.077 | 15.693 | -2.501 | 1.00 | 28.72 | G |
| | | C | | | | | | | | | |
| ATOM | 7526 | CG | GLN | C | 81 | 37.391 | 16.249 | -2.118 | 1.00 | 32.69 | G |
| | | C | | | | | | | | | |
| ATOM | 7529 | CD | GLN | C | 81 | 38.581 | 15.567 | -2.842 | 1.00 | 41.81 | G |
| | | C | | | | | | | | | |
| ATOM | 7530 | OE1 | GLN | C | 81 | 39.744 | 15.942 | -2.605 | 1.00 | 45.73 | G |
| | | O | | | | | | | | | |
| ATOM | 7531 | NE2 | GLN | C | 81 | 38.299 | 14.563 | -3.721 | 1.00 | 43.01 | G |
| | | N | | | | | | | | | |
| ATOM | 7534 | C | GLN | C | 81 | 34.641 | 17.513 | -1.599 | 1.00 | 26.48 | G |
| | | C | | | | | | | | | |
| ATOM | 7535 | O | GLN | C | 81 | 34.102 | 18.079 | -2.549 | 1.00 | 26.00 | G |

FIG 8 — CONT.

| | | | | | | | | | | |
|---|---|---|---|---|---|---|---|---|---|---|
| ATOM | 7537 | N | TRP | C | 82 | 35.112 | 18.161 | -0.558 | 1.00 26.70 | G N |
| ATOM | 7538 | CA | TRP | C | 82 | 34.920 | 19.590 | -0.378 | 1.00 26.39 | G C |
| ATOM | 7540 | CB | TRP | C | 82 | 33.960 | 19.853 | 0.770 | 1.00 26.56 | G C |
| ATOM | 7543 | CG | TRP | C | 82 | 32.578 | 19.560 | 0.541 | 1.00 23.29 | G C |
| ATOM | 7544 | CD1 | TRP | C | 82 | 31.642 | 20.402 | 0.057 | 1.00 25.47 | G C |
| ATOM | 7546 | NE1 | TRP | C | 82 | 30.406 | 19.786 | 0.040 | 1.00 26.51 | G N |
| ATOM | 7548 | CE2 | TRP | C | 82 | 30.549 | 18.520 | 0.552 | 1.00 25.94 | G C |
| ATOM | 7549 | CD2 | TRP | C | 82 | 31.905 | 18.357 | 0.894 | 1.00 25.28 | G C |
| ATOM | 7550 | CE3 | TRP | C | 82 | 32.321 | 17.141 | 1.454 | 1.00 26.63 | G C |
| ATOM | 7552 | CZ3 | TRP | C | 82 | 31.393 | 16.148 | 1.643 | 1.00 25.87 | G C |
| ATOM | 7554 | CH2 | TRP | C | 82 | 30.053 | 16.339 | 1.307 | 1.00 23.45 | G C |
| ATOM | 7556 | CZ2 | TRP | C | 82 | 29.617 | 17.519 | 0.740 | 1.00 25.29 | G C |
| ATOM | 7558 | C | TRP | C | 82 | 36.251 | 20.099 | 0.050 | 1.00 26.65 | G C |
| ATOM | 7559 | O | TRP | C | 82 | 36.891 | 19.489 | 0.907 | 1.00 26.70 | G O |
| ATOM | 7561 | N | SER | C | 82A | 36.679 | 21.205 | -0.521 | 1.00 26.58 | G N |
| ATOM | 7562 | CA | SER | C | 82A | 37.953 | 21.787 | -0.135 | 1.00 27.09 | G C |
| ATOM | 7564 | CB | SER | C | 82A | 38.599 | 22.399 | -1.390 | 1.00 27.79 | G C |
| ATOM | 7567 | OG | SER | C | 82A | 37.763 | 23.404 | -1.956 | 1.00 27.84 | G O |
| ATOM | 7569 | C | SER | C | 82A | 37.796 | 22.856 | 0.995 | 1.00 27.24 | G C |
| ATOM | 7570 | O | SER | C | 82A | 38.714 | 23.073 | 1.777 | 1.00 27.69 | G O |
| ATOM | 7572 | N | SER | C | 82B | 36.639 | 23.510 | 1.056 | 1.00 27.25 | G N |
| ATOM | 7573 | CA | SER | C | 82B | 36.349 | 24.569 | 2.039 | 1.00 27.29 | G C |
| ATOM | 7575 | CB | SER | C | 82B | 36.584 | 25.938 | 1.383 | 1.00 26.88 | G C |
| ATOM | 7578 | OG | SER | C | 82B | 36.417 | 27.017 | 2.302 | 1.00 30.00 | G O |
| ATOM | 7580 | C | SER | C | 82B | 34.891 | 24.460 | 2.479 | 1.00 26.70 | G C |
| ATOM | 7581 | O | SER | C | 82B | 33.992 | 24.995 | 1.835 | 1.00 26.34 | G O |
| ATOM | 7583 | N | LEU | C | 82C | 34.627 | 23.732 | 3.552 | 1.00 26.46 | G N |
| ATOM | 7584 | CA | LEU | C | 82C | 33.228 | 23.519 | 3.949 | 1.00 25.58 | G C |
| ATOM | 7586 | CB | LEU | C | 82C | 33.124 | 22.528 | 5.093 | 1.00 25.31 | G C |
| ATOM | 7589 | CG | LEU | C | 82C | 33.356 | 21.038 | 4.778 | 1.00 24.46 | G C |

FIG 8 – CONT.

| ATOM | 7591 | CD1 | LEU | C | 82C | 33.720 | 20.271 | 6.064 | 1.00 | 23.38 | G |
|---|---|---|---|---|---|---|---|---|---|---|---|
| ATOM | 7595 | CD2 | LEU | C | 82C | 32.198 | 20.381 | 4.051 | 1.00 | 18.90 | G |
| ATOM | 7599 | C | LEU | C | 82C | 32.556 | 24.819 | 4.360 | 1.00 | 26.15 | G |
| ATOM | 7600 | O | LEU | C | 82C | 33.218 | 25.701 | 4.916 | 1.00 | 25.06 | G |
| ATOM | 7602 | N | LYS | C | 83 | 31.253 | 24.919 | 4.061 | 1.00 | 26.40 | G |
| ATOM | 7603 | CA | LYS | C | 83 | 30.377 | 25.932 | 4.614 | 1.00 | 27.16 | G |
| ATOM | 7605 | CB | LYS | C | 83 | 29.511 | 26.518 | 3.515 | 1.00 | 27.97 | G |
| ATOM | 7608 | CG | LYS | C | 83 | 30.289 | 27.030 | 2.319 | 1.00 | 30.71 | G |
| ATOM | 7611 | CD | LYS | C | 83 | 29.411 | 27.275 | 1.110 | 1.00 | 34.25 | G |
| ATOM | 7614 | CE | LYS | C | 83 | 30.268 | 27.121 | -0.186 | 1.00 | 37.96 | G |
| ATOM | 7617 | NZ | LYS | C | 83 | 29.706 | 27.889 | -1.295 | 1.00 | 38.79 | G |
| ATOM | 7621 | C | LYS | C | 83 | 29.453 | 25.306 | 5.692 | 1.00 | 27.88 | G |
| ATOM | 7622 | O | LYS | C | 83 | 29.127 | 24.085 | 5.635 | 1.00 | 28.20 | G |
| ATOM | 7624 | N | ALA | C | 84 | 29.061 | 26.135 | 6.664 | 1.00 | 26.50 | G |
| ATOM | 7625 | CA | ALA | C | 84 | 27.984 | 25.830 | 7.614 | 1.00 | 27.19 | G |
| ATOM | 7627 | CB | ALA | C | 84 | 27.496 | 27.121 | 8.349 | 1.00 | 26.15 | C |
| ATOM | 7631 | C | ALA | C | 84 | 26.816 | 25.181 | 6.902 | 1.00 | 27.03 | G |
| ATOM | 7632 | O | ALA | C | 84 | 26.327 | 24.117 | 7.341 | 1.00 | 26.72 | G |
| ATOM | 7634 | N | SER | C | 85 | 26.419 | 25.810 | 5.786 | 1.00 | 26.61 | G |
| ATOM | 7635 | CA | SER | C | 85 | 25.268 | 25.401 | 4.989 | 1.00 | 26.44 | G |
| ATOM | 7637 | CB | SER | C | 85 | 24.973 | 26.456 | 3.903 | 1.00 | 27.80 | G |
| ATOM | 7640 | OG | SER | C | 85 | 26.101 | 26.654 | 3.026 | 1.00 | 28.40 | G |
| ATOM | 7642 | C | SER | C | 85 | 25.414 | 24.034 | 4.332 | 1.00 | 26.07 | G |
| ATOM | 7643 | O | SER | C | 85 | 24.446 | 23.511 | 3.813 | 1.00 | 25.95 | G |
| ATOM | 7645 | N | ASP | C | 86 | 26.609 | 23.441 | 4.376 | 1.00 | 26.53 | G |
| ATOM | 7646 | CA | ASP | C | 86 | 26.817 | 22.046 | 3.918 | 1.00 | 25.45 | G |
| ATOM | 7648 | CB | ASP | C | 86 | 28.278 | 21.791 | 3.563 | 1.00 | 24.76 | G |
| ATOM | 7651 | CG | ASP | C | 86 | 28.757 | 22.602 | 2.379 | 1.00 | 24.35 | G |
| ATOM | 7652 | OD1 | ASP | C | 86 | 28.019 | 22.719 | 1.379 | 1.00 | 24.74 | G |
| ATOM | 7653 | OD2 | ASP | C | 86 | 29.927 | 23.054 | 2.416 | 1.00 | 22.99 | G |
| ATOM | 7654 | C | ASP | C | 86 | 26.430 | 21.029 | 4.964 | 1.00 | 24.96 | G |

FIG 8 – CONT.

| | | | | | | | | | | |
|---|---|---|---|---|---|---|---|---|---|---|
| ATOM | 7655 | O | ASP | C | 86 | 26.569 | 19.812 | 4.732 | 1.00 24.09 | G |
| ATOM | 7657 | N | THR | C | 87 | 26.013 | 21.500 | 6.144 | 1.00 24.33 | G |
| ATOM | 7658 | CA | THR | C | 87 | 25.459 | 20.586 | 7.175 | 1.00 23.50 | G |
| ATOM | 7660 | CB | THR | C | 87 | 25.105 | 21.352 | 8.458 | 1.00 23.88 | G |
| ATOM | 7662 | OG1 | THR | C | 87 | 26.315 | 21.894 | 8.996 | 1.00 23.20 | G |
| ATOM | 7664 | CG2 | THR | C | 87 | 24.405 | 20.421 | 9.520 | 1.00 21.55 | G |
| ATOM | 7668 | C | THR | C | 87 | 24.235 | 19.836 | 6.637 | 1.00 22.70 | G |
| ATOM | 7669 | O | THR | C | 87 | 23.268 | 20.434 | 6.230 | 1.00 22.40 | G |
| ATOM | 7671 | N | ALA | C | 88 | 24.314 | 18.513 | 6.609 | 1.00 23.01 | G |
| ATOM | 7672 | CA | ALA | C | 88 | 23.295 | 17.696 | 6.002 | 1.00 22.41 | G |
| ATOM | 7674 | CB | ALA | C | 88 | 23.151 | 18.050 | 4.528 | 1.00 23.66 | G |
| ATOM | 7678 | C | ALA | C | 88 | 23.693 | 16.257 | 6.117 | 1.00 23.78 | G |
| ATOM | 7679 | O | ALA | C | 88 | 24.795 | 15.942 | 6.547 | 1.00 23.79 | G |
| ATOM | 7681 | N | ILE | C | 89 | 22.801 | 15.367 | 5.711 | 1.00 24.47 | G |
| ATOM | 7682 | CA | ILE | C | 89 | 23.178 | 13.976 | 5.539 | 1.00 25.37 | G |
| ATOM | 7684 | CB | ILE | C | 89 | 22.116 | 13.084 | 6.138 | 1.00 26.03 | C |
| ATOM | 7686 | CG1 | ILE | C | 89 | 22.531 | 11.623 | 6.116 | 1.00 30.07 | C |
| ATOM | 7689 | CD1 | ILE | C | 89 | 21.855 | 10.814 | 7.303 | 1.00 35.70 | C |
| ATOM | 7693 | CG2 | ILE | C | 89 | 20.838 | 13.230 | 5.383 | 1.00 27.94 | C |
| ATOM | 7697 | C | ILE | C | 89 | 23.391 | 13.743 | 4.035 | 1.00 25.29 | G |
| ATOM | 7698 | O | ILE | C | 89 | 22.680 | 14.320 | 3.211 | 1.00 25.65 | G |
| ATOM | 7700 | N | TYR | C | 90 | 24.426 | 12.974 | 3.683 | 1.00 25.40 | G |
| ATOM | 7701 | CA | TYR | C | 90 | 24.770 | 12.684 | 2.289 | 1.00 24.84 | G |
| ATOM | 7703 | CB | TYR | C | 90 | 26.201 | 13.119 | 1.950 | 1.00 24.31 | G |
| ATOM | 7706 | CG | TYR | C | 90 | 26.312 | 14.614 | 2.056 | 1.00 24.46 | G |
| ATOM | 7707 | CD1 | TYR | C | 90 | 26.549 | 15.251 | 3.291 | 1.00 22.89 | G |
| ATOM | 7709 | CE1 | TYR | C | 90 | 26.556 | 16.636 | 3.375 | 1.00 23.13 | G |
| ATOM | 7711 | CZ | TYR | C | 90 | 26.327 | 17.379 | 2.238 | 1.00 23.22 | G |
| ATOM | 7712 | OH | TYR | C | 90 | 26.314 | 18.759 | 2.250 | 1.00 22.93 | G |
| ATOM | 7714 | CE2 | TYR | C | 90 | 26.089 | 16.752 | 1.031 | 1.00 23.74 | C |

FIG 8 – CONT.

| ATOM | 7716 | CD2 | TYR | C | 90 | 26.055 | 15.405 | 0.958 | 1.00 | 24.66 | G |
|---|---|---|---|---|---|---|---|---|---|---|---|
| ATOM | 7718 | C | TYR | C | 90 | 24.550 | 11.225 | 2.069 | 1.00 | 25.16 | G |
| ATOM | 7719 | O | TYR | C | 90 | 25.147 | 10.393 | 2.759 | 1.00 | 25.50 | G |
| ATOM | 7721 | N | TYR | C | 91 | 23.678 | 10.916 | 1.116 | 1.00 | 25.30 | G |
| ATOM | 7722 | CA | TYR | C | 91 | 23.440 | 9.535 | 0.709 | 1.00 | 26.15 | G |
| ATOM | 7724 | CB | TYR | C | 91 | 21.959 | 9.260 | 0.562 | 1.00 | 25.68 | G |
| ATOM | 7727 | CG | TYR | C | 91 | 21.089 | 9.529 | 1.780 | 1.00 | 26.79 | G |
| ATOM | 7728 | CD1 | TYR | C | 91 | 20.978 | 8.603 | 2.816 | 1.00 | 28.37 | G |
| ATOM | 7730 | CE1 | TYR | C | 91 | 20.137 | 8.838 | 3.940 | 1.00 | 28.93 | G |
| ATOM | 7732 | CZ | TYR | C | 91 | 19.406 | 10.024 | 3.978 | 1.00 | 30.71 | G |
| ATOM | 7733 | OH | TYR | C | 91 | 18.578 | 10.324 | 5.014 | 1.00 | 31.81 | G |
| ATOM | 7735 | CE2 | TYR | C | 91 | 19.496 | 10.939 | 2.940 | 1.00 | 29.79 | G |
| ATOM | 7737 | CD2 | TYR | C | 91 | 20.324 | 10.686 | 1.853 | 1.00 | 28.44 | G |
| ATOM | 7739 | C | TYR | C | 91 | 24.084 | 9.280 | -0.658 | 1.00 | 27.10 | G |
| ATOM | 7740 | O | TYR | C | 91 | 23.967 | 10.095 | -1.585 | 1.00 | 26.88 | G |
| ATOM | 7742 | N | CYS | C | 92 | 24.770 | 8.151 | -0.773 | 1.00 | 27.84 | G |
| ATOM | 7743 | CA | CYS | C | 92 | 25.237 | 7.686 | -2.057 | 1.00 | 28.21 | G |
| ATOM | 7745 | CB | CYS | C | 92 | 26.614 | 7.018 | -1.954 | 1.00 | 28.08 | G |
| ATOM | 7748 | SG | CYS | C | 92 | 26.720 | 5.510 | -1.062 | 1.00 | 28.09 | G |
| ATOM | 7750 | C | CYS | C | 92 | 24.167 | 6.735 | -2.559 | 1.00 | 29.25 | G |
| ATOM | 7751 | O | CYS | C | 92 | 23.486 | 6.102 | -1.776 | 1.00 | 29.32 | G |
| ATOM | 7753 | N | VAL | C | 93 | 23.996 | 6.693 | -3.869 | 1.00 | 29.73 | G |
| ATOM | 7754 | CA | VAL | C | 93 | 22.944 | 5.928 | -4.496 | 1.00 | 30.02 | G |
| ATOM | 7756 | CB | VAL | C | 93 | 21.865 | 6.829 | -5.054 | 1.00 | 30.39 | C |
| ATOM | 7758 | CG1 | VAL | C | 93 | 20.853 | 6.018 | -5.877 | 1.00 | 29.82 | C |
| ATOM | 7762 | CG2 | VAL | C | 93 | 21.168 | 7.585 | -3.909 | 1.00 | 29.75 | C |
| ATOM | 7766 | C | VAL | C | 93 | 23.561 | 5.121 | -5.638 | 1.00 | 30.93 | G |
| ATOM | 7767 | O | VAL | C | 93 | 24.383 | 5.631 | -6.414 | 1.00 | 30.29 | G |
| ATOM | 7769 | N | GLY | C | 94 | 23.178 | 3.858 | -5.700 | 1.00 | 31.17 | G |
| ATOM | 7770 | CA | GLY | C | 94 | 23.707 | 2.941 | -6.688 | 1.00 | 32.18 | G |
| ATOM | 7773 | C | GLY | C | 94 | 22.705 | 2.862 | -7.813 | 1.00 | 32.31 | G |

FIG 8 – CONT.

| | | | | | | | | | | |
|---|---|---|---|---|---|---|---|---|---|---|
| ATOM | 7774 | O | GLY | C | 94 | 21.551 | 2.565 | -7.566 | 1.00 31.95 | G O |
| ATOM | 7776 | N | LEU | C | 95 | 23.135 | 3.176 | -9.036 | 1.00 32.46 | G N |
| ATOM | 7777 | CA | LEU | C | 95 | 22.257 | 3.025 | -10.196 | 1.00 33.05 | G C |
| ATOM | 7779 | CB | LEU | C | 95 | 21.650 | 4.335 | -10.714 | 1.00 32.71 | G C |
| ATOM | 7782 | CG | LEU | C | 95 | 22.092 | 5.794 | -10.507 | 1.00 33.37 | G C |
| ATOM | 7784 | CD1 | LEU | C | 95 | 22.732 | 6.077 | -9.163 | 1.00 32.33 | G C |
| ATOM | 7788 | CD2 | LEU | C | 95 | 20.861 | 6.703 | -10.726 | 1.00 29.16 | G C |
| ATOM | 7792 | C | LEU | C | 95 | 22.931 | 2.249 | -11.317 | 1.00 33.60 | G C |
| ATOM | 7793 | O | LEU | C | 95 | 24.142 | 2.379 | -11.574 | 1.00 33.68 | G O |
| ATOM | 7795 | N | ASP | C | 96 | 22.108 | 1.459 | -11.978 | 1.00 34.18 | G N |
| ATOM | 7796 | CA | ASP | C | 96 | 22.546 | 0.570 | -13.018 | 1.00 35.15 | G C |
| ATOM | 7798 | CB | ASP | C | 96 | 21.373 | -0.253 | -13.498 | 1.00 35.66 | C |
| ATOM | 7801 | CG | ASP | C | 96 | 20.900 | -1.177 | -12.460 | 1.00 36.62 | C |
| ATOM | 7802 | OD1 | ASP | C | 96 | 21.732 | -1.637 | -11.643 | 1.00 43.92 | C O |
| ATOM | 7803 | OD2 | ASP | C | 96 | 19.704 | -1.434 | -12.437 | 1.00 41.23 | C O |
| ATOM | 7804 | C | ASP | C | 96 | 23.177 | 1.317 | -14.166 | 1.00 35.23 | G C |
| ATOM | 7805 | O | ASP | C | 96 | 24.181 | 0.875 | -14.714 | 1.00 35.12 | G O |
| ATOM | 7807 | N | TRP | C | 97 | 22.608 | 2.455 | -14.519 | 1.00 34.98 | G N |
| ATOM | 7808 | CA | TRP | C | 97 | 23.292 | 3.337 | -15.427 | 1.00 35.31 | G C |
| ATOM | 7810 | CB | TRP | C | 97 | 23.066 | 2.912 | -16.891 | 1.00 35.05 | C |
| ATOM | 7813 | CG | TRP | C | 97 | 24.110 | 3.450 | -17.806 | 1.00 33.98 | C |
| ATOM | 7814 | CD1 | TRP | C | 97 | 24.000 | 4.548 | -18.607 | 1.00 33.95 | C |
| ATOM | 7816 | NE1 | TRP | C | 97 | 25.166 | 4.763 | -19.280 | 1.00 33.93 | C N |
| ATOM | 7818 | CE2 | TRP | C | 97 | 26.069 | 3.797 | -18.930 | 1.00 34.40 | C |
| ATOM | 7819 | CD2 | TRP | C | 97 | 25.442 | 2.959 | -17.987 | 1.00 34.31 | C |
| ATOM | 7820 | CE3 | TRP | C | 97 | 26.172 | 1.887 | -17.444 | 1.00 34.20 | C |
| ATOM | 7822 | CZ3 | TRP | C | 97 | 27.478 | 1.683 | -17.877 | 1.00 35.16 | C |
| ATOM | 7824 | CH2 | TRP | C | 97 | 28.081 | 2.540 | -18.821 | 1.00 34.31 | C |
| ATOM | 7826 | CZ2 | TRP | C | 97 | 27.400 | 3.605 | -19.349 | 1.00 34.51 | C |
| ATOM | 7828 | C | TRP | C | 97 | 22.807 | 4.740 | -15.201 | 1.00 35.76 | G C |

FIG 8 – CONT.

| ATOM | 7829 | O | TRP | C | 97 | 21.795 | 4.952 | -14.513 | 1.00 | 35.39 | O | G |
| --- | --- | --- | --- | --- | --- | --- | --- | --- | --- | --- | --- | --- |
| ATOM | 7831 | N | ASN | C | 98 | 23.528 | 5.705 | -15.760 | 1.00 | 36.07 | N | C |
| ATOM | 7832 | CA | ASN | C | 98 | 22.997 | 7.053 | -15.834 | 1.00 | 37.46 | C | C |
| ATOM | 7834 | CB | ASN | C | 98 | 23.841 | 7.968 | -16.761 | 1.00 | 37.50 | C | C |
| ATOM | 7837 | CG | ASN | C | 98 | 23.579 | 9.457 | -16.494 | 1.00 | 38.37 | C | C |
| ATOM | 7838 | OD1 | ASN | C | 98 | 22.922 | 9.803 | -15.501 | 1.00 | 38.86 | O | C |
| ATOM | 7839 | ND2 | ASN | C | 98 | 24.084 | 10.332 | -17.363 | 1.00 | 35.74 | N | C |
| ATOM | 7842 | C | ASN | C | 98 | 21.555 | 6.958 | -16.311 | 1.00 | 38.29 | C | C |
| ATOM | 7843 | O | ASN | C | 98 | 21.205 | 6.003 | -17.034 | 1.00 | 38.36 | O | C |
| ATOM | 7845 | N | TYR | C | 99 | 20.715 | 7.892 | -15.864 | 1.00 | 39.09 | N | C |
| ATOM | 7846 | CA | TYR | C | 99 | 19.305 | 7.978 | -16.299 | 1.00 | 40.49 | C | C |
| ATOM | 7848 | CB | TYR | C | 99 | 19.196 | 8.003 | -17.827 | 1.00 | 41.32 | C | C |
| ATOM | 7851 | CG | TYR | C | 99 | 19.499 | 9.330 | -18.462 | 1.00 | 46.56 | C | C |
| ATOM | 7852 | CD1 | TYR | C | 99 | 18.469 | 10.245 | -18.715 | 1.00 | 51.64 | C | C |
| ATOM | 7854 | CE1 | TYR | C | 99 | 18.721 | 11.485 | -19.327 | 1.00 | 53.91 | C | C |
| ATOM | 7856 | CZ | TYR | C | 99 | 20.017 | 11.818 | -19.711 | 1.00 | 55.38 | C | C |
| ATOM | 7857 | OH | TYR | C | 99 | 20.230 | 13.052 | -20.319 | 1.00 | 57.45 | O | C |
| ATOM | 7859 | CE2 | TYR | C | 99 | 21.076 | 10.924 | -19.468 | 1.00 | 53.26 | C | C |
| ATOM | 7861 | CD2 | TYR | C | 99 | 20.799 | 9.667 | -18.856 | 1.00 | 51.37 | C | C |
| ATOM | 7863 | C | TYR | C | 99 | 18.381 | 6.880 | -15.801 | 1.00 | 40.20 | C | C |
| ATOM | 7864 | O | TYR | C | 99 | 17.200 | 6.876 | -16.133 | 1.00 | 40.60 | O | C |
| ATOM | 7866 | N | ASN | C | 100 | 18.897 | 5.940 | -15.027 | 1.00 | 39.92 | N | G |
| ATOM | 7867 | CA | ASN | C | 100 | 18.077 | 4.835 | -14.534 | 1.00 | 39.25 | C | G |
| ATOM | 7869 | CB | ASN | C | 100 | 18.892 | 3.532 | -14.591 | 1.00 | 39.25 | C | C |
| ATOM | 7872 | CG | ASN | C | 100 | 19.041 | 3.002 | -16.025 | 1.00 | 37.78 | C | C |
| ATOM | 7873 | OD1 | ASN | C | 100 | 19.642 | 3.648 | -16.871 | 1.00 | 37.76 | O | C |
| ATOM | 7874 | ND2 | ASN | C | 100 | 18.473 | 1.849 | -16.289 | 1.00 | 36.56 | N | C |
| ATOM | 7877 | C | ASN | C | 100 | 17.559 | 5.149 | -13.120 | 1.00 | 39.40 | C | G |
| ATOM | 7878 | O | ASN | C | 100 | 17.832 | 6.233 | -12.591 | 1.00 | 39.47 | O | G |
| ATOM | 7880 | N | PRO | C | 100A | 16.773 | 4.236 | -12.529 | 1.00 | 38.81 | N | G |
| ATOM | 7881 | CA | PRO | C | 100A | 16.198 | 4.526 | -11.211 | 1.00 | 38.95 | C | G |

FIG 8 – CONT.

| | | | | | | | | | | |
|---|---|---|---|---|---|---|---|---|---|---|
| C | | | | | | | | | | |
| ATOM | 7883 | CB | PRO | C | 100A | 15.211 | 3.364 | -10.984 | 1.00 38.71 | C |
| ATOM | 7886 | CG | PRO | C | 100A | 14.978 | 2.774 | -12.338 | 1.00 39.46 | C |
| ATOM | 7889 | CD | PRO | C | 100A | 16.267 | 2.963 | -13.074 | 1.00 39.23 | C |
| ATOM | 7892 | C | PRO | C | 100A | 17.250 | 4.559 | -10.086 | 1.00 38.07 | G |
| ATOM | 7893 | O | PRO | C | 100A | 18.222 | 3.813 | -10.134 | 1.00 38.78 | O |
| ATOM | 7894 | N | LEU | C | 100B | 17.057 | 5.433 | -9.105 | 1.00 36.95 | N |
| ATOM | 7895 | CA | LEU | C | 100B | 17.923 | 5.477 | -7.919 | 1.00 36.15 | C |
| ATOM | 7897 | CB | LEU | C | 100B | 17.697 | 6.768 | -7.117 | 1.00 36.32 | C |
| ATOM | 7900 | CG | LEU | C | 100B | 17.565 | 8.122 | -7.831 | 1.00 36.33 | C |
| ATOM | 7902 | CD1 | LEU | C | 100B | 17.968 | 9.274 | -6.878 | 1.00 36.13 | C |
| ATOM | 7906 | CD2 | LEU | C | 100B | 18.323 | 8.193 | -9.091 | 1.00 36.14 | C |
| ATOM | 7910 | C | LEU | C | 100B | 17.627 | 4.220 | -7.079 | 1.00 34.96 | G |
| ATOM | 7911 | O | LEU | C | 100B | 16.764 | 4.211 | -6.201 | 1.00 33.32 | O |
| ATOM | 7913 | N | ARG | C | 101 | 18.335 | 3.147 | -7.389 | 1.00 34.34 | N |
| ATOM | 7914 | CA | ARG | C | 101 | 17.897 | 1.817 | -6.980 | 1.00 34.45 | C |
| ATOM | 7916 | CB | ARG | C | 101 | 18.273 | 0.774 | -8.069 | 1.00 35.27 | C |
| ATOM | 7919 | CG | ARG | C | 101 | 18.262 | -0.692 | -7.567 | 1.00 38.36 | C |
| ATOM | 7922 | CD | ARG | C | 101 | 17.341 | -1.601 | -8.366 | 1.00 44.96 | C |
| ATOM | 7925 | NE | ARG | C | 101 | 17.980 | -2.201 | -9.532 | 1.00 47.96 | N |
| ATOM | 7927 | CZ | ARG | C | 101 | 17.949 | -3.505 | -9.865 | 1.00 50.57 | C |
| ATOM | 7928 | NH1 | ARG | C | 101 | 17.311 | -4.426 | -9.139 | 1.00 49.87 | N |
| ATOM | 7931 | NH2 | ARG | C | 101 | 18.581 | -3.896 | -10.966 | 1.00 50.72 | C |
| ATOM | 7934 | C | ARG | C | 101 | 18.415 | 1.408 | -5.603 | 1.00 32.80 | G |
| ATOM | 7935 | O | ARG | C | 101 | 17.674 | 0.828 | -4.805 | 1.00 32.38 | O |
| ATOM | 7937 | N | TYR | C | 102 | 19.686 | 1.658 | -5.335 | 1.00 31.35 | N |
| ATOM | 7938 | CA | TYR | C | 102 | 20.262 | 1.228 | -4.055 | 1.00 31.67 | G |
| ATOM | 7940 | CB | TYR | C | 102 | 21.452 | 0.287 | -4.235 | 1.00 31.60 | C |
| ATOM | 7943 | CG | TYR | C | 102 | 21.141 | -0.929 | -5.048 | 1.00 32.92 | C |
| ATOM | 7944 | CD1 | TYR | C | 102 | 20.548 | -2.044 | -4.456 | 1.00 35.41 | C |
| ATOM | 7946 | CE1 | TYR | C | 102 | 20.250 | -3.173 | -5.192 | 1.00 36.85 | C |

FIG 8 – CONT.

| ATOM | 7948 | CZ | TYR | C | 102 | 20.569 | -3.213 | -6.552 | 1.00 | 36.79 | C |
|---|---|---|---|---|---|---|---|---|---|---|---|
| ATOM | 7949 | OH | TYR | C | 102 | 20.253 | -4.335 | -7.260 | 1.00 | 39.93 | O |
| ATOM | 7951 | CE2 | TYR | C | 102 | 21.157 | -2.126 | -7.182 | 1.00 | 35.07 | C |
| ATOM | 7953 | CD2 | TYR | C | 102 | 21.430 | -0.971 | -6.423 | 1.00 | 34.76 | C |
| ATOM | 7955 | C | TYR | C | 102 | 20.698 | 2.459 | -3.298 | 1.00 | 30.94 | G |
| ATOM | 7956 | O | TYR | C | 102 | 21.264 | 3.399 | -3.875 | 1.00 | 31.81 | G |
| ATOM | 7958 | N | TRP | C | 103 | 20.415 | 2.473 | -2.008 | 1.00 | 29.81 | G |
| ATOM | 7959 | CA | TRP | C | 103 | 20.705 | 3.661 | -1.195 | 1.00 | 28.37 | G |
| ATOM | 7961 | CB | TRP | C | 103 | 19.407 | 4.207 | -0.655 | 1.00 | 28.53 | G |
| ATOM | 7964 | CG | TRP | C | 103 | 18.584 | 4.880 | -1.686 | 1.00 | 27.25 | G |
| ATOM | 7965 | CD1 | TRP | C | 103 | 17.859 | 4.285 | -2.657 | 1.00 | 27.43 | G |
| ATOM | 7967 | NE1 | TRP | C | 103 | 17.251 | 5.231 | -3.431 | 1.00 | 29.46 | G |
| ATOM | 7969 | CE2 | TRP | C | 103 | 17.585 | 6.473 | -2.972 | 1.00 | 26.95 | G |
| ATOM | 7970 | CD2 | TRP | C | 103 | 18.410 | 6.294 | -1.862 | 1.00 | 28.24 | G |
| ATOM | 7971 | CE3 | TRP | C | 103 | 18.886 | 7.424 | -1.188 | 1.00 | 27.83 | G |
| ATOM | 7973 | CZ3 | TRP | C | 103 | 18.504 | 8.655 | -1.634 | 1.00 | 26.85 | G |
| ATOM | 7975 | CH2 | TRP | C | 103 | 17.674 | 8.800 | -2.731 | 1.00 | 25.38 | G |
| ATOM | 7977 | CZ2 | TRP | C | 103 | 17.192 | 7.714 | -3.406 | 1.00 | 28.02 | G |
| ATOM | 7979 | C | TRP | C | 103 | 21.665 | 3.265 | -0.080 | 1.00 | 27.86 | G |
| ATOM | 7980 | O | TRP | C | 103 | 21.528 | 2.185 | 0.512 | 1.00 | 28.12 | G |
| ATOM | 7982 | N | GLY | C | 104 | 22.692 | 4.077 | 0.153 | 1.00 | 26.62 | G |
| ATOM | 7983 | CA | GLY | C | 104 | 23.535 | 3.894 | 1.343 | 1.00 | 27.19 | G |
| ATOM | 7986 | C | GLY | C | 104 | 22.788 | 4.428 | 2.570 | 1.00 | 26.63 | G |
| ATOM | 7987 | O | GLY | C | 104 | 21.719 | 4.988 | 2.406 | 1.00 | 25.36 | G |
| ATOM | 7989 | N | PRO | C | 105 | 23.321 | 4.217 | 3.787 | 1.00 | 27.23 | G |
| ATOM | 7990 | CA | PRO | C | 105 | 22.611 | 4.672 | 4.997 | 1.00 | 27.97 | G |
| ATOM | 7992 | CB | PRO | C | 105 | 23.208 | 3.819 | 6.128 | 1.00 | 28.10 | C |
| ATOM | 7995 | CG | PRO | C | 105 | 24.490 | 3.340 | 5.630 | 1.00 | 28.11 | C |
| ATOM | 7998 | CD | PRO | C | 105 | 24.352 | 3.219 | 4.120 | 1.00 | 28.46 | C |
| ATOM | 8001 | C | PRO | C | 105 | 22.777 | 6.153 | 5.275 | 1.00 | 27.92 | C |
| ATOM | 8002 | O | PRO | C | 105 | 22.010 | 6.714 | 6.060 | 1.00 | 28.03 | G |

FIG 8 – CONT.

| | | | | | | | | | | |
|---|---|---|---|---|---|---|---|---|---|---|
| ATOM | 8003 | N | GLY | C | 106 | 23.719 | 6.790 | 4.587 | 1.00 27.48 | G |
| ATOM | 8004 | CA | GLY | C | 106 | 23.894 | 8.236 | 4.690 | 1.00 26.28 | G |
| ATOM | 8007 | C | GLY | C | 106 | 25.098 | 8.529 | 5.561 | 1.00 25.73 | G |
| ATOM | 8008 | O | GLY | C | 106 | 25.491 | 7.714 | 6.410 | 1.00 25.41 | G |
| ATOM | 8010 | N | THR | C | 107 | 25.703 | 9.690 | 5.343 | 1.00 25.11 | G |
| ATOM | 8011 | CA | THR | C | 107 | 26.810 | 10.152 | 6.187 | 1.00 24.75 | G |
| ATOM | 8013 | CB | THR | C | 107 | 28.151 | 10.216 | 5.371 | 1.00 25.07 | G |
| ATOM | 8015 | OG1 | THR | C | 107 | 28.634 | 8.894 | 5.163 | 1.00 24.03 | G |
| ATOM | 8017 | CG2 | THR | C | 107 | 29.222 | 11.014 | 6.142 | 1.00 27.91 | G |
| ATOM | 8021 | C | THR | C | 107 | 26.410 | 11.524 | 6.671 | 1.00 24.23 | G |
| ATOM | 8022 | O | THR | C | 107 | 26.136 | 12.374 | 5.850 | 1.00 22.36 | G |
| ATOM | 8024 | N | LEU | C | 108 | 26.308 | 11.706 | 7.997 | 1.00 24.22 | G |
| ATOM | 8025 | CA | LEU | C | 108 | 25.956 | 12.975 | 8.580 | 1.00 24.74 | G |
| ATOM | 8027 | CB | LEU | C | 108 | 25.507 | 12.885 | 10.080 | 1.00 26.35 | G |
| ATOM | 8030 | CG | LEU | C | 108 | 24.374 | 13.810 | 10.581 | 1.00 27.84 | G |
| ATOM | 8032 | CD1 | LEU | C | 108 | 24.482 | 14.089 | 12.098 | 1.00 30.69 | G |
| ATOM | 8036 | CD2 | LEU | C | 108 | 24.200 | 15.110 | 9.866 | 1.00 27.39 | G |
| ATOM | 8040 | C | LEU | C | 108 | 27.190 | 13.789 | 8.557 | 1.00 23.49 | G |
| ATOM | 8041 | O | LEU | C | 108 | 28.242 | 13.340 | 8.985 | 1.00 22.18 | G |
| ATOM | 8043 | N | VAL | C | 109 | 27.044 | 14.999 | 8.076 | 1.00 22.84 | G |
| ATOM | 8044 | CA | VAL | C | 109 | 28.115 | 15.948 | 8.105 | 1.00 23.30 | G |
| ATOM | 8046 | CB | VAL | C | 109 | 28.612 | 16.323 | 6.684 | 1.00 23.61 | G |
| ATOM | 8048 | CG1 | VAL | C | 109 | 29.733 | 17.416 | 6.766 | 1.00 20.71 | G |
| ATOM | 8052 | CG2 | VAL | C | 109 | 29.097 | 15.046 | 5.981 | 1.00 22.35 | G |
| ATOM | 8056 | C | VAL | C | 109 | 27.605 | 17.193 | 8.814 | 1.00 23.83 | G |
| ATOM | 8057 | O | VAL | C | 109 | 26.628 | 17.789 | 8.389 | 1.00 23.29 | G |
| ATOM | 8059 | N | THR | C | 110 | 28.303 | 17.553 | 9.889 | 1.00 25.43 | G |
| ATOM | 8060 | CA | THR | C | 110 | 27.940 | 18.702 | 10.737 | 1.00 25.96 | G |
| ATOM | 8062 | CB | THR | C | 110 | 27.778 | 18.320 | 12.243 | 1.00 25.77 | G |
| ATOM | 8064 | OG1 | THR | C | 110 | 26.816 | 17.290 | 12.364 | 1.00 26.90 | G |

FIG 8 – CONT.

| ATOM | 8066 | CG2 | THR C 110 | 27.288 | 19.540 | 13.049 | 1.00 26.85 | G |
|---|---|---|---|---|---|---|---|---|
| ATOM | 8070 | C | THR C 110 | 29.030 | 19.696 | 10.615 | 1.00 25.23 | C |
| ATOM | 8071 | O | THR C 110 | 30.159 | 19.405 | 10.958 | 1.00 25.07 | G |
| ATOM | 8073 | N | VAL C 111 | 28.698 | 20.862 | 10.086 | 1.00 26.98 | G |
| ATOM | 8074 | CA | VAL C 111 | 29.702 | 21.879 | 9.869 | 1.00 27.93 | G |
| ATOM | 8076 | CB | VAL C 111 | 29.741 | 22.337 | 8.398 | 1.00 28.46 | G |
| ATOM | 8078 | CG1 | VAL C 111 | 30.868 | 23.365 | 8.199 | 1.00 27.63 | G |
| ATOM | 8082 | CG2 | VAL C 111 | 29.920 | 21.119 | 7.419 | 1.00 26.38 | G |
| ATOM | 8086 | C | VAL C 111 | 29.357 | 23.042 | 10.799 | 1.00 28.74 | G |
| ATOM | 8087 | O | VAL C 111 | 28.296 | 23.635 | 10.685 | 1.00 29.40 | G |
| ATOM | 8089 | N | SER C 112 | 30.242 | 23.360 | 11.730 | 1.00 28.82 | C |
| ATOM | 8090 | CA | SER C 112 | 29.938 | 24.472 | 12.622 | 1.00 29.77 | C |
| ATOM | 8092 | CB | SER C 112 | 29.017 | 23.969 | 13.759 | 1.00 30.04 | C |
| ATOM | 8095 | OG | SER C 112 | 29.189 | 24.718 | 14.947 | 1.00 31.35 | C |
| ATOM | 8097 | C | SER C 112 | 31.207 | 25.089 | 13.186 | 1.00 29.44 | C |
| ATOM | 8098 | O | SER C 112 | 32.223 | 24.416 | 13.335 | 1.00 27.44 | C |
| ATOM | 8100 | N | SER C 113 | 31.115 | 26.370 | 13.520 | 1.00 30.82 | C |
| ATOM | 8101 | CA | SER C 113 | 32.244 | 27.072 | 14.121 | 1.00 32.05 | C |
| ATOM | 8103 | CB | SER C 113 | 32.046 | 28.581 | 14.006 | 1.00 32.71 | C |
| ATOM | 8106 | OG | SER C 113 | 32.034 | 28.971 | 12.632 | 1.00 31.62 | C |
| ATOM | 8108 | C | SER C 113 | 32.502 | 26.655 | 15.577 | 1.00 32.69 | C |
| ATOM | 8109 | O | SER C 113 | 33.592 | 26.865 | 16.079 | 1.00 34.04 | C |
| ATOM | 8111 | N | ALA C 114 | 31.542 | 25.998 | 16.233 | 1.00 32.97 | C |
| ATOM | 8112 | CA | ALA C 114 | 31.722 | 25.567 | 17.619 | 1.00 31.96 | C |
| ATOM | 8114 | CB | ALA C 114 | 30.422 | 24.898 | 18.172 | 1.00 31.54 | C |
| ATOM | 8118 | C | ALA C 114 | 32.865 | 24.602 | 17.658 | 1.00 32.25 | C |
| ATOM | 8119 | O | ALA C 114 | 33.146 | 23.943 | 16.649 | 1.00 31.77 | C |
| ATOM | 8121 | N | SER C 115 | 33.534 | 24.524 | 18.808 | 1.00 31.90 | C |
| ATOM | 8122 | CA | SER C 115 | 34.638 | 23.581 | 19.003 | 1.00 32.64 | C |
| ATOM | 8124 | CB | SER C 115 | 35.875 | 24.339 | 19.551 | 1.00 33.46 | C |
| ATOM | 8127 | OG | SER C 115 | 36.172 | 25.505 | 18.765 | 1.00 35.92 | C |

FIG 8 – CONT.

| | | | | | | | | | | |
|---|---|---|---|---|---|---|---|---|---|---|
| ATOM | 8129 | C | SER | C | 115 | 34.251 | 22.469 | 19.972 | 1.00 32.30 | C |
| ATOM | 8130 | O | SER | C | 115 | 33.405 | 22.683 | 20.852 | 1.00 31.01 | C |
| ATOM | 8132 | N | THR | C | 116 | 34.866 | 21.299 | 19.847 | 1.00 32.42 | C |
| ATOM | 8133 | CA | THR | C | 116 | 34.535 | 20.239 | 20.793 | 1.00 33.85 | C |
| ATOM | 8135 | CB | THR | C | 116 | 35.039 | 18.797 | 20.438 | 1.00 34.15 | C |
| ATOM | 8137 | OG1 | THR | C | 116 | 35.548 | 18.160 | 21.622 | 1.00 37.17 | C |
| ATOM | 8139 | CG2 | THR | C | 116 | 36.032 | 18.733 | 19.351 | 1.00 35.06 | C |
| ATOM | 8143 | C | THR | C | 116 | 34.773 | 20.575 | 22.299 | 1.00 33.55 | C |
| ATOM | 8144 | O | THR | C | 116 | 35.767 | 21.199 | 22.689 | 1.00 33.29 | C |
| ATOM | 8146 | N | LYS | C | 117 | 33.785 | 20.195 | 23.113 | 1.00 32.98 | C |
| ATOM | 8147 | CA | LYS | C | 117 | 33.680 | 20.616 | 24.498 | 1.00 32.12 | C |
| ATOM | 8149 | CB | LYS | C | 117 | 33.060 | 22.001 | 24.541 | 1.00 32.51 | C |
| ATOM | 8152 | CG | LYS | C | 117 | 33.011 | 22.612 | 25.954 | 1.00 32.13 | C |
| ATOM | 8155 | CD | LYS | C | 117 | 32.069 | 23.787 | 26.031 | 1.00 32.99 | C |
| ATOM | 8158 | CE | LYS | C | 117 | 31.919 | 24.279 | 27.485 | 1.00 34.64 | C |
| ATOM | 8161 | NZ | LYS | C | 117 | 31.413 | 23.199 | 28.449 | 1.00 38.23 | C |
| ATOM | 8165 | C | LYS | C | 117 | 32.824 | 19.639 | 25.284 | 1.00 32.27 | C |
| ATOM | 8166 | O | LYS | C | 117 | 31.668 | 19.402 | 24.936 | 1.00 31.28 | C |
| ATOM | 8168 | N | GLY | C | 118 | 33.404 | 19.031 | 26.320 | 1.00 32.86 | C |
| ATOM | 8169 | CA | GLY | C | 118 | 32.663 | 18.111 | 27.225 | 1.00 32.50 | C |
| ATOM | 8172 | C | GLY | C | 118 | 31.586 | 18.862 | 27.995 | 1.00 31.89 | C |
| ATOM | 8173 | O | GLY | C | 118 | 31.673 | 20.054 | 28.171 | 1.00 31.48 | C |
| ATOM | 8175 | N | PRO | C | 119 | 30.524 | 18.171 | 28.415 | 1.00 32.73 | G |
| ATOM | 8176 | CA | PRO | C | 119 | 29.430 | 18.850 | 29.105 | 1.00 32.72 | G |
| ATOM | 8178 | CB | PRO | C | 119 | 28.321 | 17.819 | 29.063 | 1.00 32.80 | G |
| ATOM | 8181 | CG | PRO | C | 119 | 29.042 | 16.546 | 29.189 | 1.00 32.91 | G |
| ATOM | 8184 | CD | PRO | C | 119 | 30.326 | 16.715 | 28.410 | 1.00 32.83 | G |
| ATOM | 8187 | C | PRO | C | 119 | 29.772 | 19.152 | 30.553 | 1.00 32.81 | G |
| ATOM | 8188 | O | PRO | C | 119 | 30.628 | 18.493 | 31.129 | 1.00 32.32 | G |
| ATOM | 8189 | N | SER | C | 120 | 29.136 | 20.184 | 31.093 | 1.00 33.70 | G |

FIG 8 – CONT.

| | | | | | | | | | | |
|---|---|---|---|---|---|---|---|---|---|---|
| ATOM | 8190 | CA | SER | C | 120 | 28.948 | 20.314 | 32.537 | 1.00 34.56 | G |
| C | | | | | | | | | | |
| ATOM | 8192 | CB | SER | C | 120 | 28.944 | 21.780 | 32.952 | 1.00 34.54 | G |
| C | | | | | | | | | | |
| ATOM | 8195 | OG | SER | C | 120 | 30.218 | 22.342 | 32.781 | 1.00 36.56 | G |
| O | | | | | | | | | | |
| ATOM | 8197 | C | SER | C | 120 | 27.588 | 19.692 | 32.915 | 1.00 33.97 | G |
| C | | | | | | | | | | |
| ATOM | 8198 | O | SER | C | 120 | 26.579 | 20.016 | 32.315 | 1.00 34.87 | G |
| O | | | | | | | | | | |
| ATOM | 8200 | N | VAL | C | 121 | 27.584 | 18.843 | 33.930 | 1.00 34.12 | G |
| N | | | | | | | | | | |
| ATOM | 8201 | CA | VAL | C | 121 | 26.387 | 18.153 | 34.404 | 1.00 34.35 | G |
| C | | | | | | | | | | |
| ATOM | 8203 | CB | VAL | C | 121 | 26.644 | 16.654 | 34.563 | 1.00 34.05 | G |
| C | | | | | | | | | | |
| ATOM | 8205 | CG1 | VAL | C | 121 | 25.350 | 15.926 | 34.938 | 1.00 35.46 | G |
| C | | | | | | | | | | |
| ATOM | 8209 | CG2 | VAL | C | 121 | 27.201 | 16.081 | 33.302 | 1.00 31.53 | G |
| C | | | | | | | | | | |
| ATOM | 8213 | C | VAL | C | 121 | 25.891 | 18.714 | 35.746 | 1.00 34.63 | G |
| C | | | | | | | | | | |
| ATOM | 8214 | O | VAL | C | 121 | 26.615 | 18.761 | 36.737 | 1.00 34.78 | G |
| O | | | | | | | | | | |
| ATOM | 8216 | N | PHE | C | 122 | 24.639 | 19.155 | 35.764 | 1.00 35.09 | G |
| N | | | | | | | | | | |
| ATOM | 8217 | CA | PHE | C | 122 | 24.048 | 19.652 | 36.980 | 1.00 34.53 | G |
| C | | | | | | | | | | |
| ATOM | 8219 | CB | PHE | C | 122 | 23.650 | 21.067 | 36.757 | 1.00 34.55 | G |
| C | | | | | | | | | | |
| ATOM | 8222 | CG | PHE | C | 122 | 24.806 | 21.949 | 36.478 | 1.00 35.92 | G |
| C | | | | | | | | | | |
| ATOM | 8223 | CD1 | PHE | C | 122 | 25.773 | 22.150 | 37.445 | 1.00 38.08 | G |
| C | | | | | | | | | | |
| ATOM | 8225 | CE1 | PHE | C | 122 | 26.881 | 22.946 | 37.196 | 1.00 38.13 | G |
| C | | | | | | | | | | |
| ATOM | 8227 | CZ | PHE | C | 122 | 27.025 | 23.562 | 35.964 | 1.00 38.12 | G |
| C | | | | | | | | | | |
| ATOM | 8229 | CE2 | PHE | C | 122 | 26.071 | 23.360 | 34.983 | 1.00 38.95 | G |
| C | | | | | | | | | | |
| ATOM | 8231 | CD2 | PHE | C | 122 | 24.968 | 22.541 | 35.241 | 1.00 37.95 | G |
| C | | | | | | | | | | |
| ATOM | 8233 | C | PHE | C | 122 | 22.880 | 18.779 | 37.412 | 1.00 35.17 | G |
| C | | | | | | | | | | |
| ATOM | 8234 | O | PHE | C | 122 | 22.124 | 18.282 | 36.571 | 1.00 36.46 | G |
| O | | | | | | | | | | |
| ATOM | 8236 | N | PRO | C | 123 | 22.755 | 18.528 | 38.730 | 1.00 34.89 | G |
| N | | | | | | | | | | |
| ATOM | 8237 | CA | PRO | C | 123 | 21.650 | 17.664 | 39.169 | 1.00 33.77 | G |
| C | | | | | | | | | | |
| ATOM | 8239 | CB | PRO | C | 123 | 22.014 | 17.363 | 40.630 | 1.00 33.92 | G |
| C | | | | | | | | | | |
| ATOM | 8242 | CG | PRO | C | 123 | 22.724 | 18.615 | 41.090 | 1.00 33.48 | G |
| C | | | | | | | | | | |
| ATOM | 8245 | CD | PRO | C | 123 | 23.504 | 19.101 | 39.877 | 1.00 34.30 | G |
| C | | | | | | | | | | |
| ATOM | 8248 | C | PRO | C | 123 | 20.351 | 18.437 | 39.067 | 1.00 32.88 | G |
| C | | | | | | | | | | |
| ATOM | 8249 | O | PRO | C | 123 | 20.360 | 19.641 | 39.277 | 1.00 32.99 | G |
| O | | | | | | | | | | |
| ATOM | 8250 | N | LEU | C | 124 | 19.262 | 17.785 | 38.678 | 1.00 32.38 | G |

FIG 8 – CONT.

| ATOM | 8251 | CA | LEU | C | 124 | 17.932 | 18.426 | 38.744 | 1.00 | 32.81 | G |
|---|---|---|---|---|---|---|---|---|---|---|---|
| ATOM | 8253 | CB | LEU | C | 124 | 17.165 | 18.308 | 37.423 | 1.00 | 32.17 | G |
| ATOM | 8256 | CG | LEU | C | 124 | 17.909 | 19.001 | 36.246 | 1.00 | 31.24 | G |
| ATOM | 8258 | CD1 | LEU | C | 124 | 17.375 | 18.571 | 34.903 | 1.00 | 28.25 | G |
| ATOM | 8262 | CD2 | LEU | C | 124 | 17.879 | 20.526 | 36.367 | 1.00 | 28.75 | G |
| ATOM | 8266 | C | LEU | C | 124 | 17.202 | 17.769 | 39.929 | 1.00 | 33.68 | G |
| ATOM | 8267 | O | LEU | C | 124 | 16.676 | 16.658 | 39.825 | 1.00 | 32.67 | G |
| ATOM | 8269 | N | ALA | C | 125 | 17.263 | 18.449 | 41.071 | 1.00 | 35.33 | G |
| ATOM | 8270 | CA | ALA | C | 125 | 16.900 | 17.840 | 42.378 | 1.00 | 37.19 | G |
| ATOM | 8272 | CB | ALA | C | 125 | 17.390 | 18.748 | 43.563 | 1.00 | 36.92 | G |
| ATOM | 8276 | C | ALA | C | 125 | 15.385 | 17.592 | 42.510 | 1.00 | 38.27 | G |
| ATOM | 8277 | O | ALA | C | 125 | 14.575 | 18.441 | 42.136 | 1.00 | 38.48 | G |
| ATOM | 8279 | N | PRO | C | 126 | 15.001 | 16.431 | 43.035 | 1.00 | 40.09 | G |
| ATOM | 8280 | CA | PRO | C | 126 | 13.580 | 16.272 | 43.357 | 1.00 | 41.47 | G |
| ATOM | 8282 | CB | PRO | C | 126 | 13.464 | 14.814 | 43.776 | 1.00 | 41.13 | G |
| ATOM | 8285 | CG | PRO | C | 126 | 14.829 | 14.493 | 44.367 | 1.00 | 41.37 | G |
| ATOM | 8288 | CD | PRO | C | 126 | 15.817 | 15.301 | 43.523 | 1.00 | 40.76 | G |
| ATOM | 8291 | C | PRO | C | 126 | 13.193 | 17.178 | 44.502 | 1.00 | 42.80 | G |
| ATOM | 8292 | O | PRO | C | 126 | 13.944 | 17.297 | 45.474 | 1.00 | 43.39 | G |
| ATOM | 8293 | N | SER | C | 127 | 12.056 | 17.847 | 44.348 | 1.00 | 44.90 | G |
| ATOM | 8294 | CA | SER | C | 127 | 11.495 | 18.719 | 45.381 | 1.00 | 46.56 | G |
| ATOM | 8296 | CB | SER | C | 127 | 11.709 | 20.196 | 45.023 | 1.00 | 46.14 | G |
| ATOM | 8299 | OG | SER | C | 127 | 10.735 | 20.608 | 44.087 | 1.00 | 45.21 | G |
| ATOM | 8301 | C | SER | C | 127 | 9.993 | 18.448 | 45.491 | 1.00 | 48.16 | G |
| ATOM | 8302 | O | SER | C | 127 | 9.458 | 17.595 | 44.786 | 1.00 | 48.60 | G |
| ATOM | 8304 | N | SER | C | 128 | 9.312 | 19.210 | 46.341 | 1.00 | 49.81 | G |
| ATOM | 8305 | CA | SER | C | 128 | 7.871 | 19.080 | 46.481 | 1.00 | 51.03 | G |
| ATOM | 8307 | CB | SER | C | 128 | 7.371 | 19.759 | 47.765 | 1.00 | 51.34 | G |
| ATOM | 8310 | OG | SER | C | 128 | 7.545 | 21.165 | 47.728 | 1.00 | 50.88 | G |
| ATOM | 8312 | C | SER | C | 128 | 7.170 | 19.638 | 45.239 | 1.00 | 51.99 | G |

FIG 8 – CONT.

| ATOM | 8313 | O   | SER | C | 128 | 6.039  | 19.263 | 44.976 | 1.00 | 52.67 | G |
|------|------|-----|-----|---|-----|--------|--------|--------|------|-------|---|
| ATOM | 8315 | N   | LYS | C | 129 | 7.842  | 20.500 | 44.464 | 1.00 | 52.66 | G |
| ATOM | 8316 | CA  | LYS | C | 129 | 7.302  | 20.955 | 43.165 | 1.00 | 53.03 | G |
| ATOM | 8318 | CB  | LYS | C | 129 | 7.979  | 22.249 | 42.694 | 1.00 | 53.54 | G |
| ATOM | 8321 | CG  | LYS | C | 129 | 7.507  | 23.524 | 43.413 | 1.00 | 54.83 | G |
| ATOM | 8324 | CD  | LYS | C | 129 | 6.136  | 24.030 | 42.902 | 1.00 | 55.80 | G |
| ATOM | 8327 | CE  | LYS | C | 129 | 6.076  | 25.568 | 42.889 | 1.00 | 55.77 | G |
| ATOM | 8330 | NZ  | LYS | C | 129 | 4.873  | 26.120 | 43.552 | 1.00 | 55.96 | G |
| ATOM | 8334 | C   | LYS | C | 129 | 7.443  | 19.894 | 42.074 | 1.00 | 52.94 | G |
| ATOM | 8335 | O   | LYS | C | 129 | 6.698  | 19.907 | 41.110 | 1.00 | 52.70 | G |
| ATOM | 8337 | N   | SER | C | 130 | 8.399  | 18.984 | 42.214 | 1.00 | 53.02 | G |
| ATOM | 8338 | CA  | SER | C | 130 | 8.575  | 17.908 | 41.223 | 1.00 | 53.23 | G |
| ATOM | 8340 | CB  | SER | C | 130 | 10.078 | 17.682 | 40.945 | 1.00 | 52.99 | G |
| ATOM | 8343 | OG  | SER | C | 130 | 10.660 | 16.803 | 41.909 | 1.00 | 52.84 | G |
| ATOM | 8345 | C   | SER | C | 130 | 7.917  | 16.570 | 41.639 | 1.00 | 53.25 | G |
| ATOM | 8346 | O   | SER | C | 130 | 8.006  | 15.587 | 40.900 | 1.00 | 52.18 | G |
| ATOM | 8348 | N   | THR | C | 133 | 7.286  | 16.525 | 42.819 | 1.00 | 54.01 | G |
| ATOM | 8349 | CA  | THR | C | 133 | 6.717  | 15.261 | 43.328 | 1.00 | 54.59 | G |
| ATOM | 8351 | CB  | THR | C | 133 | 7.363  | 14.779 | 44.669 | 1.00 | 54.74 | G |
| ATOM | 8353 | OG1 | THR | C | 133 | 6.517  | 15.103 | 45.783 | 1.00 | 55.66 | G |
| ATOM | 8355 | CG2 | THR | C | 133 | 8.752  | 15.371 | 44.887 | 1.00 | 53.40 | G |
| ATOM | 8359 | C   | THR | C | 133 | 5.187  | 15.353 | 43.474 | 1.00 | 54.96 | G |
| ATOM | 8360 | O   | THR | C | 133 | 4.640  | 16.386 | 43.883 | 1.00 | 54.81 | G |
| ATOM | 8362 | N   | SER | C | 134 | 4.508  | 14.268 | 43.116 | 1.00 | 54.72 | G |
| ATOM | 8363 | CA  | SER | C | 134 | 3.060  | 14.242 | 43.149 | 1.00 | 54.58 | G |
| ATOM | 8365 | CB  | SER | C | 134 | 2.476  | 15.051 | 41.980 | 1.00 | 54.99 | G |
| ATOM | 8368 | OG  | SER | C | 134 | 1.139  | 15.465 | 42.255 | 1.00 | 56.46 | G |
| ATOM | 8370 | C   | SER | C | 134 | 2.573  | 12.805 | 43.075 | 1.00 | 54.20 | G |
| ATOM | 8371 | O   | SER | C | 134 | 3.199  | 11.959 | 42.416 | 1.00 | 53.03 | G |
| ATOM | 8373 | N   | GLY | C | 135 | 1.452  | 12.539 | 43.758 | 1.00 | 53.98 | G |
| ATOM | 8374 | CA  | GLY | C | 135 | 0.819  | 11.214 | 43.740 | 1.00 | 53.45 | G |

FIG 8 – CONT.

| | | | | | | | | | | |
|---|---|---|---|---|---|---|---|---|---|---|
| ATOM | 8377 | C | GLY | C | 135 | 1.774 | 10.118 | 44.159 | 1.00 52.95 | G |
| ATOM | 8378 | O | GLY | C | 135 | 1.740 | 9.020 | 43.619 | 1.00 53.15 | G |
| ATOM | 8380 | N | GLY | C | 136 | 2.647 | 10.428 | 45.109 | 1.00 52.57 | G |
| ATOM | 8381 | CA | GLY | C | 136 | 3.661 | 9.471 | 45.536 | 1.00 52.53 | G |
| ATOM | 8384 | C | GLY | C | 136 | 4.766 | 9.139 | 44.521 | 1.00 52.27 | G |
| ATOM | 8385 | O | GLY | C | 136 | 5.442 | 8.108 | 44.648 | 1.00 52.47 | G |
| ATOM | 8387 | N | THR | C | 137 | 4.971 | 9.997 | 43.524 | 1.00 51.49 | G |
| ATOM | 8388 | CA | THR | C | 137 | 6.078 | 9.811 | 42.595 | 1.00 50.91 | G |
| ATOM | 8390 | CB | THR | C | 137 | 5.665 | 9.052 | 41.286 | 1.00 51.04 | G |
| ATOM | 8392 | OG1 | THR | C | 137 | 6.201 | 9.719 | 40.138 | 1.00 52.71 | G |
| ATOM | 8394 | CG2 | THR | C | 137 | 4.169 | 8.938 | 41.135 | 1.00 51.63 | G |
| ATOM | 8398 | C | THR | C | 137 | 6.767 | 11.154 | 42.349 | 1.00 49.81 | G |
| ATOM | 8399 | O | THR | C | 137 | 6.110 | 12.188 | 42.152 | 1.00 49.86 | G |
| ATOM | 8401 | N | ALA | C | 138 | 8.100 | 11.133 | 42.412 | 1.00 48.43 | G |
| ATOM | 8402 | CA | ALA | C | 138 | 8.914 | 12.346 | 42.257 | 1.00 47.33 | G |
| ATOM | 8404 | CB | ALA | C | 138 | 9.796 | 12.547 | 43.496 | 1.00 47.81 | G |
| ATOM | 8408 | C | ALA | C | 138 | 9.773 | 12.332 | 40.982 | 1.00 45.78 | G |
| ATOM | 8409 | O | ALA | C | 138 | 10.365 | 11.301 | 40.628 | 1.00 44.62 | G |
| ATOM | 8411 | N | ALA | C | 139 | 9.812 | 13.477 | 40.294 | 1.00 44.31 | G |
| ATOM | 8412 | CA | ALA | C | 139 | 10.689 | 13.665 | 39.111 | 1.00 43.42 | G |
| ATOM | 8414 | CB | ALA | C | 139 | 10.037 | 14.565 | 38.068 | 1.00 42.71 | G |
| ATOM | 8418 | C | ALA | C | 139 | 12.013 | 14.269 | 39.569 | 1.00 42.25 | G |
| ATOM | 8419 | O | ALA | C | 139 | 12.022 | 15.294 | 40.264 | 1.00 42.47 | G |
| ATOM | 8421 | N | LEU | C | 140 | 13.107 | 13.600 | 39.215 | 1.00 40.47 | G |
| ATOM | 8422 | CA | LEU | C | 140 | 14.464 | 14.114 | 39.388 | 1.00 39.35 | G |
| ATOM | 8424 | CB | LEU | C | 140 | 15.210 | 13.366 | 40.503 | 1.00 39.33 | G |
| ATOM | 8427 | CG | LEU | C | 140 | 15.409 | 11.846 | 40.346 | 1.00 38.53 | G |
| ATOM | 8429 | CD1 | LEU | C | 140 | 16.840 | 11.495 | 40.065 | 1.00 36.20 | G |
| ATOM | 8433 | CD2 | LEU | C | 140 | 14.953 | 11.098 | 41.617 | 1.00 40.61 | G |
| ATOM | 8437 | C | LEU | C | 140 | 15.206 | 13.939 | 38.069 | 1.00 38.58 | G |

FIG 8 – CONT.

| ATOM | 8438 | O | LEU | C | 140 | 14.815 | 13.109 | 37.227 | 1.00 | 38.02 | G |
|---|---|---|---|---|---|---|---|---|---|---|---|
| ATOM | 8440 | N | GLY | C | 141 | 16.277 | 14.708 | 37.885 | 1.00 | 37.60 | G |
| ATOM | 8441 | CA | GLY | C | 141 | 17.032 | 14.615 | 36.623 | 1.00 | 37.23 | G |
| ATOM | 8444 | C | GLY | C | 141 | 18.496 | 15.014 | 36.652 | 1.00 | 36.12 | G |
| ATOM | 8445 | O | GLY | C | 141 | 19.081 | 15.282 | 37.731 | 1.00 | 33.67 | G |
| ATOM | 8447 | N | CYS | C | 142 | 19.058 | 15.029 | 35.432 | 1.00 | 35.21 | G |
| ATOM | 8448 | CA | CYS | C | 142 | 20.380 | 15.566 | 35.137 | 1.00 | 34.17 | G |
| ATOM | 8450 | CB | CYS | C | 142 | 21.364 | 14.442 | 34.897 | 1.00 | 35.16 | G |
| ATOM | 8453 | SG | CYS | C | 142 | 22.161 | 13.915 | 36.424 | 1.00 | 37.24 | G |
| ATOM | 8455 | C | CYS | C | 142 | 20.317 | 16.491 | 33.931 | 1.00 | 33.56 | G |
| ATOM | 8456 | O | CYS | C | 142 | 19.780 | 16.125 | 32.878 | 1.00 | 32.39 | G |
| ATOM | 8458 | N | LEU | C | 143 | 20.808 | 17.718 | 34.138 | 1.00 | 32.37 | G |
| ATOM | 8459 | CA | LEU | C | 143 | 21.032 | 18.699 | 33.089 | 1.00 | 32.21 | G |
| ATOM | 8461 | CB | LEU | C | 143 | 20.870 | 20.111 | 33.659 | 1.00 | 31.74 | G |
| ATOM | 8464 | CG | LEU | C | 143 | 21.177 | 21.329 | 32.794 | 1.00 | 32.26 | G |
| ATOM | 8466 | CD1 | LEU | C | 143 | 20.352 | 21.365 | 31.516 | 1.00 | 27.85 | G |
| ATOM | 8470 | CD2 | LEU | C | 143 | 20.919 | 22.608 | 33.602 | 1.00 | 29.15 | G |
| ATOM | 8474 | C | LEU | C | 143 | 22.454 | 18.493 | 32.564 | 1.00 | 31.74 | G |
| ATOM | 8475 | O | LEU | C | 143 | 23.424 | 18.560 | 33.309 | 1.00 | 32.18 | G |
| ATOM | 8477 | N | VAL | C | 144 | 22.560 | 18.156 | 31.292 | 1.00 | 32.17 | G |
| ATOM | 8478 | CA | VAL | C | 144 | 23.849 | 18.023 | 30.604 | 1.00 | 31.46 | G |
| ATOM | 8480 | CB | VAL | C | 144 | 23.846 | 16.763 | 29.767 | 1.00 | 31.63 | G |
| ATOM | 8482 | CG1 | VAL | C | 144 | 25.209 | 16.526 | 29.182 | 1.00 | 32.33 | G |
| ATOM | 8486 | CG2 | VAL | C | 144 | 23.415 | 15.557 | 30.632 | 1.00 | 26.59 | G |
| ATOM | 8490 | C | VAL | C | 144 | 24.025 | 19.272 | 29.753 | 1.00 | 31.43 | G |
| ATOM | 8491 | O | VAL | C | 144 | 23.366 | 19.415 | 28.738 | 1.00 | 32.24 | G |
| ATOM | 8493 | N | LYS | C | 145 | 24.899 | 20.181 | 30.186 | 1.00 | 31.78 | G |
| ATOM | 8494 | CA | LYS | C | 145 | 24.949 | 21.563 | 29.650 | 1.00 | 33.09 | G |
| ATOM | 8496 | CB | LYS | C | 145 | 24.882 | 22.561 | 30.815 | 1.00 | 33.79 | G |
| ATOM | 8499 | CG | LYS | C | 145 | 24.345 | 24.028 | 30.487 | 1.00 | 37.70 | G |
| ATOM | 8502 | CD | LYS | C | 145 | 24.900 | 25.054 | 31.550 | 1.00 | 41.11 | G |

FIG 8 – CONT.

| ATOM | 8505 | CE | LYS | C | 145 | 24.713 | 26.540 | 31.171 | 1.00 | 44.39 | G |
| --- | --- | --- | --- | --- | --- | --- | --- | --- | --- | --- | --- |
| ATOM | 8508 | NZ | LYS | C | 145 | 25.695 | 27.098 | 30.124 | 1.00 | 46.51 | G |
| ATOM | 8512 | C | LYS | C | 145 | 26.194 | 21.870 | 28.787 | 1.00 | 32.27 | G |
| ATOM | 8513 | O | LYS | C | 145 | 27.325 | 21.557 | 29.144 | 1.00 | 32.13 | G |
| ATOM | 8515 | N | ASP | C | 146 | 25.948 | 22.495 | 27.646 | 1.00 | 32.72 | G |
| ATOM | 8516 | CA | ASP | C | 146 | 26.986 | 23.126 | 26.829 | 1.00 | 32.44 | G |
| ATOM | 8518 | CB | ASP | C | 146 | 27.570 | 24.334 | 27.566 | 1.00 | 33.15 | G |
| ATOM | 8521 | CG | ASP | C | 146 | 26.636 | 25.493 | 27.576 | 1.00 | 33.01 | G |
| ATOM | 8522 | OD1 | ASP | C | 146 | 25.626 | 25.465 | 26.859 | 1.00 | 38.84 | G |
| ATOM | 8523 | OD2 | ASP | C | 146 | 26.895 | 26.447 | 28.313 | 1.00 | 38.44 | G |
| ATOM | 8524 | C | ASP | C | 146 | 28.097 | 22.201 | 26.394 | 1.00 | 31.92 | G |
| ATOM | 8525 | O | ASP | C | 146 | 29.253 | 22.367 | 26.745 | 1.00 | 33.07 | G |
| ATOM | 8527 | N | TYR | C | 147 | 27.735 | 21.214 | 25.622 | 1.00 | 31.01 | G |
| ATOM | 8528 | CA | TYR | C | 147 | 28.703 | 20.317 | 25.033 | 1.00 | 30.71 | G |
| ATOM | 8530 | CB | TYR | C | 147 | 28.424 | 18.886 | 25.462 | 1.00 | 29.76 | G |
| ATOM | 8533 | CG | TYR | C | 147 | 27.102 | 18.367 | 24.959 | 1.00 | 30.83 | G |
| ATOM | 8534 | CD1 | TYR | C | 147 | 25.925 | 18.531 | 25.695 | 1.00 | 31.36 | G |
| ATOM | 8536 | CE1 | TYR | C | 147 | 24.712 | 18.042 | 25.212 | 1.00 | 30.62 | G |
| ATOM | 8538 | CZ | TYR | C | 147 | 24.668 | 17.376 | 24.004 | 1.00 | 29.92 | G |
| ATOM | 8539 | OH | TYR | C | 147 | 23.488 | 16.884 | 23.517 | 1.00 | 28.04 | G |
| ATOM | 8541 | CE2 | TYR | C | 147 | 25.808 | 17.213 | 23.262 | 1.00 | 29.94 | G |
| ATOM | 8543 | CD2 | TYR | C | 147 | 27.014 | 17.698 | 23.741 | 1.00 | 31.78 | G |
| ATOM | 8545 | C | TYR | C | 147 | 28.614 | 20.432 | 23.492 | 1.00 | 30.44 | G |
| ATOM | 8546 | O | TYR | C | 147 | 27.641 | 20.964 | 22.927 | 1.00 | 29.58 | G |
| ATOM | 8548 | N | PHE | C | 148 | 29.643 | 19.926 | 22.835 | 1.00 | 30.51 | G |
| ATOM | 8549 | CA | PHE | C | 148 | 29.702 | 19.929 | 21.381 | 1.00 | 30.20 | G |
| ATOM | 8551 | CB | PHE | C | 148 | 30.093 | 21.302 | 20.785 | 1.00 | 29.90 | G |
| ATOM | 8554 | CG | PHE | C | 148 | 30.200 | 21.276 | 19.283 | 1.00 | 30.30 | G |
| ATOM | 8555 | CD1 | PHE | C | 148 | 29.106 | 21.573 | 18.491 | 1.00 | 29.11 | G |
| ATOM | 8557 | CE1 | PHE | C | 148 | 29.191 | 21.477 | 17.101 | 1.00 | 31.35 | G |

FIG 8 – CONT.

| ATOM | 8559 | CZ | PHE | C | 148 | 30.377 | 21.076 | 16.478 | 1.00 | 27.25 | G |
| --- | --- | --- | --- | --- | --- | --- | --- | --- | --- | --- | --- |
| C | | | | | | | | | | | |
| ATOM | 8561 | CE2 | PHE | C | 148 | 31.452 | 20.769 | 17.235 | 1.00 | 30.79 | G |
| C | | | | | | | | | | | |
| ATOM | 8563 | CD2 | PHE | C | 148 | 31.365 | 20.854 | 18.661 | 1.00 | 30.21 | G |
| C | | | | | | | | | | | |
| ATOM | 8565 | C | PHE | C | 148 | 30.711 | 18.881 | 21.005 | 1.00 | 30.13 | G |
| C | | | | | | | | | | | |
| ATOM | 8566 | O | PHE | C | 148 | 31.771 | 18.806 | 21.589 | 1.00 | 30.96 | G |
| O | | | | | | | | | | | |
| ATOM | 8568 | N | PRO | C | 149 | 30.392 | 18.040 | 20.031 | 1.00 | 30.49 | G |
| N | | | | | | | | | | | |
| ATOM | 8569 | CA | PRO | C | 149 | 29.179 | 17.922 | 19.265 | 1.00 | 30.58 | G |
| C | | | | | | | | | | | |
| ATOM | 8571 | CB | PRO | C | 149 | 29.698 | 17.465 | 17.898 | 1.00 | 31.17 | G |
| C | | | | | | | | | | | |
| ATOM | 8574 | CG | PRO | C | 149 | 30.839 | 16.630 | 18.203 | 1.00 | 31.10 | G |
| C | | | | | | | | | | | |
| ATOM | 8577 | CD | PRO | C | 149 | 31.444 | 17.157 | 19.504 | 1.00 | 31.29 | G |
| C | | | | | | | | | | | |
| ATOM | 8580 | C | PRO | C | 149 | 28.274 | 16.854 | 19.868 | 1.00 | 29.81 | G |
| C | | | | | | | | | | | |
| ATOM | 8581 | O | PRO | C | 149 | 28.677 | 16.218 | 20.827 | 1.00 | 28.68 | G |
| O | | | | | | | | | | | |
| ATOM | 8582 | N | GLU | C | 150 | 27.074 | 16.676 | 19.300 | 1.00 | 28.93 | G |
| N | | | | | | | | | | | |
| ATOM | 8583 | CA | GLU | C | 150 | 26.295 | 15.434 | 19.512 | 1.00 | 29.26 | G |
| C | | | | | | | | | | | |
| ATOM | 8585 | CB | GLU | C | 150 | 25.056 | 15.388 | 18.631 | 1.00 | 28.49 | G |
| C | | | | | | | | | | | |
| ATOM | 8588 | CG | GLU | C | 150 | 24.027 | 16.380 | 19.001 | 1.00 | 29.12 | G |
| C | | | | | | | | | | | |
| ATOM | 8591 | CD | GLU | C | 150 | 23.110 | 15.866 | 20.074 | 1.00 | 27.80 | G |
| C | | | | | | | | | | | |
| ATOM | 8592 | OE1 | GLU | C | 150 | 23.599 | 15.375 | 21.117 | 1.00 | 28.93 | G |
| O | | | | | | | | | | | |
| ATOM | 8593 | OE2 | GLU | C | 150 | 21.889 | 15.951 | 19.851 | 1.00 | 30.10 | G |
| O | | | | | | | | | | | |
| ATOM | 8594 | C | GLU | C | 150 | 27.138 | 14.238 | 19.157 | 1.00 | 29.01 | G |
| C | | | | | | | | | | | |
| ATOM | 8595 | O | GLU | C | 150 | 28.039 | 14.357 | 18.375 | 1.00 | 29.31 | G |
| O | | | | | | | | | | | |
| ATOM | 8597 | N | PRO | C | 151 | 26.836 | 13.077 | 19.715 | 1.00 | 29.94 | G |
| N | | | | | | | | | | | |
| ATOM | 8598 | CA | PRO | C | 151 | 25.791 | 12.741 | 20.666 | 1.00 | 30.70 | G |
| C | | | | | | | | | | | |
| ATOM | 8600 | CB | PRO | C | 151 | 25.386 | 11.333 | 20.207 | 1.00 | 30.58 | G |
| C | | | | | | | | | | | |
| ATOM | 8603 | CG | PRO | C | 151 | 26.716 | 10.719 | 19.851 | 1.00 | 30.88 | G |
| C | | | | | | | | | | | |
| ATOM | 8606 | CD | PRO | C | 151 | 27.606 | 11.874 | 19.354 | 1.00 | 29.86 | G |
| C | | | | | | | | | | | |
| ATOM | 8609 | C | PRO | C | 151 | 26.306 | 12.634 | 22.103 | 1.00 | 31.06 | G |
| C | | | | | | | | | | | |
| ATOM | 8610 | O | PRO | C | 151 | 27.508 | 12.410 | 22.353 | 1.00 | 30.86 | G |
| O | | | | | | | | | | | |
| ATOM | 8611 | N | VAL | C | 152 | 25.376 | 12.763 | 23.036 | 1.00 | 32.42 | G |
| N | | | | | | | | | | | |
| ATOM | 8612 | CA | VAL | C | 152 | 25.565 | 12.286 | 24.390 | 1.00 | 33.57 | G |
| C | | | | | | | | | | | |
| ATOM | 8614 | CB | VAL | C | 152 | 25.325 | 13.393 | 25.389 | 1.00 | 33.61 | G |

FIG 8 – CONT.

| | | | | | | | | | | |
|---|---|---|---|---|---|---|---|---|---|---|
| ATOM | 8616 | CG1 | VAL | C | 152 | 24.768 | 12.829 | 26.712 | 1.00 33.36 | G |
| ATOM | 8620 | CG2 | VAL | C | 152 | 26.613 | 14.153 | 25.589 | 1.00 34.19 | G |
| ATOM | 8624 | C | VAL | C | 152 | 24.588 | 11.162 | 24.653 | 1.00 34.71 | G |
| ATOM | 8625 | O | VAL | C | 152 | 23.457 | 11.218 | 24.184 | 1.00 35.71 | G |
| ATOM | 8627 | N | THR | C | 153 | 25.030 | 10.148 | 25.389 | 1.00 35.58 | G |
| ATOM | 8628 | CA | THR | C | 153 | 24.127 | 9.157 | 25.952 | 1.00 36.23 | G |
| ATOM | 8630 | CB | THR | C | 153 | 24.544 | 7.709 | 25.592 | 1.00 36.72 | G |
| ATOM | 8632 | OG1 | THR | C | 153 | 25.850 | 7.425 | 26.097 | 1.00 37.45 | G |
| ATOM | 8634 | CG2 | THR | C | 153 | 24.590 | 7.545 | 24.090 | 1.00 37.52 | G |
| ATOM | 8638 | C | THR | C | 153 | 24.070 | 9.338 | 27.463 | 1.00 36.61 | G |
| ATOM | 8639 | O | THR | C | 153 | 25.050 | 9.742 | 28.095 | 1.00 35.53 | G |
| ATOM | 8641 | N | VAL | C | 154 | 22.890 | 9.075 | 28.031 | 1.00 37.46 | G |
| ATOM | 8642 | CA | VAL | C | 154 | 22.692 | 9.079 | 29.469 | 1.00 37.71 | G |
| ATOM | 8644 | CB | VAL | C | 154 | 21.761 | 10.201 | 29.920 | 1.00 38.02 | G |
| ATOM | 8646 | CG1 | VAL | C | 154 | 21.683 | 10.219 | 31.455 | 1.00 37.71 | G |
| ATOM | 8650 | CG2 | VAL | C | 154 | 22.214 | 11.549 | 29.370 | 1.00 35.07 | G |
| ATOM | 8654 | C | VAL | C | 154 | 22.053 | 7.776 | 29.908 | 1.00 39.34 | G |
| ATOM | 8655 | O | VAL | C | 154 | 21.145 | 7.266 | 29.261 | 1.00 39.59 | G |
| ATOM | 8657 | N | SER | C | 156 | 22.539 | 7.243 | 31.017 | 1.00 40.64 | G |
| ATOM | 8658 | CA | SER | C | 156 | 21.877 | 6.157 | 31.723 | 1.00 40.81 | G |
| ATOM | 8660 | CB | SER | C | 156 | 22.620 | 4.850 | 31.505 | 1.00 40.84 | G |
| ATOM | 8663 | OG | SER | C | 156 | 23.857 | 4.875 | 32.181 | 1.00 40.66 | G |
| ATOM | 8665 | C | SER | C | 156 | 21.816 | 6.503 | 33.210 | 1.00 41.37 | G |
| ATOM | 8666 | O | SER | C | 156 | 22.319 | 7.543 | 33.645 | 1.00 40.15 | G |
| ATOM | 8668 | N | TRP | C | 157 | 21.159 | 5.636 | 33.980 | 1.00 42.46 | G |
| ATOM | 8669 | CA | TRP | C | 157 | 20.983 | 5.850 | 35.424 | 1.00 42.73 | G |
| ATOM | 8671 | CB | TRP | C | 157 | 19.553 | 6.270 | 35.725 | 1.00 42.25 | G |
| ATOM | 8674 | CG | TRP | C | 157 | 19.176 | 7.638 | 35.270 | 1.00 39.71 | G |
| ATOM | 8675 | CD1 | TRP | C | 157 | 18.704 | 7.984 | 34.049 | 1.00 38.52 | G |
| ATOM | 8677 | NE1 | TRP | C | 157 | 18.419 | 9.326 | 34.009 | 1.00 36.23 | G |

FIG 8 – CONT.

| ATOM | 8679 | CE2 | TRP | C | 157 | 18.709 | 9.870 | 35.231 | 1.00 | 36.12 | G |
|---|---|---|---|---|---|---|---|---|---|---|---|
| C | | | | | | | | | | | |
| ATOM | 8680 | CD2 | TRP | C | 157 | 19.178 | 8.838 | 36.051 | 1.00 | 36.99 | G |
| C | | | | | | | | | | | |
| ATOM | 8681 | CE3 | TRP | C | 157 | 19.542 | 9.136 | 37.363 | 1.00 | 38.38 | G |
| C | | | | | | | | | | | |
| ATOM | 8683 | CZ3 | TRP | C | 157 | 19.419 | 10.429 | 37.805 | 1.00 | 37.75 | G |
| C | | | | | | | | | | | |
| ATOM | 8685 | CH2 | TRP | C | 157 | 18.949 | 11.442 | 36.956 | 1.00 | 38.54 | G |
| C | | | | | | | | | | | |
| ATOM | 8687 | CZ2 | TRP | C | 157 | 18.594 | 11.176 | 35.671 | 1.00 | 36.31 | G |
| C | | | | | | | | | | | |
| ATOM | 8689 | C | TRP | C | 157 | 21.358 | 4.597 | 36.223 | 1.00 | 44.03 | G |
| C | | | | | | | | | | | |
| ATOM | 8690 | O | TRP | C | 157 | 21.138 | 3.475 | 35.777 | 1.00 | 43.81 | G |
| O | | | | | | | | | | | |
| ATOM | 8692 | N | ASN | C | 162 | 21.970 | 4.808 | 37.387 | 1.00 | 45.91 | G |
| N | | | | | | | | | | | |
| ATOM | 8693 | CA | ASN | C | 162 | 22.531 | 3.715 | 38.193 | 1.00 | 47.32 | G |
| C | | | | | | | | | | | |
| ATOM | 8695 | CB | ASN | C | 162 | 21.463 | 3.204 | 39.169 | 1.00 | 47.15 | G |
| C | | | | | | | | | | | |
| ATOM | 8698 | CG | ASN | C | 162 | 21.038 | 4.282 | 40.174 | 1.00 | 48.12 | G |
| C | | | | | | | | | | | |
| ATOM | 8699 | OD1 | ASN | C | 162 | 21.680 | 5.338 | 40.283 | 1.00 | 46.79 | G |
| O | | | | | | | | | | | |
| ATOM | 8700 | ND2 | ASN | C | 162 | 19.966 | 4.018 | 40.916 | 1.00 | 48.98 | G |
| N | | | | | | | | | | | |
| ATOM | 8703 | C | ASN | C | 162 | 23.140 | 2.611 | 37.320 | 1.00 | 48.53 | G |
| C | | | | | | | | | | | |
| ATOM | 8704 | O | ASN | C | 162 | 22.791 | 1.443 | 37.423 | 1.00 | 49.11 | G |
| O | | | | | | | | | | | |
| ATOM | 8706 | N | SER | C | 163 | 24.054 | 3.037 | 36.448 | 1.00 | 50.24 | G |
| N | | | | | | | | | | | |
| ATOM | 8707 | CA | SER | C | 163 | 24.724 | 2.203 | 35.428 | 1.00 | 51.15 | G |
| C | | | | | | | | | | | |
| ATOM | 8709 | CB | SER | C | 163 | 25.829 | 1.361 | 36.071 | 1.00 | 51.23 | G |
| C | | | | | | | | | | | |
| ATOM | 8712 | OG | SER | C | 163 | 26.806 | 2.213 | 36.652 | 1.00 | 52.68 | G |
| O | | | | | | | | | | | |
| ATOM | 8714 | C | SER | C | 163 | 23.815 | 1.325 | 34.559 | 1.00 | 52.12 | G |
| C | | | | | | | | | | | |
| ATOM | 8715 | O | SER | C | 163 | 24.208 | 0.227 | 34.139 | 1.00 | 52.57 | G |
| O | | | | | | | | | | | |
| ATOM | 8717 | N | GLY | C | 164 | 22.620 | 1.814 | 34.254 | 1.00 | 52.73 | G |
| N | | | | | | | | | | | |
| ATOM | 8718 | CA | GLY | C | 164 | 21.689 | 1.064 | 33.417 | 1.00 | 53.40 | G |
| C | | | | | | | | | | | |
| ATOM | 8721 | C | GLY | C | 164 | 20.784 | 0.109 | 34.179 | 1.00 | 53.64 | G |
| C | | | | | | | | | | | |
| ATOM | 8722 | O | GLY | C | 164 | 19.956 | -0.558 | 33.576 | 1.00 | 53.89 | G |
| O | | | | | | | | | | | |
| ATOM | 8724 | N | ALA | C | 165 | 20.927 | 0.049 | 35.500 | 1.00 | 54.07 | G |
| N | | | | | | | | | | | |
| ATOM | 8725 | CA | ALA | C | 165 | 20.068 | -0.790 | 36.323 | 1.00 | 54.18 | G |
| C | | | | | | | | | | | |
| ATOM | 8727 | CB | ALA | C | 165 | 20.680 | -0.975 | 37.715 | 1.00 | 54.10 | G |
| C | | | | | | | | | | | |
| ATOM | 8731 | C | ALA | C | 165 | 18.657 | -0.184 | 36.424 | 1.00 | 54.39 | G |
| C | | | | | | | | | | | |
| ATOM | 8732 | O | ALA | C | 165 | 17.662 | -0.912 | 36.533 | 1.00 | 54.77 | G |

FIG 8 – CONT.

| | | | | | | | | | | |
|---|---|---|---|---|---|---|---|---|---|---|
| ATOM | 8734 | N | LEU | C | 166 | 18.577 | 1.146 | 36.383 | 1.00 54.07 | G N |
| ATOM | 8735 | CA | LEU | C | 166 | 17.308 | 1.860 | 36.471 | 1.00 53.73 | G C |
| ATOM | 8737 | CB | LEU | C | 166 | 17.427 | 3.016 | 37.475 | 1.00 53.37 | G C |
| ATOM | 8740 | CG | LEU | C | 166 | 16.248 | 3.979 | 37.616 | 1.00 53.31 | G C |
| ATOM | 8742 | CD1 | LEU | C | 166 | 14.967 | 3.221 | 37.983 | 1.00 53.53 | G C |
| ATOM | 8746 | CD2 | LEU | C | 166 | 16.537 | 5.093 | 38.641 | 1.00 52.02 | G C |
| ATOM | 8750 | C | LEU | C | 166 | 16.929 | 2.368 | 35.079 | 1.00 54.11 | G C |
| ATOM | 8751 | O | LEU | C | 166 | 17.544 | 3.314 | 34.550 | 1.00 54.32 | G O |
| ATOM | 8753 | N | THR | C | 167 | 15.938 | 1.723 | 34.474 | 1.00 54.11 | G N |
| ATOM | 8754 | CA | THR | C | 167 | 15.485 | 2.093 | 33.142 | 1.00 54.28 | G C |
| ATOM | 8756 | CB | THR | C | 167 | 15.739 | 0.946 | 32.145 | 1.00 54.62 | G C |
| ATOM | 8758 | OG1 | THR | C | 167 | 15.127 | -0.255 | 32.629 | 1.00 56.47 | G O |
| ATOM | 8760 | CG2 | THR | C | 167 | 17.238 | 0.708 | 31.981 | 1.00 54.32 | G C |
| ATOM | 8764 | C | THR | C | 167 | 14.010 | 2.511 | 33.117 | 1.00 54.10 | G C |
| ATOM | 8765 | O | THR | C | 167 | 13.591 | 3.317 | 32.278 | 1.00 54.05 | G O |
| ATOM | 8767 | N | SER | C | 168 | 13.232 | 1.977 | 34.055 | 1.00 53.81 | G N |
| ATOM | 8768 | CA | SER | C | 168 | 11.817 | 2.241 | 34.123 | 1.00 53.26 | G C |
| ATOM | 8770 | CB | SER | C | 168 | 11.161 | 1.216 | 35.070 | 1.00 53.85 | G C |
| ATOM | 8773 | OG | SER | C | 168 | 9.781 | 1.056 | 34.781 | 1.00 56.05 | G O |
| ATOM | 8775 | C | SER | C | 168 | 11.608 | 3.680 | 34.607 | 1.00 52.04 | G C |
| ATOM | 8776 | O | SER | C | 168 | 12.177 | 4.087 | 35.627 | 1.00 52.18 | G O |
| ATOM | 8778 | N | GLY | C | 169 | 10.809 | 4.444 | 33.867 | 1.00 50.44 | G N |
| ATOM | 8779 | CA | GLY | C | 169 | 10.526 | 5.857 | 34.188 | 1.00 49.64 | G C |
| ATOM | 8782 | C | GLY | C | 169 | 11.527 | 6.895 | 33.661 | 1.00 48.22 | G C |
| ATOM | 8783 | O | GLY | C | 169 | 11.381 | 8.098 | 33.911 | 1.00 47.47 | G O |
| ATOM | 8785 | N | VAL | C | 171 | 12.529 | 6.431 | 32.919 | 1.00 46.75 | G N |
| ATOM | 8786 | CA | VAL | C | 171 | 13.609 | 7.292 | 32.433 | 1.00 45.40 | G C |
| ATOM | 8788 | CB | VAL | C | 171 | 14.927 | 6.485 | 32.272 | 1.00 45.40 | G C |
| ATOM | 8790 | CG1 | VAL | C | 171 | 15.989 | 7.279 | 31.481 | 1.00 43.58 | G C |
| ATOM | 8794 | CG2 | VAL | C | 171 | 15.442 | 6.103 | 33.636 | 1.00 45.03 | G C |

FIG 8 – CONT.

| ATOM | 8798 | C | VAL | C | 171 | 13.240 | 7.890 | 31.099 | 1.00 | 44.03 | G | C |
|---|---|---|---|---|---|---|---|---|---|---|---|---|
| ATOM | 8799 | O | VAL | C | 171 | 12.911 | 7.154 | 30.176 | 1.00 | 44.42 | G | O |
| ATOM | 8801 | N | HIS | C | 172 | 13.274 | 9.220 | 31.015 | 1.00 | 42.72 | G | N |
| ATOM | 8802 | CA A | HIS | C | 172 | 13.117 | 9.942 | 29.756 | 0.50 | 42.38 | G | C |
| ATOM | 8803 | CA B | HIS | C | 172 | 13.160 | 9.906 | 29.730 | 0.50 | 41.67 | G | C |
| ATOM | 8806 | CB A | HIS | C | 172 | 11.853 | 10.831 | 29.787 | 0.50 | 42.55 | G | C |
| ATOM | 8807 | CB B | HIS | C | 172 | 11.854 | 10.698 | 29.616 | 0.50 | 41.37 | G | C |
| ATOM | 8812 | CG A | HIS | C | 172 | 10.574 | 10.095 | 30.083 | 0.50 | 44.32 | G | C |
| ATOM | 8813 | CG B | HIS | C | 172 | 11.470 | 11.019 | 28.201 | 0.50 | 39.94 | G | C |
| ATOM | 8814 | ND1A | HIS | C | 172 | 9.908 | 9.339 | 29.140 | 0.50 | 45.48 | G | N |
| ATOM | 8815 | ND1B | HIS | C | 172 | 12.327 | 10.838 | 27.136 | 0.50 | 36.38 | G | N |
| ATOM | 8818 | CE1A | HIS | C | 172 | 8.815 | 8.827 | 29.680 | 0.50 | 45.87 | G | C |
| ATOM | 8819 | CE1B | HIS | C | 172 | 11.730 | 11.214 | 26.023 | 0.50 | 36.08 | G | C |
| ATOM | 8822 | NE2A | HIS | C | 172 | 8.741 | 9.232 | 30.936 | 0.50 | 45.53 | G | N |
| ATOM | 8823 | NE2B | HIS | C | 172 | 10.521 | 11.653 | 26.327 | 0.50 | 37.45 | G | N |
| ATOM | 8826 | CD2A | HIS | C | 172 | 9.823 | 10.031 | 31.212 | 0.50 | 45.03 | G | C |
| ATOM | 8827 | CD2B | HIS | C | 172 | 10.331 | 11.536 | 27.681 | 0.50 | 38.58 | G | C |
| ATOM | 8830 | C | HIS | C | 172 | 14.366 | 10.828 | 29.509 | 1.00 | 41.58 | G | C |
| ATOM | 8831 | O | HIS | C | 172 | 14.599 | 11.801 | 30.244 | 1.00 | 40.35 | G | O |
| ATOM | 8833 | N | THR | C | 173 | 15.164 | 10.498 | 28.489 | 1.00 | 40.76 | G | N |
| ATOM | 8834 | CA | THR | C | 173 | 16.277 | 11.340 | 28.079 | 1.00 | 39.37 | G | C |
| ATOM | 8836 | CB | THR | C | 173 | 17.520 | 10.507 | 27.772 | 1.00 | 39.36 | G | C |
| ATOM | 8838 | OG1 | THR | C | 173 | 17.992 | 9.950 | 28.988 | 1.00 | 41.04 | G | O |
| ATOM | 8840 | CG2 | THR | C | 173 | 18.637 | 11.357 | 27.178 | 1.00 | 40.10 | G | C |
| ATOM | 8844 | C | THR | C | 173 | 15.805 | 12.077 | 26.856 | 1.00 | 37.98 | G | C |
| ATOM | 8845 | O | THR | C | 173 | 15.479 | 11.446 | 25.862 | 1.00 | 37.49 | G | O |
| ATOM | 8847 | N | PHE | C | 174 | 15.776 | 13.405 | 26.929 | 1.00 | 36.44 | G | N |
| ATOM | 8848 | CA | PHE | C | 174 | 15.227 | 14.231 | 25.881 | 1.00 | 36.10 | G | C |
| ATOM | 8850 | CB | PHE | C | 174 | 14.682 | 15.538 | 26.469 | 1.00 | 36.32 | G | C |
| ATOM | 8853 | CG | PHE | C | 174 | 13.439 | 15.341 | 27.295 | 1.00 | 37.48 | G | C |
| ATOM | 8854 | CD1 | PHE | C | 174 | 12.212 | 15.815 | 26.848 | 1.00 | 39.31 | G |

FIG 8 – CONT.

| ATOM | 8856 | CE1 | PHE | C | 174 | 11.070 | 15.629 | 27.582 | 1.00 | 38.18 | G |
|---|---|---|---|---|---|---|---|---|---|---|---|
| ATOM | 8858 | CZ | PHE | C | 174 | 11.126 | 14.921 | 28.754 | 1.00 | 38.86 | G |
| ATOM | 8860 | CE2 | PHE | C | 174 | 12.337 | 14.408 | 29.199 | 1.00 | 38.94 | G |
| ATOM | 8862 | CD2 | PHE | C | 174 | 13.483 | 14.619 | 28.472 | 1.00 | 36.98 | G |
| ATOM | 8864 | C | PHE | C | 174 | 16.286 | 14.550 | 24.828 | 1.00 | 36.47 | G |
| ATOM | 8865 | O | PHE | C | 174 | 17.474 | 14.517 | 25.145 | 1.00 | 36.33 | G |
| ATOM | 8867 | N | PRO | C | 175 | 15.854 | 14.844 | 23.578 | 1.00 | 36.43 | G |
| ATOM | 8868 | CA | PRO | C | 175 | 16.713 | 15.370 | 22.523 | 1.00 | 36.83 | G |
| ATOM | 8870 | CB | PRO | C | 175 | 15.770 | 15.474 | 21.300 | 1.00 | 36.81 | G |
| ATOM | 8873 | CG | PRO | C | 175 | 14.733 | 14.456 | 21.540 | 1.00 | 37.76 | G |
| ATOM | 8876 | CD | PRO | C | 175 | 14.562 | 14.379 | 23.035 | 1.00 | 37.07 | G |
| ATOM | 8879 | C | PRO | C | 175 | 17.255 | 16.755 | 22.866 | 1.00 | 36.28 | G |
| ATOM | 8880 | O | PRO | C | 175 | 16.527 | 17.598 | 23.407 | 1.00 | 36.42 | G |
| ATOM | 8881 | N | ALA | C | 176 | 18.507 | 16.999 | 22.500 | 1.00 | 35.16 | G |
| ATOM | 8882 | CA | ALA | C | 176 | 19.179 | 18.244 | 22.860 | 1.00 | 34.15 | G |
| ATOM | 8884 | CB | ALA | C | 176 | 20.647 | 18.168 | 22.441 | 1.00 | 33.66 | G |
| ATOM | 8888 | C | ALA | C | 176 | 18.531 | 19.446 | 22.213 | 1.00 | 33.77 | G |
| ATOM | 8889 | O | ALA | C | 176 | 17.873 | 19.316 | 21.218 | 1.00 | 33.59 | G |
| ATOM | 8891 | N | VAL | C | 177 | 18.701 | 20.620 | 22.806 | 1.00 | 34.25 | G |
| ATOM | 8892 | CA | VAL | C | 177 | 18.559 | 21.898 | 22.094 | 1.00 | 34.60 | G |
| ATOM | 8894 | CB | VAL | C | 177 | 18.099 | 23.071 | 23.015 | 1.00 | 34.52 | G |
| ATOM | 8896 | CG1 | VAL | C | 177 | 16.635 | 23.084 | 23.191 | 1.00 | 36.30 | G |
| ATOM | 8900 | CG2 | VAL | C | 177 | 18.775 | 23.009 | 24.359 | 1.00 | 33.62 | G |
| ATOM | 8904 | C | VAL | C | 177 | 19.926 | 22.339 | 21.580 | 1.00 | 34.90 | G |
| ATOM | 8905 | O | VAL | C | 177 | 20.953 | 22.106 | 22.215 | 1.00 | 35.27 | G |
| ATOM | 8907 | N | LEU | C | 178 | 19.936 | 23.026 | 20.458 | 1.00 | 35.82 | G |
| ATOM | 8908 | CA | LEU | C | 178 | 21.158 | 23.618 | 19.957 | 1.00 | 35.50 | G |
| ATOM | 8910 | CB | LEU | C | 178 | 21.261 | 23.385 | 18.458 | 1.00 | 35.36 | G |
| ATOM | 8913 | CG | LEU | C | 178 | 22.394 | 24.161 | 17.774 | 1.00 | 34.89 | G |
| ATOM | 8915 | CD1 | LEU | C | 178 | 23.707 | 23.841 | 18.473 | 1.00 | 30.35 | G |

FIG 8 – CONT.

| ATOM | 8919 | CD2 | LEU | C | 178 | 22.404 | 23.833 | 16.284 | 1.00 | 31.34 | G |
|---|---|---|---|---|---|---|---|---|---|---|---|
| ATOM | 8923 | C | LEU | C | 178 | 21.053 | 25.099 | 20.283 | 1.00 | 36.18 | G |
| ATOM | 8924 | O | LEU | C | 178 | 20.140 | 25.761 | 19.852 | 1.00 | 35.24 | G |
| ATOM | 8926 | N | GLN | C | 179 | 21.966 | 25.620 | 21.079 | 1.00 | 37.63 | G |
| ATOM | 8927 | CA | GLN | C | 179 | 21.839 | 27.017 | 21.481 | 1.00 | 39.16 | G |
| ATOM | 8929 | CB | GLN | C | 179 | 22.471 | 27.214 | 22.865 | 1.00 | 39.73 | G |
| ATOM | 8932 | CG | GLN | C | 179 | 21.965 | 26.193 | 23.949 | 1.00 | 42.76 | G |
| ATOM | 8935 | CD | GLN | C | 179 | 23.036 | 25.881 | 24.998 | 1.00 | 47.10 | G |
| ATOM | 8936 | OE1 | GLN | C | 179 | 23.526 | 24.746 | 25.114 | 1.00 | 46.66 | G |
| ATOM | 8937 | NE2 | GLN | C | 179 | 23.434 | 26.912 | 25.742 | 1.00 | 51.15 | G |
| ATOM | 8940 | C | GLN | C | 179 | 22.485 | 27.940 | 20.438 | 1.00 | 39.59 | G |
| ATOM | 8941 | O | GLN | C | 179 | 23.245 | 27.488 | 19.589 | 1.00 | 38.11 | G |
| ATOM | 8943 | N | SER | C | 180 | 22.190 | 29.242 | 20.543 | 1.00 | 40.27 | G |
| ATOM | 8944 | CA | SER | C | 180 | 22.787 | 30.275 | 19.693 | 1.00 | 40.54 | G |
| ATOM | 8946 | CB | SER | C | 180 | 22.200 | 31.663 | 20.033 | 1.00 | 41.25 | G |
| ATOM | 8949 | OG | SER | C | 180 | 20.899 | 31.802 | 19.476 | 1.00 | 43.24 | G |
| ATOM | 8951 | C | SER | C | 180 | 24.307 | 30.348 | 19.810 | 1.00 | 39.77 | G |
| ATOM | 8952 | O | SER | C | 180 | 24.956 | 30.945 | 18.971 | 1.00 | 39.71 | G |
| ATOM | 8954 | N | SER | C | 182 | 24.851 | 29.777 | 20.875 | 1.00 | 38.64 | G |
| ATOM | 8955 | CA | SER | C | 182 | 26.290 | 29.678 | 21.085 | 1.00 | 37.71 | G |
| ATOM | 8957 | CB | SER | C | 182 | 26.536 | 29.312 | 22.550 | 1.00 | 37.87 | G |
| ATOM | 8960 | OG | SER | C | 182 | 26.092 | 27.981 | 22.807 | 1.00 | 34.88 | G |
| ATOM | 8962 | C | SER | C | 182 | 26.968 | 28.587 | 20.246 | 1.00 | 37.42 | G |
| ATOM | 8963 | O | SER | C | 182 | 28.191 | 28.508 | 20.234 | 1.00 | 37.30 | G |
| ATOM | 8965 | N | GLY | C | 183 | 26.167 | 27.708 | 19.625 | 1.00 | 36.83 | G |
| ATOM | 8966 | CA | GLY | C | 183 | 26.665 | 26.532 | 18.912 | 1.00 | 35.69 | G |
| ATOM | 8969 | C | GLY | C | 183 | 26.782 | 25.282 | 19.763 | 1.00 | 34.66 | G |
| ATOM | 8970 | O | GLY | C | 183 | 27.122 | 24.210 | 19.271 | 1.00 | 34.92 | G |
| ATOM | 8972 | N | LEU | C | 184 | 26.494 | 25.402 | 21.045 | 1.00 | 33.49 | G |
| ATOM | 8973 | CA | LEU | C | 184 | 26.641 | 24.279 | 21.967 | 1.00 | 32.48 | G |
| ATOM | 8975 | CB | LEU | C | 184 | 27.256 | 24.747 | 23.284 | 1.00 | 32.31 | G |

FIG 8 – CONT.

```
ATOM   8978  CG   LEU C 184      28.764  24.912  23.480  1.00 34.73           C
ATOM   8980  CD1  LEU C 184      29.605  24.873  22.203  1.00 34.30           C
ATOM   8984  CD2  LEU C 184      29.031  26.157  24.322  1.00 32.85           C
ATOM   8988  C    LEU C 184      25.267  23.682  22.227  1.00 31.11           C
ATOM   8989  O    LEU C 184      24.250  24.354  22.084  1.00 30.75           O
ATOM   8991  N    TYR C 185      25.261  22.402  22.586  1.00 29.81           N
ATOM   8992  CA   TYR C 185      24.036  21.694  22.901  1.00 29.39           C
ATOM   8994  CB   TYR C 185      24.106  20.272  22.366  1.00 28.51           C
ATOM   8997  CG   TYR C 185      24.195  20.206  20.857  1.00 28.08           C
ATOM   8998  CD1  TYR C 185      23.041  20.163  20.083  1.00 25.38           C
ATOM   9000  CE1  TYR C 185      23.111  20.111  18.706  1.00 29.39           C
ATOM   9002  CZ   TYR C 185      24.369  20.087  18.080  1.00 27.73           C
ATOM   9003  OH   TYR C 185      24.438  20.011  16.715  1.00 29.22           O
ATOM   9005  CE2  TYR C 185      25.526  20.127  18.823  1.00 25.90           C
ATOM   9007  CD2  TYR C 185      25.441  20.166  20.206  1.00 26.78           C
ATOM   9009  C    TYR C 185      23.825  21.594  24.413  1.00 28.72           C
ATOM   9010  O    TYR C 185      24.772  21.474  25.162  1.00 27.66           O
ATOM   9012  N    SER C 186      22.571  21.573  24.835  1.00 29.43           N
ATOM   9013  CA   SER C 186      22.238  21.043  26.150  1.00 30.16           C
ATOM   9015  CB   SER C 186      21.852  22.191  27.067  1.00 30.44           C
ATOM   9018  OG   SER C 186      22.997  23.015  27.351  1.00 29.21           O
ATOM   9020  C    SER C 186      21.117  20.001  26.023  1.00 31.34           C
ATOM   9021  O    SER C 186      20.241  20.120  25.163  1.00 31.06           O
ATOM   9023  N    LEU C 187      21.134  18.996  26.898  1.00 31.87           N
ATOM   9024  CA   LEU C 187      19.978  18.124  27.036  1.00 31.92           C
ATOM   9026  CB   LEU C 187      20.130  16.872  26.168  1.00 31.56           C
ATOM   9029  CG   LEU C 187      21.156  15.781  26.470  1.00 31.50           C
ATOM   9031  CD1  LEU C 187      20.846  15.087  27.799  1.00 29.61           C
ATOM   9035  CD2  LEU C 187      21.174  14.744  25.287  1.00 28.55           C
ATOM   9039  C    LEU C 187      19.707  17.773  28.502  1.00 32.15           C
```

FIG 8 – CONT.

| ATOM | 9040 | O | LEU | C | 187 | 20.504 | 18.119 | 29.392 | 1.00 | 32.37 | G |
|---|---|---|---|---|---|---|---|---|---|---|---|
| ATOM | 9042 | N | SER | C | 188 | 18.566 | 17.125 | 28.741 | 1.00 | 31.55 | G |
| ATOM | 9043 | CA | SER | C | 188 | 18.178 | 16.689 | 30.078 | 1.00 | 31.66 | G |
| ATOM | 9045 | CB | SER | C | 188 | 17.055 | 17.546 | 30.582 | 1.00 | 31.36 | G |
| ATOM | 9048 | OG | SER | C | 188 | 17.513 | 18.882 | 30.776 | 1.00 | 30.72 | G |
| ATOM | 9050 | C | SER | C | 188 | 17.744 | 15.253 | 30.071 | 1.00 | 33.08 | G |
| ATOM | 9051 | O | SER | C | 188 | 17.169 | 14.790 | 29.079 | 1.00 | 33.87 | G |
| ATOM | 9053 | N | SER | C | 189 | 18.075 | 14.524 | 31.134 | 1.00 | 33.83 | G |
| ATOM | 9054 | CA | SER | C | 189 | 17.480 | 13.220 | 31.385 | 1.00 | 34.88 | G |
| ATOM | 9056 | CB | SER | C | 189 | 18.517 | 12.126 | 31.407 | 1.00 | 34.86 | G |
| ATOM | 9059 | OG | SER | C | 189 | 17.896 | 10.853 | 31.404 | 1.00 | 36.04 | G |
| ATOM | 9061 | C | SER | C | 189 | 16.737 | 13.285 | 32.720 | 1.00 | 36.00 | G |
| ATOM | 9062 | O | SER | C | 189 | 17.232 | 13.892 | 33.672 | 1.00 | 36.08 | G |
| ATOM | 9064 | N | VAL | C | 190 | 15.537 | 12.694 | 32.780 | 1.00 | 36.85 | G |
| ATOM | 9065 | CA | VAL | C | 190 | 14.751 | 12.692 | 34.020 | 1.00 | 37.49 | G |
| ATOM | 9067 | CB | VAL | C | 190 | 13.528 | 13.609 | 33.904 | 1.00 | 37.67 | G |
| ATOM | 9069 | CG1 | VAL | C | 190 | 13.971 | 15.038 | 33.718 | 1.00 | 37.79 | G |
| ATOM | 9073 | CG2 | VAL | C | 190 | 12.659 | 13.157 | 32.772 | 1.00 | 37.84 | G |
| ATOM | 9077 | C | VAL | C | 190 | 14.242 | 11.316 | 34.386 | 1.00 | 37.55 | G |
| ATOM | 9078 | O | VAL | C | 190 | 13.821 | 10.579 | 33.506 | 1.00 | 37.73 | G |
| ATOM | 9080 | N | VAL | C | 191 | 14.260 | 10.983 | 35.681 | 1.00 | 38.32 | G |
| ATOM | 9081 | CA | VAL | C | 191 | 13.597 | 9.753 | 36.176 | 1.00 | 38.67 | G |
| ATOM | 9083 | CB | VAL | C | 191 | 14.481 | 8.823 | 37.076 | 1.00 | 38.92 | G |
| ATOM | 9085 | CG1 | VAL | C | 191 | 14.329 | 7.336 | 36.658 | 1.00 | 38.51 | G |
| ATOM | 9089 | CG2 | VAL | C | 191 | 15.918 | 9.245 | 37.123 | 1.00 | 38.87 | G |
| ATOM | 9093 | C | VAL | C | 191 | 12.434 | 10.150 | 37.089 | 1.00 | 38.81 | G |
| ATOM | 9094 | O | VAL | C | 191 | 12.555 | 11.058 | 37.919 | 1.00 | 37.29 | G |
| ATOM | 9096 | N | THR | C | 192 | 11.336 | 9.420 | 36.936 | 1.00 | 39.58 | G |
| ATOM | 9097 | CA | THR | C | 192 | 10.223 | 9.408 | 37.888 | 1.00 | 40.10 | G |
| ATOM | 9099 | CB | THR | C | 192 | 8.880 | 9.386 | 37.159 | 1.00 | 40.24 | G |
| ATOM | 9101 | OG1 | THR | C | 192 | 8.837 | 8.258 | 36.273 | 1.00 | 41.43 | G |

FIG 8 – CONT.

| ATOM | 9103 | CG2 | THR | C | 192 | 8.698  | 10.657 | 36.331 | 1.00 | 39.66 | G |
|------|------|-----|-----|---|-----|--------|--------|--------|------|-------|---|
| ATOM | 9107 | C   | THR | C | 192 | 10.367 | 8.169  | 38.793 | 1.00 | 40.54 | G |
| ATOM | 9108 | O   | THR | C | 192 | 10.437 | 7.035  | 38.313 | 1.00 | 39.91 | G |
| ATOM | 9110 | N   | VAL | C | 193 | 10.437 | 8.408  | 40.104 | 1.00 | 41.17 | G |
| ATOM | 9111 | CA  | VAL | C | 193 | 10.668 | 7.354  | 41.096 | 1.00 | 42.03 | G |
| ATOM | 9113 | CB  | VAL | C | 193 | 12.112 | 7.415  | 41.638 | 1.00 | 41.92 | G |
| ATOM | 9115 | CG1 | VAL | C | 193 | 13.139 | 7.301  | 40.493 | 1.00 | 42.48 | G |
| ATOM | 9119 | CG2 | VAL | C | 193 | 12.327 | 8.720  | 42.454 | 1.00 | 41.17 | G |
| ATOM | 9123 | C   | VAL | C | 193 | 9.723  | 7.527  | 42.308 | 1.00 | 43.25 | G |
| ATOM | 9124 | O   | VAL | C | 193 | 9.219  | 8.633  | 42.540 | 1.00 | 42.96 | G |
| ATOM | 9126 | N   | PRO | C | 194 | 9.505  | 6.446  | 43.096 | 1.00 | 44.80 | G |
| ATOM | 9127 | CA  | PRO | C | 194 | 8.653  | 6.557  | 44.303 | 1.00 | 46.15 | G |
| ATOM | 9129 | CB  | PRO | C | 194 | 8.782  | 5.168  | 44.976 | 1.00 | 46.41 | G |
| ATOM | 9132 | CG  | PRO | C | 194 | 9.131  | 4.221  | 43.845 | 1.00 | 46.23 | G |
| ATOM | 9135 | CD  | PRO | C | 194 | 9.940  | 5.052  | 42.843 | 1.00 | 44.67 | G |
| ATOM | 9138 | C   | PRO | C | 194 | 9.162  | 7.637  | 45.226 | 1.00 | 47.31 | G |
| ATOM | 9139 | O   | PRO | C | 194 | 10.360 | 7.691  | 45.482 | 1.00 | 47.66 | G |
| ATOM | 9140 | N   | SER | C | 195 | 8.284  | 8.517  | 45.698 | 1.00 | 48.94 | G |
| ATOM | 9141 | CA  | SER | C | 195 | 8.739  | 9.604  | 46.574 | 1.00 | 50.41 | G |
| ATOM | 9143 | CB  | SER | C | 195 | 7.694  | 10.733 | 46.689 | 1.00 | 50.47 | G |
| ATOM | 9146 | OG  | SER | C | 195 | 6.372  | 10.233 | 46.843 | 1.00 | 51.21 | G |
| ATOM | 9148 | C   | SER | C | 195 | 9.192  | 9.085  | 47.950 | 1.00 | 51.48 | G |
| ATOM | 9149 | O   | SER | C | 195 | 9.992  | 9.744  | 48.634 | 1.00 | 51.47 | G |
| ATOM | 9151 | N   | SER | C | 196 | 8.702  | 7.895  | 48.325 | 1.00 | 52.96 | G |
| ATOM | 9152 | CA  | SER | C | 196 | 9.082  | 7.214  | 49.578 | 1.00 | 53.59 | G |
| ATOM | 9154 | CB  | SER | C | 196 | 8.286  | 5.906  | 49.737 | 1.00 | 53.56 | G |
| ATOM | 9157 | OG  | SER | C | 196 | 8.529  | 5.007  | 48.658 | 1.00 | 52.65 | G |
| ATOM | 9159 | C   | SER | C | 196 | 10.565 | 6.875  | 49.641 | 1.00 | 54.46 | G |
| ATOM | 9160 | O   | SER | C | 196 | 11.144 | 6.850  | 50.725 | 1.00 | 54.52 | G |
| ATOM | 9162 | N   | SER | C | 197 | 11.157 | 6.613  | 48.470 | 1.00 | 55.48 | G |

FIG 8 – CONT.

| ATOM | 9163 | CA | SER | C | 197 | 12.544 | 6.128 | 48.344 | 1.00 | 55.91 | G |
|------|------|-----|-----|---|-----|--------|-------|--------|------|-------|---|
| ATOM | 9165 | CB | SER | C | 197 | 12.677 | 5.358 | 47.029 | 1.00 | 56.25 | G |
| ATOM | 9168 | OG | SER | C | 197 | 12.734 | 6.266 | 45.931 | 1.00 | 56.59 | G |
| ATOM | 9170 | C | SER | C | 197 | 13.633 | 7.223 | 48.368 | 1.00 | 55.94 | G |
| ATOM | 9171 | O | SER | C | 197 | 14.835 | 6.915 | 48.351 | 1.00 | 55.76 | G |
| ATOM | 9173 | N | LEU | C | 198 | 13.225 | 8.489 | 48.390 | 1.00 | 56.08 | G |
| ATOM | 9174 | CA | LEU | C | 198 | 14.170 | 9.594 | 48.252 | 1.00 | 56.39 | G |
| ATOM | 9176 | CB | LEU | C | 198 | 13.424 | 10.927 | 48.119 | 1.00 | 56.43 | G |
| ATOM | 9179 | CG | LEU | C | 198 | 12.598 | 11.152 | 46.850 | 1.00 | 55.05 | G |
| ATOM | 9181 | CD1 | LEU | C | 198 | 11.987 | 12.531 | 46.919 | 1.00 | 53.85 | G |
| ATOM | 9185 | CD2 | LEU | C | 198 | 13.454 | 11.012 | 45.589 | 1.00 | 54.98 | G |
| ATOM | 9189 | C | LEU | C | 198 | 15.171 | 9.666 | 49.413 | 1.00 | 57.12 | G |
| ATOM | 9190 | O | LEU | C | 198 | 16.353 | 9.943 | 49.205 | 1.00 | 57.72 | G |
| ATOM | 9192 | N | GLY | C | 199 | 14.704 | 9.412 | 50.634 | 1.00 | 57.39 | G |
| ATOM | 9193 | CA | GLY | C | 199 | 15.600 | 9.318 | 51.787 | 1.00 | 57.36 | G |
| ATOM | 9196 | C | GLY | C | 199 | 16.593 | 8.155 | 51.751 | 1.00 | 57.24 | G |
| ATOM | 9197 | O | GLY | C | 199 | 17.618 | 8.205 | 52.430 | 1.00 | 57.67 | G |
| ATOM | 9199 | N | THR | C | 200 | 16.308 | 7.124 | 50.960 | 1.00 | 56.79 | G |
| ATOM | 9200 | CA | THR | C | 200 | 17.057 | 5.873 | 51.030 | 1.00 | 56.65 | G |
| ATOM | 9202 | CB | THR | C | 200 | 16.134 | 4.799 | 51.573 | 1.00 | 56.91 | G |
| ATOM | 9204 | OG1 | THR | C | 200 | 15.119 | 4.523 | 50.601 | 1.00 | 56.87 | G |
| ATOM | 9206 | CG2 | THR | C | 200 | 15.475 | 5.286 | 52.876 | 1.00 | 57.50 | G |
| ATOM | 9210 | C | THR | C | 200 | 17.699 | 5.352 | 49.711 | 1.00 | 56.05 | G |
| ATOM | 9211 | O | THR | C | 200 | 18.746 | 4.699 | 49.765 | 1.00 | 56.71 | G |
| ATOM | 9213 | N | GLN | C | 203 | 17.094 | 5.594 | 48.545 | 1.00 | 54.78 | G |
| ATOM | 9214 | CA | GLN | C | 203 | 17.702 | 5.124 | 47.265 | 1.00 | 53.79 | G |
| ATOM | 9216 | CB | GLN | C | 203 | 16.641 | 4.723 | 46.218 | 1.00 | 54.24 | G |
| ATOM | 9219 | CG | GLN | C | 203 | 16.527 | 3.195 | 45.944 | 1.00 | 56.06 | G |
| ATOM | 9222 | CD | GLN | C | 203 | 17.551 | 2.659 | 44.933 | 1.00 | 57.90 | G |
| ATOM | 9223 | OE1 | GLN | C | 203 | 17.371 | 1.574 | 44.364 | 1.00 | 59.62 | G |
| ATOM | 9224 | NE2 | GLN | C | 203 | 18.624 | 3.406 | 44.717 | 1.00 | 58.73 | G |

FIG 8 – CONT.

| ATOM | 9227 | C | GLN | C | 203 | 18.658 | 6.155 | 46.661 | 1.00 | 51.75 | G |
|---|---|---|---|---|---|---|---|---|---|---|---|
| ATOM | 9228 | O | GLN | C | 203 | 18.351 | 7.351 | 46.587 | 1.00 | 51.33 | G |
| ATOM | 9230 | N | THR | C | 205 | 19.813 | 5.669 | 46.225 | 1.00 | 49.75 | G |
| ATOM | 9231 | CA | THR | C | 205 | 20.801 | 6.498 | 45.530 | 1.00 | 48.21 | G |
| ATOM | 9233 | CB | THR | C | 205 | 22.240 | 5.971 | 45.794 | 1.00 | 48.14 | G |
| ATOM | 9235 | OG1 | THR | C | 205 | 22.752 | 6.626 | 46.965 | 1.00 | 48.66 | G |
| ATOM | 9237 | CG2 | THR | C | 205 | 23.172 | 6.226 | 44.619 | 1.00 | 47.28 | G |
| ATOM | 9241 | C | THR | C | 205 | 20.502 | 6.593 | 44.016 | 1.00 | 46.80 | G |
| ATOM | 9242 | O | THR | C | 205 | 20.339 | 5.570 | 43.319 | 1.00 | 46.54 | G |
| ATOM | 9244 | N | TYR | C | 206 | 20.437 | 7.826 | 43.519 | 1.00 | 44.54 | G |
| ATOM | 9245 | CA | TYR | C | 206 | 20.211 | 8.059 | 42.083 | 1.00 | 43.41 | G |
| ATOM | 9247 | CB | TYR | C | 206 | 18.881 | 8.822 | 41.880 | 1.00 | 43.26 | G |
| ATOM | 9250 | CG | TYR | C | 206 | 17.673 | 8.057 | 42.426 | 1.00 | 43.70 | G |
| ATOM | 9251 | CD1 | TYR | C | 206 | 17.251 | 6.877 | 41.820 | 1.00 | 43.13 | G |
| ATOM | 9253 | CE1 | TYR | C | 206 | 16.177 | 6.149 | 42.326 | 1.00 | 45.12 | G |
| ATOM | 9255 | CZ | TYR | C | 206 | 15.501 | 6.606 | 43.450 | 1.00 | 44.89 | G |
| ATOM | 9256 | OH | TYR | C | 206 | 14.438 | 5.877 | 43.914 | 1.00 | 46.70 | G |
| ATOM | 9258 | CE2 | TYR | C | 206 | 15.902 | 7.779 | 44.092 | 1.00 | 43.25 | G |
| ATOM | 9260 | CD2 | TYR | C | 206 | 16.990 | 8.495 | 43.581 | 1.00 | 43.37 | G |
| ATOM | 9262 | C | TYR | C | 206 | 21.412 | 8.751 | 41.371 | 1.00 | 41.58 | G |
| ATOM | 9263 | O | TYR | C | 206 | 21.744 | 9.905 | 41.620 | 1.00 | 41.34 | G |
| ATOM | 9265 | N | ILE | C | 207 | 22.050 | 8.025 | 40.476 | 1.00 | 40.24 | G |
| ATOM | 9266 | CA | ILE | C | 207 | 23.229 | 8.528 | 39.757 | 1.00 | 39.58 | G |
| ATOM | 9268 | CB | ILE | C | 207 | 24.472 | 7.678 | 40.114 | 1.00 | 39.36 | G |
| ATOM | 9270 | CG1 | ILE | C | 207 | 24.829 | 7.833 | 41.600 | 1.00 | 40.90 | G |
| ATOM | 9273 | CD1 | ILE | C | 207 | 26.051 | 6.996 | 42.051 | 1.00 | 40.43 | G |
| ATOM | 9277 | CG2 | ILE | C | 207 | 25.673 | 8.092 | 39.297 | 1.00 | 40.16 | G |
| ATOM | 9281 | C | ILE | C | 207 | 22.999 | 8.510 | 38.236 | 1.00 | 38.12 | G |
| ATOM | 9282 | O | ILE | C | 207 | 22.801 | 7.453 | 37.651 | 1.00 | 37.03 | G |
| ATOM | 9284 | N | CYS | C | 208 | 23.028 | 9.676 | 37.596 | 1.00 | 37.80 | G |

FIG 8 – CONT.

| ATOM | 9285 | CA | CYS | C | 208 | 23.040 | 9.709 | 36.120 | 1.00 | 37.89 | G C |
| --- | --- | --- | --- | --- | --- | --- | --- | --- | --- | --- | --- |
| ATOM | 9287 | CB | CYS | C | 208 | 22.401 | 10.993 | 35.591 | 1.00 | 38.12 | G C |
| ATOM | 9290 | SG | CYS | C | 208 | 23.404 | 12.453 | 35.809 | 1.00 | 40.14 | G S |
| ATOM | 9292 | C | CYS | C | 208 | 24.465 | 9.496 | 35.579 | 1.00 | 37.54 | G C |
| ATOM | 9293 | O | CYS | C | 208 | 25.423 | 10.095 | 36.072 | 1.00 | 37.82 | G O |
| ATOM | 9295 | N | ASN | C | 209 | 24.602 | 8.598 | 34.611 | 1.00 | 37.03 | G N |
| ATOM | 9296 | CA | ASN | C | 209 | 25.862 | 8.339 | 33.935 | 1.00 | 36.95 | G C |
| ATOM | 9298 | CB | ASN | C | 209 | 26.103 | 6.848 | 33.785 | 1.00 | 36.76 | G C |
| ATOM | 9301 | CG | ASN | C | 209 | 25.574 | 6.069 | 34.959 | 1.00 | 39.32 | G C |
| ATOM | 9302 | OD1 | ASN | C | 209 | 26.219 | 5.998 | 36.007 | 1.00 | 41.88 | G O |
| ATOM | 9303 | ND2 | ASN | C | 209 | 24.367 | 5.516 | 34.811 | 1.00 | 38.75 | G N |
| ATOM | 9306 | C | ASN | C | 209 | 25.821 | 8.960 | 32.546 | 1.00 | 36.69 | G C |
| ATOM | 9307 | O | ASN | C | 209 | 25.095 | 8.468 | 31.679 | 1.00 | 37.20 | G O |
| ATOM | 9309 | N | VAL | C | 210 | 26.597 | 10.025 | 32.347 | 1.00 | 35.74 | G N |
| ATOM | 9310 | CA | VAL | C | 210 | 26.588 | 10.809 | 31.112 | 1.00 | 35.84 | G C |
| ATOM | 9312 | CB | VAL | C | 210 | 26.567 | 12.297 | 31.411 | 1.00 | 35.42 | G C |
| ATOM | 9314 | CG1 | VAL | C | 210 | 26.430 | 13.110 | 30.123 | 1.00 | 35.78 | G C |
| ATOM | 9318 | CG2 | VAL | C | 210 | 25.433 | 12.647 | 32.367 | 1.00 | 34.36 | G C |
| ATOM | 9322 | C | VAL | C | 210 | 27.846 | 10.498 | 30.289 | 1.00 | 36.43 | G C |
| ATOM | 9323 | O | VAL | C | 210 | 28.954 | 10.562 | 30.803 | 1.00 | 37.62 | G O |
| ATOM | 9325 | N | ASN | C | 211 | 27.678 | 10.119 | 29.033 | 1.00 | 36.42 | G N |
| ATOM | 9326 | CA | ASN | C | 211 | 28.814 | 9.800 | 28.179 | 1.00 | 37.19 | G C |
| ATOM | 9328 | CB | ASN | C | 211 | 28.770 | 8.327 | 27.760 | 1.00 | 37.04 | G C |
| ATOM | 9331 | CG | ASN | C | 211 | 30.103 | 7.831 | 27.190 | 1.00 | 41.43 | G C |
| ATOM | 9332 | OD1 | ASN | C | 211 | 31.027 | 8.616 | 26.903 | 1.00 | 44.33 | G O |
| ATOM | 9333 | ND2 | ASN | C | 211 | 30.200 | 6.512 | 27.006 | 1.00 | 44.14 | G N |
| ATOM | 9336 | C | ASN | C | 211 | 28.837 | 10.706 | 26.953 | 1.00 | 36.48 | G C |
| ATOM | 9337 | O | ASN | C | 211 | 27.855 | 10.765 | 26.198 | 1.00 | 36.26 | G O |
| ATOM | 9339 | N | HIS | C | 212 | 29.957 | 11.397 | 26.771 | 1.00 | 35.92 | G N |
| ATOM | 9340 | CA | HIS | C | 212 | 30.207 | 12.240 | 25.589 | 1.00 | 36.28 | G C |
| ATOM | 9342 | CB | HIS | C | 212 | 30.354 | 13.694 | 26.026 | 1.00 | 35.39 | |

FIG 8 – CONT.

| | | | | | | | | | | |
|---|---|---|---|---|---|---|---|---|---|---|
| ATOM | 9345 | CG | HIS | C | 212 | 30.446 | 14.664 | 24.897 | 1.00 35.58 | G |
| ATOM | 9346 | ND1 | HIS | C | 212 | 31.418 | 15.632 | 24.829 | 1.00 35.76 | G |
| ATOM | 9348 | CE1 | HIS | C | 212 | 31.231 | 16.366 | 23.750 | 1.00 35.79 | G |
| ATOM | 9350 | NE2 | HIS | C | 212 | 30.182 | 15.898 | 23.105 | 1.00 33.86 | G |
| ATOM | 9352 | CD2 | HIS | C | 212 | 29.686 | 14.821 | 23.789 | 1.00 36.13 | G |
| ATOM | 9354 | C | HIS | C | 212 | 31.486 | 11.769 | 24.863 | 1.00 37.11 | G |
| ATOM | 9355 | O | HIS | C | 212 | 32.572 | 12.365 | 25.006 | 1.00 36.48 | G |
| ATOM | 9357 | N | LYS | C | 213 | 31.351 | 10.688 | 24.091 | 1.00 38.33 | G |
| ATOM | 9358 | CA | LYS | C | 213 | 32.495 | 10.084 | 23.410 | 1.00 39.27 | G |
| ATOM | 9360 | CB | LYS | C | 213 | 32.064 | 8.947 | 22.478 | 1.00 39.94 | G |
| ATOM | 9363 | CG | LYS | C | 213 | 31.614 | 7.678 | 23.209 | 1.00 43.36 | G |
| ATOM | 9366 | CD | LYS | C | 213 | 31.034 | 6.665 | 22.217 | 1.00 47.65 | G |
| ATOM | 9369 | CE | LYS | C | 213 | 30.600 | 5.340 | 22.880 | 1.00 50.36 | G |
| ATOM | 9372 | NZ | LYS | C | 213 | 31.746 | 4.361 | 23.060 | 1.00 53.67 | G |
| ATOM | 9376 | C | LYS | C | 213 | 33.375 | 11.122 | 22.675 | 1.00 38.37 | G |
| ATOM | 9377 | O | LYS | C | 213 | 34.575 | 11.131 | 22.865 | 1.00 38.36 | G |
| ATOM | 9379 | N | PRO | C | 214 | 32.776 | 12.026 | 21.899 | 1.00 38.02 | G |
| ATOM | 9380 | CA | PRO | C | 214 | 33.597 | 12.962 | 21.116 | 1.00 38.24 | G |
| ATOM | 9382 | CB | PRO | C | 214 | 32.556 | 13.875 | 20.479 | 1.00 37.98 | G |
| ATOM | 9385 | CG | PRO | C | 214 | 31.341 | 12.995 | 20.375 | 1.00 37.97 | G |
| ATOM | 9388 | CD | PRO | C | 214 | 31.340 | 12.226 | 21.638 | 1.00 37.72 | G |
| ATOM | 9391 | C | PRO | C | 214 | 34.604 | 13.797 | 21.902 | 1.00 38.52 | G |
| ATOM | 9392 | O | PRO | C | 214 | 35.596 | 14.229 | 21.321 | 1.00 39.02 | G |
| ATOM | 9393 | N | SER | C | 215 | 34.353 | 14.051 | 23.188 | 1.00 38.28 | G |
| ATOM | 9394 | CA | SER | C | 215 | 35.320 | 14.769 | 24.023 | 1.00 38.23 | G |
| ATOM | 9396 | CB | SER | C | 215 | 34.666 | 15.935 | 24.758 | 1.00 38.47 | G |
| ATOM | 9399 | OG | SER | C | 215 | 33.981 | 15.495 | 25.933 | 1.00 39.53 | G |
| ATOM | 9401 | C | SER | C | 215 | 35.939 | 13.836 | 25.034 | 1.00 37.80 | G |
| ATOM | 9402 | O | SER | C | 215 | 36.554 | 14.277 | 25.999 | 1.00 37.73 | G |
| ATOM | 9404 | N | ASN | C | 216 | 35.792 | 12.543 | 24.814 | 1.00 37.67 | G |

FIG 8 – CONT.

| ATOM | 9405 | CA | ASN | C | 216 | 36.305 | 11.567 | 25.749 | 1.00 | 38.41 | G |
|---|---|---|---|---|---|---|---|---|---|---|---|
| C | | | | | | | | | | | |
| ATOM | 9407 | CB | ASN | C | 216 | 37.824 | 11.510 | 25.601 | 1.00 | 39.27 | G |
| C | | | | | | | | | | | |
| ATOM | 9410 | CG | ASN | C | 216 | 38.258 | 10.997 | 24.247 | 1.00 | 39.99 | G |
| C | | | | | | | | | | | |
| ATOM | 9411 | OD1 | ASN | C | 216 | 37.789 | 9.956 | 23.793 | 1.00 | 39.18 | G |
| O | | | | | | | | | | | |
| ATOM | 9412 | ND2 | ASN | C | 216 | 39.178 | 11.725 | 23.600 | 1.00 | 41.98 | G |
| N | | | | | | | | | | | |
| ATOM | 9415 | C | ASN | C | 216 | 35.958 | 11.832 | 27.225 | 1.00 | 38.54 | G |
| C | | | | | | | | | | | |
| ATOM | 9416 | O | ASN | C | 216 | 36.807 | 11.617 | 28.095 | 1.00 | 39.25 | G |
| O | | | | | | | | | | | |
| ATOM | 9418 | N | THR | C | 217 | 34.734 | 12.296 | 27.506 | 1.00 | 37.80 | G |
| N | | | | | | | | | | | |
| ATOM | 9419 | CA | THR | C | 217 | 34.303 | 12.637 | 28.867 | 1.00 | 37.73 | G |
| C | | | | | | | | | | | |
| ATOM | 9421 | CB | THR | C | 217 | 33.931 | 14.131 | 28.962 | 1.00 | 37.92 | G |
| C | | | | | | | | | | | |
| ATOM | 9423 | OG1 | THR | C | 217 | 34.942 | 14.906 | 28.309 | 1.00 | 36.44 | G |
| O | | | | | | | | | | | |
| ATOM | 9425 | CG2 | THR | C | 217 | 33.807 | 14.587 | 30.426 | 1.00 | 36.80 | G |
| C | | | | | | | | | | | |
| ATOM | 9429 | C | THR | C | 217 | 33.105 | 11.788 | 29.288 | 1.00 | 37.63 | G |
| C | | | | | | | | | | | |
| ATOM | 9430 | O | THR | C | 217 | 32.095 | 11.797 | 28.600 | 1.00 | 37.98 | G |
| O | | | | | | | | | | | |
| ATOM | 9432 | N | LYS | C | 218 | 33.248 | 11.015 | 30.374 | 1.00 | 37.58 | G |
| N | | | | | | | | | | | |
| ATOM | 9433 | CA | LYS | C | 218 | 32.109 | 10.362 | 31.075 | 1.00 | 37.05 | G |
| C | | | | | | | | | | | |
| ATOM | 9435 | CB | LYS | C | 218 | 32.263 | 8.845 | 31.195 | 1.00 | 36.10 | G |
| C | | | | | | | | | | | |
| ATOM | 9442 | C | LYS | C | 218 | 31.972 | 10.969 | 32.464 | 1.00 | 37.29 | G |
| C | | | | | | | | | | | |
| ATOM | 9443 | O | LYS | C | 218 | 32.964 | 11.075 | 33.211 | 1.00 | 37.13 | G |
| O | | | | | | | | | | | |
| ATOM | 9445 | N | VAL | C | 219 | 30.749 | 11.361 | 32.817 | 1.00 | 37.57 | G |
| N | | | | | | | | | | | |
| ATOM | 9446 | CA | VAL | C | 219 | 30.482 | 11.978 | 34.115 | 1.00 | 38.05 | G |
| C | | | | | | | | | | | |
| ATOM | 9448 | CB | VAL | C | 219 | 30.156 | 13.471 | 33.973 | 1.00 | 37.84 | G |
| C | | | | | | | | | | | |
| ATOM | 9450 | CG1 | VAL | C | 219 | 29.973 | 14.099 | 35.326 | 1.00 | 37.56 | G |
| C | | | | | | | | | | | |
| ATOM | 9454 | CG2 | VAL | C | 219 | 31.255 | 14.209 | 33.155 | 1.00 | 37.80 | G |
| C | | | | | | | | | | | |
| ATOM | 9458 | C | VAL | C | 219 | 29.323 | 11.262 | 34.851 | 1.00 | 39.14 | G |
| C | | | | | | | | | | | |
| ATOM | 9459 | O | VAL | C | 219 | 28.248 | 11.026 | 34.285 | 1.00 | 39.52 | G |
| O | | | | | | | | | | | |
| ATOM | 9461 | N | ASP | C | 220 | 29.575 | 10.908 | 36.105 | 1.00 | 39.60 | G |
| N | | | | | | | | | | | |
| ATOM | 9462 | CA | ASP | C | 220 | 28.574 | 10.386 | 37.005 | 1.00 | 40.14 | G |
| C | | | | | | | | | | | |
| ATOM | 9464 | CB | ASP | C | 220 | 29.119 | 9.153 | 37.740 | 1.00 | 40.81 | G |
| C | | | | | | | | | | | |
| ATOM | 9467 | CG | ASP | C | 220 | 29.350 | 7.988 | 36.810 | 1.00 | 42.53 | G |
| C | | | | | | | | | | | |
| ATOM | 9468 | OD1 | ASP | C | 220 | 29.050 | 8.119 | 35.610 | 1.00 | 46.72 | G |

FIG 8 – CONT.

```
ATOM   9469  OD2 ASP C 220      29.824    6.936   37.258  1.00 45.89           G
ATOM   9470  C   ASP C 220      28.220   11.490   37.980  1.00 39.88           G
ATOM   9471  O   ASP C 220      29.105   12.156   38.527  1.00 39.81           G
ATOM   9473  N   LYS C 221      26.919   11.699   38.166  1.00 40.18           G
ATOM   9474  CA  LYS C 221      26.401   12.734   39.029  1.00 40.27           G
ATOM   9476  CB  LYS C 221      25.921   13.925   38.226  1.00 40.01           G
ATOM   9479  CG  LYS C 221      25.669   15.152   39.072  1.00 40.48           G
ATOM   9482  CD  LYS C 221      27.003   15.645   39.656  1.00 41.86           G
ATOM   9485  CE  LYS C 221      26.961   17.061   40.098  1.00 42.21           G
ATOM   9488  NZ  LYS C 221      28.255   17.707   39.855  1.00 44.38           G
ATOM   9492  C   LYS C 221      25.247   12.185   39.874  1.00 41.70           G
ATOM   9493  O   LYS C 221      24.148   11.903   39.369  1.00 41.85           G
ATOM   9495  N   LYS C 222      25.509   12.030   41.169  1.00 42.78           G
ATOM   9496  CA  LYS C 222      24.488   11.595   42.108  1.00 43.28           G
ATOM   9498  CB  LYS C 222      25.140   11.116   43.423  1.00 44.13           G
ATOM   9501  CG  LYS C 222      24.209   10.648   44.556  1.00 46.48           G
ATOM   9504  CD  LYS C 222      25.000   10.572   45.905  1.00 48.69           G
ATOM   9507  CE  LYS C 222      24.312    9.680   46.951  1.00 50.48           G
ATOM   9510  NZ  LYS C 222      23.172   10.320   47.687  1.00 50.58           G
ATOM   9514  C   LYS C 222      23.592   12.799   42.310  1.00 42.19           G
ATOM   9515  O   LYS C 222      24.067   13.927   42.426  1.00 41.19           G
ATOM   9517  N   VAL C 225      22.295   12.539   42.326  1.00 41.85           G
ATOM   9518  CA  VAL C 225      21.280   13.582   42.430  1.00 42.27           G
ATOM   9520  CB  VAL C 225      20.338   13.524   41.222  1.00 41.93           G
ATOM   9522  CG1 VAL C 225      19.222   14.558   41.353  1.00 41.42           G
ATOM   9526  CG2 VAL C 225      21.132   13.719   39.922  1.00 42.66           G
ATOM   9530  C   VAL C 225      20.460   13.369   43.712  1.00 43.37           G
ATOM   9531  O   VAL C 225      19.848   12.307   43.915  1.00 42.62           G
ATOM   9533  N   GLU C 226      20.443   14.370   44.571  1.00 44.25           G
ATOM   9534  CA  GLU C 226      19.795   14.207   45.848  1.00 45.58           G
```

FIG 8 – CONT.

| | | | | | | | | | | |
|---|---|---|---|---|---|---|---|---|---|---|
| ATOM | 9536 | CB | GLU | C | 226 | 20.807 | 13.869 | 46.972 | 1.00 46.05 | G C |
| ATOM | 9539 | CG | GLU | C | 226 | 22.197 | 14.446 | 46.807 | 1.00 47.53 | G C |
| ATOM | 9542 | CD | GLU | C | 226 | 23.196 | 14.070 | 47.915 | 1.00 48.27 | G C |
| ATOM | 9543 | OE1 | GLU | C | 226 | 23.356 | 12.863 | 48.226 | 1.00 49.13 | G O |
| ATOM | 9544 | OE2 | GLU | C | 226 | 23.858 | 15.002 | 48.441 | 1.00 48.05 | G O |
| ATOM | 9545 | C | GLU | C | 226 | 18.912 | 15.421 | 46.149 | 1.00 46.16 | G C |
| ATOM | 9546 | O | GLU | C | 226 | 19.087 | 16.478 | 45.551 | 1.00 45.77 | G O |
| ATOM | 9548 | N | PRO | C | 227 | 17.907 | 15.235 | 47.034 | 1.00 46.82 | G N |
| ATOM | 9549 | CA | PRO | C | 227 | 16.871 | 16.217 | 47.335 | 1.00 47.19 | G C |
| ATOM | 9551 | CB | PRO | C | 227 | 16.204 | 15.630 | 48.574 | 1.00 47.75 | G C |
| ATOM | 9554 | CG | PRO | C | 227 | 16.393 | 14.116 | 48.433 | 1.00 47.28 | G C |
| ATOM | 9557 | CD | PRO | C | 227 | 17.563 | 13.886 | 47.546 | 1.00 46.87 | G C |
| ATOM | 9560 | C | PRO | C | 227 | 17.339 | 17.662 | 47.574 | 1.00 47.42 | G C |
| ATOM | 9561 | O | PRO | C | 227 | 18.002 | 17.951 | 48.559 | 1.00 48.31 | G O |
| TER | | | | | | | | | | |
| ATOM | 9562 | N | SER | D | 2 | 12.430 | 23.465 | -5.562 | 1.00 56.31 | D N |
| ATOM | 9563 | CA | SER | D | 2 | 12.061 | 22.023 | -5.755 | 1.00 56.53 | D C |
| ATOM | 9565 | CB | SER | D | 2 | 11.112 | 21.546 | -4.655 | 1.00 56.98 | D C |
| ATOM | 9568 | OG | SER | D | 2 | 10.355 | 20.419 | -5.089 | 1.00 57.69 | D O |
| ATOM | 9570 | C | SER | D | 2 | 11.408 | 21.822 | -7.123 | 1.00 56.09 | D C |
| ATOM | 9571 | O | SER | D | 2 | 10.284 | 22.280 | -7.357 | 1.00 55.90 | D O |
| ATOM | 9575 | N | VAL | D | 3 | 12.106 | 21.105 | -8.005 | 1.00 55.32 | D N |
| ATOM | 9576 | CA | VAL | D | 3 | 11.759 | 21.063 | -9.424 | 1.00 54.58 | D C |
| ATOM | 9578 | CB | VAL | D | 3 | 12.940 | 20.472 | -10.252 | 1.00 54.69 | D C |
| ATOM | 9580 | CG1 | VAL | D | 3 | 12.527 | 20.243 | -11.705 | 1.00 54.06 | D C |
| ATOM | 9584 | CG2 | VAL | D | 3 | 14.170 | 21.410 | -10.163 | 1.00 53.86 | D C |
| ATOM | 9588 | C | VAL | D | 3 | 10.404 | 20.364 | -9.710 | 1.00 53.86 | D C |
| ATOM | 9589 | O | VAL | D | 3 | 9.676 | 20.774 | -10.617 | 1.00 53.54 | D O |
| ATOM | 9591 | N | LEU | D | 4 | 10.067 | 19.334 | -8.932 | 1.00 52.87 | D N |
| ATOM | 9592 | CA | LEU | D | 4 | 8.737 | 18.682 | -8.998 | 1.00 52.18 | D C |
| ATOM | 9594 | CB | LEU | D | 4 | 8.866 | 17.158 | -8.902 | 1.00 51.65 | D C |

FIG 8 – CONT.

| ATOM | 9597 | CG  | LEU | D | 4 | 9.161  | 16.342 | -10.164 | 1.00 | 51.65 | D |
|------|------|-----|-----|---|---|--------|--------|---------|------|-------|---|
| ATOM | 9599 | CD1 | LEU | D | 4 | 9.574  | 14.941 | -9.795  | 1.00 | 49.63 | D |
| ATOM | 9603 | CD2 | LEU | D | 4 | 10.213 | 16.985 | -11.034 | 1.00 | 51.19 | D |
| ATOM | 9607 | C   | LEU | D | 4 | 7.884  | 19.206 | -7.838  | 1.00 | 51.77 | D |
| ATOM | 9608 | O   | LEU | D | 4 | 8.432  | 19.519 | -6.785  | 1.00 | 51.94 | D |
| ATOM | 9610 | N   | THR | D | 5 | 6.561  | 19.294 | -8.017  | 1.00 | 51.25 | D |
| ATOM | 9611 | CA  | THR | D | 5 | 5.680  | 19.872 | -6.981  | 1.00 | 50.49 | D |
| ATOM | 9613 | CB  | THR | D | 5 | 4.849  | 21.051 | -7.521  | 1.00 | 50.60 | D |
| ATOM | 9615 | OG1 | THR | D | 5 | 5.727  | 22.116 | -7.910  | 1.00 | 50.20 | D |
| ATOM | 9617 | CG2 | THR | D | 5 | 3.901  | 21.569 | -6.461  | 1.00 | 50.55 | D |
| ATOM | 9621 | C   | THR | D | 5 | 4.748  | 18.837 | -6.405  | 1.00 | 49.99 | D |
| ATOM | 9622 | O   | THR | D | 5 | 3.944  | 18.263 | -7.125  | 1.00 | 50.19 | D |
| ATOM | 9624 | N   | GLN | D | 6 | 4.887  | 18.589 | -5.106  | 1.00 | 49.34 | D |
| ATOM | 9625 | CA  | GLN | D | 6 | 3.999  | 17.724 | -4.355  | 1.00 | 49.05 | D |
| ATOM | 9627 | CB  | GLN | D | 6 | 4.776  | 16.617 | -3.653  | 1.00 | 49.11 | D |
| ATOM | 9630 | CG  | GLN | D | 6 | 5.631  | 15.730 | -4.547  | 1.00 | 47.70 | D |
| ATOM | 9633 | CD  | GLN | D | 6 | 6.434  | 14.725 | -3.733  | 1.00 | 44.66 | D |
| ATOM | 9634 | OE1 | GLN | D | 6 | 5.884  | 13.994 | -2.906  | 1.00 | 41.87 | D |
| ATOM | 9635 | NE2 | GLN | D | 6 | 7.744  | 14.699 | -3.961  | 1.00 | 39.42 | D |
| ATOM | 9638 | C   | GLN | D | 6 | 3.304  | 18.543 | -3.271  | 1.00 | 49.62 | D |
| ATOM | 9639 | O   | GLN | D | 6 | 3.728  | 19.673 | -2.958  | 1.00 | 49.48 | D |
| ATOM | 9641 | N   | PRO | D | 7 | 2.231  | 17.985 | -2.695  | 1.00 | 49.98 | D |
| ATOM | 9642 | CA  | PRO | D | 7 | 1.593  | 18.592 | -1.526  | 1.00 | 50.51 | D |
| ATOM | 9644 | CB  | PRO | D | 7 | 0.199  | 17.940 | -1.498  | 1.00 | 50.26 | D |
| ATOM | 9647 | CG  | PRO | D | 7 | 0.357  | 16.664 | -2.234  | 1.00 | 50.46 | D |
| ATOM | 9650 | CD  | PRO | D | 7 | 1.377  | 16.950 | -3.305  | 1.00 | 50.23 | D |
| ATOM | 9653 | C   | PRO | D | 7 | 2.360  | 18.291 | -0.231  | 1.00 | 51.10 | D |
| ATOM | 9654 | O   | PRO | D | 7 | 2.773  | 17.142 | -0.019  | 1.00 | 50.66 | D |
| ATOM | 9655 | N   | PRO | D | 8 | 2.536  | 19.314 | 0.638   | 1.00 | 51.71 | D |
| ATOM | 9656 | CA  | PRO | D | 8 | 3.321  | 19.153 | 1.870   | 1.00 | 52.10 | D |
| ATOM | 9658 | CB  | PRO | D | 8 | 3.094  | 20.478 | 2.609   | 1.00 | 52.02 | D |

FIG 8 – CONT.

```
C
ATOM   9661  CG   PRO D   8       2.869   21.467   1.521  1.00 51.89        D
C
ATOM   9664  CD   PRO D   8       2.149   20.724   0.422  1.00 51.83        D
C
ATOM   9667  C    PRO D   8       2.886   17.983   2.737  1.00 52.45        D
C
ATOM   9668  O    PRO D   8       3.717   17.364   3.393  1.00 52.79        D
O
ATOM   9669  N    SER D   9       1.599   17.686   2.747  1.00 53.05        D
N
ATOM   9670  CA   SER D   9       1.102   16.625   3.592  1.00 54.08        D
C
ATOM   9672  CB   SER D   9       0.987   17.088   5.071  1.00 54.96        D
C
ATOM   9675  OG   SER D   9       0.613   18.461   5.165  1.00 55.03        D
O
ATOM   9677  C    SER D   9      -0.231   16.085   3.111  1.00 54.47        D
C
ATOM   9678  O    SER D   9      -0.887   16.652   2.230  1.00 54.26        D
O
ATOM   9680  N    VAL D  11      -0.596   14.970   3.727  1.00 54.87        D
N
ATOM   9681  CA   VAL D  11      -1.723   14.182   3.338  1.00 55.34        D
C
ATOM   9683  CB   VAL D  11      -1.414   13.398   2.036  1.00 55.68        D
C
ATOM   9685  CG1  VAL D  11      -2.003   12.012   2.073  1.00 54.96        D
C
ATOM   9689  CG2  VAL D  11      -1.884   14.196   0.803  1.00 55.54        D
C
ATOM   9693  C    VAL D  11      -2.008   13.261   4.517  1.00 55.94        D
C
ATOM   9694  O    VAL D  11      -1.106   12.889   5.275  1.00 55.38        D
O
ATOM   9696  N    SER D  12      -3.282   12.920   4.672  1.00 56.71        D
N
ATOM   9697  CA   SER D  12      -3.782   12.323   5.901  1.00 56.84        D
C
ATOM   9699  CB   SER D  12      -4.050   13.433   6.917  1.00 56.91        D
C
ATOM   9702  OG   SER D  12      -4.072   14.701   6.269  1.00 56.01        D
O
ATOM   9704  C    SER D  12      -5.045   11.540   5.617  1.00 56.95        D
C
ATOM   9705  O    SER D  12      -5.842   11.935   4.770  1.00 57.42        D
O
ATOM   9707  N    ALA D  13      -5.211   10.421   6.314  1.00 57.04        D
N
ATOM   9708  CA   ALA D  13      -6.389    9.572   6.157  1.00 56.97        D
C
ATOM   9710  CB   ALA D  13      -6.454    8.988   4.744  1.00 56.94        D
C
ATOM   9714  C    ALA D  13      -6.391    8.454   7.209  1.00 57.01        D
C
ATOM   9715  O    ALA D  13      -5.338    8.091   7.751  1.00 56.86        D
O
ATOM   9717  N    ALA D  14      -7.582    7.920   7.493  1.00 56.74        D
N
ATOM   9718  CA   ALA D  14      -7.774    6.976   8.591  1.00 56.47        D
C
```

FIG 8 – CONT.

| ATOM | 9720 | CB | ALA | D | 14 | -9.255 | 6.859 | 8.934 | 1.00 | 56.34 | D |
|---|---|---|---|---|---|---|---|---|---|---|---|
| C | | | | | | | | | | | |
| ATOM | 9724 | C | ALA | D | 14 | -7.239 | 5.644 | 8.149 | 1.00 | 56.01 | D |
| C | | | | | | | | | | | |
| ATOM | 9725 | O | ALA | D | 14 | -7.096 | 5.430 | 6.962 | 1.00 | 56.16 | D |
| O | | | | | | | | | | | |
| ATOM | 9727 | N | PRO | D | 15 | -6.934 | 4.740 | 9.089 | 1.00 | 55.98 | D |
| N | | | | | | | | | | | |
| ATOM | 9728 | CA | PRO | D | 15 | -6.551 | 3.422 | 8.603 | 1.00 | 56.10 | D |
| C | | | | | | | | | | | |
| ATOM | 9730 | CB | PRO | D | 15 | -6.389 | 2.593 | 9.877 | 1.00 | 56.15 | D |
| C | | | | | | | | | | | |
| ATOM | 9733 | CG | PRO | D | 15 | -6.072 | 3.577 | 10.942 | 1.00 | 56.51 | D |
| C | | | | | | | | | | | |
| ATOM | 9736 | CD | PRO | D | 15 | -6.651 | 4.914 | 10.522 | 1.00 | 56.07 | D |
| C | | | | | | | | | | | |
| ATOM | 9739 | C | PRO | D | 15 | -7.624 | 2.832 | 7.689 | 1.00 | 56.35 | D |
| C | | | | | | | | | | | |
| ATOM | 9740 | O | PRO | D | 15 | -8.811 | 3.152 | 7.829 | 1.00 | 56.11 | D |
| O | | | | | | | | | | | |
| ATOM | 9741 | N | GLY | D | 16 | -7.185 | 1.999 | 6.749 | 1.00 | 56.55 | D |
| N | | | | | | | | | | | |
| ATOM | 9742 | CA | GLY | D | 16 | -8.061 | 1.346 | 5.804 | 1.00 | 56.57 | D |
| C | | | | | | | | | | | |
| ATOM | 9745 | C | GLY | D | 16 | -8.251 | 2.149 | 4.536 | 1.00 | 56.65 | D |
| C | | | | | | | | | | | |
| ATOM | 9746 | O | GLY | D | 16 | -8.371 | 1.572 | 3.470 | 1.00 | 57.46 | D |
| O | | | | | | | | | | | |
| ATOM | 9748 | N | GLN | D | 17 | -8.282 | 3.474 | 4.632 | 1.00 | 56.47 | D |
| N | | | | | | | | | | | |
| ATOM | 9749 | CA | GLN | D | 17 | -8.659 | 4.291 | 3.483 | 1.00 | 56.37 | D |
| C | | | | | | | | | | | |
| ATOM | 9751 | CB | GLN | D | 17 | -8.898 | 5.754 | 3.883 | 1.00 | 56.53 | D |
| C | | | | | | | | | | | |
| ATOM | 9758 | C | GLN | D | 17 | -7.628 | 4.211 | 2.361 | 1.00 | 56.37 | D |
| C | | | | | | | | | | | |
| ATOM | 9759 | O | GLN | D | 17 | -6.617 | 3.508 | 2.460 | 1.00 | 56.82 | D |
| O | | | | | | | | | | | |
| ATOM | 9761 | N | LYS | D | 18 | -7.938 | 4.898 | 1.271 | 1.00 | 55.96 | D |
| N | | | | | | | | | | | |
| ATOM | 9762 | CA | LYS | D | 18 | -7.043 | 5.041 | 0.164 | 1.00 | 55.75 | D |
| C | | | | | | | | | | | |
| ATOM | 9764 | CB | LYS | D | 18 | -7.774 | 4.798 | -1.166 | 1.00 | 55.88 | D |
| C | | | | | | | | | | | |
| ATOM | 9771 | C | LYS | D | 18 | -6.563 | 6.472 | 0.242 | 1.00 | 55.60 | D |
| C | | | | | | | | | | | |
| ATOM | 9772 | O | LYS | D | 18 | -7.351 | 7.391 | 0.496 | 1.00 | 56.12 | D |
| O | | | | | | | | | | | |
| ATOM | 9774 | N | VAL | D | 19 | -5.267 | 6.679 | 0.062 | 1.00 | 54.96 | D |
| N | | | | | | | | | | | |
| ATOM | 9775 | CA | VAL | D | 19 | -4.786 | 8.030 | -0.092 | 1.00 | 54.40 | D |
| C | | | | | | | | | | | |
| ATOM | 9777 | CB | VAL | D | 19 | -3.880 | 8.488 | 1.075 | 1.00 | 54.42 | D |
| C | | | | | | | | | | | |
| ATOM | 9779 | CG1 | VAL | D | 19 | -2.428 | 8.205 | 0.791 | 1.00 | 54.17 | D |
| C | | | | | | | | | | | |
| ATOM | 9783 | CG2 | VAL | D | 19 | -4.091 | 9.987 | 1.329 | 1.00 | 54.61 | D |
| C | | | | | | | | | | | |
| ATOM | 9787 | C | VAL | D | 19 | -4.082 | 8.067 | -1.414 | 1.00 | 53.81 | D |
| C | | | | | | | | | | | |
| ATOM | 9788 | O | VAL | D | 19 | -3.734 | 7.028 | -1.952 | 1.00 | 53.05 | D |

FIG 8 – CONT.

| | | | | | | | | | | |
|---|---|---|---|---|---|---|---|---|---|---|
| O | | | | | | | | | | |
| ATOM | 9790 | N | THR | D | 20 | -3.903 | 9.279 | -1.918 | 1.00 53.52 | D |
| N | | | | | | | | | | |
| ATOM | 9791 | CA | THR | D | 20 | -3.408 | 9.536 | -3.255 | 1.00 53.84 | D |
| C | | | | | | | | | | |
| ATOM | 9793 | CB | THR | D | 20 | -4.603 | 9.832 | -4.229 | 1.00 53.91 | D |
| C | | | | | | | | | | |
| ATOM | 9795 | OG1 | THR | D | 20 | -4.383 | 11.059 | -4.946 | 1.00 54.22 | D |
| O | | | | | | | | | | |
| ATOM | 9797 | CG2 | THR | D | 20 | -5.922 | 9.975 | -3.447 | 1.00 54.18 | D |
| C | | | | | | | | | | |
| ATOM | 9801 | C | THR | D | 20 | -2.451 | 10.743 | -3.146 | 1.00 53.86 | D |
| C | | | | | | | | | | |
| ATOM | 9802 | O | THR | D | 20 | -2.762 | 11.730 | -2.474 | 1.00 53.60 | D |
| O | | | | | | | | | | |
| ATOM | 9804 | N | ILE | D | 21 | -1.279 | 10.653 | -3.768 | 1.00 53.80 | D |
| N | | | | | | | | | | |
| ATOM | 9805 | CA | ILE | D | 21 | -0.315 | 11.745 | -3.686 | 1.00 53.53 | D |
| C | | | | | | | | | | |
| ATOM | 9807 | CB | ILE | D | 21 | 0.935 | 11.380 | -2.856 | 1.00 53.59 | D |
| C | | | | | | | | | | |
| ATOM | 9809 | CG1 | ILE | D | 21 | 0.538 | 10.939 | -1.452 | 1.00 53.41 | D |
| C | | | | | | | | | | |
| ATOM | 9812 | CD1 | ILE | D | 21 | 1.721 | 10.469 | -0.621 | 1.00 54.20 | D |
| C | | | | | | | | | | |
| ATOM | 9816 | CG2 | ILE | D | 21 | 1.887 | 12.585 | -2.759 | 1.00 52.72 | D |
| C | | | | | | | | | | |
| ATOM | 9820 | C | ILE | D | 21 | 0.090 | 12.143 | -5.081 | 1.00 53.71 | D |
| C | | | | | | | | | | |
| ATOM | 9821 | O | ILE | D | 21 | 0.567 | 11.315 | -5.867 | 1.00 54.06 | D |
| O | | | | | | | | | | |
| ATOM | 9823 | N | SER | D | 22 | -0.103 | 13.420 | -5.375 | 1.00 53.32 | D |
| N | | | | | | | | | | |
| ATOM | 9824 | CA | SER | D | 22 | 0.130 | 13.948 | -6.695 | 1.00 53.46 | D |
| C | | | | | | | | | | |
| ATOM | 9826 | CB | SER | D | 22 | -0.837 | 15.105 | -6.963 | 1.00 53.50 | D |
| C | | | | | | | | | | |
| ATOM | 9829 | OG | SER | D | 22 | -0.284 | 16.335 | -6.511 | 1.00 55.11 | D |
| O | | | | | | | | | | |
| ATOM | 9831 | C | SER | D | 22 | 1.573 | 14.448 | -6.823 | 1.00 53.00 | D |
| C | | | | | | | | | | |
| ATOM | 9832 | O | SER | D | 22 | 2.185 | 14.879 | -5.839 | 1.00 52.89 | D |
| O | | | | | | | | | | |
| ATOM | 9834 | N | CYS | D | 23 | 2.098 | 14.390 | -8.045 | 1.00 52.17 | D |
| N | | | | | | | | | | |
| ATOM | 9835 | CA | CYS | D | 23 | 3.399 | 14.957 | -8.381 | 1.00 51.41 | D |
| C | | | | | | | | | | |
| ATOM | 9837 | CB | CYS | D | 23 | 4.475 | 13.851 | -8.426 | 1.00 51.07 | D |
| C | | | | | | | | | | |
| ATOM | 9840 | SG | CYS | D | 23 | 6.129 | 14.394 | -8.887 | 1.00 50.70 | D |
| S | | | | | | | | | | |
| ATOM | 9842 | C | CYS | D | 23 | 3.248 | 15.641 | -9.737 | 1.00 51.25 | D |
| C | | | | | | | | | | |
| ATOM | 9843 | O | CYS | D | 23 | 2.809 | 15.023 | -10.712 | 1.00 51.15 | D |
| O | | | | | | | | | | |
| ATOM | 9845 | N | SER | D | 24 | 3.627 | 16.906 | -9.793 | 1.00 50.86 | D |
| N | | | | | | | | | | |
| ATOM | 9846 | CA | SER | D | 24 | 3.351 | 17.725 | -10.935 | 1.00 51.34 | D |
| C | | | | | | | | | | |
| ATOM | 9848 | CB | SER | D | 24 | 2.374 | 18.835 | -10.533 | 1.00 51.51 | D |
| C | | | | | | | | | | |

FIG 8 – CONT.

| ATOM | 9851 | OG  | SER | D | 24  | 2.509  | 19.953 | -11.386 | 1.00 52.85 | D | O |
| ATOM | 9853 | C   | SER | D | 24  | 4.632  | 18.334 | -11.443 | 1.00 51.11 | D | C |
| ATOM | 9854 | O   | SER | D | 24  | 5.368  | 18.956 | -10.683 | 1.00 51.65 | D | O |
| ATOM | 9856 | N   | GLY | D | 25  | 4.875  | 18.196 | -12.738 | 1.00 50.97 | D | N |
| ATOM | 9857 | CA  | GLY | D | 25  | 6.147  | 18.591 | -13.308 | 1.00 51.04 | D | C |
| ATOM | 9860 | C   | GLY | D | 25  | 6.042  | 19.393 | -14.582 | 1.00 50.91 | D | C |
| ATOM | 9861 | O   | GLY | D | 25  | 5.145  | 20.216 | -14.742 | 1.00 50.88 | D | O |
| ATOM | 9863 | N   | SER | D | 26  | 6.983  | 19.161 | -15.485 | 1.00 50.83 | D | N |
| ATOM | 9864 | CA  | SER | D | 26  | 7.054  | 19.907 | -16.721 | 1.00 50.83 | D | C |
| ATOM | 9866 | CB  | SER | D | 26  | 8.139  | 20.997 | -16.638 | 1.00 50.79 | D | C |
| ATOM | 9869 | OG  | SER | D | 26  | 9.422  | 20.506 | -16.990 | 1.00 52.39 | D | O |
| ATOM | 9871 | C   | SER | D | 26  | 7.307  | 18.964 | -17.886 | 1.00 50.69 | D | C |
| ATOM | 9872 | O   | SER | D | 26  | 7.469  | 17.744 | -17.708 | 1.00 50.61 | D | O |
| ATOM | 9874 | N   | SER | D | 27  | 7.317  | 19.552 | -19.078 | 1.00 50.05 | D | N |
| ATOM | 9875 | CA  | SER | D | 27  | 7.468  | 18.822 | -20.331 | 1.00 49.96 | D | C |
| ATOM | 9877 | CB  | SER | D | 27  | 7.292  | 19.821 | -21.495 | 1.00 50.16 | D | C |
| ATOM | 9880 | OG  | SER | D | 27  | 7.669  | 19.279 | -22.740 | 1.00 51.09 | D | O |
| ATOM | 9882 | C   | SER | D | 27  | 8.811  | 18.074 | -20.412 | 1.00 49.00 | D | C |
| ATOM | 9883 | O   | SER | D | 27  | 8.866  | 16.913 | -20.792 | 1.00 48.94 | D | O |
| ATOM | 9885 | N   | SER | D | 27A | 9.879  | 18.754 | -20.014 | 1.00 48.71 | D | N |
| ATOM | 9886 | CA  | SER | D | 27A | 11.245 | 18.220 | -20.067 | 1.00 47.91 | D | C |
| ATOM | 9888 | CB  | SER | D | 27A | 12.251 | 19.377 | -20.003 | 1.00 47.92 | D | C |
| ATOM | 9891 | OG  | SER | D | 27A | 12.216 | 20.022 | -18.735 | 1.00 47.58 | D | O |
| ATOM | 9893 | C   | SER | D | 27A | 11.568 | 17.197 | -18.967 | 1.00 47.42 | D | C |
| ATOM | 9894 | O   | SER | D | 27A | 12.520 | 16.426 | -19.111 | 1.00 47.01 | D | O |
| ATOM | 9896 | N   | ASP | D | 27B | 10.809 | 17.197 | -17.868 | 1.00 46.84 | D | N |
| ATOM | 9897 | CA  | ASP | D | 27B | 11.018 | 16.190 | -16.826 | 1.00 46.25 | D | C |
| ATOM | 9899 | CB  | ASP | D | 27B | 11.193 | 16.796 | -15.418 | 1.00 46.39 | D | C |
| ATOM | 9902 | CG  | ASP | D | 27B | 10.057 | 17.724 | -14.988 | 1.00 45.80 | D | C |
| ATOM | 9903 | OD1 | ASP | D | 27B | 10.304 | 18.945 | -14.859 | 1.00 44.75 | D | O |
| ATOM | 9904 | OD2 | ASP | D | 27B | 8.941  | 17.227 | -14.734 | 1.00 45.26 | D | |

FIG 8 – CONT.

```
     O
ATOM 9905 C   ASP D 27B  10.006 15.037 -16.906 1.00 45.78  D
     C
ATOM 9906 O   ASP D 27B  10.218 14.140 -17.701 1.00 45.41  D
     O
ATOM 9908 N   ILE D 28    8.941 15.040 -16.109 1.00 45.40  D
     N
ATOM 9909 CA  ILE D 28    7.910 13.973 -16.159 1.00 45.96  D
     C
ATOM 9911 CB  ILE D 28    6.705 14.274 -15.222 1.00 46.02  D
     C
ATOM 9913 CG1 ILE D 28    7.146 14.339 -13.761 1.00 46.87  D
     C
ATOM 9916 CD1 ILE D 28    5.958 14.544 -12.788 1.00 48.33  D
     C
ATOM 9920 CG2 ILE D 28    5.577 13.239 -15.387 1.00 44.78  D
     C
ATOM 9924 C   ILE D 28    7.340 13.801 -17.559 1.00 46.00  D
     C
ATOM 9925 O   ILE D 28    6.969 12.694 -17.962 1.00 45.81  D
     O
ATOM 9927 N   GLY D 29    7.271 14.906 -18.293 1.00 46.19  D
     N
ATOM 9928 CA  GLY D 29    6.775 14.879 -19.669 1.00 46.83  D
     C
ATOM 9931 C   GLY D 29    7.575 13.966 -20.581 1.00 46.82  D
     C
ATOM 9932 O   GLY D 29    7.018 13.374 -21.519 1.00 47.01  D
     O
ATOM 9934 N   SER D 30    8.865 13.809 -20.280 1.00 45.93  D
     N
ATOM 9935 CA  SER D 30    9.761 13.102 -21.169 1.00 45.48  D
     C
ATOM 9937 CB  SER D 30   10.889 14.037 -21.580 1.00 45.46  D
     C
ATOM 9940 OG  SER D 30   10.391 15.257 -22.096 1.00 46.68  D
     O
ATOM 9942 C   SER D 30   10.373 11.829 -20.590 1.00 44.72  D
     C
ATOM 9943 O   SER D 30   11.154 11.169 -21.286 1.00 44.18  D
     O
ATOM 9945 N   ASN D 31   10.027 11.482 -19.346 1.00 43.43  D
     N
ATOM 9946 CA  ASN D 31   10.816 10.510 -18.593 1.00 42.43  D
     C
ATOM 9948 CB  ASN D 31   11.926 11.219 -17.811 1.00 42.32  D
     C
ATOM 9951 CG  ASN D 31   13.045 11.754 -18.719 1.00 41.41  D
     C
ATOM 9952 OD1 ASN D 31   13.852 10.980 -19.243 1.00 43.36  D
     O
ATOM 9953 ND2 ASN D 31   13.083 13.068 -18.921 1.00 38.48  D
     N
ATOM 9956 C   ASN D 31    9.979  9.684 -17.652 1.00 42.13  D
     C
ATOM 9957 O   ASN D 31    8.853 10.043 -17.337 1.00 42.26  D
     O
ATOM 9959 N   TYR D 32   10.524  8.548 -17.233 1.00 41.63  D
     N
ATOM 9960 CA  TYR D 32    9.852  7.694 -16.274 1.00 41.65  D
     C
```

FIG 8 – CONT.

| | | | | | | | | | | |
|---|---|---|---|---|---|---|---|---|---|---|
| ATOM | 9962 | CB | TYR | D | 32 | 10.537 | 6.351 | -16.186 | 1.00 42.36 | D C |
| ATOM | 9965 | CG | TYR | D | 32 | 10.392 | 5.484 | -17.408 | 1.00 44.43 | D C |
| ATOM | 9966 | CD1 | TYR | D | 32 | 9.254 | 4.688 | -17.586 | 1.00 46.05 | D C |
| ATOM | 9968 | CE1 | TYR | D | 32 | 9.121 | 3.861 | -18.694 | 1.00 47.28 | D C |
| ATOM | 9970 | CZ | TYR | D | 32 | 10.130 | 3.820 | -19.640 | 1.00 48.66 | D C |
| ATOM | 9971 | OH | TYR | D | 32 | 9.988 | 3.002 | -20.753 | 1.00 53.24 | D O |
| ATOM | 9973 | CE2 | TYR | D | 32 | 11.269 | 4.609 | -19.494 | 1.00 46.65 | D C |
| ATOM | 9975 | CD2 | TYR | D | 32 | 11.402 | 5.429 | -18.374 | 1.00 44.79 | D C |
| ATOM | 9977 | C | TYR | D | 32 | 9.871 | 8.352 | -14.893 | 1.00 40.51 | D C |
| ATOM | 9978 | O | TYR | D | 32 | 10.692 | 9.203 | -14.633 | 1.00 39.89 | D O |
| ATOM | 9980 | N | VAL | D | 33 | 8.941 | 7.960 | -14.038 | 1.00 39.86 | D N |
| ATOM | 9981 | CA | VAL | D | 33 | 8.742 | 8.607 | -12.743 | 1.00 39.60 | D C |
| ATOM | 9983 | CB | VAL | D | 33 | 7.314 | 9.199 | -12.603 | 1.00 39.51 | D C |
| ATOM | 9985 | CG1 | VAL | D | 33 | 6.983 | 9.533 | -11.122 | 1.00 38.31 | D C |
| ATOM | 9989 | CG2 | VAL | D | 33 | 7.163 | 10.435 | -13.494 | 1.00 37.88 | D C |
| ATOM | 9993 | C | VAL | D | 33 | 8.960 | 7.570 | -11.676 | 1.00 39.68 | D C |
| ATOM | 9994 | O | VAL | D | 33 | 8.496 | 6.466 | -11.814 | 1.00 40.19 | D O |
| ATOM | 9996 | N | SER | D | 34 | 9.677 | 7.941 | -10.619 | 1.00 39.91 | D N |
| ATOM | 9997 | CA | SER | D | 34 | 9.919 | 7.067 | -9.486 | 1.00 40.05 | D C |
| ATOM | 9999 | CB | SER | D | 34 | 11.432 | 6.848 | -9.333 | 1.00 40.49 | D C |
| ATOM | 10002 | OG | SER | D | 34 | 11.918 | 5.905 | -10.266 | 1.00 41.02 | D O |
| ATOM | 10004 | C | SER | D | 34 | 9.376 | 7.708 | -8.203 | 1.00 39.59 | D C |
| ATOM | 10005 | O | SER | D | 34 | 9.238 | 8.933 | -8.112 | 1.00 39.15 | D O |
| ATOM | 10007 | N | TRP | D | 35 | 9.119 | 6.864 | -7.216 | 1.00 39.67 | D N |
| ATOM | 10008 | CA | TRP | D | 35 | 8.735 | 7.283 | -5.873 | 1.00 39.75 | D C |
| ATOM | 10010 | CB | TRP | D | 35 | 7.293 | 6.885 | -5.576 | 1.00 40.39 | D C |
| ATOM | 10013 | CG | TRP | D | 35 | 6.310 | 7.603 | -6.430 | 1.00 42.98 | D C |
| ATOM | 10014 | CD1 | TRP | D | 35 | 5.846 | 7.211 | -7.662 | 1.00 42.31 | D C |
| ATOM | 10016 | NE1 | TRP | D | 35 | 4.985 | 8.144 | -8.150 | 1.00 44.65 | D N |
| ATOM | 10018 | CE2 | TRP | D | 35 | 4.850 | 9.161 | -7.244 | 1.00 44.85 | D C |
| ATOM | 10019 | CD2 | TRP | D | 35 | 5.683 | 8.859 | -6.147 | 1.00 44.94 | D |

FIG 8 – CONT.

| | | | | | | | | | | |
|---|---|---|---|---|---|---|---|---|---|---|
| ATOM | 10020 | CE3 | TRP | D | 35 | 5.736 | 9.753 | -5.071 | 1.00 47.22 | D C |
| ATOM | 10022 | CZ3 | TRP | D | 35 | 4.957 | 10.904 | -5.125 | 1.00 47.98 | D C |
| ATOM | 10024 | CH2 | TRP | D | 35 | 4.138 | 11.167 | -6.238 | 1.00 47.51 | D C |
| ATOM | 10026 | CZ2 | TRP | D | 35 | 4.082 | 10.310 | -7.303 | 1.00 45.81 | D C |
| ATOM | 10028 | C | TRP | D | 35 | 9.631 | 6.634 | -4.836 | 1.00 39.20 | D C |
| ATOM | 10029 | O | TRP | D | 35 | 10.003 | 5.459 | -4.990 | 1.00 38.14 | D O |
| ATOM | 10031 | N | TYR | D | 36 | 9.949 | 7.403 | -3.781 | 1.00 38.36 | D N |
| ATOM | 10032 | CA | TYR | D | 36 | 10.785 | 6.940 | -2.684 | 1.00 38.14 | D C |
| ATOM | 10034 | CB | TYR | D | 36 | 12.120 | 7.687 | -2.714 | 1.00 38.60 | D C |
| ATOM | 10037 | CG | TYR | D | 36 | 12.787 | 7.620 | -4.064 | 1.00 38.04 | D C |
| ATOM | 10038 | CD1 | TYR | D | 36 | 13.596 | 6.557 | -4.394 | 1.00 38.96 | D C |
| ATOM | 10040 | CE1 | TYR | D | 36 | 14.180 | 6.451 | -5.633 | 1.00 38.28 | D C |
| ATOM | 10042 | CZ | TYR | D | 36 | 13.953 | 7.403 | -6.578 | 1.00 36.78 | D C |
| ATOM | 10043 | OH | TYR | D | 36 | 14.568 | 7.261 | -7.823 | 1.00 39.74 | D O |
| ATOM | 10045 | CE2 | TYR | D | 36 | 13.132 | 8.466 | -6.292 | 1.00 36.81 | D C |
| ATOM | 10047 | CD2 | TYR | D | 36 | 12.548 | 8.571 | -5.036 | 1.00 38.19 | D C |
| ATOM | 10049 | C | TYR | D | 36 | 10.087 | 7.115 | -1.324 | 1.00 37.91 | D C |
| ATOM | 10050 | O | TYR | D | 36 | 9.446 | 8.120 | -1.065 | 1.00 38.73 | D O |
| ATOM | 10052 | N | GLN | D | 37 | 10.202 | 6.115 | -0.475 | 1.00 37.14 | D N |
| ATOM | 10053 | CA | GLN | D | 37 | 9.647 | 6.146 | 0.869 | 1.00 37.47 | D C |
| ATOM | 10055 | CB | GLN | D | 37 | 8.973 | 4.810 | 1.197 | 1.00 37.13 | D C |
| ATOM | 10058 | CG | GLN | D | 37 | 8.288 | 4.793 | 2.545 | 1.00 38.71 | D C |
| ATOM | 10061 | CD | GLN | D | 37 | 7.711 | 3.433 | 2.914 | 1.00 41.31 | D C |
| ATOM | 10062 | OE1 | GLN | D | 37 | 6.513 | 3.315 | 3.176 | 1.00 43.96 | D O |
| ATOM | 10063 | NE2 | GLN | D | 37 | 8.556 | 2.412 | 2.950 | 1.00 41.14 | D N |
| ATOM | 10066 | C | GLN | D | 37 | 10.753 | 6.344 | 1.898 | 1.00 37.46 | D C |
| ATOM | 10067 | O | GLN | D | 37 | 11.642 | 5.505 | 2.000 | 1.00 37.62 | D O |
| ATOM | 10069 | N | GLN | D | 38 | 10.655 | 7.395 | 2.700 | 1.00 37.29 | D N |
| ATOM | 10070 | CA | GLN | D | 38 | 11.616 | 7.636 | 3.789 | 1.00 37.51 | D C |
| ATOM | 10072 | CB | GLN | D | 38 | 12.337 | 8.964 | 3.573 | 1.00 37.07 | D C |

FIG 8 – CONT.

| ATOM | 10075 | CG | GLN | D | 38 | 13.515 | 9.179 | 4.550 | 1.00 | 36.00 | D |
|---|---|---|---|---|---|---|---|---|---|---|---|
| ATOM | 10078 | CD | GLN | D | 38 | 14.295 | 10.438 | 4.269 | 1.00 | 31.81 | D |
| ATOM | 10079 | OE1 | GLN | D | 38 | 13.760 | 11.433 | 3.768 | 1.00 | 29.78 | D |
| ATOM | 10080 | NE2 | GLN | D | 38 | 15.566 | 10.413 | 4.620 | 1.00 | 31.14 | D |
| ATOM | 10083 | C | GLN | D | 38 | 10.953 | 7.651 | 5.182 | 1.00 | 38.30 | D |
| ATOM | 10084 | O | GLN | D | 38 | 10.288 | 8.593 | 5.550 | 1.00 | 37.27 | D |
| ATOM | 10086 | N | PHE | D | 39 | 11.164 | 6.591 | 5.941 | 1.00 | 39.63 | D |
| ATOM | 10087 | CA | PHE | D | 39 | 10.840 | 6.587 | 7.340 | 1.00 | 40.57 | D |
| ATOM | 10089 | CB | PHE | D | 39 | 11.031 | 5.192 | 7.896 | 1.00 | 40.45 | D |
| ATOM | 10092 | CG | PHE | D | 39 | 10.101 | 4.191 | 7.301 | 1.00 | 43.78 | D |
| ATOM | 10093 | CD1 | PHE | D | 39 | 8.729 | 4.350 | 7.423 | 1.00 | 45.92 | D |
| ATOM | 10095 | CE1 | PHE | D | 39 | 7.854 | 3.416 | 6.868 | 1.00 | 46.30 | D |
| ATOM | 10097 | CZ | PHE | D | 39 | 8.352 | 2.315 | 6.191 | 1.00 | 47.45 | D |
| ATOM | 10099 | CE2 | PHE | D | 39 | 9.722 | 2.137 | 6.064 | 1.00 | 46.96 | D |
| ATOM | 10101 | CD2 | PHE | D | 39 | 10.589 | 3.070 | 6.623 | 1.00 | 46.61 | D |
| ATOM | 10103 | C | PHE | D | 39 | 11.729 | 7.593 | 8.074 | 1.00 | 40.37 | D |
| ATOM | 10104 | O | PHE | D | 39 | 12.720 | 8.032 | 7.517 | 1.00 | 40.22 | D |
| ATOM | 10106 | N | PRO | D | 40 | 11.345 | 8.003 | 9.301 | 1.00 | 41.00 | D |
| ATOM | 10107 | CA | PRO | D | 40 | 12.158 | 9.018 | 9.992 | 1.00 | 41.24 | D |
| ATOM | 10109 | CB | PRO | D | 40 | 11.268 | 9.442 | 11.183 | 1.00 | 41.65 | D |
| ATOM | 10112 | CG | PRO | D | 40 | 9.874 | 9.152 | 10.732 | 1.00 | 41.44 | D |
| ATOM | 10115 | CD | PRO | D | 40 | 10.004 | 7.876 | 9.918 | 1.00 | 41.56 | D |
| ATOM | 10118 | C | PRO | D | 40 | 13.468 | 8.435 | 10.460 | 1.00 | 40.74 | D |
| ATOM | 10119 | O | PRO | D | 40 | 13.510 | 7.258 | 10.845 | 1.00 | 41.35 | D |
| ATOM | 10120 | N | GLY | D | 41 | 14.541 | 9.223 | 10.389 | 1.00 | 40.26 | D |
| ATOM | 10121 | CA | GLY | D | 41 | 15.882 | 8.701 | 10.694 | 1.00 | 39.76 | D |
| ATOM | 10124 | C | GLY | D | 41 | 16.360 | 7.514 | 9.839 | 1.00 | 39.73 | D |
| ATOM | 10125 | O | GLY | D | 41 | 17.242 | 6.753 | 10.268 | 1.00 | 40.13 | D |
| ATOM | 10127 | N | THR | D | 42 | 15.798 | 7.353 | 8.636 | 1.00 | 38.47 | D |
| ATOM | 10128 | CA | THR | D | 42 | 16.148 | 6.245 | 7.743 | 1.00 | 37.93 | D |
| ATOM | 10130 | CB | THR | D | 42 | 14.996 | 5.185 | 7.707 | 1.00 | 38.20 | D |

FIG 8 – CONT.

```
C
ATOM   10132  OG1  THR  D  42      14.886    4.585    9.003  1.00 41.96      D
O
ATOM   10134  CG2  THR  D  42      15.281    4.061    6.745  1.00 39.42      D
C
ATOM   10138  C    THR  D  42      16.482    6.760    6.332  1.00 36.13      D
C
ATOM   10139  O    THR  D  42      16.037    7.836    5.913  1.00 35.78      D
O
ATOM   10141  N    ALA  D  43      17.302    6.006    5.616  1.00 34.70      D
N
ATOM   10142  CA   ALA  D  43      17.574    6.289    4.214  1.00 34.32      D
C
ATOM   10144  CB   ALA  D  43      18.661    5.352    3.661  1.00 33.79      D
C
ATOM   10148  C    ALA  D  43      16.287    6.114    3.428  1.00 33.54      D
C
ATOM   10149  O    ALA  D  43      15.439    5.306    3.775  1.00 32.65      D
O
ATOM   10151  N    PRO  D  44      16.129    6.894    2.371  1.00 33.53      D
N
ATOM   10152  CA   PRO  D  44      15.053    6.633    1.466  1.00 33.84      D
C
ATOM   10154  CB   PRO  D  44      15.225    7.700    0.400  1.00 33.39      D
C
ATOM   10157  CG   PRO  D  44      15.989    8.739    1.014  1.00 33.57      D
C
ATOM   10160  CD   PRO  D  44      16.932    8.032    1.918  1.00 34.07      D
C
ATOM   10163  C    PRO  D  44      15.214    5.277    0.835  1.00 34.34      D
C
ATOM   10164  O    PRO  D  44      16.308    4.719    0.825  1.00 33.88      D
O
ATOM   10165  N    LYS  D  45      14.120    4.793    0.273  1.00 35.80      D
N
ATOM   10166  CA   LYS  D  45      14.049    3.490   -0.355  1.00 36.72      D
C
ATOM   10168  CB   LYS  D  45      13.396    2.518    0.603  1.00 37.26      D
C
ATOM   10171  CG   LYS  D  45      13.419    1.074    0.126  1.00 40.39      D
C
ATOM   10174  CD   LYS  D  45      12.937    0.113    1.237  1.00 41.56      D
C
ATOM   10177  CE   LYS  D  45      11.504    0.378    1.621  1.00 42.39      D
C
ATOM   10180  NZ   LYS  D  45      10.886   -0.852    2.187  1.00 44.14      D
N
ATOM   10184  C    LYS  D  45      13.199    3.637   -1.595  1.00 37.23      D
C
ATOM   10185  O    LYS  D  45      12.151    4.284   -1.576  1.00 37.15      D
O
ATOM   10187  N    LEU  D  46      13.665    3.051   -2.688  1.00 38.23      D
N
ATOM   10188  CA   LEU  D  46      12.901    3.010   -3.935  1.00 37.85      D
C
ATOM   10190  CB   LEU  D  46      13.712    2.306   -5.042  1.00 37.11      D
C
ATOM   10193  CG   LEU  D  46      13.054    2.297   -6.439  1.00 37.00      D
C
ATOM   10195  CD1  LEU  D  46      12.719    3.740   -6.900  1.00 31.89      D
C
```

FIG 8 – CONT.

| ATOM | 10199 | CD2 | LEU | D | 46 | 13.904 | 1.552 | -7.488 | 1.00 | 34.56 | D |
|---|---|---|---|---|---|---|---|---|---|---|---|
| ATOM | 10203 | C | LEU | D | 46 | 11.577 | 2.276 | -3.707 | 1.00 | 37.55 | D |
| ATOM | 10204 | O | LEU | D | 46 | 11.584 | 1.136 | -3.289 | 1.00 | 37.79 | D |
| ATOM | 10206 | N | LEU | D | 47 | 10.466 | 2.943 | -4.012 | 1.00 | 37.91 | D |
| ATOM | 10207 | CA | LEU | D | 47 | 9.123 | 2.415 | -3.777 | 1.00 | 38.12 | D |
| ATOM | 10209 | CB | LEU | D | 47 | 8.320 | 3.513 | -3.122 | 1.00 | 38.36 | D |
| ATOM | 10212 | CG | LEU | D | 47 | 6.884 | 3.226 | -2.726 | 1.00 | 37.64 | D |
| ATOM | 10214 | CD1 | LEU | D | 47 | 6.869 | 2.239 | -1.606 | 1.00 | 36.60 | D |
| ATOM | 10218 | CD2 | LEU | D | 47 | 6.215 | 4.545 | -2.360 | 1.00 | 37.84 | D |
| ATOM | 10222 | C | LEU | D | 47 | 8.397 | 1.997 | -5.062 | 1.00 | 38.67 | D |
| ATOM | 10223 | O | LEU | D | 47 | 7.765 | 0.936 | -5.129 | 1.00 | 37.80 | D |
| ATOM | 10225 | N | ILE | D | 48 | 8.444 | 2.899 | -6.037 | 1.00 | 38.93 | D |
| ATOM | 10226 | CA | ILE | D | 48 | 7.924 | 2.684 | -7.374 | 1.00 | 39.31 | D |
| ATOM | 10228 | CB | ILE | D | 48 | 6.648 | 3.522 | -7.642 | 1.00 | 39.47 | D |
| ATOM | 10230 | CG1 | ILE | D | 48 | 5.467 | 3.075 | -6.779 | 1.00 | 39.00 | D |
| ATOM | 10233 | CD1 | ILE | D | 48 | 4.875 | 1.751 | -7.186 | 1.00 | 38.14 | D |
| ATOM | 10237 | CG2 | ILE | D | 48 | 6.252 | 3.457 | -9.153 | 1.00 | 40.77 | D |
| ATOM | 10241 | C | ILE | D | 48 | 8.969 | 3.200 | -8.372 | 1.00 | 39.08 | D |
| ATOM | 10242 | O | ILE | D | 48 | 9.589 | 4.263 | -8.150 | 1.00 | 39.19 | D |
| ATOM | 10244 | N | TYR | D | 49 | 9.143 | 2.450 | -9.461 | 1.00 | 38.58 | D |
| ATOM | 10245 | CA | TYR | D | 49 | 9.913 | 2.893 | -10.624 | 1.00 | 38.87 | D |
| ATOM | 10247 | CB | TYR | D | 49 | 11.293 | 2.227 | -10.622 | 1.00 | 39.46 | D |
| ATOM | 10250 | CG | TYR | D | 49 | 11.277 | 0.730 | -10.862 | 1.00 | 39.35 | D |
| ATOM | 10251 | CD1 | TYR | D | 49 | 11.636 | 0.195 | -12.106 | 1.00 | 40.77 | D |
| ATOM | 10253 | CE1 | TYR | D | 49 | 11.618 | -1.183 | -12.327 | 1.00 | 39.42 | D |
| ATOM | 10255 | CZ | TYR | D | 49 | 11.230 | -2.013 | -11.300 | 1.00 | 39.01 | D |
| ATOM | 10256 | OH | TYR | D | 49 | 11.211 | -3.367 | -11.471 | 1.00 | 36.37 | D |
| ATOM | 10258 | CE2 | TYR | D | 49 | 10.872 | -1.491 | -10.068 | 1.00 | 39.21 | D |
| ATOM | 10260 | CD2 | TYR | D | 49 | 10.890 | -0.137 | -9.867 | 1.00 | 38.29 | D |
| ATOM | 10262 | C | TYR | D | 49 | 9.215 | 2.611 | -11.974 | 1.00 | 39.16 | D |
| ATOM | 10263 | O | TYR | D | 49 | 8.307 | 1.769 | -12.085 | 1.00 | 38.19 | D |

FIG 8 – CONT.

| | | | | | | | | | | |
|---|---|---|---|---|---|---|---|---|---|---|
| ATOM | 10265 | N | ASP | D | 50 | 9.691 | 3.307 | -13.002 | 1.00 39.95 | D |
| ATOM | 10266 | CA | ASP | D | 50 | 9.200 | 3.136 | -14.374 | 1.00 40.67 | D |
| ATOM | 10268 | CB | ASP | D | 50 | 9.581 | 1.746 | -14.962 | 1.00 40.10 | D |
| ATOM | 10271 | CG | ASP | D | 50 | 11.072 | 1.630 | -15.342 | 1.00 39.83 | D |
| ATOM | 10272 | OD1 | ASP | D | 50 | 11.810 | 2.629 | -15.338 | 1.00 35.53 | D |
| ATOM | 10273 | OD2 | ASP | D | 50 | 11.522 | 0.513 | -15.690 | 1.00 41.41 | D |
| ATOM | 10274 | C | ASP | D | 50 | 7.690 | 3.351 | -14.304 | 1.00 41.09 | D |
| ATOM | 10275 | O | ASP | D | 50 | 6.896 | 2.508 | -14.723 | 1.00 40.89 | D |
| ATOM | 10277 | N | ASN | D | 51 | 7.326 | 4.484 | -13.712 | 1.00 42.12 | D |
| ATOM | 10278 | CA | ASN | D | 51 | 5.931 | 4.918 | -13.528 | 1.00 42.57 | D |
| ATOM | 10280 | CB | ASN | D | 51 | 5.215 | 5.044 | -14.880 | 1.00 42.83 | D |
| ATOM | 10283 | CG | ASN | D | 51 | 5.888 | 6.034 | -15.807 | 1.00 43.52 | D |
| ATOM | 10284 | OD1 | ASN | D | 51 | 6.705 | 6.847 | -15.388 | 1.00 45.31 | D |
| ATOM | 10285 | ND2 | ASN | D | 51 | 5.515 | 5.990 | -17.076 | 1.00 43.78 | D |
| ATOM | 10288 | C | ASN | D | 51 | 5.072 | 4.066 | -12.608 | 1.00 42.74 | D |
| ATOM | 10289 | O | ASN | D | 51 | 4.343 | 4.605 | -11.785 | 1.00 42.92 | D |
| ATOM | 10291 | N | ASN | D | 52 | 5.115 | 2.753 | -12.751 | 1.00 43.52 | D |
| ATOM | 10292 | CA | ASN | D | 52 | 4.125 | 1.912 | -12.082 | 1.00 44.51 | D |
| ATOM | 10294 | CB | ASN | D | 52 | 2.902 | 1.709 | -13.004 | 1.00 44.52 | D |
| ATOM | 10297 | CG | ASN | D | 52 | 3.281 | 1.179 | -14.376 | 1.00 45.48 | D |
| ATOM | 10298 | OD1 | ASN | D | 52 | 4.069 | 0.247 | -14.501 | 1.00 43.30 | D |
| ATOM | 10299 | ND2 | ASN | D | 52 | 2.720 | 1.794 | -15.420 | 1.00 47.50 | D |
| ATOM | 10302 | C | ASN | D | 52 | 4.584 | 0.567 | -11.577 | 1.00 45.03 | D |
| ATOM | 10303 | O | ASN | D | 52 | 3.751 | -0.222 | -11.130 | 1.00 44.77 | D |
| ATOM | 10305 | N | LYS | D | 53 | 5.884 | 0.291 | -11.623 | 1.00 46.42 | D |
| ATOM | 10306 | CA | LYS | D | 53 | 6.386 | -1.003 | -11.158 | 1.00 47.74 | D |
| ATOM | 10308 | CB | LYS | D | 53 | 7.549 | -1.482 | -12.032 | 1.00 47.77 | D |
| ATOM | 10311 | CG | LYS | D | 53 | 7.232 | -1.638 | -13.520 | 1.00 48.16 | D |
| ATOM | 10314 | CD | LYS | D | 53 | 8.377 | -2.381 | -14.274 | 1.00 48.37 | D |
| ATOM | 10317 | CE | LYS | D | 53 | 8.482 | -1.969 | -15.758 | 1.00 49.03 | D |

FIG 8 -- CONT.

| ATOM | 10320 | NZ | LYS | D | 53 | 9.871 | -2.203 | -16.330 | 1.00 | 49.85 | D |
|---|---|---|---|---|---|---|---|---|---|---|---|
| ATOM | 10324 | C | LYS | D | 53 | 6.836 | -0.951 | -9.695 | 1.00 | 48.95 | D |
| ATOM | 10325 | O | LYS | D | 53 | 7.266 | 0.101 | -9.182 | 1.00 | 49.29 | D |
| ATOM | 10327 | N | ARG | D | 54 | 6.764 | -2.110 | -9.046 | 1.00 | 49.97 | D |
| ATOM | 10328 | CA | ARG | D | 54 | 7.192 | -2.276 | -7.667 | 1.00 | 50.91 | D |
| ATOM | 10330 | CB | ARG | D | 54 | 6.090 | -2.926 | -6.837 | 1.00 | 51.34 | D |
| ATOM | 10333 | CG | ARG | D | 54 | 5.062 | -1.959 | -6.309 | 1.00 | 53.56 | D |
| ATOM | 10336 | CD | ARG | D | 54 | 3.996 | -2.696 | -5.555 | 1.00 | 55.85 | D |
| ATOM | 10339 | NE | ARG | D | 54 | 3.463 | -3.791 | -6.362 | 1.00 | 59.35 | D |
| ATOM | 10341 | CZ | ARG | D | 54 | 2.582 | -3.656 | -7.354 | 1.00 | 60.82 | D |
| ATOM | 10342 | NH1 | ARG | D | 54 | 2.184 | -4.739 | -8.017 | 1.00 | 61.25 | D |
| ATOM | 10345 | NH2 | ARG | D | 54 | 2.086 | -2.460 | -7.685 | 1.00 | 60.25 | D |
| ATOM | 10348 | C | ARG | D | 54 | 8.391 | -3.184 | -7.555 | 1.00 | 51.15 | D |
| ATOM | 10349 | O | ARG | D | 54 | 8.361 | -4.303 | -8.068 | 1.00 | 50.99 | D |
| ATOM | 10351 | N | PRO | D | 55 | 9.426 | -2.739 | -6.823 | 1.00 | 51.35 | D |
| ATOM | 10352 | CA | PRO | D | 55 | 10.425 | -3.678 | -6.313 | 1.00 | 51.48 | D |
| ATOM | 10354 | CB | PRO | D | 55 | 11.265 | -2.814 | -5.369 | 1.00 | 51.43 | D |
| ATOM | 10357 | CG | PRO | D | 55 | 11.142 | -1.441 | -5.906 | 1.00 | 51.10 | D |
| ATOM | 10360 | CD | PRO | D | 55 | 9.759 | -1.341 | -6.491 | 1.00 | 51.41 | D |
| ATOM | 10363 | C | PRO | D | 55 | 9.763 | -4.837 | -5.567 | 1.00 | 51.85 | D |
| ATOM | 10364 | O | PRO | D | 55 | 8.657 | -4.673 | -5.058 | 1.00 | 50.75 | D |
| ATOM | 10365 | N | SER | D | 56 | 10.446 | -5.983 | -5.521 | 1.00 | 52.96 | D |
| ATOM | 10366 | CA | SER | D | 56 | 9.900 | -7.247 | -4.973 | 1.00 | 53.80 | D |
| ATOM | 10368 | CB | SER | D | 56 | 10.995 | -8.333 | -4.874 | 1.00 | 53.95 | D |
| ATOM | 10371 | OG | SER | D | 56 | 11.925 | -8.273 | -5.943 | 1.00 | 54.80 | D |
| ATOM | 10373 | C | SER | D | 56 | 9.305 | -7.096 | -3.587 | 1.00 | 54.35 | D |
| ATOM | 10374 | O | SER | D | 56 | 8.216 | -7.597 | -3.307 | 1.00 | 54.14 | D |
| ATOM | 10376 | N | ALA | D | 57 | 10.058 | -6.428 | -2.716 | 1.00 | 54.97 | D |
| ATOM | 10377 | CA | ALA | D | 57 | 9.701 | -6.323 | -1.313 | 1.00 | 55.49 | D |
| ATOM | 10379 | CB | ALA | D | 57 | 10.908 | -5.857 | -0.489 | 1.00 | 55.73 | D |
| ATOM | 10383 | C | ALA | D | 57 | 8.520 | -5.391 | -1.096 | 1.00 | 55.86 | D |

FIG 8 – CONT.

| | | | | | | | | | |
|---|---|---|---|---|---|---|---|---|---|
| ATOM | 10384 | O | ALA | D | 57 | 7.861 | -5.481 | -0.064 | 1.00 56.55 | D |
| ATOM | 10386 | N | ILE | D | 58 | 8.245 | -4.507 | -2.055 | 1.00 56.26 | D |
| ATOM | 10387 | CA | ILE | D | 58 | 7.140 | -3.552 | -1.930 | 1.00 56.81 | D |
| ATOM | 10389 | CB | ILE | D | 58 | 7.307 | -2.366 | -2.907 | 1.00 56.63 | D |
| ATOM | 10391 | CG1 | ILE | D | 58 | 8.672 | -1.695 | -2.709 | 1.00 57.32 | D |
| ATOM | 10394 | CD1 | ILE | D | 58 | 9.083 | -1.468 | -1.244 | 1.00 56.86 | D |
| ATOM | 10398 | CG2 | ILE | D | 58 | 6.176 | -1.354 | -2.748 | 1.00 55.95 | D |
| ATOM | 10402 | C | ILE | D | 58 | 5.778 | -4.242 | -2.156 | 1.00 57.41 | D |
| ATOM | 10403 | O | ILE | D | 58 | 5.572 | -4.865 | -3.205 | 1.00 58.33 | D |
| ATOM | 10405 | N | PRO | D | 59 | 4.859 | -4.160 | -1.165 | 1.00 57.52 | D |
| ATOM | 10406 | CA | PRO | D | 59 | 3.544 | -4.796 | -1.332 | 1.00 57.42 | D |
| ATOM | 10408 | CB | PRO | D | 59 | 2.946 | -4.779 | 0.092 | 1.00 57.70 | D |
| ATOM | 10411 | CG | PRO | D | 59 | 3.685 | -3.700 | 0.823 | 1.00 57.32 | D |
| ATOM | 10414 | CD | PRO | D | 59 | 5.067 | -3.669 | 0.216 | 1.00 57.54 | D |
| ATOM | 10417 | C | PRO | D | 59 | 2.603 | -4.088 | -2.299 | 1.00 57.40 | D |
| ATOM | 10418 | O | PRO | D | 59 | 2.780 | -2.915 | -2.608 | 1.00 57.14 | D |
| ATOM | 10419 | N | ASP | D | 60 | 1.568 | -4.820 | -2.694 | 1.00 57.50 | D |
| ATOM | 10420 | CA | ASP | D | 60 | 0.619 | -4.439 | -3.743 | 1.00 57.75 | D |
| ATOM | 10422 | CB | ASP | D | 60 | -0.443 | -5.538 | -3.918 | 1.00 58.29 | D |
| ATOM | 10425 | CG | ASP | D | 60 | 0.110 | -6.955 | -3.692 | 1.00 60.37 | D |
| ATOM | 10426 | OD1 | ASP | D | 60 | 1.144 | -7.100 | -2.985 | 1.00 62.26 | D |
| ATOM | 10427 | OD2 | ASP | D | 60 | -0.509 | -7.926 | -4.209 | 1.00 62.89 | D |
| ATOM | 10428 | C | ASP | D | 60 | -0.115 | -3.135 | -3.458 | 1.00 57.23 | D |
| ATOM | 10429 | O | ASP | D | 60 | -0.544 | -2.444 | -4.378 | 1.00 57.16 | D |
| ATOM | 10431 | N | ARG | D | 61 | -0.261 | -2.821 | -2.174 | 1.00 56.70 | D |
| ATOM | 10432 | CA | ARG | D | 61 | -1.005 | -1.654 | -1.703 | 1.00 55.89 | D |
| ATOM | 10434 | CB | ARG | D | 61 | -0.994 | -1.635 | -0.170 | 1.00 56.32 | D |
| ATOM | 10437 | CG | ARG | D | 61 | -1.623 | -2.888 | 0.454 | 1.00 57.52 | D |
| ATOM | 10440 | CD | ARG | D | 61 | -1.668 | -2.848 | 1.984 | 1.00 58.67 | D |
| ATOM | 10443 | NE | ARG | D | 61 | -0.346 | -2.756 | 2.622 | 1.00 58.67 | D |

FIG 8 – CONT.

| ATOM | 10445 | CZ | ARG | D | 61 | 0.184 | -1.643 | 3.144 | 1.00 | 58.38 | D |
|------|-------|-----|-----|---|----|-------|--------|-------|------|-------|---|
| ATOM | 10446 | NH1 | ARG | D | 61 | -0.454 | -0.470 | 3.114 | 1.00 | 56.72 | D |
| ATOM | 10449 | NH2 | ARG | D | 61 | 1.380 | -1.703 | 3.707 | 1.00 | 59.71 | D |
| ATOM | 10452 | C | ARG | D | 61 | -0.483 | -0.329 | -2.262 | 1.00 | 54.56 | D |
| ATOM | 10453 | O | ARG | D | 61 | -1.233 | 0.640 | -2.389 | 1.00 | 54.41 | D |
| ATOM | 10455 | N | PHE | D | 62 | 0.798 | -0.301 | -2.613 | 1.00 | 53.31 | D |
| ATOM | 10456 | CA | PHE | D | 62 | 1.410 | 0.877 | -3.232 | 1.00 | 52.29 | D |
| ATOM | 10458 | CB | PHE | D | 62 | 2.872 | 1.004 | -2.803 | 1.00 | 52.41 | D |
| ATOM | 10461 | CG | PHE | D | 62 | 3.045 | 1.260 | -1.337 | 1.00 | 51.94 | D |
| ATOM | 10462 | CD1 | PHE | D | 62 | 3.094 | 2.556 | -0.849 | 1.00 | 51.72 | D |
| ATOM | 10464 | CE1 | PHE | D | 62 | 3.234 | 2.793 | 0.513 | 1.00 | 52.62 | D |
| ATOM | 10466 | CZ | PHE | D | 62 | 3.324 | 1.731 | 1.398 | 1.00 | 51.35 | D |
| ATOM | 10468 | CE2 | PHE | D | 62 | 3.279 | 0.454 | 0.927 | 1.00 | 53.01 | D |
| ATOM | 10470 | CD2 | PHE | D | 62 | 3.130 | 0.216 | -0.448 | 1.00 | 52.36 | D |
| ATOM | 10472 | C | PHE | D | 62 | 1.346 | 0.766 | -4.740 | 1.00 | 51.73 | D |
| ATOM | 10473 | O | PHE | D | 62 | 1.578 | -0.294 | -5.299 | 1.00 | 50.85 | D |
| ATOM | 10475 | N | SER | D | 63 | 1.039 | 1.869 | -5.400 | 1.00 | 50.98 | D |
| ATOM | 10476 | CA | SER | D | 63 | 0.918 | 1.855 | -6.832 | 1.00 | 50.81 | D |
| ATOM | 10478 | CB | SER | D | 63 | -0.509 | 1.431 | -7.227 | 1.00 | 51.26 | D |
| ATOM | 10481 | OG | SER | D | 63 | -1.485 | 2.385 | -6.799 | 1.00 | 51.55 | D |
| ATOM | 10483 | C | SER | D | 63 | 1.250 | 3.229 | -7.369 | 1.00 | 50.42 | D |
| ATOM | 10484 | O | SER | D | 63 | 1.283 | 4.204 | -6.611 | 1.00 | 49.66 | D |
| ATOM | 10486 | N | GLY | D | 64 | 1.507 | 3.302 | -8.672 | 1.00 | 50.14 | D |
| ATOM | 10487 | CA | GLY | D | 64 | 1.803 | 4.571 | -9.328 | 1.00 | 50.31 | D |
| ATOM | 10490 | C | GLY | D | 64 | 1.255 | 4.662 | -10.740 | 1.00 | 50.55 | D |
| ATOM | 10491 | O | GLY | D | 64 | 1.005 | 3.648 | -11.394 | 1.00 | 50.80 | D |
| ATOM | 10493 | N | SER | D | 65 | 1.069 | 5.887 | -11.210 | 1.00 | 50.65 | D |
| ATOM | 10494 | CA | SER | D | 65 | 0.684 | 6.126 | -12.584 | 1.00 | 50.86 | D |
| ATOM | 10496 | CB | SER | D | 65 | -0.841 | 6.150 | -12.718 | 1.00 | 50.88 | D |
| ATOM | 10499 | OG | SER | D | 65 | -1.431 | 7.097 | -11.850 | 1.00 | 50.60 | D |
| ATOM | 10501 | C | SER | D | 65 | 1.282 | 7.449 | -13.013 | 1.00 | 51.09 | D |

FIG 8 – CONT.

| | | | | | | | | | | |
|---|---|---|---|---|---|---|---|---|---|---|
| ATOM | 10502 | O | SER | D | 65 | 1.672 | 8.250 | -12.177 | 1.00 50.81 | O D |
| ATOM | 10504 | N | LYS | D | 66 | 1.379 | 7.655 | -14.322 | 1.00 51.45 | N D |
| ATOM | 10505 | CA | LYS | D | 66 | 1.837 | 8.915 | -14.881 | 1.00 51.52 | C D |
| ATOM | 10507 | CB | LYS | D | 66 | 3.257 | 8.793 | -15.444 | 1.00 51.27 | C D |
| ATOM | 10510 | CG | LYS | D | 66 | 3.750 | 10.025 | -16.218 | 1.00 50.67 | C D |
| ATOM | 10513 | CD | LYS | D | 66 | 5.094 | 9.775 | -16.915 | 1.00 50.91 | C D |
| ATOM | 10516 | CE | LYS | D | 66 | 5.087 | 10.256 | -18.368 | 1.00 50.43 | C D |
| ATOM | 10519 | NZ | LYS | D | 66 | 6.337 | 9.903 | -19.103 | 1.00 48.61 | N D |
| ATOM | 10523 | C | LYS | D | 66 | 0.871 | 9.296 | -15.982 | 1.00 52.00 | C D |
| ATOM | 10524 | O | LYS | D | 66 | 0.419 | 8.443 | -16.747 | 1.00 52.37 | O D |
| ATOM | 10526 | N | SER | D | 67 | 0.551 | 10.582 | -16.056 | 1.00 52.49 | N D |
| ATOM | 10527 | CA | SER | D | 67 | -0.269 | 11.094 | -17.136 | 1.00 52.62 | C D |
| ATOM | 10529 | CB | SER | D | 67 | -1.744 | 11.077 | -16.743 | 1.00 52.95 | C D |
| ATOM | 10532 | OG | SER | D | 67 | -2.515 | 11.877 | -17.634 | 1.00 54.93 | O D |
| ATOM | 10534 | C | SER | D | 67 | 0.180 | 12.503 | -17.440 | 1.00 52.25 | C D |
| ATOM | 10535 | O | SER | D | 67 | 0.063 | 13.384 | -16.597 | 1.00 52.40 | O D |
| ATOM | 10537 | N | GLY | D | 68 | 0.692 | 12.698 | -18.653 | 1.00 51.73 | N D |
| ATOM | 10538 | CA | GLY | D | 68 | 1.186 | 13.982 | -19.092 | 1.00 51.36 | C D |
| ATOM | 10541 | C | GLY | D | 68 | 2.406 | 14.357 | -18.274 | 1.00 51.49 | C D |
| ATOM | 10542 | O | GLY | D | 68 | 3.398 | 13.598 | -18.208 | 1.00 51.55 | O D |
| ATOM | 10544 | N | THR | D | 69 | 2.318 | 15.524 | -17.642 | 1.00 51.16 | N D |
| ATOM | 10545 | CA | THR | D | 69 | 3.369 | 16.064 | -16.790 | 1.00 50.70 | C D |
| ATOM | 10547 | CB | THR | D | 69 | 3.491 | 17.571 | -17.019 | 1.00 50.77 | C D |
| ATOM | 10549 | OG1 | THR | D | 69 | 2.200 | 18.166 | -16.866 | 1.00 51.14 | O D |
| ATOM | 10551 | CG2 | THR | D | 69 | 4.029 | 17.862 | -18.427 | 1.00 51.43 | C D |
| ATOM | 10555 | C | THR | D | 69 | 3.063 | 15.786 | -15.312 | 1.00 50.13 | C D |
| ATOM | 10556 | O | THR | D | 69 | 3.629 | 16.417 | -14.422 | 1.00 49.97 | O D |
| ATOM | 10558 | N | SER | D | 70 | 2.174 | 14.828 | -15.056 | 1.00 49.69 | N D |
| ATOM | 10559 | CA | SER | D | 70 | 1.795 | 14.488 | -13.700 | 1.00 49.28 | C D |
| ATOM | 10561 | CB | SER | D | 70 | 0.343 | 14.868 | -13.425 | 1.00 49.59 | C D |

FIG 8 – CONT.

| | | | | | | | | | | |
|---|---|---|---|---|---|---|---|---|---|---|
| ATOM | 10564 | OG | SER | D | 70 | 0.158 | 16.248 | -13.637 | 1.00 50.20 | D O |
| ATOM | 10566 | C | SER | D | 70 | 1.926 | 13.010 | -13.462 | 1.00 48.48 | D C |
| ATOM | 10567 | O | SER | D | 70 | 1.836 | 12.200 | -14.377 | 1.00 48.48 | D O |
| ATOM | 10569 | N | ALA | D | 71 | 2.109 | 12.676 | -12.196 | 1.00 47.46 | D N |
| ATOM | 10570 | CA | ALA | D | 71 | 2.071 | 11.308 | -11.743 | 1.00 46.99 | D C |
| ATOM | 10572 | CB | ALA | D | 71 | 3.496 | 10.709 | -11.680 | 1.00 46.96 | D C |
| ATOM | 10576 | C | ALA | D | 71 | 1.436 | 11.336 | -10.379 | 1.00 46.14 | D C |
| ATOM | 10577 | O | ALA | D | 71 | 1.313 | 12.396 | -9.764 | 1.00 46.02 | D O |
| ATOM | 10579 | N | THR | D | 72 | 1.006 | 10.183 | -9.916 | 1.00 45.53 | D N |
| ATOM | 10580 | CA | THR | D | 72 | 0.430 | 10.107 | -8.606 | 1.00 45.63 | D C |
| ATOM | 10582 | CB | THR | D | 72 | -1.130 | 10.368 | -8.606 | 1.00 46.04 | D C |
| ATOM | 10584 | OG1 | THR | D | 72 | -1.831 | 9.205 | -8.155 | 1.00 45.80 | D O |
| ATOM | 10586 | CG2 | THR | D | 72 | -1.640 | 10.820 | -9.976 | 1.00 45.08 | D C |
| ATOM | 10590 | C | THR | D | 72 | 0.759 | 8.746 | -8.033 | 1.00 45.80 | D C |
| ATOM | 10591 | O | THR | D | 72 | 0.808 | 7.750 | -8.750 | 1.00 45.32 | D O |
| ATOM | 10593 | N | LEU | D | 73 | 1.020 | 8.732 | -6.737 | 1.00 45.70 | D N |
| ATOM | 10594 | CA | LEU | D | 73 | 1.279 | 7.522 | -6.011 | 1.00 45.69 | D C |
| ATOM | 10596 | CB | LEU | D | 73 | 2.373 | 7.744 | -4.956 | 1.00 45.23 | D C |
| ATOM | 10599 | CG | LEU | D | 73 | 2.531 | 6.679 | -3.871 | 1.00 43.28 | D C |
| ATOM | 10601 | CD1 | LEU | D | 73 | 3.279 | 5.488 | -4.357 | 1.00 42.17 | D C |
| ATOM | 10605 | CD2 | LEU | D | 73 | 3.269 | 7.281 | -2.703 | 1.00 45.50 | D C |
| ATOM | 10609 | C | LEU | D | 73 | -0.016 | 7.142 | -5.339 | 1.00 46.38 | D C |
| ATOM | 10610 | O | LEU | D | 73 | -0.769 | 8.004 | -4.917 | 1.00 47.36 | D O |
| ATOM | 10612 | N | GLY | D | 74 | -0.261 | 5.847 | -5.229 | 1.00 47.11 | D N |
| ATOM | 10613 | CA | GLY | D | 74 | -1.442 | 5.350 | -4.565 | 1.00 47.75 | D C |
| ATOM | 10616 | C | GLY | D | 74 | -1.059 | 4.389 | -3.477 | 1.00 48.35 | D C |
| ATOM | 10617 | O | GLY | D | 74 | -0.175 | 3.546 | -3.679 | 1.00 47.97 | D O |
| ATOM | 10619 | N | ILE | D | 75 | -1.707 | 4.545 | -2.322 | 1.00 49.18 | D N |
| ATOM | 10620 | CA | ILE | D | 75 | -1.532 | 3.664 | -1.184 | 1.00 50.25 | D C |
| ATOM | 10622 | CB | ILE | D | 75 | -0.765 | 4.358 | -0.019 | 1.00 50.62 | D C |
| ATOM | 10624 | CG1 | ILE | D | 75 | 0.500 | 5.074 | -0.531 | 1.00 50.39 | D |

FIG 8 – CONT.

| | | | | | | | | | | |
|---|---|---|---|---|---|---|---|---|---|---|
| ATOM | 10627 | CD1 | ILE | D | 75 | 1.217 | 5.925 | 0.512 | 1.00 50.03 | D C |
| ATOM | 10631 | CG2 | ILE | D | 75 | -0.434 | 3.344 | 1.080 | 1.00 49.20 | D C |
| ATOM | 10635 | C | ILE | D | 75 | -2.933 | 3.315 | -0.713 | 1.00 51.54 | D C |
| ATOM | 10636 | O | ILE | D | 75 | -3.761 | 4.210 | -0.519 | 1.00 52.06 | D O |
| ATOM | 10638 | N | THR | D | 76 | -3.200 | 2.029 | -0.542 | 1.00 52.92 | D N |
| ATOM | 10639 | CA | THR | D | 76 | -4.520 | 1.546 | -0.137 | 1.00 54.18 | D C |
| ATOM | 10641 | CB | THR | D | 76 | -5.197 | 0.646 | -1.227 | 1.00 54.40 | D C |
| ATOM | 10643 | OG1 | THR | D | 76 | -4.729 | -0.707 | -1.092 | 1.00 53.25 | D O |
| ATOM | 10645 | CG2 | THR | D | 76 | -4.940 | 1.178 | -2.658 | 1.00 53.63 | D C |
| ATOM | 10649 | C | THR | D | 76 | -4.344 | 0.704 | 1.106 | 1.00 55.14 | D C |
| ATOM | 10650 | O | THR | D | 76 | -3.248 | 0.238 | 1.380 | 1.00 55.35 | D O |
| ATOM | 10652 | N | GLY | D | 77 | -5.430 | 0.488 | 1.841 | 1.00 56.48 | D N |
| ATOM | 10653 | CA | GLY | D | 77 | -5.362 | -0.239 | 3.105 | 1.00 57.16 | D C |
| ATOM | 10656 | C | GLY | D | 77 | -4.323 | 0.369 | 4.028 | 1.00 57.68 | D C |
| ATOM | 10657 | O | GLY | D | 77 | -3.451 | -0.346 | 4.536 | 1.00 58.02 | D O |
| ATOM | 10659 | N | LEU | D | 78 | -4.409 | 1.688 | 4.224 | 1.00 58.32 | D N |
| ATOM | 10660 | CA | LEU | D | 78 | -3.471 | 2.426 | 5.096 | 1.00 58.74 | D C |
| ATOM | 10662 | CB | LEU | D | 78 | -3.956 | 3.831 | 5.408 | 1.00 58.75 | D C |
| ATOM | 10665 | CG | LEU | D | 78 | -3.441 | 4.959 | 4.534 | 1.00 59.84 | D C |
| ATOM | 10667 | CD1 | LEU | D | 78 | -3.954 | 4.778 | 3.103 | 1.00 60.30 | D C |
| ATOM | 10671 | CD2 | LEU | D | 78 | -3.875 | 6.305 | 5.121 | 1.00 58.71 | D C |
| ATOM | 10675 | C | LEU | D | 78 | -3.296 | 1.743 | 6.421 | 1.00 59.11 | D C |
| ATOM | 10676 | O | LEU | D | 78 | -4.262 | 1.245 | 7.010 | 1.00 59.21 | D O |
| ATOM | 10678 | N | GLN | D | 79 | -2.056 | 1.728 | 6.885 | 1.00 59.08 | D N |
| ATOM | 10679 | CA | GLN | D | 79 | -1.748 | 1.217 | 8.193 | 1.00 59.22 | D C |
| ATOM | 10681 | CB | GLN | D | 79 | -0.954 | -0.069 | 8.103 | 1.00 59.31 | D C |
| ATOM | 10684 | CG | GLN | D | 79 | -1.463 | -1.061 | 7.100 | 1.00 60.09 | D C |
| ATOM | 10687 | CD | GLN | D | 79 | -0.530 | -2.225 | 7.013 | 1.00 60.47 | D C |
| ATOM | 10688 | OE1 | GLN | D | 79 | 0.531 | -2.210 | 7.643 | 1.00 60.66 | D O |
| ATOM | 10689 | NE2 | GLN | D | 79 | -0.894 | -3.237 | 6.226 | 1.00 59.85 | D N |

FIG 8 – CONT.

| ATOM | 10692 | C   | GLN | D | 79 | -0.905 | 2.243 | 8.918  | 1.00 | 59.06 | D | C |
| --- | --- | --- | --- | --- | --- | --- | --- | --- | --- | --- | --- | --- |
| ATOM | 10693 | O   | GLN | D | 79 | -0.465 | 3.248 | 8.334  | 1.00 | 59.37 | D | O |
| ATOM | 10695 | N   | THR | D | 80 | -0.673 | 1.957 | 10.193 | 1.00 | 58.27 | D | N |
| ATOM | 10696 | CA  | THR | D | 80 | 0.179  | 2.778 | 11.016 | 1.00 | 57.65 | D | C |
| ATOM | 10698 | CB  | THR | D | 80 | 0.189  | 2.264 | 12.487 | 1.00 | 57.69 | D | C |
| ATOM | 10700 | OG1 | THR | D | 80 | 0.794  | 3.255 | 13.327 | 1.00 | 60.07 | D | O |
| ATOM | 10702 | CG2 | THR | D | 80 | 0.949  | 0.929 | 12.630 | 1.00 | 57.43 | D | C |
| ATOM | 10706 | C   | THR | D | 80 | 1.594  | 2.786 | 10.415 | 1.00 | 56.30 | D | C |
| ATOM | 10707 | O   | THR | D | 80 | 2.224  | 3.841 | 10.317 | 1.00 | 56.19 | D | O |
| ATOM | 10709 | N   | GLY | D | 81 | 2.052  | 1.612 | 9.972  | 1.00 | 54.82 | D | N |
| ATOM | 10710 | CA  | GLY | D | 81 | 3.373  | 1.448 | 9.377  | 1.00 | 53.48 | D | C |
| ATOM | 10713 | C   | GLY | D | 81 | 3.749  | 2.390 | 8.237  | 1.00 | 51.96 | D | C |
| ATOM | 10714 | O   | GLY | D | 81 | 4.928  | 2.645 | 8.034  | 1.00 | 52.16 | D | O |
| ATOM | 10716 | N   | ASP | D | 82 | 2.773  | 2.918 | 7.505  | 1.00 | 50.08 | D | N |
| ATOM | 10717 | CA  | ASP | D | 82 | 3.056  | 3.681 | 6.277  | 1.00 | 48.87 | D | C |
| ATOM | 10719 | CB  | ASP | D | 82 | 1.860  | 3.626 | 5.313  | 1.00 | 48.71 | D | C |
| ATOM | 10722 | CG  | ASP | D | 82 | 1.385  | 2.198 | 5.013  | 1.00 | 49.11 | D | C |
| ATOM | 10723 | OD1 | ASP | D | 82 | 2.096  | 1.219 | 5.314  | 1.00 | 49.49 | D | O |
| ATOM | 10724 | OD2 | ASP | D | 82 | 0.267  | 2.067 | 4.473  | 1.00 | 51.18 | D | O |
| ATOM | 10725 | C   | ASP | D | 82 | 3.409  | 5.154 | 6.522  | 1.00 | 48.00 | D | C |
| ATOM | 10726 | O   | ASP | D | 82 | 3.697  | 5.904 | 5.567  | 1.00 | 46.89 | D | O |
| ATOM | 10728 | N   | GLU | D | 83 | 3.364  | 5.565 | 7.791  | 1.00 | 46.73 | D | N |
| ATOM | 10729 | CA  | GLU | D | 83 | 3.661  | 6.944 | 8.196  | 1.00 | 46.05 | D | C |
| ATOM | 10731 | CB  | GLU | D | 83 | 3.398  | 7.105 | 9.708  | 1.00 | 46.66 | D | C |
| ATOM | 10734 | CG  | GLU | D | 83 | 2.831  | 8.463 | 10.147 | 1.00 | 49.27 | D | C |
| ATOM | 10737 | CD  | GLU | D | 83 | 2.023  | 8.384 | 11.468 | 1.00 | 51.64 | D | C |
| ATOM | 10738 | OE1 | GLU | D | 83 | 2.273  | 7.464 | 12.286 | 1.00 | 53.81 | D | O |
| ATOM | 10739 | OE2 | GLU | D | 83 | 1.115  | 9.230 | 11.660 | 1.00 | 53.28 | D | O |
| ATOM | 10740 | C   | GLU | D | 83 | 5.127  | 7.258 | 7.846  | 1.00 | 43.83 | D | C |
| ATOM | 10741 | O   | GLU | D | 83 | 6.022  | 6.556 | 8.273  | 1.00 | 42.86 | D | O |
| ATOM | 10743 | N   | ALA | D | 84 | 5.342  | 8.294 | 7.037  | 1.00 | 42.35 | D |   |

FIG 8 – CONT.

| | | | | | | | | | | |
|---|---|---|---|---|---|---|---|---|---|---|
| ATOM | 10744 | CA | ALA | D | 84 | 6.627 | 8.506 | 6.365 | 1.00 41.46 | D N |
| ATOM | 10746 | CB | ALA | D | 84 | 7.054 | 7.246 | 5.616 | 1.00 40.92 | D C |
| ATOM | 10750 | C | ALA | D | 84 | 6.572 | 9.670 | 5.401 | 1.00 40.52 | D C |
| ATOM | 10751 | O | ALA | D | 84 | 5.527 | 10.266 | 5.176 | 1.00 40.52 | D O |
| ATOM | 10753 | N | ASP | D | 85 | 7.723 | 9.987 | 4.830 | 1.00 39.43 | D N |
| ATOM | 10754 | CA | ASP | D | 85 | 7.806 | 10.990 | 3.808 | 1.00 38.55 | D C |
| ATOM | 10756 | CB | ASP | D | 85 | 9.018 | 11.883 | 4.065 | 1.00 38.42 | D C |
| ATOM | 10759 | CG | ASP | D | 85 | 8.794 | 12.879 | 5.204 | 1.00 39.98 | D C |
| ATOM | 10760 | OD1 | ASP | D | 85 | 7.620 | 13.244 | 5.459 | 1.00 42.64 | D O |
| ATOM | 10761 | OD2 | ASP | D | 85 | 9.788 | 13.322 | 5.812 | 1.00 37.53 | D O |
| ATOM | 10762 | C | ASP | D | 85 | 7.923 | 10.289 | 2.456 | 1.00 37.58 | D C |
| ATOM | 10763 | O | ASP | D | 85 | 8.678 | 9.335 | 2.310 | 1.00 37.32 | D O |
| ATOM | 10765 | N | TYR | D | 86 | 7.204 | 10.812 | 1.474 | 1.00 36.66 | D N |
| ATOM | 10766 | CA | TYR | D | 86 | 7.125 | 10.244 | 0.156 | 1.00 36.06 | D C |
| ATOM | 10768 | CB | TYR | D | 86 | 5.691 | 9.787 | -0.117 | 1.00 36.39 | D C |
| ATOM | 10771 | CG | TYR | D | 86 | 5.305 | 8.623 | 0.748 | 1.00 35.96 | D C |
| ATOM | 10772 | CD1 | TYR | D | 86 | 5.659 | 7.352 | 0.392 | 1.00 33.69 | D C |
| ATOM | 10774 | CE1 | TYR | D | 86 | 5.325 | 6.273 | 1.171 | 1.00 36.08 | D C |
| ATOM | 10776 | CZ | TYR | D | 86 | 4.639 | 6.455 | 2.364 | 1.00 34.99 | D C |
| ATOM | 10777 | OH | TYR | D | 86 | 4.339 | 5.346 | 3.115 | 1.00 34.59 | D O |
| ATOM | 10779 | CE2 | TYR | D | 86 | 4.280 | 7.719 | 2.769 | 1.00 34.41 | D C |
| ATOM | 10781 | CD2 | TYR | D | 86 | 4.623 | 8.807 | 1.961 | 1.00 37.03 | D C |
| ATOM | 10783 | C | TYR | D | 86 | 7.523 | 11.276 | -0.850 | 1.00 35.89 | D C |
| ATOM | 10784 | O | TYR | D | 86 | 6.965 | 12.365 | -0.876 | 1.00 35.81 | D O |
| ATOM | 10786 | N | TYR | D | 87 | 8.476 | 10.899 | -1.696 | 1.00 35.68 | D N |
| ATOM | 10787 | CA | TYR | D | 87 | 9.048 | 11.769 | -2.693 | 1.00 35.58 | D C |
| ATOM | 10789 | CB | TYR | D | 87 | 10.547 | 11.900 | -2.429 | 1.00 34.87 | D C |
| ATOM | 10792 | CG | TYR | D | 87 | 10.918 | 12.637 | -1.161 | 1.00 31.39 | D C |
| ATOM | 10793 | CD1 | TYR | D | 87 | 11.160 | 14.010 | -1.179 | 1.00 29.39 | D C |
| ATOM | 10795 | CE1 | TYR | D | 87 | 11.524 | 14.694 | -0.011 | 1.00 31.27 | D C |

FIG 8 – CONT.

| ATOM | 10797 | CZ | TYR | D | 87 | 11.653 | 13.989 | 1.173 | 1.00 | 30.60 | D |
|------|-------|-----|-----|---|----|--------|--------|-------|------|-------|---|
| C | | | | | | | | | | | |
| ATOM | 10798 | OH | TYR | D | 87 | 12.013 | 14.634 | 2.340 | 1.00 | 35.88 | D |
| O | | | | | | | | | | | |
| ATOM | 10800 | CE2 | TYR | D | 87 | 11.450 | 12.622 | 1.193 | 1.00 | 31.25 | D |
| C | | | | | | | | | | | |
| ATOM | 10802 | CD2 | TYR | D | 87 | 11.083 | 11.956 | 0.031 | 1.00 | 29.33 | D |
| C | | | | | | | | | | | |
| ATOM | 10804 | C | TYR | D | 87 | 8.889 | 11.163 | -4.096 | 1.00 | 36.66 | D |
| C | | | | | | | | | | | |
| ATOM | 10805 | O | TYR | D | 87 | 9.072 | 9.963 | -4.281 | 1.00 | 35.17 | D |
| O | | | | | | | | | | | |
| ATOM | 10807 | N | CYS | D | 88 | 8.583 | 11.999 | -5.076 | 1.00 | 37.88 | D |
| N | | | | | | | | | | | |
| ATOM | 10808 | CA | CYS | D | 88 | 8.621 | 11.552 | -6.452 | 1.00 | 39.63 | D |
| C | | | | | | | | | | | |
| ATOM | 10810 | CB | CYS | D | 88 | 7.456 | 12.091 | -7.295 | 1.00 | 40.24 | D |
| C | | | | | | | | | | | |
| ATOM | 10813 | SG | CYS | D | 88 | 7.301 | 13.896 | -7.274 | 1.00 | 43.57 | D |
| S | | | | | | | | | | | |
| ATOM | 10815 | C | CYS | D | 88 | 9.916 | 12.066 | -6.995 | 1.00 | 39.60 | D |
| C | | | | | | | | | | | |
| ATOM | 10816 | O | CYS | D | 88 | 10.494 | 13.006 | -6.461 | 1.00 | 39.61 | D |
| O | | | | | | | | | | | |
| ATOM | 10818 | N | GLY | D | 89 | 10.372 | 11.418 | -8.057 | 1.00 | 40.26 | D |
| N | | | | | | | | | | | |
| ATOM | 10819 | CA | GLY | D | 89 | 11.554 | 11.841 | -8.775 | 1.00 | 40.16 | D |
| C | | | | | | | | | | | |
| ATOM | 10822 | C | GLY | D | 89 | 11.483 | 11.380 | -10.200 | 1.00 | 39.68 | D |
| C | | | | | | | | | | | |
| ATOM | 10823 | O | GLY | D | 89 | 10.719 | 10.500 | -10.525 | 1.00 | 40.12 | D |
| O | | | | | | | | | | | |
| ATOM | 10825 | N | THR | D | 90 | 12.274 | 12.005 | -11.051 | 1.00 | 39.91 | D |
| N | | | | | | | | | | | |
| ATOM | 10826 | CA | THR | D | 90 | 12.352 | 11.618 | -12.440 | 1.00 | 40.09 | D |
| C | | | | | | | | | | | |
| ATOM | 10828 | CB | THR | D | 90 | 11.149 | 12.195 | -13.285 | 1.00 | 40.47 | D |
| C | | | | | | | | | | | |
| ATOM | 10830 | OG1 | THR | D | 90 | 11.174 | 11.643 | -14.611 | 1.00 | 40.57 | D |
| O | | | | | | | | | | | |
| ATOM | 10832 | CG2 | THR | D | 90 | 11.205 | 13.741 | -13.380 | 1.00 | 39.21 | D |
| C | | | | | | | | | | | |
| ATOM | 10836 | C | THR | D | 90 | 13.685 | 12.136 | -12.927 | 1.00 | 40.28 | D |
| C | | | | | | | | | | | |
| ATOM | 10837 | O | THR | D | 90 | 14.548 | 12.471 | -12.092 | 1.00 | 39.63 | D |
| O | | | | | | | | | | | |
| ATOM | 10839 | N | TRP | D | 91 | 13.846 | 12.188 | -14.261 | 1.00 | 39.91 | D |
| N | | | | | | | | | | | |
| ATOM | 10840 | CA | TRP | D | 91 | 15.007 | 12.800 | -14.914 | 1.00 | 40.08 | D |
| C | | | | | | | | | | | |
| ATOM | 10842 | CB | TRP | D | 91 | 15.707 | 11.737 | -15.780 | 1.00 | 40.09 | D |
| C | | | | | | | | | | | |
| ATOM | 10845 | CG | TRP | D | 91 | 16.276 | 10.647 | -14.909 | 1.00 | 38.30 | D |
| C | | | | | | | | | | | |
| ATOM | 10846 | CD1 | TRP | D | 91 | 15.606 | 9.574 | -14.370 | 1.00 | 36.20 | D |
| C | | | | | | | | | | | |
| ATOM | 10848 | NE1 | TRP | D | 91 | 16.447 | 8.832 | -13.603 | 1.00 | 35.63 | D |
| N | | | | | | | | | | | |
| ATOM | 10850 | CE2 | TRP | D | 91 | 17.684 | 9.427 | -13.607 | 1.00 | 35.47 | D |
| C | | | | | | | | | | | |
| ATOM | 10851 | CD2 | TRP | D | 91 | 17.600 | 10.579 | -14.419 | 1.00 | 35.46 | D |

FIG 8 – CONT.

```
C
ATOM   10852  CE3 TRP D  91      18.741  11.354 -14.618  1.00 34.42      D
C
ATOM   10854  CZ3 TRP D  91      19.908  10.964 -14.007  1.00 35.37      D
C
ATOM   10856  CH2 TRP D  91      19.952   9.819 -13.192  1.00 31.90      D
C
ATOM   10858  CZ2 TRP D  91      18.857   9.044 -12.982  1.00 31.29      D
C
ATOM   10860  C   TRP D  91      14.593  14.015 -15.747  1.00 40.89      D
C
ATOM   10861  O   TRP D  91      13.426  14.133 -16.144  1.00 41.10      D
O
ATOM   10863  N   ASP D  92      15.522  14.939 -15.973  1.00 41.87      D
N
ATOM   10864  CA  ASP D  92      15.261  16.041 -16.872  1.00 43.13      D
C
ATOM   10866  CB  ASP D  92      15.504  17.391 -16.221  1.00 43.85      D
C
ATOM   10869  CG  ASP D  92      15.237  18.545 -17.191  1.00 45.28      D
C
ATOM   10870  OD1 ASP D  92      14.092  19.059 -17.198  1.00 47.08      D
O
ATOM   10871  OD2 ASP D  92      16.157  18.897 -17.975  1.00 48.00      D
O
ATOM   10872  C   ASP D  92      16.100  15.937 -18.139  1.00 43.83      D
C
ATOM   10873  O   ASP D  92      17.334  15.940 -18.086  1.00 43.72      D
O
ATOM   10875  N   SER D  93      15.411  15.905 -19.279  1.00 44.46      D
N
ATOM   10876  CA  SER D  93      16.047  15.695 -20.574  1.00 45.28      D
C
ATOM   10878  CB  SER D  93      15.003  15.339 -21.631  1.00 45.26      D
C
ATOM   10881  OG  SER D  93      14.554  14.001 -21.426  1.00 46.87      D
O
ATOM   10883  C   SER D  93      16.857  16.885 -21.036  1.00 45.64      D
C
ATOM   10884  O   SER D  93      17.827  16.706 -21.754  1.00 46.24      D
O
ATOM   10886  N   ARG D  94      16.480  18.095 -20.632  1.00 46.04      D
N
ATOM   10887  CA  ARG D  94      17.248  19.277 -21.028  1.00 46.36      D
C
ATOM   10889  CB  ARG D  94      16.445  20.580 -20.837  1.00 46.66      D
C
ATOM   10898  C   ARG D  94      18.568  19.325 -20.255  1.00 46.19      D
C
ATOM   10899  O   ARG D  94      19.625  19.579 -20.845  1.00 46.59      D
O
ATOM   10901  N   LEU D  95      18.518  19.072 -18.944  1.00 46.06      D
N
ATOM   10902  CA  LEU D  95      19.718  19.207 -18.073  1.00 45.31      D
C
ATOM   10904  CB  LEU D  95      19.309  19.735 -16.695  1.00 45.55      D
C
ATOM   10907  CG  LEU D  95      19.267  21.234 -16.312  1.00 45.87      D
C
ATOM   10909  CD1 LEU D  95      19.556  22.193 -17.450  1.00 46.37      D
C
```

FIG 8 – CONT.

| | | | | | | | | | | |
|---|---|---|---|---|---|---|---|---|---|---|
| ATOM | 10913 | CD2 | LEU | D | 95 | 17.920 | 21.540 | -15.653 | 1.00 45.57 | D C |
| ATOM | 10917 | C | LEU | D | 95 | 20.483 | 17.877 | -17.934 | 1.00 44.71 | D C |
| ATOM | 10918 | O | LEU | D | 95 | 21.694 | 17.860 | -17.769 | 1.00 45.54 | D O |
| ATOM | 10920 | N | GLY | D | 95A | 19.775 | 16.762 | -18.002 | 1.00 43.80 | D N |
| ATOM | 10921 | CA | GLY | D | 95A | 20.420 | 15.461 | -17.974 | 1.00 42.96 | D C |
| ATOM | 10924 | C | GLY | D | 95A | 20.815 | 15.017 | -16.580 | 1.00 42.36 | D C |
| ATOM | 10925 | O | GLY | D | 95A | 21.826 | 14.315 | -16.413 | 1.00 42.49 | D O |
| ATOM | 10927 | N | ILE | D | 95B | 20.013 | 15.412 | -15.586 | 1.00 41.07 | D N |
| ATOM | 10928 | CA | ILE | D | 95B | 20.213 | 15.028 | -14.194 | 1.00 39.41 | D C |
| ATOM | 10930 | CB | ILE | D | 95B | 20.728 | 16.227 | -13.373 | 1.00 39.90 | D C |
| ATOM | 10932 | CG1 | ILE | D | 95B | 19.626 | 17.306 | -13.219 | 1.00 39.80 | D C |
| ATOM | 10935 | CD1 | ILE | D | 95B | 20.100 | 18.638 | -12.620 | 1.00 38.35 | D C |
| ATOM | 10939 | CG2 | ILE | D | 95B | 22.051 | 16.744 | -14.017 | 1.00 39.84 | D C |
| ATOM | 10943 | C | ILE | D | 95B | 18.899 | 14.539 | -13.631 | 1.00 38.30 | D C |
| ATOM | 10944 | O | ILE | D | 95B | 17.866 | 14.754 | -14.246 | 1.00 37.72 | D O |
| ATOM | 10946 | N | ALA | D | 96 | 18.946 | 13.862 | -12.482 | 1.00 37.03 | D N |
| ATOM | 10947 | CA | ALA | D | 96 | 17.739 | 13.473 | -11.742 | 1.00 36.26 | D C |
| ATOM | 10949 | CB | ALA | D | 96 | 18.073 | 12.449 | -10.692 | 1.00 36.15 | D C |
| ATOM | 10953 | C | ALA | D | 96 | 17.122 | 14.676 | -11.059 | 1.00 35.64 | D C |
| ATOM | 10954 | O | ALA | D | 96 | 17.816 | 15.609 | -10.745 | 1.00 34.12 | D O |
| ATOM | 10956 | N | VAL | D | 97 | 15.820 | 14.615 | -10.796 | 1.00 35.97 | D N |
| ATOM | 10957 | CA | VAL | D | 97 | 15.128 | 15.637 | -10.032 | 1.00 36.36 | D C |
| ATOM | 10959 | CB | VAL | D | 97 | 14.381 | 16.667 | -10.923 | 1.00 36.79 | D C |
| ATOM | 10961 | CG1 | VAL | D | 97 | 15.371 | 17.600 | -11.629 | 1.00 36.74 | D C |
| ATOM | 10965 | CG2 | VAL | D | 97 | 13.467 | 15.966 | -11.928 | 1.00 37.40 | D C |
| ATOM | 10969 | C | VAL | D | 97 | 14.170 | 15.002 | -9.051 | 1.00 36.98 | D C |
| ATOM | 10970 | O | VAL | D | 97 | 13.774 | 13.852 | -9.203 | 1.00 36.89 | D O |
| ATOM | 10972 | N | PHE | D | 98 | 13.819 | 15.751 | -8.009 | 1.00 37.80 | D N |
| ATOM | 10973 | CA | PHE | D | 98 | 12.932 | 15.239 | -6.985 | 1.00 37.95 | D C |
| ATOM | 10975 | CB | PHE | D | 98 | 13.639 | 15.134 | -5.631 | 1.00 37.94 | D C |
| ATOM | 10978 | CG | PHE | D | 98 | 14.642 | 14.012 | -5.540 | 1.00 34.68 | D |

FIG 8 – CONT.

```
C
ATOM   10979  CD1  PHE D  98      14.225   12.706   -5.430  1.00 32.27        D
C
ATOM   10981  CE1  PHE D  98      15.124   11.689   -5.326  1.00 31.34        D
C
ATOM   10983  CZ   PHE D  98      16.474   11.964   -5.342  1.00 31.68        D
C
ATOM   10985  CE2  PHE D  98      16.905   13.254   -5.433  1.00 32.93        D
C
ATOM   10987  CD2  PHE D  98      15.986   14.277   -5.530  1.00 33.15        D
C
ATOM   10989  C    PHE D  98      11.795   16.192   -6.799  1.00 38.99        D
C
ATOM   10990  O    PHE D  98      11.911   17.380   -7.091  1.00 39.22        D
O
ATOM   10992  N    GLY D  99      10.707   15.670   -6.250  1.00 39.52        D
N
ATOM   10993  CA   GLY D  99       9.702   16.534   -5.657  1.00 40.03        D
C
ATOM   10996  C    GLY D  99      10.124   16.906   -4.256  1.00 39.81        D
C
ATOM   10997  O    GLY D  99      11.142   16.451   -3.773  1.00 39.12        D
O
ATOM   10999  N    GLY D 100       9.305   17.719   -3.605  1.00 40.22        D
N
ATOM   11000  CA   GLY D 100       9.651   18.325   -2.328  1.00 40.25        D
C
ATOM   11003  C    GLY D 100       9.257   17.501   -1.126  1.00 40.59        D
C
ATOM   11004  O    GLY D 100       9.504   17.903   -0.001  1.00 41.29        D
O
ATOM   11006  N    GLY D 101       8.639   16.354   -1.349  1.00 40.51        D
N
ATOM   11007  CA   GLY D 101       8.241   15.479   -0.259  1.00 40.56        D
C
ATOM   11010  C    GLY D 101       6.798   15.693    0.160  1.00 41.03        D
C
ATOM   11011  O    GLY D 101       6.263   16.807    0.074  1.00 40.76        D
O
ATOM   11013  N    THR D 102       6.170   14.619    0.613  1.00 41.27        D
N
ATOM   11014  CA   THR D 102       4.858   14.698    1.204  1.00 42.08        D
C
ATOM   11016  CB   THR D 102       3.784   14.105    0.300  1.00 41.86        D
C
ATOM   11018  OG1  THR D 102       3.777   14.805   -0.947  1.00 41.36        D
O
ATOM   11020  CG2  THR D 102       2.443   14.222    0.968  1.00 40.10        D
C
ATOM   11024  C    THR D 102       4.851   13.884    2.470  1.00 43.45        D
C
ATOM   11025  O    THR D 102       5.117   12.681    2.436  1.00 43.03        D
O
ATOM   11027  N    GLN D 103       4.542   14.544    3.583  1.00 44.87        D
N
ATOM   11028  CA   GLN D 103       4.424   13.852    4.860  1.00 46.57        D
C
ATOM   11030  CB   GLN D 103       4.654   14.788    6.062  1.00 46.87        D
C
ATOM   11033  CG   GLN D 103       4.774   14.022    7.408  1.00 49.00        D
C
```

FIG 8 – CONT.

| ATOM | 11036 | CD | GLN | D | 103 | 4.721 | 14.918 | 8.652 | 1.00 | 52.25 | D |
|---|---|---|---|---|---|---|---|---|---|---|---|
| ATOM | 11037 | OE1 | GLN | D | 103 | 4.056 | 15.962 | 8.665 | 1.00 | 55.91 | D |
| ATOM | 11038 | NE2 | GLN | D | 103 | 5.413 | 14.499 | 9.709 | 1.00 | 53.97 | D |
| ATOM | 11041 | C | GLN | D | 103 | 3.041 | 13.232 | 4.935 | 1.00 | 46.85 | D |
| ATOM | 11042 | O | GLN | D | 103 | 2.042 | 13.880 | 4.663 | 1.00 | 45.84 | D |
| ATOM | 11044 | N | LEU | D | 104 | 3.010 | 11.961 | 5.294 | 1.00 | 48.40 | D |
| ATOM | 11045 | CA | LEU | D | 104 | 1.772 | 11.226 | 5.390 | 1.00 | 49.61 | D |
| ATOM | 11047 | CB | LEU | D | 104 | 1.868 | 9.909 | 4.622 | 1.00 | 49.50 | D |
| ATOM | 11050 | CG | LEU | D | 104 | 0.633 | 8.980 | 4.597 | 1.00 | 50.41 | D |
| ATOM | 11052 | CD1 | LEU | D | 104 | 0.630 | 8.101 | 3.335 | 1.00 | 49.62 | D |
| ATOM | 11056 | CD2 | LEU | D | 104 | 0.543 | 8.083 | 5.855 | 1.00 | 49.72 | D |
| ATOM | 11060 | C | LEU | D | 104 | 1.494 | 10.983 | 6.859 | 1.00 | 50.28 | D |
| ATOM | 11061 | O | LEU | D | 104 | 2.316 | 10.400 | 7.560 | 1.00 | 50.71 | D |
| ATOM | 11063 | N | THR | D | 105 | 0.342 | 11.449 | 7.321 | 1.00 | 51.48 | D |
| ATOM | 11064 | CA | THR | D | 105 | -0.090 | 11.217 | 8.691 | 1.00 | 52.38 | D |
| ATOM | 11066 | CB | THR | D | 105 | -0.592 | 12.515 | 9.334 | 1.00 | 52.75 | D |
| ATOM | 11068 | OG1 | THR | D | 105 | 0.386 | 13.546 | 9.130 | 1.00 | 52.70 | D |
| ATOM | 11070 | CG2 | THR | D | 105 | -0.837 | 12.311 | 10.835 | 1.00 | 53.13 | D |
| ATOM | 11074 | C | THR | D | 105 | -1.216 | 10.214 | 8.640 | 1.00 | 52.91 | D |
| ATOM | 11075 | O | THR | D | 105 | -2.144 | 10.361 | 7.838 | 1.00 | 52.87 | D |
| ATOM | 11077 | N | VAL | D | 106 | -1.129 | 9.187 | 9.476 | 1.00 | 53.93 | D |
| ATOM | 11078 | CA | VAL | D | 106 | -2.203 | 8.205 | 9.595 | 1.00 | 54.84 | D |
| ATOM | 11080 | CB | VAL | D | 106 | -1.635 | 6.795 | 9.803 | 1.00 | 54.87 | D |
| ATOM | 11082 | CG1 | VAL | D | 106 | -2.714 | 5.856 | 10.319 | 1.00 | 55.86 | D |
| ATOM | 11086 | CG2 | VAL | D | 106 | -1.029 | 6.279 | 8.494 | 1.00 | 55.85 | D |
| ATOM | 11090 | C | VAL | D | 106 | -3.118 | 8.621 | 10.763 | 1.00 | 55.52 | D |
| ATOM | 11091 | O | VAL | D | 106 | -2.719 | 8.535 | 11.937 | 1.00 | 55.41 | D |
| ATOM | 11093 | N | LEU | D | 106A | -4.334 | 9.071 | 10.431 | 1.00 | 56.04 | D |
| ATOM | 11094 | CA | LEU | D | 106A | -5.261 | 9.653 | 11.429 | 1.00 | 56.61 | D |
| ATOM | 11096 | CB | LEU | D | 106A | -6.431 | 10.400 | 10.739 | 1.00 | 56.67 | D |
| ATOM | 11099 | CG | LEU | D | 106A | -6.049 | 11.714 | 10.026 | 1.00 | 57.60 | D |

FIG 8 – CONT.

```
ATOM  11101  CD1  LEU  D  106A   -7.233  12.344   9.261  1.00  57.67     C
ATOM  11105  CD2  LEU  D  106A   -5.434  12.740  10.995  1.00  57.57     C
ATOM  11109  C    LEU  D  106A   -5.810   8.672  12.472  1.00  56.47     C
ATOM  11110  O    LEU  D  106A   -5.662   7.448  12.362  1.00  56.34     O
ATOM  11112  N    GLY  D  107    -6.402   9.253  13.519  1.00  56.89     N
ATOM  11113  CA   GLY  D  107    -7.136   8.509  14.537  1.00  56.71     C
ATOM  11116  C    GLY  D  107    -6.304   7.822  15.601  1.00  56.68     C
ATOM  11117  O    GLY  D  107    -6.835   6.982  16.339  1.00  57.54     O
ATOM  11119  N    GLN  D  108    -5.012   8.143  15.699  1.00  56.26     N
ATOM  11120  CA   GLN  D  108    -4.237   7.697  16.859  1.00  55.43     C
ATOM  11122  CB   GLN  D  108    -2.729   7.855  16.643  1.00  55.87     C
ATOM  11129  C    GLN  D  108    -4.740   8.541  18.043  1.00  54.62     C
ATOM  11130  O    GLN  D  108    -5.111   9.714  17.860  1.00  53.34     O
ATOM  11132  N    PRO  D  109    -4.768   7.937  19.245  1.00  53.46     N
ATOM  11133  CA   PRO  D  109    -5.449   8.503  20.409  1.00  53.31     C
ATOM  11135  CB   PRO  D  109    -5.500   7.323  21.395  1.00  53.58     C
ATOM  11138  CG   PRO  D  109    -4.298   6.487  21.049  1.00  53.76     C
ATOM  11141  CD   PRO  D  109    -4.073   6.673  19.563  1.00  54.30     C
ATOM  11144  C    PRO  D  109    -4.732   9.698  21.037  1.00  52.06     C
ATOM  11145  O    PRO  D  109    -3.516   9.665  21.213  1.00  51.73     O
ATOM  11146  N    LYS  D  110    -5.486  10.740  21.370  1.00  50.71     N
ATOM  11147  CA   LYS  D  110    -4.898  11.900  22.037  1.00  50.05     C
ATOM  11149  CB   LYS  D  110    -5.923  12.999  22.291  1.00  50.22     C
ATOM  11152  CG   LYS  D  110    -6.203  13.863  21.069  1.00  52.22     C
ATOM  11155  CD   LYS  D  110    -7.372  14.824  21.305  1.00  54.89     C
ATOM  11158  CE   LYS  D  110    -7.031  15.913  22.343  1.00  56.16     C
ATOM  11161  NZ   LYS  D  110    -8.155  16.878  22.536  1.00  54.50     N
ATOM  11165  C    LYS  D  110    -4.218  11.514  23.341  1.00  48.52     C
ATOM  11166  O    LYS  D  110    -4.646  10.597  24.033  1.00  48.37     O
ATOM  11168  N    ALA  D  111    -3.108  12.190  23.623  1.00  47.23     N
```

FIG 8 – CONT.

| ATOM | 11169 | CA | ALA | D | 111 | -2.424 | 12.084 | 24.905 | 1.00 | 46.10 | D C |
| --- | --- | --- | --- | --- | --- | --- | --- | --- | --- | --- | --- |
| ATOM | 11171 | CB | ALA | D | 111 | -1.226 | 11.179 | 24.797 | 1.00 | 46.02 | D C |
| ATOM | 11175 | C | ALA | D | 111 | -2.024 | 13.509 | 25.346 | 1.00 | 45.04 | D C |
| ATOM | 11176 | O | ALA | D | 111 | -1.507 | 14.317 | 24.544 | 1.00 | 44.69 | D O |
| ATOM | 11178 | N | ALA | D | 112 | -2.321 | 13.842 | 26.598 | 1.00 | 43.09 | D N |
| ATOM | 11179 | CA | ALA | D | 112 | -2.012 | 15.179 | 27.112 | 1.00 | 41.82 | D C |
| ATOM | 11181 | CB | ALA | D | 112 | -2.995 | 15.578 | 28.252 | 1.00 | 41.48 | D C |
| ATOM | 11185 | C | ALA | D | 112 | -0.553 | 15.228 | 27.596 | 1.00 | 40.49 | D C |
| ATOM | 11186 | O | ALA | D | 112 | -0.037 | 14.259 | 28.175 | 1.00 | 39.93 | D O |
| ATOM | 11188 | N | PRO | D | 113 | 0.112 | 16.368 | 27.381 | 1.00 | 39.14 | D N |
| ATOM | 11189 | CA | PRO | D | 113 | 1.514 | 16.437 | 27.776 | 1.00 | 39.29 | D C |
| ATOM | 11191 | CB | PRO | D | 113 | 1.978 | 17.797 | 27.226 | 1.00 | 38.90 | D C |
| ATOM | 11194 | CG | PRO | D | 113 | 0.735 | 18.603 | 27.095 | 1.00 | 39.72 | D C |
| ATOM | 11197 | CD | PRO | D | 113 | -0.387 | 17.643 | 26.845 | 1.00 | 39.13 | D C |
| ATOM | 11200 | C | PRO | D | 113 | 1.698 | 16.397 | 29.272 | 1.00 | 38.53 | D C |
| ATOM | 11201 | O | PRO | D | 113 | 1.023 | 17.126 | 29.983 | 1.00 | 38.87 | D O |
| ATOM | 11202 | N | SER | D | 114 | 2.612 | 15.567 | 29.740 | 1.00 | 37.69 | D N |
| ATOM | 11203 | CA | SER | D | 114 | 3.089 | 15.691 | 31.103 | 1.00 | 37.63 | D C |
| ATOM | 11205 | CB | SER | D | 114 | 3.540 | 14.354 | 31.637 | 1.00 | 37.90 | D C |
| ATOM | 11208 | OG | SER | D | 114 | 4.349 | 14.585 | 32.768 | 1.00 | 41.57 | D O |
| ATOM | 11210 | C | SER | D | 114 | 4.226 | 16.738 | 31.151 | 1.00 | 36.68 | D C |
| ATOM | 11211 | O | SER | D | 114 | 5.068 | 16.796 | 30.244 | 1.00 | 37.42 | D O |
| ATOM | 11213 | N | VAL | D | 115 | 4.234 | 17.584 | 32.181 | 1.00 | 34.76 | D N |
| ATOM | 11214 | CA | VAL | D | 115 | 5.118 | 18.734 | 32.213 | 1.00 | 33.30 | D C |
| ATOM | 11216 | CB | VAL | D | 115 | 4.336 | 20.037 | 32.010 | 1.00 | 32.67 | D C |
| ATOM | 11218 | CG1 | VAL | D | 115 | 5.254 | 21.234 | 32.016 | 1.00 | 31.42 | D C |
| ATOM | 11222 | CG2 | VAL | D | 115 | 3.581 | 19.986 | 30.705 | 1.00 | 32.08 | D C |
| ATOM | 11226 | C | VAL | D | 115 | 5.879 | 18.802 | 33.518 | 1.00 | 33.83 | D C |
| ATOM | 11227 | O | VAL | D | 115 | 5.285 | 18.833 | 34.592 | 1.00 | 32.91 | D O |
| ATOM | 11229 | N | THR | D | 116 | 7.207 | 18.850 | 33.411 | 1.00 | 34.09 | D N |
| ATOM | 11230 | CA | THR | D | 116 | 8.074 | 18.978 | 34.563 | 1.00 | 33.79 | D |

FIG 8 – CONT.

```
C
ATOM   11232  CB   THR D 116       8.881   17.736   34.729  1.00 33.81        D
C
ATOM   11234  OG1  THR D 116       8.008   16.614   34.631  1.00 33.78        D
O
ATOM   11236  CG2  THR D 116       9.572   17.745   36.092  1.00 35.09        D
C
ATOM   11240  C    THR D 116       9.010   20.154   34.387  1.00 33.88        D
C
ATOM   11241  O    THR D 116       9.677   20.282   33.353  1.00 34.24        D
O
ATOM   11243  N    LEU D 117       9.082   20.995   35.408  1.00 32.87        D
N
ATOM   11244  CA   LEU D 117       9.832   22.228   35.357  1.00 31.90        D
C
ATOM   11246  CB   LEU D 117       8.875   23.385   35.460  1.00 31.65        D
C
ATOM   11249  CG   LEU D 117       9.503   24.749   35.689  1.00 32.32        D
C
ATOM   11251  CD1  LEU D 117      10.403   25.077   34.460  1.00 32.64        D
C
ATOM   11255  CD2  LEU D 117       8.430   25.826   35.919  1.00 32.81        D
C
ATOM   11259  C    LEU D 117      10.803   22.271   36.524  1.00 32.23        D
C
ATOM   11260  O    LEU D 117      10.376   22.183   37.672  1.00 32.51        D
O
ATOM   11262  N    PHE D 118      12.097   22.397   36.238  1.00 31.99        D
N
ATOM   11263  CA   PHE D 118      13.111   22.477   37.266  1.00 32.19        D
C
ATOM   11265  CB   PHE D 118      14.216   21.446   37.065  1.00 31.62        D
C
ATOM   11268  CG   PHE D 118      13.780   20.022   37.212  1.00 31.42        D
C
ATOM   11269  CD1  PHE D 118      13.688   19.432   38.476  1.00 32.57        D
C
ATOM   11271  CE1  PHE D 118      13.305   18.127   38.619  1.00 32.84        D
C
ATOM   11273  CZ   PHE D 118      13.022   17.363   37.483  1.00 34.39        D
C
ATOM   11275  CE2  PHE D 118      13.126   17.952   36.214  1.00 31.51        D
C
ATOM   11277  CD2  PHE D 118      13.488   19.262   36.100  1.00 30.25        D
C
ATOM   11279  C    PHE D 118      13.745   23.873   37.218  1.00 33.19        D
C
ATOM   11280  O    PHE D 118      14.007   24.386   36.130  1.00 33.74        D
O
ATOM   11282  N    PRO D 119      14.000   24.489   38.400  1.00 33.14        D
N
ATOM   11283  CA   PRO D 119      14.833   25.679   38.518  1.00 33.41        D
C
ATOM   11285  CB   PRO D 119      14.490   26.206   39.936  1.00 33.56        D
C
ATOM   11288  CG   PRO D 119      14.186   24.988   40.713  1.00 33.95        D
C
ATOM   11291  CD   PRO D 119      13.558   23.997   39.720  1.00 33.70        D
C
ATOM   11294  C    PRO D 119      16.336   25.370   38.427  1.00 33.13        D
C
```

FIG 8 – CONT.

| ATOM | 11295 | O | PRO | D | 119 | 16.740 | 24.211 | 38.405 | 1.00 | 32.34 | D |
|---|---|---|---|---|---|---|---|---|---|---|---|
| ATOM | 11296 | N | PRO | D | 120 | 17.173 | 26.408 | 38.450 | 1.00 | 33.80 | D |
| ATOM | 11297 | CA | PRO | D | 120 | 18.614 | 26.164 | 38.392 | 1.00 | 34.31 | D |
| ATOM | 11299 | CB | PRO | D | 120 | 19.196 | 27.560 | 38.243 | 1.00 | 34.10 | D |
| ATOM | 11302 | CG | PRO | D | 120 | 18.119 | 28.502 | 38.470 | 1.00 | 33.62 | D |
| ATOM | 11305 | CD | PRO | D | 120 | 16.832 | 27.828 | 38.315 | 1.00 | 33.62 | D |
| ATOM | 11308 | C | PRO | D | 120 | 19.146 | 25.470 | 39.639 | 1.00 | 35.15 | D |
| ATOM | 11309 | O | PRO | D | 120 | 18.731 | 25.809 | 40.715 | 1.00 | 35.74 | D |
| ATOM | 11310 | N | SER | D | 121 | 20.024 | 24.484 | 39.494 | 1.00 | 36.06 | D |
| ATOM | 11311 | CA | SER | D | 121 | 20.700 | 23.887 | 40.640 | 1.00 | 37.19 | D |
| ATOM | 11313 | CB | SER | D | 121 | 21.553 | 22.718 | 40.181 | 1.00 | 37.36 | D |
| ATOM | 11316 | OG | SER | D | 121 | 22.553 | 23.154 | 39.252 | 1.00 | 36.99 | D |
| ATOM | 11318 | C | SER | D | 121 | 21.606 | 24.901 | 41.356 | 1.00 | 38.58 | D |
| ATOM | 11319 | O | SER | D | 121 | 22.028 | 25.914 | 40.766 | 1.00 | 39.51 | D |
| ATOM | 11321 | N | SER | D | 122 | 21.951 | 24.644 | 42.613 | 1.00 | 39.15 | D |
| ATOM | 11322 | CA | SER | D | 122 | 22.922 | 25.538 | 43.271 | 1.00 | 39.73 | D |
| ATOM | 11324 | CB | SER | D | 122 | 22.958 | 25.343 | 44.802 | 1.00 | 39.96 | D |
| ATOM | 11327 | OG | SER | D | 122 | 22.954 | 23.976 | 45.159 | 1.00 | 41.00 | D |
| ATOM | 11329 | C | SER | D | 122 | 24.323 | 25.443 | 42.629 | 1.00 | 39.70 | D |
| ATOM | 11330 | O | SER | D | 122 | 25.008 | 26.460 | 42.493 | 1.00 | 39.22 | D |
| ATOM | 11332 | N | GLU | D | 123 | 24.729 | 24.247 | 42.200 | 1.00 | 40.25 | D |
| ATOM | 11333 | CA | GLU | D | 123 | 26.008 | 24.080 | 41.482 | 1.00 | 41.17 | D |
| ATOM | 11335 | CB | GLU | D | 123 | 26.150 | 22.681 | 40.879 | 1.00 | 41.59 | D |
| ATOM | 11338 | CG | GLU | D | 123 | 26.512 | 21.625 | 41.880 | 1.00 | 44.20 | D |
| ATOM | 11341 | CD | GLU | D | 123 | 26.927 | 20.295 | 41.277 | 1.00 | 45.58 | D |
| ATOM | 11342 | OE1 | GLU | D | 123 | 26.441 | 19.280 | 41.835 | 1.00 | 49.93 | D |
| ATOM | 11343 | OE2 | GLU | D | 123 | 27.750 | 20.259 | 40.319 | 1.00 | 44.71 | D |
| ATOM | 11344 | C | GLU | D | 123 | 26.178 | 25.064 | 40.348 | 1.00 | 40.95 | D |
| ATOM | 11345 | O | GLU | D | 123 | 27.252 | 25.651 | 40.199 | 1.00 | 40.94 | D |
| ATOM | 11347 | N | GLU | D | 124 | 25.123 | 25.212 | 39.546 | 1.00 | 40.90 | D |
| ATOM | 11348 | CA | GLU | D | 124 | 25.154 | 26.038 | 38.356 | 1.00 | 40.88 | D |

FIG 8 – CONT.

| ATOM | | | | | | | | | | |
|---|---|---|---|---|---|---|---|---|---|---|
| ATOM | 11350 | CB | GLU | D | 124 | 23.913 | 25.813 | 37.457 | 1.00 40.80 | D C |
| ATOM | 11353 | CG | GLU | D | 124 | 24.021 | 26.458 | 36.052 | 1.00 39.08 | D C |
| ATOM | 11356 | CD | GLU | D | 124 | 22.733 | 26.391 | 35.220 | 1.00 38.89 | D C |
| ATOM | 11357 | OE1 | GLU | D | 124 | 21.672 | 25.995 | 35.753 | 1.00 33.93 | D O |
| ATOM | 11358 | OE2 | GLU | D | 124 | 22.781 | 26.786 | 34.027 | 1.00 38.32 | D O |
| ATOM | 11359 | C | GLU | D | 124 | 25.204 | 27.486 | 38.734 | 1.00 41.26 | D C |
| ATOM | 11360 | O | GLU | D | 124 | 25.869 | 28.269 | 38.076 | 1.00 41.90 | D O |
| ATOM | 11362 | N | LEU | D | 125 | 24.450 | 27.867 | 39.743 | 1.00 41.84 | D N |
| ATOM | 11363 | CA | LEU | D | 125 | 24.531 | 29.237 | 40.244 | 1.00 42.79 | D C |
| ATOM | 11365 | CB | LEU | D | 125 | 23.459 | 29.520 | 41.293 | 1.00 42.48 | D C |
| ATOM | 11368 | CG | LEU | D | 125 | 22.022 | 29.403 | 40.771 | 1.00 41.95 | D C |
| ATOM | 11370 | CD1 | LEU | D | 125 | 21.024 | 29.341 | 41.937 | 1.00 39.50 | D C |
| ATOM | 11374 | CD2 | LEU | D | 125 | 21.676 | 30.510 | 39.797 | 1.00 39.21 | D C |
| ATOM | 11378 | C | LEU | D | 125 | 25.935 | 29.567 | 40.769 | 1.00 43.54 | D C |
| ATOM | 11379 | O | LEU | D | 125 | 26.375 | 30.688 | 40.596 | 1.00 44.07 | D O |
| ATOM | 11381 | N | GLN | D | 126 | 26.655 | 28.606 | 41.351 | 1.00 44.85 | D N |
| ATOM | 11382 | CA | GLN | D | 126 | 28.076 | 28.839 | 41.703 | 1.00 46.31 | D C |
| ATOM | 11384 | CB | GLN | D | 126 | 28.691 | 27.701 | 42.545 | 1.00 46.63 | D C |
| ATOM | 11387 | CG | GLN | D | 126 | 28.856 | 28.019 | 44.068 | 1.00 48.55 | D C |
| ATOM | 11390 | CD | GLN | D | 126 | 29.699 | 29.279 | 44.376 | 1.00 47.46 | D C |
| ATOM | 11391 | OE1 | GLN | D | 126 | 30.892 | 29.354 | 44.067 | 1.00 48.49 | D O |
| ATOM | 11392 | NE2 | GLN | D | 126 | 29.066 | 30.258 | 44.988 | 1.00 47.38 | D N |
| ATOM | 11395 | C | GLN | D | 126 | 28.972 | 29.065 | 40.463 | 1.00 47.23 | D C |
| ATOM | 11396 | O | GLN | D | 126 | 30.009 | 29.728 | 40.564 | 1.00 47.67 | D O |
| ATOM | 11398 | N | ALA | D | 127 | 28.581 | 28.529 | 39.305 | 1.00 47.01 | D N |
| ATOM | 11399 | CA | ALA | D | 127 | 29.283 | 28.819 | 38.055 | 1.00 47.00 | D C |
| ATOM | 11401 | CB | ALA | D | 127 | 29.153 | 27.627 | 37.077 | 1.00 46.85 | D C |
| ATOM | 11405 | C | ALA | D | 127 | 28.799 | 30.124 | 37.411 | 1.00 47.05 | D C |
| ATOM | 11406 | O | ALA | D | 127 | 29.186 | 30.444 | 36.283 | 1.00 48.37 | D O |
| ATOM | 11408 | N | ASN | D | 128 | 27.982 | 30.873 | 38.147 | 1.00 46.54 | D N |

FIG 8 – CONT.

| | | | | | | | | | | |
|---|---|---|---|---|---|---|---|---|---|---|
| ATOM | 11409 | CA | ASN | D | 128 | 27.329 | 32.114 | 37.695 | 1.00 46.73 | D C |
| ATOM | 11411 | CB | ASN | D | 128 | 28.323 | 33.271 | 37.559 | 1.00 47.32 | D C |
| ATOM | 11414 | CG | ASN | D | 128 | 27.663 | 34.640 | 37.833 | 1.00 50.17 | D C |
| ATOM | 11415 | OD1 | ASN | D | 128 | 27.003 | 34.838 | 38.864 | 1.00 55.62 | D O |
| ATOM | 11416 | ND2 | ASN | D | 128 | 27.823 | 35.578 | 36.903 | 1.00 54.72 | D N |
| ATOM | 11419 | C | ASN | D | 128 | 26.406 | 32.016 | 36.454 | 1.00 45.83 | D C |
| ATOM | 11420 | O | ASN | D | 128 | 26.216 | 32.989 | 35.692 | 1.00 45.97 | D O |
| ATOM | 11422 | N | LYS | D | 129 | 25.755 | 30.862 | 36.323 | 1.00 44.41 | D N |
| ATOM | 11423 | CA | LYS | D | 129 | 24.772 | 30.629 | 35.278 | 1.00 42.39 | D C |
| ATOM | 11425 | CB | LYS | D | 129 | 25.321 | 29.541 | 34.359 | 1.00 42.66 | D C |
| ATOM | 11428 | CG | LYS | D | 129 | 26.567 | 29.946 | 33.499 | 1.00 42.10 | D C |
| ATOM | 11431 | CD | LYS | D | 129 | 27.721 | 28.858 | 33.559 | 1.00 42.79 | D C |
| ATOM | 11434 | CE | LYS | D | 129 | 27.306 | 27.375 | 33.189 | 1.00 41.94 | D C |
| ATOM | 11437 | NZ | LYS | D | 129 | 28.259 | 26.313 | 33.676 | 1.00 37.35 | D N |
| ATOM | 11441 | C | LYS | D | 129 | 23.466 | 30.186 | 35.931 | 1.00 41.43 | D C |
| ATOM | 11442 | O | LYS | D | 129 | 23.486 | 29.599 | 37.012 | 1.00 41.89 | D O |
| ATOM | 11444 | N | ALA | D | 130 | 22.336 | 30.481 | 35.286 | 1.00 39.79 | D N |
| ATOM | 11445 | CA | ALA | D | 130 | 21.023 | 29.992 | 35.710 | 1.00 38.00 | D C |
| ATOM | 11447 | CB | ALA | D | 130 | 20.267 | 31.098 | 36.385 | 1.00 37.82 | D C |
| ATOM | 11451 | C | ALA | D | 130 | 20.212 | 29.454 | 34.512 | 1.00 36.36 | D C |
| ATOM | 11452 | O | ALA | D | 130 | 19.899 | 30.184 | 33.596 | 1.00 35.68 | D O |
| ATOM | 11454 | N | THR | D | 131 | 19.877 | 28.171 | 34.524 | 1.00 35.17 | D N |
| ATOM | 11455 | CA | THR | D | 131 | 18.989 | 27.615 | 33.492 | 1.00 33.26 | D C |
| ATOM | 11457 | CB | THR | D | 131 | 19.700 | 26.511 | 32.695 | 1.00 33.20 | D C |
| ATOM | 11459 | OG1 | THR | D | 131 | 20.971 | 26.974 | 32.243 | 1.00 30.97 | D O |
| ATOM | 11461 | CG2 | THR | D | 131 | 18.841 | 26.044 | 31.504 | 1.00 30.92 | D C |
| ATOM | 11465 | C | THR | D | 131 | 17.718 | 26.987 | 34.096 | 1.00 32.72 | D C |
| ATOM | 11466 | O | THR | D | 131 | 17.814 | 26.082 | 34.945 | 1.00 31.76 | D O |
| ATOM | 11468 | N | LEU | D | 132 | 16.545 | 27.429 | 33.628 | 1.00 31.79 | D N |
| ATOM | 11469 | CA | LEU | D | 132 | 15.286 | 26.759 | 33.958 | 1.00 31.57 | D C |
| ATOM | 11471 | CB | LEU | D | 132 | 14.135 | 27.748 | 34.030 | 1.00 31.61 | |

FIG 8 – CONT.

```
ATOM  11474  CG   LEU D 132      14.019  28.633  35.290  1.00 33.15      D
C
ATOM  11476  CD1  LEU D 132      15.283  29.348  35.516  1.00 32.29      D
C
ATOM  11480  CD2  LEU D 132      12.889  29.627  35.112  1.00 30.76      D
C
ATOM  11484  C    LEU D 132      14.983  25.739  32.868  1.00 31.50      D
C
ATOM  11485  O    LEU D 132      15.060  26.063  31.682  1.00 31.63      D
O
ATOM  11487  N    VAL D 133      14.603  24.538  33.273  1.00 30.95      D
N
ATOM  11488  CA   VAL D 133      14.424  23.395  32.388  1.00 31.08      D
C
ATOM  11490  CB   VAL D 133      15.300  22.262  32.858  1.00 30.69      D
C
ATOM  11492  CG1  VAL D 133      15.172  21.070  31.941  1.00 30.13      D
C
ATOM  11496  CG2  VAL D 133      16.746  22.745  32.967  1.00 32.01      D
C
ATOM  11500  C    VAL D 133      12.954  22.913  32.380  1.00 31.46      D
C
ATOM  11501  O    VAL D 133      12.453  22.381  33.385  1.00 31.87      D
O
ATOM  11503  N    CYS D 134      12.250  23.158  31.279  1.00 31.37      D
N
ATOM  11504  CA   CYS D 134      10.866  22.714  31.120  1.00 30.92      D
C
ATOM  11506  CB   CYS D 134      10.009  23.839  30.570  1.00 31.21      D
C
ATOM  11509  SG   CYS D 134       8.166  23.524  30.709  1.00 29.39      D
S
ATOM  11511  C    CYS D 134      10.817  21.519  30.187  1.00 31.27      D
C
ATOM  11512  O    CYS D 134      11.042  21.676  28.987  1.00 31.91      D
O
ATOM  11514  N    LEU D 135      10.524  20.344  30.748  1.00 30.86      D
N
ATOM  11515  CA   LEU D 135      10.408  19.098  30.023  1.00 30.75      D
C
ATOM  11517  CB   LEU D 135      11.149  18.021  30.792  1.00 30.32      D
C
ATOM  11520  CG   LEU D 135      12.563  18.459  31.156  1.00 28.97      D
C
ATOM  11522  CD1  LEU D 135      13.190  17.361  31.936  1.00 32.37      D
C
ATOM  11526  CD2  LEU D 135      13.399  18.810  29.927  1.00 27.45      D
C
ATOM  11530  C    LEU D 135       8.938  18.682  29.780  1.00 32.28      D
C
ATOM  11531  O    LEU D 135       8.120  18.667  30.713  1.00 32.86      D
O
ATOM  11533  N    VAL D 136       8.624  18.331  28.531  1.00 32.61      D
N
ATOM  11534  CA   VAL D 136       7.283  18.041  28.092  1.00 33.55      D
C
ATOM  11536  CB   VAL D 136       6.799  19.077  27.077  1.00 33.45      D
C
ATOM  11538  CG1  VAL D 136       5.295  18.956  26.871  1.00 32.49      D
C
```

FIG 8 – CONT.

```
ATOM  11542  CG2  VAL D 136      7.194  20.485  27.505  1.00 31.23      D
C
ATOM  11546  C    VAL D 136      7.235  16.674  27.422  1.00 35.80      D
C
ATOM  11547  O    VAL D 136      7.898  16.471  26.392  1.00 36.79      D
O
ATOM  11549  N    SER D 137      6.466  15.728  27.966  1.00 37.09      D
N
ATOM  11550  CA   SER D 137      6.488  14.389  27.398  1.00 38.98      D
C
ATOM  11552  CB   SER D 137      7.437  13.496  28.187  1.00 39.08      D
C
ATOM  11555  OG   SER D 137      6.979  13.276  29.500  1.00 41.74      D
O
ATOM  11557  C    SER D 137      5.154  13.695  27.264  1.00 40.55      D
C
ATOM  11558  O    SER D 137      4.171  14.026  27.943  1.00 41.63      D
O
ATOM  11560  N    ASP D 138      5.152  12.705  26.374  1.00 41.94      D
N
ATOM  11561  CA   ASP D 138      4.076  11.740  26.215  1.00 42.94      D
C
ATOM  11563  CB   ASP D 138      3.802  11.002  27.544  1.00 43.73      D
C
ATOM  11566  CG   ASP D 138      4.811   9.889  27.803  1.00 47.39      D
C
ATOM  11567  OD1  ASP D 138      5.098   9.135  26.838  1.00 51.98      D
O
ATOM  11568  OD2  ASP D 138      5.290   9.736  28.958  1.00 52.60      D
O
ATOM  11569  C    ASP D 138      2.823  12.363  25.649  1.00 42.76      D
C
ATOM  11570  O    ASP D 138      1.737  11.960  25.993  1.00 43.16      D
O
ATOM  11572  N    PHE D 139      2.987  13.323  24.746  1.00 42.98      D
N
ATOM  11573  CA   PHE D 139      1.856  13.971  24.136  1.00 43.17      D
C
ATOM  11575  CB   PHE D 139      1.941  15.488  24.266  1.00 42.85      D
C
ATOM  11578  CG   PHE D 139      3.132  16.126  23.593  1.00 42.67      D
C
ATOM  11579  CD1  PHE D 139      4.331  16.288  24.280  1.00 42.33      D
C
ATOM  11581  CE1  PHE D 139      5.421  16.904  23.692  1.00 41.73      D
C
ATOM  11583  CZ   PHE D 139      5.323  17.420  22.400  1.00 43.07      D
C
ATOM  11585  CE2  PHE D 139      4.114  17.297  21.702  1.00 44.76      D
C
ATOM  11587  CD2  PHE D 139      3.021  16.659  22.310  1.00 43.21      D
C
ATOM  11589  C    PHE D 139      1.623  13.543  22.671  1.00 44.39      D
C
ATOM  11590  O    PHE D 139      2.559  13.151  21.949  1.00 43.52      D
O
ATOM  11592  N    TYR D 140      0.351  13.608  22.270  1.00 45.00      D
N
ATOM  11593  CA   TYR D 140     -0.074  13.280  20.912  1.00 46.04      D
C
ATOM  11595  CB   TYR D 140     -0.306  11.777  20.705  1.00 45.71      D
```

FIG 8 – CONT.

| ATOM | 11598 | CG | TYR | D | 140 | -0.513 | 11.501 | 19.234 | 1.00 | 49.04 | D C |
| ATOM | 11599 | CD1 | TYR | D | 140 | 0.554 | 11.127 | 18.418 | 1.00 | 51.02 | D C |
| ATOM | 11601 | CE1 | TYR | D | 140 | 0.364 | 10.917 | 17.038 | 1.00 | 53.13 | D C |
| ATOM | 11603 | CZ | TYR | D | 140 | -0.900 | 11.101 | 16.473 | 1.00 | 53.35 | D C |
| ATOM | 11604 | OH | TYR | D | 140 | -1.102 | 10.917 | 15.124 | 1.00 | 54.96 | D O |
| ATOM | 11606 | CE2 | TYR | D | 140 | -1.965 | 11.494 | 17.268 | 1.00 | 52.48 | D C |
| ATOM | 11608 | CD2 | TYR | D | 140 | -1.766 | 11.703 | 18.632 | 1.00 | 50.61 | D C |
| ATOM | 11610 | C | TYR | D | 140 | -1.344 | 14.064 | 20.556 | 1.00 | 46.36 | D C |
| ATOM | 11611 | O | TYR | D | 140 | -2.297 | 14.080 | 21.326 | 1.00 | 46.13 | D O |
| ATOM | 11613 | N | PRO | D | 141 | -1.369 | 14.693 | 19.375 | 1.00 | 47.10 | D N |
| ATOM | 11614 | CA | PRO | D | 141 | -0.335 | 14.728 | 18.325 | 1.00 | 47.85 | D C |
| ATOM | 11616 | CB | PRO | D | 141 | -1.077 | 15.316 | 17.119 | 1.00 | 47.97 | D C |
| ATOM | 11619 | CG | PRO | D | 141 | -2.158 | 16.166 | 17.720 | 1.00 | 48.27 | D C |
| ATOM | 11622 | CD | PRO | D | 141 | -2.574 | 15.442 | 18.990 | 1.00 | 47.55 | D C |
| ATOM | 11625 | C | PRO | D | 141 | 0.877 | 15.591 | 18.697 | 1.00 | 48.31 | D C |
| ATOM | 11626 | O | PRO | D | 141 | 0.905 | 16.192 | 19.770 | 1.00 | 48.54 | D O |
| ATOM | 11627 | N | GLY | D | 142 | 1.882 | 15.634 | 17.826 | 1.00 | 48.65 | D N |
| ATOM | 11628 | CA | GLY | D | 142 | 3.167 | 16.259 | 18.152 | 1.00 | 48.40 | D C |
| ATOM | 11631 | C | GLY | D | 142 | 3.240 | 17.718 | 17.769 | 1.00 | 48.52 | D C |
| ATOM | 11632 | O | GLY | D | 142 | 4.099 | 18.119 | 16.968 | 1.00 | 49.95 | D O |
| ATOM | 11634 | N | ALA | D | 143 | 2.351 | 18.513 | 18.334 | 1.00 | 48.03 | D N |
| ATOM | 11635 | CA | ALA | D | 143 | 2.329 | 19.936 | 18.095 | 1.00 | 47.74 | D C |
| ATOM | 11637 | CB | ALA | D | 143 | 1.282 | 20.277 | 17.043 | 1.00 | 47.87 | D C |
| ATOM | 11641 | C | ALA | D | 143 | 2.002 | 20.628 | 19.418 | 1.00 | 47.39 | D C |
| ATOM | 11642 | O | ALA | D | 143 | 0.904 | 20.452 | 19.951 | 1.00 | 47.07 | D O |
| ATOM | 11644 | N | VAL | D | 144 | 2.968 | 21.383 | 19.946 | 1.00 | 46.73 | D N |
| ATOM | 11645 | CA | VAL | D | 144 | 2.798 | 22.137 | 21.183 | 1.00 | 46.17 | D C |
| ATOM | 11647 | CB | VAL | D | 144 | 3.530 | 21.507 | 22.406 | 1.00 | 45.78 | D C |
| ATOM | 11649 | CG1 | VAL | D | 144 | 2.630 | 20.605 | 23.159 | 1.00 | 46.40 | D C |
| ATOM | 11653 | CG2 | VAL | D | 144 | 4.790 | 20.783 | 22.003 | 1.00 | 45.77 | D C |

FIG 8 – CONT.

| ATOM | 11657 | C   | VAL | D | 144 | 3.364  | 23.506 | 21.018 | 1.00 | 45.76 | D | C |
| --- | --- | --- | --- | --- | --- | --- | --- | --- | --- | --- | --- | --- |
| ATOM | 11658 | O   | VAL | D | 144 | 4.300  | 23.698 | 20.251 | 1.00 | 46.66 | D | O |
| ATOM | 11660 | N   | THR | D | 145 | 2.802  | 24.458 | 21.748 | 1.00 | 44.72 | D | N |
| ATOM | 11661 | CA  | THR | D | 145 | 3.426  | 25.751 | 21.936 | 1.00 | 44.18 | D | C |
| ATOM | 11663 | CB  | THR | D | 145 | 2.431  | 26.877 | 21.678 | 1.00 | 44.22 | D | C |
| ATOM | 11665 | OG1 | THR | D | 145 | 2.264  | 27.007 | 20.265 | 1.00 | 46.91 | D | O |
| ATOM | 11667 | CG2 | THR | D | 145 | 2.912  | 28.196 | 22.232 | 1.00 | 44.98 | D | C |
| ATOM | 11671 | C   | THR | D | 145 | 3.950  | 25.776 | 23.373 | 1.00 | 43.14 | D | C |
| ATOM | 11672 | O   | THR | D | 145 | 3.262  | 25.301 | 24.297 | 1.00 | 42.39 | D | O |
| ATOM | 11674 | N   | VAL | D | 146 | 5.180  | 26.271 | 23.534 | 1.00 | 41.41 | D | N |
| ATOM | 11675 | CA  | VAL | D | 146 | 5.760  | 26.518 | 24.842 | 1.00 | 40.56 | D | C |
| ATOM | 11677 | CB  | VAL | D | 146 | 7.055  | 25.725 | 25.073 | 1.00 | 40.40 | D | C |
| ATOM | 11679 | CG1 | VAL | D | 146 | 7.545  | 25.950 | 26.497 | 1.00 | 39.03 | D | C |
| ATOM | 11683 | CG2 | VAL | D | 146 | 6.849  | 24.233 | 24.803 | 1.00 | 39.09 | D | C |
| ATOM | 11687 | C   | VAL | D | 146 | 6.070  | 28.003 | 24.982 | 1.00 | 40.30 | D | C |
| ATOM | 11688 | O   | VAL | D | 146 | 6.724  | 28.569 | 24.121 | 1.00 | 39.97 | D | O |
| ATOM | 11690 | N   | ALA | D | 147 | 5.610  | 28.606 | 26.076 | 1.00 | 40.27 | D | N |
| ATOM | 11691 | CA  | ALA | D | 147 | 5.889  | 30.005 | 26.398 | 1.00 | 40.69 | D | C |
| ATOM | 11693 | CB  | ALA | D | 147 | 4.630  | 30.846 | 26.179 | 1.00 | 40.33 | D | C |
| ATOM | 11697 | C   | ALA | D | 147 | 6.366  | 30.143 | 27.850 | 1.00 | 41.20 | D | C |
| ATOM | 11698 | O   | ALA | D | 147 | 6.047  | 29.292 | 28.693 | 1.00 | 41.22 | D | O |
| ATOM | 11700 | N   | TRP | D | 148 | 7.074  | 31.238 | 28.146 | 1.00 | 41.39 | D | N |
| ATOM | 11701 | CA  | TRP | D | 148 | 7.609  | 31.491 | 29.466 | 1.00 | 41.82 | D | C |
| ATOM | 11703 | CB  | TRP | D | 148 | 9.129  | 31.505 | 29.432 | 1.00 | 41.79 | D | C |
| ATOM | 11706 | CG  | TRP | D | 148 | 9.782  | 30.188 | 29.214 | 1.00 | 39.07 | D | C |
| ATOM | 11707 | CD1 | TRP | D | 148 | 10.084 | 29.624 | 28.015 | 1.00 | 37.53 | D | C |
| ATOM | 11709 | NE1 | TRP | D | 148 | 10.722 | 28.431 | 28.198 | 1.00 | 37.41 | D | N |
| ATOM | 11711 | CE2 | TRP | D | 148 | 10.864 | 28.205 | 29.538 | 1.00 | 37.15 | D | C |
| ATOM | 11712 | CD2 | TRP | D | 148 | 10.280 | 29.297 | 30.213 | 1.00 | 37.74 | D | C |
| ATOM | 11713 | CE3 | TRP | D | 148 | 10.299 | 29.315 | 31.610 | 1.00 | 36.33 | D | C |
| ATOM | 11715 | CZ3 | TRP | D | 148 | 10.872 | 28.262 | 32.276 | 1.00 | 36.22 | D |   |

FIG 8 – CONT.

| | | | | | | | | | | |
|---|---|---|---|---|---|---|---|---|---|---|
| ATOM | 11717 | CH2 | TRP | D | 148 | 11.431 | 27.175 | 31.574 | 1.00 37.61 | D C |
| ATOM | 11719 | CZ2 | TRP | D | 148 | 11.437 | 27.133 | 30.208 | 1.00 37.27 | D C |
| ATOM | 11721 | C | TRP | D | 148 | 7.157 | 32.815 | 30.032 | 1.00 43.46 | D C |
| ATOM | 11722 | O | TRP | D | 148 | 7.007 | 33.795 | 29.303 | 1.00 43.86 | D O |
| ATOM | 11724 | N | LYS | D | 149 | 6.945 | 32.848 | 31.344 | 1.00 45.33 | D N |
| ATOM | 11725 | CA | LYS | D | 149 | 6.592 | 34.093 | 32.022 | 1.00 47.13 | D C |
| ATOM | 11727 | CB | LYS | D | 149 | 5.122 | 34.102 | 32.464 | 1.00 47.72 | D C |
| ATOM | 11730 | CG | LYS | D | 149 | 4.155 | 34.509 | 31.362 | 1.00 49.60 | D C |
| ATOM | 11733 | CD | LYS | D | 149 | 2.797 | 33.815 | 31.471 | 1.00 52.03 | D C |
| ATOM | 11736 | CE | LYS | D | 149 | 1.966 | 34.014 | 30.177 | 1.00 53.37 | D C |
| ATOM | 11739 | NZ | LYS | D | 149 | 1.371 | 35.400 | 30.039 | 1.00 53.10 | D N |
| ATOM | 11743 | C | LYS | D | 149 | 7.502 | 34.364 | 33.210 | 1.00 47.80 | D C |
| ATOM | 11744 | O | LYS | D | 149 | 8.092 | 33.442 | 33.765 | 1.00 47.66 | D O |
| ATOM | 11746 | N | ALA | D | 150 | 7.647 | 35.651 | 33.529 | 1.00 49.21 | D N |
| ATOM | 11747 | CA | ALA | D | 150 | 8.294 | 36.129 | 34.755 | 1.00 50.47 | D C |
| ATOM | 11749 | CB | ALA | D | 150 | 9.552 | 36.893 | 34.432 | 1.00 50.11 | D C |
| ATOM | 11753 | C | ALA | D | 150 | 7.283 | 37.032 | 35.464 | 1.00 51.82 | D C |
| ATOM | 11754 | O | ALA | D | 150 | 6.924 | 38.092 | 34.940 | 1.00 52.25 | D O |
| ATOM | 11756 | N | ASP | D | 151 | 6.783 | 36.585 | 36.617 | 1.00 53.10 | D N |
| ATOM | 11757 | CA | ASP | D | 151 | 5.736 | 37.303 | 37.342 | 1.00 54.38 | D C |
| ATOM | 11759 | CB | ASP | D | 151 | 6.306 | 38.545 | 38.026 | 1.00 54.91 | D C |
| ATOM | 11762 | CG | ASP | D | 151 | 7.469 | 38.224 | 38.905 | 1.00 56.72 | D C |
| ATOM | 11763 | OD1 | ASP | D | 151 | 7.559 | 37.063 | 39.370 | 1.00 59.24 | D O |
| ATOM | 11764 | OD2 | ASP | D | 151 | 8.296 | 39.133 | 39.119 | 1.00 60.32 | D O |
| ATOM | 11765 | C | ASP | D | 151 | 4.616 | 37.732 | 36.431 | 1.00 54.75 | D C |
| ATOM | 11766 | O | ASP | D | 151 | 4.236 | 38.901 | 36.431 | 1.00 54.23 | D O |
| ATOM | 11768 | N | GLY | D | 152 | 4.118 | 36.790 | 35.633 | 1.00 55.83 | D N |
| ATOM | 11769 | CA | GLY | D | 152 | 2.956 | 37.032 | 34.787 | 1.00 56.50 | D C |
| ATOM | 11772 | C | GLY | D | 152 | 3.241 | 37.625 | 33.423 | 1.00 57.41 | D C |
| ATOM | 11773 | O | GLY | D | 152 | 2.380 | 37.538 | 32.544 | 1.00 58.35 | D O |

FIG 8 – CONT.

| ATOM | 11775 | N   | SER | D | 153 | 4.431  | 38.216 | 33.237 | 1.00 | 57.81 | D | N |
|------|-------|-----|-----|---|-----|--------|--------|--------|------|-------|---|---|
| ATOM | 11776 | CA  | SER | D | 153 | 4.826  | 38.864 | 31.970 | 1.00 | 57.75 | D | C |
| ATOM | 11778 | CB  | SER | D | 153 | 5.798  | 40.014 | 32.238 | 1.00 | 57.94 | D | C |
| ATOM | 11781 | OG  | SER | D | 153 | 5.180  | 41.063 | 32.945 | 1.00 | 58.44 | D | O |
| ATOM | 11783 | C   | SER | D | 153 | 5.555  | 37.884 | 31.063 | 1.00 | 57.61 | D | C |
| ATOM | 11784 | O   | SER | D | 153 | 6.392  | 37.131 | 31.549 | 1.00 | 57.85 | D | O |
| ATOM | 11786 | N   | PRO | D | 154 | 5.291  | 37.924 | 29.739 | 1.00 | 57.13 | D | N |
| ATOM | 11787 | CA  | PRO | D | 154 | 6.001  | 37.016 | 28.839 | 1.00 | 56.38 | D | C |
| ATOM | 11789 | CB  | PRO | D | 154 | 5.364  | 37.286 | 27.472 | 1.00 | 56.53 | D | C |
| ATOM | 11792 | CG  | PRO | D | 154 | 4.115  | 38.049 | 27.754 | 1.00 | 56.73 | D | C |
| ATOM | 11795 | CD  | PRO | D | 154 | 4.399  | 38.830 | 28.994 | 1.00 | 57.24 | D | C |
| ATOM | 11798 | C   | PRO | D | 154 | 7.479  | 37.331 | 28.780 | 1.00 | 55.85 | D | C |
| ATOM | 11799 | O   | PRO | D | 154 | 7.866  | 38.501 | 28.861 | 1.00 | 56.07 | D | O |
| ATOM | 11800 | N   | VAL | D | 155 | 8.289  | 36.283 | 28.680 | 1.00 | 54.95 | D | N |
| ATOM | 11801 | CA  | VAL | D | 155 | 9.725  | 36.396 | 28.512 | 1.00 | 54.25 | D | C |
| ATOM | 11803 | CB  | VAL | D | 155 | 10.490 | 35.686 | 29.658 | 1.00 | 54.25 | D | C |
| ATOM | 11805 | CG1 | VAL | D | 155 | 11.984 | 35.711 | 29.410 | 1.00 | 54.24 | D | C |
| ATOM | 11809 | CG2 | VAL | D | 155 | 10.173 | 36.318 | 30.996 | 1.00 | 54.06 | D | C |
| ATOM | 11813 | C   | VAL | D | 155 | 10.064 | 35.708 | 27.194 | 1.00 | 53.87 | D | C |
| ATOM | 11814 | O   | VAL | D | 155 | 9.688  | 34.558 | 26.986 | 1.00 | 53.16 | D | O |
| ATOM | 11816 | N   | LYS | D | 156 | 10.764 | 36.424 | 26.316 | 1.00 | 53.51 | D | N |
| ATOM | 11817 | CA  | LYS | D | 156 | 11.229 | 35.898 | 25.019 | 1.00 | 53.17 | D | C |
| ATOM | 11819 | CB  | LYS | D | 156 | 10.771 | 36.830 | 23.885 | 1.00 | 52.94 | D | C |
| ATOM | 11826 | C   | LYS | D | 156 | 12.762 | 35.717 | 24.971 | 1.00 | 52.44 | D | C |
| ATOM | 11827 | O   | LYS | D | 156 | 13.271 | 34.753 | 24.369 | 1.00 | 52.57 | D | O |
| ATOM | 11829 | N   | VAL | D | 157 | 13.497 | 36.626 | 25.601 | 1.00 | 51.40 | D | N |
| ATOM | 11830 | CA  | VAL | D | 157 | 14.961 | 36.577 | 25.558 | 1.00 | 50.97 | D | C |
| ATOM | 11832 | CB  | VAL | D | 157 | 15.587 | 37.951 | 25.935 | 1.00 | 51.18 | D | C |
| ATOM | 11834 | CG1 | VAL | D | 157 | 15.244 | 38.348 | 27.377 | 1.00 | 52.05 | D | C |
| ATOM | 11838 | CG2 | VAL | D | 157 | 17.081 | 37.936 | 25.723 | 1.00 | 52.02 | D | C |
| ATOM | 11842 | C   | VAL | D | 157 | 15.489 | 35.452 | 26.454 | 1.00 | 50.04 | D |   |

FIG 8 – CONT.

```
C
ATOM  11843  O    VAL D 157      15.064  35.314  27.605  1.00 50.98      D
O
ATOM  11845  N    GLY D 158      16.378  34.625  25.914  1.00 48.43      D
N
ATOM  11846  CA   GLY D 158      16.991  33.533  26.669  1.00 46.90      D
C
ATOM  11849  C    GLY D 158      16.320  32.193  26.476  1.00 46.10      D
C
ATOM  11850  O    GLY D 158      16.789  31.182  26.999  1.00 44.86      D
O
ATOM  11852  N    VAL D 159      15.232  32.180  25.707  1.00 45.57      D
N
ATOM  11853  CA   VAL D 159      14.479  30.964  25.458  1.00 45.25      D
C
ATOM  11855  CB   VAL D 159      12.989  31.272  25.262  1.00 45.36      D
C
ATOM  11857  CG1  VAL D 159      12.202  29.970  25.055  1.00 44.29      D
C
ATOM  11861  CG2  VAL D 159      12.449  32.065  26.443  1.00 43.92      D
C
ATOM  11865  C    VAL D 159      14.981  30.172  24.235  1.00 45.37      D
C
ATOM  11866  O    VAL D 159      15.159  30.714  23.139  1.00 46.10      D
O
ATOM  11868  N    GLU D 160      15.192  28.881  24.430  1.00 44.90      D
N
ATOM  11869  CA   GLU D 160      15.515  27.979  23.339  1.00 44.76      D
C
ATOM  11871  CB   GLU D 160      17.041  27.709  23.268  1.00 44.85      D
C
ATOM  11874  CG   GLU D 160      17.824  28.803  22.408  1.00 46.95      D
C
ATOM  11877  CD   GLU D 160      19.250  29.165  22.916  1.00 48.91      D
C
ATOM  11878  OE1  GLU D 160      19.644  28.764  24.051  1.00 49.03      D
O
ATOM  11879  OE2  GLU D 160      19.984  29.866  22.166  1.00 45.52      D
O
ATOM  11880  C    GLU D 160      14.654  26.718  23.503  1.00 44.15      D
C
ATOM  11881  O    GLU D 160      14.757  25.991  24.485  1.00 43.22      D
O
ATOM  11883  N    THR D 161      13.761  26.504  22.545  1.00 43.89      D
N
ATOM  11884  CA   THR D 161      12.822  25.398  22.593  1.00 43.94      D
C
ATOM  11886  CB   THR D 161      11.407  25.908  22.439  1.00 44.31      D
C
ATOM  11888  OG1  THR D 161      11.112  26.777  23.537  1.00 44.51      D
O
ATOM  11890  CG2  THR D 161      10.427  24.734  22.375  1.00 44.26      D
C
ATOM  11894  C    THR D 161      13.061  24.408  21.473  1.00 43.43      D
C
ATOM  11895  O    THR D 161      13.263  24.780  20.338  1.00 43.26      D
O
ATOM  11897  N    THR D 162      13.011  23.146  21.837  1.00 43.89      D
N
ATOM  11898  CA   THR D 162      13.176  22.019  20.954  1.00 44.40      D
C
```

FIG 8 – CONT.

| ATOM | 11900 | CB | THR | D | 162 | 13.340 | 20.776 | 21.836 | 1.00 | 44.47 | D |
|---|---|---|---|---|---|---|---|---|---|---|---|
| ATOM | 11902 | OG1 | THR | D | 162 | 14.726 | 20.399 | 21.898 | 1.00 | 45.68 | D |
| ATOM | 11904 | CG2 | THR | D | 162 | 12.491 | 19.653 | 21.408 | 1.00 | 43.46 | D |
| ATOM | 11908 | C | THR | D | 162 | 11.949 | 21.887 | 20.066 | 1.00 | 45.57 | D |
| ATOM | 11909 | O | THR | D | 162 | 10.840 | 22.177 | 20.496 | 1.00 | 44.65 | D |
| ATOM | 11911 | N | LYS | D | 163 | 12.146 | 21.491 | 18.811 | 1.00 | 46.84 | D |
| ATOM | 11912 | CA | LYS | D | 163 | 11.022 | 21.010 | 18.001 | 1.00 | 47.85 | D |
| ATOM | 11914 | CB | LYS | D | 163 | 11.417 | 20.815 | 16.523 | 1.00 | 48.63 | D |
| ATOM | 11917 | CG | LYS | D | 163 | 11.811 | 22.109 | 15.762 | 1.00 | 51.65 | D |
| ATOM | 11920 | CD | LYS | D | 163 | 12.546 | 21.778 | 14.432 | 1.00 | 54.63 | D |
| ATOM | 11923 | CE | LYS | D | 163 | 13.274 | 23.004 | 13.837 | 1.00 | 56.90 | D |
| ATOM | 11926 | NZ | LYS | D | 163 | 14.467 | 23.498 | 14.646 | 1.00 | 58.35 | D |
| ATOM | 11930 | C | LYS | D | 163 | 10.559 | 19.671 | 18.601 | 1.00 | 47.28 | D |
| ATOM | 11931 | O | LYS | D | 163 | 11.368 | 18.922 | 19.128 | 1.00 | 46.00 | D |
| ATOM | 11933 | N | PRO | D | 164 | 9.256 | 19.369 | 18.513 | 1.00 | 47.97 | D |
| ATOM | 11934 | CA | PRO | D | 164 | 8.740 | 18.074 | 18.984 | 1.00 | 48.60 | D |
| ATOM | 11936 | CB | PRO | D | 164 | 7.262 | 18.111 | 18.590 | 1.00 | 48.36 | D |
| ATOM | 11939 | CG | PRO | D | 164 | 6.928 | 19.576 | 18.396 | 1.00 | 48.47 | D |
| ATOM | 11942 | CD | PRO | D | 164 | 8.197 | 20.237 | 17.960 | 1.00 | 48.06 | D |
| ATOM | 11945 | C | PRO | D | 164 | 9.410 | 16.910 | 18.285 | 1.00 | 49.59 | D |
| ATOM | 11946 | O | PRO | D | 164 | 9.644 | 16.999 | 17.090 | 1.00 | 49.42 | D |
| ATOM | 11947 | N | SER | D | 165 | 9.697 | 15.834 | 19.009 | 1.00 | 50.77 | D |
| ATOM | 11948 | CA | SER | D | 165 | 10.291 | 14.656 | 18.406 | 1.00 | 52.35 | D |
| ATOM | 11950 | CB | SER | D | 165 | 11.785 | 14.590 | 18.729 | 1.00 | 52.51 | D |
| ATOM | 11953 | OG | SER | D | 165 | 12.021 | 13.713 | 19.821 | 1.00 | 54.94 | D |
| ATOM | 11955 | C | SER | D | 165 | 9.612 | 13.380 | 18.896 | 1.00 | 53.17 | D |
| ATOM | 11956 | O | SER | D | 165 | 9.382 | 13.212 | 20.086 | 1.00 | 52.77 | D |
| ATOM | 11958 | N | LYS | D | 166 | 9.336 | 12.462 | 17.972 | 1.00 | 54.50 | D |
| ATOM | 11959 | CA | LYS | D | 166 | 8.606 | 11.236 | 18.293 | 1.00 | 55.49 | D |
| ATOM | 11961 | CB | LYS | D | 166 | 8.335 | 10.421 | 17.021 | 1.00 | 55.97 | D |
| ATOM | 11964 | CG | LYS | D | 166 | 7.283 | 9.329 | 17.170 | 1.00 | 57.10 | D |

FIG 8 – CONT.

```
C
ATOM  11967  CD   LYS D 166      6.788   8.816  15.807  1.00 59.01        D
C
ATOM  11970  CE   LYS D 166      7.683   7.711  15.230  1.00 60.22        D
C
ATOM  11973  NZ   LYS D 166      6.909   6.791  14.323  1.00 61.04        D
N
ATOM  11977  C    LYS D 166      9.378  10.392  19.277  1.00 55.72        D
C
ATOM  11978  O    LYS D 166     10.546  10.131  19.070  1.00 56.27        D
O
ATOM  11980  N    GLN D 167      8.719   9.970  20.349  1.00 56.45        D
N
ATOM  11981  CA   GLN D 167      9.323   9.094  21.340  1.00 56.84        D
C
ATOM  11983  CB   GLN D 167      8.602   9.188  22.692  1.00 56.98        D
C
ATOM  11986  CG   GLN D 167      8.611  10.576  23.361  1.00 57.36        D
C
ATOM  11989  CD   GLN D 167      7.815  10.615  24.679  1.00 56.67        D
C
ATOM  11990  OE1  GLN D 167      7.314   9.593  25.158  1.00 55.70        D
O
ATOM  11991  NE2  GLN D 167      7.713  11.797  25.265  1.00 54.10        D
N
ATOM  11994  C    GLN D 167      9.261   7.652  20.865  1.00 57.49        D
C
ATOM  11995  O    GLN D 167      8.640   7.345  19.851  1.00 57.52        D
O
ATOM  11997  N    SER D 168      9.927   6.795  21.633  1.00 58.28        D
N
ATOM  11998  CA   SER D 168      9.928   5.341  21.504  1.00 58.93        D
C
ATOM  12000  CB   SER D 168     10.552   4.774  22.797  1.00 58.99        D
C
ATOM  12003  OG   SER D 168     10.626   3.367  22.818  1.00 60.16        D
O
ATOM  12005  C    SER D 168      8.520   4.772  21.297  1.00 59.60        D
C
ATOM  12006  O    SER D 168      8.298   3.904  20.429  1.00 59.79        D
O
ATOM  12008  N    ASN D 170      7.573   5.298  22.084  1.00 59.67        D
N
ATOM  12009  CA   ASN D 170      6.199   4.802  22.158  1.00 59.16        D
C
ATOM  12011  CB   ASN D 170      5.712   4.947  23.600  1.00 59.57        D
C
ATOM  12014  CG   ASN D 170      5.478   6.412  24.000  1.00 60.29        D
C
ATOM  12015  OD1  ASN D 170      5.609   7.333  23.187  1.00 60.37        D
O
ATOM  12016  ND2  ASN D 170      5.116   6.619  25.254  1.00 62.07        D
N
ATOM  12019  C    ASN D 170      5.221   5.528  21.246  1.00 58.51        D
C
ATOM  12020  O    ASN D 170      4.019   5.496  21.489  1.00 58.49        D
O
ATOM  12022  N    ASN D 171      5.734   6.224  20.236  1.00 57.66        D
N
ATOM  12023  CA   ASN D 171      4.915   6.995  19.274  1.00 57.01        D
C
```

FIG 8 – CONT.

| ATOM | 12025 | CB | ASN | D | 171 | 3.898 | 6.104 | 18.561 | 1.00 | 57.59 | D | C |
| ATOM | 12028 | CG | ASN | D | 171 | 4.558 | 4.978 | 17.785 | 1.00 | 60.12 | D | C |
| ATOM | 12029 | OD1 | ASN | D | 171 | 5.150 | 5.192 | 16.715 | 1.00 | 64.15 | D | O |
| ATOM | 12030 | ND2 | ASN | D | 171 | 4.454 | 3.766 | 18.317 | 1.00 | 61.69 | D | N |
| ATOM | 12033 | C | ASN | D | 171 | 4.218 | 8.265 | 19.799 | 1.00 | 55.54 | D | C |
| ATOM | 12034 | O | ASN | D | 171 | 3.606 | 9.001 | 19.018 | 1.00 | 54.88 | D | O |
| ATOM | 12036 | N | LYS | D | 172 | 4.317 | 8.537 | 21.097 | 1.00 | 54.12 | D | N |
| ATOM | 12037 | CA | LYS | D | 172 | 3.952 | 9.855 | 21.613 | 1.00 | 52.94 | D | C |
| ATOM | 12039 | CB | LYS | D | 172 | 3.468 | 9.742 | 23.066 | 1.00 | 52.82 | D | C |
| ATOM | 12046 | C | LYS | D | 172 | 5.189 | 10.763 | 21.453 | 1.00 | 51.63 | D | C |
| ATOM | 12047 | O | LYS | D | 172 | 6.292 | 10.270 | 21.234 | 1.00 | 51.75 | D | O |
| ATOM | 12049 | N | TYR | D | 173 | 5.004 | 12.074 | 21.530 | 1.00 | 49.83 | D | N |
| ATOM | 12050 | CA | TYR | D | 173 | 6.084 | 13.034 | 21.305 | 1.00 | 48.52 | D | C |
| ATOM | 12052 | CB | TYR | D | 173 | 5.563 | 14.190 | 20.451 | 1.00 | 48.93 | D | C |
| ATOM | 12055 | CG | TYR | D | 173 | 5.411 | 13.834 | 18.980 | 1.00 | 52.15 | D | C |
| ATOM | 12056 | CD1 | TYR | D | 173 | 6.440 | 14.109 | 18.061 | 1.00 | 54.32 | D | C |
| ATOM | 12058 | CE1 | TYR | D | 173 | 6.308 | 13.792 | 16.702 | 1.00 | 56.71 | D | C |
| ATOM | 12060 | CZ | TYR | D | 173 | 5.126 | 13.188 | 16.246 | 1.00 | 57.96 | D | C |
| ATOM | 12061 | OH | TYR | D | 173 | 4.985 | 12.861 | 14.921 | 1.00 | 58.69 | D | O |
| ATOM | 12063 | CE2 | TYR | D | 173 | 4.091 | 12.904 | 17.139 | 1.00 | 57.15 | D | C |
| ATOM | 12065 | CD2 | TYR | D | 173 | 4.239 | 13.232 | 18.501 | 1.00 | 55.10 | D | C |
| ATOM | 12067 | C | TYR | D | 173 | 6.718 | 13.595 | 22.593 | 1.00 | 46.53 | D | C |
| ATOM | 12068 | O | TYR | D | 173 | 6.110 | 13.547 | 23.676 | 1.00 | 45.78 | D | O |
| ATOM | 12070 | N | ALA | D | 174 | 7.945 | 14.119 | 22.456 | 1.00 | 43.83 | D | N |
| ATOM | 12071 | CA | ALA | D | 174 | 8.632 | 14.858 | 23.538 | 1.00 | 41.88 | D | C |
| ATOM | 12073 | CB | ALA | D | 174 | 9.702 | 14.020 | 24.201 | 1.00 | 41.08 | D | C |
| ATOM | 12077 | C | ALA | D | 174 | 9.203 | 16.182 | 23.028 | 1.00 | 40.23 | D | C |
| ATOM | 12078 | O | ALA | D | 174 | 9.412 | 16.375 | 21.829 | 1.00 | 40.66 | D | O |
| ATOM | 12080 | N | ALA | D | 175 | 9.396 | 17.112 | 23.947 | 1.00 | 37.82 | D | N |
| ATOM | 12081 | CA | ALA | D | 175 | 10.030 | 18.396 | 23.654 | 1.00 | 36.65 | D | C |
| ATOM | 12083 | CB | ALA | D | 175 | 9.060 | 19.348 | 22.987 | 1.00 | 35.92 | D |

FIG 8 – CONT.

| | | | | | | | | | | |
|---|---|---|---|---|---|---|---|---|---|---|
| ATOM | 12087 | C | ALA | D | 175 | 10.584 | 19.015 | 24.948 | 1.00 35.67 | D C |
| ATOM | 12088 | O | ALA | D | 175 | 10.236 | 18.556 | 26.044 | 1.00 35.62 | D O |
| ATOM | 12090 | N | SER | D | 176 | 11.423 | 20.044 | 24.804 | 1.00 34.20 | D N |
| ATOM | 12091 | CA | SER | D | 176 | 12.150 | 20.654 | 25.916 | 1.00 33.76 | D C |
| ATOM | 12093 | CB | SER | D | 176 | 13.575 | 20.151 | 25.996 | 1.00 33.90 | D C |
| ATOM | 12096 | OG | SER | D | 176 | 13.657 | 18.767 | 26.182 | 1.00 37.95 | D O |
| ATOM | 12098 | C | SER | D | 176 | 12.229 | 22.127 | 25.603 | 1.00 33.49 | D C |
| ATOM | 12099 | O | SER | D | 176 | 12.349 | 22.486 | 24.422 | 1.00 33.36 | D O |
| ATOM | 12101 | N | SER | D | 177 | 12.171 | 22.962 | 26.640 | 1.00 32.74 | D N |
| ATOM | 12102 | CA | SER | D | 177 | 12.469 | 24.390 | 26.530 | 1.00 32.58 | D C |
| ATOM | 12104 | CB | SER | D | 177 | 11.222 | 25.217 | 26.545 | 1.00 32.36 | D C |
| ATOM | 12107 | OG | SER | D | 177 | 11.505 | 26.574 | 26.261 | 1.00 34.79 | D O |
| ATOM | 12109 | C | SER | D | 177 | 13.381 | 24.774 | 27.679 | 1.00 33.21 | D C |
| ATOM | 12110 | O | SER | D | 177 | 13.381 | 24.141 | 28.756 | 1.00 33.36 | D O |
| ATOM | 12112 | N | TYR | D | 178 | 14.214 | 25.771 | 27.425 | 1.00 32.74 | D N |
| ATOM | 12113 | CA | TYR | D | 178 | 15.252 | 26.151 | 28.343 | 1.00 32.69 | D C |
| ATOM | 12115 | CB | TYR | D | 178 | 16.585 | 25.660 | 27.813 | 1.00 32.53 | D C |
| ATOM | 12118 | CG | TYR | D | 178 | 16.801 | 24.173 | 27.913 | 1.00 31.05 | D C |
| ATOM | 12119 | CD1 | TYR | D | 178 | 17.414 | 23.623 | 29.030 | 1.00 29.97 | D C |
| ATOM | 12121 | CE1 | TYR | D | 178 | 17.650 | 22.254 | 29.122 | 1.00 30.03 | D C |
| ATOM | 12123 | CZ | TYR | D | 178 | 17.243 | 21.410 | 28.103 | 1.00 28.47 | D C |
| ATOM | 12124 | OH | TYR | D | 178 | 17.483 | 20.058 | 28.228 | 1.00 27.38 | D O |
| ATOM | 12126 | CE2 | TYR | D | 178 | 16.631 | 21.932 | 26.979 | 1.00 28.84 | D C |
| ATOM | 12128 | CD2 | TYR | D | 178 | 16.430 | 23.325 | 26.887 | 1.00 30.12 | D C |
| ATOM | 12130 | C | TYR | D | 178 | 15.254 | 27.659 | 28.430 | 1.00 33.35 | D C |
| ATOM | 12131 | O | TYR | D | 178 | 15.254 | 28.299 | 27.392 | 1.00 34.52 | D O |
| ATOM | 12133 | N | LEU | D | 179 | 15.188 | 28.216 | 29.636 | 1.00 33.82 | D N |
| ATOM | 12134 | CA | LEU | D | 179 | 15.346 | 29.675 | 29.868 | 1.00 35.35 | D C |
| ATOM | 12136 | CB | LEU | D | 179 | 14.212 | 30.256 | 30.712 | 1.00 35.27 | D C |
| ATOM | 12139 | CG | LEU | D | 179 | 14.240 | 31.759 | 31.057 | 1.00 36.37 | D C |

FIG 8 – CONT.

| ATOM | 12141 | CD1 | LEU | D | 179 | 14.476 | 32.644 | 29.806 | 1.00 | 36.69 | D | C |
|---|---|---|---|---|---|---|---|---|---|---|---|---|
| ATOM | 12145 | CD2 | LEU | D | 179 | 12.959 | 32.183 | 31.748 | 1.00 | 32.79 | D | C |
| ATOM | 12149 | C | LEU | D | 179 | 16.698 | 29.934 | 30.555 | 1.00 | 36.44 | D | C |
| ATOM | 12150 | O | LEU | D | 179 | 16.995 | 29.369 | 31.624 | 1.00 | 36.04 | D | O |
| ATOM | 12152 | N | SER | D | 180 | 17.531 | 30.729 | 29.886 | 1.00 | 37.72 | D | N |
| ATOM | 12153 | CA | SER | D | 180 | 18.853 | 31.041 | 30.359 | 1.00 | 38.93 | D | C |
| ATOM | 12155 | CB | SER | D | 180 | 19.843 | 31.004 | 29.210 | 1.00 | 38.65 | D | C |
| ATOM | 12158 | OG | SER | D | 180 | 19.946 | 29.685 | 28.714 | 1.00 | 39.89 | D | O |
| ATOM | 12160 | C | SER | D | 180 | 18.774 | 32.425 | 30.981 | 1.00 | 40.04 | D | C |
| ATOM | 12161 | O | SER | D | 180 | 18.109 | 33.317 | 30.457 | 1.00 | 40.07 | D | O |
| ATOM | 12163 | N | LEU | D | 181 | 19.420 | 32.591 | 32.122 | 1.00 | 41.31 | D | N |
| ATOM | 12164 | CA | LEU | D | 181 | 19.303 | 33.839 | 32.887 | 1.00 | 41.95 | D | C |
| ATOM | 12166 | CB | LEU | D | 181 | 18.173 | 33.737 | 33.918 | 1.00 | 42.36 | D | C |
| ATOM | 12169 | CG | LEU | D | 181 | 16.743 | 33.526 | 33.479 | 1.00 | 41.07 | D | C |
| ATOM | 12171 | CD1 | LEU | D | 181 | 15.907 | 33.441 | 34.726 | 1.00 | 40.77 | D | C |
| ATOM | 12175 | CD2 | LEU | D | 181 | 16.284 | 34.649 | 32.571 | 1.00 | 41.79 | D | C |
| ATOM | 12179 | C | LEU | D | 181 | 20.558 | 34.011 | 33.654 | 1.00 | 42.12 | D | C |
| ATOM | 12180 | O | LEU | D | 181 | 21.181 | 33.016 | 33.986 | 1.00 | 42.53 | D | O |
| ATOM | 12182 | N | THR | D | 182 | 20.918 | 35.256 | 33.965 | 1.00 | 43.83 | D | N |
| ATOM | 12183 | CA | THR | D | 182 | 21.993 | 35.533 | 34.951 | 1.00 | 44.97 | D | C |
| ATOM | 12185 | CB | THR | D | 182 | 22.450 | 37.002 | 35.003 | 1.00 | 45.29 | D | C |
| ATOM | 12187 | OG1 | THR | D | 182 | 21.334 | 37.839 | 35.365 | 1.00 | 47.80 | D | O |
| ATOM | 12189 | CG2 | THR | D | 182 | 23.018 | 37.448 | 33.654 | 1.00 | 46.09 | D | C |
| ATOM | 12193 | C | THR | D | 182 | 21.415 | 35.215 | 36.314 | 1.00 | 45.24 | D | C |
| ATOM | 12194 | O | THR | D | 182 | 20.179 | 35.256 | 36.502 | 1.00 | 45.07 | D | O |
| ATOM | 12196 | N | PRO | D | 183 | 22.291 | 34.899 | 37.273 | 1.00 | 46.00 | D | N |
| ATOM | 12197 | CA | PRO | D | 183 | 21.733 | 34.669 | 38.596 | 1.00 | 46.99 | D | C |
| ATOM | 12199 | CB | PRO | D | 183 | 22.957 | 34.277 | 39.417 | 1.00 | 47.11 | D | C |
| ATOM | 12202 | CG | PRO | D | 183 | 23.795 | 33.538 | 38.416 | 1.00 | 46.40 | D | C |
| ATOM | 12205 | CD | PRO | D | 183 | 23.655 | 34.368 | 37.160 | 1.00 | 45.50 | D | C |
| ATOM | 12208 | C | PRO | D | 183 | 21.003 | 35.870 | 39.152 | 1.00 | 47.41 | D | |

FIG 8 – CONT.

```
ATOM  12209  O    PRO D 183      19.998  35.694  39.828  1.00 48.22      D
ATOM  12210  N    GLU D 184      21.443  37.078  38.823  1.00 48.38      D
ATOM  12211  CA   GLU D 184      20.732  38.276  39.274  1.00 48.99      D
ATOM  12213  CB   GLU D 184      21.479  39.576  38.895  1.00 49.01      D
ATOM  12220  C    GLU D 184      19.283  38.243  38.758  1.00 49.18      D
ATOM  12221  O    GLU D 184      18.353  38.302  39.556  1.00 49.89      D
ATOM  12223  N    GLN D 185      19.076  38.077  37.451  1.00 49.35      D
ATOM  12224  CA   GLN D 185      17.692  38.006  36.908  1.00 48.70      D
ATOM  12226  CB   GLN D 185      17.692  37.745  35.413  1.00 49.41      D
ATOM  12229  CG   GLN D 185      18.379  38.781  34.539  1.00 51.29      D
ATOM  12232  CD   GLN D 185      19.042  38.134  33.340  1.00 51.64      D
ATOM  12233  OE1  GLN D 185      18.576  37.118  32.820  1.00 48.59      D
ATOM  12234  NE2  GLN D 185      20.166  38.692  32.932  1.00 54.14      D
ATOM  12237  C    GLN D 185      16.854  36.888  37.519  1.00 47.67      D
ATOM  12238  O    GLN D 185      15.659  37.031  37.689  1.00 46.95      D
ATOM  12240  N    TRP D 186      17.457  35.741  37.791  1.00 47.16      D
ATOM  12241  CA   TRP D 186      16.686  34.641  38.393  1.00 46.72      D
ATOM  12243  CB   TRP D 186      17.560  33.416  38.536  1.00 46.03      D
ATOM  12246  CG   TRP D 186      17.122  32.363  39.529  1.00 44.74      D
ATOM  12247  CD1  TRP D 186      17.866  31.868  40.566  1.00 44.40      D
ATOM  12249  NE1  TRP D 186      17.171  30.878  41.225  1.00 43.48      D
ATOM  12251  CE2  TRP D 186      15.965  30.699  40.607  1.00 42.01      D
ATOM  12252  CD2  TRP D 186      15.898  31.613  39.530  1.00 42.71      D
ATOM  12253  CE3  TRP D 186      14.754  31.619  38.726  1.00 41.97      D
ATOM  12255  CZ3  TRP D 186      13.722  30.738  39.036  1.00 41.75      D
ATOM  12257  CH2  TRP D 186      13.818  29.864  40.118  1.00 39.93      D
ATOM  12259  CZ2  TRP D 186      14.930  29.825  40.910  1.00 40.24      D
ATOM  12261  C    TRP D 186      16.131  35.077  39.757  1.00 47.68      D
ATOM  12262  O    TRP D 186      14.914  35.041  39.974  1.00 46.70      D
ATOM  12264  N    LYS D 187      17.038  35.510  40.645  1.00 48.40      D
```

FIG 8 – CONT.

| ATOM | 12265 | CA | LYS | D | 187 | 16.695 | 35.848 | 42.038 | 1.00 | 49.14 | D |
|---|---|---|---|---|---|---|---|---|---|---|---|
| ATOM | 12267 | CB | LYS | D | 187 | 17.955 | 36.032 | 42.900 | 1.00 | 48.68 | D |
| ATOM | 12270 | CG | LYS | D | 187 | 18.781 | 34.753 | 43.136 | 1.00 | 48.91 | D |
| ATOM | 12273 | CD | LYS | D | 187 | 18.387 | 33.996 | 44.416 | 1.00 | 48.78 | D |
| ATOM | 12278 | C | LYS | D | 187 | 15.831 | 37.099 | 42.132 | 1.00 | 49.74 | D |
| ATOM | 12279 | O | LYS | D | 187 | 15.143 | 37.296 | 43.125 | 1.00 | 50.12 | D |
| ATOM | 12281 | N | SER | D | 188 | 15.831 | 37.922 | 41.088 | 1.00 | 50.58 | D |
| ATOM | 12282 | CA | SER | D | 188 | 15.156 | 39.214 | 41.155 | 1.00 | 51.07 | D |
| ATOM | 12284 | CB | SER | D | 188 | 15.909 | 40.225 | 40.281 | 1.00 | 51.52 | D |
| ATOM | 12287 | OG | SER | D | 188 | 15.764 | 39.883 | 38.912 | 1.00 | 52.85 | D |
| ATOM | 12289 | C | SER | D | 188 | 13.669 | 39.198 | 40.771 | 1.00 | 50.81 | D |
| ATOM | 12290 | O | SER | D | 188 | 13.057 | 40.271 | 40.670 | 1.00 | 51.42 | D |
| ATOM | 12292 | N | HIS | D | 189 | 13.085 | 38.020 | 40.549 | 1.00 | 50.20 | D |
| ATOM | 12293 | CA | HIS | D | 189 | 11.628 | 37.903 | 40.326 | 1.00 | 49.84 | D |
| ATOM | 12295 | CB | HIS | D | 189 | 11.303 | 37.502 | 38.883 | 1.00 | 50.71 | D |
| ATOM | 12298 | CG | HIS | D | 189 | 11.635 | 38.548 | 37.868 | 1.00 | 53.06 | D |
| ATOM | 12299 | ND1 | HIS | D | 189 | 10.792 | 39.602 | 37.583 | 1.00 | 57.11 | D |
| ATOM | 12301 | CE1 | HIS | D | 189 | 11.336 | 40.361 | 36.647 | 1.00 | 57.54 | D |
| ATOM | 12303 | NE2 | HIS | D | 189 | 12.504 | 39.837 | 36.316 | 1.00 | 57.63 | D |
| ATOM | 12305 | CD2 | HIS | D | 189 | 12.710 | 38.697 | 37.059 | 1.00 | 55.78 | D |
| ATOM | 12307 | C | HIS | D | 189 | 11.010 | 36.867 | 41.279 | 1.00 | 48.63 | D |
| ATOM | 12308 | O | HIS | D | 189 | 11.698 | 35.972 | 41.778 | 1.00 | 47.50 | D |
| ATOM | 12310 | N | ARG | D | 190 | 9.709 | 37.002 | 41.517 | 1.00 | 47.17 | D |
| ATOM | 12311 | CA | ARG | D | 190 | 9.028 | 36.219 | 42.538 | 1.00 | 46.92 | D |
| ATOM | 12313 | CB | ARG | D | 190 | 7.709 | 36.893 | 42.969 | 1.00 | 46.62 | D |
| ATOM | 12322 | C | ARG | D | 190 | 8.732 | 34.823 | 42.034 | 1.00 | 46.26 | D |
| ATOM | 12323 | O | ARG | D | 190 | 8.583 | 33.897 | 42.814 | 1.00 | 45.98 | D |
| ATOM | 12325 | N | SER | D | 191 | 8.649 | 34.680 | 40.721 | 1.00 | 45.96 | D |
| ATOM | 12326 | CA | SER | D | 191 | 8.066 | 33.505 | 40.115 | 1.00 | 45.44 | D |
| ATOM | 12328 | CB | SER | D | 191 | 6.549 | 33.618 | 40.241 | 1.00 | 45.52 | D |
| ATOM | 12331 | OG | SER | D | 191 | 5.887 | 32.757 | 39.346 | 1.00 | 47.64 | D |

FIG 8 – CONT.

```
O
ATOM  12333  C    SER D 191       8.446  33.458  38.637  1.00 44.67      D
C
ATOM  12334  O    SER D 191       8.533  34.495  37.989  1.00 44.91      D
O
ATOM  12336  N    TYR D 192       8.677  32.256  38.120  1.00 43.05      D
N
ATOM  12337  CA   TYR D 192       8.727  32.038  36.690  1.00 42.53      D
C
ATOM  12339  CB   TYR D 192      10.134  31.664  36.247  1.00 42.53      D
C
ATOM  12342  CG   TYR D 192      11.109  32.807  36.213  1.00 44.43      D
C
ATOM  12343  CD1  TYR D 192      11.364  33.481  35.028  1.00 44.79      D
C
ATOM  12345  CE1  TYR D 192      12.276  34.521  34.981  1.00 46.29      D
C
ATOM  12347  CZ   TYR D 192      12.950  34.894  36.127  1.00 45.99      D
C
ATOM  12348  OH   TYR D 192      13.844  35.932  36.060  1.00 48.64      D
O
ATOM  12350  CE2  TYR D 192      12.731  34.228  37.322  1.00 45.25      D
C
ATOM  12352  CD2  TYR D 192      11.816  33.193  37.365  1.00 44.51      D
C
ATOM  12354  C    TYR D 192       7.780  30.899  36.337  1.00 41.45      D
C
ATOM  12355  O    TYR D 192       7.592  29.975  37.116  1.00 39.70      D
O
ATOM  12357  N    SER D 193       7.225  30.933  35.136  1.00 40.41      D
N
ATOM  12358  CA   SER D 193       6.399  29.832  34.722  1.00 40.18      D
C
ATOM  12360  CB   SER D 193       4.942  30.227  34.857  1.00 40.16      D
C
ATOM  12363  OG   SER D 193       4.757  31.453  34.222  1.00 43.26      D
O
ATOM  12365  C    SER D 193       6.718  29.329  33.318  1.00 39.45      D
C
ATOM  12366  O    SER D 193       7.060  30.098  32.427  1.00 39.36      D
O
ATOM  12368  N    CYS D 194       6.623  28.021  33.158  1.00 38.90      D
N
ATOM  12369  CA   CYS D 194       6.616  27.381  31.872  1.00 39.36      D
C
ATOM  12371  CB   CYS D 194       7.515  26.160  31.861  1.00 38.92      D
C
ATOM  12374  SG   CYS D 194       7.468  25.294  30.297  1.00 38.33      D
S
ATOM  12376  C    CYS D 194       5.185  26.976  31.535  1.00 40.29      D
C
ATOM  12377  O    CYS D 194       4.556  26.225  32.273  1.00 40.39      D
O
ATOM  12379  N    ARG D 195       4.700  27.462  30.399  1.00 40.97      D
N
ATOM  12380  CA   ARG D 195       3.319  27.305  29.997  1.00 42.00      D
C
ATOM  12382  CB   ARG D 195       2.680  28.688  29.986  1.00 42.61      D
C
ATOM  12385  CG   ARG D 195       1.346  28.828  29.278  1.00 47.40      D
C
```

FIG 8 – CONT.

```
ATOM   12388  CD   ARG D 195      0.872  30.300  29.361  1.00 53.15       D
C
ATOM   12391  NE   ARG D 195     -0.279  30.559  28.498  1.00 58.12       D
N
ATOM   12393  CZ   ARG D 195     -1.554  30.317  28.825  1.00 62.91       D
C
ATOM   12394  NH1  ARG D 195     -1.875  29.806  30.012  1.00 64.34       D
N
ATOM   12397  NH2  ARG D 195     -2.527  30.584  27.952  1.00 64.38       D
N
ATOM   12400  C    ARG D 195      3.237  26.590  28.637  1.00 41.41       D
C
ATOM   12401  O    ARG D 195      3.657  27.121  27.595  1.00 41.72       D
O
ATOM   12403  N    VAL D 196      2.678  25.390  28.662  1.00 40.62       D
N
ATOM   12404  CA   VAL D 196      2.621  24.515  27.508  1.00 40.49       D
C
ATOM   12406  CB   VAL D 196      3.165  23.138  27.882  1.00 40.41       D
C
ATOM   12408  CG1  VAL D 196      3.026  22.172  26.707  1.00 40.35       D
C
ATOM   12412  CG2  VAL D 196      4.623  23.244  28.359  1.00 39.06       D
C
ATOM   12416  C    VAL D 196      1.183  24.347  27.001  1.00 41.18       D
C
ATOM   12417  O    VAL D 196      0.324  23.821  27.721  1.00 41.23       D
O
ATOM   12419  N    THR D 197      0.908  24.794  25.776  1.00 41.50       D
N
ATOM   12420  CA   THR D 197     -0.425  24.610  25.180  1.00 41.73       D
C
ATOM   12422  CB   THR D 197     -0.892  25.880  24.477  1.00 41.81       D
C
ATOM   12424  OG1  THR D 197     -0.832  26.983  25.390  1.00 41.23       D
O
ATOM   12426  CG2  THR D 197     -2.320  25.736  23.999  1.00 42.52       D
C
ATOM   12430  C    THR D 197     -0.456  23.402  24.206  1.00 42.41       D
C
ATOM   12431  O    THR D 197      0.383  23.310  23.305  1.00 42.31       D
O
ATOM   12433  N    HIS D 198     -1.407  22.483  24.414  1.00 42.79       D
N
ATOM   12434  CA   HIS D 198     -1.596  21.303  23.560  1.00 44.10       D
C
ATOM   12436  CB   HIS D 198     -1.004  20.070  24.229  1.00 43.83       D
C
ATOM   12439  CG   HIS D 198     -1.189  18.787  23.459  1.00 44.73       D
C
ATOM   12440  ND1  HIS D 198     -0.501  18.501  22.295  1.00 44.77       D
N
ATOM   12442  CE1  HIS D 198     -0.823  17.287  21.884  1.00 43.76       D
C
ATOM   12444  NE2  HIS D 198     -1.680  16.764  22.743  1.00 44.22       D
N
ATOM   12446  CD2  HIS D 198     -1.922  17.681  23.738  1.00 43.54       D
C
ATOM   12448  C    HIS D 198     -3.080  21.044  23.273  1.00 45.45       D
C
ATOM   12449  O    HIS D 198     -3.867  20.774  24.208  1.00 45.08       D
```

FIG 8 – CONT.

```
O
ATOM  12451  N    GLU D 199      -3.445  21.117  21.987  1.00 46.36      D
N
ATOM  12452  CA   GLU D 199      -4.816  20.900  21.542  1.00 47.79      D
C
ATOM  12454  CB   GLU D 199      -5.167  19.398  21.586  1.00 48.43      D
C
ATOM  12457  CG   GLU D 199      -4.371  18.510  20.588  1.00 50.76      D
C
ATOM  12460  CD   GLU D 199      -4.585  18.918  19.131  1.00 52.67      D
C
ATOM  12461  OE1  GLU D 199      -5.767  19.078  18.746  1.00 56.09      D
O
ATOM  12462  OE2  GLU D 199      -3.585  19.082  18.382  1.00 51.68      D
O
ATOM  12463  C    GLU D 199      -5.790  21.696  22.410  1.00 47.83      D
C
ATOM  12464  O    GLU D 199      -6.659  21.122  23.067  1.00 48.55      D
O
ATOM  12466  N    GLY D 200      -5.607  23.009  22.468  1.00 47.81      D
N
ATOM  12467  CA   GLY D 200      -6.545  23.869  23.177  1.00 48.10      D
C
ATOM  12470  C    GLY D 200      -6.363  23.956  24.677  1.00 48.26      D
C
ATOM  12471  O    GLY D 200      -6.686  24.980  25.273  1.00 49.17      D
O
ATOM  12473  N    SER D 203      -5.837  22.913  25.305  1.00 47.94      D
N
ATOM  12474  CA   SER D 203      -5.622  22.956  26.736  1.00 47.96      D
C
ATOM  12476  CB   SER D 203      -6.106  21.645  27.378  1.00 47.81      D
C
ATOM  12479  OG   SER D 203      -5.035  20.768  27.612  1.00 51.20      D
O
ATOM  12481  C    SER D 203      -4.149  23.322  27.077  1.00 47.51      D
C
ATOM  12482  O    SER D 203      -3.208  22.964  26.364  1.00 47.50      D
O
ATOM  12484  N    THR D 204      -3.987  24.081  28.156  1.00 46.64      D
N
ATOM  12485  CA   THR D 204      -2.709  24.623  28.599  1.00 45.65      D
C
ATOM  12487  CB   THR D 204      -2.782  26.138  28.685  1.00 45.40      D
C
ATOM  12489  OG1  THR D 204      -2.722  26.722  27.379  1.00 44.50      D
O
ATOM  12491  CG2  THR D 204      -1.649  26.665  29.522  1.00 45.84      D
C
ATOM  12495  C    THR D 204      -2.342  24.119  30.004  1.00 45.52      D
C
ATOM  12496  O    THR D 204      -3.115  24.288  30.954  1.00 45.03      D
O
ATOM  12498  N    VAL D 205      -1.162  23.517  30.132  1.00 45.34      D
N
ATOM  12499  CA   VAL D 205      -0.585  23.164  31.426  1.00 44.99      D
C
ATOM  12501  CB   VAL D 205      -0.022  21.764  31.414  1.00 44.91      D
C
ATOM  12503  CG1  VAL D 205       0.590  21.450  32.740  1.00 44.97      D
C
```

FIG 8 – CONT.

| ATOM | 12507 | CG2 | VAL | D | 205 | -1.086 | 20.777 | 31.066 | 1.00 | 45.39 | D C |
|---|---|---|---|---|---|---|---|---|---|---|---|
| ATOM | 12511 | C | VAL | D | 205 | 0.570 | 24.108 | 31.764 | 1.00 | 45.13 | D C |
| ATOM | 12512 | O | VAL | D | 205 | 1.516 | 24.274 | 30.974 | 1.00 | 44.93 | D O |
| ATOM | 12514 | N | GLU | D | 206 | 0.513 | 24.686 | 32.959 | 1.00 | 44.54 | D N |
| ATOM | 12515 | CA | GLU | D | 206 | 1.449 | 25.690 | 33.362 | 1.00 | 44.59 | D C |
| ATOM | 12517 | CB | GLU | D | 206 | 0.722 | 27.027 | 33.396 | 1.00 | 45.06 | D C |
| ATOM | 12520 | CG | GLU | D | 206 | 1.356 | 28.067 | 34.284 | 1.00 | 47.42 | D C |
| ATOM | 12523 | CD | GLU | D | 206 | 0.928 | 29.474 | 33.904 | 1.00 | 50.28 | D C |
| ATOM | 12524 | OE1 | GLU | D | 206 | -0.195 | 29.633 | 33.348 | 1.00 | 50.11 | D O |
| ATOM | 12525 | OE2 | GLU | D | 206 | 1.742 | 30.409 | 34.130 | 1.00 | 52.94 | D O |
| ATOM | 12526 | C | GLU | D | 206 | 2.065 | 25.361 | 34.718 | 1.00 | 44.07 | D C |
| ATOM | 12527 | O | GLU | D | 206 | 1.346 | 25.188 | 35.710 | 1.00 | 44.87 | D O |
| ATOM | 12529 | N | LYS | D | 207 | 3.391 | 25.293 | 34.770 | 1.00 | 42.68 | D N |
| ATOM | 12530 | CA | LYS | D | 207 | 4.100 | 24.991 | 36.013 | 1.00 | 41.74 | D C |
| ATOM | 12532 | CB | LYS | D | 207 | 4.983 | 23.765 | 35.869 | 1.00 | 40.89 | D C |
| ATOM | 12535 | CG | LYS | D | 207 | 4.244 | 22.548 | 35.468 | 1.00 | 40.76 | D C |
| ATOM | 12538 | CD | LYS | D | 207 | 3.792 | 21.691 | 36.658 | 1.00 | 39.60 | D C |
| ATOM | 12541 | CE | LYS | D | 207 | 2.851 | 20.586 | 36.156 | 1.00 | 39.02 | D C |
| ATOM | 12544 | NZ | LYS | D | 207 | 3.296 | 19.207 | 36.592 | 1.00 | 39.28 | D N |
| ATOM | 12548 | C | LYS | D | 207 | 4.936 | 26.172 | 36.442 | 1.00 | 41.46 | D C |
| ATOM | 12549 | O | LYS | D | 207 | 5.328 | 26.999 | 35.619 | 1.00 | 41.28 | D O |
| ATOM | 12551 | N | THR | D | 208 | 5.188 | 26.263 | 37.747 | 1.00 | 40.96 | D N |
| ATOM | 12552 | CA | THR | D | 208 | 5.826 | 27.429 | 38.300 | 1.00 | 40.93 | D C |
| ATOM | 12554 | CB | THR | D | 208 | 4.790 | 28.369 | 38.978 | 1.00 | 41.32 | D C |
| ATOM | 12556 | OG1 | THR | D | 208 | 3.700 | 28.647 | 38.064 | 1.00 | 42.13 | D O |
| ATOM | 12558 | CG2 | THR | D | 208 | 5.409 | 29.688 | 39.313 | 1.00 | 40.95 | D C |
| ATOM | 12562 | C | THR | D | 208 | 6.989 | 27.051 | 39.221 | 1.00 | 41.01 | D C |
| ATOM | 12563 | O | THR | D | 208 | 7.052 | 25.972 | 39.835 | 1.00 | 40.80 | D O |
| ATOM | 12565 | N | VAL | D | 209 | 7.944 | 27.953 | 39.267 | 1.00 | 40.96 | D N |
| ATOM | 12566 | CA | VAL | D | 209 | 9.111 | 27.769 | 40.064 | 1.00 | 41.48 | D C |
| ATOM | 12568 | CB | VAL | D | 209 | 10.230 | 27.194 | 39.164 | 1.00 | 41.27 | D |

FIG 8 – CONT.

```
C
ATOM   12570  CG1  VAL D 209      11.131  28.296  38.608  1.00 39.44      D
ATOM   12574  CG2  VAL D 209      10.991  26.133  39.897  1.00 41.52      D
C
ATOM   12578  C    VAL D 209       9.418  29.142  40.688  1.00 42.15      D
C
ATOM   12579  O    VAL D 209       9.230  30.162  40.038  1.00 42.03      D
O
ATOM   12581  N    ALA D 210       9.855  29.151  41.946  1.00 43.26      D
N
ATOM   12582  CA   ALA D 210      10.060  30.379  42.720  1.00 43.96      D
C
ATOM   12584  CB   ALA D 210       8.978  30.520  43.752  1.00 44.60      D
C
ATOM   12588  C    ALA D 210      11.435  30.353  43.388  1.00 44.83      D
C
ATOM   12589  O    ALA D 210      11.779  29.393  44.085  1.00 44.93      D
O
ATOM   12591  N    PRO D 211      12.243  31.397  43.154  1.00 45.74      D
N
ATOM   12592  CA   PRO D 211      13.605  31.450  43.662  1.00 46.72      D
C
ATOM   12594  CB   PRO D 211      14.206  32.660  42.941  1.00 46.85      D
C
ATOM   12597  CG   PRO D 211      13.096  33.432  42.466  1.00 46.21      D
C
ATOM   12600  CD   PRO D 211      11.953  32.522  42.250  1.00 45.68      D
C
ATOM   12603  C    PRO D 211      13.759  31.638  45.166  1.00 47.93      D
C
ATOM   12604  O    PRO D 211      14.873  31.494  45.667  1.00 47.80      D
O
ATOM   12605  N    ALA D 212      12.675  31.968  45.876  1.00 49.38      D
N
ATOM   12606  CA   ALA D 212      12.686  32.004  47.356  1.00 50.03      D
C
ATOM   12608  CB   ALA D 212      11.503  32.817  47.875  1.00 50.26      D
C
ATOM   12612  C    ALA D 212      12.667  30.596  47.957  1.00 50.62      D
C
ATOM   12613  O    ALA D 212      11.831  29.757  47.591  1.00 52.02      D
O
TER
HETATM12615  O    HOH W   1       8.499   8.717 -20.872  1.00 54.80      W
O
HETATM12618  O    HOH W   2      37.448   9.905 -10.211  1.00 25.85      W
O
HETATM12621  O    HOH W   3      29.708  29.260  11.327  1.00 27.99      W
O
HETATM12624  O    HOH W   4      63.316  17.379  33.894  1.00 37.34      W
O
HETATM12627  O    HOH W   5      36.314  20.342  -4.375  1.00 44.17      W
O
HETATM12630  O    HOH W   6      35.007  29.277  69.872  1.00 58.84      W
O
HETATM12633  O    HOH W   7      44.071  22.582  29.748  1.00 23.48      W
O
HETATM12636  O    HOH W   8      34.312   6.070   8.656  1.00 43.31      W
O
HETATM12639  O    HOH W   9      59.638  31.927  26.532  1.00 32.96      W
O
```

FIG 8 – CONT.

| | | | | | | | | | |
|---|---|---|---|---|---|---|---|---|---|
| HETATM12642 | O | HOH | W | 10 | 27.115 | 11.253 | 56.356 | 1.00 38.81 | W |
| HETATM12645 | O | HOH | W | 11 | 28.294 | -6.137 | -10.164 | 1.00 31.54 | W |
| HETATM12648 | O | HOH | W | 12 | 34.818 | 16.225 | -11.086 | 1.00 33.68 | W |
| HETATM12651 | O | HOH | W | 13 | 47.769 | 37.345 | 39.862 | 1.00 50.62 | W |
| HETATM12654 | O | HOH | W | 14 | 18.469 | 23.752 | 36.003 | 1.00 29.88 | W |
| HETATM12657 | O | HOH | W | 15 | 30.267 | 23.685 | 80.641 | 1.00 34.93 | W |
| HETATM12660 | O | HOH | W | 16 | 17.046 | 17.680 | -6.893 | 1.00 30.90 | W |
| HETATM12663 | O | HOH | W | 17 | 22.819 | 19.161 | 59.741 | 1.00 29.98 | W |
| HETATM12666 | O | HOH | W | 18 | 44.724 | 11.382 | 81.514 | 1.00 27.92 | W |
| HETATM12669 | O | HOH | W | 19 | 61.537 | 10.174 | 22.001 | 1.00 43.13 | W |
| HETATM12672 | O | HOH | W | 20 | 26.557 | 23.517 | 44.888 | 1.00 40.68 | W |
| HETATM12675 | O | HOH | W | 21 | 33.514 | 25.296 | 21.920 | 1.00 42.47 | W |
| HETATM12678 | O | HOH | W | 22 | 45.098 | 23.719 | 75.029 | 1.00 42.10 | W |
| HETATM12681 | O | HOH | W | 23 | 22.326 | 14.765 | 75.026 | 1.00 32.89 | W |
| HETATM12684 | O | HOH | W | 24 | 19.144 | 26.752 | 63.928 | 1.00 48.17 | W |
| HETATM12687 | O | HOH | W | 25 | 43.593 | 7.634 | 65.187 | 1.00 31.66 | W |
| HETATM12690 | O | HOH | W | 26 | 20.716 | 15.939 | 69.752 | 1.00 34.66 | W |
| HETATM12693 | O | HOH | W | 27 | 22.712 | -0.187 | 0.996 | 1.00 33.05 | W |
| HETATM12696 | O | HOH | W | 28 | 20.770 | 9.753 | 75.577 | 1.00 47.55 | W |
| HETATM12699 | O | HOH | W | 29 | 29.522 | 7.212 | 12.652 | 1.00 35.83 | W |
| HETATM12702 | O | HOH | W | 30 | 32.325 | 20.205 | -9.402 | 1.00 42.82 | W |
| HETATM12705 | O | HOH | W | 31 | 33.175 | 12.637 | 53.403 | 1.00 41.33 | W |
| HETATM12708 | O | HOH | W | 32 | 36.513 | 13.681 | 46.869 | 1.00 32.99 | W |
| HETATM12711 | O | HOH | W | 33 | 38.942 | 5.050 | 0.309 | 1.00 35.93 | W |
| HETATM12714 | O | HOH | W | 34 | 34.100 | 20.006 | 53.810 | 1.00 36.76 | W |
| HETATM12717 | O | HOH | W | 35 | 5.326 | 33.632 | 36.271 | 1.00 41.06 | W |
| HETATM12720 | O | HOH | W | 36 | 23.279 | 21.733 | 42.977 | 1.00 38.08 | W |
| HETATM12723 | O | HOH | W | 37 | 6.776 | -6.427 | -7.418 | 1.00 57.94 | W |
| HETATM12726 | O | HOH | W | 38 | 1.077 | 4.801 | -15.716 | 1.00 45.59 | W |
| HETATM12729 | O | HOH | W | 39 | 65.931 | 12.105 | 27.759 | 1.00 53.27 | W |
| HETATM12732 | O | HOH | W | 40 | 20.842 | 8.323 | 26.257 | 1.00 28.44 | W |

FIG 8 – CONT.

```
O
HETATM12735  O    HOH W  41      38.625  14.048   4.947  1.00 32.67      W
O
HETATM12738  O    HOH W  42      28.579  10.282  23.151  1.00 31.23      W
O
HETATM12741  O    HOH W  43      31.755  24.040   0.417  1.00 36.84      W
O
HETATM12744  O    HOH W  44      15.072  20.966  17.849  1.00 29.23      W
O
HETATM12747  O    HOH W  45      44.349   6.057  69.623  1.00 36.20      W
O
HETATM12750  O    HOH W  46      36.793  -0.115 -16.795  1.00 41.09      W
O
HETATM12753  O    HOH W  47      39.617   5.353  84.589  1.00 43.83      W
O
HETATM12756  O    HOH W  48      23.570  25.025   0.081  1.00 41.75      W
O
HETATM12759  O    HOH W  49      41.095  13.478  25.345  1.00 38.24      W
O
HETATM12762  O    HOH W  50      29.038  29.312  65.036  1.00 38.19      W
O
HETATM12765  O    HOH W  51      47.562  25.843  21.241  1.00 39.82      W
O
HETATM12768  O    HOH W  52      14.555  19.039  -7.350  1.00 47.21      W
O
HETATM12771  O    HOH W  53      23.973  14.109 -12.665  1.00 27.75      W
O
HETATM12774  O    HOH W  54      39.736  29.832  39.102  1.00 39.96      W
O
HETATM12777  O    HOH W  55      46.857  30.068  37.735  1.00 30.68      W
O
HETATM12780  O    HOH W  56      44.275   0.662  79.441  1.00 49.95      W
O
HETATM12783  O    HOH W  57      36.070  17.880  30.052  1.00 52.65      W
O
HETATM12786  O    HOH W  58      69.397  13.883  41.355  1.00 38.05      W
O
HETATM12789  O    HOH W  59      44.282   8.836  84.222  1.00 50.89      W
O
HETATM12792  O    HOH W  60      19.863  14.967  20.860  1.00 32.92      W
O
HETATM12795  O    HOH W  61      22.267  23.144   6.068  1.00 34.05      W
O
HETATM12798  O    HOH W  62      34.189  33.876  60.427  1.00 32.90      W
O
HETATM12801  O    HOH W  63      15.845   1.130  -2.723  1.00 30.02      W
O
HETATM12804  O    HOH W  64      43.467   2.746  71.761  1.00 54.18      W
O
HETATM12807  O    HOH W  65      38.773   3.393 -18.299  1.00 50.52      W
O
HETATM12810  O    HOH W  66      27.075  19.459  53.431  1.00 38.24      W
O
HETATM12813  O    HOH W  67      28.870  26.769  51.401  1.00 34.72      W
O
HETATM12816  O    HOH W  68      13.371  28.745  20.458  1.00 40.66      W
O
HETATM12819  O    HOH W  69      41.636  10.410  59.405  1.00 41.53      W
O
HETATM12822  O    HOH W  70      26.590   9.160   9.621  1.00 31.13      W
O
```

FIG 8 – CONT.

| | | | | | | | | | | |
|---|---|---|---|---|---|---|---|---|---|---|
| HETATM12825 | O | HOH W | 71 | 41.581 | 13.691 | -3.357 | 1.00 | 43.03 | | W |
| HETATM12828 | O | HOH W | 72 | 14.821 | 20.798 | 41.625 | 1.00 | 30.01 | | W |
| HETATM12831 | O | HOH W | 73 | 26.262 | 4.254 | 38.332 | 1.00 | 42.12 | | W |
| HETATM12834 | O | HOH W | 74 | 27.479 | 11.760 | -18.915 | 1.00 | 55.62 | | W |
| HETATM12837 | O | HOH W | 75 | 41.226 | 9.385 | -1.031 | 1.00 | 42.86 | | W |
| HETATM12840 | O | HOH W | 76 | 34.334 | 23.532 | -1.043 | 1.00 | 29.93 | | W |
| HETATM12843 | O | HOH W | 77 | 2.309 | 17.723 | 34.408 | 1.00 | 44.11 | | W |
| HETATM12846 | O | HOH W | 78 | 31.455 | 28.397 | 66.670 | 1.00 | 41.63 | | W |
| HETATM12849 | O | HOH W | 79 | 63.618 | 29.904 | 38.501 | 1.00 | 39.06 | | W |
| HETATM12852 | O | HOH W | 80 | 36.420 | 12.120 | -11.305 | 1.00 | 43.01 | | W |
| HETATM12855 | O | HOH W | 81 | 22.273 | 4.873 | 81.281 | 1.00 | 39.77 | | W |
| HETATM12858 | O | HOH W | 82 | 35.640 | 14.837 | 56.431 | 1.00 | 35.41 | | W |
| HETATM12861 | O | HOH W | 83 | 24.778 | 21.217 | 76.560 | 1.00 | 37.29 | | W |
| HETATM12864 | O | HOH W | 84 | 55.535 | 23.856 | 61.149 | 1.00 | 58.84 | | W |
| HETATM12867 | O | HOH W | 85 | 24.224 | 18.712 | 69.596 | 1.00 | 34.76 | | W |
| HETATM12870 | O | HOH W | 86 | 27.039 | 4.310 | 7.910 | 1.00 | 51.25 | | W |
| HETATM12873 | O | HOH W | 87 | 32.930 | 22.041 | 14.455 | 1.00 | 31.02 | | W |
| HETATM12876 | O | HOH W | 88 | 33.662 | 8.919 | 26.695 | 1.00 | 39.91 | | W |
| HETATM12879 | O | HOH W | 89 | 53.135 | 14.621 | 46.280 | 1.00 | 52.45 | | W |
| HETATM12882 | O | HOH W | 90 | 45.277 | 4.200 | 39.474 | 1.00 | 47.20 | | W |
| HETATM12885 | O | HOH W | 91 | 2.897 | 18.910 | 39.485 | 1.00 | 48.52 | | W |
| HETATM12888 | O | HOH W | 92 | 27.999 | 15.072 | 11.945 | 1.00 | 29.07 | | W |
| HETATM12891 | O | HOH W | 93 | 42.039 | 30.938 | 31.576 | 1.00 | 54.70 | | W |
| HETATM12894 | O | HOH W | 94 | 22.713 | 24.460 | -3.405 | 1.00 | 59.56 | | W |
| HETATM12897 | O | HOH W | 95 | 26.490 | 20.865 | 0.388 | 1.00 | 24.68 | | W |
| HETATM12900 | O | HOH W | 96 | 11.929 | 10.404 | 17.110 | 1.00 | 48.87 | | W |
| HETATM12903 | O | HOH W | 97 | 50.590 | 25.095 | 48.654 | 1.00 | 38.98 | | W |
| HETATM12906 | O | HOH W | 98 | 36.736 | 7.493 | -11.448 | 1.00 | 29.60 | | W |
| HETATM12909 | O | HOH W | 99 | 24.959 | -1.505 | -15.524 | 1.00 | 40.10 | | W |
| HETATM12912 | O | HOH W | 100 | 34.813 | 14.581 | 51.040 | 1.00 | 35.62 | | W |
| HETATM12915 | O | HOH W | 101 | 29.060 | 23.482 | -0.894 | 1.00 | 33.54 | | W |

FIG 8 – CONT.

```
HETATM12918  O   HOH W 102      28.273   8.795  62.221  1.00 33.24           W
HETATM12921  O   HOH W 103       8.261  32.675  25.988  1.00 37.09           W
HETATM12924  O   HOH W 104      47.189  22.289  69.915  1.00 34.59           W
HETATM12927  O   HOH W 105      47.303  25.688  66.663  1.00 43.74           W
HETATM12930  O   HOH W 106      46.241  18.321  26.378  1.00 25.44           W
HETATM12933  O   HOH W 107      28.649  18.493 -14.805  1.00 36.16           W
HETATM12936  O   HOH W 108      32.733  10.315   6.456  1.00 30.75           W
HETATM12939  O   HOH W 109       8.116  -0.071   2.569  1.00 47.27           W
HETATM12942  O   HOH W 110      16.974  22.896  19.017  1.00 43.46           W
HETATM12945  O   HOH W 111      33.952   7.842  59.493  1.00 41.83           W
HETATM12948  O   HOH W 112      18.225  28.742  26.922  1.00 30.17           W
HETATM12951  O   HOH W 113      28.786  15.405  58.888  1.00 33.82           W
HETATM12954  O   HOH W 114       1.703  10.486  14.020  1.00 55.58           W
HETATM12957  O   HOH W 115      35.195  17.046  51.749  1.00 42.18           W
HETATM12960  O   HOH W 116       7.468  11.951  13.160  1.00 47.98           W
HETATM12963  O   HOH W 117      34.311  25.896  65.642  1.00 22.19           W
HETATM12966  O   HOH W 118      37.229  30.306  65.813  1.00 49.82           W
HETATM12969  O   HOH W 119      57.092  26.796  70.768  1.00 52.51           W
HETATM12972  O   HOH W 120       1.029  18.937  -6.903  1.00 49.85           W
HETATM12975  O   HOH W 121      21.871  23.307  66.081  1.00 46.42           W
HETATM12978  O   HOH W 122      52.669   4.847  64.738  1.00 61.08           W
HETATM12981  O   HOH W 123      17.884  19.234   1.672  1.00 31.80           W
HETATM12984  O   HOH W 124       9.457   4.037  31.649  1.00 50.32           W
HETATM12987  O   HOH W 125      10.344  18.337   8.751  1.00 56.85           W
HETATM12990  O   HOH W 126      50.808   7.227  18.692  1.00 58.78           W
HETATM12993  O   HOH W 127      72.592  26.019  46.425  1.00 50.44           W
HETATM12996  O   HOH W 128       0.442  14.595  33.847  1.00 46.64           W
HETATM12999  O   HOH W 129      43.773   4.694  -7.777  1.00 62.49           W
HETATM13002  O   HOH W 130      20.496   9.909  45.114  1.00 38.47           W
HETATM13005  O   HOH W 131      50.298  18.101  25.912  1.00 30.67           W
```

FIG 8 – CONT.

```
HETATM13008  O   HOH W 132      33.785  28.021   2.902  1.00 32.49           W
                                                                             O
HETATM13011  O   HOH W 133      27.271  28.580   5.200  1.00 33.21           W
                                                                             O
HETATM13014  O   HOH W 134      48.265   9.766  62.966  1.00 37.46           W
                                                                             O
HETATM13017  O   HOH W 135      37.021   2.431   0.305  1.00 36.52           W
                                                                             O
HETATM13020  O   HOH W 136      58.329  30.019  43.124  1.00 34.03           W
                                                                             O
HETATM13023  O   HOH W 137      18.872  21.057  41.323  1.00 32.97           W
                                                                             O
HETATM13026  O   HOH W 138      57.704  18.806  29.741  1.00 37.32           W
                                                                             O
HETATM13029  O   HOH W 139      16.331  18.568  26.230  1.00 31.09           W
                                                                             O
HETATM13032  O   HOH W 140      52.236  31.737  43.552  1.00 46.38           W
                                                                             O
HETATM13035  O   HOH W 141      47.863   8.758  25.332  1.00 41.57           W
                                                                             O
HETATM13038  O   HOH W 142      39.004   3.296  33.589  1.00 45.97           W
                                                                             O
HETATM13041  O   HOH W 143      41.129   1.331  31.049  1.00 49.57           W
                                                                             O
HETATM13044  O   HOH W 144      12.199  11.241  22.745  1.00 52.88           W
                                                                             O
HETATM13047  O   HOH W 145      46.878   4.444  70.328  1.00 36.97           W
                                                                             O
HETATM13050  O   HOH W 146      25.678  28.153  25.562  1.00 39.98           W
                                                                             O
HETATM13053  O   HOH W 147      35.532  31.966  19.304  1.00 48.23           W
                                                                             O
HETATM13056  O   HOH W 148      10.826  20.707 -23.109  1.00 50.27           W
                                                                             O
HETATM13059  O   HOH W 149      20.700  17.253  17.915  1.00 43.86           W
                                                                             O
HETATM13062  O   HOH W 150      24.013  19.699 -16.290  1.00 55.10           W
                                                                             O
HETATM13065  O   HOH W 151      41.955  19.032  24.546  1.00 40.60           W
                                                                             O
HETATM13068  O   HOH W 152      35.497  18.957  79.079  1.00 37.13           W
                                                                             O
HETATM13071  O   HOH W 153      26.573  17.885  16.613  1.00 38.56           W
                                                                             O
HETATM13074  O   HOH W 154      11.748   4.410  37.962  1.00 43.54           W
                                                                             O
HETATM13077  O   HOH W 155      -4.172  18.122  25.333  1.00 40.85           W
                                                                             O
HETATM13080  O   HOH W 156       5.790   2.201  16.874  1.00 63.13           W
                                                                             O
HETATM13083  O   HOH W 157      -8.987   9.924   1.682  1.00 60.14           W
                                                                             O
HETATM13086  O   HOH W 158      -2.664  14.790  31.938  1.00 50.82           W
                                                                             O
HETATM13089  O   HOH W 159      29.505  31.854  41.404  1.00 54.03           W
                                                                             O
HETATM13092  O   HOH W 160      54.018  14.562  19.190  1.00 46.93           W
                                                                             O
HETATM13095  O   HOH W 161      32.869  -0.254  77.655  1.00 53.38           W
                                                                             O
HETATM13098  O   HOH W 162      34.858  -1.063  -9.543  1.00 39.16           W
```

FIG 8 – CONT.

```
O
HETATM13101  O    HOH W 163      42.941  24.392  65.791  1.00 22.64           W
O
HETATM13104  O    HOH W 164      12.950  27.417  43.218  1.00 48.59           W
O
HETATM13107  O    HOH W 165      13.759  17.726  23.762  1.00 30.05           W
O
HETATM13110  O    HOH W 166      26.137  29.393   2.666  1.00 43.49           W
O
HETATM13113  O    HOH W 167      26.164  18.591  82.779  1.00 51.62           W
O
HETATM13116  O    HOH W 168      42.496  22.888  74.171  1.00 42.18           W
O
HETATM13119  O    HOH W 169      41.308   7.385  64.288  1.00 41.53           W
O
HETATM13122  O    HOH W 170      29.598   8.899   2.504  1.00 28.64           W
O
HETATM13125  O    HOH W 171      21.364  16.942  43.864  1.00 42.77           W
O
HETATM13128  O    HOH W 172      23.413  19.047  75.386  1.00 46.27           W
O
HETATM13131  O    HOH W 173      61.987  35.026  35.208  1.00 54.60           W
O
HETATM13134  O    HOH W 174      17.504   0.546  -0.587  1.00 41.34           W
O
HETATM13137  O    HOH W 175      14.169   0.090  36.572  1.00 45.83           W
O
HETATM13140  O    HOH W 176      33.952  12.061  58.319  1.00 39.34           W
O
HETATM13143  O    HOH W 177      -1.095   9.644 -12.829  1.00 54.40           W
O
HETATM13146  O    HOH W 178       1.974  28.087  25.746  1.00 42.14           W
O
HETATM13149  O    HOH W 179       9.522   2.376  18.092  1.00 56.59           W
O
HETATM13152  O    HOH W 180      43.576  13.688  25.135  1.00 38.37           W
O
HETATM13155  O    HOH W 181      56.933  34.309  36.994  1.00 34.14           W
O
HETATM13158  O    HOH W 182      24.881   3.851  74.243  1.00 43.80           W
O
HETATM13161  O    HOH W 183      60.883  19.217  61.842  1.00 55.47           W
O
HETATM13164  O    HOH W 184      27.188  33.044  61.924  1.00 36.12           W
O
HETATM13167  O    HOH W 185      35.035  14.216  11.761  1.00 38.83           W
O
HETATM13170  O    HOH W 186       5.187  21.392 -19.097  1.00 54.47           W
O
HETATM13173  O    HOH W 187      41.205   3.919   0.968  1.00 47.36           W
O
HETATM13176  O    HOH W 188      53.372  26.330  78.972  1.00 58.68           W
O
HETATM13179  O    HOH W 189      62.735   3.195  73.452  1.00 53.71           W
O
HETATM13182  O    HOH W 190      60.387  15.071  81.554  1.00 62.79           W
O
HETATM13185  O    HOH W 191      54.796  24.202  69.273  1.00 47.77           W
O
HETATM13188  O    HOH W 192      26.097   7.024 -20.722  1.00 41.55           W
O
```

FIG 8 – CONT.

| HETATM13191 | O | HOH W 193 | 35.939 | 13.422 | -15.584 | 1.00 | 55.86 | W |
|---|---|---|---|---|---|---|---|---|
| HETATM13194 | O | HOH W 194 | 14.386 | 11.198 | 8.905 | 1.00 | 69.27 | W |
| HETATM13197 | O | HOH W 195 | 35.727 | 9.704 | 10.011 | 1.00 | 56.20 | W |
| HETATM13200 | O | HOH W 196 | 25.920 | 6.986 | 29.435 | 1.00 | 55.85 | W |
| HETATM13203 | O | HOH W 197 | 35.662 | 8.906 | 28.712 | 1.00 | 61.97 | W |
| HETATM13206 | O | HOH W 198 | 26.351 | -5.162 | -11.568 | 1.00 | 42.69 | W |
| HETATM13209 | O | HOH W 199 | 40.930 | 6.899 | -9.162 | 1.00 | 56.25 | W |
| HETATM13212 | O | HOH W 200 | 39.054 | 4.494 | -15.378 | 1.00 | 59.13 | W |
| HETATM13215 | O | HOH W 201 | 69.554 | 3.510 | 65.950 | 1.00 | 66.41 | W |
| HETATM13218 | O | HOH W 202 | 53.576 | 24.614 | 71.550 | 1.00 | 40.01 | W |
| HETATM13221 | O | HOH W 203 | 48.954 | 20.598 | 41.453 | 1.00 | 28.69 | W |
| HETATM13224 | O | HOH W 204 | 21.520 | -4.294 | -9.976 | 1.00 | 49.20 | W |
| HETATM13227 | O | HOH W 205 | 40.444 | 6.819 | 78.202 | 1.00 | 37.87 | W |
| HETATM13230 | O | HOH W 206 | 16.878 | 21.956 | 39.905 | 1.00 | 33.54 | W |
| HETATM13233 | O | HOH W 207 | 9.310 | 28.289 | 23.064 | 1.00 | 36.86 | W |
| HETATM13236 | O | HOH W 208 | 38.852 | 7.415 | 85.809 | 1.00 | 49.26 | W |
| HETATM13239 | O | HOH W 209 | 26.082 | 25.051 | 0.943 | 1.00 | 36.23 | W |
| HETATM13242 | O | HOH W 210 | 49.127 | 18.465 | 63.114 | 1.00 | 33.90 | W |
| HETATM13245 | O | HOH W 211 | 17.833 | 22.833 | 7.609 | 1.00 | 38.97 | W |
| HETATM13248 | O | HOH W 212 | 53.019 | 39.558 | 34.389 | 1.00 | 45.17 | W |
| HETATM13251 | O | HOH W 213 | 44.294 | 6.598 | 25.802 | 1.00 | 46.90 | W |
| HETATM13254 | O | HOH W 214 | 52.129 | 31.440 | 18.663 | 1.00 | 35.79 | W |
| HETATM13257 | O | HOH W 215 | 39.799 | 24.425 | 74.498 | 1.00 | 45.45 | W |
| HETATM13260 | O | HOH W 216 | 7.617 | 16.477 | 31.612 | 1.00 | 40.00 | W |
| HETATM13263 | O | HOH W 217 | 27.286 | 23.255 | 48.836 | 1.00 | 34.86 | W |
| HETATM13266 | O | HOH W 218 | 45.520 | 18.723 | 47.786 | 1.00 | 31.88 | W |
| HETATM13269 | O | HOH W 219 | 6.153 | 19.056 | -0.800 | 1.00 | 43.25 | W |
| HETATM13272 | O | HOH W 220 | 38.075 | 18.606 | -8.258 | 1.00 | 65.29 | W |
| HETATM13275 | O | HOH W 221 | 16.138 | 15.511 | 7.854 | 1.00 | 39.86 | W |
| HETATM13278 | O | HOH W 222 | 31.345 | 14.315 | 63.218 | 1.00 | 29.83 | W |
| HETATM13281 | O | HOH W 223 | 21.677 | 23.411 | 57.573 | 1.00 | 31.12 | W |

FIG 8 – CONT.

```
O
HETATM13284  O    HOH W 224      41.674  21.953   0.552  1.00 38.62        W
O
HETATM13287  O    HOH W 225      25.022  -8.952  -4.794  1.00 44.03        W
O
HETATM13290  O    HOH W 226      44.653  10.838  44.361  1.00 36.27        W
O
HETATM13293  O    HOH W 227      37.644  23.555  53.304  1.00 33.36        W
O
HETATM13296  O    HOH W 228      49.393  30.317  45.055  1.00 50.55        W
O
HETATM13299  O    HOH W 229      20.873  21.520  63.477  1.00 43.41        W
O
HETATM13302  O    HOH W 230      12.528  -5.563  -3.548  1.00 51.28        W
O
HETATM13305  O    HOH W 231      27.498   7.051   8.155  1.00 39.44        W
O
HETATM13308  O    HOH W 232       9.952  31.704  23.588  1.00 61.76        W
O
HETATM13311  O    HOH W 233      35.663  17.209  14.711  1.00 47.40        W
O
HETATM13314  O    HOH W 234      35.363  10.043 -18.715  1.00 53.17        W
O
HETATM13317  O    HOH W 235      54.420  29.372  18.428  1.00 50.27        W
O
HETATM13320  O    HOH W 236      47.495   5.978  24.430  1.00 46.00        W
O
HETATM13323  O    HOH W 237      17.223   2.553   1.613  1.00 32.10        W
O
HETATM13326  O    HOH W 238      43.086  16.769  46.994  1.00 39.24        W
O
HETATM13329  O    HOH W 239       1.646   0.597  -9.743  1.00 46.45        W
O
HETATM13332  O    HOH W 240      22.641  13.095  22.274  1.00 39.55        W
O
HETATM13335  O    HOH W 241      19.111  18.774  67.607  1.00 50.47        W
O
HETATM13338  O    HOH W 242      28.922  18.621  49.902  1.00 46.77        W
O
HETATM13341  O    HOH W 243      12.052  -4.049 -14.944  1.00 60.17        W
O
HETATM13344  O    HOH W 244      34.986  20.682  14.955  1.00 37.24        W
O
HETATM13347  O    HOH W 245      32.599  31.315  26.856  1.00 60.88        W
O
HETATM13350  O    HOH W 246      26.708  13.944  55.450  1.00 50.41        W
O
HETATM13353  O    HOH W 247      48.007  20.471  61.655  1.00 39.05        W
O
HETATM13356  O    HOH W 248      30.082  17.946  35.051  1.00 33.73        W
O
HETATM13359  O    HOH W 249      -0.199  -1.680 -10.444  1.00 55.46        W
O
HETATM13362  O    HOH W 250      73.782  13.682  48.272  1.00 50.41        W
O
HETATM13365  O    HOH W 251      36.508  21.154  17.443  1.00 33.16        W
O
HETATM13368  O    HOH W 252      14.507  -2.860  -7.946  1.00 48.06        W
O
HETATM13371  O    HOH W 253       5.330  18.078  14.743  1.00 54.35        W
O
```

FIG 8 – CONT.

```
HETATM13374  O  HOH W 254   24.667  24.836  52.199  1.00 41.21           O                                                                                W
HETATM13377  O  HOH W 255   30.813   9.200  56.747  1.00 50.99           O                                                                                W
HETATM13380  O  HOH W 256    9.116  20.719 -13.254  1.00 38.69           O                                                                                W
HETATM13383  O  HOH W 257   66.753  24.921  46.310  1.00 50.35           O                                                                                W
HETATM13386  O  HOH W 258   40.947   6.010  -3.390  1.00 54.55           O                                                                                W
HETATM13389  O  HOH W 259   45.481  22.402  21.009  1.00 54.16           O                                                                                W
HETATM13392  O  HOH W 260   33.871   6.641  12.221  1.00 49.10           O                                                                                W
HETATM13395  O  HOH W 261   58.206  18.850  55.241  1.00 50.68           O                                                                                W
HETATM13398  O  HOH W 262   34.490  30.044  65.088  1.00 33.32           O                                                                                W
HETATM13401  O  HOH W 263    7.339  20.632  37.593  1.00 43.07           O                                                                                W
HETATM13404  O  HOH W 264   68.985  28.058  44.005  1.00 49.79           O                                                                                W
HETATM13407  O  HOH W 265   43.530  -0.357  25.493  1.00 51.46           O                                                                                W
HETATM13410  O  HOH W 266   25.233   8.905  12.400  1.00 49.12           O                                                                                W
HETATM13413  O  HOH W 267   15.451  19.773  15.069  1.00 54.64           O                                                                                W
HETATM13416  O  HOH W 268   27.804  13.841  14.599  1.00 25.88           O                                                                                W
HETATM13419  O  HOH W 269   26.020  11.800  14.851  1.00 50.63           O                                                                                W
HETATM13422  O  HOH W 270   20.288  21.837  43.617  1.00 33.97           O                                                                                W
HETATM13425  O  HOH W 271   35.227   2.506   2.531  1.00 37.05           O                                                                                W
HETATM13428  O  HOH W 272   40.312   4.872 -12.008  1.00 43.59           O                                                                                W
HETATM13431  O  HOH W 273   21.243  19.206  74.266  1.00 37.94           O                                                                                W
HETATM13434  O  HOH W 274   15.114  19.518  12.264  1.00 54.52           O                                                                                W
HETATM13437  O  HOH W 275   38.526   0.128   0.704  1.00 30.62           O                                                                                W
HETATM13440  O  HOH W 276   11.339  24.847  43.134  1.00 49.71           O                                                                                W
HETATM13443  O  HOH W 277   44.832  18.711  23.887  1.00 41.06           O                                                                                W
HETATM13446  O  HOH W 278   25.616   7.716  62.404  1.00 43.55           O                                                                                W
HETATM13449  O  HOH W 279   38.328  17.331  15.548  1.00 49.19           O                                                                                W
HETATM13452  O  HOH W 280   38.135  25.991  53.111  1.00 38.86           O                                                                                W
HETATM13455  O  HOH W 281   13.491  -5.811  -7.223  1.00 56.79           O                                                                                W
HETATM13458  O  HOH W 282   39.829  26.600  55.087  1.00 48.43           O                                                                                W
HETATM13461  O  HOH W 283   34.225  16.042  16.700  1.00 50.88           O                                                                                W
HETATM13464  O  HOH W 284   68.897   2.089  67.883  1.00 57.28
```

FIG 8 – CONT.

```
O
HETATM13467  O    HOH W 285      23.172  24.777  69.352  1.00 39.00           W
O
HETATM13470  O    HOH W 286      37.687   5.150  65.275  1.00 34.97           W
O
HETATM13473  O    HOH W 287      25.875  21.851  15.223  1.00 27.72           W
O
HETATM13476  O    HOH W 288      26.945  24.110  16.597  1.00 31.48           W
O
HETATM13479  O    HOH W 289      24.350  26.910  72.951  1.00 52.83           W
O
HETATM13482  O    HOH W 290      26.309  15.941  14.678  1.00 27.95           W
O
HETATM13485  O    HOH W 291      26.117  28.539  66.258  1.00 35.02           W
O
HETATM13488  O    HOH W 292      39.156  18.090  -0.671  1.00 50.30           W
O
HETATM13491  O    HOH W 293      28.407  27.834  12.913  1.00 37.67           W
O
HETATM13494  O    HOH W 294      29.583  13.171  16.181  1.00 32.50           W
O
HETATM13497  O    HOH W 295      39.584  -1.886  70.145  1.00 38.79           W
O
HETATM13500  O    HOH W 296      31.165  -0.828  75.815  1.00 33.82           W
O
HETATM13503  O    HOH W 297      39.551  10.039  -5.579  1.00 48.79           W
O
HETATM13506  O    HOH W 298      27.343  25.683  74.918  1.00 37.84           W
O
HETATM13509  O    HOH W 299      50.292  10.273  43.723  1.00 46.48           W
O
HETATM13512  O    HOH W 300      75.684  11.955  66.594  1.00 61.93           W
O
HETATM13515  O    HOH W 301      20.975  23.880  36.704  1.00 31.31           W
O
HETATM13518  O    HOH W 302      32.921   3.899   2.917  1.00 32.70           W
O
HETATM13521  O    HOH W 303      46.916  22.566  30.447  1.00 24.61           W
O
HETATM13524  O    HOH W 304      37.413  29.458  69.887  1.00 60.20           W
O
HETATM13527  O    HOH W 305       9.882  33.249  44.962  1.00 42.97           W
O
HETATM13530  O    HOH W 306      53.398  10.967  46.392  1.00 51.81           W
O
HETATM13533  O    HOH W 307      44.010   2.442  -4.760  1.00 47.20           W
O
HETATM13536  O    HOH W 308      37.802   5.098 -11.011  1.00 35.78           W
O
HETATM13539  O    HOH W 309      20.340   5.115   7.733  1.00 47.00           W
O
HETATM13542  O    HOH W 310      18.846   3.711   6.523  1.00 39.88           W
O
HETATM13545  O    HOH W 311      32.943   5.685  36.049  1.00 60.24           W
O
HETATM13548  O    HOH W 312      10.229  12.834  15.255  1.00 59.00           W
O
HETATM13551  O    HOH W 313      26.326  29.124  77.222  1.00 51.16           W
O
HETATM13554  O    HOH W 314      32.643  24.044 -12.221  1.00 49.49           W
O
```

FIG 8 – CONT.

| | | | | | | | | |
|---|---|---|---|---|---|---|---|---|
| HETATM13557 | O | HOH W 315 | 17.710 | 34.398 | 22.977 | 1.00 | 60.44 | W |
| HETATM13560 | O | HOH W 316 | 52.804 | 25.552 | 17.953 | 1.00 | 52.57 | W |
| HETATM13563 | O | HOH W 317 | 56.529 | 10.546 | 43.008 | 1.00 | 57.50 | W |
| HETATM13566 | O | HOH W 318 | 21.995 | 10.253 | 64.317 | 1.00 | 36.37 | W |
| HETATM13569 | O | HOH W 319 | 22.711 | 12.565 | 76.552 | 1.00 | 40.48 | W |
| HETATM13572 | O | HOH W 320 | 29.939 | 10.635 | 16.308 | 1.00 | 41.25 | W |
| HETATM13575 | O | HOH W 321 | 11.963 | 33.143 | 22.437 | 1.00 | 53.86 | W |
| HETATM13578 | O | HOH W 322 | 57.503 | 16.661 | 37.041 | 1.00 | 48.80 | W |
| HETATM13581 | O | HOH W 323 | 26.078 | 15.356 | 49.969 | 1.00 | 63.05 | W |
| HETATM13584 | O | HOH W 324 | 33.999 | 8.882 | 11.833 | 1.00 | 52.96 | W |
| HETATM13587 | O | HOH W 325 | 46.549 | 34.186 | 39.426 | 1.00 | 57.86 | W |
| HETATM13590 | O | HOH W 326 | 19.510 | 11.663 | 82.345 | 1.00 | 55.17 | W |
| HETATM13593 | O | HOH W 327 | 32.348 | 13.618 | 16.161 | 1.00 | 44.89 | W |
| HETATM13596 | O | HOH W 328 | 35.787 | 28.989 | 37.222 | 1.00 | 56.27 | W |
| HETATM13599 | O | HOH W 329 | 13.754 | 4.520 | -15.135 | 1.00 | 37.01 | W |
| HETATM13602 | O | HOH W 330 | 56.620 | 12.938 | 36.580 | 1.00 | 54.48 | W |
| HETATM13605 | O | HOH W 331 | 7.424 | 19.035 | 2.916 | 1.00 | 48.53 | W |
| HETATM13608 | O | HOH W 332 | 10.325 | 15.240 | 8.222 | 1.00 | 55.26 | W |
| HETATM13611 | O | HOH W 333 | 28.815 | -10.109 | -6.736 | 1.00 | 24.77 | W |
| HETATM13614 | O | HOH W 334 | 28.130 | -8.302 | -9.093 | 1.00 | 37.30 | W |
| HETATM13617 | O | HOH W 335 | 20.573 | -7.027 | -3.479 | 1.00 | 41.58 | W |
| HETATM13620 | O | HOH W 336 | 9.311 | 17.249 | 4.241 | 1.00 | 54.20 | W |
| HETATM13623 | O | HOH W 337 | 31.134 | -5.136 | 71.708 | 1.00 | 23.44 | W |
| HETATM13626 | O | HOH W 338 | 31.988 | -3.920 | 73.912 | 1.00 | 43.99 | W |
| HETATM13629 | O | HOH W 339 | 34.354 | 3.477 | 80.976 | 1.00 | 35.34 | W |
| HETATM13632 | O | HOH W 340 | 40.007 | 3.137 | 84.507 | 1.00 | 61.88 | W |
| HETATM13635 | O | HOH W 341 | 25.706 | 25.953 | 15.235 | 1.00 | 42.51 | W |
| HETATM13638 | O | HOH W 342 | 29.239 | 29.638 | 16.700 | 1.00 | 45.16 | W |
| HETATM13641 | O | HOH W 343 | 24.445 | 22.926 | 13.349 | 1.00 | 44.13 | W |
| HETATM13644 | O | HOH W 344 | 23.910 | 12.531 | 16.405 | 1.00 | 43.84 | W |
| HETATM13647 | O | HOH W 345 | 20.214 | 15.656 | 9.349 | 1.00 | 49.51 | W |

FIG 8 – CONT.

```
O
HETATM13650  O    HOH W 346      12.177  13.389   4.668  1.00 35.16           W
O
HETATM13653  O    HOH W 347      36.141  19.193  27.635  1.00 34.78           W
O
HETATM13656  O    HOH W 348      44.000  15.949  58.466  1.00 44.92           W
O
HETATM13659  O    HOH W 349      37.611  11.312  56.206  1.00 50.63           W
O
HETATM13662  O    HOH W 350      40.807   4.407  67.716  1.00 51.05           W
O
HETATM13665  O    HOH W 351      27.686  32.142  65.492  1.00 32.43           W
O
HETATM13668  O    HOH W 352      28.494  34.547  64.050  1.00 43.73           W
O
HETATM13671  O    HOH W 353      29.365  36.266  65.838  1.00 29.00           W
O
HETATM13674  O    HOH W 354      41.221   9.733 -12.445  1.00 50.02           W
O
HETATM13677  O    HOH W 355      18.955   2.971  75.403  1.00 40.59           W
O
HETATM13680  O    HOH W 356      19.397  14.578  65.553  1.00 45.45           W
O
HETATM13683  O    HOH W 357      51.200  13.105  88.192  1.00 52.01           W
O
HETATM13686  O    HOH W 358      35.910  21.816  87.123  1.00 50.82           W
O
HETATM13689  O    HOH W 359      31.737  17.297  84.947  1.00 41.46           W
O
HETATM13692  O    HOH W 360      13.466  37.940  32.697  1.00 47.66           W
O
HETATM13695  O    HOH W 361      61.915  11.485  30.317  1.00 54.44           W
O
HETATM13698  O    HOH W 362      60.285  16.233  29.215  1.00 58.14           W
O
HETATM13701  O    HOH W 363      61.941   8.797  23.833  1.00 51.29           W
O
TER
END
```

Figure 9A Representation of K1-70 Fab structure in JOY format
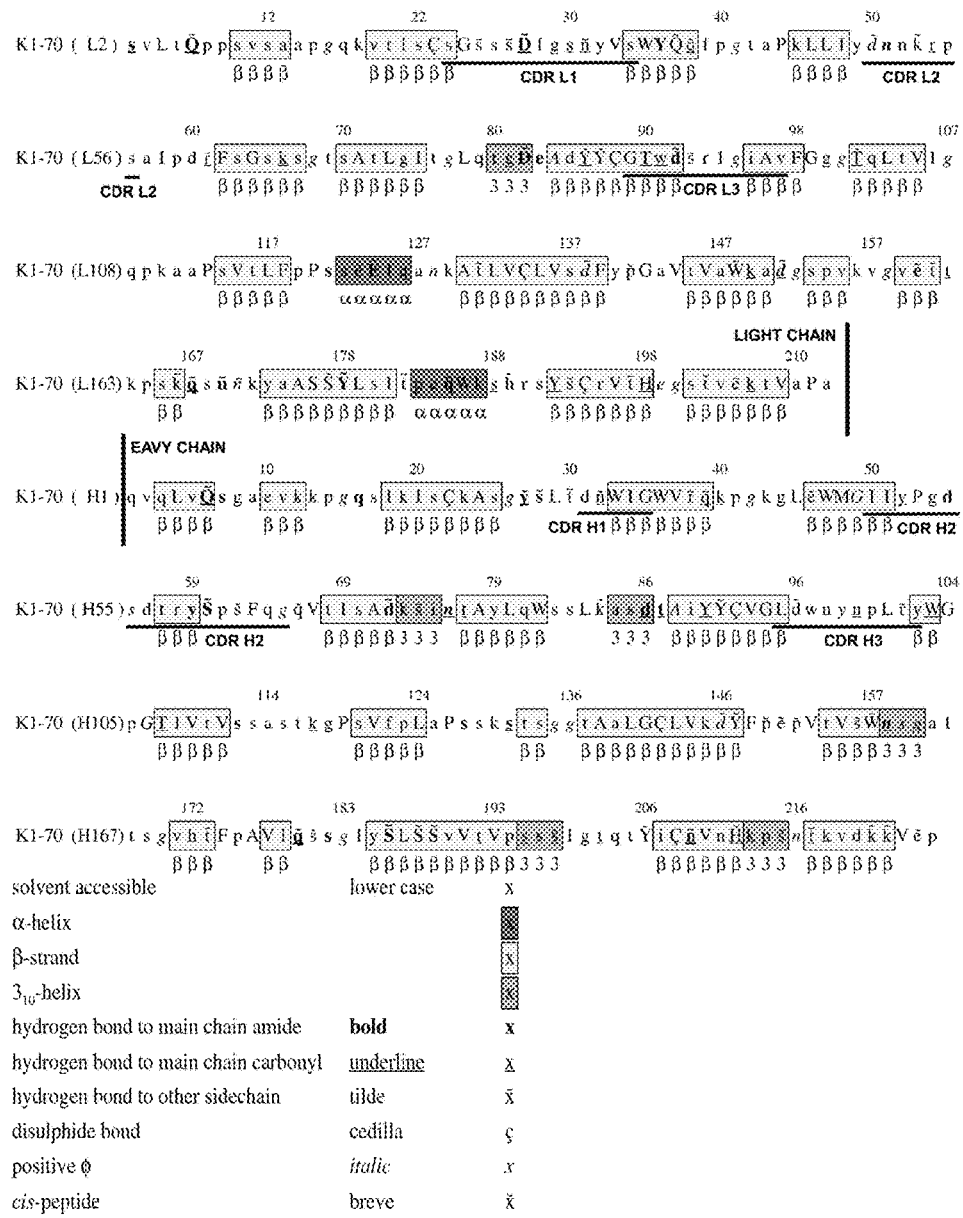
The residues are numbered according to Kabat's system (Kabat E *et al* 1991 *supra*) as shown in Figure 8.

Figure 9B    Electrostatic potential of the combining site of K1-70
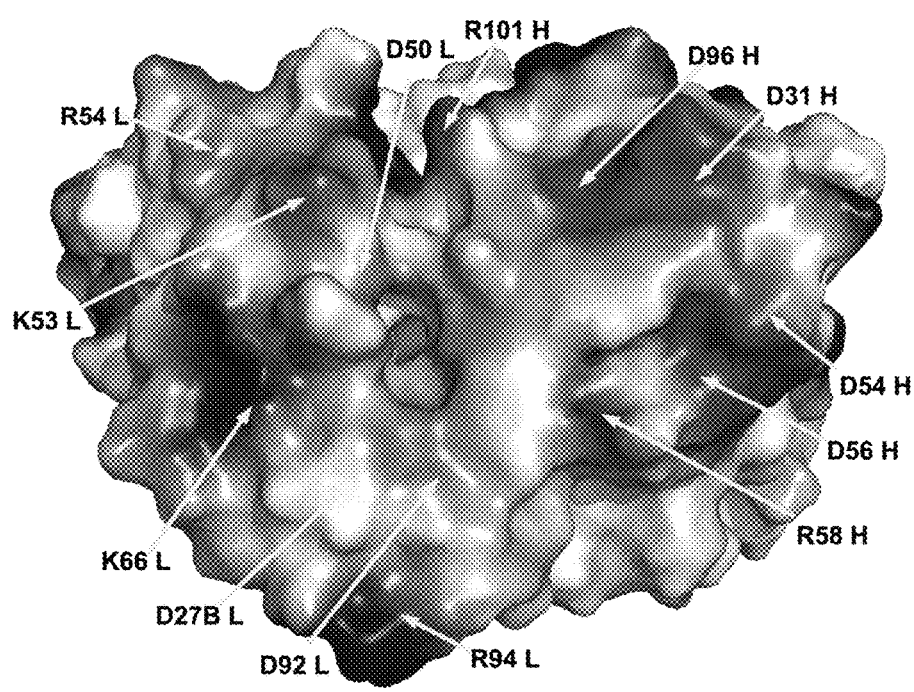
The residues are numbered according to Kabat's system (Kabat E *et al* 1991 *supra*) as shown in Figures 8 and 9A Figure 9C    Aromatic amino acids of the combining site of K1-70
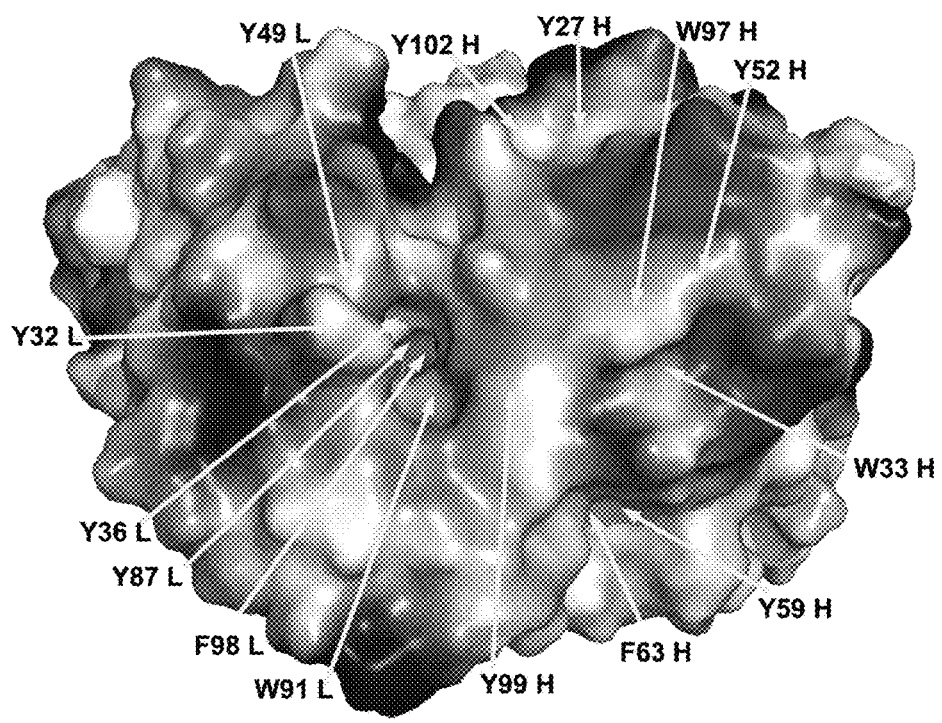
The residues are numbered according to Kabat's system (Kabat E *et al* 1991 *supra*) as shown in Figures 8 and 9A.

HUMAN ANTI TSHR ANTIBODIES

CLAIM OF PRIORITY

This application is a divisional application of U.S. application Ser. No. 13/142,217 having a filing date Jul. 2, 2015, now U.S. Pat. No. 9,073,992, which claims the benefit of priority under 35 U.S.C. §119(a) of International Application No. PCT/GB2009/002946 having an International Filing Date of Dec. 23, 2009, which claims the benefit of priority of GB 0908945.9 having a filing date of May 22, 2009 and GB 0823562.4 having a filing date of Dec. 24, 2008.

FIELD OF THE INVENTION

The present invention relates to human monoclonal autoantibodies (MAbs) reactive with the thyroid stimulating hormone (TSH) receptor (TSHR). One of the human MAbs (K1-18) has the ability to bind to the TSHR and to stimulate TSHR cyclic AMP activity. The other human MAb (K1-70) has the ability to bind to the TSHR and to block stimulation of cyclic AMP mediated by TSH and TSHR stimulating antibodies. Both human MAbs were isolated from the peripheral lymphocytes of a patient who presented with clinical symptoms of hypothyroidism.

BACKGROUND

Thyroid function is regulated by TSH secreted by the pituitary (Szkudlinski M W, et al 2002. Physiological Reviews 82: 473-502). TSH binds to the TSHR on the surface of thyrocytes and this is the first step in initiating the TSHR signalling cascade. Binding of TSH to the TSHR leads to stimulation of formation and release of thyroid hormones; thyroxine (T4) and tri-iodothyronine (T3). A feedback mechanism involving the levels of T4 and T3 in the circulation and thyrotropin releasing hormone (TRH) secreted by the hypothalamus controls the release of TSH that in turn controls thyroid stimulation and the levels of thyroid hormones in serum (Szkudlinski M W, et al, 2002 supra). The TSHR is a G-protein coupled receptor and is composed of three domains:—a leucine rich repeat domain (LRD), a cleavage domain (CD) and a transmembrane domain (TMD) (Núñez Miguel R, et al 2004. Thyroid 14: 991-1011).

It is well documented in the art that some patients with autoimmune thyroid disease (AITD) develop autoantibodies which are reactive with the TSHR (Rees Smith B, et al 1988. Endocrine Reviews 9: 106-121). There are two main types of TSHR autoantibodies (TRAbs); a stimulating type and a blocking type. Thyroid stimulating type autoantibodies bind to the TSHR and mimic the actions of TSH thereby stimulating the thyroid to produce high levels of T4 and T3; these autoantibodies are also described as TRAbs with stimulating activity or TSH agonist activity (Rees Smith B, et al 2007. Thyroid 17: 923-938). The feedback control mechanism of thyroid function is no longer effective in the presence of thyroid stimulating autoantibodies and patients present with the clinical symptoms of a hyperactive thyroid characterised by an excess of thyroid hormones in serum and its metabolic consequences. This condition is known as Graves' disease. TRAbs with stimulating activity may also interact with the TSHRs in retroorbital tissue and contribute to the development of the eye signs of Graves' disease. A human monoclonal autoantibody which acts as a powerful thyroid stimulator (hMAb TSHR1; also referred to as M22) has been described in detail in WO 2004/050708A2. The structure of the complex of M22 Fab bound to the TSHR LRD has been solved by x-ray crystallography at 2.55 Å resolution as described in WO2008/025991A1. Analysis of the structure of the TSHR-M22 complex provides detailed information about the receptor residues and the stimulating autoantibody residues involved in interactions with each other.

M22 has been used in ELISA for TSHR antibody measurement (Zöphel, K et al, Clinica Chimica Acta 2009 and Zöphel, K et al, Clinica Chimica Acta 2008.

Blocking type TRAbs occur less frequently in patients with AITD than stimulating autoantibodies. Blocking type autoantibodies bind to the TSHR, prevent TSH from binding to the receptor but have no ability to stimulate TSHR activity. Consequently formation and secretion of thyroid hormones (T4 and T3) is greatly reduced and the patients with this type of TRAb can present with clinical symptoms of an under-active thyroid (hypothyroidism). Blocking type autoantibodies are known as TRAbs with blocking activity or TSH antagonist activity (Rees Smith B, et al 1988 supra and Rees Smith B, 2007 et al supra). TRAbs with blocking activity when present in serum of pregnant women cross the placenta and may block the TSHRs in the foetal thyroid leading to neonatal hypothyroidism and serious consequences for development. Furthermore, TRAbs with blocking activity can be found in breast milk of affected mothers and may cause clinical hypothyroidism in the baby (Evans C, et al 2004 European Journal of Endocrinology 150: 265-268). A human autoantibody to the TSHR with TSH antagonist activity (5C9) has been described in detail in WO 2008/099185A1. Clinical symptoms in patients with AITD and circulating TRAbs are related to the effect of autoantibodies on TSHR activity i.e. whether the TRAbs cause stimulation or blocking. It has been proposed, however, that in some patients a mixture of stimulating and blocking TRAbs may be present simultaneously with the overall clinical presentation related to higher concentration and/or activity of one type of the TRAbs (Rees Smith B et al 1988 supra; Furmaniak J et al 1993 Springer Seminars in Immunopathology 14: 309-321 and Schott M et al 2005 Trends in Endocrinology and Metabolism 16: 243-248). Furthermore, the concentrations and/or activities of stimulating or blocking TRAb may vary in the same patient during the course of the disease and indeed fluctuation of symptoms from hypo- to hyperthyroidism in the same patient over time has been reported (Rees Smith B et al 1988 supra; Furmaniak J and Rees Smith B 1993 supra and Schott M et al 2005 supra). However, attempts to separate the TRAbs with different bioactivity or to differentiate between these TRAbs in serum samples using currently available bioassays is difficult. More recently, the invention described in WO2006/016121A1 provides a means to discriminate between stimulating and blocking types of TRAbs using bioassays that employ TSHR mutated at R255.

Human recombinant TSH (Thyrogen®) is a preparation of human TSH produced under cGMP regulations as a recombinant protein and approved by the US FDA as an aid in the diagnosis of residual or recurrent thyroid cancer (Duntas L H, Cooper D S 2008 Thyroid 18: 509-516). Monitoring of thyroid cancer patients after treatment includes stimulation of thyroid remnants or metastases with recombinant human TSH followed by a thyroid scan and/or measurement of serum thyroglobulin levels (Duntas L H and Cooper D S 2008 supra). Human chorionic gonadotropin is a hormone produced during pregnancy which has mild thyroid stimulating effects (Grossmann M et al 1997 Endocrine Reviews 18: 476-501). Characterisation of stimulating or blocking types of TRAbs and how they interact with the TSHR is of critical importance for development of improved methods to diagnose and manage different forms of AITD. In addition these studies are critical for developing new strategies for the management of diseases associated with an autoimmune response to the TSHR. The availability of potent thyroid stimulators other than recombinant human TSH provides new alternatives for monitoring and managing thyroid cancer patients.

RELATED PREVIOUS PATENT APPLICATIONS

The invention described in WO2004/050708A2 provides details of the properties of a human monoclonal autoantibody (MAb) with powerful stimulating activity and its interaction with the TSHR. The interactions between this autoantibody (M22) and the TSHR LRD have been solved at the molecular level from an X-ray diffraction analysis (2.55 Å resolution) of a complex between the two molecules as described in WO2008/025991A1. WO2006/016121A1 discloses a mutated TSHR preparation including at least one point mutation which can be used in the differential screening and identification of patient serum stimulating TSHR autoantibodies, patient serum blocking TSHR autoantibodies and TSH in a sample of body fluid from a patient being screened. Generation and characterisation of a mouse MAb (9D33) with TSHR blocking activity is also described in WO2004/050708A2. 9D33 binds to the TSHR with high affinity ($2 \times 10^{10}$ L/mol) and is an effective antagonist of TSH, hMAb TSHR1 (M22) and patient serum TRAbs with stimulating or blocking activities. WO2008/099185A1 discloses the isolation and characterisation of human MAb (5C9) to the TSHR that is an effective antagonist of TSH and of stimulating TRAbs in patient sera. 5C9 has been found unexpectedly to inhibit TSHR constitutive activity (also referred to as the TSHR basal activity), that is to say the production of cyclic AMP in a test system in the absence of TSH or M22. Furthermore, 5C9 has been found to inhibit TSHR cyclic AMP activity associated with TSHR activating mutations. WO2008/091981A2 describes a mouse MAb that has the ability to suppress the constitutive activity of TSHR and the methods of using the MAb to treat thyroid diseases including hyperthyroidism and thyroid cancer. The properties of the MAb described in WO2008/091981A2 are also disclosed in Chen C R et al 2007 Endocrinology 148: 2375-2382.

PRESENT INVENTION

Antibodies K1-18 and K1-70 have been isolated from the peripheral blood lymphocytes of a 54 year old female patient with hypothyroidism and high levels of TSHR autoantibodies. The patient had an 8 year history of AITD and first presented with hyperthyroidism and responded to treatment with methimazole which continued for 3 years. However, approximately 10 months after reaching the euthyroid state (i.e. having normal function) the patient developed hypothyroidism and was treated with thyroxine. The patient had been hypothyroid for approximately 4.5 years at the time of blood collection. At the time of lymphocyte isolation serum TRAb levels were 160 Units/L measured by TSH binding inhibition assay. The serum also showed an ability to block TSH stimulation of the TSHR (cyclic AMP based assay). Serum autoantibodies to thyroid peroxidase were positive at >500 Units/mL (Units are of the reference preparation 66/387 from National Institute for Standards and Control (NIBSC) Potters Bar, UK).

The patient's lymphocytes were immortalised by infection with Epstein Barr virus (EBV) and supernatants of cultures of the infected cells screened for their ability to inhibit $^{125}$I-TSH binding to TSHR coated tubes. Cells from positive cell cultures were fused with a mouse/human cell line and screened as above. 2 stable clones secreting TSHR autoantibodies were obtained. IgGs were purified from supernatants of the clone cultures and the ability of the 2 MAbs (K1-18 and K1-70) IgGs to bind to the TSHR and influence TSHR activity assessed. In particular, the ability of K1-18 or K1-70 to inhibit TSH binding to the TSHR was studied. The ability of K1-18 to stimulate the TSHR was also studied and compared to the activity of various other thyroid stimulators. The ability of K1-70 to inhibit the ability of TSH to stimulate the TSHR was studied and compared to the activities of other TSH antagonists. Furthermore, the ability of stimulating or blocking patient serum TRAbs to inhibit TSHR binding and biological activity of K1-18 and K1-70 was assessed. In addition, the use of K1-18 and K1-70 in assays for TSHR antibodies, TSH and related compounds was investigated. Variable region (V region) genes of the heavy (HC) and light chains (LC) of K1-18 and K1-70 were sequenced and the complementarity determining regions (CDRs) assigned. Furthermore, purified preparations of K1-70 Fab were crystallised and analysed using X-ray diffraction methods. These analyses provided molecular level details about the overall structure of K1-70 Fab and the topography of the antigen binding site of K1-70.

SUMMARY OF THE INVENTION

According to one aspect of the invention there is provided an isolated human antibody molecule which binds to a TSHR and which reduces ligand induced stimulation of said TSHR but has no effect on constitutive activity of said TSHR.

Preferably, there is provided an isolated human antibody molecule or fragment thereof which binds to the TSHR and which reduces ligand-induced stimulation of the TSHR but has no effect on said TSHR constitutive activity wherein said human antibody or fragment thereof has the characteristics of patient serum TSH receptor autoantibodies of inhibiting TSH and M22 binding to the TSHR. More preferably the isolated human antibody molecule or fragment thereof has at least one further characteristic of patient serum TSH receptor autoantibodies selected from having a binding affinity for the TSHR of at least $10^8$ L/mol and the ability to cause detectable blocking of ligand-induced TSHR stimulation at an antibody concentration of less than 10 μg/mL. Even more preferably the further characteristics of patient serum TSH receptor autoantibodies are selected from having a binding affinity for the TSHR of at least $10^9$ L/mol and the ability to cause detectable blocking of ligand-induced TSHR stimulation at an antibody concentration of less than 1 μg/mL, preferably less than 0.1 μg/mL. The isolated human antibody may be an antagonist of TSH and/or thyroid stimulating autoantibodies, and/or thyroid stimulating animal antibodies and/or of human chorionic gonadotropin.

The isolated antibody molecule may be an inhibitor of TSH receptor binding by at least one of TSH, M22 or K1-18.

The isolated antibody molecule may comprise an antibody VH domain selected from the amino acid sequence of FIGS. 5B and 5D (SEQ ID No 41 and 51, respectively). The isolated antibody molecule may comprise an antibody VH domain consisting preferably of the amino acid sequence of FIGS. 5B and 5D (SEQ ID No 41 and 51, respectively). The isolated antibody molecule may comprise a CDR selected from CDR I (SEQ ID No 42 and 52), II (SEQ ID No 43 and 53) and III (SEQ ID No 44 and 54) of FIGS. 5B and 5D respectively. An antibody molecule according to the invention may comprise a VH region which comprises one or more amino acid sequences having substantial homology to those CDRs. Preferably an antibody according to the invention shows 70-99.9% amino acid homology to the CDRs shown in FIG. 5D (SEQ ID No 52, 53 and 54). Preferably, the isolated antibody molecule comprises CDR I, II and III of FIG. 5D (SEQ ID No 52, 53 and 54). In preferred embodiments a corresponding portion of the isolated antibody molecule is at least 70% identical, more preferably at least 80% identical, highly preferably at least 90% identical, particularly preferred at least 95% identical and especially preferred 99.9% identical to one of those CDRs. The isolated antibody molecule may comprise an antibody VL domain selected preferably from an amino acid sequence of FIG. 6D (SEQ ID No 69). The isolated antibody molecule may comprise an antibody VL domain consisting preferably of an amino acid sequence of FIG. 6D (SEQ ID No 69). The isolated antibody molecule thereof may comprise a CDR selected from CDR I (SEQ ID No 70), II (SEQ ID No 71) or III (SEQ ID No 72) of FIG. 6D. Additionally or alternatively, an isolated antibody molecule according to the invention may comprise one or more amino acid sequences having substantial homology to those CDRs. Preferably the CDRs of an isolated antibody molecule according to the invention shows 70-99.9% amino acid homology to the CDRs shown in FIG. 6D (SEQ ID No 70, 71 and 72). In preferred embodiments the isolated antibody molecule is at least 70% identical, more preferably at least 80% identical, highly preferably at least 90% identical, particularly preferred at least 95% identical and especially preferred 99.9% identical.

Preferably, the isolated antibody molecule comprises CDR I, II and III of FIG. 6D (SEQ ID No 70, 71 and 72).

The isolated antibody molecule may have a molecular structure as shown in FIG. 9A with the distribution of charged and aromatic residues in the antigen binding site as shown in FIGS. 9B and 9C. According to another aspect of the invention there is provided an isolated antibody molecule which binds to the TSHR so as to stimulate the TSHR, the antibody molecule comprising an antibody VL domain selected from the amino acid sequences of FIGS. 4B and 4D (SEQ ID No 23 and 33, respectively) and/or comprising one or more CDRs selected from CDR I (SEQ ID No 24 and 34), II (SEQ ID No 25 and 35) and III (SEQ ID No 26 and 36) of FIGS. 4B and 4D respectively, and/or an antibody VH domain selected from the amino acid sequences of FIGS. 3B and 3D (SEQ ID No 5 and 15, respectively) and/or comprising one or more CDRs selected from CDR I (SEQ ID No 6 and 16), II (SEQ ID No 7 and 17) and III (SEQ ID No 8 and 18) of FIGS. 3B and 3D respectively. Preferably the antibody molecule comprises: (i) an antibody VL domain comprising one or more CDRs selected from CDR I (SEQ ID No 24 and 34), II (SEQ ID No 25 and 35) and III (SEQ ID No 26 and 36) of FIGS. 4B and 4D respectively; and/or (ii) an antibody VH domain comprising one or more CDRs selected from CDR I (SEQ ID No 6 and 16), II (SEQ ID No 7 and 17) and III (SEQ ID No 8 and 18) of FIGS. 3B and 3D respectively.

Binding of the isolated antibody molecule to the TSHR may be inhibited by patient serum TSHR antibodies with thyroid stimulating or blocking activities.

Binding of the isolated antibody molecule to the TSHR may be inhibited by at least one of M22, K1-70, 5C9, 9D33 and thyroid stimulating mouse monoclonal antibodies.

The isolated antibody molecule may comprise an antibody VL domain selected from the amino acid sequences of FIGS. 4B and 4D (SEQ ID No 23 and 33, respectively) and an antibody VH domain selected from the amino acid sequences of FIGS. 3B and 3D (SEQ ID No 5 and 15, respectively). Preferably, the isolated antibody molecule comprises CDR I (SEQ ID No 6 and 16), II (SEQ ID No 7 and 17) and III (SEQ ID No 8 and 18) of FIGS. 3B and 3D respectively. An antibody according to the invention may comprise a VH region which comprises one or more amino acid sequences having substantial homology to those CDRs. Preferably an antibody molecule according to the invention shows 70-99.9% amino acid homology to the CDRs (SEQ ID No 6-8 and 16-18) shown in FIGS. 3B and 3D respectively. In preferred embodiments the isolated antibody molecule is at least 70% identical, more preferably at least 80% identical, highly preferably at least 90% identical, particularly preferred at least 95% identical and especially preferred 99.9% identical.

The isolated antibody molecule may comprise an antibody VL domain consisting of an amino acid sequence of FIG. 4B or 4D (SEQ ID No 23 and 33, respectively). The isolated antibody molecule may comprise an antibody VH domain consisting of an amino acid sequence of FIG. 3B or 3D (SEQ ID No 5 and 15, respectively). Preferably, the isolated antibody molecule comprises CDR I (SEQ ID No 24 and 34), II (SEQ ID No 25 and 35) and III (SEQ ID No 26 and 36) of FIGS. 4B and 4D respectively. Additionally or alternatively, an antibody according to the invention may comprise one or more amino acid sequences having substantial homology to those CDRs. Preferably the antibody shows 70-99.9% amino acid homology to the CDRs (SEQ ID No 24-26 and 34-36) shown in FIGS. 4B and 4D respectively. In preferred embodiments the isolated antibody molecule is at least 70% identical, more preferably at least 80% identical, highly preferably at least 90% identical, particularly preferred at least 95% identical and especially preferred 99.9% identical.

In most applications a VH domain in an antibody molecule according to the invention will be arranged with a VL domain to provide a TSHR binding site. In some applications a VH domain alone may be provided to bind a TSHR.

Methods of grafting antibody domains are well known in the art such that an antibody molecule in accordance with the invention can be constructed using VH and VL domains or portions thereof from different sources.

The term "antibody molecule" and cognate terms, such as "antibody molecules", used herein in relation to antibody molecules of the invention embraces, according to context, immunoglobulin-based binding moieties such as monoclonal, recombinant, synthetic and polyclonal antibodies, single chain antibodies, multi-specific antibodies and also binding moieties, which may be substituted by the skilled addressee for such immunoglobulin-based binding moieties, such as domain antibodies, diabodies, as well as IgG[Delta]CH2, F(ab')$_2$, Fab, scFv, VL, VH, dsFv, Minibody, Triabody, Tetrabody, (scFv)$_2$, scFv-Fc, F(ab')$_3$ moieties (Holliger P, et al 1993 Proc Natl Acad Sci USA 90: 6444-6448.), (Carter P J 2006 Nat Rev Immunol 6: 343-357). The term also embraces fragments of such entities, preferably fragments which bind TSHRs, and more preferably have the effects of K1-18 or K1-70.

The terms "thyroid stimulating hormone receptor" and "TSHR" refer to full length human TSHR having the amino acid sequence shown in FIG. 7A (SEQ ID No 74) or variants or fragments thereof having high homology with such TSHR. Preferably, such variants and fragments have 70 to 99.9% homology with the amino acid sequence shown in FIG. 7A (SEQ ID No 74). In preferred embodiments such variants or fragments are at least 70% identical, more preferably at least 80% identical, highly preferably at least 90% identical, particularly preferred at least 95% identical and especially preferred 99.9% identical to that sequence.

The isolated antibody of the invention may preferably be in the form of a monoclonal antibody, a recombinant antibody or a synthetic antibody. CDRs I, II or III from the K1-18 or K1-70 VH or VL domains may be incorporated into a suitable framework. Variants of the K1-18 and K1-70 VH and VL domains and their CDRs can be produced by modifications using methods well known to those skilled in the field.

Such variants may comprise one or more amino acid sequence variations, including the addition, deletion, substitution or insertion mutations. The framework of K1-18 or K1-70 may also be modified in antibody molecules according to the invention. The isolated antibody according to the invention may have a framework which is human or non-human.

According to another aspect of the invention there is provided an isolated nucleotide encoding an isolated antibody molecule or fragment thereof according to the invention, comprising an antibody VL domain comprising an amino acid sequence of FIG. 4B (SEQ ID No 23) or 4D (SEQ ID No 33) or 6D (SEQ ID No 69), an antibody VH domain comprising an amino acid sequence of FIG. 3B (SEQ ID No 5), 3D (SEQ ID No 15) or 5B (SEQ ID No 41) and 5D (SEQ ID No 51), or CDR I, II or III of FIG. 3B (SEQ ID No 6-8), 3D (SEQ ID No 16-18), 4B (SEQ ID No 24-26), 4D (SEQ ID No 34-36), 5B (SEQ ID No 42-44), 5D (SEQ ID No 52-54) or 6D (SEQ ID No 70-72), or a combination thereof.

The isolated nucleotide may comprise a nucleotide sequence of FIG. 3A (SEQ ID No 1), 3C (SEQ ID No 10), 4A (SEQ ID No 19), 4C (SEQ ID No 28), 5A (SEQ ID No 37), 5C (SEQ ID No 46) or 6C (SEQ ID No 64).

A plurality of such nucleotides may be provided, for example in a bacteriophage display library. Such bacteriophage display libraries may be used to express a variety of antibody molecules or fragments thereof such as isolated domains.

The invention also provides a vector including an isolated nucleotide according to the invention, or a host cell including such a vector or a nucleotide according to the invention. The vector may be a plasmid, virus or fragment thereof. Many different types of vectors are known to the skilled addressee. The isolated cell may express an antibody according to the invention. Preferably, the isolated cell secretes an antibody according to the invention. Preferably an isolated cell according to the invention is from a stable heterohybridoma cell line.

Another aspect of the invention provides a method of producing an isolated antibody molecule or a fragment thereof such as an isolated domain in accordance with the invention, the method comprising expressing a nucleotide encoding such an antibody molecule, or a fragment thereof.

According to a further aspect of the invention there is provided a method of producing an antibody according to the invention, the method comprising culturing one or more isolated host cells according to the invention whereby the antibody is expressed by the cell. Preferably, the antibody is secreted by the cell, According to another aspect of the invention there is provided a pharmaceutical composition comprising an isolated antibody molecule according to the invention, and a carrier.

A pharmaceutical composition according to the invention may be suitable for human administration. Preferably a pharmaceutical composition according to the invention has no significant adverse effect on the immune system of the subject.

Various formats are contemplated for pharmaceutical compositions according to the invention. A pharmaceutical composition according to the invention for use in the treatment of a thyroid-related condition may be in an injectable format. A pharmaceutical composition according to the invention for use in the treatment of ophthalmic Graves' disease is preferably in the form of eye drops. Pharmaceutical compositions of this invention comprise an isolated antibody in accordance with the invention, with a pharmaceutically acceptable carrier, adjuvant or vehicle. Pharmaceutically acceptable carriers, adjuvants and vehicles that may be used in the pharmaceutical compositions of this invention include, but are not limited to, ion exchangers, alumina, aluminium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulphate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. The pharmaceutical compositions of the invention may be administered orally, parenterally, by inhalation spray, topically, by eyedrops, rectally, nasally, buccally, vaginally or via an implanted reservoir. We prefer oral administration or administration by injection. The term "parenteral" as used herein includes subcutaneous, intracutaneous, intravenous, intramuscular, intra-articular, intrasynovial, intrasternal, intrathecal, intralesional and intracranial injection or infusion techniques. The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as Ph. Helv or a similar alcohol. The pharmaceutical compositions of this invention may be orally administered in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are administered orally, the active ingredient is combined with emulsifying and suspending agents. If desired, certain sweetening and/or flavouring and/or colouring agents may be added. The pharmaceutical compositions of this invention may also be provided in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols. Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention. The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilising or dispersing agents known in the art.

Antibodies according to the first mentioned aspect of the invention such as K1-70 have potential applications for management and control of conditions associated with TSHR activation for example: Graves' disease, Graves' opthalmopathy or hyperthyroidism due to abnormal levels of TSH or hCG. Antibodies according to the second mentioned aspect of the invention such as K1-18 have applications for stimulating the TSHR in different clinical conditions and treatment situations. These conditions include diagnosis and management of thyroid cancer and its metastases, multinodular goitre or congenital hypothyroidism.

According to another aspect of the invention there is provided the use of an isolated antibody molecule or a pharmaceutical composition according to the invention in therapy. The invention also provides an isolated antibody molecule or a pharmaceutical composition according to the invention for use in therapy. According to another aspect of the invention there is provided a method of characterising the activity of TSHR antibodies, TSH or human chorionic gonadotropin, the method comprising a step including the use of an isolated antibody molecule according to the invention.

According to another aspect of the invention there is provided an in vitro method of stimulating the TSHR in mammalian cells, the method comprising contacting the cells with an isolated antibody molecule according to the invention.

According to another aspect of the invention there is provided an in vivo method of stimulating the TSHR in mammalian cells, the method comprising contacting the cells with an isolated antibody molecule according to the invention. Preferably, cells of a subject with thyroid cancer and its metastases, multinodular goitre and/or congenital hypothyroidism are contacted with an isolated antibody according to the invention.

According to another aspect of the invention there is provided an in vivo method of preventing ligand induced stimulation of TSHRs in mammalian cells, the method comprising contacting a TSHR with an isolated antibody molecule according to the invention. The ligand may be a thyroid stimulating autoantibody, TSH or human chorionic gonadotropin. The mammalian cells may be thyroid cells or extra-thyroidal cells. Mammalian extra-thyroidal cells may be in retro-orbital tissue or pre-tibial tissue.

In methods according to this aspect of the invention the isolated antibody molecule may be used in combination with another TSHR binding antibody such as 5C9 or 9D33 referred to above.

The thyroid-related condition may be selected from hyperthyroidism, Graves' disease, ophthalmic Graves' disease and neonatal hyperthyroidism. Alternatively, the thyroid-related condition may be hypothyroidism related to the presence of TRAbs with blocking activity in patients with AITD, neonatal hypothyroidism due to transfer of maternal TRAbs (via placenta or breast milk).

The subject treated in the various methods of the invention described above is preferably human. According to another aspect of the invention there is provided a diagnostic method for detecting autoantibodies to TSHRs, the method comprising contacting a sample, which has been isolated from a subject believed to contain such autoantibodies, and an antibody molecule according to the invention with a TSHR.

According to another aspect of the invention there is provided a diagnostic method for detecting an antibody in accordance with the invention, preferably a human antibody, to the TSHR or antibodies to the TSHR in human serum comprising contacting any one of the antibodies to the TSHR with a TSHR fragment comprising amino acids 22-260 of the TSHR (TSHR260) (FIG. 7B; SEQ ID No 75).

A suitable detectable label that can be employed in a method according to the present invention can be selected from the group consisting of enzymic labels, isotopic labels, chemiluminescent labels, fluorescent, dyes and the like.

In the case where an isotopic label (such as $^{125}$I, $^{14}$C, $^{3}$H or $^{35}$S) is employed, monitoring may therefore comprise measuring radioactivity dependent on binding of an antibody molecule according to the present invention. Radioactivity is generally measured using a gamma counter, or liquid scintillation counter. According to another aspect of the invention there is provided a method of identifying small molecules that bind to TSHR260 (SEQ ID No 75), the method comprising contacting a candidate small molecule with TSHR260 for example in an ELISA and selecting small molecules that bind to TSHR260. Further, there is provided a method of identifying small molecules that have the ability to prevent TSHR autoantibody binding to TSHR260, the method comprising determining inhibition of binding of TSHR autoantibody (stimulating or blocking) to TSHR260 in the presence of a candidate small molecule and selecting small molecules that inhibit TSHR autoantibody binding. Small molecules identified in this way may be developed to provide new drugs to control autoimmune thyroid disease caused by TSHR autoantibodies (stimulating or blocking).

The present invention provides new and/or improved means to:

1. Stimulate the TSHR in the thyroid or tissues expressing the TSHR such as thyroid cancer and thyroid cancer metastases.
2. Prevent thyroid stimulating autoantibodies binding to the TSHR in the thyroid and thereby providing a new treatment for Graves' disease.
3. Prevent TSHR autoantibodies binding to the extra-thyroidal TSHRs (for example in retro-orbital tissue or pre-tibial tissue) and thereby providing improved opportunities for the management of Graves' ophthalmopathy and pre-tibial myxoedema.
4. Determine TSHR amino acids critical for binding TRAbs with stimulating activities.
5. Determine TSHR amino acids critical for binding TRAbs with blocking activities.
6. Compare the TSHR amino acids critical for binding of TRAbs with stimulating and blocking activities.
7. Develop new assays for TRAbs that differentiate between blocking and stimulating antibodies.
8. Develop new assays for TRAb based on using thermostable TSHR fragments.
9. Determine TSHR amino acids critical for ligand-induced TSHR activation.
10. Determine TSHR amino acids critical for ligand-induced TSHR inactivation.
11. Determine the blocking autoantibody amino acids critical for binding to the TSHR.
12. Determine the blocking autoantibody amino acids critical for affecting TSH or thyroid stimulating antibody-mediated TSHR activation.
13. Control hyperthyroidism of Graves' disease, neonatal hyperthyroidism and the eye signs of Graves' disease. Alternatively, the thyroid-related condition may be hypothyroidism related to the presence of TRAbs with blocking activity in patients with AITD, or neonatal hypothyroidism due to transfer of maternal blocking type TRAbs (via placenta or breast milk).
14. Develop new means to screen for small molecule drug candidates to control thyroid disease caused by the autoantibodies that bind to the TSHR.
15. Understand molecular differences between TSHR autoantibodies with thyroid stimulating or blocking activity produced by the immune system of the same patient and by the immune system of different patients.
16. Understand the immunological mechanisms involved in development and production of stimulating and blocking TSHR autoantibodies.
17. Understand the mechanisms including evolutionary driving forces which are the basis of the molecular mimicry between TSH and TSHR autoantibodies.

BRIEF DESCRIPTION OF THE DRAWINGS

Antibody molecules and methods in accordance with the invention will now be described, by way of example only, with reference to the accompanying drawings, FIGS. 1 to 9, in which:

FIG. 1A shows the time course of binding of $^{125}$I-labelled K1-70 IgG and Fab to full length TSHR;

FIG. 1B shows the time course of binding of 125I-labelled K1-70 IgG to TSHR260;

FIG. 1C shows the time course of 125I-labelled K1-70 Fab to TSHR260;

FIG. 1D shows the dissociation of 125I-labelled K1-70 IgG from the TSHR (full length) in the presence of various ligands;

FIG. 1E shows the dissociation of 125I-labelled K1-70 IgG from TSHR (full length) in the presence of K1-18 Fab;

FIG. 1F shows the dissociation 125I-labelled K1-70 Fab from the TSHR (full length) in the presence of various ligands;

FIG. 1G shows the dissociation of 125I-labelled K1-70 IgG from TSHR260 in the presence of various ligands;

FIG. 1H shows the dissociation of 125I-labelled K1-70 IgG from TSHR260 in the presence of K1-18 Fab;

FIG. 1I shows the dissociation of 125I-labelled K1-70 Fab from the TSHR260 in the presence of various ligands;

FIG. 1J shows the time course of binding of 125I-labelled K1-18 IgG to full length TSHR and TSHR260;

FIG. 1K shows the dissociation of 125I-labelled K1-18 IgG from full length TSHR in the presence of various ligands;

FIG. 1L shows the dissociation of 125I-labelled K1-18 IgG from TSHR260 in the presence of various ligands FIG. 2A shows the comparison of the measurements in a TRAb coated tube assay (based on inhibition of TSH binding) and in a TSHR260-AP ELISA;

FIG. 2B shows the comparison of measurements by ELISAs based on inhibition of M22 binding to full length TSHR and by inhibition of M22 Fab binding to TSHR260 in the ELISA;

FIG. 2C shows the comparison of measurements in a TRAb coated tube assay (based on inhibition of TSH binding) and by inhibition of M22 Fab binding to TSHR260 coated plates in an ELISA;

FIG. 2D shows the comparison of the measurements in a TRAb ELISA (based on inhibition of M22 binding) and in a TSHR260-AP ELISA;

FIG. 3A gives the oligonucleotide sequence of K1-18 HC (SEQ ID No 1) shown in unannotated and annotated forms. In the annotated forms, sequences used for PCR primers are underlined; for individual Complementarity Determining Regions (CDRs) are boxed; and constant regions are in bold;

FIG. 3B gives the amino acid sequence of K1-18 HC (SEQ ID No 5) derived from the oligonucleotide sequence shown in (FIG. 3A) in unannotated and annotated forms;

FIG. 3C gives the preferred oligonucleotide sequence of K1-18 HC (SEQ ID No 10) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold;

FIG. 3D gives the preferred amino acid sequence of K1-18 HC (SEQ ID No 15) with the leader sequence derived from the oligonucleotide sequence shown in FIG. 3C in unannotated and annotated forms;

FIG. 4A gives the oligonucleotide sequence of K1-18 LC (SEQ ID No 19) shown in unannotated and annotated forms. In the annotated forms, sequences used for PCR primers are underlined; individual CDRs are boxed; and constant regions are in bold;

FIG. 4B gives the amino acid sequence of K1-18 LC (SEQ ID No 23) derived from the oligonucleotide sequence shown in FIG. 4A in unannotated and annotated forms;

FIG. 4C gives the preferred oligonucleotide sequence of K1-18 LC (SEQ ID No 28) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold;

FIG. 4D gives the preferred amino acid sequence of K1-18 LC (SEQ ID No 33) with the leader sequence derived from the oligonucleotide sequence shown in FIG. 4C in unannotated and annotated forms;

FIG. 5A gives the oligonucleotide sequence of K1-70 HC (SEQ ID No 37) shown in unannotated and annotated forms. In the annotated forms, sequences used for PCR primers are underlined; individual CDRs are boxed; and constant regions are in bold;

FIG. 5B gives the amino acid sequence of K1-70 HC (SEQ ID No 41) derived from the oligonucleotide sequence shown in FIG. 5A in unannotated and annotated forms;

FIG. 5C gives the preferred oligonucleotide sequence of K1-70 HC (SEQ ID No 46) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold;

FIG. 5D gives the preferred amino acid sequence of K1-70 HC (SEQ ID No 51) with the leader sequence derived from the oligonucleotide sequence shown in FIG. 5C in unannotated and annotated forms;

FIG. 6A gives the oligonucleotide sequence of K1-70 LC (SEQ ID No 55) shown in unannotated and annotated forms. In the annotated forms, sequences used for PCR primers are underlined; individual CDRs are boxed; and constant regions are in bold;

FIG. 6B gives the amino acid sequence of K1-70 LC (SEQ ID No 59) derived from the oligonucleotide sequence shown in FIG. 6A in unannotated and annotated forms;

FIG. 6C gives the preferred oligonucleotide sequence of K1-70 LC (SEQ ID No 64) with the actual N-terminal sequence (the leader sequence) shown in unannotated and annotated forms. In the annotated forms, sequences used for PCR primers are underlined, the leader sequence is shown in lowercase letters; individual CDRs are boxed; and constant regions are in bold;

FIG. 6D gives the preferred amino acid sequence of K1-70 LC (SEQ ID No 69) with the leader sequence derived from the oligonucleotide sequence shown in FIG. 6C in unannotated and annotated forms;

FIG. 6E gives the actual N-terminal amino acid sequence (amino acids 2-21) (SEQ ID No 73) determined by Edman degradation reaction;

FIG. 7A illustrates the consensus amino acid sequence of the human TSHR (amino acids 1-764 (SEQ ID No 74) (accession no. P16473, at ncbi.nlm.nih.gov/entrez/viewer.fcgi?db=protein&val=62298994 on the World Wide Web);

FIG. 7B illustrates the consensus amino acid sequence of the human TSHR amino acids 1-260. The leader sequence (amino acids 1-21) is shown in lowercase and the histidine sequence added for purification purposes is shown at the C-terminus in bold (SEQ ID No 75);

FIG. 7C illustrates the amino acid sequence of the human TSHR LRD C-CAP. The leader sequence (amino acids 1-21) is shown in lowercase and the histidine sequence added for purification purposes is shown at the C-terminus in bold (SEQ ID No 76);

FIG. 8 gives the coordinates of K1-70 Fab at 2.22 Å resolution.

FIG. 9A shows the structure of K1-70 Fab—representation of structure in Joy format;

FIG. 9B shows the electrostatic potential of the combining site of K1-70 Fab;

FIG. 9C shows the aromatic amino acids of the combining site of K1-70 Fab.

METHODS

Lymphocyte Isolation and Cloning of Human Monoclonal TSHR Autoantibodies.

The monoclonal autoantibodies K1-18 and K1-70 were isolated using the procedure described in WO2004/050708A2. Lymphocytes were isolated from a blood sample collected from a patient with an 8 year clinical history of AITD and high levels of TRAbs. Patient consent and Local Ethical Committee approval were obtained. The patient was first diagnosed with hyperthyroidism, reached the euthyroid state after treatment with methimazole, however, approximately 4.5 years prior to blood collection she developed hypothyroidism. At the time of blood collection the patient was being treated with thyroxine (50 µg daily). The lymphocytes were infected with Epstein Barr Virus (EBV) (European Collection of Cell Cultures—ECACC; Porton Down, SP4 0JG, UK) and cultured on mouse macrophage feeder layers as described in WO2004/050708A2. Immortalised lymphocytes secreting TSHR autoantibodies were fused with a mouse/human hybrid cell line K6H6/B5 (ECACC) and cloned four times by limiting dilution to obtain a single colony. The presence of TSHR autoantibody in cell culture supernatants at different stages of cloning was detected by inhibition of labelled TSH binding to the TSHR (WO2004/050708A2). Two single clones producing the TSHR autoantibodies were expanded and supernatants from the cultures were harvested for autoantibody purification. One clone was designated as K1-18 and the other as K1-70.

Purification, Characterisation and Labelling of K1-18 and K1-70

TSHR human MAbs IgGs were purified from culture supernatants using protein A affinity chromatography on MABSELECT™ (GE Healthcare, UK) as described in Sanders J et al 2004. Thyroid 2004 14: 560-570) and purity assessed by SDS-polyacrylamide gel electrophoresis (PAGE). The heavy chain isotype was determined using a radial diffusion assay (The Binding Site; Birmingham, B29 6AT, UK), and the light 15 chain isotype was determined by Western blotting with anti-human kappa chain and anti-human lambda chain specific mouse monoclonal antibodies (Sigma-Aldrich Company Ltd, Poole, UK). Purified K1-18 IgG was treated with mercuripapain (Sigma Aldrich, Poole, UK) at a IgG/enzyme ratio of 100:1 in phosphate buffered saline (PBS; 137 mmol/L NaCl, 8.1 mmol/L $Na_2HPO_4$, 2.7 mmol/L KCL, 1.47 mmol/L $KH_2PO_4$, pH 7.4 containing cysteine at final concentration of 1 mmol/L and EDTA at final concentration of 2 mmol/L) for 4 hours at 37° C. The reaction was stopped by addition of iodoacetamide (final concentration of 50 mmol/L) for 30 minutes at room temperature. The reaction mixture was then passed through a MABSELECT column to remove any intact IgG or Fc fragments from the Fab preparation. The Fab containing solution was dialysed into PBS containing 3.1 mmol/L NaN3 and concentrated using a CENTRIPREP concentrator (Millipore, Watford, WD18 8YH, UK) when appropriate. K1-70 Fab were 25 obtained using similar method except that an IgG/enzyme ratio of 200:1 was used and the digestion with enzyme was for 1 hour at 37° C. Analysis by SDS-PAGE indicated that intact IgG was undetectable in the Fab preparations. IgG preparations were labelled with 125I as described in Sanders J et al 1999. Journal of Clinical Endocrinology and Metabolism. 1999 84: 3797-3802) or with biotin hydrazide (Perbio Science, Cramlington, UK) (Rees Smith et al 2004. Thyroid 14: 830-835).

Inhibition of $^{125}$I-TSH or $^{125}$I-Labelled Human MAbs Binding to the TSHR Binding inhibition assays were carried out using TSHR coated tubes as described in W02004/050708A2. In the assay, 100 μL of test sample (MAb preparation, patient serum or unlabelled TSH) and 50 μL of start buffer (RSR Ltd) were incubated in TSHR coated tubes for 2 hours at room temperature with gentle shaking. After aspiration, the tubes were washed and 100 μL $^{125}$I-labelled protein ($5\times10^4$ cpm) added and incubated for 1 hour at room temperature with shaking. The tubes were then aspirated, washed and counted in a gamma counter. Inhibition of labelled protein binding was calculated as 100×[1-(cpm bound in the presence of test material/cpm bound in the presence of control material)]. MAb preparations used in these experiments were K1-18, K1-70, M22, 5C9, 9D33 described above. TSMAbs 1-7 are mouse thyroid stimulating MAbs (WO 03/01862 and Sanders J et al 2002 supra). Control material was a pool of healthy blood donor sera or individual healthy blood donor sera or other materials as indicated in the results of various experiments.

Scatchard Analysis of Human MAb IgG Binding to the TSHR

Unlabelled K1-18 or K1-70 IgG in 50 μL of assay buffer (50 mmol/L NaCl, 10 mmol/L Tris pH 7.8 and 0.1% Triton X-100) and 50 μL start buffer (RSR Ltd) and 50 μL of $^{125}$I-labelled K1-18 or K1-70 IgG respectively (30,000 cpm in assay buffer) were incubated in TSHR coated tubes for 2 hours at room temperature with shaking (maximum binding occurred under these conditions), aspirated, washed twice with 1 mL of assay buffer and counted in a gamma counter. The concentration of IgG bound vs bound/free was plotted (Scatchard G 1949. Annals of the New York Academy of Sciences 51: 660-672) to derive the association constant.

Inhibition of TSH Binding to the TSHR Measured by ELISA

A TRAb ELISA based on TSH-biotin binding to TSHR coated ELISA wells was used as described previously (Bolton J, et al 1999 Clinical Chemistry 45: 2285-2287). In the assay 75 μL of test sample was added to 75 μL of start buffer in the plate wells and incubated for 2 hours at room temperature with shaking at about 500 shakes/minute. After washing 100 μL of TSH-biotin was added and incubation continued for 25 minutes without shaking. The wells were washed again, the reaction developed using described standard procedures and the absorbance of each well read at 450 nm.

Inhibition of TSH-biotin binding was calculated as: 100× [1-(test sample absorbance at 450 nm/negative control sample absorbance at 450 nm)]. MAb preparations used in these experiments were K1-18, K1-70, M22, 5C9, 9D33 described above. TSMAbs 1-7 are mouse thyroid stimulating MAbs (WO03/01863 and Sanders J, et al 2002 supra). Control sample material was a pool of healthy blood donor sera or other materials as indicated in the results of various experiments.

Inhibition of M22 Binding to the TSHR in ELISA

A TRAb ELISA based on labelled M22 (M22 Fab-POD) binding to TSHR coated ELISA wells was used (Rees Smith B, et al 2004 supra). The assay was carried out as the TSH-biotin based ELISA except the first incubation was for 1 hour. Results were expressed as inhibition of M22 binding using the formula: 100×[1-(test sample absorbance at 450 nm/negative control sample absorbance at 450 nm)]. MAb preparations used in these experiments were K1-18, K1-70, M22, 5C9, 9D33 described above. TSMAbs 1-7 are mouse thyroid stimulating MAbs (Patent application number WO03/01863 and Sanders J, 2002 supra). Control material was a pool of healthy blood donor sera or other materials as indicated in the results of various experiments.

Analysis of TSHR Stimulation

The ability of K1-18 or K1-70 IgG and other preparations to stimulate production of cyclic AMP in Chinese hamster ovary (CHO) cells transfected with the human TSHR was tested as described in WO2004/050708A2. CHO cells expressing either approximately $5\times10^4$ or approximately $5\times10^5$ TSHR per cell were seeded into 96-well plates at $3\times10^4$ cells per well, adapted into DMEM (Invitrogen Ltd, Paisley, UK) without foetal calf serum and then test samples (TSH, IgG or patient serum) added (100 μL diluted in cyclic AMP assay buffer i.e. NaCl free Hank's Buffered Salts solution containing 1 g/L glucose, 20 mmol/L HEPES, 222 mmol/L sucrose, 15 g/L bovine serum albumin and 0.5 mmol/L 3 isobutyl-1-methylxanthine pH 7.4; cyclic AMP assay hypotonic buffer) and incubated for 1 hour at 37° C. After removal of test solutions, cells were lysed and cyclic AMP concentration in the lysates assayed using Direct Cyclic AMP Correlate—EIA kits from Assay Designs; Cambridge Bioscience, UK. Results are expressed as pmol/mL of cyclic AMP in the cell lysate (200 μL). Some experiments were carried out under isotonic buffer condition. In these experiments Krebs Ringer Hepes buffer (KRH buffer) was used (124 mmol/L NaCl, 5 mmol/L KCl, 1.25 mmol/L MgSO$_4$, 1.45 mmol/L CaCl$_2$, 1.25 mmol/L KH$_2$PO$_4$, 25 mmol/L HEPES, 8 mmol/glucose, 0.5 g/L bovine serum albumin, 0.5 mmol/L 3 isobutyl-1-methylxanthine, pH 7.4). Cells were allowed to reach the required density, the culture medium removed and the cells washed with 1 mL of KRH buffer. Fresh KRH buffer was then added and the cells incubated for 30 minutes at 37° C. The buffer was then removed and replaced with fresh KRH buffer containing test sample (TSH, MAb preparations, serum samples etc). The next steps were then carried out as described above for the experiments under the hypotonic conditions (i.e. in cyclic AMP assay buffer). In some experiments the effect of various MAbs on the TSHR stimulating activity of various preparations (for example, TSH, human MAbs, patient sera) measured as described above was assessed. This was carried out by comparing (a) the stimulating activity of the sample alone with (b) stimulating activity in the presence of various MAbs.

Measurement of Antagonist (Blocking) Activity

The ability of K1-70 IgG and other preparations to inhibit the stimulating activity of porcine (p) TSH, native human (h) TSH and recombinant human (rh) TSH, MAb M22, MAb K1-18 and patient serum TRAbs in CHO cells expressing TSHRs was assessed. This was carried out by comparing the stimulatory effect of TSH, M22, K1-18 or TRAbs in the absence and in the presence of K1-70 IgG (or other preparations being tested). The assay was carried out as described above except 50 μL of K1-70 (or other preparations being tested) diluted in cyclic AMP assay buffer was added to the cell wells followed by 50 μL of TSH or M22 or K1-18 or patient serum (diluted as appropriate in cyclic AMP assay buffer) and incubated and tested as for the stimulating assay described above. Other MAbs and sera from patients with blocking type TRAbs were tested in this assay in addition to K1-70.

Association and Dissociation of K1-18 and K1-70 Binding to the TSHR

The association and dissociation of K1-18 IgG, K1-18 Fab, K1-70 IgG and K1-70 Fab binding to the full length TSHR and the TSHR260 was studied using the method as described in: Nakatake N, et al Thyroid 2006, 16; 1077-1084. The full length TSHR or TSHR260 were coated onto plastic tubes which had been pre-coated with an appropriate mouse MAb to the TSHR. In association experiments 100 µL of $^{125}$I-labelled IgG or Fab were incubated in the TSHR coated tubes at room temperature for 5-180 min. The tubes were then aspirated, washed with assay buffer and counted in a gamma counter. In the dissociation experiments 100 µL of $^{125}$I-labelled IgG or Fab were incubated in TSHR coated tubes for 180 min at room temperature followed by the addition of 10 µL of 1 mg/mL of various MAb IgG or Fab preparations and incubation for 0-180 min at room temperature. At different time points the tubes were aspirated, washed and counted. In some experiments TSH or buffer was added instead of a MAb preparation.

Amino Acid Mutations in the TSHR

The methods used to introduce specific mutations into the TSHR sequence have been described in patent application WO2006/016121A. Furthermore, transfection of mutated TSHR constructs into CHO cells using the Flp-In system is also described in WO2006/016121A. Flp-In-CHO cells expressing either wild type or mutated TSHRs were seeded into 96 well plates and used to test the ability of various preparations to stimulate cyclic AMP activity in the CHO cells expressing the TSHR containing amino acid mutations. These experiments were compared to similar experiments carried out using CHO cells expressing wild type TSHR. Flp-In-CHO cells expressing either wild type or mutated TSHRs were also used in experiments to study the ability of various preparations to block the stimulating activity of TSH, stimulating antibodies or patient serum TRAbs as described above.

Production of TSHR260-Alkaline Phosphatase (TSHR260-AP) Construct

The TSHR 260 construct (coding amino acids 1-260 of the human TSHR; amino acids 1-21 being the leader sequence) was amplified using full length human TSHR as the template (Oda Y, et al 1998. Journal of Molecular Endocrinology 20: 233-244) and joined to the coding sequence of a secreted alkaline phosphatase (minus the 17 amino acid alkaline phosphatase leader sequence) using the cloning vector pSEAP2-basic (Clontech) as the template. Two PCR reactions were carried out, the first used the full length TSHR amplified with specific primers SEQ ID No 77 and SEQ ID No 78 primers (Sigma Genosys) which added an EcoRI restriction site at the N-terminus, and a 1 amino acid linker (Asparagine) and the first 8 amino acids (excluding the 17 amino acid leader sequence) of the secreted alkaline phosphatase at the C terminus. The second PCR was carried out using the cloning vector pSEAP2-basic amplified with the primersSEQ ID No 79 and SEQ ID No 80 which adds amino acids 254-260 of the TSHR and a 1 amino acid linker (Asparagine) to the N terminus of the secreted alkaline phosphatase and a 6 histidine tag, a stop codon and an XhoI restriction site at the C-terminus of the secreted alkaline phosphatase gene. The PCR reactions were carried out for 30 cycles of 1 minute at 94° C., 1 minute at 40° C. and 1 minute at 72° C. followed by 7 minutes at 72° C. The PCR products were run on 1% agarose gels and the DNA extracted using a geneclean II kit (Anachem Ltd, Luton) following the manufacturer's instructions. Purified PCR products 1 and 2 were then used to set up a third PCR to construct the whole TSHR 260-alkaline phosphatase gene. The PCR 3 reaction contained 200 ng of PCR 1 and 200 ng of PCR 2 product and PCR 3 was carried out for 7 cycles at 94° C. for 1.5 minutes, 65° C. for 1.5 minutes and 72° C. for 1.5 minutes. The temperature was then increased to 94° C. again for 2 minutes and primers SEQ ID No 77 and 80 added followed by 30 cycles of 94° C. for 1 minute, 52° C. for 1 minute and 72° C. for 2 minutes. The PCR 3 product was cloned into pFastBac1 using EcoRI and XhoI restriction sites and the presence of the mutation was verified using sequencing by the Sanger-Coulson method (Sanger F et al 1997. Proceedings of the National Academy of Sciences of the USA 74: 5463-5467). Recombinant DNA was made using the Bac to Bac Baculovirus expression system (Invitrogen, UK) and transfected into Sf-9 cells to obtain and amplify recombinant baculovirus stock as described in WO02008/025991A1. TSHR260-AP was expressed in insect cells as described in WO02008/025991A1.

ELISA Based on TSHR260-AP

An ELISA was established based on the ability of divalent TSHR antibodies to bind with one antigen binding site to TSHR coated onto an ELISA plate well and with the other antigen binding site to TSHR260-AP in a liquid phase i.e. forming a bridge. TSHR in the form of full length detergent-solubilised receptor expressed in CHO cells was coated onto ELISA plate wells via a C-terminal antibody as described previously (Bolton J et al 1999 supra). In the assay 75 µL of start buffer (as described for TRAb ELISA; Bolton J, et al 1999 supra) and 75 µL of test sample (patient sera or monoclonal antibodies) were added to the ELISA plate wells coated with the full length detergent solubilised TSHR and incubated for 2 hours at room temperature with shaking (500 rpm). Then the contents of the wells were removed, the wells washed 3 times with wash buffer (50 mmol/L NaCl, 20 mmol/L Tris pH 7.8, 1% Triton X-100) followed by addition of 100 µL of TSHR260-AP (diluted in wash buffer containing 0.2 g/L $MgCl_2$-$6H_2O$ and 2 g/L BSA). After incubation for 1 hour at room temperature with shaking (500 rpm) the wells were emptied, washed (3 times) and 100 µL of p-nitrophenyl phosphate (pNpp) substrate (Europa Bioproducts Ltd, Ely, Cambridge UK) added and the plate incubated in the dark for 45 minutes. Thereafter 100 µL of stop solution (1 mol/L NaOH) was added and the absorbance read at 405 nm in an ELISA plate reader. The results were expressed as $OD_{405}$ nm absorbance values, values higher than those observed with a panel of healthy blood donor (HBD) sera indicated the presence of TSHR autoantibodies in the sample. In some experiments solubilised preparations of recombinant TSHR containing mutation R255D expressed in CHO cells were used to coat the ELISA plate wells.

Production of TSHR LRD C-CAP Construct

The TSHR LRD C-CAP construct coding amino acids 1-409 of the human TSHR with amino acids 306-384 removed, was amplified using full length human TSHR as the template (Oda Y, et al 1998. Journal of Molecular Endocrinology 20: 233-244). Two PCR reactions were carried out, the first used the full length TSHR amplified with T7 primer (SEQ ID No 81) and specific primer SEQ ID No 82 (Sigma Genosys, Gillingham, Dorset, UK) which added amino acids 385-342 of the TSHR to the C terminus of amino acid 305 of the TSHR. The second PCR was carried out using the full length TSHR amplified with BGH reverse primer SEQ ID No 83 and the specific primer (SEQ ID No 84), which adds amino acids 298-305 of the TSHR to the N terminus of amino acid 385 of the TSHR. The PCR reactions were carried out for 30 cycles of 1 minute at 94° C., 1 minute at 40° C. and 2 minutes at 72° C. followed by 7 minutes at 72° C. The PCR products were run on 1% agarose gels and the DNA extracted using a Geneclean II kit (Anachem Ltd, Luton, UK) following the manufacturer's instructions. Purified PCR products 1 and 2 were then used to set up a third PCR to construct a continuous TSHR sequence joining Ser305 to Tyr385 with amino acids 306-384 removed. The PCR 3 reaction which contained 200 ng of PCR 1 and 200 ng of PCR 2 product and PCR 3 was carried out for 7 cycles at 94° C. for 1.5 minutes, 65° C. for 1.5 minutes and 72° C. for 1.5 minutes. The temperature was then increased to 94° C. again for 2 minutes and T7 primer (SEQ ID No 81) and BGHR primer (SEQ ID No 83) were added followed by 30 cycles of 94° C. for 1 minute, 52° C. for 1 minute and 72° C. for 2 minutes. The PCR 3 product containing TSHR sequence omitting amino acids 306-384 was then run on a 1% agarose gel and the DNA extracted using a Geneclean II kit (Anachem Ltd) following the manufacturer's instructions. Purified PCR3 product was used as the template for construction of the TSHR LRD C-CAP gene in PCR 4. The PCR 4 reaction contained 200 ng of PCR 3 as template DNA and was amplified with T7 primer (SEQ ID No 81) and the specific primer (SEQ ID No 85) which adds a 6 histidine tag, a stop codon and an XhoI restriction site to the C-terminus of amino acid 409 of the TSHR sequence (1-409 with amino acids 306-384 deleted). PCR 4 was carried out for 30 cycles of 1 minute at 94° C., 1 minute at 40° C. and 1 minute at 72° C., followed by 10 minutes at 72° C. The PCR 4 product was cloned into pFastBac1 using BamHI and XhoI restriction sites and the presence of the mutation was verified using sequencing by the Sanger-Coulson method (Sanger F. et al 1997. Proceedings of the National Academy of Sciences of the USA 74: 5463-5467). Recombinant DNA was made using the Bac to Bac Baculovirus expression system (Invitrogen, Paisley, UK) and transfected into Sf-9 cells to obtain and amplify recombinant baculovirus stock as described in WO2008/025991A1. TSHR LRD C-CAP (FIG. 7C; SEQ ID No 76) was expressed in insect cells using the procedure described in WO2008/025991A1.

Comparison of Stability of Different TSHR Preparations

Temperature stability of different preparations of recombinant TSHR was compared. Full length solubilised TSHR expressed in CHO cells, TSHR260 expressed in insect cells, TSHR260-AP expressed in insect cells and TSHR. LRD C-CAP expressed in insect cells were tested. An aliquot of each of the above listed preparations was removed from −80° C. storage, thawed on ice, a sample returned to −80° C. as a control while the bulk was stored at room temperature (20-25° C.) for 24 or 48 hours. After 24 or 48 hours at room temperature the TSHR preparations were stored at −80° C. and then tested as described below. ELISA plate wells were coated with a F(ab')$_2$ preparation of the mouse TSHR MAb 14C4 (Jeffreys J et al 2002, Thyroid 12: 1051-1061 and Sanders J et al 2007 Thyroid 17: 395-410) at 1 μg/mL in coating buffer (Bolton J et al 1999 supra). TSHR preparations under investigation were diluted in 20 mmol/L NaCl, 10 mmol/L Tris pH7.8, 1% v/v Triton X-100, 1 g/L BSA, 200 mg/L NaN3 and 150 μL added to ELISA plate wells (in quadruplicate). After incubation overnight at 4° C. to allow the TSHR preparations to bind to the antibody (14C4 F(ab')2) coated wells, the wells were washed and incubated with 75 μL of assay buffer (50 mmol/L NaCl, 20 mmol/L Tris pH7.8, 1% v/v Triton X-100, 1 g/L BSA) and 75 μL of healthy blood donor serum for 1 hour at room temperature at 500 shakes per minute on an ELISA plate shaker. Thereafter the contents of the wells were emptied, the wells washed and 100 μL of M22 Fab-peroxidase conjugate (see above) added to each well. After 25 minutes incubation at room temp without shaking the plate wells were washed again followed by addition of 100 μL of tetramethylbenzidine and a further incubation of 25 minutes at room temperature without shaking. The reaction was stopped by addition of 50 μL of 0.5 mol/L $H_2SO_4$ and the absorbance of each well read at 450 nm on an ELISA plate reader.

Variable Region Gene Analysis

The variable (V) region genes of K1-18 or K1-70 heavy and light chains were determined as described in WO2004/050708A2, using total RNA prepared from 1×10$^7$ heterohybridoma cells (secreting K1-18 IgG or K1-70 IgG) to produce mRNA for RT-PCR (reverse transcriptase PCR) reactions. Specific IgG1 HC and kappa LC sense and antisense strand oligonucleotide primers designed using the Medical Research Council's V-base (http://vbase.mrc-cpe.cam.ac.uk/) and synthesised by Invitrogen (Paisley, PA4 9RF, UK) were used in RT-PCR reactions with K1-18 mRNA. Specific IgG1 HC and lambda LC primers prepared as described above were used in RT-PCR reactions with K1-70 mRNA. The RT reaction was carried out at 50° C. for 15 minutes followed by 40 cycles of PCR at 94° C. for 15 seconds, 50° C. for 30 seconds and 72° C. for 30 seconds. DNA products were cloned into pUC18 and sequenced by the Sanger-Coulson method (Sanger F, et al 1977 supra). V region sequences were compared with available sequences of human Ig genes using Ig blast (http://www.ncbi.nlm.nih.gov/igblast/). The CDRs were assigned by the method of Kabat (Kabat E et al 1991 Sequences of proteins of immunological interest (US Public Health service, Bethesda, Md.) Fifth edition) and Ig blast (http://www.ncbi.nlm.nih.gov/igblast/). A second round of mRNA isolation was carried out from both the K1-70 and K1-18 hybridoma cell lines that had undergone further recloning by limiting dilution. The V-region sequences (K1-18 HC, K1-18 LC, K1-70 HC and K1-70 LC) were obtained by RT-PCR from the mRNA followed by cloning and sequencing as described above. In addition the RT-PCR reactions were also carried out using specifically designed PCR primers corresponding to the 5' end of the respective leader sequences for each of the V regions. This allowed the identification of the actual oligonucleotide sequences (and derived amino acid sequences) at the N-termini of the HC and LC V regions of K1-18 and K1-70. In addition, the N-terminal amino acid sequence of K1-70 LC protein was analysed by Edman degradation reaction by Alta Bioscience (Birmingham, UK). This was possible after the N-terminal "deblocking" of the K1-70 LC protein preparation with pyroglutamate aminopeptidase. Purified K1-70 Fab (10 μg) was treated with 2.5 mU of pyroglutamate aminopeptidase (in 50 mmol/L $Na_2HPO_4$ pH 7.0; 10 mmol/L dithiothreitol and 1 mmol/L EDTA) for 6 hours at 75° C. An equal volume of SDS-PAGE sample buffer was added and after heating at 100° C. for 5 minutes, K1-70 Fab was resolved into the HC (Fd part) and the LC on 15% SDS-PAGE. The LC band was carefully cut out of the gel and the N-terminal protein sequence determined. Repeat rounds of RT-PCR and sequencing of K1-18 HC, K1-18 LC and K1-70 HC confirmed the V region sequences were the same as obtained before while the K1-70 LC V region sequence differed. The K1-70 LC sequence obtained in the repeat round of experiments was consistent with the protein sequence of the 2-21 consecutive N-terminal amino acids obtained by Edman reaction (FIG. 6E; SEQ ID No 73) and the electron density of the LC amino acids in the crystal structure of K1-70 Fab (FIG. 8) and consequently concluded as the preferred K1-70 LC sequence (FIGS. 6C and 6D; (SEQ ID No 64 and 69, respectively).

X-Ray Diffraction Analysis of K1-70 Fab

K1-70 Fab solutions prepared as described above were concentrated to 15.5 mg/mL using iCON concentrators (ThermoFisher Scientific, Loughborough, UK) with a 9000 Da cut off and stored at −20° C. in aliquots. Crystals of K1-70 Fab were grown using the hanging drop method of vapour diffusion using the Structure Screen 1 sparse matrix screen from Molecular Dimensions (Newmarket, UK). Several crystals were obtained in a number of conditions and all were screened to identify the crystal most suitable for the X-ray diffraction analysis at Biofocus DPI (Saffron Walden, UK). A crystal grown in 30% PEG 400, 0.1 M sodium Hepes pH 7.5, 0.2 M magnesium chloride was chosen. It was washed in well solution and flash frozen by plunging into liquid nitrogen. The data set was collected on a Rigaku R-Axis IV image plate detector and was indexed, integrated and scaled using MOSFLM and SCALA (from CCP4 program suite (Collaborative computational project, number 4. 1994. "The CCP4 Suite: Programs for Protein Crystallography". Acta Cryst. D50, 760-763). Three structures from the Protein Data Bank (http://www.rcsb.org/pdb/home/home.do) 1LIL (VL and CL domains), 2B0S (VH domain) and 2EH7 (VL domain) were chosen for use in molecular replacement, based on sequence alignment. There were two complete Fab K1-70 molecules in the asymmetric unit and the resulting model was given ten cycles of atomic refinement with tight geometric weights using REFMAC5 (CCP4). The electron density maps calculated after molecular replacement and initial refinement were examined in the model building program COOT (Emsley P, Cowtan K 2004. Nature 355: 472-475) and automated model rebuilding was performed using BUCCANEER (CCP4). The model was reexamined and any remaining missing features were built by hand and the model was refined using REFMAC5 (CCP4). Water molecules were then added using the water placement option in COOT and refined using REFMAC5 (CCP4). The structural geometry of Fab K1-70 was checked using PROCHECK (CCP4) and RAMPAGE (CCP4). Finally, the residues in the model were renumbered in accordance with the Kabat numbering system (Kabat E et al 1991 supra).

Cloning and Expression of Recombinant K1-70 Fab in *E. coli*

The K1-70 HC RT-PCR product was cut with XhoI and SpeI restriction endonucleases and the K1-70 LC PCR product was cut with SacI and XbaI restriction endonucleases and both HC and LC cDNAs cloned into the Immunozap H/L vector (Stratagene Europe; Amsterdam, Netherlands) (Matthews I, et al 2002 Laboratory Investigation 82: 1-11) under the control of the lacZ promoter. Plasmid DNA was prepared using the Qiagen midi plasmid purification kit (Qiagen Ltd, Crawley, UK) and the presence of K1-70 HC and LC cDNAs confirmed by sequencing using the Sanger-Coulson method (Sanger F, et al 1977 supra). Plasmid DNA was transformed into the *E coli* strain HB2151 (GE Life Sciences, Little Chalfont, UK) and grown overnight at 37° C. on LB ampicillin (Tryptone 10 g/L, Yeast Extract 5 g/L, NaCl 10 g/L, 100 μg/mL final concentration ampicillin) agar plates (15 g/L agar). Precultures (one colony in 3 mL LB ampicillin+1% glucose) were grown overnight at 30° C. with shaking. Production of the recombinant Fab is inhibited in the presence of glucose. Precultures after overnight incubation were diluted 1/100 (0.5 mL in 50 mL LB ampicillin) and grown at 30° C. until the $OD_{600}$ was 1.2 followed by addition of sucrose (final concentration 0.3 mol/L) and culture grown at 30° C. until $OD_{600}$ returned to 1.2. Thereafter isopropyl-β-D thiogalactoside (IPTG) was added to a final concentration of 1 mmol/L and cultures continued to be incubated for 24 hours at 23° C. with shaking. The cultures were then centrifuged at 3000 rpm for 30 minutes at 4° C. and the culture supernatants recovered. The culture supernatants were filtered through a 0.45 μm filter and dialysed overnight into PBS (8.1 mmol/L $Na_2HPO_4$, 1.5 mmol/L $KH_2PO_4$, 2.7 mmol/L KCl, 137 mmol/L NaCl pH 7.4). Culture supernatant from HB2151 cells transformed with K1-70 plasmid (HB2151/K1-70) grown with glucose without IPTG ie non-induced were used as negative controls. The culture supernatants were assayed for (a) their ability to inhibit TSH binding to the TSHR and (b) their ability to inhibit TSH mediated stimulation of cyclic AMP production in CHO cells expressing TSHR.

Results

Isolation and Cloning of Stable Cell Lines Secreting K1-18 or K1-70

Lymphocytes ($26 \times 10^6$) obtained from 20 mL of patient's blood were infected with EBV and plated out at $1 \times 10^6$ cells per well in a 48 well plate on feeder layers of mouse macrophages. On day 13 post EBV infection the plate well supernatants were monitored for inhibition of $^{125}$I-TSH binding. Positive clones were tested further for their effects (stimulating or blocking) on the TSHR. Cells from positive wells (positive in any of the assays used) were expanded and fused with the K6H6/B5 hybridoma cell line and plated out in 96 well plates. Two clones stably producing antibodies with $^{125}$I-TSH binding inhibiting activity were obtained and re-cloned 4 times. One of the clones secreted a human MAb designated as K1-18 that had TSHR stimulating activity. K1-18 antibody purified from the hetero-hybridoma culture supernatants was subclass IgG1 with kappa light chains. The other stable clone secreted a human MAb designated as K1-70 that had the ability to block TSH stimulation of cyclic AMP production in TSHR transfected CHO cells. K1-70 antibody purified from hetero-hybridoma culture supernatants was subclass IgG1 with lambda light chains.

Inhibition of $^{125}$I-TSH Binding to TSHR Coated Tubes

The ability of different concentrations of K1-18 or K1-70 IgGs to inhibit binding of labelled TSH to TSHR coated tubes is shown in Tables 1a and 1b. As shown in Table 1a, K1-18 IgG diluted in healthy blood donor (HBD) serum showed maximum inhibition of $^{125}$I-TSH binding of approx 95% at 1 μg/mL concentrations. The inhibiting effect of K1-18 IgG at concentrations between 1-0.001 μg/mL was dose dependent. The inhibiting effect of K1-18 was comparable to the effect of M22 IgG at the same concentrations. K1-18 IgG at 1 μg/mL is a more potent inhibitor of $^{125}$I-TSH binding than 5C9 IgG, TSMAb 1-7 IgGs or 9D33 IgG (Table 1a). K1-70 IgG or Fab inhibiting effects on $^{125}$I-TSH binding are shown in Table 1b. K1-70 IgG diluted in HBD serum showed dose dependent inhibition ranging from 13.5±2.3% at 0.03 μg/mL to 95.9±0.8% at 100 μg/mL. The inhibiting effects of K1-70 Fab was comparable to the effects of K1-70 IgG at the same concentrations (Table 1b). Tables 1a and 1b also show the effects on $^{125}$I-TSH binding to TSHR coated tubes by K1-18 and K1-70 and different MAbs IgGs diluted in the coated tube assay buffer; in the case of all MAbs except 5C9 these effects were comparable to the results observed when MAbs were diluted in HBD serum. Table 2a shows inhibition of $^{125}$I-TSH binding to TSHR coated tubes by different preparations of K1-18, K1 donor serum and K1-donor serum IgG. In this experiment, approximately 12% inhibition was observed with as little as 0.01 µg/mL of K1-18 IgG diluted in HBD sera and the inhibition increased in a dose dependent manner up to 95% inhibition at 10 µg/mL of K1-18 IgG. K1-18 Fab at 0.01 µg/mL in HBD sera showed 5.6±7.3% inhibition and the inhibition increased in a dose dependent manner to a maximum inhibition of 82.2±0.9% at 10 µg/mL. This can be compared to $^{125}$I-TSH binding inhibition by donor serum IgG diluted in HBD sera; 13.7±1.3% inhibition at 0.125 mg/mL increasing in a dose dependent manner to 76.5±1.5% inhibition at 1 mg/mL. Donor serum at different dilutions also showed dose dependent inhibition of $^{125}$I-TSH binding; 9.1±0.8% inhibition and 1/160 dilution to 81.1±0.4% inhibition at 1/10 dilution. The data in Table 2a showed that purified K1-18 IgG was 6600 times more active in terms of inhibition of TSH binding compared to K1 donor serum IgG. When K1-18 IgG and donor serum IgG were diluted in assay buffer the ability of K1-18 IgG to inhibit TSH binding was 4700 times greater than that of the donor serum IgG (Table 2a). Table 2b shows inhibition of $^{125}$I-TSH binding to the TSHR in coated tube assay by different preparations of K1-18 compared to the effect of Thyroid Stimulating Autoantibody reference preparation 90/672 from National Institute for Biological Standards and Control (NIBSC; Potters Bar, UK). K1-18 IgG diluted in HBD serum showed $^{125}$I-TSH binding inhibiting activity of 69 NIBSC 90/672 units/mg (mean of activity calculated at three concentrations of K1-18 IgG; 30 ng/mL, 100 ng/mL and 300 ng/mL) (Table 2b). $^{125}$I-TSH binding inhibiting activity of K1-18 Fab (diluted in serum) calculated in the same experiment was 46 NIBSC 90/672 units/mg (activity at 30 ng/mL, 100 ng/mL and 300 ng/mL of K1-18 Fab was used for the calculations) (Table 2b). This can be compared with M22 IgG $^{125}$I-TSH binding inhibiting activity of 131 NIBSC units/mg (Table 2b). $^{125}$I-TSH binding inhibiting activities of dilutions of donor serum and donor serum IgG compared to the activity of NIBSC 90/672 are shown in Table 2c. $^{125}$I-TSH binding inhibiting activity of the donor serum was 0.075 NIBSC 90/672 units/mL (mean of values at 40× and 20× dilutions) and of donor serum IgG diluted in HBD serum was 0.011 units/mg (mean of values at 0.1; 0.3 and 1.0 mg/mL) (Table 2c). This can be compared to the activity of K1-18 IgG (diluted in HBD serum) measured in the same experiment of 63.3 NIBSC 90/672 units/mg (mean of values at 30, 100 and 300 ng/mL) and the activity of K1-70 IgG (diluted in HBD serum) of 114 units/mg (mean of values at 10, 30 and 100 ng/mL) (Table 2c). Consequently in this assay system the specific activity of K1-18 IgG was 5755× that of the donor serum IgG. Similarly, the specific activity of K1-70 IgG was 10,364× that of the donor serum IgG.

Scatchard Analysis of K1-18 and K1-70 Binding to TSHR Coated Tubes

The binding affinity of K1-18 IgG for the TSHR (full length) was $6.7±1.0×10^9$ L/mol (mean±SD; n=3) while binding affinity of K1-18 Fab was $1.8±1.0×10^9$ L/mol (mean±SD; n=3). Binding affinity of K1-18 IgG for the TSHR260 was $5.9±1.0×10^9$ L/mol (mean±SD; n=3). K1-70 IgG binding affinity for the TSHR (full length) was $3.9±0.8×10^{10}$ L/mol (mean±SD; n=3) while binding affinity of K1-70 Fab was $2.3±0.3×10^{10}$ L/mol (mean±SD; n=3). Binding affinity of K1-70 IgG for the TSHR260 was $3.1±0.4×10^{10}$ L/mol (mean±SD; n=3) and of K1-70 Fab it was $9.3±0.4×10^9$ L/mol (mean±SD; n=3). This can be compared to binding affinity of porcine TSH to the TSHR (full length) of $6.0±0.9×10^9$ L/mol (mean±SD, n=5) (Nakatake et al 2006 supra).

Inhibition of TSH-Biotin Binding to the TSHR Measured by ELISA

The effects of K1-18 IgG on TSH-biotin binding to TSHR coated ELISA plate wells was studied and compared to the effects of various other MAbs. As shown in Table 3a K1-18 IgG diluted in HBD serum had a dose dependent inhibiting effect on TSH-biotin binding with 10.0±0.8% inhibition at 0.01 µg/mL, essentially maximum inhibition of 96.2±0.2% at 1 µg/mL and a maximum inhibition plateau at concentrations of 3 µg/mL and above. This can be compared to M22 IgG (diluted in HBD serum) inhibiting effect of 17.5±2.0% at 0.01 µg/mL and 98.3±0.0% at 1 µg/mL (Table 3a). TSH-biotin binding inhibiting activity of K1-18 IgG at 1 µg/mL (diluted in HBD serum) was greater than 5C9 IgG, TSMAb 1-7 IgGs and 9D33 IgG as illustrated by the examples shown in Table 3a. When K1-18 IgG was tested diluted in ELISA assay buffer (50 mmol/L NaCl, 10 mmol/L Tris pH 7.8, 0.1% v/v Triton X-100, 1 mg/mL BSA) the inhibiting effects were essentially the same as when the dilutions were made in HBD serum (Table 3a). As shown by the examples in Table 3b K1-18 Fab diluted in HBD serum or in ELISA assay buffer was also an effective inhibitor of TSH-biotin binding in the ELISA. The inhibiting effects of K1-18 IgG diluted in ELISA assay buffer with addition of control MAb IgG (5B3 which is a human MAb to glutamic acid decarboxylase) at 100 µg/mL is shown in Table 3c. When diluted in the buffer containing control MAb K1-18 IgG showed similar TSH-biotin binding inhibition activity as when diluted in buffer containing BSA or in HBD serum (Table 3c). Consequently, the presence of an unrelated human MAb IgG at high concentration (100 µg/mL) had no effect on the inhibiting activity of K1-18 IgG nor M22 IgG nor 5C9 IgG. Table 3d shows the effects of K1-70 on TSH-biotin binding to the TSHR and these are comparable to the effects of K1-18 or M22 (Tables 3a & 3b). K1-70 IgG diluted in HBD serum had a dose dependent inhibiting effect on TSH-biotin binding with 13.6±1.4%; 74.1±0.4% and 97.4±0.2% inhibition at 0.01 µg/mL; 0.1 µg/mL and 1 µg/mL, respectively. K1-70 Fab was similarly active with inhibitions of 18.2±0.6%; 88.3±0.3% and 96.9±0.1% at 0.01 µg/mL; 0.1 µg/mL and 1 µg/mL, respectively. When K1-70 IgG or Fab preparations were diluted in ELISA assay buffer the inhibiting activities were essentially the same compared to dilutions made in HBD serum (Table 3d). The ability of K1-18 IgG to inhibit binding of M22 Fab-POD to TSHR coated ELISA plate wells is shown in Table 4a. K1-18 IgG diluted in HBD serum inhibited M22 Fab-POD binding in a dose dependent manner; in particular 21.0±1.3%, 81.6±0.5% and 97.2±0.1% inhibitions were observed at 0.03 µg/mL, 0.3 µg/mL and 3 µg/mL, respectively. This effect was comparable to the inhibiting effect of M22 IgG (diluted in HBD serum) of 51.0±2.4%, 93.2±0.3% and 98.0±0.2% at 0.03 µg/mL, 0.3 µg/mL and 3 µg/mL, respectively. K1-18 Fab showed similar ability to inhibit M22 Fab-POD binding as K1-18 IgG (Table 4b). As shown in Table 4a, K1-18 and M22 ability to inhibit labelled M22 binding to the TSHR were greater than the inhibiting activities of 5C9, TSMAbs 1-7 and 9D33. Inhibiting effects of all MAbs studied when diluted in ELISA assay buffer were similar to those observed when diluted in HBD serum (Table 4a and b). The inhibiting effects of K1-18 on M22 Fab-POD binding to the TSHR can be compared to the effects of K1-70 (Table 4c). K1-70 IgG diluted in HBD serum showed 34.5±3.8%, 91.1±0.3% and 97.6±0.1% inhibition at 0.03 µg/mL, 0.3 µg/mL and 3 µg/mL, respectively. Similar percentage inhibitions were observed when K1-70 IgG was diluted in ELISA assay buffer (Table 4c). As illustrated in Table 4c K1-70 Fab diluted in HBD serum or in ELISA assay buffer showed similar M22-POD binding inhibiting activity as K1-70 IgG.

Inhibition of $^{125}$I-Labelled K1-18 IgG or Fab Binding to TSHR Coated Tubes

In the presence of a control human MAb 4B4 IgG at concentrations from 0.01-100 µg/mL (diluted in HBD serum) binding of $^{125}$I-K1-18 IgG was essentially not affected (Table 5a). This can be compared with the effects of different concentrations of unlabelled K1-18 IgG (diluted in HBD serum); increasing doses of 0.001; 0.01; 0.1 and 1.0 µg/mL caused inhibition of binding of $^{125}$I-labelled K1-18 of 11.1±4.4%, 22.9±2.4%, 69.0±0.5% and 91.7±0.8%, respectively. Unlabelled K1-18 Fab tested at concentrations from 0.001-100 µg/mL showed inhibitions ranged from 10.3±2.2% (at 0.03 µg/mL) to 84.8±0.9% (at 100 µg/mL) (Table 5b). K1-70 IgG and Fab (both tested in the range of concentrations from 0.001-100 µg/mL) also inhibited $^{125}$I-K1-18 IgG binding in a dose dependent manner to an essentially complete inhibition of 95.1±0.3% at 10 µg/mL of K1-70 IgG and 92.8±1.1% at 3 µg/mL of K1-70 Fab (Table 5b). In addition, binding of $^{125}$I-K1-18 IgG was inhibited in a dose dependent manner by M22 IgG, M22 Fab, 5C9 IgG, TSMAb 1-7 IgGs and 9D33 IgG (Table 5a and 5b). When the same experiments were carried out using various MAb preparations diluted in coated tube assay buffer the inhibiting effects of the respective preparations were comparable to the effect observed when diluted in HBD serum except in the case of 5C9 IgG (Table 5a). In the case of 5C9 diluted in assay buffer the maximum inhibition at 100 µg/mL was 91.3±0.4% compared to 57.7±2.4% when diluted in HBD serum and the inhibitions at 0.01 µg/mL were 11.7±1.8% and −1.8±2.7%, respectively (Table 5a). Binding of $^{125}$I-K1-18 IgG to TSHR coated tubes was inhibited by the lymphocyte donor serum resulting in 35.2% and 59.3% inhibition at serum dilutions of 1:20 and 1:10, respectively (Table 5c). Sera from 20 Graves' patients inhibited binding of $^{125}$I-K1-18 IgG and the inhibiting effect was comparable to the inhibiting effect on $^{125}$I-TSH binding (Table 5c). Table 5c also shows the effect of dilutions of sera from two patients with blocking TRAbs (B1 and B2) and sera from two patients with stimulating TRAbs (S1 and S2) on both $^{125}$I-K1-18 IgG and $^{125}$I-TSH binding. Effect of various MAbs on $^{125}$I-K1-18 Fab binding to the TSHR coated tubes is shown in Table 5d. Both, unlabelled K1-18 IgG and K1-18 Fab had dose dependent inhibiting effect on $^{125}$I-K1-18 Fab binding and these effects were comparable to the effects of M22 IgG, M22 Fab and K1-70 IgG (Table 5d). 5C9 IgG, TSMAbs 1-7 IgGs and 9D33 IgG also inhibited on $^{125}$I-K1-18 Fab binding, however, their effects were smaller compared to M22, K1-18 and K1-70 preparations (Table 5d).

Stimulation of Cyclic AMP Production in CHO Cells Expressing the TSHR

K1-18 IgG stimulated cyclic AMP production in CHO cells expressing the TSHR in a dose dependent manner as shown in Table 6a. In hypotonic buffer, the levels of cyclic AMP in the presence of 0.1 ng/mL K1-18 IgG were 1.56±0.32 pmol/L, at 1.0 ng/mL were 4.08±0.28 pmol/L, at 10 ng/mL were 31.66±5.06 pmol/L, at 100 ng/mL were 64.95±9.61 pmol/L and at 1000 ng/mL they were 67.90±10.44 pmol/L. The cyclic AMP levels at different concentrations of K1-18 Fab in hypotonic buffer were 1.72±0.82 pmol/L, 9.99±3.52 pmol/L, 53.22 pmol/L and 66.94±6.93 pmol/L at 1 ng/mL, 10 ng/mL, 100 ng/mL and 1000 ng/mL of K1-18 Fab, respectively. M22 Fab at 1 ng/mL in hypotonic buffer stimulated cyclic AMP production of 29.80±0.97 pmol/L and at 10 ng/mL of 57.41±5.05 pmol/L (Table 6a). Table 6a also shows the effect of K1-18 IgG or Fab on cyclic AMP stimulation in CHO cells expressing the TSHR tested under the isotonic conditions. As illustrated by examples in Table 6a both K1-18 and K1-70 caused increase of cyclic AMP production under isotonic conditions although the levels of cyclic AMP produced were lower compared to experiments using hypotonic conditions. Comparison of stimulating activity of M22 IgG and K1-18 IgG tested in hypotonic buffer is shown in Table 6b. At 3 ng/mL concentration M22 IgG stimulated 24.3±2.3 pmol/mL of cyclic AMP while K1-18 IgG 8.3±0.5 pmol/mL. At 10 ng/mL M22 IgG and K1-18 IgG caused stimulation of 50.3±1.6 and 25.0±1.0 pmol/mL of cyclic AMP respectively and at 100 ng/mL 64.6±1.9 and 62.6±2.7 pmol/mL respectively. The stimulating activity of K1-18 IgG and Fab was also assessed relative to the activity of NIBSC reference preparation 90/672 (Table 6c). Calculated cyclic AMP stimulating activity of K1-18 IgG was 155 NIBSC 90/672 units/mg (mean of activity calculated at three concentrations of K1-18 IgG; 1 ng/mL, 3 ng/mL and 10 ng/mL) (Table 6c). Cyclic AMP stimulating activity of K1-18 Fab calculated in the same experiment was 22 NIBSC 90/672 units/mg (activity at 10 ng/mL, 30 ng/mL and 100 ng/mL of K1-18 Fab were used for the calculations) (Table 6c). This can be compared with M22 IgG cyclic AMP stimulating activity of 286 NIBSC units/mg (Table 6c). For comparative purposes the stimulating activities of porcine TSH, native human TSH and recombinant human TSH in isotonic and in hypotonic buffers are shown in Table 6d.

Further examples shown in Table 6e concern the stimulating effects of K1-18 IgG, M22 IgG or pTSH when mixed together in different combinations. The stimulating effect of pTSH, M22 or K1-18 appeared to be enhanced when two stimulators were mixed together compared to the effect of the stimulator alone at the same concentrations. In particular, cyclic AMP production of 11.01±0.99 pmol/mL (mean±SD) at 0.1 ng/mL pTSH alone and 35.17±6.38 pmol/mL (mean±SD) at 1 ng/mL of M22 IgG increased to 47.22±3.89 pmol/mL (mean±SD) when 0.1 ng/mL pTSH and 1 ng/mL of M22 IgG were mixed together. Also a mixture of 0.1 ng/mL of pTSH and 10 ng/mL of K1-18 IgG had a greater stimulating effect than these stimulators alone (Table 6e). Furthermore, two stimulating antibodies mixed together were more potent than a single antibody at the same concentrations. For example, 29.95±1.18 pmol/mL (mean±SD) of cyclic AMP was produced in response to 5 ng/mL of K1-18 IgG, 20.20±2.48 pmol/mL (mean±SD) was produced in response to 0.5 ng/mL of M22 IgG while 44.01±7.19 pmol/mL (mean±SD) cyclic AMP was produced in response to 5 ng/mL of K1-18 and 0.5 ng/mL of M22 mixed together (Table 6e).

The results of two experiments in which the ability of the K1-18 and K1-70 donor serum and donor serum IgG to stimulate cyclic AMP were compared to the stimulating activity of NIBSC 90/672 are shown in Tables 6f and 6g. In experiment 1, the stimulating activity of donor serum was 4.7±0.1 pmol/mL of cyclic AMP at 30 times dilution compared to the effect of HBD serum at the same dilution of 1.7±0.4 pmol/mL while the stimulating activity of donor serum IgG was 7.7±1.0 pmol/mL at 30 µg/mL which represented activity relative to NIBSC 90/672 of 0.013 units/mg (Table 6f). In experiment 2, donor serum diluted 30 times caused stimulation of cyclic AMP to 9.5±0.7 pmol/mL while donor serum IgG at 30 µg/mL caused stimulation to 15.6±0.7 pmol/mL which represented activity relative to NIBSC 90/672 of 0.014 units/mg (Table 6g). K1-18 IgG TSHR stimulating activity was inhibited by human MAbs with TSH antagonist activity (K1-70 and 5C9) as illustrated by the examples shown in Table 6h. In particular, K1-18 IgG at 10 ng/mL caused stimulation of cyclic AMP to 50.0±3.3 pmol/mL and this was reduced to 3.8±1.0 pmol/mL in the presence of 0.1 µg/mL of K1-70 IgG (92% inhibition). In the presence of 10 ng/mL of K1-18 IgG and 0.1 µg/mL of 5C9 IgG cyclic AMP levels were 4.4±1.5 pmol/mL (91% inhibition). At higher concentrations of K1-70 IgG or 5C9 IgG the inhibiting effect was complete (100% inhibition) (Table 6h). In further experiments the effect of K1-70 IgG mixed together with 5C9 IgG on K1-18 IgG stimulating activity was studied (Table 6i). As shown in the Table 6i K1-18 IgG stimulation at 10 ng/mL was effectively inhibited by 0.1 µg/mL of 5C9 IgG or 0.1 µg/mL of K1-70 IgG. When K1-70 IgG and 5C9 IgG were mixed to give a final total concentration of 0.1 µg/mL the stimulating activity of K1-18 IgG was also effectively inhibited (97.3% inhibition). However at lower concentrations K1-70 IgG and 5C9 IgG when mixed together were more effective inhibitors of K1-18 IgG stimulating activity than one antibody alone. For example, at 0.001 µg/mL K1-70 IgG and 5C9 IgG individually caused no inhibition (0% and 1% respectively) while when mixed together to the same final concentration of total IgG (ie 0.001 µg/mL) the inhibition was 25.5%. Table 6i also shows that cyclic AMP concentration in the presence of K1-70 IgG (100 µg/mL) was similar to that observed in the presence of assay buffer while in the presence of 5C9 IgG (100 µg/mL) the concentration of cyclic AMP was lower (0.89±0.13; 0.89±0.15 and 0.55±0.14, respectively) (mean±SD of triplicate determinations). When K1-70 IgG and 5C9 IgG were mixed together (final concentration of 100 µg/mL of total IgG) cyclic AMP concentrations were not reduced below the levels observed in the presence of buffer (ie not lower than basal or constitutive activity levels). For comparison essentially complete inhibition of M22 IgG (3 ng/mL) stimulating activity was observed at 1 µg/mL of 5C9 IgG or 1 µg/mL of K1-70 IgG (97.1% and 96.6% inhibition respectively) and inhibitions at 0.1 µg/mL of 5C9 IgG or 0.1 µg/mL of K1-70 IgG were 92.8% and 75.5%, respectively (Table 6j). However, when 5C9 and K1-70 were mixed together to a final total IgG concentration of 0.1 µg/mL 91.9% inhibition was observed (Table 6j). The effects of mixtures of K1-70 IgG and 9D33 IgG on K1-18 IgG stimulating activity are shown in Table 6k. In the case of 9D33 IgG 95% inhibition was observed at 1 µg/mL while K1-70 IgG at 0.1 µg/mL showed the same inhibition (95% inhibition). When the two blocking MAbs (9D33 and K1-70) were mixed together to a final total IgG concentration of 0.1 µg/mL 95% inhibition was also observed (Table 6k). 9D33 IgG at 10 µg/mL was able to essentially completely inhibit M22 IgG cyclic AMP stimulation (94% inhibition) while lower concentrations of K1-70 IgG (1 µg/mL) had similar effect (96% inhibition) (Table 6l). Essentially complete inhibition of M22 activity (96% inhibition) was evident at 1 µg/mL of the 9D33 and K1-70 mixture (Table 6l). This is comparable to the inhibiting effect of a mixture of 9D33 and K1-70 (1 µg/mL) on TSH stimulating activity (97% inhibition) (Table 6m). However, it should be noted that TSH stimulating activity was inhibited more effectively by K1-70 IgG alone (98% inhibition at 1 µg/mL) than by 9D33 IgG alone (95% inhibition at 100 µg/mL) (Table 6m). Table 6n shows the effect of the lymphocyte donor serum and three patient sera containing TRAbs with blocking activity (B1-B3) on TSHR stimulating activity of TSH, M22 IgG and K1-18 IgG. The donor serum inhibited TSH, M22 IgG and K1-18 IgG stimulating activities (63.8%, 80.1% and 79.5% inhibitions, respectively). Three different sera with blocking TRAbs that had a strong inhibiting effect on TSH and M22 IgG stimulation also inhibited the stimulating activity of K1-18 IgG (Table 6n). The inhibiting effects of the different patient sera on TSH, M22 IgG or K1-18 IgG stimulating activities were comparable.

Measurement of Antagonist (Blocking) Activity

Incubation of CHO cells expressing the TSHR with porcine TSH at 3 ng/mL caused stimulation of cyclic AMP production to 62.6±3.9 pmol/mL (Table 7a). In the presence of increasing amounts of K1-70 IgG stimulating activity of porcine TSH was inhibited in a dose dependent manner. In particular in the presence of 0.01, 0.05, 0.1 and 1 µg/mL of K1-70 IgG the levels of cyclic AMP were 60.1±1.6, 31.4±1.9, 5.8±2.8 and 2.0±0.2 pmol/mL respectively which represent 4.0%, 49.8%, 90.7% and 96.8% inhibition respectively relative to the effect of control MAb IgG (5B3) (Table 7a). Table 7a also show the inhibiting effects of 5C9 IgG for comparison. The effects of K1-70 Fab on stimulating activity of porcine TSH under 2 different experimental conditions are shown in Table 7b. In the presence of K1-70 Fab at 1 µg/mL porcine TSH stimulating activity was essentially completely inhibited in both conditions (ie in isotonic and in hypotonic medium). The effect of K1-70 Fab was dose dependent in the range of concentrations studied (0.003 µg/mL to 3 µg/mL) with as little as 0.05 µg/mL of Fab showing an ability to reduce porcine TSH stimulation down to 28.9±1.1 pmol/mL cyclic AMP from 39.5±1.9 pmol/mL in the presence of 1 µg/mL of control MAb (under isotonic conditions) (Table 7b). The potency of K1-70 Fab under hypotonic conditions was similar to that observed under isotonic conditions (Table 7b). Increasing concentrations of K1-70 IgG (range 0.001-100 µg/mL) did not show any ability to inhibit TSHR constitutive (basal) activity as illustrated by the examples shown in Table 7c. This contrasts with the effects of 5C9 IgG as shown in Table 7c for comparison. The blocking mouse antibody 9D33 tested in the same experiment had no ability to affect TSHR constitutive activity (Table 7c) and some weak stimulating activity (about 2× basal) was observed with high concentrations of 9D33.

Blocking activity of K1-70 IgG was compared to the blocking activity of the lymphocyte donor serum as shown in Table 7d. Cyclic AMP levels after incubation with porcine TSH at 1 ng/mL were 61.7±4.3 pmol/mL and the levels dropped in the presence of donor serum (10× dilution) to 14.9±1.2 pmol/mL (75.9% inhibition) and to 51.6±2.6 pmol/mL with serum diluted 20 times (16.4% inhibition). Donor serum at higher dilutions did not have a detectable effect on TSH stimulating activity. The effect of donor serum can be compared to the effect of K1-70 IgG that at 0.1 µg/mL had a similar effect as serum diluted 10 times (67.6% and 75.9% inhibition respectively) (Table 7d). K1-70 IgG had the ability to block cyclic AMP stimulating activity of porcine TSH, human TSH and human recombinant TSH as illustrated by the examples in Table 7e. K1-70 IgG at 0.1 µg/mL was an effective blocker of stimulating activity of all three TSH preparations tested under hypotonic medium conditions. Blocking activity of K1-70 IgG was less effective under isotonic medium conditions (Table 7e). Effects of K1-70 IgG on M22 IgG mediated stimulation of cyclic AMP production in CHO cells expressing the TSHR are shown in Table 7f. Cyclic AMP levels observed at 3 ng/mL of M22 IgG were 33.1±1.8 pmol/mL and these decreased in the presence of K1-70 IgG for example, 4.3±2.4 pmol/mL at 0.1 µg/mL (87% inhibition) (Table 7f). The effects of K1-70 IgG were comparable to the effects of 5C9 IgG tested in the same experiment (Table 7f). Furthermore, K1-70 IgG showed the ability to block cyclic AMP stimulating activity of TRAbs in sera from patients with Graves' disease and the examples in Tables 7g-7k illustrate that 100 µg/mL concentrations of K1-70 IgG caused complete inhibition of stimulating activity in all 15 sera studied (inhibition of T1-T15 ranged from 90.8% to 98.7%). The effects of K1-70 IgG on the stimulating activities of sera T1-T15 were comparable to the effects of 5C9 IgG and 9D33 IgG tested in the same experiment except for one serum ie T11 (Table 7j). Stimulating activity of serum T11 was only weakly inhibited by 100 µg/mL of 5C9 IgG (8.5% inhibition) while in the presence of 100 µg/mL of K1-70 the inhibition was essentially complete (95.1% inhibition) (Table 7j). Effective inhibition (87.1%) of T11 was also observed with 100 µg/mL 9D33 (Table 7j). The effect of different blocking MAbs at different concentrations (0.01-100 µg/mL) on the stimulating activities of three Graves' sera (including serum T11) is shown in more detail in Tables 7l-7n. These experiments showed that K1-70 IgG, 5C9 IgG and 9D33 IgG are effective inhibitors at concentrations as low as 0.1 µg/mL except in the case of serum T11 on which 5C9 IgG had little or no effect (Table 7n). Table 7o shows inhibition of porcine TSH stimulation by K1-70 IgG and 5C9 IgG when the two blocking MAbs were mixed together in one experiment. These experiments showed that the two blocking MAbs were effective in combination in their ability to inhibit TSH stimulation of cyclic AMP production. In addition the effect of K1-70 IgG and 5C9 IgG mixed together on the constitutive activity of the TSHR was tested. As shown in Tables 7c and 7p K1-70 IgG had no effect on TSHR basal activity in contrast to 5C9 IgG. When K1-70 and 5C9 IgGs were mixed together to give a final IgG concentration of 2 µg/mL cyclic AMP levels dropped slightly from 58.04±8.52 pmol/mL (mean±SD, n=3) in the presence of buffer only to 55.28±6.17 pmol/mL (mean±SD, n=3) ie 4.8% inhibition (Table 7p). However, when 5C9 IgG was mixed with 5B3 IgG (control antibody to glutamic acid decarboxylase) to give a final IgG concentration of 2 µg/mL constitutive activity of the TSHR was inhibited to 52.1% of basal values (cyclic AMP level 27.78±2.96 pmol/mL; mean±SD, n=3) (Table 7p). These experiments show that in the presence of K1-70 IgG, 5C9 IgG is unable to act as an effective inhibitor of TSHR constitutive activity.

Effect of the TSHR Mutations on K1-18 Stimulating Activity

The effect of K1-18 IgG on stimulation of cyclic AMP production was tested using CHO cells expressing TSHRs with the following amino acid mutations: Lys58Ala, Arg80Ala, Tyr82Ala, Glu107Ala, Arg109Ala, Lys129Ala, Phe130Ala, Phe134Ala, Lys183Ala, Asp203Ala, Arg255Asp (Table 8a-k and summarised in Table 10). Mutation of TSHR amino acids Lys58, Arg80, Tyr82, Glu107, Arg109, Lys129, Phe130, Phe 134 and Asp203 to alanine had no effect on K1-18 IgG's ability to stimulate cyclic AMP production. The ability of K-18 IgG to stimulate cyclic AMP production was lost completely with CHO cells expressing TSHR containing mutations Lys183Ala and Arg255Asp and cyclic AMP concentrations in response to K1-18 IgG were similar to the concentrations observed in the presence of cyclic AMP buffer only (Table 8i and 8k). However, responsiveness to TSH was retained with the Lys183Ala and Arg255Asp mutations. In an additional series of experiments the effects of mutations of various amino acids of the TSHR on K1-18 IgG cyclic AMP stimulating activity was tested further (Tables 14a-14v and summarised in Table 16). Mutations (to alanine) of TSHR residues Asp43, Ile60, Glu61, Thr104, His105, Lys250, Arg255, Thr257, Asp276 and Ser281 had no effect on K1-18 IgG's ability to stimulate cyclic AMP production. Mutations of TSHR Asp151, Glu178, Lys209, Gln235, Glu251 to alanine caused a small reduction of K1-18 IgG stimulating activity, however, these mutations also affected TSH stimulating activity therefore the interactions with these TSHR residues were not considered specific for K1-18. In contrast, mutations of TSHR Glu157Ala, Lys183Asp, Tyr185Ala and Asp232Ala resulted in loss of the ability of K1-18 IgG to stimulate cyclic AMP (less than 20% of the wild type activity; Tables 14g, 14i, 14j, 14m). Furthermore, the ability of K1-18 IgG to stimulate the TSHR mutated at Tyr206, Trp258 and Arg274 to alanine was reduced to approximately 40-60% of the wild type activity (Tables 14k, 14s, 14t).

Effect of the TSHR Mutations on K1-70 Blocking Activity

The effect of K1-70 IgG on TSH stimulation of cyclic AMP production was tested in CHO cells expressing TSHRs containing mutations of the following amino acids to alanine: Lys58, Arg80, Tyr82, Glu107, Arg109, Lys129, Phe130, Phe134, Lys183 and Asp203. In addition the effect of TSHR mutation Arg255Asp was tested. (Table 9 a-k and summarised in Table 10). Mutation of TSHR amino acids Arg80, Glu107, Lys129, Phe130, Phe134 and Asp203 to alanine had no effect on K1-70 IgG's ability to inhibit TSH stimulated cyclic AMP production. The ability of K1-70 to inhibit TSH stimulated cyclic AMP production was reduced by mutation of TSHR Lys58, Tyr82, Arg109 and Lys183 to alanine. The mutation Lys58Ala had the greatest effect (Table 9a) followed by Arg109Ala, Lys183Ala and Tyr82Ala that had the smallest effect (Tables 9e, 9i, 9c respectively and Table 10). However, none of the mutations studied caused a complete loss of K1-70 IgG ability to block TSH stimulated cyclic AMP production. In an additional series of experiments the effects of mutations of various amino acids of the TSHR on K1-70 IgG blocking activity was tested further (Tables 15a-15v and summarised in Table 16). The ability of K1-70 to inhibit TSH stimulated cyclic AMP production in TSHR transfected CHO cells was not affected by the TSHR mutations Asp43, Thr104, His105, Asp151, Tyr185, Tyr206, Lys209, Asp232, Gln235, Glu251, Arg255, Thr257, Trp258, and Arg274 to alanine nor mutations Asp160Lys and Lys183Asp. Mutations (to alanine) at TSHR Glu178 and Ser281 had a small effect on the ability of K1-70 IgG to block the stimulating activity of TSH (80-100% of the wild type activity; Tables 15h and 15v). TSHR mutations Glu61, Lys250 and Asp276 to alanine caused some effect (60-80% of the wild type) on K1-70 IgG blocking activity (Tables 15c, 15o, 15u) while TSHR mutation Ile60Ala caused reduction of K1-70 IgG blocking activity to 40-60% of the wild type activity (Table 15b).

Inhibition of $^{125}$I-labelled K1-70 IgG or Fab binding to the TSHR Binding of $^{125}$I-K1-70 IgG to TSHR coated tubes was inhibited in a dose dependent manner by unlabelled K1-70 IgG and at concentrations of 0.003 µg/mL, 0.03 µg/mL, 0.3 µg/mL and 3 µg/mL (diluted in HBD serum) the inhibitions were 10.2±2.4%; 36.5±1.9%; 84.4±0.8% and 92.0±0.5%, respectively (Table 11 a). As shown in Table 11a binding of $^{125}$I-K1-70 IgG was inhibited in a very similar way by M22 IgG (diluted in HBD serum); 6.2% (mean of duplicate determinations); 33.8±0.9%; 84.6±1.1% and 91.6±0.5% inhibitions at 0.003 µg/mL, 0.03 µg/mL, 0.3 µg/mL and 3 µg/mL concentrations. M22 Fab showed a greater potency to inhibit $^{125}$I-K1-70 IgG binding at lower concentrations with the inhibitions of 16.7±6.0%; 60.2±1.8%; 89.9±01% and 92.0±0.3% at 0.003 µg/mL, 0.03 µg/mL, 0.3 µg/mL and 3 µg/mL concentrations (in HBD serum) (Table 11a). Also, K1-18 IgG and Fab inhibited $^{125}$I-K1-70 IgG binding to the TSHR in a dose dependent manner (Table 11b). Dilutions of K1-18 IgG at 0.03 µg/mL, 0.3 µg/mL and 3 µg/mL (in HBD serum) showed 20.0±1.9%, 73.9±0.6% and 91.0±0.3% inhibition respectively and K1-18 Fab at 0.03 µg/mL, 0.3 µg/mL and 3 µg/mL (in HBD serum) showed 10.2±2.1%, 60.9±1.1% and 80.5±0.6% inhibition respectively (Table 11b). In contrast higher concentrations of 5C9 IgG were required to inhibit $^{125}$I-K1-70 IgG binding; 1 µg/mL was needed for 15.4±3.4% inhibition and 100 µg/mL showed 68.5±0.7% inhibition (Table 11a). Tables 11a and 11b also show the effects of various human MAbs on $^{125}$I-K1-70 binding in assay buffer. The effects are stronger when dilutions were made in assay buffer compared with HBD sera. The effects of different mouse monoclonal antibodies to the TSHR with TSHR stimulating activity (TSMAbs 1-7) and with TSHR blocking activity (9D33) on $^{125}$I-K1-70 IgG binding to the TSHR are shown in Table 11c. All TSMAbs tested had the ability to inhibit $^{125}$I-K1-70 IgG binding and 100 µg/mL concentrations (in HBD serum) caused inhibition ranging from 33.5±3.7% (TSMAb 3) to 59.6±0.6% (TSMAb 5) (Table 11c). 9D33 IgG at 100 µg/mL (in HBD serum) showed 51.1±1.7% inhibition (Table 11c). When these MAbs were diluted in assay buffer the % inhibitions were slightly higher compared with HBD sera in some cases and slightly lower in others (Table 11c). Further experiments showed that $^{125}$I-K1-70 Fab binding to the TSHR was also effectively inhibited by K1-18 IgG, K1-18 Fab, M22 IgG, M22 Fab, K1-70 IgG, K1-70 Fab, and mouse TSMAbs in a dose dependent manner (Table 11d). Graves' patient sera n=20) containing TSHR autoantibodies with $^{125}$I-TSH binding inhibition activity in the range from 15.9% to 80.0% (in the TSHR coated tube assay) also showed the ability to inhibit $^{125}$I-K1-70 IgG or Fab binding to the TSHR (range 19.2% to 77.6% and 15.9% to 72.8%, respectively) (Table 11e). The % inhibitions for the three labelled ligands tested were comparable in the case of each serum (Table 11e). None of the HBD sera (n=10) had an effect on $^{125}$I-labelled TSH, K1-70 IgG or Fab binding (Table 11e). Table 11e shows examples of experiments using two sera with TSHR stimulating activity (S1 and S2) and two sera with TSHR blocking activity (B1 and B2). Sera with either type of activity inhibited $^{125}$I-labelled TSH, K1-70 IgG or Fab binding in a dose dependent manner and the degree of inhibition of binding of the different ligands was comparable for each serum (Table 11e).

Kinetics of K1-18 and K1-70 Binding to the TSHR $^{125}$I-labelled K1-70 IgG and Fab binding to TSHR (full length) coated tubes at room temperature reached a maximum after 180 min (45.5% and 37.1% binding respectively). 50% maximal binding occurred after about 35 min (FIG. 1A). $^{125}$I-labelled K1-70 IgG binding to TSHR260 coated tubes reached 36.2% at 180 min and 50% maximal binding was observed after 60 min incubation (FIG. 1B). Time course of $^{125}$I-labelled K1-70 Fab binding to the TSHR260 was similar to that observed for K1-70 IgG with the maximum binding after 60 min incubation of 37.3% and 50% maximal binding after approximately 60 min (FIG. 1C). Addition of unlabelled K1-70 IgG or Fab, K1-18 IgG or Fab, M22 IgG (all at 1 mg/mL), porcine TSH (100 mU/mL) or assay buffer to either $^{125}$I-K1-70 IgG or $^{125}$I-K1-70 Fab bound to TSHR (full length) coated tubes did not result in detectable dissociation even after 180 min of incubation (FIGS. 1D, 1E and 1F). However, after addition of unlabelled M22 Fab (1 mg/mL) to $^{125}$I-K1-70 IgG or $^{125}$I-K1-70 Fab bound to TSHR coated tubes 41.2% and 27.9% respectively of the counts bound dissociated after 180 min incubation (FIGS. 1D and 1F). The dissociating effect of various unlabelled ligands on $^{125}$I-labelled K1-70 IgG bound to TSHR260 is shown in FIG. 1G. Porcine TSH, M22 IgG and K1-18 IgG had no effect while M22 Fab and K1-70 Fab caused approximately 30% of bound $^{125}$I-labelled K1-70 IgG to dissociate from TSHR260 after 30 min incubation and thereafter dissociation did not increase further up to 180 min (FIG. 1G). K1-18 Fab had similar effect as shown in FIG. 1H. $^{125}$I-K1-70 Fab binding to TSHR260 coated tubes was not dissociated by incubation with unlabelled K1-70 IgG, K1-18 IgG, M22 IgG (all at 1 mg/mL), porcine TSH (100 mU/mL) or assay buffer. Incubation with unlabelled M22 Fab or K1-70 Fab (1 mg/mL) caused dissociation of $^{125}$I-K1-70 Fab binding to TSHR260 (58.9% and 62% respectively) (FIG. 1I). $^{125}$I-labelled K1-18 IgG binding to TSHR coated tubes at room temperature reached a maximum after 180 min of 32.7% in the case of tubes coated with the full length TSHR and 23.3% in the case of tubes coated with TSHR260 (FIG. 1J). 50% maximal binding was observed after approx. 45 min in the case of full length TSHR and after approx. 50 min in the case of TSHR260 (FIG. 1J). $^{125}$I-labelled K1-18 IgG bound to full length TSHR coated tubes was not dissociated to a small extent by incubation with unlabelled porcine TSH while incubation with unlabelled K1-18 IgG, M22 IgG, K1-70 IgG, K1-18 Fab and K1-70 Fab had a slightly greater effect (approx. 25% dissociation after 180 min) (FIG. 1K). In contrast, M22 Fab caused 29% dissociation of $^{125}$I-K1-18 IgG bound to full length TSHR after 60 min incubation increasing to 43% dissociation after 180 min incubation (34.5% of $^{125}$I-K1-18 IgG bound in the absence of M22 Fab compared to 24.5% and 19.8% after 60 and 180 min incubation with M22 Fab respectively) (FIG. 1K). In the case of $^{125}$I-labelled K1-18 IgG bound to TSHR260 coated tubes incubation with porcine TSH had no dissociating effect (FIG. 1L). In contrast incubation with unlabelled M22 Fab, K1-70 Fab and K1-18 Fab caused bound $^{125}$I-K1-18 IgG to dissociate from TSHR260. In the presence of M22 Fab and K1-70 Fab dissociation was rapid (approximately 50% after 30 min incubation) while incubation with K1-18 Fab caused 50% dissociation after 90 min (FIG. 1L). Intact M22 IgG, K1-70 IgG and K1-18 IgG had lesser ability to dissociate $^{125}$I-K1-18 IgG from TSHR260 with approximately 30% dissociation observed after 180 min incubation (FIG. 1L). A separate series of experiments showed that $^{125}$I-labelled porcine TSH was not able to bind to TSHR260 coated tubes. Binding of $^{125}$I-TSH to tubes coated with the full length TSHR was described before (Nakatake et al 2006 supra).

Effects of K1-18 or K1-70 IgG in an ELISA Based on TSHR260-AP

The ability of K1-18 IgG to form a "bridge" between the full length TSHR immobilised on ELISA plate wells and TSHR260-AP in the liquid phase is illustrated by the examples shown in Table 12a. OD405 nm values increased in a dose dependent manner with increasing concentrations of K1-18 IgG (diluted in HBD sera). In particular, OD405 nm values were 0.013, 0.191, 0.511, 0.660 and 0.706 at 0.005, 0.05, 0.5, 10 and 100 µg/mL K1-18 IgG respectively compared to OD405 nm of −0.002 in the presence of HBD serum alone. K1-70 IgG (diluted in HBD sera) also bound well in the bridging ELISA and showed OD 405 nm values of 0.045, 0.290, 0.661, 0.738 and 0.794 at 0.005, 0.05, 0.5, 10 and 100 µg/mL K1-70 IgG concentrations respectively (Table 12a). The effects of K1-18 and K1-70 IgGs can be compared to the ability of M22 IgG to bind to TSHR260-AP preparations as shown in Table 12a. In the assay, increasing doses of M22 IgG (ranging from 0.005 µg/mL to 10 µg/mL diluted in HBD sera) bound increasing amounts of the TSHRs with the OD405 nm values ranging between 0.045 and 0.796. When dilutions of MAbs were made in ELISA assay buffer rather than HBD sera, absorbances at 450 nm were higher particularly in the case of 5C9 (Table 12a). The principle of the "bridge type" ELISA on which divalent IgG binds to two molecules of the TSHR has been validated further by the results of the experiments shown in Table 12b. Intact IgGs of human MAbs to the TSHR (M22, 5C9, K1-18 and K1-70) showed dose dependent binding in the ELISA while the monovalent Fab fragments of the same MAbs showed little or no response (Table 12b). Mouse TSMAbs 1-7 also bound well in the TSHR260-AP ELISA as illustrated by the examples in Table 12c. OD 405 nm signal ranged from 0.103 to 0.561 at 10 µg/mL concentrations of TSMAbs 1-7 (Table 12c). Mouse TSHR blocking MAb 9D33 also bound in this assay system with an OD 405 nm signal of 0.481 at 10 µg/mL (Table 12d). Patient sera containing TRAbs with stimulating activity i.e. sera that showed an ability to stimulate cyclic AMP activity in CHO cells expressing the TSHR reacted well in the TSHR260-AP ELISA. Table 12e shows examples of 6 different sera tested at different dilutions and the OD405 nm signal ranged from 0.407 to 0.924 at 1/5 dilutions in HBD sera. Furthermore sera from patients with blocking type TSHR autoantibodies bound well in the TSHR260-AP ELISA as illustrated by the examples in Table 12f with the OD 405 nm signal ranging from 0.323 to 0.896 at 1/10 dilutions in HBD sera. Table 12g shows more examples of binding of patient sera in the TSHR260-AP ELISA. TRAb concentrations in the TSHR260-AP ELISA were calculated from a calibration curve prepared from the NIBSC reference preparation 90/672 and compared to TRAb concentrations (expressed as NIBSC U/L) measured in the same sera using a TSHR coated tubes assay. There was good overall agreement in TRAb measurements made using the TSHR260-AP ELISA and by inhibition of TSH binding to full length TSHR (coated tube assay) (r=0.913, n=57) (FIG. 2A). Table 12h shows that patient serum TRAbs have the ability to inhibit binding of M22 Fab labelled with peroxidase to TSHR260 coated onto ELISA plate wells. Comparison of TRAb measurement in an assay based on inhibition of M22 Fab binding to full length TSHR correlated well with results in the assay based on inhibition of M22 Fab binding to TSHR260 (r=0.761; n=56) (FIG. 2B). Other comparison data are shown in FIGS. 2C and 2D. The effect of TSHR R255 mutation on binding of antibodies in the TSHR260-AP ELISA was tested. In these experiments full length preparations of TSHR containing the mutation R255D were coated on the plate wells and the ELISA carried out using the standard protocol described above. As shown in Table 12i binding of K1-70 IgG or 9D33 IgG were only affected slightly by the TSHR R255D mutation. In contrast, M22 IgG binding was markedly affected by TSHR R255D mutation with the OD signal reduced at all concentrations studied (Table 12i). The TSHR R255D mutation had little effect on higher concentrations of K1-18 IgG but lower concentrations (0.1 µg/mL and below) were much less effective in the assay using the mutated receptor (Table 12i). Table 12j also shows that OD 405 nm signal with 10 Graves' sera (not selected for TSHR stimulating or blocking activity) was reduced when TSHR R255D coated plates were used compared to wild type TSHR. The degree of the signal reduction varied with different sera (Table 12j). Patient TSHR blocking sera bound well in the TSHR260-AP ELISA (Table 12f) and the binding of the same sera to TSHR R255D is shown in Table 12k. The OD 405 nm signal values in experiments with wild type TSHR and TSHR mutated at R255D are similar and consequently the effect of TSHR R255D mutation on binding of the blocking sera does not appear evident in this assay system. The effect of R255D mutation on binding of patient blocking sera in the TSHR260-AP ELISA can be compared to the effect of the same mutation on binding of patient sera with thyroid stimulating activity. Table 12l shows binding of six stimulating sera (S1-S6 sera are the same as in Table 12e) to TSHR R255D. In the case of all six sera the OD 405 nm values were lower in the assays with TSHR R255D compared to wild type TSHR. The degree of the signal reduction varied; in the case of sera S4, S5 and S6 (diluted 1:5 in HBD pool serum) the signal dropped from 0.646, 0.407 and 0.531 in the experiments with the wild type TSHR to 0.193, 0.133 and 0.342 in the experiments with TSHR R255D, respectively (Table 12l). The reduction in OD 405 nm values in the case of sera with high levels of TRAb (sera S1-S3 in Table 12e and 12l) was clearly evident at higher serum dilutions. For example, OD 405 nm signal in the case of sera S1, S2 and S3 (diluted 1:20 in HBD pool) of 0.583, 0.407 and 0.453 in the experiments with the wild type TSHR were clearly reduced to 0.193, 0.117 and 0.210 in the experiments with TSHR R255D, respectively. The examples shown in Tables 12k and 12l suggest that sera with TSHR stimulating activities can be differentiated from sera with TSHR blocking activities in some cases at least on the basis of differences in binding to the TSHR containing R255D mutation. Binding of patient sera with stimulating activities tends to be affected by the mutation while binding of patient sera with blocking activities tends not to be.

Temperature Stability of Different TSHR Preparations

In the temperature stability experiments $OD_{450}$ nm values of binding of M22 Fab-peroxidase to the full length TSHR in the ELISA were 1.748, 0.268 and 0.126 respectively for (a) preparations stored at −80° C. (untreated), (b) incubated for 24 hours at room temperature followed by return to −80° C. and (c) incubated for 48 hours at room temperature followed by return to −80° C., respectively. Consequently full length TSHR preparations stored at room temperature for 48 and 24 hours showed respectively only 7% and 15% activity relative to untreated preparations. M22 Fab-peroxidase binding $OD_{450}$ nm values were 2.293 for untreated TSHR260 and 1.836 and 1.676 for TSHR260 stored at room temperature for 24 and 48 hours respectively. The activity of TSHR260 stored at room temperature for 24 and 48 hours relative to untreated preparations was 80% and 73% respectively. Similar results were observed in the case of TSHR260-AP with $OD_{450}$ nm of 2.106 and 1.983 for samples stored at room temperature for 24 and 48 hours respectively compared to 2.395 for untreated samples. This represented 88% and 83% binding activity after 24 and 48 hours room temperature storage relative to untreated TSHR260-AP. In the experiments with untreated TSHR LRD C-CAP the $OD_{450}$ nm was 1.826 and after 24 and 48 hour room temp storage 1.158 and 1.155, respectively. TSHR LRD C-CAP showed 63% activity relative to untreated preparations after 24 and 48 hour storage at room temperature. The above described experiments showed that the ability to bind M22 of TSHR260, TSHR260-AP and TSHR LRD C-CAP after room temp treatment was greater than the full length TSHR preparations. This indicates that TSHR260, TSHR260-AP and TSHR LRD C-CAP are more stable at room temperature compared to full length TSHR.

Variable Region Sequences

Sequence analysis of the genes coding for K1-18 indicated that the HC V region genes were from the VH5-51*01 family, the D genes from the D3-16*02 (or D3-16*01)

family and the JH genes from the J3*02 family. In the case of the LC, V region genes were from the V3-20*01 family and J region genes from the JK-1*01 germline. The HC nucleotide and amino acid sequences are shown in FIG. 3 (SEQ ID No 1-18) and the LC nucleotide and amino acid sequences are shown in FIG. 4 (SEQ ID No 19-36). There are somatic mutations in the HC gene sequence compared to the germline sequences; in particular 1 silent mutation and, 1 replacement mutation in CDR 1, 1 silent and 3 replacement mutations in CDR 2, 3 replacement mutations in FRW3 and 1 silent and 1 replacement mutation in CDR 3. The replacement/silent mutation (R/S) ratio for the CDRs is 2.7, however, in addition to the mutations there is an 8 base pair long insertion in the CDR 3. The HC CDR1 (SEQ ID No 6 and 16) is 5 amino acids long, CDR 2 (SEQ ID No 7 and 17) is 17 amino acids long and the CDR 3 (SEQ ID No 8 and 18) is 13 amino acids long (FIGS. 3B and 3D, respectively). In the LC sequence there are: 2 replacement mutations in CDR1, 1 silent mutation in FWR2 and 3 replacement mutations in CDR 3 with the overall R/S mutation ratio of 5.0 (FWRs and CDRs). The LC CDR 1 (SEQ ID No 24 and 34) is made up of 12 amino acids, CDR 2 (SEQ ID No 25 and 35) of 7 amino acids and CDR 3 (SEQ ID No 26 and 36) of 9 amino acids (FIGS. 4B and 4D, respectively). K1-70 HC V region is from the VH5-51*01 germline, D genes from the D1-7*01 family and JH genes from the J4*02 family. LC genes are from the LV1-51*01 germline combined with JL genes from the LJ7*01. The HC nucleotide and amino acid sequences are shown in FIG. 5 (SEQ ID No 37-54) the preferred LC nucleotide and amino acid sequences are shown in FIGS. 6C and 6D (SEQ ID No 63-72). In the K1-70 HC sequence there are three replacement mutations in FWR1, 3 replacement mutations in CDR1, 1 replacement mutation in FWR2, 2 silent mutation in CDR 2, 4 replacement mutations in FWR3 and 1 replacement mutation in FWR4. Overall (FWRs and CDRs) R/S mutation ratio is 6.0. In addition there are 2 insertions in the CDR 3; a 5 base pair insertion in the junction between V and D genes and a 12 base pair insertion at the junction between D and J genes (FIGS. 5B and 5D; SEQ ID No 41 and 51)). The HC CDR 1 (SEQ ID No 42 and 52) is 5 amino acids long, CDR 2 (SEQ ID No 43 and 53) is 17 amino acids long and CDR 3 (SEQ ID No 44 and 54) is 10 amino acids long (FIGS. 5B and 5D, respectively). K1-70 LC genes show 1 silent mutation in FWR1, 1 silent and 1 replacement mutations in FWR2 and 1 replacement mutation in FWR3. There are 1 silent and 2 replacement mutations in the CDR1 and 2 replacement mutations in the CDR3. Overall (FWRs and CDRs) R/S mutation ratio is 2.0. In addition there is a 2 base pair insertion between the LC V and J genes. The LC CDR 1 (SEQ ID No 70) is made up of 13 amino acids, CDR 2 (SEQ ID No 71) of 7 amino acids and CDR 3 (SEQ ID No 72) 11 amino acids (FIG. 6D).

K1-70 Fab Structure

The structure of Fab K1-70 has been determined at 2.22 Å resolution (FIG. 8). The Ramachandran plot parameters and the refinement statistics were within the range acceptable for correct structure refinement. The asymmetric unit contains two complete Fab K1-70 molecules, Fab A and Fab B. Fab A contains heavy chain A and light chain B, while Fab B contains heavy chain C and light chain D. The two Fab molecules are not related by non-crystallographic symmetry due to differences in the elbow angles (Fab A=145.5°, Fab B=163.1°). There are no breaks in main chain electron density in the structure, but some residues are missing at the termini. In Fab A heavy chain A and light chain B consist of residues 1 to 227 and 4 to 211, respectively, and in Fab B heavy chain C and light chain D consist of residues 1 to 227 and 2 to 212, respectively. The residues in Fab A and Fab B are numbered according to Kabat's system (Kabat E et al 1991 supra). See FIGS. 8 and 9A for details. Electron density could not be observed for the side chains of residues 1, 58, 129 and 213 of heavy chain A; side chains of residues 18, 94, 110, 126, 156, 163 and 166 of light chain B; side chains of residues 1, 58 and 218 of heavy chain C; and side chains of residues 17, 18, 94, 108, 156, 172, 184, 187 and 190 of light chain D. The absence of these side chains in the electron density map indicates that they are highly mobile, mainly due to their being positioned in solvent accessible regions of the crystal structure. The root mean square deviation (r.m.s.d) for the two molecules of Fab, calculated using LSQKAB (CCP4), are 0.20 Å for VH domains (117 Cα atoms), 0.23 Å for VL domains (106 Cα atoms), 0.22 Å for CH domains (96 Cα atoms) and 0.29 Å for CL domains (97 Cα atoms). This demonstrates that even though the elbow angles between the two Fab molecules differ, the domains themselves show minimal differences. The structure of K1-70 Fab is standard (FIG. 9A); the canonical structures adopted by the six CDRs are 1,1 and 2 for LC CDR1, LC CDR2 and LC CDR3 respectively and 1 and 2A for HC CDR1 and HC CDR2 respectively. The HC CDR3 has not been assigned any canonical class due to greater variations in sequence and conformation. Disulphide bonds are present between cysteine residues LC23-LC88, LC134-LC194, HC22-HC92, HC142-HC208. In the crystal structure of K1-70 Fab LC CDR1 is 13 residues long, LC CDR2 is 7 residues long and LC CDR3 is 11 residues long. HC CDR1 is made up of 5 residues, HC CDR2 of 17 residues and HC CDR3 of 12 residues. For further analysis of the structure the side chains of LC CDR3 Arg94 and HC CDR2 Arg58 (for which the electron density was missing in the diffraction data set) were added. In the description of the structure below the values in brackets refer to the values obtained including these side chains. There are 158 hydrogen bonds within the LC and 177 within the HC. 52 (52) residues from the LC are involved in interface contact with 44 (45) residues from the HC. There are 7 hydrogen bonds and 2 salt bridges that keep the two chains in their relative position. The solvent accessible surface area (ASA) for the LC CDR1 is 525 (485) Å$^2$, LC CDR2 is 508 (508) Å$^2$, LC CDR3 is 257 (442) Å$^2$, HC CDR1 is 120 Å$^2$, HC CDR2 is 759 (842) Å$^2$ and HC CDR3 is 557 (528) Å$^2$. The distribution of charged amino acids on the surface of the antigen binding site of K1-70 Fab has been analysed and is shown in FIG. 9B. The surface of the combining site is dominated by negatively charged residues on one side and by positively charged residues on the other side. The acidic patches on the antigen binding surface are contributed from LC residues: Asp27B (CDR1), Asp50 (CDR2), Asp92 (CDR3) and from HC residues: Asp31 (CDR1), Asp54 and Asp56 (CDR2) and Asp96 (CDR3). The basic patches are contributed from the LC residues: Lys53 and Arg54 (CDR1) and Arg94 (CDR3) and from the HC residues: Arg58 (CDR2) and Arg 101 (CDR3). In addition, LC Lys 66 which is outside the CDR regions also contributes to a basic patch on the surface. Overall, the positively charged area on the antigen binding surface of K1-70 is made up predominantly by the LC residues while the negatively charged area by the HC residues. The antigen binding surface of K1-70 is also rich in aromatic residues with 5 tyrosines, one phenylalanine and three tryptophans from the HC and the LC CDRs (FIG. 9C). In addition, four tyrosines and one phenylalanine from the FRW regions contribute to the surface area.

The overall surface of the K1-70 antigen binding area is highly irregular with a cavity near to the centre. The cavity is surrounded mostly by aromatic residues and by LC Asp50 (FIGS. 9B and 9C). Furthermore, the interior of the cavity is also populated by aromatic residues. This suggests that aromatic contacts may be important for the interaction between K1-70 and the TSHR with the prominent aromatic residue on the surface of the TSHR "fitting" into the cavity on the K1-70 surface.

Recombinant K1-70 Fab

Table 17a shows that recombinant K1-70 Fab in *E. coli* culture supernatant had the ability to inhibit $^{125}$I-TSH binding to the TSHR. The inhibiting effect was complete at lower dilutions of the culture supernatants (91.9% at 1:2 dilution) while increasing dilutions of the supernatant cause dose dependent inhibiting effect (27.9% inhibition at 1:256 dilution) (Table 17a). The effect of recombinant K1-70 Fab on TSH mediated stimulation of cyclic AMP production in CHO cells expressing the TSHR is shown in Table 17b. Different dilutions of culture supernatants showed dose dependent inhibition of cyclic AMP stimulation; from 89.3% inhibition at 1:5 dilution to 39.7% inhibition at 1:40 dilution (Table 17b). Control culture supernatants from non-induced *E. coli* cultures did not produced detectable inhibition of TSH binding or inhibition of TSH mediated cyclic AMP stimulation (Tables 17a &b).

SUMMARY AND CONCLUSIONS

The experiments described above show that two monoclonal autoantibodies to the TSHR with very different biological activities (K1-18 stimulating and K1-70 blocking) can be isolated from a single preparation of a patient's lymphocytes. Consequently, the patient's immune system was producing both types of TSHR autoantibody ie stimulating type and blocking type at the same time. Once isolated (as described above) in the form of monoclonal autoantibodies, the properties of the two types of TSHR autoantibody can be investigated without interference from each other. The characteristics of the new human MAb with TSHR stimulating activity (K1-18) have been described and compared to the characteristics of some other known TSHR MAbs. Specifically of a stimulating human MAb (M22), a blocking human MAb (5C9), a blocking human Mab (K1-70), a blocking mouse MAb (9D33) and mouse stimulating MAbs (TSMAbs 1-7). Also the characteristics of the new human MAb with TSH antagonist activity (K1-70) have been described and compared to the characteristics of known MAbs. Specifically of a blocking human MAb (5C9), a blocking mouse MAb (9D33), a stimulating human MAb (M22), a stimulating human MAb (K1-18) and mouse stimulating MAbs (TSMAbs 1-7). It has been shown that the new human stimulating TSHR MAb K1-18 has properties similar to M22 in terms of:—inhibition of binding of labelled TSH to the TSHR, inhibition of binding of each other to the TSHR, inhibition of binding of blocking human MAbs (5C9 and K1-70) to the TSHR, inhibition of binding of mouse blocking and stimulating MAbs (9D33 and TSMAbs 1-7). Also the patient serum TRAbs inhibited binding of K1-18 to the TSHR. Furthermore, both M22 and K1-18 bind to the TSHR with a high affinity and are able to bind to a TSHR fragment consisting of amino acids 22-260 linked to alkaline phosphatase. Antibodies such as M22 and K1-18 have the ability to stimulate TSHR cyclic AMP activity although the potency of the two antibodies differs by about 1.5 fold. The studies show that the properties of TSHR stimulating autoantibodies are similar in different patients and they are representative of the properties of TSHR stimulating autoantibodies in all patients with Graves' disease studied so far. A summary of K1-18 characteristics is shown in Table 13a. Our experiments also showed that the new blocking type human MAb K1-70 (obtained from the same sample of lymphocytes as the stimulating MAb K1-18) has the ability to:—inhibit binding of labelled TSH to the TSHR, inhibit binding of human MAbs (M22, K1-18 and 5C9) to the TSHR, inhibit binding of mouse blocking and stimulating MAbs (9D33 and TSMAbs 1-7) to the TSHR. Furthermore binding of K1-70 to the TSHR was inhibited by patient serum TRAbs. K1-70 showed potent TSH antagonist activity and the ability to block stimulation of the TSHR by all patient serum TRAbs tested. K1-70 was shown to be a more effective inhibitor of TSH binding to the TSHR than 5C9. K1-70 binds to the TSHR with a high affinity and is able to bind to the TSHR fragment of amino acids 22-260 linked to the alkaline phosphatase. Consequently, K1-70 has the characteristics of patient sera with blocking TRAbs including the high binding affinity for the TSHR, the ability to inhibit TSH and M22 binding to the TSHR and the ability to block ligand induced TSHR stimulation at low concentrations of antibody. However, K1-70 has no effect on TSHR constitutive activity while 5C9 does. A summary of K1-70 characteristics is shown in Table 13b. K1-18 ability to stimulate cyclic AMP activity in CHO cells expressing TSHRs was lost when TSHR was mutated at Glu157Ala, Lys183Ala, Tyr185Ala, Asp232Ala or Arg255Asp. K1-70 ability to block TSH mediated cyclic AMP activity in CHO cells expressing TSHRs was reduced in the case of TSHR mutations Lys58Ala, Ile60Ala, Arg109Ala, Lys183Ala, Lys250Ala and slightly reduced by the TSHR mutation Tyr82Ala. Both K1-18 and K1-70 as well as M22 reacted well with the TSHR fragment of 22-260 in an ELISA based on TSHR 260-AP. Furthermore a panel of patient serum TSHR autoantibodies reacted well with TSHR amino acids 22-260 in the same assay. Patient sera with either type of TRAb activities (stimulating and blocking) bound to TSHR260 in the ELISA. In addition, ELISA plate wells coated with the TSHR fragment of amino acids 22-260 bound M22-peroxidase (from RSR Ltd) well and this M22-peroxidase binding was inhibited by a panel of patient serum TSHR autoantibodies. This inhibition of M22-peroxidase binding by the patient serum TSHR autoantibodies was similar to inhibition of M22-peroxidase binding to full length TSHR. Surprisingly therefore the TSHR fragment of amino acids 22-260 (or perhaps a smaller fragment) appears to be sufficient for routine assays of TSHR autoantibodies. Furthermore, M22 also bound well to a longer fragment of the TSHR (TSHR LRD C-CAP). In stability studies, the ability of M22 to bind TSHR260, TSHR260-AP and TSHR LRD C-CAP after they had been pre-incubated at room temperature was greater than the full length TSHR preparations which had been pre-incubated under the same conditions. This indicates that TSHR260, TSHR260-AP and TSHR LRD C-CAP are more stable at room temperature compared to full length TSHR. The TSHR mutation Arg255Asp had no effect on binding of K1-70 IgG while K1-18 IgG (at lower concentrations ie 0.1 µg/mL and below) bound less effectively to the mutated receptor. The experiments with different patient serum TRAbs indicate that sera with TSHR stimulating activities can be differentiated from sera with TSHR blocking activities on the basis of differences in binding to the TSHR containing R255D mutation. Binding of patient sera with stimulating activities is affected by the mutation while binding of patient sera with blocking activities is affected less or not at all. The experiments provide nucleotide and amino acid sequences of K1-18 and K1-70. Although heavy chain V genes of K1-18, K1-70 are derived from the same germline which belongs to the same family as the other stimulating human MAb M22 heavy chain V genes they are all combined with D and J genes from different families; furthermore K1-18 uses the kappa light chain, whereas M22 and K1-70 use lambda light chains. 5C9 (the other blocking type human MAb) germline genes are different from M22, K1-18 and K1-70 except that 5C9 and K1-70 use J4 heavy chain genes. Amino acid sequences of the CDRs of stimulating MAbs (M22 and K1-18) and blocking MAbs (5C9 and K1-70) are essentially different in particular within the heavy and the light chains CDR3s. These observations indicate that each of the 4 human autoantibodies is derived from distinct germlines. Also different CDR sequences may show similar biological activities towards the TSHR. The X-ray diffraction data provide molecular details of K1-70 Fab structure including the topography of the antigen binding site. A recombinant K1-70 Fab produced by cloning and expression of the K1-70 HC (SEQ ID No 46) and K1-70 LC (SEQ ID No 63 with SEQ ID No 64) in *E. coli* showed the ability to inhibit $^{125}$I-labelled TSH binding to the TSHR and the ability to inhibit TSH mediated stimulation of TSHR cyclic AMP activity. Overall the results indicate that antibodies in accordance with the invention such as K1-18 and K1-70 show similar TSHR binding activity and similar biological effects on TSHR function as TSHR MAbs described previously (M22 and 5C9) and as TSHR autoantibodies found in different sera from patients with autoimmune thyroid disease.

TABLE 1a

Inhibition of $^{125}$I-TSH binding to TSHR coated tubes by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 91.4 ± 0.7 | 95.9 ± 0.2 |
| 30 µg/mL | 89.5 ± 1.0 | 96.0 ± 0.3 |
| 10 µg/mL | 91.1 ± 1.1 | 96.0 ± 0.5 |
| 3 µg/mL | 89.1 ± 0.4 | 95.3 ± 0.5 |
| 1 µg/mL | 89.3 ± 1.3 | 94.0 ± 0.7 |
| 0.3 µg/mL | 89.7 ± 0.7 | 82.6 ± 1.0 |
| 0.1 µg/mL | 78.5 ± 0.6 | 62.0 ± 1.6 |
| 0.03 µg/mL | 45.2 ± 2.3 | 26.6 ± 1.2 |
| 0.01 µg/mL | 21.1 ± 2.3 | 9.3 ± 2.1 |
| 0.003 µg/mL | 0.5* | 11.4 ± 3.0 |
| 0.001 µg/mL | −4.6* | 1.6 ± 3.2 |
| M22 IgG | | |
| 100 µg/mL | 91.4 ± 1.8 | 96.5 ± 0.1 |
| 30 µg/mL | 89.2 ± 0.5 | 96.1 ± 0.5 |
| 10 µg/mL | 89.3 ± 0.6 | 96.1 ± 0.5 |
| 3 µg/mL | 89.6 ± 0.4 | 96.0 ± 0.6 |
| 1 µg/mL | 89.9 ± 1.7 | 95.5 ± 0.3 |
| 0.3 µg/mL | 88.6 ± 1.2 | 89.9 ± 0.2 |
| 0.1 µg/mL | 87.2 ± 1.2 | 76.1 ± 2.2 |
| 0.03 µg/mL | 58.3 ± 1.5 | 41.6 ± 3.5 |
| 0.01 µg/mL | 23.4 ± 3.4 | 18.0 ± 0.8 |
| 0.003 µg/mL | 7.1* | 11.1 ± 2.9 |
| 0.001 µg/mL | 1.5* | 10.6 ± 8.7 |
| 5C9 IgG | | |
| 100 µg/mL | 82.9 ± 1.0 | 35.3 ± 2.8 |
| 10 µg/mL | 40.5 ± 0.3 | 40.9 ± 1.1 |
| 1 µg/mL | 23.5 ± 2.9 | 19.7 ± 1.2 |
| 0.1 µg/mL | 21.3* | 16.2 ± 4.3 |
| 0.01 µg/mL | 15.9* | 4.1 ± 2.2 |
| TSMAb 1 IgG | | |
| 100 µg/mL | 61.1 ± 4.1 | 54.1 ± 4.1 |
| 10 µg/mL | 48.1 ± 1.7 | 43.4 ± 1.1 |
| 1 µg/mL | 29.3 ± 1.5 | 26.5 ± 0.5 |
| 0.1 µg/mL | 11.0 ± 1.7 | 6.8 ± 1.7 |
| 0.01 µg/mL | 2.6 ± 2.1 | 2.4* |
| TSMAb 2 IgG | | |
| 100 µg/mL | 77.6 ± 7.7 | 48.0 ± 4.4 |
| 10 µg/mL | 37.7 ± 2.6 | 39.0 ± 0.5 |
| 1 µg/mL | 29.1 ± 2.5 | 33.6* |
| 0.1 µg/mL | 23.4 ± 2.7 | 15.9 ± 0.8 |
| 0.01 µg/mL | 1.6 ± 1.5 | 0.7 ± 1.7 |
| TSMAb 3 IgG | | |
| 100 µg/mL | 81.1 ± 2.9 | 54.3 ± 3.3 |
| 10 µg/mL | 58.1 ± 1.1 | 44.7 ± 2.8 |
| 1 µg/mL | 35.2 ± 1.5 | 37.7 ± 0.7 |
| 0.1 µg/mL | 30.7 ± 0.8 | 15.7 ± 4.9 |
| 0.01 µg/mL | 9.0 ± 0.5 | −2.5 ± 4.1 |
| TSMAb 4 IgG | | |
| 100 µg/mL | 57.2 ± 4.7 | 63.5 ± 5.6 |
| 10 µg/mL | 40.8 ± 1.3 | 56.5 ± 1.2 |
| 1 µg/mL | 39.8 ± 0.8 | 53.9 ± 2.3 |
| 0.1 µg/mL | 42.8 ± 1.4 | 32.1 ± 3.3 |
| 0.01 µg/mL | 33.3* | 8.6 ± 7.2 |
| TSMAb 5 IgG | | |
| 100 µg/mL | 87.8 ± 1.0 | 61.9 ± 2.8 |
| 10 µg/mL | 64.6 ± 1.1 | 56.9 ± 1.9 |
| 1 µg/mL | 43.9 ± 1.1 | 53.8 ± 2.6 |
| 0.1 µg/mL | 39.7 ± 0.9 | 38.6 ± 2.4 |
| 0.01 µg/mL | 15.9 ± 9.4 | 7.5 ± 0.6 |
| TSMAb 6 IgG | | |
| 100 µg/mL | 68.6 ± 2.5 | 46.9 ± 2.6 |
| 10 µg/mL | 32.8 ± 0.9 | 40.8 ± 2.3 |
| 1 µg/mL | 28.9 ± 3.0 | 40.2 ± 0.9 |
| 0.1 µg/mL | 24.6 ± 0.6 | 30.2 ± 1.3 |
| 0.01 µg/mL | 9.5 ± 5.8 | 19.6 ± 0.6 |
| TSMAb 7 IgG | | |
| 100 µg/mL | 69.4 ± 3.4 | 45.9 ± 1.1 |
| 10 µg/mL | 43.9 ± 0.6 | 42.0 ± 0.7 |
| 1 µg/mL | 28.5 ± 4.8 | 37.7 ± 1.6 |
| 0.1 µg/mL | 19.8 ± 1.5 | 19.9 ± 1.5 |
| 0.01 µg/mL | −3.1 ± 5.2 | 8.0 ± 2.1 |
| 9D33 IgG | | |
| 100 µg/mL | 75.6 ± 1.2 | 67.4 ± 4.6 |
| 10 µg/mL | 58.7 ± 4.1 | 60.5 ± 2.6 |
| 1 µg/mL | 50.9 ± 2.9 | 50.8 ± 2.2 |
| 0.1 µg/mL | 48.3 ± 2.6 | 30.5 ± 2.7 |
| 0.01 µg/mL | 15.8 ± 3.0 | 3.6 ± 3.3 |
| 5B3 IgG | | |
| 100 µg/mL | 22.4 ± 1.5 | −3.9 ± 5.7 |
| 10 µg/mL | −5.7 ± 2.1 | −1.9 ± 1.5 |
| 1 µg/mL | −1.7 ± 5.3 | −4.9 ± 3.4 |
| 0.1 µg/mL | −5.0 ± 3.7 | 4.4 ± 2.5 |
| 0.01 µg/mL | −5.8* | 2.6* |

Results shown are mean ± SD of triplicate determinations.
*mean of duplicate determinations.
HBD = pool of healthy blood donor sera. 5B3 is a human MAb to glutamic acid decarboxylase (negative control).
$^{125}$I-TSH binding in the presence of assay buffer was 11%. $^{125}$I-TSH binding in the presence of HBD pool was 11.5%. Assay buffer is 50 mmol/L NaCl, 10 mmol/L Tris pH 7.8, 0.1% Triton X-100.

TABLE 1b

Inhibition of $^{125}$I-TSH binding to TSHR coated tubes by K1-70 IgG and K1-70 Fab and by various TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 µg/mL | 94.6 ± 0.2 | 95.9 ± 0.8 |
| 30 µg/mL | 93.3 ± 0.4 | 94.9 ± 0.4 |
| 10 µg/mL | 92.7 ± 0.8 | 93.9 ± 1.4 |
| 3 µg/mL | 91.8 ± 0.5 | 94.1 ± 0.4 |
| 1 µg/mL | 92.3 ± 0.4 | 91.9 ± 0.9 |
| 0.3 µg/mL | 91.3 ± 1.1 | 83.5 ± 1.3 |
| 0.1 µg/mL | 86.9 ± 1.1 | 50.0 ± 1.6 |
| 0.03 µg/mL | 50.5 ± 2.0 | 13.5 ± 2.3 |
| 0.01 µg/mL | 8.3 ± 2.8 | −7.0 ± 1.9 |
| 0.003 µg/mL | −3.7 ± 1.6 | 0.8 ± 4.7 |
| 0.001 µg/mL | −6.1 ± 5.5 | −3.0 ± 2.2 |
| K1-70 Fab | | |
| 100 µg/mL | 87.3 ± 0.9 | 93.3 ± 1.2 |
| 30 µg/mL | 89.0 ± 0.1 | 92.5 ± 0.8 |
| 10 µg/mL | 87.2 ± 0.9 | 91.2 ± 0.2 |
| 3 µg/mL | 88.2 ± 0.4 | 91.6 ± 0.5 |
| 1 µg/mL | 88.1 ± 0.7 | 91.8 ± 1.3 |
| 0.3 µg/mL | 87.5 ± 0.3 | 88.1 ± 2.3 |
| 0.1 µg/mL | 85.0 ± 0.4 | 71.6 ± 3.1 |
| 0.03 µg/mL | 70.3 ± 0.6 | 40.7 ± 0.6 |
| 0.01 µg/mL | 24.8 ± 1.3 | 18.9 ± 0.5 |
| 0.003 µg/mL | 2.7 ± 2.8 | *−1.7 |
| 0.001 µg/mL | −2.6 ± 3.5 | 7.2 ± 2.8 |
| M22 IgG | | |
| 100 µg/mL | 88.5 ± 0.9 | 96.2 ± 0.5 |
| 30 µg/mL | 90.0 ± 2.4 | 94.3 ± 0.3 |
| 10 µg/mL | 87.5 ± 1.4 | 93.4 ± 1.6 |
| 3 µg/mL | 89.5 ± 2.5 | 94.6 ± 0.7 |
| 1 µg/mL | 91.6 ± 0.8 | 92.6 ± 1.6 |
| 0.3 µg/mL | 89.9 ± 0.6 | 82.2 ± 2.0 |
| 0.1 µg/mL | 84.3 ± 0.9 | 62.1 ± 1.7 |
| 0.03 µg/mL | 48.3 ± 0.9 | 31.4 ± 3.8 |
| 0.01 µg/mL | 7.5 ± 1.1 | −0.3 ± 5.5 |
| 0.003 µg/mL | −1.5 ± 5.5 | −1.8 ± 4.0 |
| 0.001 µg/mL | −11.0 ± 0.7 | 1.2 ± 6.9 |
| M22 Fab | | |
| 100 µg/mL | 91.3 ± 0.1 | 94.4 ± 0.8 |
| 30 µg/mL | 89.9 ± 3.1 | 93.5 ± 0.7 |
| 10 µg/mL | 90.1 ± 1.6 | 93.9 ± 0.7 |
| 3 µg/mL | 87.5 ± 1.2 | 93.4 ± 0.5 |
| 1 µg/mL | 89.2 ± 0.4 | 92.5 ± 0.5 |
| 0.3 µg/mL | 87.3 ± 0.7 | 90.0 ± 0.2 |
| 0.1 µg/mL | 86.7 ± 0.5 | 77.1 ± 2.9 |
| 0.03 µg/mL | 71.4 ± 1.4 | 35.3 ± 3.3 |
| 0.01 µg/mL | 27.1 ± 2.7 | 8.7 ± 4.9 |
| 0.003 µg/mL | 1.1 ± 6.8 | −7.9 ± 0.3 |
| 0.001 µg/mL | −9.3 ± 2.1 | −11.2 ± 1.9 |
| 5C9 IgG | | |
| 100 µg/mL | 92.5 ± 0.4 | 59.2 ± 5.3 |
| 10 µg/mL | 76.7 ± 1.3 | 39.9 ± 5.6 |
| 1 µg/mL | 38.7 ± 0.7 | 24.8 ± 0.8 |
| 0.1 µg/mL | 24.4 ± 4.5 | 7.0 ± 2.4 |
| 0.01 µg/mL | 8.3 ± 3.3 | −5.5 ± 4.8 |
| 0.001 µg/mL | −11.2 ± 2.9 | −8.0 ± 1.1 |

See legend to Table 1a for details. $^{125}$I-TSH binding in the presence of assay buffer was 13.4%. $^{125}$I-TSH binding in the presence of HBD pool was 11.5%.

TABLE 2a

Inhibition of $^{125}$I-TSH binding to TSHR coated tubes by K1 donor serum and IgG and by K1-18 IgG and Fab

| Test sample | Inhibition of binding (%) Dilutions in assay buffer (mean ± SD) | Inhibition of binding (%) Dilutions in HBD (mean ± SD) |
|---|---|---|
| K1 donor serum dilution | | |
| 1/10 | 94.7 ± 0.9 | 81.1 ± 0.4 |
| 1/20 | 89.3 ± 0.7 | 62.4 ± 3.5 |
| 1/40 | 67.0 ± 1.0 | 39.0 ± 0.9 |
| 1/80 | 34.0 ± 3.8 | 19.8 ± 1.9 |
| 1/160 | 13.1 ± 3.1 | 9.1 ± 0.8 |
| 1/320 | 6.6 ± 0.9 | 2.17 ± 1.5 |
| K1 donor serum IgG | | |
| 1 mg/mL | 89.6 ± 0.8 | 76.5 ± 1.5 |
| 0.5 mg/mL | 79.4 ± 0.7 | 52.3 ± 0.7 |
| 0.25 mg/mL | 52.1 ± 2.0 | 27.8 ± 0.4 |
| 0.125 mg/mL | 29.5 ± 2.6 | 13.7 ± 1.3 |
| K1-18 IgG | | |
| 100 µg/mL | 93.7 ± 0.6 | 95.7 ± 0.6 |
| 30 µg/mL | 93.3 ± 0.5 | 95.3 ± 0.0 |
| 10 µg/mL | 93.3 ± 1.1 | 95.3 ± 0.4 |
| 3 µg/mL | 94.2 ± 1.4 | 94.3 ± 0.6 |
| 1 µg/mL | 93.3 ± 1.0 | 92.0 ± 0.4 |
| 0.3 µg/mL | 90.9 ± 1.3 | 80.9 ± 2.2 |
| 0.1 µg/mL | 78.0 ± 0.4 | 54.0 ± 2.4 |
| 0.03 µg/mL | 38.8 ± 2.2 | 25.5 ± 3.2 |
| 0.01 µg/mL | 14.6 ± 5.2 | 11.8 ± 6.1 |
| 0.003 µg/mL | 0.2 ± 0.2 | 2.4 ± 4.2 |
| 0.001 µg/mL | 0.5 ± 0.9 | 0.9 ± 1.5 |
| K1-18 Fab | | |
| 100 µg/mL | 88.9 ± 0.8 | 81.7 ± 1.6 |
| 30 µg/mL | 85.6 ± 0.3 | 81.3 ± 1.4 |
| 10 µg/mL | 82.9 ± 1.1 | 82.2 ± 0.9 |
| 3 µg/mL | 79.3 ± 0.9 | 80.9 ± 2.1 |
| 1 µg/mL | 77.0 ± 1.8 | 76.8 ± 1.6 |
| 0.3 µg/mL | 72.4 ± 1.1 | 60.6 ± 1.3 |
| 0.1 µg/mL | 56.2 ± 4.2 | 35.7 ± 3.3 |
| 0.03 µg/mL | 25.6 ± 4.9 | 15.9 ± 4.6 |
| 0.01 µg/mL | 7.4 ± 4.8 | 5.6 ± 7.3 |
| 0.003 µg/mL | 2.4 ± 3.9 | 0.5 ± 0.86 |
| 0.001 µg/mL | 0.0 ± 0.0 | 2.1 ± 2.2 |

See legend to Table 1a for details. $^{125}$I-TSH binding in the presence of assay buffer was 10.8%. $^{125}$I-TSH binding in the presence of HBD pool was 12.4%.

TABLE 2b

Inhibition of $^{125}$I-TSH binding to TSHR coated tubes by WHO reference preparation NIBSC 90/672 and by K1-18 IgG and Fab preparations

| | Samples diluted in serum | | | | Samples diluted in assay buffer | | | |
|---|---|---|---|---|---|---|---|---|
| Test sample | Inhibition of binding (%) (mean ± SD) | units/L | units/ mg | mean units/ mg | Inhibition of binding (%) (mean ± SD) | units/L | units/ mg | mean units/ mg |
| NIBSC 90/672 | | | | | | | | |
| 0.125 units/L | 0 | | | | 0 | | | |
| 0.25 units/L | 0 | | | | 0 | | | |
| 0.5 units/L | 5.6 ± 2.5 | | | | 3.1 ± 1.6 | | | |
| 1.0 units/L | 8.1 ± 5.8 | | | | 14.0 ± 2.6 | | | |
| 2.0 units/L | 18.2 ± 1.2 | | | | 26.2 ± 4.2 | | | |
| 4.0 units/L | 34.8 ± 0.6 | | | | 49.0 ± 4.3 | | | |
| 8.0 units/L | 65.3 ± 0.3 | | | | 62.7 ± 0.2 | | | |
| 40.0 units/L | 90.9 ± 0.5 | | | | 91.0 ± 0.6 | | | |
| M22 IgG | | | | | | | | |
| 0.3 ng/mL | 0 | | | | 0 | | | |
| 1 ng/mL | 0 | | | | 4.5 ± 1.6 | | | |
| 3 ng/mL | 0 | | | | 10.9 ± 3.5 | | | |
| 10 ng/mL | 13.0 ± 1.51 | 1.5 | 150 | | 26.4 ± 0.1 | 2.5 | 250 | |
| 30 ng/mL | 37.6 ± 1.7 | 4.3 | 143 | 131 | 64.1 ± 3.2 | 8.6 | 287 | 266 |
| 100 ng/mL | 70.4 ± 1.1 | 9.9 | 99 | | 87.6 ± 0.6 | 26 | 260 | |
| 300 ng/mL | 87.9 ± 0.1 | | | | 87.6 ± 0.5 | | | |
| 1000 ng/mL | 92.5 ± 0.5 | | | | 91.2 ± 0.3 | | | |
| K1-18 IgG | | | | | | | | |
| 0.3 ng/mL | 0 | | | | 0.6 ± 1.9 | | | |
| 1 ng/mL | 0 | | | | 4.5 ± 2.9 | | | |
| 3 ng/mL | 0 | | | | 7.8 ± 2.1 | | | |
| 10 ng/mL | 6.4 ± 0.8 | | | | 21.4 ± 1.8 | 1.52 | 152 | |
| 30 ng/mL | 24.7 ± 4.7 | 2.7 | 90 | | 49.9 ± 4.2 | 5.3 | 177 | 181 |
| 100 ng/mL | 60.2 ± 1.7 | 7 | 70 | 69 | 84.3 ± 0.9 | 21.5 | 215 | |
| 300 ng/mL | 79.9 ± 1.7 | 14.5 | 48 | | 87.8 ± 1.1 | | | |
| 1000 ng/mL | 90.7 ± 0.8 | | | | 90.1 ± 0.3 | | | |
| K1-18 Fab | | | | | | | | |
| 0.3 ng/mL | 0 | | | | 2.0 ± 0.9 | | | |
| 1 ng/mL | 0 | | | | 5.7 ± 3.0 | | | |
| 3 ng/mL | 0 | | | | 7.8 ± 5.4 | | | |
| 10 ng/mL | 2.6 ± 3.2 | | | | 16.6 ± 1.9 | 1.2 | 120 | |
| 30 ng/mL | 17.1 ± 1.0 | 1.9 | 63 | | 34.5 ± 1.1 | 3.12 | 104 | 86 |
| 100 ng/mL | 41.0 ± 2.4 | 4.6 | 46 | 46 | 58.7 ± 0.7 | 7.1 | 71 | |
| 300 ng/mL | 66.6 ± 0.9 | 8.4 | 28 | | 70.8 ± 2.5 | 15 | 50 | |
| 1000 ng/mL | 74.4 ± 4.3 | | | | 75.7 ± 0.8 | | | |
| 4B4 IgG | | | | | | | | |
| 0.3 ng/mL | 0 | | | | 5.0 ± 3.5 | | | |
| 3 ng/mL | 0 | | | | 0.8 ± 1.9 | | | |
| 30 ng/mL | 0 | | | | 1.9 ± 0.8 | | | |
| 300 ng/mL | 0 | | | | 0.7 ± 2.0 | | | |
| 4B4 Fab | | | | | | | | |
| 0.3 ng/mL | 0 | | | | 10.7 ± 3.9 | | | |
| 3 ng/mL | 0 | | | | 8.9 ± 2.5 | | | |
| 30 ng/mL | 0 | | | | 0 | | | |
| 300 ng/mL | 0 | | | | 0.5 ± 0.5 | | | |

See legend for Table 1a for details. $^{125}$I-TSH binding in the presence of assay buffer was 17.7%. $^{125}$I-TSH binding in the presence of HBD pool was 16.0%.

TABLE 2c

Inhibition of $^{125}$I-TSH binding to TSHR coated tubes by lymphocyte donor serum IgG

| Test sample | Samples diluted in serum ||| Samples diluted in assay buffer |||
|---|---|---|---|---|---|---|
| | Inhibition of binding (%) (mean ± SD) | units/L | units/mg (or U/mL in undil serum) | mean units/mg (or mean units/mL) | Inhibition of binding (%) (mean ± SD) | units/L | units/mg (or U/mL in undil serum) | mean units/mg (or mean units/mL) |
| NIBSC 90/672 | | | | | | | | |
| 0.125 units/L | 2.4 ± 0.7 | | | | 5.1 ± 4.2 | | | |
| 0.25 units/L | 3.5 ± 2.0 | | | | 0.9 ± 1.4 | | | |
| 0.5 units/L | 9.3 ± 2.7 | | | | 2.8 ± 2.2 | | | |
| 1 unit/L | 15.5 ± 1.7 | | | | 14.1 ± 2.7 | | | |
| 2 units/L | 22.9 ± 6.4 | | | | 27.2 ± 5.4 | | | |
| 4 units/L | 49.2 ± 1.2 | | | | 53.3 ± 2.1 | | | |
| 8 units/L | 63.2 ± 1.1 | | | | 62.2 ± 1.8 | | | |
| 40 units/L | 90.0 ± 0.1 | | | | 90.9 ± 1.0 | | | |
| Donor serum | | | | | | | | |
| diluted 160× | 3.5 ± 1.9 | | | | 5.3 ± 0.7 | | | |
| diluted 80× | 10.4 ± 1.0 | | | | 17.9 ± 2.9 | 1.25 | (0.1) | |
| diluted 40× | 23.3 ± 2.6 | 2 | (0.08) | (0.075) | 39.5 ± 1.3 | 2.8 | (0.112) | (0.144) |
| diluted 20× | 39.7 ± 4.4 | 3.3 | (0.07) | | 67.8 ± 1.6 | 11 | (0.22) | |
| Donor serum IgG | | | | | | | | |
| 0.01 mg/mL | 0 | | | | 5.1 ± 8.5 | | | |
| 0.03 mg/mL | 0.4 ± 2.7 | | | | 4.4 ± 2.7 | | | |
| 0.1 mg/mL | 13.5 ± 1.6 | 0.8 | 0.008 | | 19.8 ± 1.5 | 1.4 | 0.014 | |
| 0.3 mg/mL | 36.1 ± 3.0 | 3.0 | 0.010 | 0.011 | 60.6 ± 2.8 | 7 | 0.023 | 0.024 |
| 1 mg/mL | 72.3 ± 1.2 | 13.5 | 0.014 | | 87.2 ± 2.0 | 34 | 0.034 | |
| HBD | | | | | | | | |
| diluted 160× | 0 | | | | 0 | | | |
| diluted 80× | 0 | | | | 0 | | | |
| diluted 40× | 0 | | | | 0 | | | |
| diluted 20× | 0 | | | | 0 | | | |
| HBD IgG | | | | | | | | |
| 0.01 mg/mL | 0 | | | | 0 | | | |
| 0.1 mg/mL | 0 | | | | 0 | | | |
| 1 mg/mL | 0 | | | | 0 | | | |
| K1-18 IgG | | | | | | | | |
| 0.3 ng/mL | 0 | | | | 0 | | | |
| 1 ng/mL | 0 | | | | 1.7 ± 4.4 | | | |
| 3 ng/mL | 0 | | | | 12.9 ± 7.0 | | | |
| 10 ng/mL | 6.0 ± 1.3 | | | | 20.5 ± 6.4 | 1.4 | 140 | |
| 30 ng/mL | 24.4 ± 1.8 | 2.1 | 70.0 | | 48.1 ± 5.5 | 3.5 | 116.7 | 150.4 |
| 100 ng/mL | 53.6 ± 0.6 | 5.0 | 50.0 | 63.3 | 79.7 ± 2.8 | 22.5 | 225 | |
| 300 ng/mL | 79.7 ± 0.6 | 21 | 70.0 | | 88.5 ± 2.6 | 36 | 120 | |
| 1000 ng/mL | 91.3 ± 0.7 | | | | 86.6 ± 5.3 | | | |
| K1-70 IgG | | | | | | | | |
| 0.3 ng/mL | 0 | | | | 0 | | | |
| 1 ng/mL | 0 | | | | 0 | | | |
| 3 ng/mL | 1.0 ± 5.9 | | | | 5.2 ± 4.0 | 0.56 | 186.7 | |
| 10 ng/mL | 14.9 ± 2.1 | 1.0 | 100 | | 21.1 ± 2.1 | 1.45 | 145 | 166.1 |
| 30 ng/mL | 36.4 ± 1.6 | 3.5 | 117 | 114 | 55.8 ± 0.6 | 5 | 166.7 | |
| 100 ng/mL | 71.9 ± 1.4 | 12.5 | 125 | | 89.8 ± 0.7 | | | |
| 300 ng/mL | 89.4 ± 0.6 | | | | 89.2 ± 0.6 | | | |
| 1000 ng/mL | 93.2 ± 0.7 | | | | 90.7 ± 1.4 | | | |

See legend to Table 1a for details. $^{125}$I-TSH binding in the presence of assay buffer was 12.6%. $^{125}$I-TSH binding in the presence of HBD pool was 12.9%.

TABLE 3a

Inhibition of TSH-biotin binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 96.9 ± 0.2 | 98.6 ± 0.1 |
| 30 µg/mL | 96.7 ± 0.2 | 98.4 ± 0.1 |
| 10 µg/mL | 96.2 ± 0.2 | 98.3 ± 0.1 |
| 3 µg/mL | 96.6 ± 0.2 | 98.2 ± 0.1 |
| 1 µg/mL | 96.6 ± 0.3 | 96.2 ± 0.2 |
| 0.3 µg/mL | 93.8 ± 0.4 | 90.7 ± 0.3 |
| 0.1 µg/mL | 76.3 ± 1.8 | 55.0 ± 0.2 |
| 0.03 µg/mL | 33.8 ± 1.2 | 31.9 ± 0.3 |
| 0.01 µg/mL | 12.9 ± 2.8 | 10.0 ± 0.8 |
| 0.003 µg/mL | 1.6 ± 0.5 | 1.4 ± 2.1 |
| 0.001 µg/mL | −4.2 ± 0.9 | −3.7 ± 1.1 |
| M22 IgG | | |
| 100 µg/mL | 96.8 ± 0.2 | 98.8 ± 0.1 |
| 30 µg/mL | 97.0 ± 0.1 | 98.8 ± 0.1 |
| 10 µg/mL | 97.0 ± 0.1 | 98.7 ± 0.1 |
| 3 µg/mL | 97.1 ± 0.1 | 98.6 ± 0.1 |
| 1 µg/mL | 97.0 ± 0.1 | 98.3 ± 0.0 |
| 0.3 µg/mL | 96.0 ± 0.2 | 95.5 ± 0.1 |
| 0.1 µg/mL | 88.3 ± 1.1 | 78.2 ± 0.7 |
| 0.03 µg/mL | 35.2 ± 2.4 | 33.3 ± 2.0 |
| 0.01 µg/mL | 14.9 ± 2.0 | 17.5 ± 2.0 |
| 0.003 µg/mL | 9.2 ± 3.4 | 12.1 ± 4.7 |
| 0.001 µg/mL | 0.4* | 7.8 ± 5.1 |
| 5C9 IgG | | |
| 100 µg/mL | 54.3 ± 1.3 | 37.1 ± 2.2 |
| 10 µg/mL | 37.8 ± 2.1 | 37.4 ± 0.9 |
| 1 µg/mL | 31.4 ± 1.9 | 28.5 ± 1.6 |
| 0.1 µg/mL | 26.1 ± 3.2 | 10.4 ± 1.6 |
| 0.01 µg/mL | 7.5 ± 0.9 | −2.6 ± 2.3 |
| TSMAb 1 IgG | | |
| 100 µg/mL | 84.3 ± 0.8 | 82.6 ± 2.2 |
| 10 µg/mL | 73.4 ± 2.8 | 74.6 ± 1.3 |
| 1 µg/mL | 44.3 ± 1.2 | 47.9* |
| 0.1 µg/mL | 3.8 ± 5.9 | 21.2 ± 1.5 |
| 0.01 µg/mL | −6.3 ± 3.3 | 12.8 ± 2.9 |
| TSMAb 2 IgG | | |
| 100 µg/mL | 85.2 ± 0.3 | 78.6 ± 1.4 |
| 10 µg/mL | 77.0 ± 0.7 | 75.1 ± 0.6 |
| 1 µg/mL | 67.3 ± 1.5 | 65.0 ± 1.0 |
| 0.1 µg/mL | 39.6 ± 0.8 | 29.1 ± 0.7 |
| 0.01 µg/mL | 8.8 ± 0.4 | 7.5 ± 0.1 |
| TSMAb 3 IgG | | |
| 100 µg/mL | 82.6 ± 0.1 | 78.6 ± 1.4 |
| 10 µg/mL | 77.0 ± 0.7 | 75.1 ± 0.6 |
| 1 µg/mL | 67.3 ± 1.5 | 65.0 ± 1.0 |
| 0.1 µg/mL | 39.6 ± 0.8 | 29.1 ± 0.7 |
| 0.01 µg/mL | 8.8 ± 0.4 | 7.5 ± 0.1 |
| TSMAb 4 IgG | | |
| 100 µg/mL | 73.1 ± 1.8 | 81.0 ± 1.5 |
| 10 µg/mL | 72.0 ± 0.5 | 79.6 ± 0.3 |
| 1 µg/mL | 73.1 ± 1.3 | 73.3 ± 1.3 |
| 0.1 µg/mL | 59.0 ± 1.7 | 50.1 ± 1.6 |
| 0.01 µg/mL | 18.9 ± 0.7 | 14.8 ± 3.8 |
| TSMAb 5 IgG | | |
| 100 µg/mL | 89.9 ± 0.3 | 85.2 ± 0.1 |
| 10 µg/mL | 85.8 ± 0.7 | 82.8 ± 0.4 |
| 1 µg/mL | 79.0 ± 2.2 | 79.2 ± 0.7 |
| 0.1 µg/mL | 60.9 ± 4.0 | 55.2 ± 0.9 |
| 0.01 µg/mL | 19.1 ± 3.1 | 19.3 ± 0.4 |
| TSMAb 6 IgG | | |
| 100 µg/mL | 80.3 ± 1.0 | 77.8 ± 0.6 |
| 10 µg/mL | 73.0 ± 0.6 | 75.6 ± 0.4 |
| 1 µg/mL | 69.5 ± 2.5 | 73.6 ± 0.9 |
| 0.1 µg/mL | 58.5 ± 3.1 | 54.7 ± 2.3 |
| 0.01 µg/mL | 16.9 ± 3.1 | 19.2 ± 1.8 |
| TSMAb 7 IgG | | |
| 100 µg/mL | 83.1 ± 0.7 | 77.6 ± 0.5 |
| 10 µg/mL | 75.3 ± 0.2 | 73.4 ± 0.8 |
| 1 µg/mL | 62.8 ± 2.3 | 67.4 ± 1.9 |
| 0.1 µg/mL | 38.2 ± 7.1 | 36.8 ± 3.4 |
| 0.01 µg/mL | 14.1 ± 3.8 | 20.5 ± 1.7 |
| 9D33 IgG | | |
| 100 µg/mL | 86.8 ± 0.3 | 84.0 ± 0.3 |
| 10 µg/mL | 84.8 ± 0.2 | 83.2 ± 0.2 |
| 1 µg/mL | 81.8 ± 0.1 | 76.0 ± 0.4 |
| 0.1 µg/mL | 59.7 ± 0.5 | 39.0 ± 1.5 |
| 0.01 µg/mL | 15.3 ± 0.9 | 10.1 ± 4.2 |
| 5B3 IgG | | |
| 100 µg/mL | 1.3 ± 1.9 | −2.3 ± 2.2 |
| 10 µg/mL | −8.4 ± 2.3 | −1.6 ± 3.3 |
| 1 µg/mL | −8.3 ± 3.8 | −3.5 ± 0.5 |
| 0.1 µg/mL | −7.8 ± 10.0 | −1.2 ± 4.3 |
| 0.01 µg/mL | −5.9 ± 4.4 | −5.1 ± 3.3 |

Results shown are mean ± SD of triplicate determinations.

*mean of duplicate determinations

HBD = pool of healthy blood donor sera. 5B3 is a human MAb to glutamic acid decarboxylase (negative control). Assay buffer is 50 mmol/L NaCl, 10 mmol/L Tris pH 7.8, 0.1% Triton X-100, 1 mg/mL BSA.

TABLE 3b

Inhibition of TSH-biotin binding to TSHR coated ELISA plate wells by K1-18 IgG and K1-18 Fab

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 97.0 ± 0.2 | 98.1 ± 0.0 |
| 30 µg/mL | 97.0 ± 0.1 | 97.9 ± 0.2 |
| 10 µg/mL | 96.9 ± 0.1 | 97.9 ± 0.1 |
| 3 µg/mL | 96.8 ± 0.2 | 97.9 ± 0.0 |
| 1 µg/mL | 96.3 ± 0.1 | 96.8 ± 0.0 |
| 0.3 µg/mL | 94.2 ± 0.1 | 87.8 ± 0.1 |
| 0.1 µg/mL | 78.1 ± 0.3 | 61.8 ± 0.1 |
| 0.03 µg/mL | 34.9 ± 0.3 | 26.3 ± 1.1 |
| 0.01 µg/mL | 13.7 ± 0.4 | 8.2 ± 1.2 |
| 0.003 µg/mL | 8.5 ± 1.1 | 3.0 ± 2.9 |
| 0.001 µg/mL | 0.8 ± 2.6 | −1.9 ± 0.1 |
| K1-18 Fab | | |
| 100 µg/mL | 93.8 ± 0.2 | 95.6 ± 0.1 |
| 30 µg/mL | 93.6 ± 0.2 | 95.6 ± 0.1 |
| 10 µg/mL | 93.3 ± 0.1 | 95.6 ± 0.3 |
| 3 µg/mL | 92.9 ± 0.6 | 95.3 ± 0.2 |
| 1 µg/mL | 91.2 ± 0.2 | 92.9 ± 0.4 |
| 0.3 µg/mL | 85.1 ± 0.4 | 80.3 ± 0.2 |
| 0.1 µg/mL | 61.7 ± 1.6 | 47.7 ± 0.7 |
| 0.03 µg/mL | 28.9 ± 2.6 | 18.2 ± 1.6 |
| 0.01 µg/mL | 10.5 ± 3.0 | 5.7* |
| 0.003 µg/mL | 5.1 ± 0.9 | 3.1 ± 4.7 |
| 0.001 µg/mL | −0.1 ± 2.3 | 0.3 ± 2.2 |

TABLE 3b-continued

Inhibition of TSH-biotin binding to TSHR coated ELISA plate wells by K1-18 IgG and K1-18 Fab

| Test sample | Inhibition of binding (%) Dilutions in assay buffer (mean ± SD) | Inhibition of binding (%) Dilutions in HBD (mean ± SD) |
|---|---|---|
| M22 Fab | | |
| 0.1 µg/mL | 92.9 ± 0.3 | 89.7 ± 0.5 |
| 0.03 µg/mL | 57.0 ± 1.5 | 49.9 ± 2.2 |
| 0.01 µg/mL | 18.6 ± 3.0 | 16.3 ± 3.2 |
| 0.003 µg/mL | 5.3 ± 1.8 | 5.4 ± 5.6 |
| 0.001 µg/mL | −0.1 ± 0.5 | −1.4 ± 7.0 |

See legend to Table 3a for details. Results of negative control MAb (5B3 IgG) are shown in Table 3a.

TABLE 3c

Inhibition of TSH-biotin binding to TSHR coated plate wells by K1-18 IgG (effect of different assay conditions)

| Test sample | % Inhibition (mean ± SD) Dilutions in assay buffer | % Inhibition (mean ± SD) Dilutions in HBD | % Inhibition (mean ± SD) Dilutions in assay buffer + 100 µg/mL 5B3 IgG |
|---|---|---|---|
| K1-18 IgG | | | |
| 100 µg/mL | 96.9 ± 0.2 | 98.6 ± 0.1 | 96.7 ± 0.1 |
| 30 µg/mL | 96.7 ± 0.2 | 98.4 ± 0.1 | 96.7 ± 0.2 |
| 10 µg/mL | 96.2 ± 0.2 | 98.3 ± 0.1 | 96.6 ± 0.1 |
| 3 µg/mL | 96.6 ± 0.2 | 98.2 ± 0.1 | 96.6 ± 0.1 |
| 1 µg/mL | 96.6 ± 0.3 | 96.2 ± 0.2 | 96.4 ± 0.0 |
| 0.3 µg/mL | 93.8 ± 0.4 | 90.7 ± 0.3 | 94.8 ± 0.1 |
| 0.1 µg/mL | 76.3 ± 1.8 | 55.0 ± 0.2 | 82.8 ± 0.4 |
| 0.03 µg/mL | 33.8 ± 1.2 | 31.9 ± 0.2 | 45.6 ± 1.1 |
| 0.01 µg/mL | 12.9 ± 2.8 | 10.0 ± 0.8 | 17.6 ± 4.9 |
| 0.003 µg/mL | 1.6 ± 0.5 | 1.4 ± 2.1 | 4.6 ± 1.3 |
| 0.001 µg/mL | −4.2 ± 0.9 | −3.7 ± 1.1 | −4.0 ± 5.2 |
| M22 IgG | | | |
| 100 µg/mL | 96.8 ± 0.2 | 98.8 ± 0.1 | 97.2 ± 0.9 |
| 30 µg/mL | 97.0 ± 0.1 | 98.8 ± 0.1 | 97.0 ± 0.1 |
| 10 µg/mL | 97.0 ± 0.1 | 98.7 ± 0.1 | 97.0 ± 0.0 |
| 3 µg/mL | 97.1 ± 0.1 | 98.6 ± 0.1 | 96.9 ± 0.0 |
| 1 µg/mL | 97.0 ± 0.1 | 98.3 ± 0.0 | 96.8 ± 0.0 |
| 0.3 µg/mL | 96.0 ± 0.2 | 95.5 ± 0.1 | 96.4 ± 0.0 |
| 0.1 µg/mL | 88.3 ± 1.1 | 78.2 ± 0.7 | 91.2 ± 0.1 |
| 0.03 µg/mL | 35.2 ± 2.4 | 33.3 ± 2.0 | 43.6 ± 3.4 |
| 0.01 µg/mL | 14.9 ± 2.0 | 17.5 ± 2.0 | 12.9 ± 2.0 |
| 0.003 µg/mL | 9.2 ± 3.4 | 12.1 ± 4.7 | −0.5 ± 5.1 |
| 0.001 µg/mL | 0.4* | 7.8 ± 5.1 | −7.7 ± 5.8 |
| 5C9 IgG | | | |
| 100 µg/mL | 91.2 ± 0.8 | 48.6 ± 1.8 | 92.3 ± 0.3 |
| 10 µg/mL | 58.2 ± 0.5 | 42.6 ± 4.6 | 63.9 ± 0.8 |
| 1 µg/mL | 42.9 ± 1.6 | 35.7 ± 4.0 | 46.7 ± 1.7 |
| 0.1 µg/mL | 34.9 ± 4.0 | 21.6 ± 4.7 | 36.3 ± 2.0 |
| 0.01 µg/mL | 16.1 ± 2.9 | 7.5 ± 5.4 | 20.7 ± 2.9 |
| 5B3 IgG | | | |
| 100 µg/mL | 8.3 ± 2.4 | 10.9 ± 2.9 | 1.1 ± 3.6 |
| 10 µg/mL | 0.9 ± 0.6 | 11.6 ± 3.3 | −4.8 ± 1.8 |
| 1 µg/mL | −1.0 ± 0.2 | 8.0 ± 1.7 | −4.8 ± 3.2 |
| 0.1 µg/mL | −2.0 ± 0.7 | 8.6 ± 1.9 | −6.4 ± 2.6 |

See legend to Table 3a for details.

TABLE 3d

Inhibition of TSH-biotin binding to TSHR coated plate wells by K1-70 IgG and K1-70 Fab

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 µg/mL | 97.2 ± 0.2 | 98.2 ± 0.1 |
| 30 µg/mL | 97.2 ± 0.1 | 98.2 ± 0.1 |
| 10 µg/mL | 97.3 ± 0.1 | 97.9 ± 0 |
| 3 µg/mL | 97.2 ± 0.2 | 97.8 ± 0.1 |
| 1 µg/mL | 97.3 ± 0.1 | 97.4 ± 0.2 |
| 0.3 µg/mL | 97.0 ± 0.1 | 93.8 ± 0.1 |
| 0.1 µg/mL | 91.3 ± 0.8 | 74.1 ± 0.4 |
| 0.03 µg/mL | 45.0 ± 3.1 | 35.0 ± 1.0 |
| 0.01 µg/mL | 10.7 ± 0.7 | 13.6 ± 1.4 |
| 0.003 µg/mL | −1.7 ± 2.6 | 12.1 ± 2.8 |
| 0.001 µg/mL | −0.1 ± 3.9 | 3.5 ± 1.8 |
| K1-70 Fab | | |
| 100 µg/mL | 96.5 ± 0.2 | 97.3 ± 0.1 |
| 30 µg/mL | 96.4 ± 0 | 97.4 ± 0.2 |
| 10 µg/mL | 96.3 ± 0.1 | 97.3 ± 0 |
| 3 µg/mL | 97.3 ± 0.2 | 97.3 ± 0.1 |
| 1 µg/mL | 96.2 ± 0.1 | 96.9 ± 0.1 |
| 0.3 µg/mL | 95.8 ± 0.1 | 95.8 ± 0.7 |
| 0.1 µg/mL | 94.2 ± 0.6 | 88.3 ± 0.3 |
| 0.03 µg/mL | 57.6 ± 1.2 | 55.5 ± 1.5 |
| 0.01 µg/mL | 23.4 ± 3.1 | 18.2 ± 0.6 |
| 0.003 µg/mL | 18.3 ± 0.6 | 9.2 ± 5.6 |
| 0.001 µg/mL | −3.2 ± 3.3 | 4.8 ± 4.7 |

See legend to Table 3a for details. Results of negative control MAb (5B3 IgG) are shown in Table 3a.

TABLE 4a

Inhibition of M22-peroxidase binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 98.4 ± 0.1 | 98.0 ± 0.1 |
| 30 µg/mL | 98.2 ± 0.1 | 97.8 ± 0.1 |
| 10 µg/mL | 98.2 ± 0.1 | 97.6 ± 0.2 |
| 3 µg/mL | 98.1 ± 0.1 | 97.2 ± 0.1 |
| 1 µg/mL | 97.2 ± 0.3 | 94.5 ± 0.0 |
| 0.3 µg/mL | 92.1 ± 0.7 | 81.6 ± 0.5 |
| 0.1 µg/mL | 73.9 ± 7.1 | 49.8 ± 0.6 |
| 0.03 µg/mL | 29.9 ± 5.3 | 21.0 ± 1.3 |
| 0.01 µg/mL | 9.1 ± 3.7 | 1.2 ± 4.6 |
| 0.003 µg/mL | −1.7 ± 4.0 | 0.4 ± 4.3 |
| 0.001 µg/mL | −5.2 ± 4.7 | −0.0 ± 2.0 |
| M22 IgG | | |
| 100 µg/mL | 98.9 ± 0.1 | 98.6 ± 0.1 |
| 30 µg/mL | 98.6 ± 0.1 | 98.4 ± 0.0 |
| 10 µg/mL | 98.6 ± 0.1 | 98.4 ± 0.1 |
| 3 µg/mL | 98.4 ± 0.1 | 98.0 ± 0.2 |
| 1 µg/mL | 98.3 ± 0.0 | 97.4 ± 0.1 |
| 0.3 µg/mL | 96.7 ± 0.3 | 93.2 ± 0.3 |
| 0.1 µg/mL | 90.6 ± 0.9 | 79.4 ± 0.5 |
| 0.03 µg/mL | 66.0 ± 2.1 | 51.0 ± 2.4 |
| 0.01 µg/mL | 29.5 ± 0.9 | 22.7 ± 3.7 |
| 0.003 µg/mL | 5.7 ± 1.4 | 8.8 ± 4.4 |
| 0.001 µg/mL | 2.0 ± 4.1 | 2.6 ± 3.4 |
| 5C9 IgG | | |
| 100 µg/mL | 24.6 ± 1.3 | 19.6 ± 5.3 |
| 10 µg/mL | 13.2 ± 2.6 | 13.0 ± 2.6 |
| 1 µg/mL | 12.1 ± 2.1 | 7.8 ± 2.4 |
| 0.1 µg/mL | 7.1 ± 0.9 | 6.3 ± 2.7 |
| 0.01 µg/mL | 0.6 ± 3.6 | 0.9 ± 1.0 |

TABLE 4a-continued

Inhibition of M22-peroxidase binding to TSHR coated ELISA plate wells by K1-18 IgG and different TSHR monoclonal antibodies

| Test sample | Inhibition of binding (%) Dilutions in assay buffer (mean ± SD) | Inhibition of binding (%) Dilutions in HBD (mean ± SD) |
|---|---|---|
| TSMAb 1 IgG | | |
| 100 µg/mL | 74.0 ± 0.6 | 71.0 ± 1.2 |
| 10 µg/mL | 68.6 ± 0.4 | 63.5 ± 1.9 |
| 1 µg/mL | 39.0 ± 1.8 | 30.6 ± 3.8 |
| 0.1 µg/mL | 8.8 ± 1.8 | 2.4 ± 3.4 |
| 0.01 µg/mL | 4.3 ± 1.7 | −6.3 ± 1.1 |
| TSMAb 2 IgG | | |
| 100 µg/mL | 63.1 ± 0.2 | 65.2 ± 3.9 |
| 10 µg/mL | 58.3 ± 1.2 | 62.4 ± 1.2 |
| 1 µg/mL | 52.8 ± 0.7 | 56.4 ± 3.9 |
| 0.1 µg/mL | 29.5 ± 1.6 | 25.8 ± 2.8 |
| 0.01 µg/mL | 5.6 ± 2.8 | 8.4 ± 3.8 |
| TSMAb 3 IgG | | |
| 100 µg/mL | 34.5 ± 0.5 | 42.7 ± 2.9 |
| 10 µg/mL | 38.4 ± 1.5 | 40.7 ± 3.1 |
| 1 µg/mL | 34.3 ± 1.5 | 29.8 ± 2.5 |
| 0.1 µg/mL | 19.4 ± 1.6 | 16.7 ± 7.1 |
| 0.01 µg/mL | 8.2 ± 1.3 | 3.8 ± 3.1 |
| TSMAb 4 IgG | | |
| 100 µg/mL | 56.6 ± 2.8 | 55.2 ± 3.1 |
| 10 µg/mL | 56.0 ± 1.7 | 55.4 ± 1.8 |
| 1 µg/mL | 55.6 ± 1.3 | 52.4 ± 1.3 |
| 0.1 µg/mL | 40.2 ± 1.6 | 25.2 ± 0.7 |
| 0.01 µg/mL | 13.7 ± 3.5 | 11.6 ± 5.0 |
| TSMAb 5 IgG | | |
| 100 µg/mL | 67.2 ± 1.2 | 63.7 ± 1.7 |
| 10 µg/mL | 65.4 ± 1.0 | 63.6 ± 2.3 |
| 1 µg/mL | 63.4 ± 1.0 | 59.2 ± 1.1 |
| 0.1 µg/mL | 54.3 ± 2.8 | 37.1 ± 1.9 |
| 0.01 µg/mL | 22.6 ± 1.3 | 9.1 ± 2.9 |
| TSMAb 6 IgG | | |
| 100 µg/mL | 62.9 ± 4.4 | 56.3 ± 2.0 |
| 10 µg/mL | 55.8 ± 1.1 | 52.2 ± 1.5 |
| 1 µg/mL | 54.7 ± 0.7 | 51.3 ± 1.1 |
| 0.1 µg/mL | 40.7 ± 2.5 | 37.3 ± 5.7 |
| 0.01 µg/mL | 11.6 ± 2.5 | 2.9 ± 1.6 |
| TSMAb 7 IgG | | |
| 100 µg/mL | 51.2 ± 1.0 | 46.8 ± 0.2 |
| 10 µg/mL | 54.1 ± 4.4 | 46.1 ± 1.2 |
| 1 µg/mL | 46.9 ± 1.1 | 44.9 ± 2.2 |
| 0.1 µg/mL | 28.9 ± 2.9 | 28.3 ± 8.5 |
| 0.01 µg/mL | 3.9 ± 1.5 | 1.4 ± 1.4 |
| 9D33 IgG | | |
| 100 µg/mL | 64.1 ± 1.7 | 65.9 ± 0.3 |
| 10 µg/mL | 64.2 ± 1.7 | 66.7 ± 1.4 |
| 1 µg/mL | 60.1 ± 0.9 | 57.8 ± 1.2 |
| 0.1 µg/mL | 35.1 ± 2.0 | 24.1 ± 1.9 |
| 0.01 µg/mL | 14.8 ± 3.5 | 6.2 ± 4.9 |
| 5B3 IgG | | |
| 100 µg/mL | 8.1 ± 0.9 | 3.8 ± 2.5 |
| 10 µg/mL | 2.4 ± 1.2 | 4.9 ± 7.1 |
| 1 µg/mL | 3.4 ± 1.7 | 9.7 ± 3.9 |
| 0.1 µg/mL | 1.4 ± 1.9 | 3.0 ± 3.1 |
| 0.01 µg/mL | 2.2 ± 6.1 | 4.3 ± 3.0 |

Results shown are mean ± SD of triplicate determinations.
*mean of duplicate determinations
HBD = pool of healthy blood donor sera. 5B3 is a human MAb to glutamic acid decarboxylase (negative control). Assay buffer is 50 mmol/L NaCl, 10 mmol/L Tris pH 7.8, 0.1% Triton X-100, 1 mg/mL BSA.

TABLE 4b

Inhibition of M22-peroxidase binding to TSHR coated ELISA plate wells by K1-18 IgG, K1-18 Fab and M22 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 3 µg/mL | 97.7 ± 0.1 | 96.7 ± 0.3 |
| 1 µg/mL | 96.5 ± 0.4 | 93.2 ± 0.3 |
| 0.3 µg/mL | 91.9 ± 0.8 | 82.2 ± 1.2 |
| 0.1 µg/mL | 71.9 ± 0.6 | 45.3 ± 1.5 |
| 0.03 µg/mL | 37.2 ± 2.6 | 24.4 ± 1.7 |
| 0.01 µg/mL | 16.7 ± 0.9 | 4.7 ± 0.6 |
| 0.003 µg/mL | 6.5* | 2.6* |
| K1-18 Fab | | |
| 100 µg/mL | 95.1 ± 0.8 | 93.4 ± 0.4 |
| 30 µg/mL | 94.8 ± 0.1 | 92.6 ± 0.2 |
| 10 µg/mL | 93.6 ± 0.4 | 92.0 ± 0.3 |
| 3 µg/mL | 92.5 ± 0.1 | 91.7 ± 0.5 |
| 1 µg/mL | 90.4 ± 0.1 | 87.5 ± 0.9 |
| 0.3 µg/mL | 79.5 ± 0.1 | 70.4 ± 1.7 |
| 0.1 µg/mL | 53.5 ± 0.3 | 47.3 ± 6.3 |
| 0.03 µg/mL | 24.6 ± 3.4 | 14.5 ± 4.7 |
| 0.01 µg/mL | 11.2 ± 1.9 | 11.7 ± 7 |
| 0.003 µg/mL | 6.3 ± 1.1 | 4.9 ± 7.9 |
| 0.001 µg/mL | 3.6* | 2.4 ± 5.0 |
| M22 Fab | | |
| 3 µg/mL | 97.5 ± 0.3 | 96.8 ± 0.3 |
| 1 µg/mL | 97.2 ± 0.3 | 96.4 ± 0.2 |
| 0.3 µg/mL | 96.9 ± 0.1 | 94.7 ± 0.3 |
| 0.1 µg/mL | 93.9 ± 0.5 | 85.2 ± 0.3 |
| 0.03 µg/mL | 80.0 ± 1.1 | 60.0 ± 4.9 |
| 0.01 µg/mL | 44.7 ± 2.0 | 28.8 ± 1.1 |
| 0.003 µg/mL | 17.4 ± 3.8 | 13.1 ± 3.1 |
| 0.001 µg/mL | 5.0* | 8.5* |

See legend to Table 4a for details. Results of negative control MAb (5B3 IgG) are shown in Table 4a.

TABLE 4c

Inhibition of M22-peroxidase binding to TSHR coated ELISA plate wells by K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-70 IgG | | |
| 100 µg/mL | 98.5 ± 0.3 | 98.3 ± 0.2 |
| 30 µg/mL | 98.2 ± 0.1 | 97.9 ± 0.1 |
| 10 µg/mL | 97.9 ± 0.2 | 97.8 ± 0.1 |
| 3 µg/mL | 98.1 ± 0.2 | 97.6 ± 0.1 |
| 1 µg/mL | 98.1 ± 0.1 | 96.4 ± 0.2 |
| 0.3 µg/mL | 97.3 ± 0.3 | 91.1 ± 0.3 |
| 0.1 µg/mL | 93.0 ± 0.3 | 69.7 ± 0.7 |
| 0.03 µg/mL | 71.8 ± 4.2 | 34.5 ± 3.8 |
| 0.01 µg/mL | 28.0 ± 2.8 | 9.2 ± 2.6 |
| 0.003 µg/mL | 6.4 ± 3.1 | 9.6* |
| 0.001 µg/mL | −5.0 ± 2.7 | 0.8* |
| K1-70 Fab | | |
| 100 µg/mL | 97.4 ± 0.1 | 97.4 ± 0.1 |
| 30 µg/mL | 97.6 ± 0.05 | 97.5 ± 0.2 |
| 10 µg/mL | 97.5 ± 0.1 | 97.1 ± 0.1 |
| 3 µg/mL | 97.2 ± 0.2 | 96.5 ± 0.5 |
| 1 µg/mL | 97.2 ± 0.1 | 96.1 ± 0.3 |
| 0.3 µg/mL | 96.8 ± 0.2 | 94.4 ± 0.1 |
| 0.1 µg/mL | 94.6 ± 0.2 | 86.0 ± 0.4 |
| 0.03 µg/mL | 82.0 ± 0.7 | 58.8 ± 1.2 |
| 0.01 µg/mL | 57.5 ± 3.7 | 27.9 ± 3.2 |
| 0.003 µg/mL | 21.8 ± 3.9 | 8.2 ± 2.1 |
| 0.001 µg/mL | 4.9 ± 0.4 | −6.6 ± 1.9 |

TABLE 4c-continued

Inhibition of M22-peroxidase binding to TSHR coated ELISA plate wells by K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 1 µg/mL | 96.3 ± 0.2 | 94.6 ± 0.2 |
| 0.1 µg/mL | 71.9 ± 0.9 | 56.3 ± 1.1 |
| 0.03 µg/mL | 35.7 ± 4.2 | 13.6 ± 0.8 |
| 0.01 µg/mL | 8.9 ± 3.2 | −4.0 ± 4.9 |
| 0.003 µg/mL | −1.9* | −1.3 ± 2.9 |

See legend to Table 4a for details. Results of negative control MAb (5B3 IgG) are shown in Table 4a.

TABLE 5a

Inhibition of $^{125}$I-K1-18 IgG binding to TSHR coated tubes by K1-18 IgG, K1-18 Fab, K1-70 IgG and other MAbs

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 94.0 ± 0.9 | 94.9 ± 0.2 |
| 30 µg/mL | 93.2 ± 0.3 | 94.7 ± 0.2 |
| 10 µg/mL | 92.4 ± 1.5 | 93.6 ± 0.9 |
| 3 µg/mL | 93.0 ± 0.3 | 93.5 ± 0.8 |
| 1 µg/mL | 92.6 ± 0.4 | 91.7 ± 0.8 |
| 0.3 µg/mL | 91.0 ± 0.5 | 84.6 ± 0.5 |
| 0.1 µg/mL | 82.9 ± 1.8 | 69.0 ± 0.5 |
| 0.03 µg/mL | 52.7 ± 0.9 | 36.0 ± 1.8 |
| 0.01 µg/mL | 19.4 ± 4.1 | 22.9 ± 2.4 |
| 0.003 µg/mL | 9.2 ± 2.6 | 7.2 ± 3.5 |
| 0.001 µg/mL | 1.9 ± 7.2 | 11.1 ± 4.4 |
| M22 IgG | | |
| 100 µg/ml | 94.5 ± 1.2 | 95.5 ± 0.9 |
| 30 µg/mL | 93.3 ± 0.9 | 94.3 ± 1.2 |
| 10 µg/mL | 93.3 ± 0.8 | 94.9 ± 0.7 |
| 3 µg/mL | 93.4 ± 0.6 | 94.6 ± 0.1 |
| 1 µg/mL | 92.3 ± 0.4 | 94.1 ± 0.4 |
| 0.3 µg/mL | 92.2 ± 0.3 | 92.4 ± 0.6 |
| 0.1 µg/mL | 87.1 ± 0.5 | 80.9 ± 0.3 |
| 0.03 µg/mL | 53.3 ± 3.4 | 56.5 ± 1.7 |
| 0.01 µg/mL | 18.3 ± 5.3 | 36.9 ± 5.4 |
| 0.003 µg/mL | 5.1 ± 3.1 | 14.3 ± 3.4 |
| 0.001 µg/mL | −1.6 ± 3.8 | 11.0 ± 0.4 |
| M22 Fab | | |
| 100 µg/ml | 95.0 ± 0.6 | 94.1 ± 0.9 |
| 10 µg/mL | 91.8 ± 0.8 | 92.6 ± 1.2 |
| 1 µg/mL | 91.6 ± 0.8 | 92.8 ± 0.2 |
| 0.1 µg/mL | 90.2 ± 0.1 | 87.4 ± 0.5 |
| 0.01 µg/mL | 39.1 ± 2.8 | 48.0 ± 1.0 |
| 0.001 µg/mL | 2.9 ± 2.8 | 9.3* |
| K1-70 IgG | | |
| 100 µg/ml | 94.6 ± 1.2 | 95.2 ± 2.0 |
| 30 µg/mL | 94.6 ± 0.6 | 95.2 ± 0.1 |
| 10 µg/mL | 93.6 ± 0.8 | 94.5 ± 0.3 |
| 3 µg/mL | 93.1 ± 1.0 | 94.6 ± 0.5 |
| 1 µg/mL | 93.6 ± 1.4 | 93.1 ± 0.1 |
| 0.3 µg/mL | 92.7 ± 0.5 | 88.6 ± 0.3 |
| 0.1 µg/mL | 89.0 ± 1.9 | 87.1 ± 1.3 |
| 0.03 µg/mL | 55.7 ± 1.4 | 58.6 ± 2.0 |
| 0.01 µg/mL | 18.5 ± 4.1 | 48.7 ± 1.3 |
| 0.003 µg/mL | 1.5 ± 2.9 | 17.5 ± 3.9 |
| 0.001 µg/mL | 1.3 ± 4.1 | 10.7 ± 0.9 |
| 4B4 IgG | | |
| 100 µg/mL | 20.7 ± 2.7 | −1.6 ± 2.3 |
| 10 µg/mL | 5.1 ± 3.9 | 0.6 ± 3.0 |
| 1 µg/mL | 4.5 ± 2.9 | 7.4 ± 5.4 |
| 0.1 µg/mL | −2.3 ± 2.0 | 1.8 ± 4.3 |
| 0.01 µg/mL | −3.5 ± 4.24 | −0.8 ± 1.3 |
| 4B4 Fab | | |
| 100 µg/mL | −6.3 ± 0.8 | −0.2 ± 1.0 |
| 10 µg/mL | −4.9 ± 3.9 | 3.0 ± 1.5 |
| 5C9 IgG | | |
| 100 µg/mL | 91.3 ± 0.4 | 57.7 ± 2.4 |
| 10 µg/mL | 65.9 ± 1.4 | 46.7 ± 0.6 |
| 1 µg/mL | 48.0 ± 7.5 | 26.8* |
| 0.1 µg/mL | 33.4 ± 0.2 | 21.3 ± 6.4 |
| 0.01 µg/mL | 11.7 ± 1.8 | −1.8 ± 2.7 |
| TSMAb 1 IgG | | |
| 100 µg/mL | 56.1 ± 2.0 | 62.5 ± 4.0 |
| 10 µg/mL | 46.0 ± 2.2 | 57.8 ± 1.5 |
| 1 µg/mL | 41.0 ± 0.4 | 36.3 ± 1.0 |
| 0.1 µg/mL | 17.6 ± 4.5 | 3.8 ± 3.8 |
| 0.01 µg/mL | 3.6 ± 9.5 | −6.9 ± 3.4 |
| TSMAb 2 IgG | | |
| 100 µg/mL | 72.8 ± 5.9 | 64.5 ± 7.3 |
| 10 µg/mL | 48.2 ± 1.5 | 62.0 ± 2.6 |
| 1 µg/mL | 43.2 ± 2.0 | 48.8 ± 2.8 |
| 0.1 µg/mL | 37.1 ± 0.6 | 30.2 ± 3.2 |
| 0.01 µg/mL | 7.6 ± 1.2 | 4.9 ± 2.0 |
| TSMAb 3 IgG | | |
| 100 µg/mL | 62.7 ± 1.2 | 64.8 ± 7.4 |
| 10 µg/mL | 54.2 ± 0.4 | 55.6 ± 0.4 |
| 1 µg/mL | 54.3 ± 1.3 | 46.1 ± 1.3 |
| 0.1 µg/mL | 45.7 ± 5.1 | 24.0 ± 8.5 |
| 0.01 µg/mL | 23.4 ± 3.8 | −1.5 ± 2.0 |
| TSMAb 4 IgG | | |
| 100 µg/mL | 64.4 ± 2.0 | 81.6 ± 3.8 |
| 10 µg/mL | 59.7 ± 0.4 | 75.7 ± 2.1 |
| 1 µg/mL | 57.5 ± 1.5 | 70.5 ± 4.6 |
| 0.1 µg/mL | 48.5 ± 0.7 | 39.2 ± 0.3 |
| 0.01 µg/mL | 12.3 ± 2.9 | 5.1 ± 0.9 |
| TSMAb 5 IgG | | |
| 100 µg/mL | 71.9 ± 1.0 | 85.3 ± 3.4 |
| 10 µg/mL | 67.7 ± 1.5 | 78.9 ± 1.6 |
| 1 µg/mL | 60.5 ± 1.0 | 70.8 ± 1.1 |
| 0.1 µg/mL | 52.7 ± 0.7 | 47.7 ± 1.8 |
| 0.01 µg/mL | 14.4 ± 1.5 | 17.5 ± 9.9 |
| TSMAb 6 IgG | | |
| 100 µg/mL | 72.0 ± 1.6 | 71.3 ± 1.6 |
| 10 µg/mL | 49.3 ± 0.6 | 60.5 ± 1.1 |
| 1 µg/mL | 46.9 ± 1.1 | 57.0 ± 0.6 |
| 0.1 µg/mL | 40.4 ± 2.4 | 38.6 ± 3.8 |
| 0.01 µg/mL | 19.1 ± 2.4 | 9.6 ± 2.4 |
| TSMAb 7 IgG | | |
| 100 µg/mL | 68.7 ± 1.0 | 65.3 ± 4.1 |
| 10 µg/mL | 53.4 ± 0.5 | 59.9 ± 1.3 |
| 1 µg/mL | 41.0 ± 0.2 | 54.8 ± 2.3 |
| 0.1 µg/mL | 29.4 ± 1.4 | 28.6 ± 1.0 |
| 0.01 µg/mL | 4.3 ± 2.0 | −1.0 ± 3.0 |
| 9D33 IgG | | |
| 100 µg/mL | 72.5 ± 0.8 | 68.7 ± 2.2 |
| 10 µg/mL | 63.2 ± 0.8 | 68.1 ± 1.5 |
| 1 µg/mL | 63.0 ± 0.9 | 62.1 ± 2.1 |
| 0.1 µg/mL | 54.8 ± 1.4 | 33.8 ± 3.0 |
| 0.01 µg/mL | 20.9 ± 0.7 | 5.3 ± 1.5 |
| 5B3 IgG | | |
| 100 µg/mL | 6.7 ± 2.1 | 29.4 ± 3.4 |
| 10 µg/mL | −2.7 ± 1.1 | −0.1* |

TABLE 5a-continued

Inhibition of $^{125}$I-K1-18 IgG binding to TSHR coated tubes by K1-18 IgG, K1-18 Fab, K1-70 IgG and other MAbs

| Test sample | Inhibition of binding (%) Dilutions in assay buffer (mean ± SD) | Inhibition of binding (%) Dilutions in HBD (mean ± SD) |
|---|---|---|
| 1 µg/mL | −3.8 ± 1.0 | −6.2 ± 0.7 |
| 0.1 µg/mL | −4.8 ± 1.8 | −7.8 ± 0.6 |
| 0.01 µg/mL | −4.2 ± 3.2 | −8.1 ± 1.4 |

Results shown are mean ± SD of triplicate determinations.
*mean of duplicate determinations
HBD = pool of healthy blood donor sera. 4B4 is a human MAb to glutamic acid decarboxylase (negative control). 5B3 is a human MAb to glutamic acid decarboxylase (negative control). $^{125}$I-K1-18 IgG binding in the presence of assay buffer was 13.6%. $^{125}$I-K1-18 IgG binding in the presence of HBD pool was 13.8%. Assay buffer is 50 mmol/L NaCl, 10 mmol/L Tris pH 7.8, 0.1% Triton X-100.

TABLE 5b

Inhibition of $^{125}$I-K1-18 IgG binding to TSHR coated tubes by K1-18 IgG, K1-18 Fab, K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/ml | 94.5 ± 0.8 | 96.1 ± 0.0 |
| 30 µg/mL | 93.8 ± 1.2 | 95.6 ± 0.8 |
| 10 µg/mL | 92.5 ± 1.4 | 94.0 ± 1.2 |
| 3 µg/mL | 93.0 ± 0.5 | 94.0 ± 0.3 |
| 1 µg/mL | 92.8 ± 1.0 | 91.1 ± 0.5 |
| 0.3 µg/mL | 90.9 ± 0.5 | 78.3 ± 3.4 |
| 0.1 µg/mL | 78.9 ± 2.9 | 49.4 ± 2.3 |
| 0.03 µg/mL | 39.3 ± 1.6 | 15.1 ± 2.9 |
| 0.01 µg/mL | 14.9 ± 2.1 | 5.8 ± 5.5 |
| 0.003 µg/mL | 2.9 ± 5.4 | −0.3 ± 2.5 |
| 0.001 µg/mL | 6.9 ± 5.1 | 2.7 ± 1.8 |
| K1-18 Fab | | |
| 100 µg/ml | 86.2 ± 2.2 | 84.8 ± 0.9 |
| 30 µg/mL | 83.0 ± 0.8 | 85.0 ± 0.8 |
| 10 µg/mL | 81.8 ± 0.7 | 83.0 ± 1.7 |
| 3 µg/mL | 81.9 ± 1.3 | 83.4 ± 1.1 |
| 1 µg/mL | 77.5 ± 1.6 | 80.2 ± 1.1 |
| 0.3 µg/mL | 71.1 ± 0.8 | 65.5 ± 1.5 |
| 0.1 µg/mL | 56.7 ± 0.8 | 39.0 ± 2.3 |
| 0.03 µg/mL | 24.8 ± 0.2 | 10.3 ± 2.2 |
| 0.01 µg/mL | 8.8 ± 2.6 | 1.8 ± 2.0 |
| 0.003 µg/mL | 0.8 ± 4.5 | 1.0 ± 1.6 |
| 0.001 µg/mL | −2.6 ± 5.2 | −1.0 ± 3.4 |
| K1-70 IgG | | |
| 100 µg/ml | 94.5 ± 0.6 | 95.3 ± 0.1 |
| 30 µg/mL | 93.1 ± 1.0 | 93.9 ± 1.9 |
| 10 µg/mL | 91.9 ± 0.4 | 95.1 ± 0.3 |
| 3 µg/mL | 92.9 ± 0.9 | 94.1 ± 0.6 |
| 1 µg/mL | 92.0 ± 0.7 | 92.9 ± 0.4 |
| 0.3 µg/mL | 91.5 ± 0.2 | 82.2 ± 0.6 |
| 0.1 µg/mL | 89.2 ± 1.5 | 55.6 ± 1.2 |
| 0.03 µg/mL | 45.6 ± 2.8 | 17.8 ± 2.1 |
| 0.01 µg/mL | 6.8 ± 1.0 | 6.1 ± 4.2 |
| 0.003 µg/mL | 0.1 ± 2.2 | 2.1 ± 3.4 |
| 0.001 µg/mL | −1.7 ± 2.2 | −0.0 ± 2.3 |
| K1-70 Fab | | |
| 100 µg/ml | 93.3 ± 0.6 | 92.5 ± 0.3 |
| 30 µg/mL | 92.2 ± 1.5 | 91.8 ± 2.1 |
| 10 µg/mL | 92.4 ± 1.2 | 92.6 ± 0.4 |
| 3 µg/mL | 91.1 ± 0.8 | 92.8 ± 1.1 |
| 1 µg/mL | 91.0 ± 0.5 | 92.1 ± 0.2 |
| 0.3 µg/mL | 89.6 ± 0.1 | 88.1 ± 1.1 |
| 0.1 µg/mL | 87.6 ± 1.5 | 75.2 ± 1.3 |
| 0.03 µg/mL | 68.8 ± 2.3 | 35.0 ± 3.5 |
| 0.01 µg/mL | 25.6 ± 4.3 | 16.2 ± 1.2 |
| 0.003 µg/mL | 4.1 ± 4.8 | 3.7 ± 2.6 |
| 0.001 µg/mL | −3.9 ± 0.8 | −3.2 ± 4.0 |

TABLE 5b-continued

Inhibition of $^{125}$I-K1-18 IgG binding to TSHR coated tubes by K1-18 IgG, K1-18 Fab, K1-70 IgG and K1-70 Fab preparations

| Test sample | Inhibition of binding (%) Dilutions in assay buffer (mean ± SD) | Inhibition of binding (%) Dilutions in HBD (mean ± SD) |
|---|---|---|
| M22 Fab | | |
| 1 µg/mL | 90.5 ± 0.7 | 91.8 ± 0.4 |
| 0.3 µg/mL | 87.7 ± 4.0 | 87.8 ± 1.8 |
| 0.01 µg/mL | 90.2 ± 0.6 | 77.0 ± 1.7 |
| 0.03 µg/mL | 77.0 ± 1.1 | 39.5 ± 0.7 |
| 0.01 µg/mL | 29.1 ± 6.0 | 10.5 ± 2.9 |
| 0.003 µg/mL | 1.9 ± 3.1 | 1.0 ± 0.5 |
| 0.001 µg/mL | −7.3 ± 3.5 | 3.8 ± 2.6 |
| 4B4 IgG | | |
| 100 µg/mL | 17.7 ± 1.8 | −3.5 ± 2.2 |
| 10 µg/mL | −0.5 ± 2.1 | 0.6 ± 5.3 |
| 1 µg/mL | 2.1 ± 1.5 | −1.2 ± 1.5 |

See legend to Table 5a for details. $^{125}$I-K1-18 IgG binding in the presence of assay buffer was 19.1%. $^{125}$I-K1-18 IgG binding in the presence of HBD pool was 15.3%.

TABLE 5c

Inhibition of $^{125}$I-K1-18 IgG binding to TSHR coated tubes by patient sera positive for TRAb (stimulating and blocking) and by donor serum K1

| Test sample | % Inhibition of $^{125}$I-K1-18 IgG binding | % Inhibition of $^{125}$I-TSH binding |
|---|---|---|
| G1 | 37.8 | 38.6 |
| G2 | 43.1 | 31.5 |
| G3 | 36.5 | 35.6 |
| G4 | 44.1 | 47.1 |
| G5 | 42.6 | 44.7 |
| G6 | 54.5 | 52.1 |
| G7 | 25.5 | 15.9 |
| G8 | 48.2 | 41.8 |
| G9 | 79.5 | 80.0 |
| G10 | 63.1 | 68.7 |
| G11 | 37.2 | 31.0 |
| G12 | 37.2 | 29.7 |
| G13 | 63.1 | 57.9 |
| G14 | 56.4 | 49.3 |
| G15 | 43.8 | 38.6 |
| G16 | 44.0 | 42.9 |
| G17 | 27.7 | 24.5 |
| G18 | 44.5 | 39.1 |
| G19 | 23.2 | 20.6 |
| G20 | 54.4 | 38.4 |
| HBD 1 | 1.9 | −12.6 |
| HBD 2 | −1.2 | −4.2 |
| HBD 3 | 7.7 | −5.4 |
| HBD 4 | 5.7 | −11.8 |
| HBD 5 | 14.7 | −4.7 |
| HBD 6 | 11.8 | 1.8 |
| HBD 7 | 0.0 | −13.7 |
| HBD 8 | 1.5 | −12.8 |
| HBD 9 | 0.2 | −11.0 |
| HBD 10 | 1.1 | −10.6 |
| K1 donor serum | | |
| diluted 10x | 59.3 | 67.2 |
| diluted 20x | 35.2 | 44.0 |
| diluted 40x | 14.2 | 24.8 |
| diluted 80x | 6.9 | 11.9 |
| diluted 160x | 5.1 | 2.7 |
| diluted 320x | 5.7 | 2.1 |
| B1 | | |
| diluted 5x | 88.1 | 91.5 |
| diluted 10x | 77.6 | 83.9 |
| diluted 20x | 57.1 | 65.8 |
| diluted 40x | 35.5 | 39.6 |

TABLE 5c-continued

Inhibition of $^{125}$I-K1-18 IgG binding to TSHR coated tubes by patient sera positive for TRAb (stimulating and blocking) and by donor serum K1

| Test sample | % Inhibition of $^{125}$I-K1-18 IgG binding | % Inhibition of $^{125}$I-TSH binding |
|---|---|---|
| diluted 80x | 18.7 | 20.7 |
| diluted 160x | 11.6 | 7.5 |
| diluted 320x | 5.4 | −2.5 |
| B2 | | |
| diluted 20x | 90.3 | 93.5 |
| diluted 40x | 79.1 | 86.5 |
| diluted 80x | 58.7 | 68.7 |
| diluted 160x | 32.9 | 42.8 |
| diluted 320x | 32.6 | 20.4 |
| diluted 640x | 10.7 | 10.5 |
| diluted 1280x | 9.6 | 14.1 |
| S1 | | |
| diluted 5x | 80.6 | 82.0 |
| diluted 10x | 66.9 | 66.5 |
| diluted 20x | 52.0 | 47.1 |
| diluted 40x | 32.4 | 32.5 |
| diluted 80x | 13.6 | 17.4 |
| diluted 160x | 15.8 | 5.2 |
| diluted 320x | 10.2 | 2.3 |
| S2 | | |
| diluted 5x | 58.0 | 55.1 |
| diluted 10x | 41.5 | 33.7 |
| diluted 20x | 27.9 | 18.4 |
| diluted 40x | 19.5 | 9.5 |
| diluted 80x | 10.6 | 7.7 |
| diluted 160x | 6.7 | −0.7 |

G1-G20 are sera from patients with Graves' disease positive for TRAbs. HBD 1-10 are individual sera from healthy blood donors. B1 and B2 are sera from patients with blocking type TRAb. S1 and S2 are sera from patients with stimulating type TRAb.

TABLE 5d

Inhibition of $^{125}$I-K1-18 Fab binding to TSHR coated tubes by K1-18 IgG, K1-18 Fab and K1-70 IgG preparations

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/ml | 94.8 ± 0.8 | 96.0 ± 0.8 |
| 30 µg/mL | 94.5 ± 0.8 | 95.7 ± 1.2 |
| 10 µg/mL | 94.8 ± 2.6 | 94.5 ± 1.6 |
| 3 µg/mL | 93.7 ± 0.5 | 94.0 ± 0.2 |
| 1 µg/mL | 93.3 ± 0.7 | 91.9 ± 0.7 |
| 0.3 µg/mL | 91.1 ± 0.9 | 83.5 ± 1.9 |
| 0.1 µg/mL | 78.5 ± 2.5 | 57.0 ± 2.8 |
| 0.3 µg/mL | 22.0 ± 1.4 | 23.5 ± 2.1 |
| 0.01 µg/mL | 8.6 ± 1.4 | 11.0 ± 2.7 |
| 0.003 µg/mL | 1.4 ± 1.7 | 9.0 ± 2.5 |
| 0.001 µg/mL | −3.0 ± 6.1 | 9.4 ± 5.3 |
| K1-18 Fab | | |
| 100 µg/ml | 86.2 ± 3.3 | 84.8 ± 1.0 |
| 30 µg/mL | 84.2 ± 2.6 | 82.6 ± 0.9 |
| 10 µg/mL | 83.5 ± 3.0 | 81.6 ± 1.8 |
| 3 µg/mL | 81.1 ± 0.1 | 82.8 ± 1.0 |
| 1 µg/mL | 81.5 ± 3.8 | 79.2 ± 1.4 |
| 0.1 µg/mL | 62.5 ± 0.9 | 43.9 ± 1.3 |
| M22 IgG | | |
| 100 µg/ml | 94.9 ± 0.3 | 95.9 ± 0.2 |
| 30 µg/mL | 93.9 ± 2.0 | 95.2 ± 2.4 |
| 10 µg/mL | 95.3 ± 1.1 | 95.5 ± 0.2 |
| 3 µg/mL | 94.4 ± 0.7 | 95.1 ± 0.4 |
| 1 µg/mL | 93.4 ± 0.5 | 93.6 ± 1.0 |
| 0.3 µg/mL | 92.5 ± 0.5 | 87.1 ± 0.6 |
| 0.1 µg/mL | 69.8 ± 2.0 | 61.5 ± 1.4 |
| 0.03 µg/mL | 14.7 ± 3.2 | 23.8 ± 1.9 |
| 0.01 µg/mL | 8.0 ± 10.2 | 10.9 ± 2.5 |
| 0.003 µg/mL | 9.0 ± 10.3 | 10.8 ± 5.8 |
| 0.001 µg/mL | 2.9 ± 2.4 | 2.9 ± 3.7 |
| M22 Fab | | |
| 100 µg/ml | 94.5 ± 0.4 | 94.5 ± 1.1 |
| 10 µg/mL | 92.0 ± 2.1 | 92.8 ± 1.5 |
| 1 µg/mL | 91.4 ± 0.5 | 92.8 ± 0.4 |
| 0.1 µg/mL | 79.5 ± 1.2 | 84.5 ± 0.2 |
| 0.01 µg/mL | 3.1 ± 3.3 | 20.4 ± 5.6 |
| 0.001 µg/mL | −0.7 ± 6.4 | 4.7 ± 3.9 |
| K1-70 IgG | | |
| 100 µg/ml | 94.8 ± 2.2 | 95.6 ± 1.8 |
| 30 µg/mL | 95.1 ± 0.4 | 95.5 ± 0.6 |
| 10 µg/mL | 94.6 ± 1.0 | 95.8 ± 0.4 |
| 3 µg/mL | 94.5 ± 0.5 | 95.3 ± 0.3 |
| 1 µg/mL | 94.0 ± 0.5 | 94.0 ± 0.2 |
| 0.3 µg/mL | 93.4 ± 0.6 | 87.7 ± 0.9 |
| 0.1 µg/mL | 73.8 ± 0.6 | 60.1 ± 2.8 |
| 0.03 µg/mL | 24.1 ± 5.8 | 28.7 ± 1.5 |
| 0.01 µg/mL | 4.8 ± 3.5 | 11.7 ± 4.6 |
| 0.003 µg/mL | 2.2 ± 2.2 | 6.4 ± 2.2 |
| 0.001 µg/mL | −3.9 ± 4.3 | 4.7 ± 3.5 |
| 4B4 IgG | | |
| 100 µg/ml | 17.9 ± 3.9 | 2.7 ± 5.2 |
| 10 µg/mL | −1.35 ± 3.2 | 1.3 ± 0.7 |
| 1 µg/mL | −2.16 ± 3.6 | 5.5 ± 3.6 |
| 0.1 µg/mL | −4.5 ± 2.4 | 1.6 ± 1.7 |
| 0.01 µg/mL | −8.9 ± 1.3 | 1.9 ± 1.1 |
| 4B4 Fab | | |
| 100 µg/ml | −7.8 ± 3.5 | −0.8 ± 2.2 |
| 10 µg/mL | −8.5 ± 1.4 | 1.6 ± 2.8 |
| 5C9 IgG | | |
| 100 µg/ml | 85.2 ± 1.0 | 61.3 ± 1.6 |
| 10 µg/mL | 63.8 ± 2.1 | 49.8 ± 1.6 |
| 1 µg/mL | 52.5 ± 1.3 | 23.2 ± 1.9 |
| 0.1 µg/mL | 27.7 ± 1.5 | 6.3 ± 0.4 |
| 0.01 µg/mL | 3.0 ± 2.7 | 5.7 ± 8.8 |
| TSMAb 1 IgG | | |
| 100 µg/ml | 67.0 ± 2.0 | 76.8 ± 1.5 |
| 10 µg/mL | 61.1 ± 3.1 | 67.7 ± 5.0 |
| 1 µg/mL | 48.5 ± 0.8 | 43.4 ± 1.6 |
| 0.1 µg/mL | 13.1 ± 2.0 | 12.8 ± 2.7 |
| 0.01 µg/mL | −0.1 ± 2.6 | 6.3 ± 2.7 |
| TSMAb 2 IgG | | |
| 100 µg/ml | 82.8 ± 1.8 | 83.9 ± 3.1 |
| 10 µg/mL | 60.5 ± 2.5 | 77.1 ± 1.4 |
| 1 µg/mL | 57.5 ± 0.9 | 63.1 ± 2.9 |
| 0.1 µg/mL | 39.5 ± 1.4 | 32.1 ± 2.8 |
| 0.01 µg/mL | 4.7 ± 4.2 | 6.5 ± 3.8 |
| TSMAb 3 IgG | | |
| 100 µg/ml | 76.5 ± 2.4 | 78.5 ± 4.1 |
| 10 µg/mL | 68.6 ± 1.3 | 72.4 ± 1.1 |
| 1 µg/mL | 66.0 ± 1.9 | 59.4 ± 1.8 |
| 0.1 µg/mL | 41.3 ± 1.2 | 19.7 ± 3.9 |
| 0.01 µg/mL | 5.5 ± 0.4 | 1.4 ± 3.9 |
| TSMAb 4 IgG | | |
| 100 µg/ml | 71.4 ± 1.5 | 82.7 ± 2.4 |
| 10 µg/mL | 67.6 ± 0.6 | 80.5 ± 1.1 |
| 1 µg/mL | 66.2 ± 0.2 | 70.3 ± 1.5 |
| 0.1 µg/mL | 46.1 ± 0.6 | 31.1 ± 4.0 |
| 0.01 µg/mL | 8.1 ± 2.1 | 2.5 ± 1.9 |

TABLE 5d-continued

Inhibition of $^{125}$I-K1-18 Fab binding to TSHR coated tubes by K1-18 IgG, K1-18 Fab and K1-70 IgG preparations

| Test sample | Inhibition of binding (%) Dilutions in assay buffer (mean ± SD) | Inhibition of binding (%) Dilutions in HBD (mean ± SD) |
|---|---|---|
| TSMAb 5 IgG | | |
| 100 μg/ml | 87.3 ± 0.9 | 86.4 ± 2.7 |
| 10 μg/mL | 79.8 ± 1.3 | 81.1 ± 2.1 |
| 1 μg/mL | 69.9 ± 0.9 | 75.9 ± 1.4 |
| 0.1 μg/mL | 50.0 ± 3.0 | 44.1 ± 0.6 |
| 0.01 μg/mL | 4.2 ± 2.5 | 3.3 ± 4.5 |
| TSMAb 6 IgG | | |
| 100 μg/ml | 75.8 ± 2.5 | 77.5 ± 1.9 |
| 10 μg/mL | 59.0 ± 0.7 | 75.4 ± 0.5 |
| 1 μg/mL | 56.3 ± 4.0 | 70.0 ± 1.8 |
| 0.1 μg/mL | 43.9 ± 0.8 | 40.2 ± 2.5 |
| 0.01 μg/mL | *5.6 | 7.1 ± 3.4 |
| TSMAb 7 IgG | | |
| 100 μg/ml | 78.0 ± 0.4 | 77.4 ± 1.3 |
| 10 μg/mL | 61.8 ± 2.2 | 72.5 ± 2.9 |
| 1 μg/mL | 51.1 ± 1.5 | 62.8 ± 1.0 |
| 0.1 μg/mL | 30.2 ± 1.2 | 31.3 ± 1.5 |
| 0.01 μg/mL | 2.0 ± 7.0 | 5.6 ± 0.8 |
| 9D33 IgG | | |
| 100 μg/ml | 81.5 ± 2.0 | 77.3 ± 2.2 |
| 10 μg/mL | 69.5 ± 3.9 | 73.9 ± 0.9 |
| 1 μg/mL | 66.5 ± 0.9 | 64.8 ± 0.7 |
| 0.1 μg/mL | 48.6 ± 2.7 | 32.2 ± 1.1 |
| 0.01 μg/mL | 7.9 ± 1.8 | 2.3 ± 3.0 |
| 5B3 IgG | | |
| 100 μg/ml | 6.3 ± 4.5 | −1.1 ± 4.8 |
| 10 μg/mL | 0.6 ± 3.9 | −0.1 ± 0.8 |
| 1 μg/mL | −0.9 ± 1.7 | −3.1 ± 3.5 |
| 0.1 μg/mL | −3.6 ± 2.5 | −8.3 ± 2.0 |
| 0.01 μg/mL | −0.0 ± 2.3 | −8.6 ± 1.3 |

See legend to Table 5a for details.
$^{125}$I-K1-18 Fab binding in the presence of assay buffer was 10%.
$^{125}$I-K1-18 Fab binding in the presence of HBD pool was 9.4%.

TABLE 6a

Comparison of stimulation of cyclic AMP production by K1-18 IgG, K1-18 Fab and M22 Fab in CHO cells expressing the TSHR

| Test sample | Stimulation of cyclic AMP production in isotonic buffer (pmol/mL cyclic AMP mean ± SD) | Stimulation of cyclic AMP production in hypotonic buffer (pmol/mL cyclic AMP mean ± SD) |
|---|---|---|
| Cyclic AMP buffer | 0.88 ± 0.12 | 1.48 ± 0.13 |
| K1-18 IgG | | |
| 1000 ng/mL | 51.16 ± 5.29 | 67.90 ± 10.44 |
| 100 ng/mL | 22.95 ± 2.90 | 64.95 ± 9.61 |
| 30 ng/mL | 9.63 ± 0.76 | 50.72 ± 3.69 |
| 10 ng/mL | 4.81 ± 0.22 | 31.66 ± 5.06 |
| 3 ng/mL | 1.61 ± 0.49 | 12.55 ± 1.75 |
| 1 ng/mL | 1.56 ± 0.40 | 4.08 ± 0.28 |
| 0.3 ng/mL | 1.14 ± 0.10 | 2.32 ± 0.47 |
| 0.1 ng/mL | 1.29 ± 0.31 | 1.56 ± 0.32 |
| 0.03 ng/mL | 0.95 ± 0.04 | 1.26 ± 0.30 |

TABLE 6a-continued

Comparison of stimulation of cyclic AMP production by K1-18 IgG, K1-18 Fab and M22 Fab in CHO cells expressing the TSHR

| Test sample | Stimulation of cyclic AMP production in isotonic buffer (pmol/mL cyclic AMP mean ± SD) | Stimulation of cyclic AMP production in hypotonic buffer (pmol/mL cyclic AMP mean ± SD) |
|---|---|---|
| K1-18 Fab | | |
| 1000 ng/mL | 35.73 ± 2.25 | 66.94 ± 6.93 |
| 100 ng/mL | 8.93 ± 0.18 | *53.22 |
| 30 ng/mL | 2.97 ± 0.82 | 27.99 ± 6.25 |
| 10 ng/mL | 1.65 ± 0.20 | 9.99 ± 3.52 |
| 3 ng/mL | 1.14 ± 0.19 | 2.93 ± 0.17 |
| 1 ng/mL | 0.79 ± 0.10 | 1.72 ± 0.82 |
| 0.3 ng/mL | 0.71 ± 0.10 | 1.13 ± 0.24 |
| 0.1 ng/mL | 0.84 ± 0.41 | 1.33 ± 0.53 |
| 0.03 ng/mL | 0.50 ± 0.44 | 0.68 ± 0.18 |
| M22 Fab | | |
| 10 ng/mL | 34.71 ± 1.43 | 57.41 ± 5.05 |
| 3 ng/mL | 16.30 ± 1.49 | 55.34 ± 7.49 |
| 1 ng/mL | 9.14 ± 0.82 | 29.80 ± 0.97 |
| 0.3 ng/mL | 2.19 ± 0.19 | 10.08 ± 0.95 |
| 0.1 ng/mL | 1.38 ± 0.07 | 3.83 ± 0.30 |

Results shown are mean ± SD of triplicate determinations.
*mean of duplicate determinations.
Test samples were diluted in cyclic AMP buffer.

TABLE 6b

Stimulation of cyclic AMP production by K1-18 IgG, M22 IgG and pTSH in CHO cells expressing the TSHR

| Test sample | Cyclic AMP production concentration (pmol/mL mean ± SD) |
|---|---|
| Cyclic AMP buffer | 1.3 ± 0.2 |
| K1-18 IgG | |
| 300 ng/mL | 63.3 ± 3.7 |
| 100 ng/mL | 62.6 ± 2.7 |
| 30 ng/mL | 38.4 ± 3.1 |
| 10 ng/mL | 25.0 ± 1.0 |
| 3 ng/mL | 8.3 ± 0.5 |
| 1 ng/mL | 3.0 ± 1.0 |
| 0.3 ng/mL | 1.7 ± 0.3 |
| 0.1 ng/mL | 0.9 ± 0.2 |
| 0.03 ng/mL | 1.0 ± 0.2 |
| 0.01 ng/mL | 1.0 ± 0.2 |
| M22 IgG | |
| 100 ng/mL | 64.6 ± 1.9 |
| 30 ng/mL | 60.9 ± 3.5 |
| 10 ng/mL | 50.3 ± 1.6 |
| 3 ng/mL | 24.3 ± 2.3 |
| 1 ng/mL | 8.1 ± 1.2 |
| 0.3 ng/mL | 2.9 ± 0.9 |
| pTSH | |
| 3 ng/mL | 55.4 ± 7.3 |
| 1 ng/mL | 51.7 ± 3.6 |
| 0.3 ng/mL | 18.5 ± 1.5 |
| 0.1 ng/mL | 7.2 ± 0.6 |
| 0.03 ng/mL | 2.4 ± 0.7 |
| 0.01 ng/mL | 1.4 ± 0.3 |

See legend to Table 6a for details.

TABLE 6c

Stimulation of cyclic AMP production by NIBSC reference preparation 90/672 and by K1-18 IgG and Fab preparations compared to M22 IgG

| Test sample | Cyclic AMP concentration (pmol/mL mean ± SD) | units/L | units/mg | mean units/mg |
|---|---|---|---|---|
| Cyclic AMP buffer | 1.36 ± 0.39 | | | |
| NIBSC 90/672 | | | | |
| 3 units/L | 60.37 ± 3.73 | | | |
| 1 unit/L | 27.43 ± 3.52 | | | |
| 0.3 units/L | 12.47 ± 0.23 | | | |
| 0.1 units/L | 5.00 ± 0.69 | | | |
| K1-18 IgG | | | | |
| 100 ng/mL | 73.05 ± 3.43 | | | |
| 30 ng/mL | 63.68 ± 1.54 | | | |
| 10 ng/mL | 41.91 ± 3.97 | 1.85 | 185 | |
| 3 ng/mL | 16.87 ± 0.96 | 0.48 | 160 | 155 |
| 1 ng/mL | 5.36 ± 0.68 | 0.12 | 120 | |
| 0.3 ng/mL | 1.91 ± 0.45 | | | |
| K1-18 Fab | | | | |
| 100 ng/mL | 51.38 ± 1.87 | 2.40 | 24 | |
| 30 ng/mL | 22.25 ± 0.81 | 0.70 | 23 | 22 |
| 10 ng/mL | 8.34 ± 1.91 | 0.18 | 18 | |
| 3 ng/mL | 3.40 ± 0.52 | | | |
| 1 ng/mL | 1.91 ± 0.30 | | | |
| 0.3 ng/mL | 1.30 ± 0.32 | | | |
| M22 IgG | | | | |
| 10 ng/mL | 58.88 ± 8.96 | 2.9 | 290 | |
| 3 ng/mL | 24.57 ± 6.55 | 0.8 | 267 | 286 |
| 1 ng/mL | 12.01 ± 2.52 | 0.3 | 300 | |
| 0.3 ng/mL | 2.36 ± 0.29 | | | |
| 4B4 IgG | | | | |
| 10 ng/mL | 1.00 ± 0.33 | | | |
| 1 ng/mL | 1.09 ± 0.22 | | | |
| 4B4 Fab | | | | |
| 10 ng/mL | 0.89 ± 0.11 | | | |
| 1 ng/mL | 0.68* | | | |

See legend to Table 6a for details.
4B4 is a human MAb to glutamic acid decarboxylase (negative control).
Test samples were diluted in hypotonic cyclic AMP buffer.

TABLE 6d

Comparison of stimulation of cyclic AMP production by porcine (p), native human (h) and recombinant human (rh) TSH in CHO cells expressing the TSHR

| Test sample | Cyclic AMP concentration in isotonic buffer (pmol/mL mean ± SD) | Cyclic AMP concentration in hypotonic buffer (pmol/mL mean ± SD) |
|---|---|---|
| Cyclic AMP buffer | 1.3 ± 0.5 | 2.0 ± 0.1 |
| pTSH | | |
| 20 ng/mL | 73.9 ± 12.7 | 89.9 ± 10.1 |
| 3 ng/mL | 46.6 ± 3.3 | 76.6 ± 0.0 |
| 2 ng/mL | 49.5 ± 3.9 | 77.6 ± 9.2 |
| 1 ng/mL | 37.5 ± 3.8 | 69.0 ± 1.4 |
| 0.3 ng/mL | 14.3 ± 1.1 | 34.1 ± 2.8 |
| 0.1 ng/mL | 4.0 ± 0.4 | 11.0 ± 0.6 |
| 0.03 ng/mL | 2.0 ± 0.3 | 4.1 ± 0.3 |
| 0.01 ng/mL | 1.4 ± 0.2 | 2.4 ± 0.2 |
| Native hTSH | | |
| 250 ng/mL | 57.9 ± 7.2 | 79.3 ± 1.0 |
| 100 ng/mL | 41.6 ± 3.0 | 74.4 ± 0.9 |
| 50 ng/mL | 29.0 ± 0.8 | 69.4 ± 11.7 |
| 25 ng/mL | 19.9 ± 1.2 | 55.2 ± 2.7 |
| 10 ng/mL | 9.6 ± 1.7 | 37.8 ± 2.0 |
| 2.5 ng/mL | 3.7 ± 0.4 | 11.6 ± 0.2 |
| 1 ng/mL | 2.0 ± 1.2 | 6.1 ± 0.6 |
| rhTSH | | |
| 250 ng/mL | 46.2 ± 10.2 | 67.4 ± 4.6 |
| 100 ng/mL | 35.4 ± 2.5 | 63.0 ± 7.9 |
| 50 ng/mL | 24.5 ± 1.3 | 44.7 ± 4.3 |
| 25 ng/mL | 14.4 ± 0.6 | 30.6 ± 1.4 |
| 10 ng/mL | 6.2 ± 1.1 | 14.3 ± 1.2 |
| 2.5 ng/mL | 2.1 ± 0.4 | 6.0 ± 1.9 |
| 1 ng/mL | 1.4 ± 0.3 | 3.0 ± 0.3 |

See legend to Table 6a for details.
pTSH was from RSR Ltd, Cardiff, CF23 8HE, UK.
Native hTSH was an NIBSC reference preparation 81/565.
rhTSH was an NIBSC reference preparation 94/674.

TABLE 6e

Stimulation of cyclic AMP production in TSHR transfected CHO cells by pTSH, M22 IgG and K1-18 IgG mixed together in different combinations

| Test sample | Cyclic AMP (pmol/mL; mean ± SD) |
|---|---|
| cyclic AMP buffer | 1.00 ± 0.72 |
| 10 ng/mL 5B3 IgG | 1.58* |
| 1 ng/mL 5B3 IgG | 1.19* |
| 0.1 ng/mL 5B3 IgG | 1.53* |
| 0.1 ng/mL pTSH | 11.01 ± 0.99 |
| 1 ng/mL M22 IgG | 35.17 ± 6.38 |
| 0.1 ng/mL pTSH + 1 ng/mL M22 IgG | 47.22 ± 3.89 |
| 0.05 ng/mL pTSH | 5.83* |
| 0.5 ng/mL M22 IgG | 20.20* |
| 0.05 ng/mL pTSH + 0.5 ng/mL M22 IgG | 25.99 ± 2.19 |
| 0.1 ng/mL pTSH | 11.01 ± 0.99 |
| 10 ng/mL K1-18 IgG | 45.09 ± 6.15 |
| 0.1 ng/mL pTSH + 10 ng/mL K1-18 IgG | 52.84 ± 6.76 |
| 0.05 ng/mL pTSH | 5.83* |
| 5 ng/mL K1-18 IgG | 29.95* |
| 0.05 ng/mL pTSH + 5 ng/mL K1-18 IgG | 29.87 ± 4.34 |
| 10 ng/mL K1-18 IgG | 45.09 ± 6.15 |
| 1 ng/mL M22 IgG | 35.17 ± 6.38 |
| 10 ng/mL K1-18 IgG + 1 ng/mL M22 IgG | 52.84 ± 6.76 |
| 5 ng/mL K1-18 IgG | 29.95* |
| 0.5 ng/mL M22 IgG | 20.20* |
| 5 ng/mL K1-18 IgG + 0.5 ng/mL M22 IgG | 44.01 ± 7.19 |

See legend to Table 6a for details.
5B3 is a human MAb to glutamic acid decarboxylase (negative control).
Test samples were diluted in hypotonic cyclic AMP buffer.

TABLE 6f

Stimulation of cyclic AMP production in TSHR transfected CHO cells by NIBSC reference preparation 90/672 and by K1-18 IgG, donor serum and donor serum IgG (experiment 1)

| Test sample | Cyclic AMP concentration (pmol/mL mean ± SD) | units/L | units/mg | mean units/mg |
|---|---|---|---|---|
| Cyclic AMP buffer | 1.5 ± 0.3 | | | |
| NIBSC 90/672 | | | | |
| 3 units/L | 37.6 ± 3.9 | | | |
| 1 unit/L | 19.0 ± 1.4 | | | |

TABLE 6f-continued

Stimulation of cyclic AMP production in TSHR transfected CHO cells by NIBSC reference preparation 90/672 and by K1-18 IgG, donor serum and donor serum IgG (experiment 1)

| Test sample | Cyclic AMP concentration (pmol/mL mean ± SD) | units/L | units/mg | mean units/mg |
|---|---|---|---|---|
| 0.3 units/L | 6.8 ± 0.5 | | | |
| 0.1 units/L | 2.7 ± 0.3 | | | |
| K1 donor IgG | | | | |
| 30 µg/mL | 7.7 ± 1.0 | 0.45 | 0.013 | 0.013 |
| 10 µg/mL | 3.3 ± 0.2 | | | |
| 3 µg/mL | 1.8 ± 0.3 | | | |
| K1 donor serum | | | | |
| diluted 10x | 3.2 ± 0.4 | | | |
| diluted 30x | 4.7 ± 0.1 | 0.29 | | |
| diluted 100x | 2.8 ± 0.0 | | | |
| diluted 300x | 2.4 ± 0.3 | | | |
| HBD serum | | | | |
| diluted 10x | 1.8 ± 0.1 | | | |
| diluted 30x | 1.7 ± 0.4 | | | |
| diluted 100x | 1.4 ± 0.4 | | | |
| HBD serum IgG | | | | |
| 30 µg/mL | 1.2 ± 0.2 | | | |
| 10 µg/mL | 1.2 ± 0.2 | | | |
| 3 µg/mL | 2.1 ± 0.2 | | | |

See legend to Table 6a for details.
HBD = serum from a healthy blood donor (HBD IgG was isolated from the same serum).
Test samples were diluted in hypotonic cyclic AMP buffer.

TABLE 6g

Stimulation of cyclic AMP production in TSHR transfected CHO cells by NIBSC reference preparation 90/672 and by K1-18 IgG, donor serum and donor serum IgG (experiment 2)

| Test sample | Cyclic AMP concentration (pmol/mL mean ± SD) | units/L | units/mg | mean units/mg |
|---|---|---|---|---|
| Cyclic AMP buffer | 2.5* | | | |
| NIBSC 90/672 | | | | |
| 3 units/L | 64.6 ± 6.9 | | | |
| 1 unit/L | 36.4 ± 4.6 | | | |
| 0.3 units/L | 10.2 ± 1.0 | | | |
| 0.1 units/L | 4.3 ± 0.5 | | | |
| K1 donor serum IgG | | | | |
| 30 µg/mL | 15.6 ± 0.7 | 0.42 | 0.014 | 0.014 |
| 10 µg/mL | *5.7 | | | |
| 3 µg/mL | 2.2 ± 0.3 | | | |
| K1 donor serum | | | | |
| Diluted 10x | 6.9 ± 0.6 | | | |
| Diluted 30x | 9.5 ± 0.7 | 0.28 | | |
| Diluted 100x | 6.6 ± 0.9 | | | |
| Diluted 300x | 3.9 ± 2.4 | | | |
| HBD serum | | | | |
| Diluted 10x | 3.0 ± 0.7 | | | |
| Diluted 30x | 1.5 ± 1.5 | | | |
| Diluted 100x | 2.1 ± 0.3 | | | |
| HBD serum IgG | | | | |
| 30 µg/mL | 2.0 ± 0.2 | | | |
| 10 µg/mL | 2.1 ± 0.2 | | | |
| 3 µg/mL | 2.3 ± 0.9 | | | |

See legend to Table 6a for details.
HBD = serum from a healthy blood donor (HBD IgG was isolated from the same serum).
Test samples were diluted in hypotonic cyclic AMP buffer.

TABLE 6h

Inhibition of K1-18 IgG TSHR stimulating activity by human MAbs K1-70 and 5C9 IgGs with TSH antagonist activity

| Test sample | Cyclic AMP concentration (pmol/mL mean ± SD) | % Inhibition |
|---|---|---|
| Cyclic AMP buffer | 1.6 ± 0.2 | |
| K1-70 IgG 100 µg/mL | 1.1 ± 0.2 | |
| 5B3 IgG 100 µg/mL | 1.6 ± 0.5 | |
| 5C9 IgG 100 µg/mL | 1.0 ± 0.1 | |
| 10 ng/mL K1-18 IgG | 50.0 ± 3.3 | |
| 10 ng/mL K1-18 IgG + 100 µg/ml 5B3 IgG | 61.1 ± 5.9 | 0 |
| 10 ng/mL K1-18 IgG + 100 µg/ml K1-70 IgG | 1.3 ± 1.7 | 97 |
| 10 ng/mL K1-18 IgG + 50 µg/ml K1-70 IgG | 0.9 ± 1.5 | 98 |
| 10 ng/mL K1-18 IgG + 10 µg/ml K1-70 IgG | 0.1 ± 0.0 | 100 |
| 10 ng/mL K1-18 IgG + 5 µg/ml K1-70 IgG | 0.0 ± 0.0 | 100 |
| 10 ng/mL K1-18 IgG + 1 µg/ml K1-70 IgG | 0.1 ± 0.0 | 100 |
| 10 ng/mL K1-18 IgG + 0.5 µg/ml K1-70 IgG | 0.0 ± 0.0 | 100 |
| 10 ng/mL K1-18 IgG + 0.1 µg/ml K1-70 IgG | 3.8 ± 1.0 | 92 |
| 10 ng/mL K1-18 IgG + 0.01 µg/ml K1-70 IgG | 48.6 ± 1.7 | 3 |
| 10 ng/mL K1-18 IgG + 0.001 µg/ml K1-70 IgG | 52.1 ± 11.4 | 0 |
| 10 ng/mL K1-18 IgG + 100 µg/ml 5C9 IgG | 0.1 ± 0.0 | 100 |
| 10 ng/mL K1-18 IgG + 50 µg/ml 5C9 IgG | 0.1* | 100 |
| 10 ng/mL K1-18 IgG + 10 µg/ml 5C9 IgG | 1.4 ± 1.5 | 97 |
| 10 ng/mL K1-18 IgG + 5 µg/ml 5C9 IgG | 1.5 ± 2.4 | 97 |
| 10 ng/mL K1-18 IgG + 1 µg/ml 5C9 IgG | 0.9 ± 1.4 | 98 |
| 10 ng/mL K1-18 IgG + 0.5 µg/ml 5C9 IgG | 0.3* | 99 |
| 10 ng/mL K1-18 IgG + 0.1 µg/ml 5C9 IgG | 4.4 ± 1.5 | 91 |
| 10 ng/mL K1-18 IgG + 0.01 µg/ml 5C9 IgG | 51.8 ± 4.9 | 0 |
| 10 ng/mL K1-18 IgG + 0.001 µg/ml 5C9 IgG | 40.4 ± 7.0 | 19 |

See legend to Table 6a for details.
5B3 is a human MAb to glutamic acid decarboxylase (negative control).
Test samples were diluted in hypotonic cyclic AMP buffer.

TABLE 6i

Inhibition of K1-18 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| Cyclic AMP buffer | 0.89 ± 0.15 | |
| 10 ng/mL K1-18 IgG | 50.3 ± 4.97 | |
| 100 µg/mL 5B3 IgG | 1.20 ± 0.24 | |
| 100 µg/mL 5C9 IgG | 0.55 ± 0.14 | |
| 100 µg/mL K1-70 IgG | 0.89 ± 0.13 | |
| 100 µg/mL (K1-70 IgG + 5C9 IgG)$^a$ | 0.86 ± 0.17 | |
| 10 ng/mL K1-18 + 100 µg/mL 5B3 IgG | 52.8 ± 0.21 | 0 |
| 10 ng/mL K1-18 + 10 µg/mL 5B3 IgG | 48.5 ± 2.16 | 3.5 |
| 10 ng/mL K1-18 + 100 µg/mL 5C9 IgG | 0.66 ± 0.25 | 98.7 |
| 10 ng/mL K1-18 + 10 µg/mL 5C9 IgG | 0.21 ± 0.18 | 99.6 |
| 10 ng/mL K1-18 + 1 µg/mL 5C9 IgG | 0.29 ± 0.25 | 99.4 |
| 10 ng/mL K1-18 + 0.1 µg/mL 5C9 IgG | 0.50 ± 0.62 | 99.0 |
| 10 ng/mL K1-18 + 0.01 µg/mL 5C9 IgG | 37.7 ± 1.75 | 25.0 |
| 10 ng/mL K1-18 + 0.001 µg/mL 5C9 IgG | 51.2 ± 2.6 | 0 |
| 10 ng/mL K1-18 + 100 µg/mL K1-70 IgG | 0.74 ± 0.12 | 98.5 |
| 10 ng/mL K1-18 + 10 µg/mL K1-70 IgG | 0.38 ± 0.19 | 99.2 |
| 10 ng/mL K1-18 + 1 µg/mL K1-70 IgG | 0.37 ± 0.15 | 99.3 |
| 10 ng/mL K1-18 + 0.1 µg/mL K1-70 IgG | 1.88 ± 0.06 | 96.3 |
| 10 ng/mL K1-18 + 0.01 µg/mL K1-70 IgG | 40.4 ± 3.19 | 19.6 |
| 10 ng/mL K1-18 + 0.001 µg/mL K1-70 | 49.74 ± 1.73 | 1.0 |
| 10 ng/mL K1-18 + 100 µg/mL (K1-70 IgG + 5C9 IgG)$^a$ | 0.57 ± 0.18 | 98.9 |
| 10 ng/mL K1-18 + 10 µg/mL (K1-70 IgG + 5C9 IgG)$^a$ | 0.59 ± 0.11 | 98.8 |
| 10 ng/mL K1-18 + 1 µg/mL (K1-70 IgG + 5C9 IgG)$^a$ | 0.39 ± 0.09 | 99.2 |

TABLE 6i-continued

Inhibition of K1-18 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| 10 ng/mL K1-18 + 0.1 µg/mL (K1-70 IgG + 5C9 IgG)[a] | 1.37 ± 0.92 | 97.3 |
| 10 ng/mL K1-18 + 0.01 µg/mL (K1-70 IgG + 5C9 IgG)[a] | 34.15 ± 0.62 | 32.0 |
| 18 10ng/mL + 0.001 µg/mL (K1-70 IgG + 5C9 IgG)[a] | 37.4 ± 1.84 | 25.5 |

See legend to Table 6a for details.

5B3 is a human MAb to glutamic acid decarboxylase (negative control).

[a]The total final concentration of IgG mixture is shown; ie in the case of 100 µg/mL (K1-70 IgG + 5C9 IgG) the mixture contains 50 µg/mL K1-70 IgG and 50 µg/mL 5C9 IgG. Consequently, the combined effect of two IgGs at 100 µg/mL can be compared to the effect of the single IgG at the same concentration (100 µg/mL).

Test samples were diluted in hypotonic cyclic AMP buffer.

µg/mL

TABLE 6j

Inhibition of M22 IgG stimulation of cyclic AMP production in TSHR transfected CHO cells by K1-70 and 5C9 IgGs mixed together

| Test sample | Cyclic AMP concentration (pmol/mL; mean ± SD) | % Inhibition |
|---|---|---|
| Cyclic AMP buffer | 1.8 ± 0.2 | |
| 3 ng/mL M22 IgG | 44.4 ± 7.1 | |
| 100 µg/mL 5B3 IgG | 2.3 ± 0.2 | |
| 100 µg/mL 5C9 IgG | 1.7 ± 0.2 | |
| 100 µg/mL K1-70 IgG | 1.8 ± 0.2 | |
| 100 µg/mL (K1-70 IgG + 5C9 IgG)[a] | 1.9 ± 0.2 | |
| 3 ng/mL M22 IgG + 100 µg/mL 5B3 IgG | 51.3 ± 1.2 | 0 |
| 3 ng/mL M22 IgG + 10 µg/mL 5B3 IgG | 44.7 ± 4.3 | 0 |
| 3 ng/mL M22 IgG + 100 µg/mL 5C9 IgG | 1.3 ± 0.2 | 97.1 |
| 3 ng/mL M22 IgG + 10 µg/mL 5C9 IgG | 2.5 ± 1.6 | 94.4 |
| 3 ng/mL M22 IgG + 1 µg/mL 5C9 IgG | 1.3 ± 0.1 | 97.1 |
| 3 ng/mL M22 IgG + 0.1 µg/mL 5C9 IgG | 3.2 ± 0.5 | 92.8 |
| 3 ng/mL M22 IgG + 0.01 µg/mL 5C9 IgG | 33.2 ± 1.5 | 25.2 |
| 3 ng/mL M22 IgG + 0.001 µg/mL 5C9 IgG | 41.0 ± 1.9 | 7.7 |
| 3 ng/mL M22 IgG + 100 µg/mL K1-70 IgG | 1.4 ± 0.1 | 96.8 |
| 3 ng/mL M22 IgG + 10 µg/mL K1-70 IgG | 1.2 ± 0.1 | 97.3 |
| 3 ng/mL M22 IgG + 1 µg/mL K1-70 IgG | 1.5 ± 0.2 | 96.6 |
| 3 ng/mL M22 IgG + 0.1 µg/mL K1-70 IgG | 10.9 ± 3.7 | 75.5 |
| 3 ng/mL M22 IgG + 0.01 µg/mL K1-70 IgG | 38.4 ± 3.2 | 13.5 |
| 3 ng/mL M22 IgG + 0.001 µg/mL K1-70 IgG | 40.5 ± 1.3 | 8.8 |
| 3 ng/mL M22 IgG + 100 µg/mL (K1-70 IgG + 5C9 IgG)[a] | 1.7 ± 0.1 | 96.2 |
| 3 ng/mL M22 IgG + 10 µg/mL (K1-70 IgG + 5C9 IgG)[a] | 1.8 ± 0.2 | 95.9 |
| 3 ng/mL M22 IgG + 1 µg/mL (K1-70 IgG + 5C9 IgG)[a] | 1.4 ± 0.1 | 96.8 |
| 3 ng/mL M22 IgG + 0.1 µg/mL (K1-70 IgG + 5C9 IgG)[a] | 3.6 ± 0.4 | 91.9 |
| 3 ng/mL M22 IgG + 0.01 µg/mL (K1-70 IgG + 5C9 IgG)[a] | 39.1 ± 7.9 | 11.9 |
| 3 ng/mL M22 IgG + 0.001 µg/mL (K1-70 IgG + 5C9 IgG)[a] | 36.5 ± 2.8 | 17.8 |

See legend to Table 6i for details.

TABLE 6k

Inhibition of K1-18 IgG stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 1.5 ± 0.05 | |
| 10 ng/mL K1-18 IgG | 37.0 ± 0.9 | |
| 100 µg/mL 5B3 IgG | 1.3 ± 0.1 | |
| 100 µg/mL 9D33 IgG | 2.0 ± 0.6 | |
| 100 µg/mL K1-70 IgG | 1.3 ± 0.1 | |
| 100 µg/mL (K1-70 IgG + 9D33 IgG)[a] | 1.3 ± 0.2 | |
| 10 ng/mL K1-18 IgG + 100 µg/mL 5B3 IgG | 41.9 ± 4.3 | −13 |
| 10 ng/mL K1-18 IgG + 10 µg/mL 5B3 IgG | 35.4 ± 1.6 | 4 |
| 10 ng/mL K1-18 IgG + 100 µg/mL 9D33 IgG | 2.2 ± 0.7 | 94 |
| 10 ng/mL K1-18 IgG + 10 µg/mL 9D33 IgG | 1.9 ± 0.6 | 95 |
| 10 ng/mL K1-18 IgG + 1 µg/mL 9D33 IgG | 1.9 ± 0.2 | 95 |
| 10 ng/mL K1-18 IgG + 0.1 µg/mL 9D33 IgG | 5.3 ± 1.1 | 86 |
| 10 ng/mL K1-18 IgG + 0.01 µg/mL 9D33 IgG | 31.32 ± 3.3 | 15 |
| 10 ng/mL K1-18 IgG + 0.001 µg/mL 9D33 IgG | 35.8 ± 2.3 | 3 |
| 10 ng/mL K1-18 IgG + 100 µg/mL K1-70 IgG | 1.4 ± 0.4 | 96 |
| 10 ng/mL K1-18 IgG + 10 µg/mL K1-70 IgG | 0.9 ± 0.1 | 98 |
| 10 ng/mL K1-18 IgG + 1 µg/mL K1-70 IgG | 1.1 ± 0.5 | 97 |
| 10 ng/mL K1-18 IgG + 0.1 µg/mL K1-70 IgG | 1.7 ± 0.8 | 95 |
| 10 ng/mL K1-18 IgG + 0.01 µg/mL K1-70 IgG | 27.7 ± 0.8 | 25 |
| 10 ng/mL K1-18 IgG + 0.001 µg/mL K1-70 IgG | 37.4 ± 1.3 | −1 |
| 10 ng/mL K1-18 IgG + 100 µg/mL (K1-70 IgG + 9D33 IgG)[a] | 1.2 ± 0.1 | 97 |
| 10 ng/mL K1-18 IgG + 10 µg/mL (K1-70 IgG + 9D33 IgG)[a] | 0.9 ± 0.2 | 98 |
| 10 ng/mL K1-18 IgG + 1 µg/mL (K1-70 IgG + 9D33 IgG)[a] | 1.1 ± 0.1 | 97 |
| 10 ng/mL K1-18 IgG + 0.1 µg/mL (K1-70 IgG + 9D33 IgG)[a] | 1.7 ± 0.05 | 95 |
| 10 ng/mL K1-18 IgG + 0.01 µg/mL (K1-70 IgG + 9D33 IgG)[a] | 29.4 ± 0.6 | 20 |
| 10 ng/mL K1-18 IgG + 0.001 µg/mL (K1-70 IgG + 9D33 IgG)[a] | 35.2 ± 1.7 | 5 |

See legend to Table 6i for details.

[a]The total final concentration of IgG mixture is shown; ie in the case of 100 µg/mL (K1-70 IgG + 9D33 IgG) the mixture contains 50 µg/mL K1-70 IgG and 50 µg/mL 9D33 IgG. Consequently, the combined effect of two IgGs at 100 µg/mL can be compared to the effect of the single IgG at the same concentration (100 µg/mL).

TABLE 6l

Inhibition of M22 IgG stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 0.52 ± 0.3 | |
| 3 ng/mL M22 IgG | 21.33 ± 1.3 | |
| 100 µg/mL 5B3 IgG | 1.10 ± 0.3 | |
| 100 µg/mL 9D33 IgG | 1.31 ± 0.4 | |
| 100 µg/mL K1-70 IgG | 0.47 ± 0.1 | |
| 100 µg/mL (K1-70 IgG + 9D33 IgG)[a] | 0.45 ± 0.02 | |
| 3 ng/mL M22 IgG + 100 µg/mL 5B3 IgG | 28.13 ± 3.9 | 0 |
| 3 ng/mL M22 IgG + 10 µg/mL 5B3 IgG | 21.55 ± 1.2 | 0 |
| 3 ng/mL M22 IgG + 100 µg/mL 9D33 IgG | 1.01 ± 0.18 | 95 |
| 3 ng/mL M22 IgG + 10 µg/mL 9D33 IgG | 1.20 ± 0.1 | 94 |
| 3 ng/mL M22 IgG + 1 µg/mL 9D33 IgG | 1.48 ± 0.1 | 93 |
| 3 ng/mL M22 IgG + 0.1 µg/mL 9D33 IgG | 7.19 ± 1.6 | 66 |
| 3 ng/mL M22 IgG + 0.01 µg/mL 9D33 IgG | 21.00 ± 1.25 | 2 |
| 3 ng/mL M22 IgG + 0.001 µg/mL 9D33 IgG | 19.36 ± 7.3 | 9 |
| 3 ng/mL M22 IgG + 100 µg/mL K1-70 IgG | 0.77 ± 0.3 | 96 |

TABLE 6l-continued

Inhibition of M22 IgG stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| 3 ng/mL M22 IgG + 10 µg/mL K1-70 IgG | 0.72 ± 0.3 | 97 |
| 3 ng/mL M22 IgG + 1 µg/mL K1-70 IgG | 0.82 ± 0.1 | 96 |
| 3 ng/mL M22 IgG + 0.1 µg/mL K1-70 IgG | 4.82 ± 0.7 | 77 |
| 3 ng/mL M22 IgG + 0.01 µg/mL K1-70 IgG | 18.67 ± 1.9 | 12 |
| 3 ng/mL M22 IgG + 0.001 µg/mL K1-70 IgG | 19.82 ± 0.3 | 7 |
| 3 ng/mL M22 IgG + 100 µg/mL (K1-70 IgG + 9D33 IgG)[a] | 0.77 ± 0.1 | 96 |
| 3 ng/mL M22 IgG + 10 µg/mL (K1-70 IgG + 9D33 IgG)[a] | 0.56 ± 0.4 | 97 |
| 3 ng/mL M22 IgG + 1 µg/mL (K1-70 IgG + 9D33 IgG)[a] | 0.90 ± 0.4 | 96 |
| 3 ng/mL M22 IgG + 0.1 µg/mL (K1-70 IgG + 9D33 IgG)[a] | 3.34 ± 2.4 | 84 |
| 3 ng/mL M22 IgG + 0.01 µg/mL (K1-70 IgG + 9D33 IgG)[a] | 18.20 ± 2.0 | 15 |
| 3 ng/mL M22 IgG + 0.001 µg/mL (K1-70 IgG + 9D33 IgG)[a] | 21.09 ± 0.6 | 1 |

See legend to Table 6i for details.

[a]The total final concentration of IgG mixture is shown; ie in the case of 100 µg/mL (K1-70 IgG + 9D33 IgG) the mixture contains 50 µg/mL K1-70 IgG and 50 µg/mL 9D33 IgG. Consequently, the combined effect of two IgGs at 100 µg/mL can be compared to the effect of the single IgG at the same concentration (100 µg/mL).

TABLE 6m

Inhibition of pTSH stimulation of cyclic AMP production in TSHR transfected CHO cells by K1-70 and 9D33 IgGs mixed together

| Test sample | Cyclic AMP concentration (pmol/mL; mean ± SD) | % Inhibition |
|---|---|---|
| Cyclic AMP buffer | 6.04 ± 1.78 | |
| 3 ng/mL pTSH | 70.82 ± 1.75 | |
| 100 µg/mL 5B3 IgG | 3.29 ± 0.18 | |
| 100 µg/mL 9D33 IgG | 1.58 ± 0.25 | |
| 100 µg/mL K1-70 IgG | 1.27 ± 0.17 | |
| 100 µg/mL (K1-70 IgG + 9D33 IgG)[a] | 0.41 ± 0.68 | |
| 3 ng/mL pTSH + 100 µg/mL 5B3 IgG | 65.74* | 7 |
| 3 ng/mL pTSH + 10 µg/mL 5B3 IgG | 65.97 ± 7.7 | 7 |
| 3 ng/mL pTSH + 100 µg/mL 9D33 IgG | 3.26 ± 0.17 | 95 |
| 3 ng/mL pTSH + 10 µg/mL 9D33 IgG | 9.17 ± 1.46 | 87 |
| 3 ng/mL pTSH + 1 µg/mL 9D33 IgG | 23.60 ± 1.33 | 67 |
| 3 ng/mL pTSH + 0.1 µg/mL 9D33 IgG | 50.73 ± 5.03 | 28 |
| 3 ng/mL pTSH + 0.01 µg/mL 9D33 IgG | 67.60 ± 7.15 | 5 |
| 3 ng/mL pTSH + 0.001 µg/mL 9D33 IgG | 61.65 ± 6.60 | 13 |
| 3 ng/mL pTSH + 100 µg/mL K1-70 IgG | 1.46 ± 0.11 | 98 |
| 3 ng/mL pTSH + 10 µg/mL K1-70 IgG | 1.52 ± 0.25 | 98 |
| 3 ng/mL pTSH + 1 µg/mL K1-70 IgG | 1.70 ± 0.09 | 98 |
| 3 ng/mL pTSH + 0.1 µg/mL K1-70 IgG | 27.50 ± 3.26 | 61 |
| 3 ng/mL pTSH + 0.01 µg/mL K1-70 IgG | 74.70 ± 9.2 | 0 |
| 3 ng/mL pTSH + 0.001 µg/mL K1-70 IgG | 86.95 ± 4.38 | 0 |
| 3 ng/mL pTSH + 100 µg/mL (K1-70 IgG + 9D33 IgG)[a] | 1.69 ± 0.12 | 98 |
| 3 ng/mL pTSH + 10 µg/mL (K1-70 IgG + 9D33 IgG)[a] | 1.39 ± 0.08 | 98 |
| 3 ng/mL pTSH + 1 µg/mL (K1-70 IgG + 9D33 IgG)[a] | 1.90 ± 0.13 | 97 |
| 3 ng/mL pTSH + 0.1 µg/mL (K1-70 IgG + 9D33 IgG)[a] | 16.30 ± 1.16 | 77 |
| 3 ng/mL pTSH + 0.01 µg/mL (K1-70 IgG + 9D33 IgG)[a] | 61.50 ± 5.06 | 13 |
| 3 ng/mL pTSH + 0.001 µg/mL (K1-70 IgG + 9D33 IgG)[a] | 72.11 ± 5.5 | 0 |

See legend to Table 6i for details.

[a]The total final concentration of IgG mixture is shown; ie in the case of 100 µg/mL (K1-70 IgG + 9D33 IgG) the mixture contains 50 µg/mL K1-70 IgG and 50 µg/mL 9D33 IgG. Consequently, the combined effect of two IgGs at 100 µg/mL can be compared to the effect of the single IgG at the same concentration (100 µg/mL).

TABLE 6n

Effect of K1 donor serum and serum TRAbs with blocking activity on stimulating activity of TSH, M22 IgG and K1-18 IgG

| Test sample | Cyclic AMP concentration (pmol/mL mean ± SD) | % Inhibition |
|---|---|---|
| Cyclic AMP buffer | 0.9 ± 0.2 | |
| 3 ng/mL pTSH | 73.7 ± 6.0 | |
| 3 ng/mL M22 IgG | 42.0 ± 9.5 | |
| 10 ng/mL K1-18 IgG | 44.1 ± 3.3 | |
| HBD control | 0.5 ± 0.4 | |
| HBD + 3 ng/mL pTSH | 99.4 ± 4.3 | 0 |
| HBD + 3 ng/mL M22 IgG | 34.7 ± 3.9 | 0 |
| HBD + 10 ng/mL K1-18 IgG | 22.0 ± 3.1 | 0 |
| B1 | 2.0 ± 0.1 | |
| B1 + 3 ng/mL pTSH | 32.0 ± 5.2 | 67.8 |
| B1 + 3 ng/mL M22 IgG | 4.5 ± 1.3 | 87.0 |
| B1 + 10 ng/mL K1-18 IgG | 3.8 ± 1.2 | 82.7 |
| B2 | 1.0 ± 0.7 | |
| B2 + 3 ng/mL pTSH | 1.7 ± 0.2 | 98.3 |
| B2 + 3 ng/mL M22 IgG | 0.9 ± 0.1 | 97.4 |
| B2 + 10 ng/mL K1-18 IgG | 0.6 ± 0.3 | 97.3 |
| B3 | 0.4 ± 0.1 | |
| B3 + 3 ng/mL pTSH | 9.3 ± 2.2 | 90.6 |
| B3 + 3 ng/mL M22 IgG | 4.9 ± 0.7 | 85.9 |
| B3 + 10 ng/mL K1-18 IgG | 6.1 ± 0.6 | 72.3 |
| Donor K1 | 3.8 ± 1.5 | |
| K1 + 3 ng/mL pTSH | 36.0 ± 3.7 | 63.8 |
| K1 + 3 ng/mL M22 IgG | 6.9 ± 0.8 | 80.1 |
| K1 + 10 ng/mL K1-18 IgG | 4.5 ± 0.2 | 79.5 |

See legend to Table 6a for details.
pTSH = porcine TSH.
B1-B3 are sera from patients with blocking type TRAb.
HBD = healthy blood donor serum.
Test samples were diluted in hypotonic cyclic AMP buffer.

TABLE 7a

Inhibition of porcine (p) TSH stimulation of cyclic AMP production in TSHR transfected CHO cells by K1-70 and 5C9 IgGs

| Test sample | Cyclic AMP concentration (pmol/mL mean ± SD) | % Inhibition |
|---|---|---|
| Cyclic AMP buffer only | 1.6 ± 0.3 | |
| 3 ng/mL pTSH | 62.6 ± 3.9 | 0 |
| 5B3 IgG | | |
| 100 µg/mL + 3 ng/mL pTSH | 66.7 ± 3.7 | 0 |
| 10 µg/mL + 3 ng/mL pTSH | 67.8 ± 3.7 | 0 |
| K1-70 IgG | | |
| 3 µg/mL + 3 ng/mL pTSH | 1.7 ± 0.6 | 97.3 |
| 1 µg/mL + 3 ng/mL pTSH | 2.0 ± 0.2 | 96.8 |
| 0.3 µg/mL + 3 ng/mL pTSH | 2.5 ± 0.9 | 96.0 |
| 0.1 µg/mL + 3 ng/mL pTSH | 5.8 ± 2.8 | 90.7 |
| 0.075 µg/mL + 3 ng/mL pTSH | 11.6 ± 2.0 | 81.5 |
| 0.05 µg/mL + 3 ng/mL pTSH | 31.4 ± 1.9 | 49.8 |
| 0.025 µg/mL + 3 ng/mL pTSH | 50.5 ± 7.3 | 19.3 |

TABLE 7a-continued

Inhibition of porcine (p) TSH stimulation of cyclic AMP production in TSHR transfected CHO cells by K1-70 and 5C9 IgGs

| Test sample | Cyclic AMP concentration (pmol/mL mean ± SD) | % Inhibition |
|---|---|---|
| 0.01 µg/mL + 3 ng/mL pTSH | 60.1 ± 1.6 | 4.0 |
| 0.003 µg/mL + 3 ng/mL pTSH | 59.5 ± 5.1 | 5.0 |
| 3 µg/mL + no pTSH | 0.8 ± 0.1 | |
| 5C9 IgG | | |
| 3 µg/mL + 3 ng/mL pTSH | 4.5 ± 1.5 | 92.8 |
| 1 µg/mL + 3 ng/mL pTSH | 4.8 ± 0.7 | 92.3 |
| 0.3 µg/mL + 3 ng/mL pTSH | 7.8 ± 2.1 | 87.5 |
| 0.1 µg/mL + 3 ng/mL pTSH | 11.4 ± 1.1 | 81.8 |
| 0.0075 µg/mL + 3 ng/mL pTSH | 14.7 ± 0.6 | 76.5 |
| 0.05 µg/mL + 3 ng/mL pTSH | 23.3 ± 2.9 | 62.8 |
| 0.025 µg/mL + 3 ng/mL pTSH | 46.3 ± 4.6 | 26.0 |
| 0.01 µg/mL + 3 ng/mL pTSH | 61.8 ± 4.8 | 1.0 |
| 0.003 µg/mL + 3 ng/mL pTSH | 56.1 ± 7.5 | 10.4 |
| 3 µg/mL + no pTSH | 0.9 ± 0.1 | |

Results shown are mean ± SD of triplicate determinations.
5B3 is a human MAb to glutamic acid decarboxylase (negative control).
Test samples were diluted in hypotonic cyclic AMP buffer.

TABLE 7b

Inhibition of porcine (p) TSH stimulation of cyclic AMP production in TSHR transfected CHO cells by K1-70 IgG and Fab preparations

| Test sample | Cyclic AMP concentration in hypotonic medium (pmol/mL mean ± SD) | Cyclic AMP concentration in isotonic medium (pmol/mL mean ± SD) |
|---|---|---|
| Cyclic AMP buffer only | 2.4 ± 0.4 | 0.7 ± 0.1 |
| 3 µg/mL 5B3 IgG | 1.9 ± 0.3 | 0.5 ± 0.1 |
| 3 µg/mL K1-70 IgG | 2.3 ± 0.9 | 0.5 ± 0.1 |
| 3 µg/mL K1-70 Fab | 2.3 ± 0.8 | 0.8 ± 0.2 |
| 3 ng/mL pTSH | 65.2 ± 11.2 | 42.4 ± 1.1 |
| 5B3 IgG | | |
| 3 µg/mL + 3 ng/mL pTSH | 75.7 ± 11.4 | 42.5 ± 2.8 |
| 1 µg/mL + 3 ng/mL pTSH | 71.9 ± 14.3 | 39.5 ± 1.9 |
| K1-70 IgG | | |
| 3 µg/mL + 3 ng/mL pTSH | 3.0 ± 1.2 | 1.1 ± 0.2 |
| 1 µg/mL + 3 ng/mL pTSH | 4.0 ± 0.7 | 2.2 ± 0.2 |
| 0.3 µg/mL + 3 ng/mL pTSH | 4.5 ± 0.6 | 8.2 ± 0.4 |
| 0.1 µg/mL + 3 ng/mL pTSH | 8.4 ± 0.9 | 27.0 ± 3.5 |
| 0.075 µg/mL + 3 ng/mL pTSH | 16.3 ± 1.3 | 33.3 ± 0.7 |
| 0.05 µg/mL + 3 ng/mL pTSH | 24.5 ± 5.2 | 36.5 ± 2.2 |
| 0.025 µg/mL + 3 ng/mL pTSH | 71.0 ± 4.5 | 38.1 ± 3.8 |
| 0.01 µg/mL + 3 ng/mL pTSH | 64.0 ± 9.9 | 45.0 ± 3.0 |
| 0.003 µg/mL + 3 ng/mL pTSH | 72.5 ± 16.2 | 40.8 ± 3.5 |
| K1-70 Fab | | |
| 3 µg/mL + 3 ng/mL pTSH | 3.7 ± 0.3 | 1.8 ± 0.5 |
| 1 µg/mL + 3 ng/mL pTSH | 3.8 ± 0.2 | 2.1 ± 0.8 |
| 0.3 µg/mL + 3 ng/mL pTSH | 5.2 ± 1.0 | 5.6 ± 1.3 |
| 0.1 µg/mL + 3 ng/mL pTSH | 12.9 ± 1.4 | 18.5 ± 2.1 |
| 0.075 µg/mL + 3 ng/mL pTSH | 14.1 ± 1.0 | 22.4 ± 0.4 |
| 0.05 µg/mL + 3 ng/mL pTSH | 28.9 ± 1.5 | 28.9 ± 1.1 |
| 0.025 µg/mL + 3 ng/mL pTSH | 59.9 ± 5.8 | 42.4 ± 1.1 |
| 0.01 µg/mL + 3 ng/mL pTSH | 58.8 ± 1.5 | 43.2 ± 4.0 |
| 0.003 µg/mL + 3 ng/mL pTSH | 56.3 ± 6.0 | 41.2 ± 1.0 |

See legend to Table 7a for details.
Test samples were diluted in cyclic AMP buffer.

TABLE 7c

The effect of human and mouse TSHR blocking MAbs (K1-70, 5C9 and 9D33) on the constitutive activity (ie basal activity) of the TSHR

| Test sample | Cyclic AMP concentration (pmol/mL mean ± SD) | % Inhibition |
|---|---|---|
| Cyclic AMP buffer only | 18.7 ± 2.3 | 0 |
| K1-70 IgG | | |
| 100 µg/mL | 17.6 ± 1.6 | 6 |
| 10 µg/mL | 17.3 ± 0.3 | 7 |
| 3 µg/mL | 18.1 ± 0.7 | 3 |
| 1 µg/mL | 16.8 ± 0.5 | 10 |
| 0.3 µg/mL | 18.9 ± 1.2 | 0 |
| 0.1 µg/mL | 19.6 ± 0.8 | 0 |
| 0.01 µg/mL | 19.1 ± 2.6 | 0 |
| 0.001 µg/mL | 20.3 ± 3.1 | 0 |
| 5C9 IgG | | |
| 100 µg/mL | 9.0 ± 1.0 | 52 |
| 10 µg/mL | 8.3 ± 0.9 | 56 |
| 3 µg/mL | 6.9 ± 0.8 | 63 |
| 1 µg/mL | 7.4 ± 1.3 | 61 |
| 0.3 µg/mL | 9.3 ± 1.2 | 50 |
| 0.1 µg/mL | 16.3 ± 0.9 | 13 |
| 0.01 µg/mL | 18.6 ± 1.7 | 1 |
| 0.001 µg/mL | 19.1 ± 0.8 | 0 |
| 9D33 IgG | | |
| 100 µg/mL | 38.0 ± 1.9 | 0 |
| 10 µg/mL | 34.3 ± 1.4 | 0 |
| 3 µg/mL | 32.3 ± 2.3 | 0 |
| 1 µg/mL | 35.5 ± 4.3 | 0 |
| 0.3 µg/mL | 26.4 ± 1.2 | 0 |
| 0.1 µg/mL | 23.9 ± 2.7 | 0 |
| 0.01 µg/mL | 20.3 ± 1.2 | 0 |
| 0.001 µg/mL | 18.8 ± 2.1 | 0 |

See legend to Table 7a for details.
The experiments were carried out using CHO cell line expressing wild type TSHR at approximately $5 \times 10^5$ receptors per cell.

TABLE 7d

Effect of K1 donor serum on TSH mediated stimulation of cyclic AMP in CHO cells expressing TSHR

| Test sample | Cyclic AMP concentration (pmol/mL mean ± SD) | % Inhibition |
|---|---|---|
| Cyclic AMP buffer | 1.7 ± 1.0 | |
| 1 ng/mL pTSH | 61.7 ± 4.3 | |
| 3 µg/mL K1-70 IgG | 1.7 ± 0.1 | |
| 1 ng/mL pTSH + 3 µg/mL K1-70 IgG | 3.6 ± 0.6 | 94.2 |
| 1 ng/mL pTSH + 1 µg/mL K1-70 IgG | 3.9 ± 0.1 | 93.7 |
| 1 ng/mL pTSH + 0.3 µg/mL K1-70 IgG | 3.3 ± 0.4 | 94.7 |
| 1 ng/mL pTSH + 0.1 µg/mL K1-70 IgG | 20.0 ± 1.2 | 67.6 |
| 1 ng/mL pTSH + 0.03 µg/mL K1-70 IgG | 52.2 ± 11.2 | 18.2 |
| 1 ng/mL pTSH + 0.01 µg/mL K1-70 IgG | 67.7 ± 3.7 | 0 |
| 1 ng/mL pTSH + 0.003 µg/mL K1-70 IgG | 72.4 ± 5.5 | 0 |
| 1 ng/mL pTSH + 0.001 µg/mL K1-70 IgG | 58.7 ± 2.2 | 4.9 |
| 1 ng/mL pTSH + 0.0003 µg/mL K1-70 IgG | 66.2 ± 1.7 | 0 |
| 100 µg/mL 5B3 IgG | 2.6 ± 0.2 | |
| 1 ng/mL pTSH + 100 µg/mL 5B3 IgG | 79.3 ± 8.9 | 0 |
| 1 ng/mL pTSH + 10 µg/mL 5B3 IgG | 80.7 ± 1.1 | 0 |
| 1 ng/mL pTSH + K1 donor serum 10x diluted | 14.9 ± 1.2 | 75.9 |
| 1 ng/mL pTSH + K1 donor serum 20x diluted | 51.6 ± 2.6 | 16.4 |
| 1 ng/mL pTSH + K1 donor serum 40x diluted | 63.0 ± 3.3 | 0 |
| 1 ng/mL pTSH + K1 donor serum 80x diluted | 64.4 ± 3.5 | 0 |
| 1 ng/mL pTSH + K1 donor serum 160x diluted | 63.9 ± 3.6 | 0 |
| K1 donor serum 10x diluted | 4.7 ± 0.3 | |
| 1 ng/mL pTSH + HBD 10x diluted | 101.3 ± 5.1 | 0 |

TABLE 7d-continued

Effect of K1 donor serum on TSH mediated stimulation of cyclic AMP in CHO cells expressing TSHR

| Test sample | Cyclic AMP concentration (pmol/mL mean ± SD) | % Inhibition |
|---|---|---|
| 1 ng/mL pTSH + HBD 20x diluted | 88.6 ± 6.4 | 0 |
| HBD 10x diluted | 2.2 ± 1.0 | |

See legend to Table 7a for details.
HBD = pool of healthy blood donor sera.
pTSH = porcine TSH.

TABLE 7e

Effect of K1-70 IgG on stimulation of cyclic AMP production by porcine (p), human (h) and recombinant human (rh) TSH in CHO cells expressing the TSHR

| Test sample | Cyclic AMP concentration in hypotonic medium (pmol/mL mean ± SD) | Cyclic AMP concentration in isotonic medium (pmol/mL mean ± SD) |
|---|---|---|
| Cyclic AMP buffer | 2.5 ± 0.5 | 1.1 ± 0.4 |
| 100 µg/mL 5B3 IgG | 2.2 ± 0.6 | 1.4 ± 0.5 |
| 100 µg/mL K1-70 IgG | 2.5 ± 0.5 | 1.1 ± 0.2 |
| pTSH 3 ng/mL | 48.1 ± 0.9 | 41.1 ± 2.2 |
| pTSH 3 ng/mL + 100 µg/mL K1-70 IgG | 0.1 ± 0.0 | 1.3 ± 0.3 |
| pTSH 3 ng/mL + 10 µg/mL K1-70 IgG | 0.2 ± 0.1 | 1.2 ± 0.3 |
| pTSH 3 ng/mL + 1 µg/mL K1-70 IgG | 0.1* | 2.0 ± 0.4 |
| pTSH 3 ng/mL + 0.1 µg/mL K1-70 IgG | 3.3 ± 2.8 | 24.4 ± 1.2 |
| pTSH 3 ng/mL + 0.01 µg/mL K1-70 IgG | 53.8 ± 3.4 | 39.7 ± 3.0 |
| pTSH 3 ng/mL + 0.001 µg/mL K1-70 IgG | 44.9 ± 1.8 | 36.6 ± 5.8 |
| 100 ng/mL hTSH | 56.8 ± 0.1 | 42.3 ± 4.5 |
| 100 ng/mL hTSH + 100 µg/mL K1-70 IgG | 0.1* | 1.3 ± 0.3 |
| 100 ng/mL hTSH + 10 µg/mL K1-70 IgG | 0.1 ± 0.0 | 1.0 ± 0.3 |
| 100 ng/mL hTSH + 1 µg/mL K1-70 IgG | 0.2 ± 0.1 | 1.9 ± 0.2 |
| 100 ng/mL hTSH + 0.1 µg/mL K1-70 IgG | 0.1 ± 0.0 | 29.8 ± 1.5 |
| 100 ng/mL hTSH + 0.01 µg/mL K1-70 IgG | 55.2* | 37.9 ± 2.7 |
| 100 ng/mL hTSH + 0.001 µg/mL K1-70 IgG | 55.0 ± 3.0 | 38.8 ± 2.8 |
| 100 ng/mL rhTSH | 37.8 ± 4.9 | 29.9 ± 2.3 |
| 100 ng/mL rhTSH + 100 µg/mL K1-70 IgG | 0.3 ± 0.1 | 0.9 ± 0.1 |
| 100 ng/mL rhTSH + 10 µg/mL K1-70 IgG | 0.2 ± 0.1 | 0.7 ± 0.2 |
| 100 ng/mL rhTSH + 1 µg/mL K1-70 IgG | 0.3* | 1.3 ± 0.6 |
| 100 ng/mL rhTSH + 0.1 µg/mL K1-70 IgG | 0.3 ± 0.1 | 10.2 ± 0.9 |
| 100 ng/mL rhTSH + 0.01 µg/mL K1-70 IgG | 27.3 ± 5.5 | 21.4 ± 1.0 |
| 100 ng/mL rhTSH + 0.001 µg/mL K1-70 IgG | 30.8 ± 1.4 | 23.0 ± 3.8 |
| 100 ng/mL rhTSH + 100 µg/mL K1-70 IgG | 36.7 ± 3.4 | 28.1 ± 1.5 |

See legend to Table 7a for details.
*mean of duplicate determinations.
Test samples were diluted in cyclic AMP buffer.

TABLE 7f

Effect of K1-70 IgG on M22 IgG mediated stimulation of cyclic AMP production in CHO cells expressing the TSHR

| Test sample | Cyclic AMP concentration (pmol/mL mean ± SD) | % Inhibition |
|---|---|---|
| Cyclic AMP buffer | 1.4 ± 0.3 | |
| K1-70 IgG 100 µg/mL | 1.1 ± 0.5 | |
| 5B3 IgG 100 µg/mL | 1.2 ± 0.5 | |
| 5C9 IgG 100 µg/mL | 0.5 ± 0.2 | |
| 3 ng/mL M22 IgG | 33.1 ± 1.8 | 0 |
| 3 ng/mL M22 IgG + 100 µg/ml 5B3 IgG | 41.8 ± 5.3 | 0 |

TABLE 7f-continued

Effect of K1-70 IgG on M22 IgG mediated stimulation of cyclic AMP production in CHO cells expressing the TSHR

| Test sample | Cyclic AMP concentration (pmol/mL mean ± SD) | % Inhibition |
|---|---|---|
| 3 ng/mL M22IgG + 100 µg/ml K1-70 IgG | 0.6 ± 0.3 | 98.2 |
| 3 ng/mL M22 IgG + 50 µg/ml K1-70 IgG | 0.8 ± 0.4 | 97.6 |
| 3 ng/mL M22 IgG + 10 µg/ml K1-70 IgG | 0.6 ± 0.4 | 98.2 |
| 3 ng/mL M22 IgG + 5 µg/ml K1-70 IgG | 0.1 ± 0.2 | 99.7 |
| 3 ng/mL M22 IgG + 1 µg/ml K1-70 IgG | 0.6 ± 0.2 | 98.2 |
| 3 ng/mL M22 IgG + 0.5 g/ml K1-70 IgG | 0.5 ± 0.3 | 98.5 |
| 3 ng/mL M22 IgG + 0.1 µg/ml K1-70 IgG | 4.3 ± 2.4 | 87.0 |
| 3 ng/mL M22 IgG + 0.01 µg/ml K1-70 IgG | 33.0 ± 3.2 | 0 |
| 3 ng/mL M22 IgG + 0.001 µg/ml K1-70 IgG | 35.9 ± 3.2 | 0 |
| 3 ng/mL M22 IgG + 100 µg/ml 5C9 IgG | 0.4 ± 0.4 | 98.8 |
| 3 ng/mL M22 IgG + 50 µg/ml 5C9 IgG | 0.3 ± 0.1 | 99.1 |
| 3 ng/mL M22 IgG + 10 µg/ml 5C9 IgG | 0.3 ± 0.1 | 99.1 |
| 3 ng/mL M22 IgG + 5 µg/ml 5C9 IgG | 0.2 ± 0.2 | 99.4 |
| 3 ng/mL M22 IgG + 1 µg/ml 5C9 IgG | 0.8 ± 0.4 | 97.6 |
| 3 ng/mL M22 IgG + 0.5 µg/ml 5C9 IgG | 1.0 ± 0.1 | 97.0 |
| 3 ng/mL M22 IgG + 0.1 µg/ml 5C9 IgG | 2.9 ± 0.6 | 91.2 |
| 3 ng/mL M22 IgG + 0.01 µg/ml 5C9 IgG | 42.3 ± 7.1 | 0 |
| 3 ng/mL M22 IgG + 0.001 µg/ml 5C9 IgG | 39.3 ± 3.6 | 0 |

See legend to Table 7a for details.
HBD = pool of healthy blood donor sera.

TABLE 7g

Effect of K1-70 IgG on TSHR stimulating activity of TRAb positive patient sera (T1-T3)

| Test sample | Cyclic AMP concentration (pmol/mL mean ± SD) | % Inhibition |
|---|---|---|
| Cyclic AMP buffer | 2.0 ± 0.6 | |
| HBD | 1.7 ± 0.2 | |
| HBD + 100 µg/mL 5B3 IgG | 2.0 ± 0.1 | |
| HBD + 100 µg/mL K1-70 IgG | 1.2 ± 0.1 | |
| HBD + 100 µg/mL 5C9 IgG | 0.9 ± 0.3 | |
| HBD + 100 µg/mL 9D33 IgG | 1.9 ± 0.1 | |
| T1 serum | 99.8 ± 6.1 | 0 |
| T1 serum + 100 µg/mL 5B3 IgG | 94.9 ± 14.2 | 4.9 |
| T1 serum + 100 µg/mL K1-70 IgG | 1.4 ± 0.3 | 98.6 |
| T1 serum + 100 µg/mL 5C9 IgG | 1.3 ± 0.2 | 98.7 |
| T1 serum + 100 µg/mL 9D33 IgG | 4.6 ± 0.7 | 95.4 |
| T2 serum | 61.8 ± 6.3 | 0 |
| T2 serum + 100 µg/mL 5B3 IgG | 62.0 ± 14.6 | 0 |
| T2 serum + 100 µg/mL K1-70 IgG | 1.5 ± 0.1 | 97.6 |
| T2 serum + 100 µg/mL 5C9 IgG | 1.1 ± 0.3 | 98.2 |
| T2 serum + 100 µg/mL 9D33 IgG | 2.0 ± 0.2 | 96.8 |
| T3 serum | 63.3 ± 9.7 | 0 |
| T3 serum + 100 µg/mL 5B3 IgG | 54.2 ± 3.8 | 14.4 |
| T3 serum + 100 µg/mL K1-70 IgG | 1.2 ± 0.3 | 98.1 |
| T3 serum + 100 µg/mL 5C9 IgG | 1.4 ± 0.2 | 97.8 |
| T3 serum + 100 µg/mL 9D33 IgG | 3.7 ± 1.0 | 94.2 |
| 100 µg/mL 5B3 IgG | 1.0 ± 0.4 | |
| 100 µg/mL K1-70 IgG | 0.8 ± 0.1 | |
| 100 µg/mL 5C9 IgG | 1.0 ± 0.5 | |
| 100 µg/mL 9D33 IgG | 2.1 ± 0.5 | |

See legend to Table 7a for details.
HBD = pool of healthy blood donor sera.
Sera were diluted to a final concentration of 1:10 in hypotonic cyclic AMP assay buffer.

TABLE 7h

Effect of K1-70 IgG on TSHR stimulating activity of TRAb positive patient sera (T4-T6)

| Test sample | Cyclic AMP concentration (pmol/mL mean ± SD) | % Inhibition |
|---|---|---|
| Cyclic AMP buffer | 1.9 ± 0.4 | |
| HBD | 2.4 ± 0.1 | |
| HBD + 100 µg/mL 5B3 IgG | 3.0 ± 0.1 | |
| HBD + 100 µg/mL K1-70 IgG | 2.1 ± 0.2 | |
| HBD + 100 µg/mL 5C9 IgG | 1.8 ± 0.9 | |
| HBD + 100 µg/mL 9D33 | 3.9 ± 0.5 | |
| T4 serum | 78.9 ± 8.2 | 0 |
| T4 serum + 100 µg/mL 5B3 IgG | 55.0 ± 14.0 | 30.3 |
| T4 serum + 100 µg/mL K1-70 IgG | 3.0 ± 0.4 | 96.2 |
| T4 serum + 100 µg/mL 5C9 IgG | 1.9 ± 0.3 | 97.6 |
| T4 serum + 100 µg/mL 9D33 | 4.1 ± 1.1 | 94.8 |
| T5 serum | 66.6* | 0 |
| T5 serum + 100 µg/mL 5B3 IgG | 66.7 ± 5.3 | 0 |
| T5 serum + µg/mL K1-70 IgG 100 | 1.6 ± 0.4 | 97.6 |
| T5 serum + 100 µg/mL 5C9 IgG | 1.1 ± 0.2 | 98.3 |
| T5 serum + 100 µg/mL 9D33 | 2.9 ± 0.2 | 95.6 |
| T6 serum | 83.0 ± 6.9 | 0 |
| T6 serum + 100 µg/mL 5B3 IgG | 81.5 ± 20.5 | 1.8 |
| T6 serum + µg/mL K1-70 IgG 100 | 2.5 ± 0.1 | 97.0 |
| T6 serum + 100 µg/mL 5C9 IgG | 1.8 ± 0.4 | 97.8 |
| T6 serum + 100 µg/mL 9D33 | 5.0 ± 1.0 | 94.0 |
| 100 µg/mL 5B3 IgG | 2.6 ± 0.7 | |
| 100 µg/mL K1-70 IgG | 1.4 ± 0.5 | |
| 100 µg/mL 5C9 IgG | 1.2 ± 0.3 | |
| 100 µg/mL 9D33 | 2.0 ± 0.6 | |

See legend to Table 7g for details.
*mean of duplicate determinations.
HBD = pool of healthy blood donor sera.

TABLE 7i

Effect of K1-70 IgG on TSHR stimulating activity of TRAb positive patient sera (T7-T9)

| Test sample | Cyclic AMP concentration (pmol/mL mean ± SD) | % Inhibition |
|---|---|---|
| Cyclic AMP buffer | 2.9 ± 1.1 | |
| HBD | 3.1 ± 0.4 | |
| HBD + 100 µg/mL 5B3 IgG | 4.0 ± 0.4 | |
| HBD + 100 µg/mL K1-70 IgG | 2.7 ± 0.1 | |
| HBD + 100 µg/mL 5C9 IgG | 2.7 ± 1.4 | |
| HBD + 100 µg/mL 9D33 IgG | 5.4 ± 0.3 | |
| T7 serum | 90.6* | |
| T7 serum + 100 µg/mL 5B3 IgG | 91.9 ± 29.6 | 0 |
| T7 serum + 100 µg/mL K1-70 IgG | 3.2 ± 0.4 | 96.5 |
| T7 serum + 100 µg/mL 5C9 IgG | 2.1 ± 0.5 | 97.7 |
| T7 serum + 100 µg/mL 9D33 IgG | 6.3 ± 1.2 | 93.0 |
| T8 serum | 85.6* | 0 |
| T8 serum + 100 µg/mL 5B3 IgG | 76.3 ± 10.7 | 10.9 |
| T8 serum + 100 µg/mL K1-70 IgG | 3.2 ± 0.5 | 96.3 |
| T8 serum + 100 µg/mL 5C9 IgG | 1.8 ± 0.3 | 97.9 |
| T8 serum + 100 µg/mL 9D33 IgG | 4.3 ± 0.6 | 95.0 |
| T9 serum | 56.4 ± 0.0 | 0 |
| T9 serum + 100 µg/mL 5B3 IgG | 53.2* | 0 |
| T9 serum + 100 µg/mL K1-70 IgG | 5.2 ± 0.5 | 90.8 |
| T9 serum + 100 µg/mL 5C9 IgG | 3.0 ± 0.4 | 94.7 |
| T9 serum + 100 µg/mL 9D33 IgG | 7.2 ± 1.1 | 87.2 |
| 100 µg/mL 5B3 IgG | 2.7 ± 0.3 | |
| 100 µg/mL K1-70 IgG | 1.6 ± 0.4 | |
| 100 µg/mL 5C9 IgG | 1.0 ± 0.5 | |
| 100 µg/mL 9D33 IgG | 2.4 ± 0.4 | |

See legend to Table 7g for details.
*mean of duplicate determinations.
HBD = pool of healthy blood donor sera.

TABLE 7j

Effect of K1-70 IgG on TSHR stimulating activity of TRAb positive patient sera (T10-T12)

| Test sample | Cyclic AMP concentration (pmol/mL mean ± SD) | % Inhibition |
|---|---|---|
| Cyclic AMP buffer | 1.8 ± 0.2 | |
| HBD | 2.2 ± 0.2 | |
| HBD + 100 µg/mL 5B3 IgG | 2.4 ± 0.4 | |
| HBD + 100 µg/mL K1-70 IgG | 1.7 ± 0.0 | |
| HBD + 100 µg/mL 5C9 IgG | 1.1 ± 0.3 | |
| HBD + 100 µg/mL 9D33 IgG | 3.2 ± 0.6 | |
| T10 serum | 56.3 ± 5.2 | 0 |
| T10 serum + 100 µg/mL 5B3 IgG | 59.3 ± 7.1 | 0 |
| T10 serum + 100 µg/mL K1-70 IgG | 1.8 ± 0.2 | 96.8 |
| T10 serum + 100 µg/mL 5C9 IgG | 0.9 ± 0.1 | 98.4 |
| T10 serum + 100 µg/mL 9D33 IgG | 2.6 ± 0.3 | 95.4 |
| T11 serum | 41.0 ± 4.5 | 0 |
| T11 serum + 100 µg/mL 5B3 IgG | 39.7 ± 1.8 | 3.2 |
| T11 serum + 100 µg/mL K1-70 IgG | 2.0 ± 0.2 | 95.1 |
| T11 serum + 100 µg/mL 5C9 IgG | 37.5 ± 3.9 | 8.5 |
| T11 serum + 100 µg/mL 9D33 IgG | 5.3 ± 1.6 | 87.1 |
| T12 serum | 43.2 ± 3.1 | 0 |
| T12 serum + 100 µg/mL 5B3 IgG | 43.3 ± 4.0 | 0 |
| T12 serum + 100 µg/mL K1-70 IgG | 1.8 ± 0.0 | 95.8 |
| T12 serum + 100 µg/mL 5C9 IgG | 1.6 ± 0.7 | 96.3 |
| T12 serum + 100 µg/mL 9D33 IgG | 3.6 ± 0.1 | 91.7 |
| 100 µg/mL 5B3 IgG | 2.0 ± 0.4 | |
| 100 µg/mL K1-70 IgG | 1.1 ± 0.1 | |
| 100 µg/mL 5C9 IgG | 0.9 ± 0.1 | |
| 100 µg/mL 9D33 IgG | 1.9 ± 0.4 | |

See legend to Table 7g for details.
HBD = pool of healthy blood donor sera.

TABLE 7k

Effect of K1-70 IgG on TSHR stimulating activity of TRAb positive patient sera (T13-T15)

| Test sample | Cyclic AMP concentration (pmol/mL mean ± SD) | % Inhibition |
|---|---|---|
| Cyclic AMP buffer | 1.6 ± 0.2 | |
| HBD | 2.2 ± 0.4 | |
| HBD + 100 µg/mL 5B3 IgG | 5.1 ± 1.2 | |
| HBD + 100 µg/mL K1-70 IgG | 2.1 ± 0.8 | |
| HBD + 100 µg/mL 5C9 IgG | 1.0 ± 0.2 | |
| HBD + 100 µg/mL 9D33 IgG | 3.3 ± 0.3 | |
| T13 serum | 48.5 ± 3.8 | 0 |
| T13 serum + 100 µg/mL 5B3 IgG | 37.6 ± 3.4 | 22.5 |
| T13 serum + 100 µg/mL K1-70 IgG | 2.1 ± 0.3 | 95.7 |
| T13 serum + 100 µg/mL 5C9 IgG | 1.2 ± 0.3 | 97.5 |
| T13 serum + 100 µg/mL 9D33 IgG | 3.8 ± 0.3 | 92.2 |
| T14 serum | 27.2 ± 3.6 | 0 |
| T14 serum + 100 µg/mL 5B3 IgG | 20.5 ± 2.3 | 24.6 |
| T14 serum + 100 µg/mL K1-70 IgG | 1.9 ± 0.4 | 93.0 |
| T14 serum + 100 µg/mL 5C9 IgG | 1.4 ± 0.5 | 94.9 |
| T14 serum + 100 µg/mL 9D33 IgG | 2.8 ± 0.3 | 89.7 |
| T15 serum | 51.3* | 0 |
| T15 serum + 100 µg/mL 5B3 IgG | 41.9 ± 4.0 | 18.3 |
| T15 serum + 100 µg/mL K1-70 IgG | 2.7 ± 0.1 | 94.7 |
| T15 serum + 100 µg/mL 5C9 IgG | 1.6 ± 0.3 | 96.9 |
| T15 serum + 100 µg/mL 9D33 IgG | 3.9 ± 0.2 | 92.4 |
| 100 µg/mL 5B3 IgG | 4.1 ± 0.9 | |
| 100 µg/mL K1-70 IgG | 2.6 ± 1.5 | |
| 100 µg/mL 5C9 IgG | 0.9 ± 0.2 | |
| 100 µg/mL 9D33 IgG | 2.3 ± 0.2 | |

See legend to Table 7g for details.
*mean of duplicate determinations.
HBD = pool of healthy blood donor sera.

TABLE 7l

Effect on T5 serum stimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.4 ± 0.5 | |
| HBD diluted 10x | 2.8 ± 0.7 | |
| Serum T5 diluted 10x | 63.9 ± 5.9 | |
| 5B3 IgG (negative control) | | |
| 100 µg/mL | 1.1 ± 0.5 | |
| 100 µg/mL + T5 | 55.9 ± 5.5 | 12.5 |
| 10 µg/mL + T5 | 61.9 ± 2.6 | 3.1 |
| 1 µg/mL + T5 | 61.3 ± 5.5 | 4.1 |
| 0.1 µg/mL + T5 | 59.4* | 7.0 |
| K1-70 IgG | | |
| 100 µg/mL | 1.0 ± 0.3 | |
| 100 µg/mL + T5 | 1.4 ± 0.6 | 97.8 |
| 10 µg/mL + T5 | 0.9 ± 0.1 | 98.6 |
| 1 µg/mL + T5 | 1.4 ± 0.1 | 97.8 |
| 0.1 µg/mL + T5 | 8.3 ± 1.1 | 87.0 |
| 0.01 µg/mL + T5 | 52.4 ± 4.8 | 18.0 |
| 5C9 IgG | | |
| 100 µg/mL | 1.1 ± 0.3 | |
| 100 µg/mL + T5 | 0.7 ± 0.1 | 98.9 |
| 10 µg/mL + T5 | 0.7 ± 0.0 | 98.9 |
| 1 µg/mL + T5 | 1.4 ± 0.5 | 97.8 |
| 0.1 µg/mL + T5 | 5.6 ± 0.3 | 91.2 |
| 0.01 µg/mL + T5 | 52.9 ± 2.0 | 17.2 |
| 9D33 IgG | | |
| 100 µg/mL | 2.4 ± 0.2 | |
| 100 µg/mL + T5 | 3.0 ± 0.2 | 95.3 |
| 10 µg/mL + T5 | 2.3 ± 0.2 | 96.4 |
| 1 µg/mL + T5 | 4.1 ± 0.3 | 93.6 |
| 0.1 µg/mL + T5 | 28.3 ± 0.8 | 55.7 |
| 0.01 µg/mL + T5 | 49.2 ± 3.5 | 23.0 |

See legend to Table 7a for details.
T5 = TRAb positive serum with thyroid stimulating activity;
T5 serum was diluted to a final concentration of 1:10 in hypotonic cyclic AMP buffer.
HBD = pool of healthy blood donor sera.

TABLE 7m

Effect on T8 serum stimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.7 ± 0.2 | |
| HBD diluted 10x | 2.5 ± 1.0 | |
| Serum T8 diluted 10x | 52.3 ± 10.5 | |
| 5B3 IgG | | |
| 100 µg/mL | 2.1 ± 0.5 | |
| 100 µg/mL + T8 | 50.5 ± 3.1 | 3 |
| 10 µg/mL + T8 | 56.0 ± 14.7 | 0 |
| 1 µg/mL + T8 | 51.4 ± 2.7 | 2 |
| 0.1 µg/mL + T8 | 50.7 ± 10.2 | 3 |
| K1-70 IgG | | |
| 100 µg/mL | 1.8 ± 0.2 | |
| 100 µg/mL + T8 | 2.4 ± 0.3 | 95 |
| 10 µg/mL + T8 | 2.1 ± 0.7 | 96 |
| 1 µg/mL + T8 | 2.5 ± 0.2 | 95 |
| 0.1 µg/mL + T8 | 5.8 ± 0.3 | 89 |
| 0.01 µg/mL + T8 | 63.4 ± 8.0 | 0 |
| 5C9 IgG | | |
| 100 µg/mL | 1.2 ± 0.2 | |
| 100 µg/mL + T8 | 1.7 ± 0.8 | 97 |
| 10 µg/mL + T8 | 1.7 ± 0.2 | 97 |
| 1 µg/mL + T8 | 2.2 ± 0.3 | 96 |
| 0.1 µg/mL + T8 | 4.6 ± 0.5 | 91 |
| 0.01 µg/mL + T8 | 53.7 ± 7.1 | 0 |
| 9D33 IgG | | |
| 100 µg/mL | 2.4 ± 0.5 | |
| 100 µg/mL + T8 | 3.6 ± 0.8 | 93 |
| 10 µg/mL + T8 | 3.7 ± 0.5 | 93 |
| 1 µg/mL + T8 | 4.7 ± 0.2 | 91 |
| 0.1 µg/mL + T8 | 22.9 ± 0.4 | 56 |
| 0.01 µg/mL + T8 | 45.8 ± 4.9 | 12 |

See legend to Table 7a for details.
T8 = TRAb positive serum with TSH receptor stimulating activity;
T8 serum was diluted to a final oncentration of 1:10 in hypotonic cyclic AMP buffer
HBD = pool of healthy blood donor sera.

TABLE 7n

Effect on T11 serumstimulating activity of different concentrations of TSHR blocking monoclonal antibodies (K1-70, 5C9, 9D33)

| Test sample | Cyclic AMP concentration (pmol/mL mean ± SD) | % Inhibition |
|---|---|---|
| Cyclic AMP buffer | 1.2 ± 0.4 | |
| HBD diluted 10x | 1.8 ± 0.4 | |
| Serum T11 diluted 10x | 25.2 ± 4.4 | |
| 5B3 IgG | | |
| 100 µg/mL | 1.0 ± 0.2 | |
| 100 µg/mL + T11 | 18.4 ± 1.3 | 27.0 |
| 10 µg/mL + T11 | 18.8 ± 1.3 | 25.4 |
| 1 µg/mL + T11 | 19.8 ± 1.2 | 21.4 |
| 0.1 µg/mL + T11 | 17.7 ± 2.1 | 29.8 |
| K1-70 IgG | | |
| 100 µg/mL | 0.9 ± 0.2 | |
| 100 µg/mL + T11 | 1.0 ± 0.3 | 96.0 |
| 10 µg/mL + T11 | 1.1 ± 0.1 | 95.6 |
| 1 µg/mL + T11 | 1.1 ± 0.1 | 95.6 |
| 0.1 µg/mL + T11 | 2.4 ± 0.3 | 90.5 |
| 0.01 µg/mL + T11 | 22.1 ± 0.8 | 12.3 |
| 5C9 IgG | | |
| 100 µg/mL | 0.9 ± 0.1 | |
| 100 µg/mL + T11 | 22.4 ± 1.9 | 11.1 |
| 10 µg/mL + T11 | 21.7 ± 0.5 | 13.9 |
| 1 µg/mL + T11 | 19.4 ± 2.2 | 23.0 |
| 0.1 µg/mL + T11 | 20.2 ± 0.4 | 19.8 |
| 0.01 µg/mL + T11 | 24.1 ± 0.5 | 4.3 |
| 9D33 IgG | | |
| 100 µg/mL | 1.3 ± 0.2 | |
| 100 µg/mL + T11 | 2.1 ± 0.1 | 94.8 |
| 10 µg/mL + T11 | 2.5 ± 0.1 | 90.1 |
| 1 µg/mL + T11 | 3.1 ± 0.3 | 87.7 |
| 0.1 µg/mL + T11 | 12.5 ± 0.3 | 50.4 |
| 0.01 µg/mL + T11 | 20.9 ± 0.3 | 17.1 |

See legend to Table 7a for details.
T11 = TRAb positive serum with TSH receptor stimulating activity;
T11 serum was diluted to a final concentration of 1:10 in hypotonic cyclic AMP buffer.
HBD = pool of healthy blood donor sera.

TABLE 7o

Inhibition of porcine (p) TSH stimulation of cyclic AMP production in TSHR transfected CHO cells by K1-70 and 5C9 mixed together

| Test Sample | Cyclic AMP concentration (pmol/mL mean ± SD) | % Inhibition |
|---|---|---|
| Cyclic AMP buffer | 0.6 ± 0.1 | |
| pTSH 3 ng/mL | 64.2 ± 3.5 | |
| 100 µg/mL 5B3 | 0.9 ± 0.2 | |
| 100 µg/mL 5C9 | 0.2 ± 0.0 | |
| 100 µg/mL K1-70 | 0.6 ± 0.2 | |
| 100 µg/mL (K1-70 + 5C9)[a] | 0.7 ± 0.5 | |
| pTSH 3 ng/mL + 100 µg/mL 5B3 | 63.9 ± 5.1 | 0.5 |
| pTSH 3 ng/mL + 10 µg/mL 5B3 | 66.9 ± 6.5 | 0 |
| pTSH 3 ng/mL + 100 µg/mL 5C9 | 0.5 ± 0.0 | 99.2 |
| pTSH 3 ng/mL + 10 µg/mL 5C9 | 1.3 ± 0.4 | 98.0 |
| pTSH 3 ng/mL + 1 µg/mL 5C9 | 4.2 ± 0.6 | 93.5 |
| pTSH 3 ng/mL + 0.1 µg/mL 5C9 | 13.7 ± 4.9 | 78.7 |
| pTSH 3 ng/mL + 0.01 µg/mL 5C9 | 64.6 ± 1.4 | 0 |
| pTSH 3 ng/mL + 0.001 µg/mL 5C9 | 64.1 ± 7.3 | 0.2 |
| pTSH 3 ng/mL + 100 µg/mL K1-70 | 0.7 ± 0.1 | 98.9 |
| pTSH 3 ng/mL + 10 µg/mL K1-70 | 1.0 ± 0.6 | 98.4 |
| pTSH 3 ng/mL + 1 µg/mL K1-70 | 0.7 ± 0.4 | 98.9 |
| pTSH 3 ng/mL + 0.1 µg/mL K1-70 | 5.9 ± 2.8 | 90.8 |
| pTSH 3 ng/mL + 0.01 µg/mL K1-70 | 52.0 ± 3.0 | 19.0 |
| pTSH 3 ng/mL + 0.001 µg/mL K1-70 | 59.4 ± 3.7 | 7.5 |
| pTSH 3 ng/mL + 100 µg/mL (K1-70 + 5C9)[a] | 1.1 ± 0.4 | 98.3 |
| pTSH 3 ng/mL + 10 µg/mL (K1-70 + 5C9)[a] | 0.5 ± 0.1 | 99.2 |
| pTSH 3 ng/mL + 1 µg/mL (K1-70 + 5C9)[a] | 2.5 ± 0.3 | 96.1 |
| pTSH 3 ng/mL + 0.1 µg/mL (K1-70 + 5C9)[a] | 9.4 ± 4.0 | 85.4 |
| pTSH 3 ng/mL + 0.01 µg/mL (K1-70 + 5C9)[a] | 49.4 ± 2.9 | 23.0 |
| pTSH 3 ng/mL + 0.001 µg/mL (K1-70 + 5C9)[a] | 48.3 ± 4.8 | 24.8 |

See legend to Table 7a for details.
K1-70, 5C9 and 5B3: purified IgG of the MAbs were used in all experiments.
[a]In some experiments the MAbs were mixed in equal proportions and the concentration shown for a mixture represents the total amount of IgG added i.e.: 100 µg/mL (K1-70 + 5C9) = 50 µg/mL of K1-70 + 50 µg/mL of 5C9 used in the experiment.

TABLE 7p

The effect of K1-70 and 5C9 IgGs mixed together on the constitutive activity (ie basal activity) of the TSHR

| Test Sample | Cyclic AMP production (pmol/mL mean ± SD) | % Inhibition |
|---|---|---|
| cyclic AMP buffer only | 58.04 ± 8.52 | |
| 0.1 µg/mL 5C9 IgG | 68.21 ± 2.81 | 0 |
| 0.2 µg/mL 5C9 IgG | 58.75 ± 3.92 | 0 |
| 1 µg/mL 5C9 IgG | 31.40 ± 0.89 | 45.9 |
| 2 µg/mL 5C9 IgG | 31.75 ± 2.73 | 45.3 |
| 0.01 µg/mL K1-70 IgG | 92.24 ± 3.92 | 0 |
| 0.1 µg/mL K1-70 IgG | 62.77 ± 2.18 | 0 |
| 0.2 µg/mL K1-70 IgG | 58.75 ± 3.92 | 0 |
| 1 µg/mL K1-70 IgG | 61.52 ± 5.04 | 0 |
| 2 µg/mL K1-70 IgG | 52.12 ± 1.84 | 10.2 |
| 0.01 µg/mL 5B3 IgG | 58.16 ± 9.42 | 0 |
| 0.1 µg/mL 5B3 IgG | 58.75 ± 3.92 | 0 |
| 0.2 µg/mL 5B3 IgG | 53.30 ± 3.36 | 8.2 |
| 1 µg/mL 5B3 IgG | 54.39 ± 2.62 | 6.3 |
| 2 µg/mL 5B3 IgG | 50.57 ± 2.39 | 12.9 |
| 0.01 µg/mL 5C9 IgG + K1-70 IgG[a] | 83.80 ± 5.12 | 0 |
| 0.1 µg/mL 5C9 IgG + K1-70 IgG[a] | 76.28 ± 1.72 | 0 |
| 0.2 µg/mL 5C9 IgG + K1-70 IgG[a] | 71.85 ± 5.96 | 0 |
| 1 µg/mL 5C9 IgG + K1-70 IgG[a] | 67.70 ± 12.58 | 0 |
| 2 µg/mL 5C9 IgG + K1-70 IgG[a] | 55.28 ± 6.17 | 4.8 |
| 0.01 µg/mL 5C9 IgG + 5B3 IgG[a] | 73.53 ± 4.31 | 0 |
| 0.1 µg/mL 5C9 IgG + 5B3 IgG[a] | 82.26 ± 12.07 | 0 |
| 0.2 µg/mL 5C9 IgG + 5B3 IgG[a] | 62.03 ± 1.22 | 0 |
| 1 µg/mL 5C9 IgG + 5B3 IgG[a] | 36.49 ± 1.10 | 37.1 |
| 2 µg/mL 5C9 IgG + 5B3 IgG[a] | 27.78 ± 2.96 | 52.1 |

See legend to Table 7a for details.
The experiments were carried out using CHO cells expressing wild type TSHR at approximately $5 \times 10^5$ receptors per cells.
[a]The total final concentration of IgG mixture is shown; ie in the case of 2 µg/mL K1-70 IgG + 5C9 IgG, the mixture contains 1 µg/mL K1-70 IgG and 1 µg/mL 5C9 IgG. Consequently, the combined effect of two IgGs at 2 µg/mL can be compared to the effect of the single IgG at the same concentration (2 µg/mL).

TABLE 8a

Cyclic AMP levels in CHO cells expressing wild type TSHR and TSHR with Lys58 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/Wild type (%) |
|---|---|---|---|
| | Wild type TSHR | Mutated TSHR | |
| Cyclic AMP assay buffer | 2.32 ± 0.37 | 8.23 ± 0.00 | 355 |
| K1-18 | | | |
| 0.3 ng/mL | 4.69 ± 0.95 | 12.02 ± 1.52 | 256 |
| 1 ng/mL | 8.95 ± 0.18 | 19.35 ± 3.45 | 216 |
| 3 ng/mL | 25.47 ± 4.30 | 43.07 ± 13.04 | 169 |
| 10 ng/mL | 66.57 ± 3.17 | 69.61 ± 1.25 | 105 |
| 30 ng/mL | 84.18 ± 11.86 | 79.39 ± 9.40 | 94 |
| 100 ng/mL TSH | 98.12 ± 5.31 | 102.88 ± 3.31 | 105 |
| 0.01 ng/mL | 3.11 ± 1.09 | 7.16 ± 0.97 | 230 |
| 0.03 ng/mL | 4.43 ± 0.67 | 10.00 ± 0.29 | 226 |
| 0.1 ng/mL | 10.11 ± 1.27 | 17.24 ± 1.77 | 171 |
| 0.3 ng/mL | 41.25 ± 5.41 | 45.94 ± 1.43 | 111 |
| 1 ng/mL | 74.52 ± 3.07 | 75.22* | 101 |
| 3 ng/mL | 95.34 ± 6.60 | 83.71 ± 7.10 | 88 |

Results shown are mean ± SD of triplicate determinations.
*duplicate determination.
Samples diluted in hypotonic cyclic AMP buffer.

TABLE 8b

Cyclic AMP levels in CHO cells expressing wild type TSHR and TSHR with Arg80 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/Wild type (%) |
|---|---|---|---|
| | Wild type TSHR | Mutated TSHR | |
| Cyclic AMP assay buffer | 1.65 ± 0.40 | 4.76 ± 1.30 | 288 |
| K1-18 | | | |
| 0.3 ng/mL | 2.46 ± 0.49 | 4.59 ± 0.41 | 187 |
| 1 ng/mL | 5.11 ± 0.77 | 7.22 ± 0.69 | 141 |
| 3 ng/mL | 10.65 ± 1.17 | 13.81 ± 2.53 | 130 |
| 10 ng/mL | 31.34 ± 5.31 | 31.72 ± 1.53 | 101 |
| 30 ng/mL | 50.15 ± 6.02 | 45.47 ± 3.59 | 91 |
| 100 ng/mL | 66.30 ± 6.93 | 64.50 ± 0.51 | 97 |

TABLE 8b-continued

Cyclic AMP levels in CHO cells expressing wild type TSHR and TSHR with Arg80 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| TSH | | | |
| 0.01 ng/mL | 2.00 ± 0.81 | 4.06 ± 0.36 | 203 |
| 0.03 ng/mL | 3.68 ± 0.28 | 6.19 ± 0.95 | 168 |
| 0.1 ng/mL | 9.10 ± 1.19 | 13.31 ± 1.94 | 146 |
| 0.3 ng/mL | 22.19 ± 1.46 | 27.66 ± 2.20 | 125 |
| 1 ng/mL | 57.48 ± 4.57 | 54.55 ± 10.40 | 95 |
| 3 ng/mL | 58.48 ± 8.87 | 56.95 ± 3.97 | 97 |

See legend to Table 8a for details.

TABLE 8c

Cyclic AMP levels in CHO cells expressing wild type TSHR and TSHR with Tyr82 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| Cyclic AMP assay buffer K1-18 | 0.52 ± 0.09 | 1.88 ± 0.25 | 362 |
| 0.3 ng/mL | 1.39 ± 0.10 | 4.72 ± 0.95 | 340 |
| 1 ng/mL | 2.95 ± 0.51 | 5.48 ± 0.91 | 186 |
| 3 ng/mL | 7.22 ± 1.08 | 13.26 ± 1.61 | 184 |
| 10 ng/mL | 26.07 ± 1.15 | 28.73 ± 2.65 | 110 |
| 30 ng/mL | 36.96 ± 2.55 | 41.91 ± 5.06 | 113 |
| 100 ng/mL | 50.72 ± 6.93 | 57.64 ± 1.84 | 114 |
| TSH | | | |
| 0.01 ng/mL | 1.01 ± 0.42 | 2.60 ± 0.44 | 257 |
| 0.03 ng/mL | 4.39 ± 1.65 | 4.10 ± 0.63 | 93 |
| 0.1 ng/mL | 9.67 ± 1.07 | 9.64 ± 1.49 | 100 |
| 0.3 ng/mL | 29.80 ± 2.51 | 33.66 ± 4.57 | 113 |
| 1 ng/mL | 53.34 ± 4.68 | 49.96 ± 0.72 | 94 |
| 3 ng/mL | 56.56 ± 4.76 | 61.34 ± 4.96 | 108 |

See legend to Table 8a for details.

TABLE 8d

Cyclic AMP levels in CHO cells expressing wild type TSHR and TSHR with Glu107 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| Cyclic AMP assay buffer K1-18 (ng/mL) | 0.91 ± 0.15 | 7.16 ± 0.17 | 787 |
| 0.3 ng/mL | 1.78 ± 0.20 | 9.30 ± 1.48 | 522 |
| 1 ng/mL | 3.73 ± 0.09 | 10.96 ± 0.69 | 294 |
| 3 ng/mL | 11.06 ± 1.45 | 20.55 ± 3.83 | 186 |
| 10 ng/mL | 30.04 ± 2.34 | 31.49 ± 2.70 | 105 |
| 30 ng/mL | 49.28 ± 3.28 | 40.92 ± 2.03 | 83 |
| 100 ng/mL | 57.80 ± 5.23 | 53.62 ± 3.86 | 93 |

TABLE 8d-continued

Cyclic AMP levels in CHO cells expressing wild type TSHR and TSHR with Glu107 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| TSH (ng/mL) | | | |
| 0.01 ng/mL | 1.41 ± 0.10 | 8.20 ± 1.87 | 582 |
| 0.03 ng/mL | 1.99 ± 0.09 | 8.92 ± 2.93 | 448 |
| 0.1 ng/mL | 5.54 ± 0.60 | 8.24 ± 0.60 | 149 |
| 0.3 ng/mL | 16.27 ± 4.48 | 15.72 ± 0.81 | 97 |
| 1 ng/mL | 44.20 ± 3.64 | 30.22 ± 2.62 | 68 |
| 3 ng/mL | 53.86 ± 7.00 | 43.91 ± 2.61 | 82 |

See legend to Table 8a for details.

TABLE 8e

Cyclic AMP levels in CHO cells expressing wild type TSHR and TSHR with Arg109 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| Cyclic AMP assay buffer K1-18 (ng/mL) | 1.75 ± 0.35 | 3.42 ± 0.41 | 195 |
| 0.3 ng/mL | 2.66 ± 0.13 | 5.31 ± 0.11 | 200 |
| 1 ng/mL | 5.81 ± 0.13 | 9.39 ± 0.88 | 162 |
| 3 ng/mL | 12.86 ± 0.77 | 17.99 ± 3.94 | 140 |
| 10 ng/mL | 40.46 ± 1.76 | 40.55 ± 3.48 | 100 |
| 30 ng/mL | 58.91 ± 9.28 | 50.84 ± 1.01 | 86 |
| 100 ng/mL | 66.01 ± 4.85 | 59.9 ± 1.25 | 91 |
| TSH (ng/mL) | | | |
| 0.01 ng/mL | 2.74 ± 0.37 | 3.15 ± 0.22 | 115 |
| 0.03 ng/mL | 4.24 ± 0.24 | 4.92 ± 0.54 | 116 |
| 0.1 ng/mL | 9.39 ± 1.16 | 8.39 ± 0.46 | 89 |
| 0.3 ng/mL | 39.63 ± 2.57 | 39.17 ± 1.70 | 99 |
| 1 ng/mL | 61.19 ± 8.50 | 43.82 ± 1.69 | 72 |
| 3 ng/mL | 70.6 ± 10.03 | 55.16 ± 2.59 | 78 |

See legend to Table 8a for details.

TABLE 8f

Cyclic AMP levels in CHO cells expressing wild type TSHR and TSHR with Lys129 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| Cyclic AMP assay buffer K1-18 | 1.72 ± 0.44 | 2.69 ± 0.25 | 156 |
| 0.3 ng/mL | 2.49 ± 0.34 | 3.24 ± 0.03 | 130 |
| 1 ng/mL | 4.78 ± 0.88 | 5.53 ± 1.04 | 116 |
| 3 ng/mL | 12.22 ± 0.32 | 10.58 ± 0.61 | 87 |
| 10 ng/mL | 30.88 ± 3.70 | 23.53 ± 1.04 | 76 |
| 30 ng/mL | 44.61 ± 4.59 | 33.46 ± 2.66 | 75 |
| 100 ng/mL | 52.57 ± 1.30 | 52.88 ± 2.31 | 101 |

TABLE 8f-continued

Cyclic AMP levels in CHO cells expressing wild type TSHR and TSHR with Lys129 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| TSH | | | |
| 0.01 ng/mL | 2.01 ± 0.40 | 2.69 ± 0.44 | 134 |
| 0.03 ng/mL | 3.32 ± 0.26 | 5.34 ± 0.05 | 161 |
| 0.1 ng/mL | 9.69 ± 0.91 | 12.69 ± 1.06 | 131 |
| 0.3 ng/mL | 26.14 ± 2.72 | 29.0 ± 1.07 | 111 |
| 1 ng/mL | 46.33 ± 2.29 | 40.78 ± 5.20 | 88 |
| 3 ng/mL | 48.07 ± 2.77 | 48.50 ± 5.38 | 101 |

See legend to Table 8a for details.

TABLE 8g

Cyclic AMP levels in CHO cells expressing wild type TSHR and TSHR with Phe130 mutated to Ala. Effect of different dilutions of human monoclonal antibody to the TSHR (K1-18) with TSH agonist activity

| | Cyclic AMP produced (pmol/mLpmol/mL) mean ± SD (n = 3) | | Mutated/ Wild type |
|---|---|---|---|
| | Wild type TSHR | Mutated TSHR | (%) |
| Cyclic AMP assay buffer K1-18 | 1.96 ± 0.22 | 3.38 ± 0.47 | 172 |
| 0.3 ng/mL | 3.23 ± 0.26 | 4.01 ± 0.03 | 124 |
| 1 ng/mL | 6.24 ± 0.70 | 6.71 ± 0.35 | 108 |
| 3 ng/mL | 15.42 ± 1.00 | 14.89 ± 12.46 | 97 |
| 10 ng/mL | 49.72 ± 5.36 | 36.36 ± 2.23 | 73 |
| 30 ng/mL | 51.57 ± 8.02 | 54.0 ± 2.20 | 66 |
| 100 ng/mL | 98.73 ± 8.67 | 78.11 ± 7.43 | 79 |
| TSH | | | |
| 0.01 ng/mL | 2.28 ± 0.15 | 3.05 ± 0.29 | 134 |
| 0.03 ng/mL | 3.77 ± 0.83 | 4.12 ± 0.55 | 109 |
| 0.1 ng/mL | 9.55 ± 0.15 | 9.61 ± 1.14 | 101 |
| 0.3 ng/mL | 28.77 ± 1.08 | 35.64 ± 3.00 | 124 |
| 1 ng/mL | 76.83 ± 10.33 | 66.16 ± 4.97 | 86 |
| 3 ng/mL | 93.08 ± 7.22 | 80.37 ± 3.05 | 86 |

See legend to Table 8a for details.

TABLE 8h

Cyclic AMP levels in CHO cells expressing wild type TSHR and TSHR with Phe134 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type |
|---|---|---|---|
| | Wild type TSHR | Mutated TSHR | (%) |
| Cyclic AMP assay buffer K1-18 | 1.85 ± 0.37 | 4.62 ± 0.89 | 250 |
| 0.3 ng/mL | 2.44 ± 0.12 | 2.71 ± 0.65 | 234 |
| 1 ng/mL | 5.97 ± 0.63 | 9.56 ± 0.52 | 160 |
| 3 ng/mL | 13.43 ± 0.46 | 24.24 ± 1.93 | 180 |
| 10 ng/mL | 35.49 ± 1.71 | 43.41 ± 1.29 | 122 |
| 30 ng/mL | 46.48 ± 3.34 | 66.25 ± 11.73 | 143 |
| 100 ng/mL | 58.93 ± 10.42 | 78.69 ± 6.43 | 134 |

TABLE 8h-continued

Cyclic AMP levels in CHO cells expressing wild type TSHR and TSHR with Phe134 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type |
|---|---|---|---|
| | Wild type TSHR | Mutated TSHR | (%) |
| TSH | | | |
| 0.01 ng/mL | 2.50 ± 0.43 | 4.73 ± 0.24 | 189 |
| 0.03 ng/mL | 4.29 ± 0.33 | 6.05 ± 0.21 | 141 |
| 0.1 ng/mL | 10.60 ± 0.56 | 12.70 ± 2.22 | 120 |
| 0.3 ng/mL | 28.93 ± 3.07 | 27.28 ± 1.96 | 94 |
| 1 ng/mL | 52.55 ± 3.97 | 53.68 ± 4.76 | 102 |
| 3 ng/mL | 61.09 ± 8.26 | 61.51 ± 0.99 | 101 |

See legend to Table 8a for details.

TABLE 8i

Cyclic AMP levels in CHO cells expressing wild type TSHR and TSHR with Lys183 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type |
|---|---|---|---|
| | Wild type TSHR | Mutated TSHR | (%) |
| Experiment 1 | | | |
| Cyclic AMP assay buffer K1-18 | 1.49 ± 0.31 | 4.54 ± 0.23 | 305 |
| 0.3 ng/mL | 2.67 ± 0.30 | 4.41 ± 0.07 | 165 |
| 1 ng/mL | 5.69 ± 0.26 | 4.72 ± 0.53 | 83 |
| 3 ng/mL | 14.43 ± 2.30 | 4.55 ± 0.32 | 32 |
| 10 ng/mL | 43.94 ± 2.59 | 4.73 ± 0.57 | 11 |
| 30 ng/mL | 73.60 ± 9.07 | 4.58 ± 0.29 | 6 |
| 100 ng/mL | 84.59 ± 5.65 | 5.31 ± 1.38 | 6 |
| TSH | | | |
| 0.01 ng/mL | 1.80 ± 0.13 | 4.95 ± 0.23 | 275 |
| 0.03 ng/mL | 3.91 ± 0.06 | 6.94 ± 1.04 | 177 |
| 0.1 ng/mL | 8.92 ± 1.47 | 13.04 ± 1.12 | 146 |
| 0.3 ng/mL | 33.01 ± 3.49 | 34.95 ± 1.12 | 106 |
| 1 ng/mL | 76.07 ± 4.42 | 57.18 ± 2.97 | 75 |
| 3 ng/mL | 86.17 ± 2.02 | 69.15 ± 3.34 | 80 |
| Experiment 2 | | | |
| Cyclic AMP assay buffer K1-18 | 0.53 ± 0.27 | 3.72 ± 0.19 | 702 |
| 0.3 ng/mL | 1.93 ± 0.92 | 3.25 ± 0.23 | 168 |
| 1 ng/mL | 3.59 ± 0.47 | 2.77 ± 1.32 | 77 |
| 3 ng/mL | 6.56 ± 2.29 | 3.24 ± 0.63 | 49 |
| 10 ng/mL | 27.79 ± 1.77 | 0.58 ± 0.89 | 2 |
| 30 ng/mL | 46.16 ± 5.72 | 1.97 ± 0.11 | 4 |
| 100 ng/mL | 61.78 ± 3.78 | 0.92 ± 1.17 | 1 |
| TSH | | | |
| 0.01 ng/mL | 1.30 ± 0.20 | 3.73 ± 0.10 | 287 |
| 0.03 ng/mL | 3.00 ± 0.12 | 5.37 ± 0.31 | 179 |
| 0.1 ng/mL | 6.69 ± 0.41 | 10.08 ± 0.82 | 151 |
| 0.3 ng/mL | 26.22 ± 6.92 | 27.84 ± 2.8 | 106 |
| 1 ng/mL | 68.12 ± 15.71 | 55.78 ± 2.52 | 82 |
| 3 ng/mL | 69.75 ± 13.30 | 72.17 ± 8.74 | 103 |

See legend to Table 8a for details.

TABLE 8j

Cyclic AMP levels in CHO cells expressing wild type TSHR and TSHR with Asp203 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type |
|---|---|---|---|
| | Wild type TSHR | Mutated TSHR | (%) |
| Cyclic AMP assay buffer | 1.64 ± 0.17 | 6.06 ± 0.16 | 370 |
| K1-18 | | | |
| 0.3 ng/mL | 2.68 ± 0.21 | 8.14 ± 0.24 | 304 |
| 1 ng/mL | 5.60 ± 0.27 | 12.54 ± 0.46 | 224 |
| 3 ng/mL | 11.54 ± 2.20 | 26.08 ± 2.19 | 226 |
| 10 ng/mL | 38.16 ± 0.90 | 49.54 ± 2.38 | 130 |
| 30 ng/mL | 60.04 ± 6.18 | 67.45 ± 4.04 | 112 |
| 100 ng/mL | 76.63 ± 4.54 | 78.94 ± 3.75 | 103 |
| TSH | | | |
| 0.01 ng/mL | 2.29 ± 0.18 | 5.30 ± 0.53 | 231 |
| 0.03 ng/mL | 3.56 ± 0.21 | 7.13 ± 0.29 | 200 |
| 0.1 ng/mL | 8.45 ± 0.07 | 13.02 ± 2.00 | 154 |
| 0.3 ng/mL | 26.33 ± 1.63 | 33.77 ± 1.37 | 128 |
| 1 ng/mL | 65.72 ± 5.74 | 58.56 ± 3.02 | 89 |
| 3 ng/mL | 77.11 ± 4.86 | 69.26 ± 0.68 | 90 |

See legend to Table 8a for details.

TABLE 8k

Cyclic AMP levels in CHO cells expressing wild type TSHR and TSHR with Arg255 mutated to Asp. Effect of different dilutions of human monoclonal antibody to the TSHR (K1-18) with TSH agonist activity

| | Cyclic AMP produced (pmol/mL) mean ± SD (n = 3) | | Mutated/ Wild type |
|---|---|---|---|
| | Wild type TSHR | Mutated TSHR | (%) |
| Experiment 1 | | | |
| Cyclic AMP assay buffer | 2.65 ± 0.20 | 1.89 ± 0.28 | 71 |
| K1-18 | | | |
| 0.3 ng/mL | 4.40 ± 0.67 | 1.93 ± 0.23 | 44 |
| 1 ng/mL | 8.93 ± 2.17 | 2.19 ± 0.25 | 25 |
| 3 ng/mL | 16.31 ± 1.29 | 4.14 ± 0.95 | 25 |
| 10 ng/mL | 42.50 ± 3.42 | 7.87 ± 0.53 | 19 |
| 30 ng/mL | 49.10 ± 9.27 | 15.59 ± 1.15 | 32 |
| 100 ng/mL | 55.17 ± 10.84 | 31.58 ± 6.83 | 57 |
| TSH | | | |
| 0.01 ng/mL | 4.36 ± 1.05 | 2.59 ± 0.31 | 59 |
| 0.03 ng/mL | v9.19 ± 1.74 | 6.47 ± 0.10 | 70 |
| 0.1 ng/mL | 26.86 ± 2.67 | 19.18 ± 2.69 | 71 |
| 0.3 ng/mL | 42.03 ± 6.15 | 51.67 ± 3.38 | 123 |
| 1 ng/mL | 60.08 ± 4.20 | 68.59 ± 7.0 7 | 114 |
| 3 ng/mL | 61.27 ± 2.99 | 57.72 ± 9.50 | 94 |
| Experiment 2 | | | |
| Cyclic AMP assay buffer | 1.80 ± 0.14 | 2.35 ± 0.45 | 131 |
| K1-18 | | | |
| 0.3 ng/mL | 2.26 ± 0.22 | 2.13 ± 0.19 | 94 |
| 1 ng/mL | 5.21 ± 0.60 | 1.93 ± 0.67 | 37 |
| 3 ng/mL | 11.23 ± 1.35 | 3.49 ± 0.08 | 31 |
| 10 ng/mL | 30.58 ± 1.89 | 6.08 ± 0.93 | 20 |
| 30 ng/mL | 51.91 ± 5.11 | 7.96 ± 0.29 | 15 |
| 100 ng/mL | 67.17 ± 5.84 | 20.23 ± 0.48 | 30 |
| TSH | | | |
| 0.01 ng/mL | 2.21 ± 0.25 | 1.49 ± 0.25 | 67 |
| 0.03 ng/mL | 3.61 ± 0.28 | 2.81 ± 0.38 | 78 |
| 0.1 ng/mL | 7.86 ± 3.02 | 6.92 ± 0.35 | 88 |
| 0.3 ng/mL | 27.07 ± 2.08 | 21.24* | 78 |
| 1 ng/mL | 54.24 ± 5.41 | 41.06 ± 1.0 | 76 |
| 3 ng/mL | 58.14 ± 3.02 | 52.35 ± 3.20 | 90 |
| Experiment 3 | | | |
| Cyclic AMP assay buffer | 4.02 ± 0.14 | 5.88 ± 0.27 | 146 |
| K1-18 | | | |
| 0.3 ng/mL | 5.65 ± 0.61 | 5.76 ± 0.33 | 102 |
| 1 ng/mL | 9.40 ± 0.97 | 5.93 ± 0 | 63 |
| 3 ng/mL | 21.39 ± 0.55 | 6.06 ± 0.40 | 28 |
| 10 ng/mL | 67.31 ± 4.56 | 9.44 ± 0.82 | 14 |
| 30 ng/mL | 131.53 ± 5.0 | 13.46 ± 1.25 | 10 |
| 100 ng/mL | 226.28 ± 15.17 | 30.07 ± 5.98 | 13 |
| TSH | | | |
| 0.01 ng/mL | 5.19 ± 0.15 | 6.46 ± 0.13 | 124 |
| 0.03 ng/mL | 9.82 ± 0.96 | 9.44 ± 0.27 | 96 |
| 0.1 ng/mL | 24.96* | 22.74 ± 2.24 | 91 |
| 0.3 ng/mL | 91.70 ± 3.45 | 68.89 ± 3.12 | 75 |
| 1 ng/mL | 191.94 ± 11.08 | 154.26 ± 4.66 | 80 |
| 3 ng/mL | 226.42 ± 16.78 | 201.17 ± 16.22 | 89 |

See legend to Table 8a for details.

TABLE 9a

TSH induced cyclic AMP production in CHO cells expressing wild type TSHR and TSHR with Lys58 mutated to Ala. Effect of different dilutions of human monoclonal antibody to the TSHR (K1-70) with TSH antagonist activity Experiment 1

| | Cyclic AMP produced (pmol/mL; mean ± SD, n = 3) | | Mutated/ wild type |
|---|---|---|---|
| Test sample[a] | Wild type TSHR | Mutated TSHR | (%) |
| Cyclic AMP assay buffer only | 1.86 ± 0.41 | 5.03 ± 0.29 | 270 |
| TSH[b] | 68.83 ± 0.70 | 78.46 ± 4.71 | 114 |
| 5B3 10 µg/mL + TSH[b] | 82.85 ± 10.89 | 81.62 ± 5.07 | 99 |
| 5B3 100 µg/mL + TSH[b] | 80.67 ± 13.25 | 81.61 ± 5.04 | 101 |
| K1-70 0.001 µg + TSH[b] | 92.76 ± 13.12 | 104.76 ± 7.65 | 113 |
| K1-70 0.01 µg + TSH[b] | 82.54 ± 2.17 | 108.22 ± 8.17 | 131 |
| K1-70 0.1 µg + TSH[b] | 4.26 ± 0.83 | 85.28 ± 6.13 | 2002 |
| K1-70 1.0 µg + TSH[b] | 1.56 ± 0.20 | 61.47 ± 2.61 | 3940 |
| K1-70 10 µg + TSH[b] | 1.72 ± 0.34 | 33.11 ± 4.67 | 1925 |
| K1-70 100 µg + TSH[b] | 1.58 ± 0.05 | 18.75 ± 4.91 | 1187 |
| K1-70 100 µg | 1.04 ± 0.61 | 4.06 ± 0.66 | 390 |
| TSH (2) | 74.30 ± 18.86 | 85.20 ± 4.48 | 115 |

| | % inhibition of TSH stimulation[c] | |
|---|---|---|
| Antibody concentration | Wild type TSHR | Mutated TSHR |
| 5B3 10 µg/mL | 0 | 0 |
| 5B3 100 µg/mL | 0 | 0 |
| K1-70 0.001 µg | 0 | 0 |
| K1-70 0.01 µg/mL | 0 | 0 |
| K1-70 0.1 µg/mL | 94 | 0 |
| K1-70 1 µg/mL | 98 | 22 |
| K1-70 10 µg/mL | 98 | 58 |
| K1-70 100 µg/mL | 98 | 76 |
| TSH (2) | 0 | 0 |

TABLE 9a-continued

TSH induced cyclic AMP production in CHO cells expressing wild type TSHR and TSHR with Lys58 mutated to Ala. Effect of different dilutions of human monoclonal antibody to the TSHR (K1-70) with TSH antagonist activity Experiment 2

| Test sample[a] | Cyclic AMP produced (pmol/mL; mean ± SD, n = 3) | | Mutated/wild type |
|---|---|---|---|
| | Wild type TSHR | Mutated TSHR | (%) |
| Cyclic AMP assay buffer only | 1.49 ± 0.21 | 3.68 ± 0.45 | 247 |
| TSH[b] | 97.87 ± 4.55 | 96.77 ± 9.54 | 99 |
| 5B3 10 µg/mL + TSH[b] | 105.71 ± 16.43 | 92.91 ± 1.17 | 88 |
| 5B3 100 µg/mL + TSH[b] | 90.43 ± 5.84 | 95.85 ± 6.56 | 106 |
| K1-70 0.001 µg + TSH[b] | 101.80 ± 13.32 | 105.33 ± 11.55 | 103 |
| K1-70 0.01 µg + TSH[b] | 115.21 ± 7.84 | 107.32 ± 11.90 | 93 |
| K1-70 0.1 µg + TSH[b] | 8.94 ± 2.47 | 83.06 ± 10.21 | 929 |
| K1-70 1.0 µg + TSH[b] | 1.71 ± 0.40 | 60.95 ± 3.72 | 3564 |
| K1-70 10 µg + TSH[b] | 1.27 ± 0.47 | 25.12 ± 4.15 | 1978 |
| K1-70 100 µg + TSH[b] | 1.31 ± 0.33 | 17.34 ± 1.35 | 1324 |
| K1-70 100 µg | 1.38 ± 1.81 | 2.56 ± 0.20 | 186 |
| TSH (2) | 102.41 ± 6.78 | 95.84 ± 1.30 | 94 |

| Antibody concentration | % inhibition of TSH stimulation[c] | |
|---|---|---|
| | Wild type TSHR | Mutated TSHR |
| 5B3 10 µg/mL | 0 | 4 |
| 5B3 100 µg/mL | 8 | 1 |
| K1-70 0.001 µg | 0 | 0 |
| K1-70 0.01 µg/mL | 0 | 0 |
| K1-70 0.1 µg/mL | 91 | 14 |
| K1-70 1 µg/mL | 98 | 37 |
| K1-70 10 µg/mL | 99 | 74 |
| K1-70 100 µg/mL | 99 | 82 |
| TSH (2) | 0 | 1 |

[a]Test samples in hypotonic cyclic AMP assay buffer.
[b]TSH final concentration = 3 ng/mL
[c]% inhibition = 100 × [1 − (cyclic AMP in the presence of test samples and TSH/cyclic AMP in the presence of cyclic AMP buffer and TSH)].
5B3 is a human monoclonal antibody to GAD (negative control for K1-70)

TABLE 9b

TSH induced cyclic AMP production in CHO cells expressing wild type TSHR and TSHR with Arg80 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type |
|---|---|---|---|
| | Wild type TSHR | Mutated TSHR | (%) |
| Cyclic AMP assay buffer only | 3.44 ± 0.35 | 4.01 ± 0.07 | 117 |
| TSH[b] | 85.04 ± 5.88 | 105.33 ± 10.10 | 124 |
| 5B3 10 µg/mL + TSH[b] | 103.34 ± 14.25 | 104.97 ± 12.48 | 102 |
| 5B3 100 µg/mL + TSH[b] | 94.76 ± 19.53 | 101.43 ± 4.34 | 107 |
| K1-70 0.001 µg + TSH[b] | 79.24 ± 9.29 | 90.78 ± 8.65 | 115 |
| K1-70 0.01 µg + TSH[b] | 83.30 ± 7.42 | 99.26 ± 7.04 | 119 |
| K1-70 0.1 µg + TSH[b] | 40.75 ± 8.82 | 38.83 ± 8.04 | 95 |
| K1-70 1.0 µg + TSH[b] | 5.0 ± 0.72 | 6.71 ± 1.42 | 134 |
| K1-70 10 µg + TSH[b] | 3.17 ± 0.18 | 5.14 ± 1.43 | 162 |
| K1-70 100 µg + TSH[b] | 4.67 ± 0.32 | 4.83 ± 0.25 | 103 |
| K1-70 100 µg | 2.98 ± 0.13 | 3.19 ± 0.51 | 107 |
| TSH (2) | 93.53 ± 17.83 | 88.18 ± 2.24 | 94 |

| Antibody concentration | % inhibition of TSH stimulation[c] | |
|---|---|---|
| | Wild type TSHR | Mutated TSHR |
| 5B3 10 µg/mL | 0 | 0.3 |
| 5B3 100 µg/mL | 0 | 4 |
| K1-70 0.001 µg | 7 | 14 |
| K1-70 0.01 µg/mL | 2 | 6 |
| K1-70 0.1 µg/mL | 52 | 63 |
| K1-70 1 µg/mL | 94 | 94 |
| K1-70 10 µg/mL | 96 | 95 |
| K1-70 100 µg/mL | 95 | 95 |
| TSH (2) | 0 | 16 |

See legend to Table 9a for details.

TABLE 9c

TSH induced cyclic AMP production in CHO cells expressing wild type TSHR and TSHR with Tyr82 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/wild type |
|---|---|---|---|
| | Wild type TSHR | Mutated TSHR | (%) |
| Cyclic AMP assay buffer only | 1.38 ± 0.19 | 2.00 ± 0.22 | 145 |
| TSH[b] | 153.65 ± 17.41 | 165.92 ± 11.45 | 108 |
| 5B3 10 µg/mL + TSH[b] | 163.14 ± 13.71 | 139.01 ± 5.40 | 85 |
| 5B3 100 µg/mL + TSH[b] | 146.23 ± 19.81 | 139.28 ± 11.07 | 95 |
| K1-70 0.001 µg + TSH[b] | 172.63 ± 16.69 | 103.81 ± 9.73 | 60 |
| K1-70 0.01 µg + TSH[b] | 146.19 ± 29.10 | 99.95 ± 12.23 | 68 |
| K1-70 0.1 µg + TSH[b] | 21.73 ± 3.85 | 69.85 ± 16.62 | 321 |
| K1-70 1.0 µg + TSH[b] | 1.88 ± 0.24 | 31.82 ± 3.29 | 1696 |
| K1-70 10 µg + TSH[b] | 1.35 ± 0.26 | 11.74 ± 1.33 | 870 |
| K1-70 100 µg + TSH[b] | 1.05 ± 0.07 | 7.88 ± 2.09 | 750 |
| K1-70 100 µg | 0.84 ± 0.12 | 1.81 ± 0.13 | 215 |
| TSH (2) | 159.76 ± 4.28 | 92.29 ± 5.79 | 58 |

| Antibody concentration | % inhibition of TSH stimulation[c] | |
|---|---|---|
| | Wild type TSHR | Mutated TSHR |
| 5B3 10 µg/mL | 0 | 16 |
| 5B3 100 µg/mL | 5 | 16 |
| K1-70 0.001 µg | 0 | 62 |
| K1-70 0.01 µg/mL | 5 | 40 |
| K1-70 0.1 µg/mL | 86 | 60 |
| K1-70 1 µg/mL | 99 | 81 |
| K1-70 10 µg/mL | 99 | 93 |
| K1-70 100 µg/mL | 99 | 95 |
| TSH (2) | 0 | 44 |

Experiment 2

| Test sample[a] | Cyclic AMP produced (pmol/mL; mean ± SD, n = 3) | | Mutated/wild type |
|---|---|---|---|
| | Wild type TSHR | Mutated TSHR | (%) |
| Cyclic AMP assay buffer only | 0.62 ± 0.16 | 5.67 ± 0.29 | 915 |
| TSH[b] | 59.91 ± 5.85 | 74.61 ± 6.62 | 125 |
| 5B3 10 µg/mL + TSH[b] | 73.66 ± 23.18 | 71.92 ± 5.39 | 96 |
| 5B3 100 µg/mL + TSH[b] | 68.87 ± 10.44 | 68.46 ± 3.41 | 99 |
| K1-70 0.001 µg + TSH[b] | 97.15 ± 2.87 | 89.47 ± 9.17 | 92 |
| K1-70 0.01 µg + TSH[b] | 81.95 ± 4.74 | 95.68 ± 7.62 | 117 |
| K1-70 0.1 µg + TSH[b] | 5.79 ± 0.68 | 50.57 ± 19.35 | 873 |
| K1-70 1.0 µg + TSH[b] | 1.01 ± 0.36 | 14.55 ± 0.65 | 1440 |
| K1-70 10 µg + TSH[b] | 1.02 ± 0.19 | 9.07 ± 0.70 | 889 |
| K1-70 100 µg + TSH[b] | 1.00 ± 0.19 | 7.28 ± 0.44 | 728 |

TABLE 9c-continued

TSH induced cyclic AMP production in CHO cells expressing wild type TSHR and TSHR with Tyr82 mutated to Ala. Effect of different dilutions of human monoclonal antibody to the TSHR (K1-70) with TSH antagonist activity

| | | | |
|---|---|---|---|
| K1-70 100 μg | 0.84 ± 0.14 | 5.32 ± 0.74 | 633 |
| TSH (2) | 61.54 ± 7.58 | 57.87 ± 1.52 | 94 |

| Antibody concentration | % inhibition of TSH stimulation[c] | |
|---|---|---|
| | Wild type TSHR | Mutated TSHR |
| 5B3 10 μg/mL | 0 | 4 |
| 5B3 100 μg/mL | 0 | 8 |
| K1-70 0.001 μg | 0 | 0 |
| K1-70 0.01 μg/mL | 0 | 0 |
| K1-70 0.1 μg/mL | 90 | 32 |
| K1-70 1 μg/mL | 98 | 80 |
| K1-70 10 μg/mL | 98 | 88 |
| K1-70 100 μg/mL | 98 | 90 |
| TSH (2) | 0 | 22 |

See legend to Table 9a for details.

TABLE 9d

TSH induced cyclic AMP production in CHO cells expressing wild type TSHR and TSHR with Glu107 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.60 ± 0.19 | 5.29 ± 0.36 | 331 |
| TSH[b] | 76.22 ± 4.52 | 83.70 ± 3.92 | 110 |
| 5B3 10 μg/mL + TSH[b] | 85.30 ± 5.68 | 70.93 ± 5.64 | 83 |
| 5B3 100 μg/mL + TSH[b] | 81.64 ± 5.48 | 66.84 ± 7.24 | 82 |
| K1-70 0.001 μg + TSH[b] | 103.6 ± 5.93 | 94.45 ± 8.21 | 91 |
| K1-70 0.01 μg + TSH[b] | 89.43 ± 19.6 | 82.88 ± 4.50 | 93 |
| K1-70 0.1 μg + TSH[b] | 12.10 ± 2.22 | 4.97 ± 0.59 | 41 |
| K1-70 1.0 μg + TSH[b] | 1.71 ± 0.32 | 2.71 ± 0.05 | 158 |
| K1-70 10 μg + TSH[b] | 1.49 ± 0.16 | 2.45 ± 0.13 | 164 |
| K1-70 100 μg + TSH[b] | 1.86 ± 0.23 | 2.75 ± 0.17 | 148 |
| K1-70 100 μg | 1.60 ± 0.07 | 1.80 ± 0.30 | 113 |
| TSH (2) | 93.75 ± 9.25 | 73.24 ± 5.57 | 78 |

| Antibody concentration | % inhibition of TSH stimulation[c] | |
|---|---|---|
| | Wild type TSHR | Mutated TSHR |
| 5B3 10 μg/mL | 0 | 15 |
| 5B3 100 μg/mL | 0 | 17 |
| K1-70 0.001 μg | 0 | 0 |
| K1-70 0.01 μg/mL | 0 | 1 |
| K1-70 0.1 μg/mL | 84 | 94 |
| K1-70 1 μg/mL | 98 | 97 |
| K1-70 10 μg/mL | 98 | 97 |
| K1-70 100 μg/mL | 98 | 97 |
| TSH (2) | 0 | 12 |

See legend to Table 9a for details.

TABLE 9e

TSH induced cyclic AMP production in CHO cells expressing wild type TSHR and TSHR with Arg109 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.94 ± 0.35 | 4.42 ± 0.55 | 228 |
| TSH[b] | 67.67 ± 4.90 | 32.90 ± 2.55 | 49 |
| 5B3 10 μg/mL + TSH[b] | 65.84 ± 1.73 | 34.41 ± 1.67 | 52 |
| 5B3 100 μg/mL + TSH[b] | 68.54 ± 1.22 | 34.51 ± 5.03 | 50 |
| K1-70 0.001 μg + TSH[b] | 66.99 ± 8.59 | 34.24 ± 0.25 | 51 |
| K1-70 0.01 μg + TSH[b] | 66.85 ± 2.02 | 32.56 ± 1.04 | 49 |
| K1-70 0.1 μg + TSH[b] | 6.41 ± 0.32 | 24.84 ± 1.94 | 388 |
| K1-70 1.0 μg + TSH[b] | 1.60 ± 0.28 | 24.45 ± 0.49 | 1528 |
| K1-70 10 μg + TSH[b] | 1.51 ± 0.08 | 18.92 ± 2.16 | 1253 |
| K1-70 100 μg + TSH[b] | 1.36 ± 0.17 | 14.05 ± 3.4 | 1033 |
| K1-70 100 μg | 1.48 ± 0.1 | 3.39 ± 0.29 | 229 |
| TSH (2) | 67.54 ± 2.56 | 33.30 ± 2.27 | 49 |

| Antibody concentration | % inhibition of TSH stimulation[c] | |
|---|---|---|
| | Wild type TSHR | Mutated TSHR |
| 5B3 10 μg/mL | 3 | 0 |
| 5B3 100 μg/mL | 0 | 0 |
| K1-70 0.001 μg | 1 | 0 |
| K1-70 0.01 μg/mL | 1 | 0 |
| K1-70 0.1 μg/mL | 91 | 24 |
| K1-70 1 μg/mL | 98 | 26 |
| K1-70 10 μg/mL | 98 | 42 |
| K1-70 100 μg/mL | 98 | 57 |
| TSH (2) | 0.1 | 0 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.89 ± 0.19 | 1.61 ± 0.14 | 181 |
| TSH[b] | 60.73 ± 7.97 | 53.41 ± 3.69 | 88 |
| 5B3 10 μg/mL + TSH[b] | 68.59 ± 2.26 | 60.65 ± 0.63 | 88 |
| 5B3 100 μg/mL + TSH[b] | 66.50 ± 2.55 | 56.57 ± 3.26 | 85 |
| K1-70 0.001 μg + TSH[b] | 55.89 ± 6.77 | 61.82 ± 17.17 | 111 |
| K1-70 0.01 μg + TSH[b] | 61.90 ± 1.57 | 46.01 ± 0.91 | 74 |
| K1-70 0.1 μg + TSH[b] | 5.54 ± 1.21 | 30.32 ± 3.35 | 547 |
| K1-70 1.0 μg + TSH[b] | 1.32 ± 0.21 | 25.25 ± 1.54 | 1913 |
| K1-70 10 μg + TSH[b] | 0.97* | 14.80 ± 0 | 1526 |
| K1-70 100 μg + TSH[b] | 0.88 ± 0.11 | 9.14 ± 0.91 | 1039 |
| K1-70 100 μg | 1.02 ± 0.06 | 1.26 ± 0.41 | 124 |
| TSH (2) | 67.80 ± 3.83 | 50.39 ± 2.52 | 74 |

| Antibody concentration | % inhibition of TSH stimulation[c] | |
|---|---|---|
| | Wild type TSHR | Mutated TSHR |
| 5B3 10 μg/mL | 0 | 0 |
| 5B3 100 μg/mL | 0 | 0 |
| K1-70 0.001 μg | 8 | 0 |
| K1-70 0.01 μg/mL | 0 | 14 |
| K1-70 0.1 μg/mL | 91 | 43 |
| K1-70 1 μg/mL | 98 | 53 |
| K1-70 10 μg/mL | 98 | 72 |
| K1-70 100 μg/mL | 99 | 83 |
| TSH (2) | 0 | 6 |

*duplicate determination
See legend to Table 9a for details.

TABLE 9f

TSH induced cyclic AMP production in CHO cells expressing
wild type TSHR and TSHR with Lys129 mutated to Ala. Effect
of different dilutions of human monoclonal antibody to
the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 3.10 ± 2.74 | 3.37 ± 0.85 | 109 |
| TSH[b] | 50.03 ± 3.0 | 49.2 ± 6.7 | 98 |
| 5B3 10 µg/mL + TSH[b] | 53.88 ± 3.67 | 50.5 ± 3.43 | 94 |
| 5B3 100 µg/mL + TSH[b] | 52.60 ± 6.43 | 42.63 ± 2.35 | 81 |
| K1-70 0.001 µg + TSH[b] | 49.48 ± 6.51 | 44.76 ± 2.58 | 90 |
| K1-70 0.01 µg + TSH[b] | 51.04 ± 0.00 | 38.66 ± 2.03 | 76 |
| K1-70 0.1 µg + TSH[b] | 4.70 ± 1.25 | 9.86 ± 1.14 | 210 |
| K1-70 1.0 µg + TSH[b] | 0.74 ± 0.06 | 3.23 ± 0.15 | 436 |
| K1-70 10 µg + TSH[b] | 0.80 ± 0.33 | 2.83 ± 0.71 | 354 |
| K1-70 100 µg + TSH[b] | 1.12 ± 0.46 | 2.82 ± 0.21 | 251 |
| K1-70 100 µg | 0.88 ± 0.21 | 3.06 ± 1.11 | 348 |
| TSH (2) | 53.1 ± 8.0 | 47.9 ± 0.41 | 90 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 13 |
| K1-70 0.001 µg | 1 | 9 |
| K1-70 0.01 µg/mL | 0 | 21 |
| K1-70 0.1 µg/mL | 91 | 80 |
| K1-70 1 µg/mL | 99 | 93 |
| K1-70 10 µg/mL | 98 | 94 |
| K1-70 100 µg/mL | 98 | 94 |
| TSH (2) | 0 | 3 |

See legend for Table 9a for details.

TABLE 9g

TSH induced cyclic AMP production in CHO cells expressing
wild type TSHR and TSHR with Phe130 mutated to Ala. Effect
of different dilutions of human monoclonal antibody to
the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.39 ± 0.29 | 3.53 ± 0.49 | 254 |
| TSH[b] | 79.42 ± 5.15 | 120.74 ± 2.87 | 152 |
| 5B3 10 µg/mL + TSH[b] | 78.18 ± 1.95 | 110.76 ± 1.49 | 142 |
| 5B3 100 µg/mL + TSH[b] | 86.94 ± 15.80 | 113.8 ± 11.11 | 131 |
| K1-70 0.001 µg + TSH[b] | 82.73 ± 3.36 | 102.43 ± 7.59 | 124 |
| K1-70 0.01 µg + TSH[b] | 83.95 ± 5.31 | 103.90 ± 7.14 | 124 |
| K1-70 0.1 µg + TSH[b] | 4.86 ± 1.52 | 12.71 ± 3.24 | 262 |
| K1-70 1.0 µg + TSH[b] | 1.56 ± 0.61 | 2.87 ± 0.28 | 184 |
| K1-70 10 µg + TSH[b] | 1.27 ± 0.15 | 2.22 ± 0.40 | 175 |
| K1-70 100 µg + TSH[b] | 1.18 ± 0.09 | 2.68 ± 0.41 | 242 |
| K1-70 100 µg | 1.23 ± 0.08 | 2.37 ± 0.26 | 193 |
| TSH (2) | 89.12 ± 4.45 | 95.39 ± 7.44 | 107 |

| Antibody concentration | % inhibition of TSH stimulation[c] | |
|---|---|---|
| | Wild type TSHR | Mutated TSHR |
| 5B3 10 µg/mL | 2 | 8 |
| 5B3 100 µg/mL | 0 | 6 |
| K1-70 0.001 µg | 0 | 15 |
| K1-70 0.01 µg/mL | 0 | 14 |
| K1-70 0.1 µg/mL | 94 | 89 |
| K1-70 1 µg/mL | 98 | 98 |
| K1-70 10 µg/mL | 98 | 98 |
| K1-70 100 µg/mL | 99 | 98 |
| TSH (2) | 0 | 0 |

See legend to Table 9a for details

TABLE 9h

TSH induced cyclic AMP production in CHO cells expressing wild type TSHR
and TSHR with Phe134 mutated to Ala. Effect of different dilutions of human
monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 6.83 ± 1.44 | 14.86 ± 2.75 | 218 |
| TSH[b] | 108.08 ± 13.83 | 111.16 ± 2.0 | 103 |
| 5B3 10 µg/mL + TSH[b] | 131.38 ± 6.77 | 101.30 ± 8.44 | 77 |
| 5B3 100 µg/mL + TSH[b] | 112.49 ± 2.66 | 115.54 ± 9.72 | 103 |
| K1-70 0.001 µg + TSH[b] | 137.02 ± 27.32 | 106.92 ± 15.54 | 78 |
| K1-70 0.01 µg + TSH[b] | 120.16 ± 3.88 | 111.84 ± 6.01 | 93 |
| K1-70 0.1 µg + TSH[b] | 8.09 ± 1.00 | 27.86 ± 3.72 | 344 |
| K1-70 1.0 µg + TSH[b] | 2.02 ± 0.39 | 5.59 ± 1.40 | 277 |
| K1-70 10 µg + TSH[b] | 1.88 ± 0.35 | 4.00 ± 1.77 | 213 |
| K1-70 100 µg + TSH[b] | 1.48 ± 0.33 | 3.50 ± 0.09 | 236 |
| K1-70 100 µg | 1.34 ± 0.40 | 2.86 ± 0.41 | 213 |
| TSH (2) | 142.29 ± 13.46 | 101.70 ± 1.33 | 71 |

| Antibody concentration | % inhibition of TSH stimulation[c] | |
|---|---|---|
| | Wild type TSHR | Mutated TSHR |
| 5B3 10 µg/mL | 0 | 9 |
| 5B3 100 µg/mL | 0 | 0 |
| K1-70 0.001 µg | 0 | 4 |
| K1-70 0.01 µg/mL | 0 | 0 |
| K1-70 0.1 µg/mL | 93 | 75 |
| K1-70 1 µg/mL | 98 | 95 |
| K1-70 10 µg/mL | 98 | 96 |

TABLE 9h-continued

TSH induced cyclic AMP production in CHO cells expressing wild type TSHR and TSHR with Phe134 mutated to Ala. Effect of different dilutions of human monoclonal antibody to the TSHR (K1-70) with TSH antagonist activity

| | | |
|---|---|---|
| K1-70 100 µg/mL | 99 | 97 |
| TSH (2) | 0 | 9 |

See legend to Table 9a for details.

TABLE 9i

TSH induced cyclic AMP production in CHO cells expressing wild type TSHR and TSHR with Lys183 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.43 ± 0.69 | 3.20 ± 0.15 | 744 |
| TSH[b] | 61.1 ± 2.48 | 75.8 ± 8.25 | 124 |
| 5B3 10 µg/mL + TSH[b] | 62.03 ± 12.77 | 57.82 ± 7.43 | 93 |
| 5B3 100 µg/mL + TSH[b] | 69.24 ± 6.19 | 63.12 ± 10.69 | 91 |
| K1-70 0.001 µg + TSH[b] | 83.86 ± 6.22 | 64.26 ± 2.45 | 77 |
| K1-70 0.01 µg + TSH[b] | 91.30 ± 15.24 | 61.76 ± 5.46 | 68 |
| K1-70 0.1 µg + TSH[b] | 9.35 ± 4.52 | 35.73 ± 5.57 | 382 |
| K1-70 1.0 µg + TSH[b] | 0.94 ± 0.34 | 4.02 ± 0.35 | 428 |
| K1-70 10 µg + TSH[b] | 0.52 ± 0.44 | 2.13 ± 0.89 | 410 |
| K1-70 100 µg + TSH[b] | 1.22 ± 0.32 | 1.88 ± 0.17 | 154 |
| K1-70 100 µg | 0.02 ± 0.01 | 1.42 ± 0.18 | 7100 |
| TSH (2) | 83.6 ± 2.95 | 62.16 ± 4.39 | 74 |

| Antibody concentration | % inhibition of TSH stimulation[c] | |
|---|---|---|
| | Wild type TSHR | Mutated TSHR |
| 5B3 10 µg/mL | 0 | 24 |
| 5B3 100 µg/mL | 0 | 17 |
| K1-70 0.001 µg | 0 | 15 |
| K1-70 0.01 µg/mL | 0 | 19 |
| K1-70 0.1 µg/mL | 85 | 53 |
| K1-70 1 µg/mL | 98 | 95 |
| K1-70 10 µg/mL | 99 | 97 |
| K1-70 100 µg/mL | 98 | 98 |
| TSH (2) | 0 | 18 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 2.28 ± 0.08 | 4.86 ± 0.69 | 213 |
| TSH[b] | 78.45 ± 5.2 | 100.68 ± 6.89 | 128 |
| 5B3 10 µg/mL + TSH[b] | 87.4 ± 1.07 | 91.25 ± 1.14 | 104 |
| 5B3 100 µg/mL + TSH[b] | 82.72 ± 3.42 | 91.89 ± 0.00 | 111 |
| K1-70 0.001 µg + TSH[b] | 94.13 ± 3.00 | 98.03 ± 9.02 | 104 |
| K1-70 0.01 µg + TSH[b] | 101.52 ± 6.79 | 103.40 ± 5.88 | 102 |
| K1-70 0.1 µg + TSH[b] | 19.94 ± 4.38 | 69.63 ± 3.65 | 349 |
| K1-70 1.0 µg + TSH[b] | 2.26 ± 0.17 | 13.36 ± 3.85 | 591 |
| K1-70 10 µg + TSH[b] | 2.24 ± 0.33 | 4.32 ± 0.30 | 193 |
| K1-70 100 µg + TSH[b] | 2.29 ± 0.42 | 4.01 ± 0.56 | 175 |
| K1-70 100 µg | 2.32 ± 0.21 | 3.26 ± 0.08 | 141 |
| TSH (2) | 79.45 ± 4.3 | 77.34 ± 3.86 | 97 |

TABLE 9i-continued

TSH induced cyclic AMP production in CHO cells expressing wild type TSHR and TSHR with Lys183 mutated to Ala. Effect of different dilutions of human monoclonal antibody to the TSHR (K1-70) with TSH antagonist activity

| Antibody concentration | % inhibition of TSH stimulation[c] | |
|---|---|---|
| | Wild type TSHR | Mutated TSHR |
| 5B3 10 µg/mL | 0 | 9 |
| 5B3 100 µg/mL | 0 | 9 |
| K1-70 0.001 µg | 0 | 3 |
| K1-70 0.01 µg/mL | 0 | 0 |
| K1-70 0.1 µg/mL | 75 | 31 |
| K1-70 1 µg/mL | 97 | 87 |
| K1-70 10 µg/mL | 97 | 96 |
| K1-70 100 µg/mL | 97 | 96 |
| TSH (2) | 0 | 23 |

See legend to Table 9a for details.

TABLE 9j

TSH induced cyclic AMP production in CHO cells expressing wild type TSHR and TSHR with Asp203 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.55 ± 0.40 | 5.22 ± 0.77 | 337 |
| TSH[b] | 71.0 ± 6.52 | 53.85 ± 2.96 | 76 |
| 5B3 10 µg/mL + TSH[b] | 72.22 ± 3.73 | 64.34 ± 5.43 | 89 |
| 5B3 100 µg/mL + TSH[b] | 72.78 ± 4.65 | 61.38 ± 1.95 | 84 |
| K1-70 0.001 µg + TSH[b] | 79.43 ± 2.28 | 65.83 ± 4.66 | 83 |
| K1-70 0.01 µg + TSH[b] | 80.84 ± 4.72 | 63.32 ± 8.41 | 78 |
| K1-70 0.1 µg + TSH[b] | 7.51 ± 0.12 | 15.13 ± 3.92 | 201 |
| K1-70 1.0 µg + TSH[b] | 1.33 ± 0.03 | 4.43 ± 0.96 | 333 |
| K1-70 10 µg + TSH[b] | 0.39 ± 0.31 | 4.37 ± 0.56 | 1121 |
| K1-70 100 µg + TSH[b] | 0.62 ± 0.45 | 4.55 ± 1.57 | 734 |
| K1-70 100 µg | 0.53 ± 0.27 | 3.79 ± 0.59 | 715 |
| TSH (2) | 68.0 ± 3.15 | 59.29 ± 9.87 | 87 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 0 | 0 |
| K1-70 0.01 µg/mL | 0 | 0 |
| K1-70 0.1 µg/mL | 89 | 72 |
| K1-70 1 µg/mL | 98 | 92 |
| K1-70 10 µg/mL | 99 | 92 |
| K1-70 100 µg/mL | 99 | 92 |
| TSH (2) | 0 | 0 |

See legend to Table 9a for details.

TABLE 9k

TSH induced cyclic AMP production in CHO cells expressing wild type TSHR and TSHR with Arg255 mutated to Asp. Effect of different dilutions of human monoclonal antibody to the TSHR (K1-70) with TSH antagonist activity

| | Cyclic AMP produced (pmol/mL; mean ± SD, n = 3) | | |
|---|---|---|---|
| Test sample[a] | Wild type TSHR | Mutated TSHR R255D | Mutated/wild type (%) |
| Cyclic AMP assay buffer only | 1.95 ± 0.25 | 2.17 ± 0.78 | 111 |
| TSH[b] | 66.48 ± 5.07 | 57.84 ± 4.45 | 87 |
| 5B3 10 µg/mL + TSH[b] | 69.15 ± 0.73 | 59.42 ± 3.05 | 86 |
| 5B3 100 µg/mL + TSH[b] | 83.38 ± 7.53 | 62.20 ± 10.14 | 75 |
| K1-70 0.001 µg + TSH[b] | 74.70 ± 1.78 | 55.65 ± 3.99 | 74 |
| K1-70 0.01 µg + TSH[b] | 77.09 ± 6.60 | 56.26 ± 3.14 | 73 |
| K1-70 0.1 µg + TSH[b] | 24.06 ± 0.32 | 5.67 ± 1.26 | 24 |
| K1-70 1.0 µg + TSH[b] | 3.22 ± 0.64 | 1.56 ± 0.34 | 48 |
| K1-70 10 µg + TSH[b] | 2.38 ± 0.28 | 0.10 ± 0.08 | 4 |
| K1-70 100 µg + TSH[b] | 1.99 ± 0.14 | 1.05 ± 0.56 | 53 |
| K1-70 100 µg | 1.85 ± 0.44 | 0.60 ± 0.47 | 32 |
| TSH (2) | 64.84 ± 8.16 | 50.21 ± 5.27 | 77 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 0 | 4 |
| K1-70 0.01 µg/mL | 0 | 3 |
| K1-70 0.1 µg/mL | 64 | 90 |
| K1-70 1 µg/mL | 95 | 97 |
| K1-70 10 µg/mL | 96 | 100 |
| K1-70 100 µg/mL | 97 | 98 |
| TSH (2) | 2 | 13 |

See legend to Table 9a for details.

TABLE 10

Summary of effects of TSHR mutations (relative to wild type) on the ability of K1-18 IgG to stimulate the TSHR and K1-70 IgG to block TSH stimulation of the TSHR

| TSHR mutation | Stimulation of cyclic AMP production by K1-18 IgG | Blocking by K1-70 of TSH stimulation of cyclic AMP production |
|---|---|---|
| Wild type | +++++ | +++++ |
| Lys58 Ala | +++++ | ++ |
| Arg80 Ala | +++++ | +++++ |
| Tyr82 Ala | +++++ | ++++ |
| Glu107 Ala | +++++ | +++++ |
| Arg109 Ala | +++++ | +++ |
| Lys129 Ala | +++++ | +++++ |
| Phe130 Ala | +++++ | +++++ |
| Phe134 Ala | +++++ | +++++ |
| Lys183 Ala | 0 | +++ |
| Asp203 Ala | +++++ | +++++ |
| Arg255 Asp | 0 | +++++ |

Effects of TSHR mutations were expressed as a percentage of activity observed with wild type as follows:-
+++++ = 100% wild type activity;
++++ = <100-80% of wild type activity;
+++ = <80-60% of wild type activity;
++ = <60-40% of wild type activity;
+ = <40-20% of wild type activity;
0 = <20% of wild type activity.

TABLE 11a

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| M22 IgG | | |
| 100 µg/mL | 92.2 ± 0.2 | 94.0 ± 0.6 |
| 30 µg/mL | 90.5 ± 0.4 | 94.4 ± 1.1 |
| 10 µg/mL | 90.2 ± 0.7 | 92.5 ± 0.1 |
| 3 µg/mL | 89.5 ± 1.0 | 91.6 ± 0.5 |
| 1 µg/mL | 89.0 ± 0.1 | 90.4 ± 0.7 |
| 0.3 µg/mL | 87.7 ± 0.4 | 84.6 ± 1.1 |
| 0.1 µg/mL | 84.5 ± 0.4 | 65.5 ± 0.2 |
| 0.03 µg/mL | 70.4 ± 1.1 | 33.8 ± 0.9 |
| 0.01 µg/mL | 43.4 ± 1.9 | 17.1 ± 2.4 |
| 0.003 µg/mL | 16.7 ± 3.7 | 6.2* |
| 0.001 µg/mL | 5.5 ± 0.7 | 3.0 ± 3.6 |
| M22 Fab | | |
| 100 µg/mL | 93.2 ± 0.5 | 93.1 ± 0.2 |
| 30 µg/mL | 92.2 ± 0.7 | 93.2 ± 0.3 |
| 10 µg/mL | 89.4 ± 1.3 | 92.6 ± 0.4 |
| 3 µg/mL | 89.1 ± 1.0 | 92.0 ± 0.3 |
| 1 µg/mL | 88.8 ± 0.8 | 91.7 ± 0.7 |
| 0.3 µg/mL | 88.0 ± 0.4 | 89.9 ± 0.1 |
| 0.1 µg/mL | 86.5 ± 0.1 | 82.5 ± 0.4 |
| 0.03 µg/mL | 79.7 ± 0.4 | 60.2 ± 1.8 |
| 0.01 µg/mL | 63.5 ± 0.8 | 34.0 ± 2.1 |
| 0.003 µg/mL | 31.0 ± 3.3 | 16.7 ± 6.0 |
| 0.001 µg/mL | 15.9 ± 3.1 | 9.3 ± 1.3 |
| K1-70 IgG | | |
| 100 µg/mL | 93.0 ± 0.3 | 94.6 ± 0.7 |
| 30 µg/mL | 92.3 ± 0.2 | 93.7 ± 0.5 |
| 10 µg/mL | 90.8 ± 1.0 | 92.6 ± 0.4 |
| 3 µg/mL | 89.7 ± 0.4 | 92.0 ± 0.5 |
| 1 µg/mL | 89.9 ± 0.7 | 91.8 ± 0.9 |
| 0.3 µg/mL | 89.0 ± 0.5 | 84.4 ± 0.8 |
| 0.1 µg/mL | 86.7 ± 0.5 | 67.4 ± 0.7 |
| 0.03 µg/mL | 77.0 ± 0.6 | 36.5 ± 1.9 |
| 0.01 µg/mL | 50.7 ± 1.5 | 19.9 ± 5.8 |
| 0.003 µg/mL | 17.0 ± 0.8 | 10.2 ± 2.4 |
| 0.001 µg/mL | 3.4 ± 0.7 | 4.8 ± 4.8 |
| 5C9 IgG | | |
| 100 µg/mL | 93.3 ± 0.2 | 68.5 ± 0.7 |
| 10 µg/mL | 84.8 ± 0.8 | 22.7 ± 1.0 |
| 1 µg/mL | 56.4 ± 0.9 | 15.4 ± 3.4 |
| 0.1 µg/mL | 24.6 ± 0.4 | 4.4 ± 2.7 |
| 0.01 µg/mL | 4.5 ± 2.4 | 2.8 ± 4.5 |
| 5B3 IgG | | |
| 100 µg/mL | 15.2 ± 2.5 | 1.1* |
| 10 µg/mL | -2.1 ± 1.3 | -0.7 ± 2.2 |
| 1 µg/mL | -2.6 ± 1.1 | 0.0* |
| 0.1 µg/mL | 1.0 ± 2.7 | 9.4 ± 4.2 |
| 0.01 µg/mL | 3.2 ± 3.4 | 3.2 ± 3.4 |
| 0.001 µg/mL | -1.5 ± 4.3 | 3.7 ± 2.1 |

Results shown are mean ± SD of triplicate determinations.
*duplicate determination.

HBD = pool of healthy blood donor sera. 5B3 is a human MAb to glutamic acid decarboxylase (negative control). $^{125}$I-K1-70 IgG in the presence of assay buffer gave 20.4% binding. $^{125}$I-K1-70 IgG in the presence of HBD pool gave 20.5% binding. Assay buffer is 50 mmol/L NaCl, 10 mmol/L Tris pH 7.8, 0.1% Triton X-100.

TABLE 11b

Inhibition of $^{125}$I-K1-70 IgG binding to TSHR coated tubes by human monoclonal TSHR autoantibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 µg/mL | 92.9 ± 0.2 | 93.5 ± 0.2 |
| 30 µg/mL | 91.2 ± 0.7 | 92.2 ± 0.6 |
| 10 µg/mL | 91.8 ± 0.3 | 92.5 ± 0.7 |
| 3 µg/mL | 90.5 ± 1.0 | 91.0 ± 0.3 |
| 1 µg/mL | 89.6 ± 1.2 | 85.8 ± 0.3 |
| 0.3 µg/mL | 86.4 ± 0.8 | 73.9 ± 0.6 |
| 0.1 µg/mL | 77.9 ± 0.2 | 48.6 ± 0.9 |
| 0.03 µg/mL | 53.9 ± 1.9 | 20.0 ± 1.9 |
| 0.01 µg/mL | 30.2 ± 2.1 | 3.1 ± 2.0 |
| 0.003 µg/mL | 17.0 ± 3.1 | −2.7 ± 7.9 |
| 0.001 µg/mL | 7.2 ± 2.5 | −3.0 ± 3.9 |
| K1-18 Fab | | |
| 100 µg/mL | 86.0 ± 1.4 | 83.6 ± 0.3 |
| 30 µg/mL | 83.3 ± 1.5 | 83.2 ± 1.4 |
| 10 µg/mL | 81.9 ± 0.9 | 82.0 ± 0.2 |
| 3 µg/mL | 79.4 ± 1.1 | 80.5 ± 0.6 |
| 1 µg/mL | 78.5 ± 1.8 | 75.6 ± 1.0 |
| 0.3 µg/mL | 71.4 ± 1.7 | 60.9 ± 1.1 |
| 0.1 µg/mL | 62.8 ± 5.1 | 38.4 ± 1.2 |
| 0.03 µg/mL | 31.3 ± 1.0 | 10.2 ± 2.1 |
| 0.01 µg/mL | 23.7 ± 5.4 | 1.1 ± 2.6 |
| 0.003 µg/mL | 15.2 ± 3.4 | −3.5 ± 3.1 |
| 0.001 µg/mL | 13.8 ± 5.9 | 0.5 ± 4.4 |
| K1-70 IgG | | |
| 100 µg/mL | 93.8 ± 0.2 | 93.6 ± 0.4 |
| 30 µg/mL | 93.1 ± 0.5 | 94.3 ± 0.2 |
| 10 µg/mL | 92.3 ± 0.3 | 93.1 ± 0.6 |
| 3 µg/mL | 90.7 ± 0.4 | 91.7 ± 0.4 |
| 1 µg/mL | 90.8 ± 0.4 | 90.4 ± 0.3 |
| 0.3 µg/mL | 89.2 ± 0.6 | 82.7 ± 0.6 |
| 0.1 µg/mL | 87.1 ± 0.6 | 62.8 ± 1.1 |
| 0.03 µg/mL | 74.2 ± 1.5 | 33.6 ± 1.8 |
| 0.01 µg/mL | 50.9 ± 0.8 | 11.4 ± 3.6 |
| 0.003 µg/mL | 24.0 ± 4.5 | 2.2 ± 6.2 |
| 0.001 µg/mL | 15.3 ± 1.1 | −7.6 ± 2.8 |
| K1-70 Fab | | |
| 100 µg/mL | 91.5 ± 0.2 | 90.8 ± 0.6 |
| 30 µg/mL | 90.7 ± 0.1 | 91.0 ± 0.7 |
| 10 µg/mL | 89.8 ± 1.2 | 90.6 ± 0.1 |
| 3 µg/mL | 89.4 ± 0.3 | 90.9 ± 0.4 |
| 1 µg/mL | 88.3 ± 0.4 | 89.5 ± 0.3 |
| 0.3 µg/mL | 88.0 ± 0.1 | 87.3 ± 0.6 |
| 0.1 µg/mL | 87.5 ± 0.8 | 76.5 ± 0.4 |
| 0.03 µg/mL | 81.7 ± 0.6 | 49.6 ± 0.4 |
| 0.01 µg/mL | 64.8 ± 2.7 | 21.6 ± 3.8 |
| 0.003 µg/mL | 32.7 ± 2.7 | 5.6 ± 6.0 |
| 0.001 µg/mL | 12.2 ± 2.3 | −3.6 ± 1.0 |

See legend to Table 11a for details. $^{125}$I-K1-70 IgG in the presence of assay buffer gave 20.4% binding. $^{125}$I-K1-70 IgG in the presence of HBD pool gave 20.5% binding. Effect of 5B3 IgG (human MAb to glutamic acid decarboxylase; negative control) is shown in Table 11a.

TABLE 11c

Inhibition of $^{125}$I-K1-70 IgG binding to TSHR coated tubes by mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| TSMAb 1 IgG | | |
| 100 µg/mL | 47.4 ± 1.2 | 44.7 ± 0.5 |
| 10 µg/mL | 23.0 ± 0.5 | 37.7 ± 1.2 |
| 1 µg/mL | 14.8 ± 0.5 | 16.8 ± 2.3 |
| 0.1 µg/mL | 2.3 ± 2.3 | −2.2 ± 1.9 |
| 0.01 µg/mL | −1.0 ± 4.4 | −3.3 ± 2.9 |
| TSMAb 2 IgG | | |
| 100 µg/mL | 53.7 ± 1.4 | 43.8 ± 0.9 |
| 10 µg/mL | 14.5 ± 1.4 | 35.5 ± 1.3 |
| 1 µg/mL | 9.3 ± 1.6 | 28.6 ± 0.6 |
| 0.1 µg/mL | 6.5 ± 2.3 | 10.2 ± 0.8 |
| 0.01 µg/mL | 0.3 ± 3.4 | 1.2 ± 3.6 |
| TSMAb 3 IgG | | |
| 100 µg/mL | 54.8 ± 2.8 | 33.5 ± 3.7 |
| 10 µg/mL | 25.4 ± 2.9 | 24.9 ± 2.8 |
| 1 µg/mL | 14.6 ± 0.9 | 18.5 ± 0.8 |
| 0.1 µg/mL | 13.1 ± 0.7 | 4.8 ± 1.7 |
| 0.01 µg/mL | 5.3 ± 0.7 | −1.3 ± 0.3 |
| TSMAb 4 IgG | | |
| 100 µg/mL | 47.7 ± 2.6 | 54.2 ± 1.7 |
| 10 µg/mL | 31.9 ± 0.7 | 52.8 ± 2.5 |
| 1 µg/mL | 29.9 ± 1.0 | 42.8 ± 1.2 |
| 0.1 µg/mL | 22.6 ± 1.6 | 18.6 ± 0.2 |
| 0.01 µg/mL | 6.7 ± 0.6 | 2.3 ± 3.1 |
| TSMAb 5 IgG | | |
| 100 µg/mL | 72.5 ± 1.3 | 59.6 ± 0.6 |
| 10 µg/mL | 53.1 ± 1.6 | 53.8 ± 0.7 |
| 1 µg/mL | 33.8 ± 3.9 | 46.3 ± 1.3 |
| 0.1 µg/mL | 25.7 ± 0.7 | 30.6 ± 1.5 |
| 0.01 µg/mL | 10.9 ± 3.1 | 7.2 ± 1.4 |
| TSMAb 6 IgG | | |
| 100 µg/mL | 59.5 ± 3.2 | 48.1 ± 2.1 |
| 10 µg/mL | 23.9 ± 3.0 | 47.4 ± 4.1 |
| 1 µg/mL | 19.2 ± 2.3 | 37.0 ± 1.4 |
| 0.1 µg/mL | 16.6 ± 1.1 | 22.0 ± 1.2 |
| 0.01 µg/mL | 7.8 ± 0.5 | 3.6 ± 1.6 |
| TSMAb 7 IgG | | |
| 100 µg/mL | 61.2 ± 0.8 | 44.7 ± 1.6 |
| 10 µg/mL | 41.2 ± 2.3 | 41.8 ± 2.7 |
| 1 µg/mL | 19.4 ± 3.7 | 33.1 ± 1.4 |
| 0.1 µg/mL | 13.4 ± 1.5 | 13.0 ± 1.2 |
| 0.01 µg/mL | 2.9 ± 1.2 | −2.1 ± 0.4 |
| 9D33 IgG | | |
| 100 µg/mL | 61.4 ± 0.4 | 51.1 ± 1.7 |
| 10 µg/mL | 41.7 ± 1.6 | 48.0 ± 2.2 |
| 1 µg/mL | 37.2 ± 4.0 | 40.5 ± 3.6 |
| 0.1 µg/mL | 24.8 ± 1.1 | 14.8 ± 0.2 |
| 0.01 µg/mL | 9.4 ± 1.1 | 0.6 ± 0.4 |
| 5B3 IgG | | |
| 100 µg/mL | 1.3 ± 0.6 | −0.9 ± 2.6 |
| 10 µg/mL | 2.3 ± 2.3 | −1.5 ± 1.5 |
| 1 µg/mL | 4.2 ± 5.3 | −1.5 ± 5.4 |
| 0.1 µg/mL | −1.2 ± 1.3 | −3.6 ± 3.3 |
| 0.01 µg/mL | −3.6 ± 1.8 | −5.8 ± 1.9 |

See legend to Table 11a for details. $^{125}$I-K1-70 IgG in the presence of assay buffer gave 20.3% binding. $^{125}$I-K1-70 IgG in the presence of HBD pool gave 19.5% binding.

TABLE 11d

Inhibition of $^{125}$I-K1-70 Fab binding to TSHR coated tubes by human and mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| K1-18 IgG | | |
| 100 μg/mL | 95.3 ± 0.2 | 96.0 ± 0.0 |
| 30 μg/mL | 94.5 ± 0.1 | 95.6 ± 0.4 |
| 10 μg/mL | 94.0 ± 0.4 | 94.8 ± 0.3 |
| 3 μg/mL | 93.3 ± 0.5 | 93.0 ± 0.5 |
| 1 μg/mL | 93.1 ± 0.3 | 89.4 ± 0.7 |
| 0.3 μg/mL | 92.6 ± 0.8 | 77.7 ± 1.5 |
| 0.1 μg/mL | 83.6 ± 0.3 | 51.0 ± 3.2 |
| 0.03 μg/mL | 63.1 ± 0.6 | 17.2 ± 2.6 |
| 0.01 μg/mL | 30.3 ± 2.1 | 2.2 ± 7.8 |
| 0.003 μg/mL | 11.4 ± 4.1 | −9.4 ± 3.1 |
| 0.001 μg/mL | 5.9 ± 5.6 | −6.8 ± 5.4 |
| K1-18 Fab | | |
| 100 μg/mL | 86.4 ± 0.5 | 85.7 ± 1.6 |
| 30 μg/mL | 83.2 ± 0.1 | 85.4 ± 0.8 |
| 10 μg/mL | 80.8 ± 0.9 | 83.2 ± 0.7 |
| 3 μg/mL | 80.6 ± 1.9 | 82.6 ± 0.5 |
| 1 μg/mL | 79.0 ± 1.5 | 78.7 ± 1.6 |
| 0.3 μg/mL | 75.9 ± 0.2 | 63.9 ± 1.3 |
| 0.1 μg/mL | 62.9 ± 0.7 | 36.9 ± 2.2 |
| 0.03 μg/mL | 38.8 ± 0.4 | 7.9 ± 1.5 |
| 0.01 μg/mL | 16.7 ± 0.4 | −0.8 ± 4.7 |
| 0.003 μg/mL | 5.0 ± 4.6 | −9.6 ± 4.8 |
| 0.001 μg/mL | 3.8 ± 5.8 | −8.2 ± 5.6 |
| M22 IgG | | |
| 100 μg/mL | 97.2 ± 0.3 | 96.5 ± 0.5 |
| 30 μg/mL | 96.3 ± 0.5 | 95.8 ± 0.3 |
| 10 μg/mL | 95.8 ± 0.5 | 95.4 ± 0.7 |
| 3 μg/mL | 95.4 ± 0.4 | 95.1 ± 0.4 |
| 1 μg/mL | 94.5 ± 0.9 | 93.1 ± 0.2 |
| 0.3 μg/mL | 93.1 ± 0.3 | 86.6 ± 3.3 |
| 0.1 μg/mL | 89.4 ± 0.4 | 68.2 ± 0.4 |
| 0.03 μg/mL | 72.7 ± 1.3 | 32.7 ± 1.3 |
| 0.01 μg/mL | 41.0 ± 2.4 | 5.7 ± 2.0 |
| 0.003 μg/mL | 19.3 ± 3.1 | −5.8 ± 2.8 |
| 0.001 μg/mL | 12.1 ± 4.8 | −3.1 ± 5.5 |
| M22 Fab | | |
| 100 μg/mL | 97.7 ± 0.1 | 94.9 ± 0.5 |
| 30 μg/mL | 96.2 ± 0.3 | 95.3 ± 0.2 |
| 10 μg/mL | 95.5 ± 0.1 | 94.8 ± 0.5 |
| 3 μg/mL | 94.2 ± 0.2 | 94.1 ± 0.4 |
| 1 μg/mL | 93.6 ± 0.5 | 93.7 ± 0.7 |
| 0.3 μg/mL | 92.7 ± 0.4 | 92.2 ± 0.7 |
| 0.1 μg/mL | 91.8 ± 0.2 | 86.4 ± 1.8 |
| 0.03 μg/mL | 83.9 ± 0.8 | 66.8 ± 0.8 |
| 0.01 μg/mL | 61.6 ± 1.2 | 36.6 ± 1.0 |
| 0.003 μg/mL | 29.7 ± 1.4 | 11.5 ± 1.9 |
| 0.001 μg/mL | 10.9 ± 0.5 | 7.7 ± 7.3 |
| K1-70 IgG | | |
| 100 μg/mL | 97.7 ± 0.2 | 97.7 ± 0.2 |
| 30 μg/mL | 97.7 ± 0.2 | 97.4 ± 0.2 |
| 10 μg/mL | 96.9 ± 0.3 | 96.6 ± 0.2 |
| 3 μg/mL | 95.5 ± 0.5 | 96.2 ± 0.5 |
| 1 μg/mL | 95.2 ± 0.3 | 94.1 ± 0.4 |
| 0.3 μg/mL | 94.2 ± 0.2 | 97.0 ± 1.0 |
| 0.1 μg/mL | 93.5 ± 0.7 | 66.5 ± 1.4 |
| 0.03 μg/mL | 89.0 ± 0.5 | 37.8 ± 3.3 |
| 0.01 μg/mL | 66.2 ± 2.1 | 10.6 ± 1.6 |
| 0.003 μg/mL | 27.7 ± 3.8 | −0.8 ± 2.6 |
| 0.001 μg/mL | 5.5 ± 1.0 | −8.8 ± 2.4 |
| K1-70 Fab | | |
| 100 μg/mL | 96.7 ± 0.4 | 96.3 ± 0.1 |
| 30 μg/mL | 95.1 ± 0.9 | 95.7 ± 0.4 |
| 10 μg/mL | 93.6 ± 0.0 | 94.8 ± 0.5 |
| 3 μg/mL | 93.5 ± 0.2 | 94.9 ± 0.3 |
| 1 μg/mL | 93.5 ± 0.1 | 94.2 ± 0.3 |
| 0.3 μg/mL | 92.7 ± 0.4 | 91.4 ± 0.8 |
| 0.1 μg/mL | 92.2 ± 0.3 | 81.9 ± 0.5 |
| 0.03 μg/mL | 89.0 ± 0.3 | 57.2 ± 2.6 |
| 0.01 μg/mL | 75.6 ± 1.3 | 25.3 ± 3.9 |
| 0.003 μg/mL | 40.0 ± 3.9 | 2.5 ± 5.8 |
| 0.001 μg/mL | 11.9 ± 2.6 | −2.5 ± 3.2 |
| 5C9 IgG | | |
| 100 μg/mL | 93.3 ± 0.9 | 40.6 ± 3.8 |
| 10 μg/mL | 80.4 ± 2.4 | 20.7 ± 1.1 |
| 1 μg/mL | 41.5 ± 3.2 | 8.1 ± 5.5 |
| 0.1 μg/mL | 21.9 ± 0.6 | 6.0 ± 8.6 |
| 0.01 μg/mL | 10.9 ± 1.6 | −4.4 ± 5.9 |
| TSMAb 1 IgG | | |
| 100 μg/mL | 48.8 ± 1.9 | 46.3 ± 1.6 |
| 10 μg/mL | 29.9 ± 0.4 | 41.4 ± 1.3 |
| 1 μg/mL | 21.9 ± 1.5 | 25.0 ± 2.0 |
| 0.1 μg/mL | 4.1 ± 3.0 | 8.4 ± 4.3 |
| 0.01 μg/mL | −2.5 ± 2.5 | 3.5 ± 3.5 |
| TSMAb 2 IgG | | |
| 100 μg/mL | 56.3 ± 2.1 | 38.3 ± 3.0 |
| 10 μg/mL | 24.0 ± 3.8 | 34.7 ± 1.2 |
| 1 μg/mL | 16.8 ± 1.4 | 26.9 ± 2.9 |
| 0.1 μg/mL | 13.0 ± 2.2 | 12.5 ± 1.7 |
| 0.01 μg/mL | 4.0 ± 2.1 | 8.6 ± 8.6 |
| TSMAb 3 IgG | | |
| 100 μg/mL | 58.9 ± 3.2 | 32.6 ± 2.6 |
| 10 μg/mL | 30.3 ± 1.8 | 29.0 ± 3.4 |
| 1 μg/mL | 29.3 ± 3.2 | 18.2 ± 2.1 |
| 0.1 μg/mL | 21.1 ± 1.9 | 3.6 ± 1.3 |
| 0.01 μg/mL | 7.2 ± 1.7 | 2.4 ± 3.7 |
| TSMAb 4 IgG | | |
| 100 μg/mL | 53.8 ± 3.4 | 57.8 ± 3.3 |
| 10 μg/mL | 41.8 ± 2.1 | 53.5 ± 1.4 |
| 1 μg/mL | 38.8 ± 2.2 | 41.2 ± 0.1 |
| 0.1 μg/mL | 29.9 ± 1.3 | 12.8 ± 1.6 |
| 0.01 μg/mL | 8.6 ± 1.2 | −1.4 ± 1.7 |
| TSMAb 5 IgG | | |
| 100 μg/mL | 81.8 ± 1.5 | 57.5 ± 1.6 |
| 10 μg/mL | 62.0 ± 5.7 | 57.0 ± 2.6 |
| 1 μg/mL | 41.2 ± 0.9 | 52.3 ± 1.2 |
| 0.1 μg/mL | 34.4 ± 1.4 | 28.8 ± 1.2 |
| 0.01 μg/mL | 14.4 ± 1.9 | 6.8 ± 0.4 |
| TSMAb 6 IgG | | |
| 100 μg/mL | 68.3 ± 2.9 | 43.9 ± 1.0 |
| 10 μg/mL | 28.9 ± 3.7 | 39.2 ± 3.8 |
| 1 μg/mL | 25.4 ± 2.4 | 36.9 ± 4.7 |
| 0.1 μg/mL | 19.5 ± 2.0 | 19.2 ± 1.6 |
| 0.01 μg/mL | 4.9 ± 0.7 | 0.2 ± 0.9 |
| TSMAb 7 IgG | | |
| 100 μg/mL | 59.8 ± 2.8 | 38.2 ± 2.1 |
| 10 μg/mL | 40.6 ± 1.2 | 39.5 ± 5.5 |
| 1 μg/mL | 21.7 ± 2.1 | 30.7 ± 2.8 |
| 0.1 μg/mL | 13.5 ± 1.7 | 9.3 ± 2.7 |
| 0.01 μg/mL | −1.7 ± 1.6 | −2.9 ± 2.3 |
| 9D33 IgG | | |
| 100 μg/mL | 62.7 ± 2.5 | 55.7 ± 7.1 |
| 10 μg/mL | 48.0 ± 2.6 | 47.7 ± 1.7 |
| 1 μg/mL | 43.8 ± 1.8 | 38.8 ± 3.3 |
| 0.1 μg/mL | 29.7 ± 3.4 | 12.7 ± 1.8 |
| 0.01 μg/mL | 5.0 ± 0.4 | −1.2 ± 2.7 |
| 5B3 IgG | | |
| 100 μg/mL | 1.4 ± 0.6 | −8.6 ± 1.2 |
| 10 μg/mL | −2.1 ± 2.6 | −5.7 ± 4.4 |
| 1 μg/mL | −1.7 ± 0.2 | −7.8 ± 2.2 |

TABLE 11d-continued

Inhibition of $^{125}$I-K1-70 Fab binding to TSHR coated tubes by human and mouse monoclonal TSHR antibodies

| Test sample | Inhibition of binding (%) Dilutions in assay buffer (mean ± SD) | Inhibition of binding (%) Dilutions in HBD (mean ± SD) |
|---|---|---|
| 0.1 µg/mL | 2.2 ± 0.8 | −8.7 ± 0.8 |
| 0.01 µg/mL | −1.7 ± 1.7 | −5.3 ± 7.0 |
| 0.001 µg/mL | −1.8 ± 3.1 | −12.1 ± 2.8 |

See legend to Table 11a for details. $^{125}$I-K1-70 Fab in the presence of assay buffer gave 20.3% binding. $^{125}$I-K1-70 Fab in the presence of HBD pool gave 19.5% binding.

TABLE 11e

Inhibition of $^{125}$I-K1-70 Fab, $^{125}$I-K1-70 IgG and $^{125}$I-TSH binding to TSHR coated tubes by patient sera

| Test Sample | % Inhibition of $^{125}$I-K1-70 Fab binding | % Inhibition of $^{125}$I-K1-70 IgG binding | % Inhibition of $^{125}$I-TSH binding |
|---|---|---|---|
| G1 | 43.7 | 47.6 | 38.6 |
| G2 | 29.0 | 33.8 | 31.5 |
| G3 | 33.3 | 44.7 | 35.6 |
| G4 | 39.2 | 47.5 | 47.1 |
| G5 | 40.9 | 41.1 | 44.7 |
| G6 | 50.2 | 55.1 | 52.1 |
| G7 | 15.9 | 19.2 | 15.9 |
| G8 | 34.6 | 41.5 | 41.8 |
| G9 | 72.8 | 77.6 | 80.0 |
| G10 | 55.2 | 62.4 | 68.7 |
| G11 | 32.7 | 38.3 | 31.0 |
| G12 | 30.8 | 42.1 | 29.7 |
| G13 | 47.3 | 51.8 | 57.9 |
| G14 | 49.7 | 53.3 | 49.3 |
| G15 | 41.1 | 48.4 | 38.6 |
| G16 | 36.9 | 43.3 | 42.9 |
| G17 | 17.5 | 23.3 | 24.5 |
| G18 | 33.9 | 40.6 | 39.1 |
| G19 | 22.2 | 33.4 | 20.6 |
| G20 | 33.5 | 38.1 | 38.4 |
| HBD1 | −4.7 | −6.5 | −12.6 |
| HBD2 | −1.7 | −3.5 | −4.2 |
| HBD3 | 1.2 | −2.8 | −5.4 |
| HBD4 | −3.4 | 0.8 | −11.8 |
| HBD5 | −0.5 | 5.6 | −4.7 |
| HBD6 | 1.6 | 4.1 | 1.8 |
| HBD7 | −9.0 | −2.4 | −13.7 |
| HBD8 | −4.6 | 0.8 | −12.8 |
| HBD9 | −0.6 | 1.2 | −11.0 |
| HBD10 | −4.3 | 2.1 | −10.6 |
| K1 donor serum | | | |
| diluted 10x | 72.9 | 73.7 | 67.2 |
| diluted 20x | 52.2 | 56.6 | 44.0 |
| diluted 40x | 29.5 | 39.5 | 24.8 |
| diluted 80x | 15.5 | 26.2 | 11.9 |
| diluted 160x | 7.8 | 15.3 | 2.7 |
| diluted 320x | 3.2 | 8.0 | 2.1 |
| B1 | | | |
| diluted 5x | 85.7 | 89.0 | 91.5 |
| diluted 10x | 76.5 | 81.7 | 83.9 |
| diluted 20x | 60.6 | 68.1 | 65.8 |
| diluted 40x | 38.4 | 51.3 | 39.6 |
| diluted 80x | 21.0 | 36.9 | 20.7 |
| diluted 160x | 8.6 | 20.4 | 7.5 |
| diluted 320x | 3.6 | 10.7 | −2.5 |
| B2 | | | |
| diluted 5x | 90.4 | 89.9 | 93.5 |
| diluted 10x | 84.6 | 86.6 | 86.5 |
| diluted 20x | 71.9 | 78.1 | 68.7 |
| diluted 40x | 52.4 | 63.1 | 42.8 |
| diluted 80x | 34.9 | 45.1 | 20.4 |
| diluted 160x | 18.6 | 29.5 | 10.5 |
| diluted 320x | 10.7 | 16.6 | 14.1 |
| S1 | | | |
| diluted 5x | 73.6 | 72.1 | 82.0 |
| diluted 10x | 58.6 | 60.2 | 66.5 |
| diluted 20x | 45.1 | 45.7 | 47.1 |
| diluted 40x | 32.9 | 34.5 | 32.5 |
| diluted 80x | 19.7 | 21.6 | 17.4 |
| diluted 160x | 9.7 | 13.7 | 5.2 |
| diluted 320x | 2.2 | 4.7 | 2.3 |
| S2 | | | |
| diluted 5x | 50.0 | 54.7 | 55.1 |
| diluted 10x | 34.8 | 38.9 | 33.7 |
| diluted 20x | 24.2 | 22.9 | 18.4 |
| diluted 40x | 11.8 | 16.0 | 9.5 |
| diluted 80x | 5.6 | 9.4 | 7.7 |
| diluted 160x | 0.3 | 4.9 | −0.7 |

See legend to Table 11a for details. Dilutions were made in HBD pool serum. HBD 1-10 = healthy blood donor sera 1-10. B1, B2 = sera from two different patients with TSHR blocking autoantibodies. S1, S2 = sera from two different patients with TSHR stimulating autoantibodies.

TABLE 12a

Binding of human MAbs to TSHR260-AP in an ELISA

| Test sample | Mean absorbance at 405 nm | |
|---|---|---|
| | Test sample diluted in HBD | Test sample diluted in assay buffer |
| Assay buffer | | −0.005 |
| HBD serum | −0.002 | |
| K1-18 IgG | | |
| 250 µg/mL | 0.722 | 1.197 |
| 100 µg/mL | 0.706 | 0.993 |
| 10 µg/mL | 0.660 | 0.800 |
| 1 µg/mL | 0.578 | 0.715 |
| 0.5 µg/mL | 0.511 | 0.673 |
| 0.1 µg/mL | 0.292 | 0.545 |
| 0.05 µg/mL | 0.191 | 0.396 |
| 0.01 µg/mL | 0.053 | 0.255 |
| 0.005 µg/mL | 0.013 | 0.136 |
| K1-70 IgG | | |
| 250 µg/mL | 0.817 | 1.134 |
| 100 µg/mL | 0.794 | 1.030 |
| 10 µg/mL | 0.738 | 0.885 |
| 1 µg/mL | 0.677 | 0.806 |
| 0.5 µg/mL | 0.661 | 0.802 |
| 0.1 µg/mL | 0.440 | 0.713 |
| 0.05 µg/mL | 0.290 | 0.593 |
| 0.01 µg/mL | 0.086 | 0.183 |
| 0.005 µg/mL | 0.045 | 0.085 |
| M22 IgG | | |
| 250 µg/mL | 0.833 | 1.007 |
| 100 µg/mL | 0.851 | 0.967 |
| 10 µg/mL | 0.796 | 0.872 |
| 1 µg/mL | 0.726 | 0.821 |
| 0.5 µg/mL | 0.657 | 0.776 |
| 0.1 µg/mL | 0.365 | 0.653 |
| 0.05 µg/mL | 0.204 | 0.484 |
| 0.01 µg/mL | 0.030 | 0.101 |
| 0.005 µg/mL | 0.045 | 0.075 |
| 5C9 IgG | | |
| 250 µg/mL | 0.058 | 1.124 |
| 100 µg/mL | 0.027 | 0.669 |
| 10 µg/mL | 0.004 | 0.099 |

TABLE 12a-continued

Binding of human MAbs to TSHR260-AP in an ELISA

| Test sample | Mean absorbance at 405 nm | |
|---|---|---|
| | Test sample diluted in HBD | Test sample diluted in assay buffer |
| 1 µg/mL | 0.045 | 0.011 |
| 0.5 µg/mL | 0.016 | −0.005 |
| 0.1 µg/mL | −0.005 | −0.013 |
| 0.05 µg/mL | −0.003 | −0.008 |
| 0.01 µg/mL | 0.017 | −0.001 |
| 0.005 µg/mL | 0.020 | −0.009 |
| 5B3 IgG | | |
| 250 µg/mL | 0.012 | 0.018 |
| 100 µg/mL | 0.003 | −0.011 |
| 10 µg/mL | −0.006 | −0.014 |
| 1 µg/mL | 0.049 | −0.004 |
| 0.5 µg/mL | −0.001 | −0.006 |
| 0.1 µg/mL | −0.002 | −0.013 |
| 0.05 µg/mL | −0.006 | −0.009 |
| 0.01 µg/mL | 0.027 | 0.012 |
| 0.005 µg/mL | −0.002 | −0.012 |

TSHR260-AP is a fusion protein consisting of a fragment of human TSHR (amino acids 22-260) e with alkaline phosphatase. HBD = pool of healthy blood donor sera. Test samples were diluted in HBD serum or assay buffer. Assay buffer is 50 mmol/L NaCl, 10 mmol/L Tris pH 7.8, 0.1% Triton X-100, 1 mg/mL BSA. 5B3 is a human MAb to glutamic acid decarboxylase (negative control). Mean absorbance = mean of duplicate determinations.

TABLE 12b

Binding of human TSHR MAbs (IgG and Fab preparations) in the TSHR260-AP based ELISA

| Test sample | Mean absorbance at 405 nm Dilutions in HBD | | Mean absorbance at 405 nm Dilutions in assay buffer | |
|---|---|---|---|---|
| | IgG | Fab | IgG | Fab |
| M22 IgG | | | | |
| 250 µg/mL | 0.833 | 0.031 | 1.007 | 0.077 |
| 100 µg/mL | 0.851 | — | 0.967 | — |
| 10 µg/mL | 0.796 | 0.010 | 0.872 | 0.034 |
| 1 µg/mL | 0.726 | — | 0.821 | — |
| 0.5 µg/mL | 0.657 | — | 0.776 | — |
| 0.1 µg/mL | 0.365 | −0.007 | 0.653 | 0.015 |
| 0.05 µg/mL | 0.204 | — | 0.484 | — |
| 0.01 µg/mL | 0.030 | — | 0.101 | — |
| 0.005 µg/mL | 0.045 | −0.013 | 0.075 | −0.004 |
| 5C9 IgG | | | | |
| 250 µg/mL | 0.058 | −0.008 | 1.124 | 0.204 |
| 100 µg/mL | 0.027 | — | 0.669 | — |
| 10 µg/mL | 0.004 | −0.008 | 0.099 | 0.016 |
| 1 µg/mL | 0.045 | — | 0.011 | — |
| 0.5 µg/mL | 0.016 | — | −0.005 | — |
| 0.1 µg/mL | −0.005 | −0.009 | −0.013 | −0.009 |
| 0.05 µg/mL | −0.003 | — | −0.008 | — |
| 0.01 µg/mL | 0.017 | — | −0.001 | — |
| 0.005 µg/mL | 0.020 | −0.012 | −0.009 | 0.000 |
| K1-18 IgG | | | | |
| 250 µg/mL | 0.722 | −0.007 | 1.197 | 0.049 |
| 100 µg/mL | 0.706 | — | 0.993 | — |
| 10 µg/mL | 0.660 | −0.002 | 0.800 | 0.008 |
| 1 µg/mL | 0.578 | — | 0.715 | — |
| 0.5 µg/mL | 0.511 | — | 0.673 | — |
| 0.1 µg/mL | 0.292 | −0.011 | 0.545 | 0.002 |
| 0.05 µg/mL | 0.191 | — | 0.396 | — |
| 0.01 µg/mL | 0.053 | — | 0.255 | — |
| 0.005 µg/mL | 0.013 | −0.011 | 0.136 | −0.004 |
| K1-70 IgG | | | | |
| 250 µg/mL | 0.817 | 0.020 | 1.134 | 0.056 |
| 100 µg/mL | 0.794 | — | 1.030 | — |
| 10 µg/mL | 0.738 | 0.018 | 0.885 | 0.033 |
| 1 µg/mL | 0.677 | — | 0.806 | — |
| 0.5 µg/mL | 0.661 | — | 0.802 | — |
| 0.1 µg/mL | 0.440 | −0.010 | 0.713 | 0.007 |
| 0.05 µg/mL | 0.290 | — | 0.593 | — |
| 0.01 µg/mL | 0.086 | — | 0.183 | — |
| 0.005 µg/mL | 0.045 | −0.010 | 0.085 | −0.004 |
| 5B3 IgG | | | | |
| 250 µg/mL | 0.012 | — | 0.018 | — |
| 100 µg/mL | 0.003 | — | −0.011 | — |
| 10 µg/mL | −0.006 | — | −0.014 | — |
| 1 µg/mL | 0.049 | — | −0.004 | — |
| 0.5 µg/mL | −0.001 | — | −0.006 | — |
| 0.1 µg/mL | −0.002 | — | −0.013 | — |
| 0.05 µg/mL | −0.006 | — | −0.009 | — |
| 0.01 µg/mL | 0.027 | — | 0.012 | — |
| 0.005 µg/mL | −0.002 | — | −0.012 | — |
| 4B4 IgG | | | | |
| 250 µg/mL | — | −0.009 | — | −0.004 |
| 100 µg/mL | — | — | — | — |
| 10 µg/mL | — | −0.009 | — | 0.012 |
| 1 µg/mL | — | — | — | — |
| 0.5 µg/mL | — | — | — | — |
| 0.1 µg/mL | — | −0.001 | — | −0.006 |
| 0.05 µg/mL | — | — | — | — |
| 0.01 µg/mL | — | — | — | — |
| 0.005 µg/mL | — | −0.014 | — | 0.000 |

See legend to Table 12a for details. 4B4 is a human MAb to glutamic acid decarboxylase (negative control).

TABLE 12c

Binding of mouse TSMAbs in the TSHR260-AP ELISA

| Test sample | Mean absorbance at 405 nm Dilutions in HBD |
|---|---|
| HBD | −0.010 |
| TSMAb 1 | |
| 10 µg/mL | 0.166 |
| 0.5 µg/mL | 0.036 |
| 0.05 µg/mL | −0.002 |
| 0.005 µg/mL | 0.006 |
| TSMAb 2 | |
| 10 µg/mL | 0.410 |
| 0.5 µg/mL | 0.191 |
| 0.05 µg/mL | 0.033 |
| 0.005 µg/mL | 0.003 |
| TSMAb 3 | |
| 10 µg/mL | 0.103 |
| 0.5 µg/mL | 0.029 |
| 0.05 µg/mL | −0.001 |
| 0.005 µg/mL | 0.003 |
| TSMAb 4 | |
| 10 µg/mL | 0.428 |
| 0.5 µg/mL | 0.253 |
| 0.05 µg/mL | 0.048 |
| 0.005 µg/mL | 0.013 |
| TSMAb 5 | |
| 10 µg/mL | 0.561 |
| 0.5 µg/mL | 0.319 |
| 0.05 µg/mL | 0.054 |
| 0.005 µg/mL | 0.011 |

TABLE 12c-continued

Binding of mouse TSMAbs in the TSHR260-AP ELISA

| Test sample | Mean absorbance at 405 nm Dilutions in HBD |
|---|---|
| TSMAb 6 | |
| 10 µg/mL | 0.486 |
| 0.5 µg/mL | 0.310 |
| 0.05 µg/mL | 0.090 |
| 0.005 µg/mL | 0.002 |
| TSMAb 7 | |
| 10 µg/mL | 0.357 |
| 0.5 µg/mL | 0.184 |
| 0.05 µg/mL | 0.027 |
| 0.005 µg/mL | 0.004 |
| K1-70 IgG | |
| 10 µg/mL | 1.252 |
| 1 µg/mL | 1.122 |
| 0.5 µg/mL | 1.038 |
| 0.1 µg/mL | 0.606 |
| 0.05 µg/mL | 0.348 |
| 0.01 µg/mL | 0.069 |
| 0.005 µg/mL | 0.076 |
| M22 IgG | |
| 10 µg/mL | 1.272 |
| 1 µg/mL | 1.094 |
| 0.5 µg/mL | 1.018 |
| 0.1 µg/mL | 0.548 |
| 0.05 µg/mL | 0.292 |
| 0.01 µg/mL | 0.043 |
| 0.005 µg/mL | 0.011 |

See legend to Table 12a for details. Binding of 5B3 and 4B4 (human MAbs to glutamic acid decarboxylase; negative controls) is shown in Table 12b.

TABLE 12d

Binding of mouse TSHR blocking MAb (9D33) in the TSHR260-AP ELISA

| Test sample | Mean absorbance at 405 nm Dilutions in HBD |
|---|---|
| HBD | 0.003 |
| 9D33 IgG | |
| 10 µg/mL | 0.481 |
| 1 µg/mL | 0.329 |
| 0.5 µg/mL | 0.273 |
| 0.1 µg/mL | 0.102 |
| 0.05 µg/mL | 0.056 |
| 0.01 µg/mL | 0.011 |
| 0.005 µg/mL | 0.006 |
| K1-70 IgG | |
| 10 µg/mL | 1.324 |
| 1 µg/mL | 1.164 |
| 0.5 µg/mL | 1.083 |
| 0.1 µg/mL | 0.639 |
| 0.05 µg/mL | 0.388 |
| 0.01 µg/mL | 0.094 |
| 0.005 µg/mL | 0.059 |
| M22 IgG | |
| 10 µg/mL | 1.360 |
| 1 µg/mL | 1.172 |
| 0.5 µg/mL | 1.093 |
| 0.1 µg/mL | 0.599 |
| 0.05 µg/mL | 0.332 |
| 0.01 µg/mL | 0.064 |
| 0.005 µg/mL | 0.032 |

See legend to Table 12a for details. Binding of 5B3 and 4B4 (human MAbs to glutamic acid decarboxylase; negative controls) is shown in Table 12b.

TABLE 12e

Binding of patient sera with TSHR stimulating activity in the TSHR260-AP ELISA

| | TSHR260-AP ELISA | | | Inhibition of TSH binding ELISA | Stimulation of cyclic AMP production[3] (pmol/mL) |
|---|---|---|---|---|---|
| Test sample | Mean absorbance at 405 nm | TRAb conc[1] (µg/mL) | TRAb conc[2] (U/L) | TRAb conc[2] (U/L) | |
| HBD | 0.003 | 0 | 0 | 0 | |
| S1 | | | | | |
| diluted 1:5 | 0.924 | 0.31 | 38.0 | >40 | 37.2 |
| diluted 1:10 | 0.788 | 0.18 | 19.7 | 31.1 | |
| diluted 1:20 | 0.583 | 0.10 | 9.5 | 16.2 | |
| diluted 1:40 | 0.378 | 0.05 | 5.2 | 7.1 | |
| S2 | | | | | |
| diluted 1:5 | 0.740 | 0.17 | 17.9 | 36.0 | 47.6 |
| diluted 1:10 | 0.595 | 0.10 | 9.8 | 23.6 | |
| diluted 1:20 | 0.407 | 0.06 | 5.7 | 13.6 | |
| diluted 1:40 | 0.235 | 0.03 | 2.9 | 6.6 | |
| S3 | | | | | |
| diluted 1:5 | 0.868 | 0.25 | 28.5 | >40 | 35.9 |
| diluted 1:10 | 0.651 | 0.12 | 11.8 | 34.0 | |
| diluted 1:20 | 0.453 | 0.06 | 6.5 | 23.5 | |
| diluted 1:40 | 0.290 | 0.04 | 3.8 | 12.2 | |
| S4 | | | | | |
| diluted 1:5 | 0.646 | 0.11 | 11.6 | 19.8 | 107.5 |
| diluted 1:10 | 0.362 | 0.05 | 4.9 | 7.6 | |
| diluted 1:20 | 0.171 | 0.02 | 2.0 | 3.1 | |
| diluted 1:40 | 0.080 | 0.01 | 1.0 | 1.4 | |
| S5 | | | | | |
| diluted 1:5 | 0.407 | 0.06 | 5.7 | 9.4 | 40.6 |
| diluted 1:10 | 0.221 | 0.03 | 2.7 | 4.4 | |
| diluted 1:20 | 0.109 | 0.01 | 1.3 | 2.1 | |
| diluted 1:40 | 0.059 | 0.01 | 0.9 | 1.1 | |
| S6 | | | | | |
| diluted 1:5 | 0.531 | 0.08 | 8.2 | 19.9 | 43.5 |
| diluted 1:10 | 0.363 | 0.05 | 5.0 | 9.2 | |
| diluted 1:20 | 0.213 | 0.03 | 2.6 | 4.7 | |
| diluted 1:40 | 0.124 | 0.02 | 1.5 | 2.0 | |

See legend to Table 12a for details
[1]Read off M22 IgG calibration curve (0.005, 0.001, 0.05, 0.1, 0.5, 1.0 and 10 µg/mL was run in each assay).
[2]Units are NIBSC 90/672.
[3]Stimulation of cyclic AMP production was tested (serum diluted 1:10 in hypotonic cyclic AMP buffer) using CHO cells expressing the full length TSHR. S1 = TSHR stimulating patient serum 1. S2 = TSHR stimulating patient serum 2. S3 = TSHR stimulating patient serum 3. S4 = TSHR stimulating patient serum 4. S5 = TSHR stimulating patient serum 5. S6 = TSHR stimulating patient serum. Serum dilutions for both ELISAs were made in HBD.

TABLE 12f

Binding of patient sera with TSHR blocking activity in the TSHR260-AP ELISA

| | TSHR260-AP ELISA | | TRAb level measured in TSHR coated tube assay |
|---|---|---|---|
| | Diluted in HBD | Diluted in assay buffer | |
| Test sample | Mean absorbance at 405 nm | Mean absorbance at 405 nm | % inhibition of $^{125}$I-TSH binding | U/L |
| B1 | | | | |
| undiluted | 0.859 | 0.859 | NT | NT |
| diluted 1:10 | 0.484 | 0.667 | 73 | 16.8 |
| diluted 1:20 | 0.284 | 0.457 | 45 | 4.3 |

TABLE 12f-continued

Binding of patient sera with TSHR blocking activity in the TSHR260-AP ELISA

| | TSHR260-AP ELISA | | TRAb level measured in TSHR coated tube assay | |
|---|---|---|---|---|
| | Diluted in HBD | Diluted in assay buffer | | |
| Test sample | Mean absorbance at 405 nm | Mean absorbance at 405 nm | % inhibition of $^{125}$I-TSH binding | U/L |
| diluted 1:40 | 0.154 | 0.243 | 22 | 1.4 |
| diluted 1:80 | 0.078 | 0.119 | 4 | 0.1 |
| diluted 1:160 | 0.037 | 0.062 | 0 | 0 |
| diluted 1:320 | 0.021 | 0.032 | NT | NT |
| B2 | | | | |
| undiluted | 0.323 | 0.323 | NT | NT |
| diluted 1:10 | 0.097 | 0.165 | 82 | 25.6 |
| diluted 1:20 | 0.052 | 0.114 | 70 | 14.6 |
| diluted 1:40 | 0.029 | 0.063 | 47 | 4.5 |
| diluted 1:80 | 0.015 | 0.036 | 23 | 2 |
| diluted 1:160 | 0.008 | 0.018 | 9 | 0.7 |
| diluted 1:320 | 0.007 | 0.014 | NT | NT |
| B3 | | | | |
| diluted 1:10 | 0.896 | 1.061 | 85[a] | NT |
| diluted 1:20 | 0.588 | 0.768 | 73[a] | NT |
| diluted 1:40 | 0.320 | 0.443 | 51[a] | NT |
| diluted 1:80 | 0.168 | 0.218 | 34[a] | NT |
| diluted 1:160 | 0.091 | 0.104 | 22[a] | NT |
| diluted 1:320 | 0.041 | 0.054 | 13[a] | NT |
| B4 | | | | |
| diluted 1:10 | 0.729 | 0.826 | 94[a] | NT |
| diluted 1:20 | 0.612 | 0.734 | 91[a] | NT |
| diluted 1:40 | 0.453 | 0.592 | 80[a] | NT |
| diluted 1:80 | 0.270 | 0.353 | 55[a] | NT |
| diluted 1:160 | 0.141 | 0.153 | 33[a] | NT |
| diluted 1:320 | 0.068 | 0.066 | 17[a] | NT |
| B5 | | | | |
| diluted 1:10 | 0.772 | 0.910 | 98 | >40 |
| diluted 1:20 | 0.652 | 0.835 | 97 | >40 |
| diluted 1:40 | 0.470 | 0.735 | 95 | >40 |
| diluted 1:80 | 0.291 | 0.522 | 90 | 36.2 |
| diluted 1:160 | 0.155 | 0.276 | 76 | 12.0 |
| diluted 1:320 | 0.077 | 0.130 | 45 | 3.0 |

See legend to Table 12a for details. NT = not tested. B1 = TSHR blocking patient serum 1 (K1 lymphocyte donor serum). B2 = TSHR blocking patient serum 2. B3 = TSHR blocking patient serum 3. B4 = TSHR blocking patient serum 4. B5 = TSHR blocking patient serum 5. Serum dilutions were made in HBD or assay buffer.
[a] the inhibition of $^{125}$I-TSH binding was carried out using the PEG precipitation assay (Southgate K, Creagh F, Teece M, Kingwood C, Rees Smith B. A receptor assay for the measurement of TSH receptor antibodies in unextracted serum. Clin Endocrinol 1984; 20: 539-548).

TABLE 12g

Binding of patient sera in the TSHR260-AP ELISA

| Test sample | Mean absorbance @ 405 nm | TRAb concentration read off M22 IgG calibration curve (µg/mL) | TRAb concentration in TSHR260-AP ELISA (U/L) | TRAb concentration in TSHR coated tube assay (U/L) |
|---|---|---|---|---|
| Serum 1 | 0.06 | 0.007 | 0.7 | 1.0 |
| Serum 2 | 0.072 | 0.008 | 0.9 | 1.0 |
| Serum 3 | 0.067 | 0.008 | 0.8 | 1.1 |
| Serum 4 | −0.004 | 0.000 | 0 | 1.1 |
| Serum 5 | 0.38 | 0.052 | 5.2 | 1.2 |
| Serum 6 | 0.099 | 0.012 | 1.2 | 1.2 |
| Serum 7 | 0.051 | 0.006 | 0.6 | 1.2 |
| Serum 8 | 0.113 | 0.014 | 1.3 | 1.4 |
| Serum 9 | 0.07 | 0.008 | 0.8 | 1.4 |
| Serum 10 | 0.157 | 0.019 | 1.9 | 1.5 |
| Serum 11 | 0.191 | 0.025 | 2.5 | 2.0 |
| Serum 12 | 0.157 | 0.019 | 1.9 | 2.1 |
| Serum 13 | 0.23 | 0.029 | 2.9 | 2.2 |
| Serum 14 | 0.047 | 0.006 | 0.7 | 2.7 |
| Serum 15 | 0.198 | 0.026 | 2.6 | 2.7 |
| Serum 16 | 0.238 | 0.032 | 3.2 | 3.0 |
| Serum 17 | 0.296 | 0.041 | 4.1 | 3.0 |
| Serum 18 | 0.322 | 0.042 | 4.3 | 3.6 |
| Serum 19 | 0.326 | 0.043 | 4.3 | 3.7 |
| Serum 20 | 0.088 | 0.011 | 1.1 | 4.7 |
| Serum 21 | 0.005 | <0.005 | <0.6 | 5.1 |
| Serum 22 | 0.383 | 0.056 | 5.5 | 5.1 |
| Serum 23 | 0.211 | 0.026 | 2.6 | 5.7 |
| Serum 24 | 0.461 | 0.071 | 7 | 6.4 |
| Serum 25 | 0.453 | 0.067 | 6.6 | 6.6 |
| Serum 26 | 0.295 | 0.038 | 3.8 | 6.7 |
| Serum 27 | 0.419 | 0.062 | 6.2 | 7.1 |
| Serum 28 | 0.363 | 0.050 | 5 | 8.1 |
| Serum 29 | 0.526 | 0.086 | 8.6 | 8.5 |
| Serum 30 | 0.611 | 0.112 | 11.3 | 11.8 |
| Serum 31 | 0.49 | 0.077 | 7.7 | 14.3 |
| Serum 32 | 0.621 | 0.116 | 11.7 | 16.9 |
| Serum 33 | 0.696 | 0.150 | 15.6 | 17.8 |
| Serum 34 | 0.592 | 0.104 | 10.4 | 19.0 |
| Serum 35 | 0.832 | 0.259 | 30.4 | 21.1 |
| Serum 36 | 0.78 | 0.222 | 24.5 | 21.2 |
| Serum 37 | 0.782 | 0.224 | 24.6 | 21.5 |
| Serum 38 | 0.754 | 0.196 | 21.1 | 21.7 |
| Serum 39 | 1.008 | 1.375 | >61 | 26.2 |
| Serum 40 | −0.008 | 0 | 0 | 0 |
| Serum 41 | −0.005 | 0 | 0 | 0 |
| Serum 42 | −0.006 | 0 | 0 | 0 |
| Serum 43 | −0.004 | 0 | 0 | 0 |
| Serum 44 | −0.007 | 0 | 0 | 0 |
| Serum 45 | −0.007 | 0 | 0 | 0 |
| Serum 46 | −0.002 | <0.005 | <0.6 | 0 |
| Serum 47 | −0.001 | 0 | 0 | 0 |
| Serum 48 | 0.0095 | <0.005 | <0.6 | 0 |
| Serum 49 | −0.002 | 0 | 0 | 0 |
| Serum 50 | 0.003 | 0 | 0 | 0 |
| Serum 51 | 0.005 | <0.005 | <0.6 | 0 |
| Serum 52 | 0.008 | <0.005 | <0.6 | 0 |
| Serum 53 | −0.003 | 0 | 0 | 0 |
| Serum 54 | −0.005 | 0 | 0 | 0 |
| Serum 55 | −0.006 | 0 | 0 | <1 |
| Serum 56 | 0.0065 | <0.005 | <0.6 | 0 |
| Serum 57 | −0.004 | 0 | 0 | 0 |
| Serum 58 | 0.001 | 0 | 0.0 | <1 |
| Serum 59 | 0.041 | 0.005 | 0.6 | 0 |

See legend to Table 12a for details. Sera 1-39 are from patients diagnosed with or suspected of having Graves' disease. Sera 1-39 were positive for TRAb in the coated tube assay (based on inhibition of $^{125}$I-binding to full length TSHR coated on the tubes). Sera 40-59 were from healthy blood donors and were negative for TRAb in the coated tube assay.

TABLE 12h

Measurement of serum TRAb by inhibition of M22-peroxidase binding to the TSHR260 in an ELISA

| Test sample | TRAb ELISA (full length TSHR coated on plates) | | | TRAb ELISA (TSHR260 coated on plates) | | |
|---|---|---|---|---|---|---|
| | Mean absorbance at 450 nm | % inhibition of TSH-biotin binding | TRAb concentr. (U/L) | Mean absorbance at 450 nm | % inhibition of M22 Fab-peroxidase binding | TRAb concentr. (U/L) |
| Serum 60 | 0.224 | 90 | 30.7 | 0.196 | 92 | >40 |
| Serum 61 | 0.514 | 77 | 15.2 | 0.569 | 77 | 14.7 |
| Serum 62 | 0.605 | 73 | 12.4 | 0.470 | 81 | 24.7 |
| Serum 63 | 1.555 | 30 | 2.1 | 1.109 | 55 | 3.7 |
| Serum 64 | 1.639 | 26 | 1.7 | 1.208 | 51 | 3.1 |
| Serum 65 | 1.488 | 33 | 2.4 | 1.341 | 45 | 2.4 |
| Serum 66 | 1.267 | 43 | 3.6 | 0.706 | 71 | 8.5 |
| Serum 67 | 1.066 | 52 | 5.1 | 0.908 | 63 | 5.3 |
| Serum 68 | 1.341 | 40 | 3.1 | 0.704 | 71 | 8.6 |
| Serum 69 | 1.414 | 37 | 2.7 | 0.764 | 69 | 7.3 |
| Serum 70 | 0.704 | 68 | 10.0 | 0.797 | 67 | 6.7 |
| Serum 71 | 1.691 | 24 | 1.5 | 0.797 | 67 | 6.7 |
| Serum 72 | 2.404 | −8 | 0 | 2.791 | −14 | 0 |
| Serum 73 | 2.203 | 1 | 0.1 | 2.509 | −3 | 0 |
| Serum 74 | 2.228 | 0 | 0.1 | 2.737 | −12 | 0 |
| Serum 75 | 2.274 | −2 | 0 | 2.758 | −13 | 0 |
| Serum 76 | 2.178 | 2 | 0.2 | 2.215 | 10 | 0.3 |
| Serum 77 | 2.292 | −3 | 0 | 2.152 | 12 | 0.3 |
| Serum 78 | 2.425 | −9 | 0 | 2.676 | −9 | 0 |
| Serum 79 | 2.397 | −8 | 0 | 3.363 | −37 | 0 |
| Serum 80 | 2.410 | −8 | 0 | 2.905 | −19 | 0 |
| Serum 81 | 2.148 | 4 | 0.2 | 2.523 | −3 | 0 |

Sera 60-71 are from patients diagnosed with or suspected of Graves' disease. Sera 60-71 were positive for TRAb in the coated tube assay (based on inhibition of $^{125}$I-TSH binding to full length TSHR coated on the tubes). Sera 72-81 were from healthy blood donors that were negative for TRAb in the coated tube assay.

TABLE 12i

Ability of TSHR MAbs to bind to full length wild type TSHR and TSHR Arg255 Asp coated on ELISA plate wells. TSHR260-AP used to detect MAb binding

| Test sample | Wild type TSHR Mean absorbance at 405 nm | Arg255 Asp TSHR Mean absorbance at 405 nm |
|---|---|---|
| HBD | 0.003 | 0.005 |
| K1-70 IgG | | |
| 10 µg/mL | 1.324 | 1.357 |
| 1 µg/mL | 1.164 | 1.141 |
| 0.5 µg/mL | 1.083 | 0.998 |
| 0.1 µg/mL | 0.639 | 0.322 |
| 0.05 µg/mL | 0.388 | 0.146 |
| 0.01 µg/mL | 0.094 | 0.021 |
| 0.005 µg/mL | 0.059 | 0.008 |
| M22 IgG | | |
| 10 µg/mL | 1.360 | 0.551 |
| 1 µg/mL | 1.172 | 0.340 |
| 0.5 µg/mL | 1.093 | 0.262 |
| 0.1 µg/mL | 0.599 | 0.050 |
| 0.05 µg/mL | 0.332 | 0.017 |
| 0.01 µg/mL | 0.064 | −0.002 |
| 0.005 µg/mL | 0.032 | −0.007 |
| K1-18 IgG | | |
| 10 µg/mL | 1.187 | 1.111 |
| 1 µg/mL | 0.986 | 0.888 |
| 0.5 µg/mL | 0.876 | 0.710 |
| 0.1 µg/mL | 0.452 | 0.176 |
| 0.05 µg/mL | 0.301 | 0.099 |
| 0.01 µg/mL | 0.072 | 0.014 |
| 0.005 µg/mL | 0.038 | 0.002 |
| 9D33 IgG | | |
| 10 µg/mL | 0.481 | 0.534 |
| 1 µg/mL | 0.329 | 0.322 |
| 0.5 µg/mL | 0.273 | 0.242 |
| 0.1 µg/mL | 0.102 | 0.053 |
| 0.05 µg/mL | 0.056 | 0.020 |
| 0.01 µg/mL | 0.011 | −0.004 |
| 0.005 µg/mL | 0.006 | 0.001 |

See legend to Table 12a for details. Serum dilutions were made in HBD.

TABLE 12j

Ability of patient sera to bind to full length wild type TSHR and TSHR Arg255 Asp coated on ELISA plate wells. TSHR260-AP used to detect binding

| Test sample | Wild type TSHR | | Arg255 Asp TSHR | | TRAb level in TSHR coated tube assay U/L |
|---|---|---|---|---|---|
| | Mean absorbance at 405 nm | µg/mL (read off K1-70 IgG calibration) | Mean absorbance at 405 nm | µg/mL (read off K1-70 IgG calibration) | |
| Patient sera | | | | | |
| Serum 1 | 0.707 | 0.121 | 0.558 | 0.176 | 14.7 |
| Serum 2 | 0.798 | 0.159 | 0.677 | 0.227 | 17.1 |
| Serum 3 | 0.647 | 0.102 | 0.237 | 0.076 | 8.1 |
| Serum 4 | 0.692 | 0.116 | 0.585 | 0.187 | 12.3 |

TABLE 12j-continued

Ability of patient sera to bind to full length wild type TSHR and TSHR Arg255 Asp coated on ELISA plate wells. TSHR260-AP used to detect binding

| Test sample | Wild type TSHR Mean absorbance at 405 nm | Wild type TSHR µg/mL (read off K1-70 IgG calibration) | Arg255 Asp TSHR Mean absorbance at 405 nm | Arg255 Asp TSHR µg/mL (read off K1-70 IgG calibration) | TRAb level in TSHR coated tube assay U/L |
|---|---|---|---|---|---|
| Serum 5 | 0.560 | 0.081 | 0.169 | 0.057 | 9.9 |
| Serum 6 | 0.278 | 0.034 | 0.096 | 0.036 | 5.9 |
| Serum 7 | 0.388 | 0.050 | 0.167 | 0.056 | 5.6 |
| Serum 8 | 0.367 | 0.047 | 0.112 | 0.040 | 8.3 |
| Serum 9 | 0.198 | 0.023 | 0.074 | 0.029 | 11.3 |
| Serum 10 | 0.788 | 0.154 | 0.447 | 0.137 | 17 |
| HBD | 0.003 | 0 | 0.005 | 0 | 0 |

See legend to Table 12a for details. Serum 1-10 are from patients with detectable TRAb levels in the coated tube assay. A calibration curve using K1-70 IgG (0.005, 0.01, 0.05, 0.1, 0.5, 1.0 and 10 µg/mL) was run in each assay.

TABLE 12k

Ability of patient sera with TSHR blocking activity to bind to full length wild type TSHR and TSHR Arg255 Asp coated on ELISA plate wells. TSHR260-AP used to detect binding

| Test sample | Wild type TSHR Mean absorbance at 405 nm | Wild type TSHR µg/mL IgG[a] read off M22 IgG calibration | Arg255 Asp TSHR Mean absorbance at 405 nm | Arg255 Asp TSHR µg/mL IgG[b] read off K1-70 IgG calibration |
|---|---|---|---|---|
| Serum 1 | | | | |
| undiluted | 0.859 | 0.30 | 0.879 | 0.47 |
| 1:10 | 0.484 | 0.09 | 0.202 | 0.08 |
| 1:20 | 0.284 | 0.05 | NT | NT |
| 1:40 | 0.154 | 0.02 | NT | NT |
| 1:50 | NT | NT | 0.027 | 0.02 |
| 1:80 | 0.078 | 0.01 | NT | NT |
| 1:100 | NT | NT | 0.015 | 0.02 |
| 1:160 | 0.037 | 0.01 | NT | NT |
| 1:320 | 0.021 | 0.00 | NT | NT |
| Serum 2 | | | | |
| undiluted | 0.323 | 0.05 | 0.274 | 0.11 |
| 1:10 | 0.097 | 0.02 | 0.021 | 0.02 |
| 1:20 | 0.052 | 0.01 | NT | NT |
| 1:40 | 0.029 | 0.00 | NT | NT |
| 1:50 | NT | NT | 0.005 | 0.00 |
| 1:80 | 0.015 | 0.00 | NT | NT |
| 1:100 | NT | NT | 0.009 | 0.00 |
| 1:160 | 0.008 | 0.00 | NT | NT |
| 1:320 | 0.007 | 0.00 | NT | NT |
| Serum 3 | | | | |
| 1:10 | 0.896 | 0.46 | 0.510 | 0.19 |
| 1:20 | 0.588 | 0.13 | NT | NT |
| 1:40 | 0.320 | 0.06 | NT | NT |
| 1:50 | NT | NT | 0.056 | 0.04 |
| 1:80 | 0.168 | 0.03 | NT | NT |
| 1:100 | NT | NT | 0.020 | 0.02 |
| 1:160 | 0.091 | 0.02 | NT | NT |
| 1:320 | 0.041 | 0.01 | NT | NT |
| Serum 4 | | | | |
| 1:10 | 0.729 | 0.21 | 0.639 | 0.25 |
| 1:20 | 0.612 | 0.14 | NT | NT |
| 1:40 | 0.453 | 0.08 | NT | NT |
| 1:50 | NT | NT | 0.107 | 0.05 |
| 1:80 | 0.270 | 0.05 | NT | NT |
| 1:100 | NT | NT | 0.040 | 0.03 |
| 1:160 | 0.141 | 0.02 | NT | NT |
| 1:320 | 0.068 | 0.01 | NT | NT |
| Serum 5 | | | | |
| 1:10 | 0.772 | 0.21 | 0.536 | 0.2 |
| 1:20 | 0.652 | 0.14 | NT | NT |
| 1:40 | 0.470 | 0.08 | NT | NT |
| 1:50 | NT | NT | 0.114 | 0.06 |
| 1:80 | 0.291 | 0.05 | NT | NT |
| 1:100 | NT | NT | 0.035 | 0.03 |
| 1:160 | 0.155 | 0.03 | NT | NT |
| 1:320 | 0.077 | 0.01 | NT | NT |

See legend to Table 12a for details. NT = not tested. Serum 1 = K1 lymphocyte donor serum. Serum 2 = patient serum with TSHR blocking autoantibodies. Serum 3 = patient serum with TSHR blocking autoantibodies. Serum 4 = patient serum with TSHR blocking autoantibodies. Serum 5 = patient serum with TSHR blocking autoantibodies. Serum dilutions were made in HBD.
[a] A calibration curve using M22 IgG (0.005, 0.01, 0.05, 0.1, 0.5, 1.0 and 10 µg/mL) was run in each assay.
[b] A calibration curve using K1-70 IgG (0.005, 0.01, 0.05, 0.1, 0.5, 1.0 and 10 µg/mL) was run in each assay.

TABLE 12l

Ability of patient sera with TSHR stimulating activity to bind to full length wild type TSHR and TSHR Arg255 Asp coated on ELISA plate wells. TSHR260-AP used to detect binding

| Test sample | Wild type TSHR Mean absorbance at 405 nm | Wild type TSHR µg/mL IgG[a] read off M22 IgG calibration | Arg255 Asp TSHR Mean absorbance at 405 nm | Arg255 Asp TSHR µg/mL IgG[b] read off K1-70 IgG calibration |
|---|---|---|---|---|
| HBD | 0.003 | 0 | −0.01 | 0 |
| S1 | | | | |
| diluted 1:5 | 0.924 | 0.31 | 0.66 | 0.26 |
| diluted 1:10 | 0.788 | 0.18 | 0.40 | 0.15 |
| diluted 1:20 | 0.583 | 0.10 | 0.19 | 0.08 |
| diluted 1:40 | 0.378 | 0.05 | 0.09 | 0.04 |
| S2 | | | | |
| diluted 1:5 | 0.740 | 0.17 | 0.50 | 0.19 |
| diluted 1:10 | 0.595 | 0.10 | 0.26 | 0.10 |
| diluted 1:20 | 0.407 | 0.06 | 0.12 | 0.05 |
| diluted 1:40 | 0.235 | 0.03 | 0.05 | 0.03 |
| S3 | | | | |
| diluted 1:5 | 0.868 | 0.25 | 0.75 | 0.32 |
| diluted 1:10 | 0.651 | 0.12 | 0.74 | 0.16 |
| diluted 1:20 | 0.453 | 0.06 | 0.21 | 0.09 |
| diluted 1:40 | 0.290 | 0.04 | 0.10 | 0.04 |
| S4 | | | | |
| diluted 1:5 | 0.646 | 0.11 | 0.19 | 0.08 |
| diluted 1:10 | 0.362 | 0.05 | 0.07 | 0.04 |
| diluted 1:20 | 0.171 | 0.02 | 0.02 | 0.02 |
| diluted 1:40 | 0.080 | 0.01 | 0.00 | 0.01 |
| S5 | | | | |
| diluted 1:5 | 0.407 | 0.06 | 0.13 | 0.06 |
| diluted 1:10 | 0.221 | 0.03 | 0.04 | 0.02 |

TABLE 12l-continued

Ability of patient sera with TSHR stimulating activity to bind to full length wild type TSHR and TSHR Arg255 Asp coated on ELISA plate wells. TSHR260-AP used to detect binding

| | TSHR260-AP ELISA | | | |
|---|---|---|---|---|
| | Wild type TSHR | | Arg255 Asp TSHR | |
| Test sample | Mean absorbance at 405 nm | μg/mL IgG[a] read off M22 IgG calibration | Mean absorbance at 405 nm | μg/mL IgG[b] read off K1-70 IgG calibration |
| diluted 1:20 | 0.109 | 0.01 | 0.01 | 0.01 |
| diluted 1:40 | 0.059 | 0.01 | 0.01 | 0.01 |
| S6 | | | | |
| diluted 1:5 | 0.531 | 0.08 | 0.34 | 0.13 |
| diluted 1:10 | 0.363 | 0.05 | 0.16 | 0.07 |
| diluted 1:20 | 0.213 | 0.03 | 0.06 | 0.03 |
| diluted 1:40 | 0.124 | 0.02 | 0.03 | 0.02 |

See legend to Table 12a for details. Serum dilutions were made in HBD. Sera S1-S6 are the same sera shown in Table 12e.
[a]A calibration curve using M22 IgG (0.005, 0.01, 0.05, 0.1, 0.5, 1.0 and 10 μg/mL) was run in each assay.
[b]A calibration curve using K1-70 IgG (0.005, 0.01, 0.05, 0.1, 0.5, 1.0 and 10 μg/mL) was run in each assay.

TABLE 13a

Summary of stimulating MAb K1-18 (IgG1 kappa) properties

| TSHR binding affinity | IgG | $0.7 \times 10^{10}$ L/mol | |
|---|---|---|---|
| | Fab | $0.13 \times 10^{10}$ L/mol | |
| Inhibition of $^{125}$I-TSH binding to the TSHR | IgG (1 μg/mL) | 94% 181 units/mg (NIBSC 90/672) | Table 1a Table 2b |
| | Fab (1 μg/mL) | 77% 86 units/mg (NIBSC 90/672) | Table 2a Table 2b |
| Inhibition of TSH-biotin binding to the TSHR | IgG (1 μg/mL) | 96% | Table 3a |
| | Fab (1 μg/mL) | 93% | Table 3b |
| Inhibition of M22 Fab peroxidase binding to the TSHR | IgG (1 μg/mL) | 95% | Table 4a |
| | Fab (1 μg/mL) | 88% | Table 4b |
| Stimulation of cyclic AMP in CHO cells expressing TSHR | IgG (100 μg/mL) | 40x basal 155 units/mg (NIBSC 90/672) | Table 6a Table 6c |
| | Fab (100 μg/mL) | 35x basal 22 units/mg (NIBSC 90/672) | Table 6a Table 6c |
| Binding to TSHR 260-AP | IgG (1 μg/mL) | OD405 = 0.828 | Table 12a |
| V regions | Heavy chain (IgG1) | VH5-51*01 D3-16*02 (D3-16*01) J3*02 | FIG. 3A and FIG. 3C |
| | Light chain (kappa) | V3-20*01 JK-1*01 | FIG. 4A and FIG. 4C |

TABLE 13b

Summary of blocking MAb K1-70 (IgG1 lambda) properties

| TSHR binding affinity | IgG | $3.9 \pm 0.8 \times 10^{10}$ L/mol | |
|---|---|---|---|
| Inhibition of $^{125}$I-TSH binding to the TSHR | IgG (1 μg/mL) | 92% 166 units/mg (NIBSC 90/672) | Table 1b |
| | Fab (1 μg/mL) | 92% | Table 1b |
| Inhibition of TSH-biotin binding to the TSHR | IgG (1 μg/mL) | 97% | Table 3d |
| | Fab (1 μg/mL) | 97% | Table 3d |
| Inhibition of M22 Fab peroxidase binding to the TSHR | IgG (1 μg/mL) | 96% | Table 4c |
| | Fab (1 μg/mL) | 96% | Table 4c |
| Blocking TSH mediated cyclic AMP stimulation in CHO cells expressing TSHR | IgG (1 μg/mL) | 94% | Table 7b |
| | Fab (1 μg/mL) | 94% | Table 7b |
| Binding to TSHR 260-AP | IgG (1 μg/mL) | OD405 = 1.016 | Table 12a |
| V regions | Heavy chain (IgG1) | VH5-51*01 D1-7*01 J4*02 | FIG. 5A and FIG. 5C |
| | Light chain (lambda) | LV1-51*01 LJ7*01 | FIG. 6C |

TABLE 14a

Cyclic AMP production in CHO cells expressing wild type TSHR and TSHR with Asp43 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild type (%) |
|---|---|---|---|
| | Wild type TSHR | Mutated TSHR | |
| Cyclic AMP assay buffer | 2.52 ± 0.23 | 2.60 ± 0.33 | 103 |
| K1-18 | | | |
| 0.3 ng/mL | 3.84 ± 0.42 | 3.35 ± 0.20 | 87 |
| 1 ng/mL | 7.35 ± 0.07 | 5.53 ± 0.15 | 75 |
| 3 ng/mL | 17.04 ± 0.62 | 11.59 ± 0.42 | 68 |
| 10 ng/mL | 37.74 ± 0.67 | 26.69 ± 1.57 | 71 |
| 30 ng/mL | 51.46 ± 2.52 | 40.80 ± 0.74 | 79 |
| 100 ng/mL | 57.08 ± 4.79 | 48.50 ± 4.25 | 85 |
| TSH | | | |
| 0.01 ng/mL | 2.85 ± 0.08 | 2.84 ± 0.14 | 100 |
| 0.03 ng/mL | 3.81 ± 0.06 | 4.30 ± 0.10 | 113 |
| 0.1 ng/mL | 8.70 ± 0.49 | 10.35 ± 2.47 | 119 |
| 0.3 ng/mL | 22.78 ± 1.49 | 19.69 ± 1.60 | 86 |
| 1 ng/mL | 46.09 ± 0.00 | 39.56 ± 0.31 | 86 |
| 3 ng/mL | 54.16 ± 3.56 | 47.87 ± 0.09 | 88 |

Results shown are mean ± SD of triplicate determinations. Test samples diluted in hypotonic cyclic AMP assay buffer.

TABLE 14b

Cyclic AMP production in CHO cells expressing wild type TSHR and TSHR with Ile60 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild type (%) |
|---|---|---|---|
| | Wild type TSHR | Mutated TSHR | |
| Cyclic AMP assay buffer | 1.00 ± 0.09 | 5.02 ± 1.03 | 502 |
| K1-18 | | | |
| 0.3 ng/mL | 2.58 ± 0.33 | 7.76 ± 0.36 | 301 |
| 1 ng/mL | 5.33 ± 0.59 | 10.94 ± 0.61 | 205 |
| 3 ng/mL | 12.64 ± 2.43 | 23.29 ± 1.42 | 184 |

TABLE 14b-continued

Cyclic AMP production in CHO cells expressing wild type TSHR and TSHR with Ile60 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild |
|---|---|---|---|
| | Wild type TSHR | Mutated TSHR | type (%) |
| 10 ng/mL | 51.08 ± 11.46 | 44.53 ± 4.03 | 87 |
| 30 ng/mL | 69.95 ± 3.59 | 57.58 ± 2.07 | 82 |
| 100 ng/mL TSH | 87.39 ± 6.54 | 67.02 ± 4.87 | 77 |
| 0.01 ng/mL | 1.51 ± 0.49 | 5.40 ± 0.84 | 358 |
| 0.03 ng/mL | 3.34 ± 1.14 | 5.93 ± 0.56 | 178 |
| 0.1 ng/mL | 5.58 ± 2.31 | 11.24 ± 1.18 | 201 |
| 0.3 ng/mL | 29.97 ± 6.61 | 28.85 ± 1.39 | 96 |
| 1 ng/mL | 64.61 ± 4.81 | 49.65 ± 5.10 | 77 |
| 3 ng/mL | 73.22 ± 4.70 | 60.45 ± 7.70 | 83 |

See legend to Table 14a for details.

TABLE 14c

Cyclic AMP production in CHO cells expressing wild type TSHR and TSHR with Glu61 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 1.47 ± 0.15 | 5.22 ± 0.71 | 355 |
| 0.3 ng/mL | 1.79 ± 0.19 | 6.02 ± 0.33 | 336 |
| 1 ng/mL | 3.68 ± 0.26 | 8.45 ± 0.76 | 230 |
| 3 ng/mL | 9.15 ± 0.43 | 15.04 ± 1.69 | 164 |
| 10 ng/mL | 32.03 ± 0.84 | 34.30 ± 1.21 | 107 |
| 30 ng/mL | 63.25 ± 0.99 | 55.51 ± 6.57 | 88 |
| 100 ng/mL TSH | 73.14 ± 1.81 | 81.13 ± 7.20 | 111 |
| 0.01 ng/mL | 1.09 ± 0.28 | 5.12 ± 0.48 | 470 |
| 0.03 ng/mL | 1.75 ± 0.06 | 6.46 ± 0.67 | 369 |
| 0.1 ng/mL | 2.91 ± 0.16 | 7.88 ± 0.56 | 271 |
| 0.3 ng/mL | 7.29 ± 0.10 | 13.74 ± 0.45 | 188 |
| 1 ng/mL | 26.58 ± 1.60 | 34.30 ± 1.21 | 129 |
| 3 ng/mL | 57.99 ± 3.45 | 63.63 ± 5.01 | 110 |

See legend to Table 14a for details.

TABLE 14d

Cyclic AMP production in CHO cells expressing wild type TSHR and TSHR with Thr104 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Experiment 1 | | | |
| Cyclic AMP assay buffer K1-18 | 1.34 ± 0.29 | 3.56 ± 0.24 | 266 |
| 0.3 ng/mL | 2.95 ± 0.47 | 4.64 ± 0.14 | 157 |
| 1 ng/mL | 6.14 ± 0.36 | 7.38 ± 0.38 | 120 |
| 3 ng/mL | 14.80 ± 1.02 | 14.53 ± 1.12 | 98 |
| 10 ng/mL | 39.45 ± 12.99 | 21.62 ± 16.74 | 55 |

TABLE 14d-continued

Cyclic AMP production in CHO cells expressing wild type TSHR and TSHR with Thr104 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| 30 ng/mL | 68.16 ± 7.99 | 35.85 ± 26.65 | 53 |
| 100 ng/mL TSH | 83.92 ± 10.03 | 62.56 ± 6.94 | 75 |
| 0.01 ng/mL | 1.37 ± 0.21 | 2.58 ± 0.21 | 188 |
| 0.03 ng/mL | 1.58 ± 0.10 | 3.20 ± 0.60 | 203 |
| 0.1 ng/mL | 1.83 ± 0.88 | 3.64 ± 0.19 | 199 |
| 0.3 ng/mL | 3.20** | 5.38 ± 0.07 | 168 |
| 1 ng/mL | 15.90 ± 0.95 | 15.80 ± 0.41 | 99 |
| 3 ng/mL | 47.64 ± 6.10 | 34.47 ± 1.54 | 72 |
| Experiment 2 | | | |
| Cyclic AMP assay buffer K1-18 | 1.04 ± 0.26 | 3.70 ± 0.49 | 356 |
| 0.3 ng/mL | 4.94 ± 0.29 | 6.65 ± 0.23 | 135 |
| 1 ng/mL | 9.47 ± 0.98 | 10.37 ± 1.18 | 110 |
| 3 ng/mL | 26.53 ± 2.22 | 21.47 ± 3.41 | 81 |
| 10 ng/mL | 54.89 ± 1.67 | 38.87 ± 3.69 | 71 |
| 30 ng/mL | 79.51 ± 5.35 | 50.95 ± 3.65 | 64 |
| 100 ng/mL TSH | 78.3 ± 6.52 | 64.82 ± 5.61 | 83 |
| 0.01 ng/mL | 2.10 ± 0.39 | 4.28 ± 0.18 | 204 |
| 0.03 ng/mL | 4.48 ± 0.53 | 5.71 ± 0.77 | 127 |
| 0.1 ng/mL | 10.27 ± 1.87 | 9.80 ± 0.53 | 95 |
| 0.3 ng/mL | 35.72 ± 5.54 | 35.74 ± 1.21 | 100 |
| 1 ng/mL | 71.99 ± 7.40 | 57.09 ± 2.53 | 79 |
| 3 ng/mL | 79.18 ± 6.82 | 58.46 ± 0.86 | 74 |

See legend to Table 14a for details.
**single determination.

TABLE 14e

Cyclic AMP production in CHO cells expressing wild type TSHR and TSHR with His105 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 2.02 ± 0.26 | 3.51 ± 0.31 | 173 |
| 0.3 ng/mL | 2.51 ± 0.14 | 3.91 ± 0.29 | 156 |
| 1 ng/mL | 4.59 ± 0.48 | 4.99 ± 0.14 | 109 |
| 3 ng/mL | 9.26 ± 0.49 | 10.42 ± 0.32 | 113 |
| 10 ng/mL | 39.21 ± 2.49 | 27.25 ± 0.37 | 69 |
| 30 ng/mL | 69.70 ± 5.97 | 51.22 ± 4.24 | 73 |
| 100 ng/mL TSH | 99.18 ± 3.63 | 78.03 ± 4.40 | 79 |
| 0.01 ng/mL | 1.56 ± 0.28 | 4.80 ± 2.60 | 308 |
| 0.03 ng/mL | 2.42 ± 0.39 | 3.55 ± 0.20 | 147 |
| 0.1 ng/mL | 4.09 ± 0.79 | 4.82 ± 0.29 | 118 |
| 0.3 ng/mL | 11.44 ± 2.32 | 11.88 ± 2.77 | 104 |
| 1 ng/mL | 45.62 ± 1.99 | 34.56 ± 1.21 | 76 |
| 3 ng/mL | 77.89 ± 8.17 | 58.28 ± 4.66 | 75 |

See legend to Table 14a for details.

TABLE 14f

Cyclic AMP production in CHO cells expressing wild type TSHR and TSHR with Asp151 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 1.90 ± 0.61 | 5.93 ± 0.60 | 312 |
| 0.3 ng/mL | 4.01 ± 0.43 | 7.36 ± 0.35 | 184 |
| 1 ng/mL | 9.64 ± 0.27 | 11.42 ± 2.31 | 118 |
| 3 ng/mL | 20.53 ± 1.64 | 18.27 ± 0.51 | 89 |
| 10 ng/mL | 54.20 ± 1.61 | 40.81 ± 7.12 | 75 |
| 30 ng/mL | 81.74 ± 5.92 | 51.20 ± 5.41 | 63 |
| 100 ng/mL | 79.82 ± 4.86 | 66.01 ± 5.14 | 83 |
| TSH | | | |
| 0.01 ng/mL | 2.96 ± 0.26 | 6.19 ± 0.36 | 209 |
| 0.03 ng/mL | 5.36 ± 0.60 | 7.99 ± 1.12 | 149 |
| 0.1 ng/mL | 14.33 ± 1.46 | 14.12 ± 0.67 | 99 |
| 0.3 ng/mL | 43.55 ± 6.31 | 35.02 ± 4.18 | 80 |
| 1 ng/mL | 73.50 ± 9.55 | 48.53 ± 6.40 | 66 |
| 3 ng/mL | 80.67 ± 3.49 | 54.55 ± 3.53 | 68 |

See legend to Table 14a for details.

TABLE 14g

Cyclic AMP production in CHO cells expressing wild type TSHR and TSHR with Glu157 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 1.89 ± 0.08 | 9.18 ± 0.08 | 485 |
| 0.3 ng/mL | 3.77 ± 0.18 | 11.44 ± 3.63 | 303 |
| 1 ng/mL | 7.52 ± 0.26 | 9.76 ± 0.93 | 130 |
| 3 ng/mL | 19.14 ± 0.40 | 9.31 ± 0.91 | 49 |
| 10 ng/mL | 45.88 ± 1.10 | 14.37 ± 6.84 | 31 |
| 30 ng/mL | 56.81 ± 5.21 | 11.01 ± 3.30 | 19 |
| 100 ng/mL | 64.73 ± 5.17 | 9.39 ± 2.46 | 15 |
| TSH | | | |
| 0.01 ng/mL | 2.55 ± 0.32 | 11.48 ± 1.63 | 450 |
| 0.03 ng/mL | 3.56 ± 0.17 | 11.67 ± 1.56 | 328 |
| 0.1 ng/mL | 8.19 ± 0.96 | 13.43 ± 1.26 | 164 |
| 0.3 ng/mL | 21.83 ± 0.73 | 25.78 ± 4.64 | 118 |
| 1 ng/mL | 46.44 ± 3.10 | 40.14 ± 1.60 | 86 |
| 3 ng/mL | 52.73 ± 2.18 | 60.81 ± 5.71 | 115 |

See legend to Table 14a for details.

TABLE 14h

Cyclic AMP production in CHO cells expressing wild type TSHR and TSHR with Glu178 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 1.39 ± 0.21 | 9.71 ± 0.36 | 699 |
| 0.3 ng/mL | 3.10 ± 0.45 | 10.89 ± 0.67 | 351 |
| 1 ng/mL | 7.67 ± 0.57 | 13.37 ± 0.56 | 174 |
| 3 ng/mL | 19.48 ± 2.03 | 20.66* | 106 |
| 10 ng/mL | 56.35 ± 2.84 | 40.02* | 71 |
| 30 ng/mL | 72.19 ± 2.66 | 46.23 ± 1.87 | 64 |
| 100 ng/mL | 77.30 ± 4.83 | 61.85 ± 3.91 | 80 |
| TSH | | | |
| 0.01 ng/mL | 1.99 ± 0.11 | 9.29 ± 1.00 | 467 |
| 0.03 ng/mL | 4.84 ± 0.30 | 11.60 ± 0.21 | 240 |
| 0.1 ng/mL | 12.93 ± 0.64 | 14.83 ± 2.25 | 115 |
| 0.3 ng/mL | 47.70 ± 4.82 | 33.72 ± 3.43 | 71 |
| 1 ng/mL | 79.36 ± 7.46 | 43.12 ± 1.05 | 54 |
| 3 ng/mL | 74.89 ± 8.91 | 54.84 ± 4.58 | 73 |

See legend to Table 14a for details.
*mean of duplicate.

TABLE 14i

Cyclic AMP production in CHO cells expressing wild type TSHR and TSHR with Lys183 mutated to Asp. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer K1-18 | 2.23 ± 0.06 | 2.51 ± 0.63 | 113 |
| 0.3 ng/mL | 4.15 ± 0.47 | 2.40 ± 0.34 | 58 |
| 1 ng/mL | 8.37 ± 2.15 | 2.20 ± 0.54 | 26 |
| 3 ng/mL | 18.71 ± 2.79 | 3.05 ± 0.46 | 16 |
| 10 ng/mL | 54.30 ± 2.14 | 2.35 ± 0.77 | 4 |
| 30 ng/mL | 89.01 ± 13.58 | 2.24 ± 0.79 | 3 |
| 100 ng/mL | 109.78 ± 16.33 | 2.30 ± 0.72 | 2 |
| TSH | | | |
| 0.01 ng/mL | 2.48 ± 0.32 | 4.08 ± 1.06 | 165 |
| 0.03 ng/mL | 4.62 ± 0.25 | 7.18 ± 0.78 | 155 |
| 0.1 ng/mL | 17.59 ± 8.60 | 19.10 ± 3.55 | 109 |
| 0.3 ng/mL | 40.35 ± 5.38 | 51.68 ± 4.48 | 128 |
| 1 ng/mL | 92.49 ± 2.61 | 93.34 ± 4.90 | 101 |
| 3 ng/mL | 103.97 ± 13.32 | 106.27 ± 8.71 | 102 |

See legend to Table 14a for details.

TABLE 14j

Cyclic AMP production in CHO cells expressing wild type TSHR and TSHR with Tyr185 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Experiment 1 | | | |
| Cyclic AMP assay buffer | 2.04 ± 0.15 | 3.02 ± 0.58 | 148 |
| K1-18 (ng/mL) | | | |
| 0.3 ng/mL | 3.69 ± 0.22 | 2.68 ± 0.19 | 73 |
| 1 ng/mL | 7.76 ± 1.36 | 2.95 ± 0.51 | 38 |
| 3 ng/mL | 22.97 ± 1.30 | 2.31 ± 0.50 | 10 |
| 10 ng/mL | 55.05 ± 5.19 | 3.21 ± 0.80 | 6 |
| 30 ng/mL | 97.56 ± 6.65 | 4.58 ± 0.63 | 5 |
| 100 ng/mL | 120.10 ± 15.75 | 5.57 ± 1.20 | 5 |
| TSH (ng/mL) | | | |
| 0.01 ng/mL | 2.60 ± 0.30 | 3.33 ± 0.81 | 128 |
| 0.03 ng/mL | 4.27 ± 0.38 | 3.85 ± 0.37 | 90 |
| 0.1 ng/mL | 10.94 ± 1.68 | 8.36 ± 0.98 | 76 |
| 0.3 ng/mL | 32.33 ± 2.26 | 21.15 ± 3.60 | 65 |
| 1 ng/mL | 84.95 ± 2.47 | 37.84 ± 1.45 | 45 |
| 3 ng/mL | 124.05 ± 7.70 | 42.9 ± 5.23 | 35 |
| Experiment 2 | | | |
| Cyclic AMP assay buffer | 2.15 ± 0.04 | 4.23 ± 0.89 | 197 |
| K1-18 (ng/mL) | | | |
| 0.3 ng/mL | 7.38 ± 0.53 | 4.33 ± 0.20 | 59 |
| 1 ng/mL | 7.51 ± 1.67 | 4.39 ± 0.45 | 58 |
| 3 ng/mL | 28.12 ± 0.86 | 4.10 ± 0.68 | 15 |
| 10 ng/mL | 50.76 ± 7.00 | 4.38 ± 1.82 | 9 |
| 30 ng/mL | 89.92 ± 4.11 | 3.90 ± 1.06 | 4 |
| 100 ng/mL | 105.22 ± 5.18 | 7.08 ± 0.31 | 7 |
| TSH (ng/mL) | | | |
| 0.01 ng/mL | 3.89 ± 0.51 | 3.82 ± 0.64 | 98 |
| 0.03 ng/mL | 5.52 ± 0.31 | 5.60 ± 1.20 | 101 |
| 0.1 ng/mL | 13.28 ± 0.63 | 12.32 ± 0.57 | 93 |
| 0.3 ng/mL | 35.35 ± 2.72 | 30.54 ± 3.00 | 86 |
| 1 ng/mL | 82.08 ± 4.80 | 50.65 ± 1.32 | 62 |
| 3 ng/mL | 91.67 ± 10.28 | 56.30 ± 6.87 | 61 |

See legend to Table 14a for details.

TABLE 14k

Cyclic AMP production in CHO cells expressing wild type TSHR and TSHR with Tyr206 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Experiment 1 | | | |
| Cyclic AMP assay buffer | 1.50 ± 0.27 | 2.47 ± 0.13 | 165 |
| K1-18 | | | |
| 0.3 ng/mL | 1.19 ± 1.22 | 2.68 ± 0.23 | 225 |
| 1 ng/mL | 6.57 ± 0.16 | 3.11 ± 0.24 | 47 |
| 3 ng/mL | 16.50 ± 1.42 | 1.75 ± 0.81 | 11 |
| 10 ng/mL | 31.40 ± 14.65 | 8.14 ± 2.38 | 26 |
| 30 ng/mL | 62.92 ± 1.83 | 15.07 ± 1.02 | 24 |
| 100 ng/mL | 61.48 ± 14.14 | 20.32 ± 12.27 | 33 |
| TSH | | | |
| 0.01 ng/mL | 2.09 ± 0.51 | 1.74 ± 1.50 | 83 |
| 0.03 ng/mL | 2.93 ± 0.48 | 3.64 ± 0.84 | 124 |
| 0.1 ng/mL | 9.04 ± 0.73 | 8.40 ± 0.72 | 93 |
| 0.3 ng/mL | 19.08 ± 12.79 | 19.83 ± 6.50 | 104 |
| 1 ng/mL | 59.48 ± 1.26 | 38.98 ± 1.84 | 66 |
| 3 ng/mL | 75.64 ± 2.36 | 46.68 ± 2.01 | 62 |
| Experiment 2 | | | |
| Cyclic AMP assay buffer | 1.96 ± 0.19 | 4.35 ± 0.24 | 222 |
| K1-18 | | | |
| 0.3 ng/mL | 5.09 ± 1.70 | 4.50 ± 0.37 | 88 |
| 1 ng/mL | 7.69 ± 1.28 | 6.23 ± 0.55 | 81 |
| 3 ng/mL | 18.47 ± 1.00 | 8.07 ± 0.28 | 44 |
| 10 ng/mL | 55.94 ± 8.77 | 22.41 ± 2.17 | 40 |
| 30 ng/mL | 69.92 ± 4.84 | 33.57 ± 1.65 | 48 |
| 100 ng/mL | 85.46 ± 15.91 | 45.40 ± 3.53 | 53 |
| TSH | | | |
| 0.01 ng/mL | 3.63 ± 1.30 | 4.90 ± 1.14 | 135 |
| 0.03 ng/mL | 4.60 ± 0.31 | 6.64 ± 0.51 | 144 |
| 0.1 ng/mL | 10.82 ± 0.50 | 19.25 ± 5.14 | 178 |
| 0.3 ng/mL | 34.70 ± 5.34 | 38.33 ± 1.28 | 110 |
| 1 ng/mL | 65.17 ± 6.68 | 60.87 ± 6.66 | 93 |
| 3 ng/mL | 75.13 ± 8.64 | 73.06 ± 3.01 | 97 |

See legend to Table 14a for details.

TABLE 14l

Cyclic AMP production in CHO cells expressing wild type TSHR and TSHR with Lys209 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer | 1.97 ± 0.24 | 4.79 ± 0.77 | 243 |
| K1-18 | | | |
| 0.3 ng/mL | 4.08 ± 0.19 | 5.52 ± 0.33 | 135 |
| 1 ng/mL | 9.47 ± 0.42 | 8.07 ± 0.57 | 85 |
| 3 ng/mL | 21.43 ± 1.03 | 12.65 ± 1.18 | 59 |
| 10 ng/mL | 62.15 ± 8.08 | 32.55 ± 4.45 | 52 |
| 30 ng/mL | 91.57 ± 5.64 | 43.71 ± 9.76 | 48 |
| 100 ng/mL | 99.88 ± 10.13 | 69.49 ± 7.10 | 70 |
| TSH | | | |
| 0.01 ng/mL | 3.02 ± 0.62 | 5.16 ± 0.11 | 171 |
| 0.03 ng/mL | 4.59 ± 0.54 | 5.87 ± 0.17 | 128 |
| 0.1 ng/mL | 14.25 ± 1.09 | 9.27 ± 0.81 | 65 |
| 0.3 ng/mL | 38.20 ± 6.84 | 24.27 ± 1.60 | 64 |
| 1 ng/mL | 87.25 ± 1.51 | 39.31 ± 5.78 | 45 |
| 3 ng/mL | 101.72 ± 11.82 | 63.25 ± 6.11 | 62 |

See legend to Table 14a for details.

TABLE 14m

Cyclic AMP production in CHO cells expressing wild type TSHR and TSHR with Asp232 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Experiment 1 | | | |
| Cyclic AMP assay buffer | 2.02 ± 0.09 | 1.33 ± 0.21 | 66 |
| K1-18 | | | |
| 0.3 ng/mL | 2.54 ± 0.06 | 0.99 ± 0.10 | 39 |
| 1 ng/mL | 6.16 ± 0.44 | 1.31 ± 0.05 | 21 |
| 3 ng/mL | 14.61 ± 0.83 | 1.80 ± 0.36 | 12 |
| 10 ng/mL | 38.90 ± 1.79 | 3.61 ± 0.02 | 9 |
| 30 ng/mL | 60.13 ± 3.16 | 8.21 ± 0.04 | 14 |
| 100 ng/mL | 65.85 ± 1.99 | 16.17 ± 0.08 | 25 |
| TSH | | | |
| 0.01 ng/mL | 1.69 ± 0.21 | 1.40 ± 0.08 | 83 |
| 0.03 ng/mL | 2.46 ± 0.20 | 2.16 ± 0.13 | 88 |
| 0.1 ng/mL | 6.18 ± 0.69 | 5.39 ± 0.28 | 87 |
| 0.3 ng/mL | 18.94 ± 0.29 | 15.11 ± 0.50 | 80 |
| 1 ng/mL | 45.19 ± 3.19 | 31.85 ± 1.24 | 70 |
| 3 ng/mL | 61.65 ± 5.29 | 40.95 ± 2.42 | 66 |
| Experiment 2 | | | |
| Cyclic AMP assay buffer | 1.74 ± 1.29 | 2.80 ± 0.16 | 161 |
| K1-18 | | | |
| 0.3 ng/mL | 4.93 ± 0.61 | 2.86 ± 0.15 | 58 |
| 1 ng/mL | 8.65 ± 0.84 | 3.53 ± 0.52 | 41 |
| 3 ng/mL | 21.61 ± 0.47 | 4.78 ± 0.27 | 22 |
| 10 ng/mL | 54.40 ± 0.93 | 1.76 ± 0.18 | 3 |
| 30 ng/mL | 86.44 ± 6.25 | 3.79 ± 0.17 | 4 |
| 100 ng/mL | 99.65 ± 10.16 | 6.49 ± 0.05 | 7 |
| TSH | | | |
| 0.01 ng/mL | 4.16 ± 1.96 | 2.58 ± 0.09 | 62 |
| 0.03 ng/mL | 4.92 ± 0.92 | 4.10 ± 0.23 | 83 |
| 0.1 ng/mL | 11.24 ± 1.01 | 9.44 ± 0.60 | 84 |
| 0.3 ng/mL | 31.44 ± 1.09 | 23.47 ± 1.51 | 75 |
| 1 ng/mL | 74.30 ± 2.40 | 44.35 ± 1.57 | 60 |
| 3 ng/mL | 96.39 ± 4.85 | 62.02 ± 8.15 | 64 |

See legend to Table 14a for details.

TABLE 14n

Cyclic AMP production in CHO cells expressing wild type TSHR and TSHR with Gln235 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Experiment 1 | | | |
| Cyclic AMP assay buffer | 0.70 ± 0.09 | 1.98 ± 0.62 | 283 |
| K1-18 | | | |
| 0.3 ng/mL | 1.80 ± 0.35 | 2.51 ± 0.43 | 139 |
| 1 ng/mL | 4.34 ± 0.52 | 4.48 ± 0.64 | 103 |
| 3 ng/mL | 9.25 ± 2.14 | 6.01 ± 1.95 | 65 |
| 10 ng/mL | 33.66 ± 5.21 | 18.80 ± 1.99 | 56 |
| 30 ng/mL | 79.70 ± 7.46 | 30.92 ± 2.83 | 39 |
| 100 ng/mL | 74.66 ± 3.56 | 47.71 ± 1.54 | 64 |
| TSH | | | |
| 0.01 ng/mL | 1.09 ± 0.35 | 1.75 ± 0.00 | 161 |
| 0.03 ng/mL | 2.31 ± 0.17 | 2.89 ± 0.03 | 125 |
| 0.1 ng/mL | 6.54 ± 0.20 | 5.97 ± 1.62 | 91 |
| 0.3 ng/mL | 26.48 ± 0.68 | 17.61 ± 0.48 | 67 |
| 1 ng/mL | 67.72 ± 7.23 | 44.19 ± 18.05 | 65 |
| 3 ng/mL | 83.50* | 46.59 ± 8.21 | 56 |
| Experiment 2 | | | |
| Cyclic AMP assay buffer | 1.85 ± 0.32 | 4.10 ± 0.42 | 222 |
| K1-18 | | | |
| 0.3 ng/mL | 2.58 ± 0.21 | 4.27 ± 1.53 | 166 |
| 1 ng/mL | 5.15 ± 0.85 | 7.30 ± 0.74 | 142 |
| 3 ng/mL | 14.11 ± 0.27 | 12.33 ± 3.43 | 87 |
| 10 ng/mL | 32.68 ± 5.49 | 24.02 ± 3.07 | 74 |
| 30 ng/mL | 58.74 ± 1.82 | 32.71 ± 2.05 | 56 |
| 100 ng/mL | 66.70 ± 2.49 | 43.93 ± 0.41 | 66 |
| TSH | | | |
| 0.01 ng/mL | 1.93 ± 0.13 | 3.42 ± 0.30 | 177 |
| 0.03 ng/mL | 2.75 ± 0.41 | 4.55 ± 0.24 | 165 |
| 0.1 ng/mL | 7.25 ± 1.02 | 7.77 ± 1.16 | 107 |
| 0.3 ng/mL | 25.26 ± 0.96 | 17.14 ± 0.56 | 68 |
| 1 ng/mL | 50.96 ± 2.69 | 31.70 ± 1.10 | 62 |
| 3 ng/mL | 69.68 ± 2.04 | 37.14 ± 1.16 | 53 |

See legend to Table 14a for details.
*mean of duplicate.

TABLE 14o

Cyclic AMP production in CHO cells expressing wild type TSHR and TSHR with Lys250 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ |
|---|---|---|---|
| | Wild type TSHR | Mutated TSHR | Wild type (%) |
| Cyclic AMP assay buffer | 1.41 ± 0.87 | 6.48 ± 0.22 | 460 |
| K1-18 | | | |
| 0.3 ng/mL | 3.20 ± 0.31 | 10.50 ± 0.55 | 328 |
| 1 ng/mL | 8.57 ± 0.31 | 23.44 ± 6.81 | 274 |
| 3 ng/mL | 27.68 ± 3.34 | 35.88 ± 0.55 | 130 |
| 10 ng/mL | 54.04 ± 4.74 | 68.33 ± 5.39 | 126 |
| 30 ng/mL | 85.58 ± 3.88 | 91.29 ± 2.75 | 107 |
| 100 ng/mL | 81.79 ± 1.55 | 100.62 ± 8.66 | 123 |
| TSH | | | |
| 0.01 ng/mL | 4.00 ± 0.10 | 8.29 ± 0.69 | 207 |
| 0.03 ng/mL | 6.66 ± 0.59 | 12.58 ± 0.44 | 189 |
| 0.1 ng/mL | 19.66 ± 2.56 | 28.81 ± 3.56 | 147 |
| 0.3 ng/mL | 44.98 ± 3.85 | 66.19 ± 0.67 | 147 |
| 1 ng/mL | 75.67 ± 6.21 | 87.90 ± 5.38 | 116 |
| 3 ng/mL | 87.19 ± 1.94 | 110.23 ± 9.68 | 126 |

See legend to Table 14a for details.

TABLE 14p

Cyclic AMP production in CHO cells expressing wild type TSHR and TSHR with Glu251 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type (%) |
|---|---|---|---|
| | Wild type TSHR | Mutated TSHR | |
| Cyclic AMP assay buffer | 1.22 ± 0.42 | 6.69 ± 2.73 | 548 |
| K1-18 | | | |
| 0.3 ng/mL | 2.36 ± 0.37 | 6.85 ± 0.56 | 290 |
| 1 ng/mL | 6.40 ± 0.43 | 9.70 ± 1.01 | 152 |
| 3 ng/mL | 19.16 ± 1.47 | 19.57 ± 1.63 | 102 |
| 10 ng/mL | 55.42 ± 4.77 | 39.70 ± 4.02 | 72 |
| 30 ng/mL | 84.02* | 66.74 ± 3.34 | 79 |
| 100 ng/mL | 111.09 ± 6.17 | 78.15 ± 0.89 | 70 |
| TSH | | | |
| 0.01 ng/mL | 1.64 ± 0.28 | 3.99 ± 0.94 | 243 |
| 0.03 ng/mL | 2.67 ± 0.32 | 5.99 ± 2.43 | 224 |
| 0.1 ng/mL | 9.75 ± 1.97 | 11.18 ± 1.33 | 115 |
| 0.3 ng/mL | 33.26 ± 9.03 | 22.15 ± 3.42 | 67 |
| 1 ng/mL | 77.73 ± 4.07 | 53.68 ± 1.90 | 69 |
| 3 ng/mL | 109.36 ± 2.78 | 71.71* | 66 |

See legend to Table 14a for details.
*mean of duplicate.

TABLE 14q

Cyclic AMP production in CHO cells expressing wild type TSHR and TSHR with Arg255 mutated to Ala. Effect of different dilutions of human monoclonal antibody to the TSHR (K1-18) with TSH agonist activity

| | Cyclic AMP produced (pmol/mL) mean ± SD (n = 3) | | Mutated/ Wild type (%) |
|---|---|---|---|
| | Wild type TSHR | Mutated TSHR | |
| Cyclic AMP assay buffer | 2.29 ± 1.04 | 4.37 ± 0.75 | 191 |
| K1-18 | | | |
| 0.3 ng/mL | 4.64 ± 0.55 | 5.46 ± 0.19 | 118 |
| 1 ng/mL | 8.87 ± 0.31 | 8.37 ± 0.20 | 94 |
| 3 ng/mL | 18.48 ± 0.81 | 13.80 ± 1.77 | 75 |
| 10 ng/mL | 55.33 ± 0.69 | 42.85 ± 1.72 | 77 |
| 30 ng/mL | 73.94 ± 4.06 | 59.25 ± 2.70 | 80 |
| 100 ng/mL | 79.57 ± 6.78 | 77.80 ± 4.90 | 98 |
| TSH | | | |
| 0.01 ng/mL | 2.94 ± 0.54 | 4.72 ± 0.33 | 161 |
| 0.03 ng/mL | 4.82 ± 0.70 | 6.78 ± 0.49 | 141 |
| 0.1 ng/mL | 9.25 ± 0.11 | 11.66 ± 0.75 | 126 |
| 0.3 ng/mL | 36.20 ± 3.81 | 36.72 ± 3.56 | 101 |
| 1 ng/mL | 69.17 ± 5.01 | 61.95 ± 3.97 | 90 |
| 3 ng/mL | 88.05* | 80.08 ± 0.72 | 91 |

See legend to Table 14a for details.
*mean of duplicate.

TABLE 14r

Cyclic AMP production in CHO cells expressing wild type TSHR and TSHR with Thr257 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild type (%) |
|---|---|---|---|
| | Wild type TSHR | Mutated TSHR | |
| Cyclic AMP assay buffer | 1.01 ± 0.34 | 1.13 ± 0.45 | 112 |
| K1-18 | | | |
| 0.3 ng/mL | 1.50 ± 0.68 | 1.54 ± 0.29 | 103 |
| 1 ng/mL | 3.60 ± 0.36 | 2.69 ± 1.11 | 75 |
| 3 ng/mL | 8.09 ± 0.45 | 7.13 ± 0.88 | 88 |
| 10 ng/mL | 27.52 ± 3.28 | 20.22 ± 1.90 | 73 |
| 30 ng/mL | 64.52 ± 1.71 | 39.26 ± 3.48 | 61 |
| 100 ng/mL | 100.30 ± 2.04 | 81.11 ± 5.12 | 81 |
| TSH | | | |
| 0.01 ng/mL | 1.67 ± 0.27 | 1.50 ± 0.29 | 90 |
| 0.03 ng/mL | 3.13 ± 0.68 | 2.92 ± 0.45 | 93 |
| 0.1 ng/mL | 8.30 ± 0.37 | 7.65 ± 1.51 | 92 |
| 0.3 ng/mL | 24.05 ± 2.75 | 25.30 ± 0.41 | 105 |
| 1 ng/mL | 64.57 ± 3.16 | 60.69 ± 3.98 | 94 |
| 3 ng/mL | 102.12 ± 9.89 | 88.24 ± 12.78 | 86 |

See legend to Table 14a for details.

TABLE 14s

Cyclic AMP production in CHO cells expressing wild type TSHR and TSHR with Trp258 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild type (%) |
|---|---|---|---|
| | Wild type TSHR | Mutated TSHR | |
| Experiment 1 | | | |
| Cyclic AMP assay buffer | 0.90 ± 0.08 | 2.05 ± 0.38 | 228 |
| K1-18 | | | |
| 0.3 ng/mL | 2.29 ± 0.25 | 2.93 ± 0.39 | 128 |
| 1 ng/mL | 5.47 ± 0.90 | 4.39 ± 0.24 | 80 |
| 3 ng/mL | 15.27 ± 1.02 | 11.47 ± 0.72 | 75 |
| 10 ng/mL | 45.65 ± 2.67 | 25.35 ± 2.59 | 56 |
| 30 ng/mL | 70.22 ± 8.09 | 40.36 ± 0.00 | 57 |
| 100 ng/mL | 77.74 ± 5.05 | 52.44 ± 4.72 | 67 |
| TSH | | | |
| 0.01 ng/mL | 1.22 ± 0.34 | 1.93 ± 0.24 | 158 |
| 0.03 ng/mL | 1.85 ± 0.62 | 2.88 ± 0.09 | 156 |
| 0.1 ng/mL | 4.89 ± 0.35 | 7.51 ± 1.57 | 154 |
| 0.3 ng/mL | 17.37 ± 0.87 | 22.29 ± 3.45 | 128 |
| 1 ng/mL | 52.88 ± 6.38 | 45.69 ± 7.63 | 86 |
| 3 ng/mL | 70.63 ± 3.87 | 53.97 ± 3.81 | 76 |
| Experiment 2 | | | |
| Cyclic AMP assay buffer | 1.45 ± 0.28 | 0.92 ± 0.21 | 63 |
| K1-18 | | | |
| 0.3 ng/mL | 1.68 ± 0.21 | 1.53 ± 0.31 | 91 |
| 1 ng/mL | 5.21 ± 0.29 | 3.29 ± 0.75 | 63 |
| 3 ng/mL | 15.99 ± 1.07 | 6.25 ± 0.22 | 39 |
| 10 ng/mL | 41.40 ± 4.90 | 15.64 ± 0.90 | 38 |
| 30 ng/mL | 77.09 ± 1.32 | 38.59 ± 1.52 | 50 |
| 100 ng/mL | 106.57 ± 3.64 | 57.31 ± 2.41 | 54 |

TABLE 14s-continued

Cyclic AMP production in CHO cells expressing wild type TSHR and TSHR with Trp258 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild |
|---|---|---|---|
| | Wild type TSHR | Mutated TSHR | type (%) |
| TSH | | | |
| 0.01 ng/mL | 2.02 ± 0.51 | 1.56 ± 0.18 | 77 |
| 0.03 ng/mL | 1.96 ± 0.06 | 2.76 ± 0.71 | 141 |
| 0.1 ng/mL | 4.49 ± 0.81 | 7.04 ± 0.83 | 156 |
| 0.3 ng/mL | 13.47 ± 1.96 | 17.26 ± 4.12 | 128 |
| 1 ng/mL | 43.24 ± 1.20 | 49.17 ± 5.52 | 114 |
| 3 ng/mL | 84.76 ± 9.98 | 84.70* | 100 |

See legend to Table 14a for details.
*mean of duplicate.

TABLE 14t

Cyclic AMP production in CHO cells expressing wild type TSHR and TSHR with Arg274 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild |
|---|---|---|---|
| | Wild type TSHR | Mutated TSHR | type (%) |
| Experiment 1 | | | |
| Cyclic AMP assay buffer K1-18 | 1.58 ± 0.21 | 1.71 ± 0.07 | 108 |
| 0.3 ng/mL | 1.75 ± 0.14 | 1.74 ± 0.17 | 99 |
| 1 ng/mL | 3.17 ± 0.20 | 1.97 ± 0.82 | 62 |
| 3 ng/mL | 10.91 ± 1.52 | 3.46 ± 0.07 | 32 |
| 10 ng/mL | 28.17 ± 2.38 | 9.44 ± 0.80 | 34 |
| 30 ng/mL | 71.50 ± 3.54 | 27.91 ± 1.72 | 39 |
| 100 ng/mL | 96.37 ± 4.71 | 70.48 ± 5.61 | 73 |
| TSH | | | |
| 0.01 ng/mL | 1.86 ± 0.23 | 1.97 ± 0.06 | 106 |
| 0.03 ng/mL | 3.32 ± 0.07 | 4.14 ± 1.36 | 125 |
| 0.1 ng/mL | 14.60 ± 1.90 | 9.38 ± 0.23 | 64 |
| 0.3 ng/mL | 48.54 ± 4.12 | 27.28 ± 1.62 | 56 |
| 1 ng/mL | 91.18 ± 4.31 | 67.63 ± 0.93 | 74 |
| 3 ng/mL | 118.63 ± 16.76 | 98.80 ± 7.10 | 83 |
| Experiment 2 | | | |
| Cyclic AMP assay buffer K1-18 | 2.08 ± 0.14 | 1.65 ± 0.12 | 79 |
| 0.3 ng/mL | 2.70 ± 0.08 | 1.71 ± 0.13 | 63 |
| 1 ng/mL | 5.96 ± 0.25 | 2.65 ± 0.20 | 44 |
| 3 ng/mL | 14.95 ± 0 | 5.45 ± 0.28 | 36 |
| 10 ng/mL | 51.80 ± 4.35 | 14.83 ± 1.86 | 29 |
| 30 ng/mL | 81.16 ± 2.80 | 35.53 ± 0.93 | 44 |
| 100 ng/mL | 97.09 ± 10.91 | 60.73 ± 3.26 | 63 |
| TSH | | | |
| 0.01 ng/mL | 2.49 ± 0.39 | 1.37 ± 0.18 | 55 |
| 0.03 ng/mL | 5.12 ± 0.22 | 2.94 ± 0.11 | 57 |
| 0.1 ng/mL | 13.66 ± 1.00 | 8.29 ± 0.74 | 61 |
| 0.3 ng/mL | 39.93 ± 2.47 | 25.47 ± 0.43 | 64 |
| 1 ng/mL | 74.35 ± 5.04 | 58.49 ± 4.84 | 79 |
| 3 ng/mL | 88.28 ± 15.49 | 73.19 ± 3.18 | 82 |

See legend to Table 14a for details.

TABLE 14u

Cyclic AMP production in CHO cells expressing wild type TSHR and TSHR with Asp276 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild |
|---|---|---|---|
| | Wild type TSHR | Mutated TSHR | type (%) |
| Cyclic AMP assay buffer K1-18 | 1.05 ± 0.23 | 13.94 ± 2.05 | 1328 |
| 0.3 ng/mL | 2.27 ± 0.23 | 17.17 ± 0.64 | 756 |
| 1 ng/mL | 6.16 ± 0.90 | 23.79 ± 1.67 | 386 |
| 3 ng/mL | 17.36 ± 0.80 | 32.67 ± 3.05 | 188 |
| 10 ng/mL | 52.57 ± 0 | 56.94 ± 0.50 | 108 |
| 30 ng/mL | 81.08 ± 11.47 | 65.05 ± 4.25 | 80 |
| 100 ng/mL | 87.81 ± 14.82 | 86.02 ± 6.77 | 98 |
| TSH | | | |
| 0.01 ng/mL | 2.45 ± 0.68 | 14.29 ± 1.97 | 583 |
| 0.03 ng/mL | 4.78 ± 0.57 | 17.64 ± 0.44 | 369 |
| 0.1 ng/mL | 16.19 ± 0.95 | 21.70 ± 4.65 | 134 |
| 0.3 ng/mL | 44.34 ± 6.02 | 45.58 ± 1.03 | 103 |
| 1 ng/mL | 77.19 ± 4.48 | 68.31 ± 7.05 | 88 |
| 3 ng/mL | 95.50 ± 7.45 | 76.02 ± 5.12 | 80 |

See legend to Table 14a for details.

TABLE 14v

Cyclic AMP production in CHO cells expressing wild type TSHR and TSHR with Ser281 mutated to Ala. Effect of different dilutions of human monoclonal antibody to the TSHR (K1-18) with TSH agonist activity

| | Cyclic AMP produced (pmol/mL) mean ± SD (n = 3) | | Mutated/Wild |
|---|---|---|---|
| | Wild type TSHR | Mutated TSHR | type (%) |
| Cyclic AMP assay buffer K1-18 (ng/mL) | 1.72 ± 0.28 | 2.04 ± 0.29 | 119 |
| 0.3 ng/mL | 3.09 ± 0.17 | 3.62 ± 0.35 | 117 |
| 1 ng/mL | 6.04 ± 0.42 | 7.01 ± 0.55 | 116 |
| 3 ng/mL | 18.37 ± 1.19 | 15.23 ± 0.92 | 83 |
| 10 ng/mL | 43.48 ± 0.76 | 31.25 ± 1.85 | 72 |
| 30 ng/mL | 72.75 ± 5.88 | 55.19 ± 0.59 | 76 |
| 100 ng/mL | 81.95 ± 2.57 | 65.22 ± 6.42 | 80 |
| TSH (ng/mL) | | | |
| 0.01 ng/mL | 2.03 ± 0.30 | 2.84 ± 0.06 | 140 |
| 0.03 ng/mL | 3.65 ± 0.64 | 4.69 ± 0.05 | 128 |
| 0.1 ng/mL | 9.65 ± 1.53 | 11.33 ± 0.62 | 117 |
| 0.3 ng/mL | 31.40 ± 0.93 | 27.48 ± 2.15 | 88 |
| 1 ng/mL | 61.04 ± 3.63 | 51.63 ± 0.54 | 85 |
| 3 ng/mL | 82.58 ± 2.92 | 67.98 ± 2.73 | 82 |

See legend to Table 14a for details.

TABLE 15a

TSH induced cyclic AMP production in CHO cells expressing wild type TSHR and TSHR with Asp43 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 3.57 ± 1.18 | 1.40 ± 0.04 | 39 |
| TSH[b] | 93.92 ± 3.88 | ND | ND |
| 5B3 10 µg/mL + TSH[b] | 106.48 ± 12.76 | 73.73 ± 6.47 | 69 |
| 5B3 100 µg/mL + TSH[b] | 104.40 ± 2.12 | 57.99 ± 7.76 | 56 |
| K1-70 0.001 µg + TSH[b] | 109.98 ± 20.13 | 65.19 ± 11.37 | 59 |
| K1-70 0.01 µg + TSH[b] | 118.99 ± 3.21 | 61.42 ± 3.26 | 52 |
| K1-70 0.1 µg + TSH[b] | 82.87 ± 6.76 | 23.56 ± 12.03 | 28 |
| K1-70 1.0 µg + TSH[b] | 3.37 ± 0.81 | 1.82 ± 0.25 | 54 |
| K1-70 10 µg + TSH[b] | 2.05 ± 0.10 | 0.97 ± 0.16 | 47 |
| K1-70 100 µg + TSH[b] | 2.34 ± 0.18 | 1.16 ± 0.25 | 50 |
| K1-70 100 µg | 1.89 ± 0.12 | 1.64 ± 0.98 | 87 |
| [b]TSH (2) | 92.19 ± 5.64 | 60.27 ± 7.64 | 65 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 4 |
| K1-70 0.001 µg | 0 | 0 |
| K1-70 0.01 µg/mL | 0 | 0 |
| K1-70 0.1 µg/mL | 12 | 61 |
| K1-70 1 µg/mL | 96 | 97 |
| K1-70 10 µg/mL | 98 | 98 |
| K1-70 100 µg/mL | 98 | 98 |
| [b]TSH (2) | 2 | 0 |

[a]Test samples in hypotonic cyclic AMP assay buffer.
[b]TSH final concentration = 3 µg/mL.
[c]% inhibition = 100 × [1 − (cyclic AMP in the presence of test samples and TSH/cyclic AMP in the presence of cyclic AMP buffer and TSH)]. 5B3 is a human monoclonal antibody to GAD (negative control for K1-70).
ND = not determined.
TSH(2) = run at the end of assay.

TABLE 15b

TSH induced cyclic AMP production in CHO cells expressing wild type TSHR and TSHR with Ile60 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.78 ± 0.12 | 4.07 ± 0.08 | 229 |
| TSH[b] | 90.09 ± 1.19 | 51.32 ± 3.85 | 57 |
| 5B3 10 µg/mL + TSH[b] | 95.17 ± 4.45 | 54.77 ± 12.78 | 58 |
| 5B3 100 µg/mL + TSH[b] | 88.16 ± 5.03 | 43.98 ± 3.05 | 50 |
| K1-70 0.001 µg + TSH[b] | 91.53 ± 28.48 | 42.91 ± 2.83 | 47 |
| K1-70 0.01 µg + TSH[b] | 92.89 ± 10.08 | 47.49 ± 2.80 | 51 |
| K1-70 0.1 µg + TSH[b] | 8.45 ± 0.58 | 44.85 ± 7.20 | 531 |
| K1-70 1.0 µg + TSH[b] | 2.39 ± 0.42 | 21.99 ± 1.61 | 920 |
| K1-70 10 µg + TSH[b] | 1.78 ± 0.21 | 10.90 ± 0.67 | 612 |
| K1-70 100 µg + TSH[b] | 1.54 ± 021 | 7.61 ± 0.53 | 494 |
| K1-70 100 µg | 1.12 ± 0.51 | 3.84 ± 0.56 | 343 |
| [b]TSH (2) | 82.90 ± 1.87 | 45.09 ± 0.90 | 54 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 2 | 14 |
| K1-70 0.001 µg | 0 | 16 |
| K1-70 0.01 µg/mL | 0 | 7 |
| K1-70 0.1 µg/mL | 91 | 13 |
| K1-70 1 µg/mL | 97 | 57 |
| K1-70 10 µg/mL | 98 | 79 |
| K1-70 100 µg/mL | 98 | 85 |
| [b]TSH (2) | 8 | 12 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.16 ± 0.21 | 5.06 ± 0.31 | 436 |
| TSH[b] | 81.69 ± 3.88 | 65.78 ± 5.98 | 81 |
| 5B3 10 µg/mL + TSH[b] | 102.63 ± 13.71 | 54.69 ± 7.88 | 53 |
| 5B3 100 µg/mL + TSH[b] | 107.64 ± 13.05 | 66.83 ± 6.83 | 62 |
| K1-70 0.001 µg + TSH[b] | 93.21 ± 9.01 | 57.98 ± 6.22 | 62 |
| K1-70 0.01 µg + TSH[b] | 92.99 ± 6.39 | 58.40 ± 1.47 | 63 |
| K1-70 0.1 µg + TSH[b] | 4.12 ± 0.54 | 54.06 ± 5.59 | 1312 |
| K1-70 1.0 µg + TSH[b] | 1.16 ± 0.09 | 14.82 ± 1.13 | 1278 |
| K1-70 10 µg + TSH[b] | 1.85 ± 0.28 | 11.15 ± 2.09 | 603 |
| K1-70 100 µg + TSH[b] | 1.71 ± 0.56 | 7.87 ± 0.63 | 460 |
| K1-70 100 µg | 1.50 ± 0.25 | 4.13 ± 0.28 | 275 |
| [b]TSH (2) | 82.55 ± 7.76 | 56.96 ± 7.01 | 69 |

| Antibody concentration | % inhibition of TSH stimulation[c] | |
|---|---|---|
| | Wild type TSHR | Mutated TSHR |
| 5B3 10 µg/mL | 0 | 17 |
| 5B3 100 µg/mL | 0 | 0 |
| K1-70 0.001 µg | 0 | 12 |
| K1-70 0.01 µg/mL | 0 | 11 |
| K1-70 0.1 µg/mL | 95 | 18 |
| K1-70 1 µg/mL | 99 | 77 |
| K1-70 10 µg/mL | 98 | 83 |
| K1-70 100 µg/mL | 98 | 88 |
| [b]TSH (2) | 0 | 13 |

See legend to Table 15a for details.

TABLE 15c

TSH induced cyclic AMP production in CHO cells expressing wild type TSHR and TSHR with Glu61 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.63 ± 0.27 | 1.49 ± 0.48 | 237 |
| TSH[b] | 115.33 ± 1.56 | 77.74 ± 6.57 | 67 |
| 5B3 10 µg/mL + TSH[b] | 114.68 ± 8.12 | 77.87 ± 8.10 | 68 |
| 5B3 100 µg/mL + TSH[b] | 127.08 ± 6.55 | 70.47 ± 2.85 | 55 |
| K1-70 0.001 µg + TSH[b] | 102.62 ± 6.91 | 72.39 ± 4.36 | 71 |
| K1-70 0.01 µg + TSH[b] | 109.66 ± 14.99 | 71.93 ± 9.10 | 66 |
| K1-70 0.1 µg + TSH[b] | 43.68 ± 13.73 | 54.35 ± 9.85 | 124 |

TABLE 15c-continued

TSH induced cyclic AMP production in CHO cells expressing wild type TSHR and TSHR with Glu61 mutated to Ala. Effect of different dilutions of human monoclonal antibody to the TSHR (K1-70) with TSH antagonist activity

| | | | |
|---|---|---|---|
| K1-70 1.0 µg + TSH[b] | 1.35 ± 0.08 | 1.18 ± 0.23 | 87 |
| K1-70 10 µg + TSH[b] | 1.25 ± 0.35 | 0.76 ± 0.23 | 60.8 |
| K1-70 100 µg + TSH[b] | 0.61 ± 0.46 | 0.91 ± 0.36 | 149 |
| K1-70 100 µg | 0.49 ± 0.47 | 1.69 ± 0.34 | 345 |
| [b]TSH (2) | 126.05 ± 6.29 | 64.74 ± 4.96 | 51 |

| Antibody concentration | % inhibition of TSH stimulation[c] | |
|---|---|---|
| | Wild type TSHR | Mutated TSHR |
| 5B3 10 µg/mL | 1 | 0 |
| 5B3 100 µg/mL | 0 | 9 |
| K1-70 0.001 µg | 11 | 7 |
| K1-70 0.01 µg/mL | 5 | 7 |
| K1-70 0.1 µg/mL | 62 | 30 |
| K1-70 1 µg/mL | 99 | 98 |
| K1-70 10 µg/mL | 99 | 99 |
| K1-70 100 µg/mL | 99 | 99 |
| [b]TSH (2) | 0 | 17 |

See legend to Table 15a for details.

TABLE 15d

TSH induced cyclic AMP production in CHO cells expressing wild type TSHR and TSHR with Thr104 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.89 ± 0.29 | 1.36 ± 0.89 | 153 |
| TSH[b] | 83.78 ± 6.86 | 63.69 ± 1.38 | 76 |
| 5B3 10 µg/mL + TSH[b] | 83.61 ± 3.29 | 59.13 ± 0.82 | 71 |
| 5B3 100 µg/mL + TSH[b] | 88.04 ± 5.58 | 60.01 ± 3.04 | 68 |
| K1-70 0.001 µg + TSH[b] | 90.15 ± 15.94 | 64.74 ± 6.20 | 72 |
| K1-70 0.01 µg + TSH[b] | 92.33 ± 8.48 | 54.64 ± 1.42 | 59 |
| K1-70 0.1 µg + TSH[b] | 34.13 ± 3.95 | 24.89 ± 3.39 | 73 |
| K1-70 1.0 µg + TSH[b] | 1.58 ± 0.16 | 2.55 ± 0.11 | 161 |
| K1-70 10 µg + TSH[b] | 1.07 ± 0.33 | 2.15 ± 1.06 | 201 |
| K1-70 100 µg + TSH[b] | 1.19 ± 0.35 | 1.86 ± 0.06 | 156 |
| K1-70 100 µg | 0.74 ± 0.30 | 1.48 ± 0.13 | 200 |
| [b]TSH (2) | 83.61 ± 3.30 | 57.01 ± 1.62 | 68 |

| Antibody concentration | % inhibition of TSH stimulation[c] | |
|---|---|---|
| | Wild type TSHR | Mutated TSHR |
| 5B3 10 µg/mL | 0 | 7 |
| 5B3 100 µg/mL | 0 | 6 |
| K1-70 0.001 µg | 0 | 0 |
| K1-70 0.01 µg/mL | 0 | 14 |
| K1-70 0.1 µg/mL | 59 | 61 |
| K1-70 1 µg/mL | 98 | 96 |
| K1-70 10 µg/mL | 99 | 97 |
| K1-70 100 µg/mL | 99 | 97 |
| [b]TSH (2) | 0.2 | 10 |

See legend to Table 15a for details.

TABLE 15e

TSH induced cyclic AMP production in CHO cells expressing wild type TSHR and TSHR with His105 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.64 ± 0.08 | 0.99 ± 0.06 | 155 |
| TSH[b] | 93.59 ± 6.12 | 65.93 ± 4.03 | 70 |
| 5B3 10 µg/mL + TSH[b] | 91.63 ± 10.00 | 75.20 ± 5.73 | 82 |
| 5B3 100 µg/mL + TSH[b] | 133.84 ± 27.40 | 66.67 ± 1.51 | 50 |
| K1-70 0.001 µg + TSH[b] | 135.86 ± 3.01 | 89.32 ± 7.04 | 66 |
| K1-70 0.01 µg + TSH[b] | 119.40 ± 22.33 | 82.69 ± 6.53 | 69 |
| K1-70 0.1 µg + TSH[b] | 24.43 ± 4.03 | 10.46 ± 2.84 | 43 |
| K1-70 1.0 µg + TSH[b] | 1.34 ± 0.26 | 1.47 ± 0.40 | 110 |
| K1-70 10 µg + TSH[b] | 1.96 ± 2.03 | 0.70 ± 0.16 | 36 |
| K1-70 100 µg + TSH[b] | 0.70 ± 0.24 | 0.80 ± 0.24 | 114 |
| K1-70 100 µg | 0.89 ± 0.19 | 0.66 ± 0.13 | 74 |
| [b]TSH (2) | 116.74 ± 5.43 | 58.53 ± 2.95 | 50 |

| Antibody concentration | % inhibition of TSH stimulation[c] | |
|---|---|---|
| | Wild type TSHR | Mutated TSHR |
| 5B3 10 µg/mL | 2 | 0 |
| 5B3 100 µg/mL | 0 | 0 |
| K1-70 0.001 µg | 0 | 0 |
| K1-70 0.01 µg/mL | 0 | 0 |
| K1-70 0.1 µg/mL | 74 | 84 |
| K1-70 1 µg/mL | 99 | 98 |
| K1-70 10 µg/mL | 98 | 99 |
| K1-70 100 µg/mL | 99 | 99 |
| [b]TSH (2) | 0 | 11 |

See legend to Table 15a for details.

TABLE 15f

TSH induced cyclic AMP production in CHO cells expressing wild type TSHR and TSHR with Asp151 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.06 ± 0.22 | 2.03 ± 0.48 | 192 |
| TSH[b] | 74.09 ± 8.63 | 45.72 ± 0.43 | 62 |
| 5B3 10 µg/mL + TSH[b] | 76.94 ± 7.67 | 40.70 ± 2.59 | 53 |
| 5B3 100 µg/mL + TSH[b] | 81.59 ± 6.54 | 46.24 ± 1.77 | 57 |
| K1-70 0.001 µg + TSH[b] | 80.09 ± 1.95 | 45.85 ± 4.25 | 57 |
| K1-70 0.01 µg + TSH[b] | 80.41 ± 8.03 | 44.71 ± 2.24 | 56 |
| K1-70 0.1 µg + TSH[b] | 13.74 ± 6.49 | 10.24 ± 0.91 | 75 |
| K1-70 1.0 µg + TSH[b] | 1.10 ± 0.24 | 2.04 ± 0.41 | 185 |
| K1-70 10 µg + TSH[b] | 1.21 ± 0.33 | 1.60 ± 0.35 | 132 |
| K1-70 100 µg + TSH[b] | 1.06 ± 0.54 | 1.68 ± 0.19 | 158 |
| K1-70 100 µg | 1.20 ± 0.13 | 1.72 ± 0.68 | 143 |
| [b]TSH (2) | 95.46 ± 17.64 | 41.53 ± 1.51 | 44 |

| Antibody concentration | % inhibition of TSH stimulation[c] | |
|---|---|---|
| | Wild type TSHR | Mutated TSHR |
| 5B3 10 µg/mL | 0 | 11 |
| 5B3 100 µg/mL | 0 | 0 |
| K1-70 0.001 µg | 0 | 0 |
| K1-70 0.01 µg/mL | 0 | 2 |
| K1-70 0.1 µg/mL | 81 | 78 |
| K1-70 1 µg/mL | 99 | 96 |

TABLE 15f-continued

TSH induced cyclic AMP production in CHO cells expressing wild type TSHR and TSHR with Asp151 mutated to Ala. Effect of different dilutions of human monoclonal antibody to the TSHR (K1-70) with TSH antagonist activity

| K1-70 10 µg/mL | 98 | 97 |
| K1-70 100 µg/mL | 99 | 96 |
| [b]TSH (2) | 0 | 9 |

See legend to Table 15a for details.

TABLE 15g

TSH induced cyclic AMP production in CHO cells expressing wild type TSHR and TSHR with Asp160 mutated to Lys. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.71 ± 0.10 | 5.83 ± 0.11 | 821 |
| M22[b] | 65.25 ± 4.95 | 51.70 ± 2.57 | 79 |
| 5B3 10 µg/mL + M22[b] | 75.97 ± 4.49 | 52.50 ± 4.25 | 69 |
| 5B3 100 µg/mL + M22[b] | 76.92 ± 9.97 | 45.83 ± 3.53 | 60 |
| K1-70 0.001 µg + M22[b] | 88.89 ± 11.87 | 51.99 ± 6.36 | 58 |
| K1-70 0.01 µg + M22[b] | 81.52 ± 12.62 | 41.02 ± 6.06 | 50 |
| K1-70 0.1 µg + M22[b] | 10.95 ± 1.07 | 9.26 ± 2.35 | 85 |
| K1-70 1.0 µg + M22[b] | 0.46 ± 0.06 | 0.25 ± 0.06 | 54 |
| K1-70 10 µg + M22[b] | 0.63 ± 0.33 | 0.07 ± 0.08 | 11 |
| K1-70 100 µg + M22[b] | 0.52 ± 0.46 | 0.27 ± 0.12 | 52 |
| K1-70 100 µg | 1.00 ± 0.68 | 0.09 ± 0.06 | 9 |
| [b]M22 (2) | 71.04 ± 1.30 | 45.81 ± 5.56 | 64 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 11 |
| K1-70 0.001 µg | 0 | 0 |
| K1-70 0.01 µg/mL | 0 | 21 |
| K1-70 0.1 µg/mL | 83 | 82 |
| K1-70 1 µg/mL | 99 | 99 |
| K1-70 10 µg/mL | 99 | 100 |
| K1-70 100 µg/mL | 99 | 99 |
| [b]M22 (2) | 0 | 11 |

See legend to Table 15a for details.

TABLE 15h

TSH induced cyclic AMP production in CHO cells expressing wild type TSHR and TSHR with Glu178 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.35 ± 0.47 | 9.18 ± 0.59 | 2623 |
| TSH[b] | 52.9 ± 3.27 | 56.61 ± 6.05 | 107 |
| 5B3 10 µg/mL + TSH[b] | 65.73 ± 1.11 | 57.61 ± 2.52 | 88 |
| 5B3 100 µg/mL + TSH[b] | 65.49 ± 4.50 | 57.04 ± 7.63 | 87 |
| K1-70 0.001 µg + TSH[b] | 63.14 ± 5.08 | 45.91 ± 1.28 | 73 |
| K1-70 0.01 µg + TSH[b] | 60.67 ± 7.43 | 47.28 ± 2.68 | 78 |
| K1-70 0.1 µg + TSH[b] | 6.32 ± 2.70 | 37.53 ± 7.25 | 594 |
| K1-70 1.0 µg + TSH[b] | 0.78 ± 0.64 | 6.96 ± 0.61 | 892 |
| K1-70 10 µg + TSH[b] | 0.66 ± 0.34 | 5.65 ± 0.22 | 856 |
| K1-70 100 µg + TSH[b] | 0.42 ± 0.22 | 6.80 ± 0.16 | 1619 |
| K1-70 100 µg | 0.01* | 6.11 ± 0.14 | 61100 |
| [b]TSH (2) | 77.16 ± 8.61 | 50.08 ± 5.73 | 65 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 0 |
| K1-70 0.001 µg | 0 | 19 |
| K1-70 0.01 µg/mL | 0 | 16 |
| K1-70 0.1 µg/mL | 88 | 34 |
| K1-70 1 µg/mL | 99 | 88 |
| K1-70 10 µg/mL | 99 | 90 |
| K1-70 100 µg/mL | 99 | 88 |
| [b]TSH (2) | 0 | 12 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.83 ± 0.13 | 6.13 ± 0.45 | 335 |
| TSH[b] | 87.25 ± 10.43 | 46.20 ± 2.13 | 53 |
| 5B3 10 µg/mL + TSH[b] | 100.35 ± 7.09 | 54.97 ± 4.10 | 55 |
| 5B3 100 µg/mL + TSH[b] | 98.11 ± 11.88 | 44.98 ± 4.80 | 46 |
| K1-70 0.001 µg + TSH[b] | 103.37 ± 16.45 | 49.40 ± 4.23 | 48 |
| K1-70 0.01 µg + TSH[b] | 96.22 ± 16.49 | 48.01 ± 5.37 | 50 |
| K1-70 0.1 µg + TSH[b] | 20.35 ± 9.35 | 30.71 ± 3.37 | 151 |
| K1-70 1.0 µg + TSH[b] | 1.13 ± 0.62 | 5.78 ± 0.42 | 512 |
| K1-70 10 µg + TSH[b] | 1.43 ± 0.34 | 4.88 ± 0.15 | 341 |
| K1-70 100 µg + TSH[b] | 1.54 ± 0.24 | 4.84 ± 0.32 | 314 |
| K1-70 100 µg | 1.08 ± 0.32 | 3.73 ± 0.64 | 345 |
| [b]TSH (2) | 88.09 ± 7.60 | 44.11 ± 1.34 | 50 |

| Antibody concentration | % inhibition of TSH stimulation[c] | |
|---|---|---|
| | Wild type TSHR | Mutated TSHR |
| 5B3 10 µg/mL | 0 | 0 |
| 5B3 100 µg/mL | 0 | 3 |
| K1-70 0.001 µg | 0 | 0 |
| K1-70 0.01 µg/mL | 0 | 0 |
| K1-70 0.1 µg/mL | 77 | 34 |
| K1-70 1 µg/mL | 99 | 87 |
| K1-70 10 µg/mL | 98 | 89 |
| K1-70 100 µg/mL | 98 | 90 |
| [b]TSH (2) | 0 | 5 |

See legend to Table 15a for details.

TABLE 15i

TSH induced cyclic AMP production in CHO cells expressing wild type TSHR and TSHR with Lys183 mutated to Asp. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.83 ± 0.70 | 1.26 ± 0.02 | 152 |
| TSH[b] | 85.81 ± 4.18 | 117.28 ± 3.46 | 137 |
| 5B3 10 µg/mL + TSH[b] | 93.70 ± 8.12 | 104.75 ± 8.56 | 112 |
| 5B3 100 µg/mL + TSH[b] | 108.83 ± 3.13 | 127.83 ± 6.64 | 117 |
| K1-70 0.001 µg + TSH[b] | 90.69 ± 2.74 | 101.41 ± 11.08 | 112 |
| K1-70 0.01 µg + TSH[b] | 97.27 ± 2.97 | 101.74 ± 14.23 | 105 |
| K1-70 0.1 µg + TSH[b] | 69.05 ± 10.81 | 33.97 ± 2.51 | 49 |
| K1-70 1.0 µg + TSH[b] | 2.33 ± 0.54 | 3.04 ± 1.07 | 130 |
| K1-70 10 µg + TSH[b] | 1.74 ± 0.11 | 0.85 ± 0.38 | 49 |
| K1-70 100 µg + TSH[b] | 1.61 ± 0.27 | 0.98 ± 0.23 | 61 |
| K1-70 100 µg | 1.46 ± 0.16 | 0.84 ± 0.26 | 58 |
| [b]TSH (2) | 97.81 ± 21.58 | 93.44 ± 3.40 | 96 |

| Antibody concentration | % inhibition of TSH stimulation[c] | |
|---|---|---|
| | Wild type TSHR | Mutated TSHR |
| 5B3 10 µg/mL | 0 | 11 |
| 5B3 100 µg/mL | 0 | 0 |
| K1-70 0.001 µg | 0 | 14 |
| K1-70 0.01 µg/mL | 0 | 13 |
| K1-70 0.1 µg/mL | 20 | 71 |
| K1-70 1 µg/mL | 97 | 97 |
| K1-70 10 µg/mL | 98 | 99 |
| K1-70 100 µg/mL | 98 | 99 |
| [b]TSH (2) | 0 | 20 |

See legend for Table 15a for details.

TABLE 15j

TSH induced cyclic AMP production in CHO cells expressing wild type TSHR and TSHR with Tyr185 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.20 ± 0.46 | 2.17 ± 0.33 | 181 |
| TSH[b] | 100.81 ± 7.98 | 52.49 ± 3.51 | 52 |
| 5B3 10 µg/mL + TSH[b] | 125.53 ± 9.18 | 47.02 ± 2.22 | 37 |
| 5B3 100 µg/mL + TSH[b] | 97.32 ± 11.29 | 56.13 ± 6.76 | 58 |
| K1-70 0.001 µg + TSH[b] | 118.92 ± 0 | 51.39 ± 4.61 | 43 |
| K1-70 0.01 µg + TSH[b] | 120.80 ± 7.93 | 46.06 ± 1.89 | 38 |
| K1-70 0.1 µg + TSH[b] | 15.05 ± 4.72 | 10.84 ± 2.53 | 72 |
| K1-70 1.0 µg + TSH[b] | 1.30 ± 0.32 | 2.10 ± 0.52 | 162 |
| K1-70 10 µg + TSH[b] | 1.61 ± 0.80 | 1.64 ± 0.49 | 102 |
| K1-70 100 µg + TSH[b] | 1.38 ± 0.09 | 2.07 ± 0.62 | 150 |
| K1-70 100 µg | 1.30 ± 0.17 | 1.54 ± 0.39 | 118 |
| [b]TSH (2) | 131.33 ± 9.02 | 41.01 ± 1.66 | 31.2 |

| Antibody concentration | % inhibition of TSH stimulation[c] | |
|---|---|---|
| | Wild type TSHR | Mutated TSHR |
| 5B3 10 µg/mL | 0 | 10 |
| 5B3 100 µg/mL | 3 | 0 |
| K1-70 0.001 µg | 0 | 2 |
| K1-70 0.01 µg/mL | 0 | 12 |
| K1-70 0.1 µg/mL | 85 | 79 |
| K1-70 1 µg/mL | 99 | 96 |
| K1-70 10 µg/mL | 98 | 97 |
| K1-70 100 µg/mL | 99 | 96 |
| [b]TSH (2) | 0 | 22 |

See legend to Table 15a for details.

TABLE 15k

TSH induced cyclic AMP production in CHO cells expressing wild type TSHR and TSHR with Tyr206 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.45 ± 0.33 | 2.33 ± 0.17 | 161 |
| TSH[b] | 92.20 ± 5.95 | 82.89 ± 7.13 | 90 |
| 5B3 10 µg/mL + TSH[b] | 94.47 ± 3.74 | 74.63 ± 5.45 | 79 |
| 5B3 100 µg/mL + TSH[b] | 101.41 ± 6.91 | 75.18 ± 4.79 | 74 |
| K1-70 0.001 µg + TSH[b] | 102.14 ± 23.36 | 68.25 ± 5.23 | 67 |
| K1-70 0.01 µg + TSH[b] | 92.18 ± 10.18 | 73.26 ± 6.48 | 79 |
| K1-70 0.1 µg + TSH[b] | 9.63 ± 0.78 | 7.55 ± 0.73 | 78 |
| K1-70 1.0 µg + TSH[b] | 2.01 ± 1.50 | 2.46 ± 0.55 | 122 |
| K1-70 10 µg + TSH[b] | 1.45 ± 0.19 | 2.18 ± 0.16 | 150 |

TABLE 15k-continued

TSH induced cyclic AMP production in CHO cells expressing wild type TSHR and TSHR with Tyr206 mutated to Ala. Effect of different dilutions of human monoclonal antibody to the TSHR (K1-70) with TSH antagonist activity

| | | | |
|---|---|---|---|
| K1-70 100 µg + TSH[b] | 1.62 ± 0.44 | 2.31 ± 0.08 | 143 |
| K1-70 100 µg | 1.44 ± 0.23 | 2.13 ± 0.38 | 148 |
| [b]TSH (2) | 107.85 ± 5.97 | 69.48 ± 2.42 | 64 |

| | % inhibition of TSH stimulation[c] | |
|---|---|---|
| Antibody concentration | Wild type TSHR | Mutated TSHR |
| 5B3 10 µg/mL | 0 | 10 |
| 5B3 100 µg/mL | 0 | 9 |
| K1-70 0.001 µg | 0 | 18 |
| K1-70 0.01 µg/mL | 0 | 12 |
| K1-70 0.1 µg/mL | 90 | 91 |
| K1-70 1 µg/mL | 98 | 97 |
| K1-70 10 µg/mL | 98 | 97 |
| K1-70 100 µg/mL | 98 | 97 |
| [b]TSH (2) | 0 | 16 |

See legend to Table 15a for details.

TABLE 15l

TSH induced cyclic AMP production in CHO cells expressing wild type TSHR and TSHR with Lys209 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/ |
|---|---|---|---|
| Test sample[a] | Wild type TSHR | Mutated TSHR | wild type (%) |
| Cyclic AMP assay buffer only | 0.88 ± 0.03 | 2.14 ± 0.56 | 243 |
| TSH[b] | 78.97 ± 8.73 | 57.94 ± 4.39 | 73 |
| 5B3 10 µg/mL + TSH[b] | 76.61 ± 6.55 | 56.52 ± 4.26 | 74 |
| 5B3 100 µg/mL + TSH[b] | 87.72 ± 5.48 | 55.93 ± 3.69 | 64 |
| K1-70 0.001 µg + TSH[b] | 97.83 ± 2.41 | 52.17 ± 7.95 | 53 |
| K1-70 0.01 µg + TSH[b] | 99.22* | 42.31 ± 6.68 | 43 |
| K1-70 0.1 µg + TSH[b] | 9.58 ± 1.13 | 5.45 ± 2.69 | 57 |
| K1-70 1.0 µg + TSH[b] | 1.36 ± 0.10 | 1.43 ± 0.13 | 105 |
| K1-70 10 µg + TSH[b] | 0.88 ± 0 | 1.37 ± 0.29 | 156 |
| K1-70 100 µg + TSH[b] | 0.98 ± 0.24 | 1.58 ± 0.10 | 161 |
| K1-70 100 µg | 0.81 ± 0.09 | 1.84 ± 0.32 | 227 |
| [b]TSH (2) | 91.50 ± 6.84 | 47.73 ± 3.41 | 52 |

| | % inhibition of TSH stimulation[c] | |
|---|---|---|
| Antibody concentration | Wild type TSHR | Mutated TSHR |
| 5B3 10 µg/mL | 3 | 2 |
| 5B3 100 µg/mL | 0 | 3 |
| K1-70 0.001 µg | 0 | 10 |
| K1-70 0.01 µg/mL | 0 | 27 |
| K1-70 0.1 µg/mL | 88 | 91 |
| K1-70 1 µg/mL | 98 | 98 |
| K1-70 10 µg/mL | 99 | 98 |
| K1-70 100 µg/mL | 99 | 97 |
| [b]TSH (2) | 0 | 18 |

See legend to Table 15a for details.

TABLE 15m

TSH induced cyclic AMP production in CHO cells expressing wild type TSHR and TSHR with Asp232 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/ |
|---|---|---|---|
| Test sample[a] | Wild type TSHR | Mutated TSHR | wild type (%) |
| Cyclic AMP assay buffer only | 1.93 ± 0.10 | 2.61 ± 0.62 | 135 |
| TSH[b] | 82.02 ± 7.26 | 57.02 ± 6.10 | 70 |
| 5B3 10 µg/mL + TSH[b] | 86.80 ± 8.83 | 51.42 ± 3.83 | 59 |
| 5B3 100 µg/mL + TSH[b] | 92.84 ± 3.94 | 53.61 ± 5.00 | 58 |
| K1-70 0.001 µg + TSH[b] | 96.66 ± 2.53 | 56.21 ± 2.78 | 58 |
| K1-70 0.01 µg + TSH[b] | 93.85 ± 4.23 | 32.28 ± 7.68 | 34 |
| K1-70 0.1 µg + TSH[b] | 4.46 ± 1.38 | 2.98 ± 0.19 | 67 |
| K1-70 1.0 µg + TSH[b] | 1.66 ± 0.13 | 2.03 ± 0.10 | 122 |
| K1-70 10 µg + TSH[b] | 1.71 ± 0.25 | 2.35 ± 0.21 | 137 |
| K1-70 100 µg + TSH[b] | 1.81 ± 0.34 | 2.62 ± 0.17 | 145 |
| K1-70 100 µg | 1.13 ± 0.97 | 2.18 ± 0.32 | 193 |
| [b]TSH (2) | 82.64 ± 7.95 | 62.58 ± 3.86 | 76 |

| | % inhibition of TSH stimulation[c] | |
|---|---|---|
| Antibody concentration | Wild type TSHR | Mutated TSHR |
| 5B3 10 µg/mL | 0 | 10 |
| 5B3 100 µg/mL | 0 | 6 |
| K1-70 0.001 µg | 0 | 1 |
| K1-70 0.01 µg/mL | 0 | 43 |
| K1-70 0.1 µg/mL | 95 | 95 |
| K1-70 1 µg/mL | 98 | 96 |
| K1-70 10 µg/mL | 98 | 96 |
| K1-70 100 µg/mL | 98 | 95 |
| [b]TSH (2) | 0 | 0 |

See legend to Table 15a for details.

TABLE 15n

TSH induced cyclic AMP production in CHO cells expressing wild type TSHR and TSHR with Gln235 mutated to Ala. Effect of different dilutions of human monoclonal antibody to the TSHR (K1-70) with TSH antagonist activity Experiment 1

| | Cyclic AMP produced (pmol/mL; mean ± SD, n = 3) | | Mutated/ |
|---|---|---|---|
| Test sample[a] | Wild type TSHR | Mutated TSHR | wild type (%) |
| Cyclic AMP assay buffer only | 1.55 ± 0.63 | 3.85 ± 0.62 | 248 |
| TSH[b] | 79.85 ± 5.00 | 55.54 ± 2.28 | 70 |
| 5B3 10 µg/mL + TSH[b] | 80.10 ± 8.09 | 63.73 ± 3.15 | 80 |
| 5B3 100 µg/mL + TSH[b] | 93.18 ± 7.43 | 58.27 ± 3.67 | 63 |
| K1-70 0.001 µg + TSH[b] | 75.94 ± 9.09 | 50.44 ± 3.80 | 66 |
| K1-70 0.01 µg + TSH[b] | 83.71 ± 2.23 | 51.03 ± 3.63 | 61 |
| K1-70 0.1 µg + TSH[b] | 7.69 ± 0.71 | 23.70 ± 3.03 | 308 |
| K1-70 1.0 µg + TSH[b] | 1.05 ± 0.12 | 5.05 ± 0.37 | 481 |
| K1-70 10 µg + TSH[b] | 1.81 ± 0.58 | 3.76 ± 0.11 | 208 |
| K1-70 100 µg + TSH[b] | 1.43 ± 0.56 | 4.93 ± 0.84 | 345 |
| K1-70 100 µg | 0.76 ± 0.42 | 3.59 ± 0.48 | 472 |
| [b]TSH (2) | 80.04 ± 7.76 | 48.55 ± 4.54 | 61 |

| | % inhibition of TSH stimulation[c] | |
|---|---|---|
| Antibody concentration | Wild type TSHR | Mutated TSHR |
| 5B3 10 µg/mL | 0 | 0 |
| 5B3 100 µg/mL | 0 | 0 |
| K1-70 0.001 µg | 5 | 9 |
| K1-70 0.01 µg/mL | 0 | 8 |

TABLE 15n-continued

TSH induced cyclic AMP production in CHO cells expressing wild type TSHR and TSHR with Gln235 mutated to Ala. Effect of different dilutions of human monoclonal antibody to the TSHR (K1-70) with TSH antagonist activity

| | | |
|---|---|---|
| K1-70 0.1 µg/mL | 90 | 57 |
| K1-70 1 µg/mL | 99 | 91 |
| K1-70 10 µg/mL | 98 | 93 |
| K1-70 100 µg/mL | 98 | 91 |
| [b]TSH (2) | 0 | 13 |

Experiment 2

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 0.88 ± 0.09 | 2.06 ± 0.39 | 234 |
| TSH[b] | 56.39 ± 3.44 | 56.59 ± 2.20 | 100 |
| 5B3 10 µg/mL + TSH[b] | 62.97 ± 1.58 | 48.72 ± 6.02 | 77 |
| 5B3 100 µg/mL + TSH[b] | 60.63 ± 1.31 | 57.90 ± 6.25 | 95 |
| K1-70 0.001 µg + TSH[b] | 61.57 ± 5.25 | 54.73 ± 13.72 | 89 |
| K1-70 0.01 µg + TSH[b] | 55.31 ± 5.21 | 61.63 ± 17.52 | 111 |
| K1-70 0.1 µg + TSH[b] | 30.91 ± 2.16 | 27.18 ± 5.31 | 88 |
| K1-70 1.0 µg + TSH[b] | 1.95 ± 1.37 | 2.82 ± 0.34 | 145 |
| K1-70 10 µg + TSH[b] | 1.15 ± 0.35 | 1.40 ± 0.15 | 122 |
| K1-70 100 µg + TSH[b] | 1.12 ± 0.41 | 1.65 ± 0.29 | 147 |
| K1-70 100 µg | 0.63 ± 0.11 | 1.20 ± 0.07 | 190 |
| [b]TSH (2) | 77.33 ± 18.51 | 55.10 ± 2.99 | 71 |

| Antibody concentration | % inhibition of TSH stimulation[c] | |
|---|---|---|
| | Wild type TSHR | Mutated TSHR |
| 5B3 10 µg/mL | 0 | 14 |
| 5B3 100 µg/mL | 0 | 0 |
| K1-70 0.001 µg | 0 | 3 |
| K1-70 0.01 µg/mL | 2 | 0 |
| K1-70 0.1 µg/mL | 45 | 52 |
| K1-70 1 µg/mL | 97 | 95 |
| K1-70 10 µg/mL | 98 | 98 |
| K1-70 100 µg/mL | 98 | 97 |
| [b]TSH (2) | 0 | 3 |

See legend to Table 15a for details.

TABLE 15o

TSH induced cyclic AMP production in CHO cells expressing wild type TSHR and TSHR with Lys250 mutated to Ala. Effect of different dilutions of human monoclonal antibody to the TSHR (K1-70) with TSH antagonist activity

Experiment 1

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.37 ± 0.11 | 5.15 ± 0.63 | 376 |
| TSH[b] | 77.89 ± 4.29 | 64.69 ± 4.82 | 83 |
| 5B3 10 µg/mL + TSH[b] | 77.80 ± 3.64 | 67.66 ± 1.21 | 87 |
| 5B3 100 µg/mL + TSH[b] | 79.92 ± 5.52 | 66.12 ± 2.92 | 83 |
| K1-70 0.001 µg + TSH[b] | 80.20 ± 4.04 | 64.15 ± 0 | 80 |
| K1-70 0.01 µg + TSH[b] | 68.64 ± 9.75 | 57.52 ± 4.14 | 84 |
| K1-70 0.1 µg + TSH[b] | 5.75 ± 0.88 | 42.40 ± 1.47 | 737 |
| K1-70 1.0 µg + TSH[b] | 1.67 ± 0.29 | 6.09 ± 0.05 | 365 |
| K1-70 10 µg + TSH[b] | 1.37 ± 0.06 | 4.29 ± 0.62 | 313 |
| K1-70 100 µg + TSH[b] | 1.48 ± 0.08 | 4.75 ± 0.08 | 319 |
| K1-70 100 µg | 1.66 ± 0.33 | 3.17 ± 0.19 | 191 |
| [b]TSH (2) | 84.45 ± 1.63 | 58.26 ± 3.24 | 69 |

TABLE 15o-continued

TSH induced cyclic AMP production in CHO cells expressing wild type TSHR and TSHR with Lys250 mutated to Ala. Effect of different dilutions of human monoclonal antibody to the TSHR (K1-70) with TSH antagonist activity

| Antibody concentration | % inhibition of TSH stimulation[c] | |
|---|---|---|
| | Wild type TSHR | Mutated TSHR |
| 5B3 10 µg/mL | 0.1 | 0 |
| 5B3 100 µg/mL | 0 | 0 |
| K1-70 0.001 µg | 0 | 1 |
| K1-70 0.01 µg/mL | 12 | 11 |
| K1-70 0.1 µg/mL | 93 | 34 |
| K1-70 1 µg/mL | 98 | 91 |
| K1-70 10 µg/mL | 98 | 93 |
| K1-70 100 µg/mL | 98 | 93 |
| [b]TSH (2) | 0 | 10 |

Experiment 2

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 0.36 ± 0.14 | 0.90 ± 0.36 | 250 |
| TSH[b] | 86.55 ± 2.19 | 54.99 ± 5.70 | 64 |
| 5B3 10 µg/mL + TSH[b] | 90.58 ± 4.34 | 47.09 ± 1.88 | 52 |
| 5B3 100 µg/mL + TSH[b] | 87.52 ± 2.25 | 54.67 ± 4.74 | 62 |
| K1-70 0.001 µg + TSH[b] | 88.48 ± 4.56 | 44.31 ± 3.00 | 50 |
| K1-70 0.01 µg + TSH[b] | 86.20 ± 7.37 | 45.44 ± 2.16 | 53 |
| K1-70 0.1 µg + TSH[b] | 8.81 ± 0.84 | 27.64 ± 1.41 | 314 |
| K1-70 1.0 µg + TSH[b] | 1.05 ± 0.35 | 1.98 ± 0.29 | 189 |
| K1-70 10 µg + TSH[b] | 0.76 ± 0.58 | 0.72 ± 0.11 | 95 |
| K1-70 100 µg + TSH[b] | 0.40 ± 0.09 | 0.64 ± 0.16 | 160 |
| K1-70 100 µg | 0.61 ± 0.20 | 0.90 ± 0.15 | 148 |
| [b]TSH (2) | 75.91 ± 7.48 | 51.08 ± 3.64 | 67 |

| Antibody concentration | % inhibition of TSH stimulation[c] | |
|---|---|---|
| | Wild type TSHR | Mutated TSHR |
| 5B3 10 µg/mL | 0 | 14 |
| 5B3 100 µg/mL | 0 | 1 |
| K1-70 0.001 µg | 0 | 19 |
| K1-70 0.01 µg/mL | 0 | 17 |
| K1-70 0.1 µg/mL | 90 | 50 |
| K1-70 1 µg/mL | 99 | 96 |
| K1-70 10 µg/mL | 99 | 99 |
| K1-70 100 µg/mL | 99 | 99 |
| [b]TSH (2) | 12 | 7 |

See legend to Table 15a for details.

TABLE 15p

TSH induced cyclic AMP production in CHO cells expressing wild type TSHR and TSHR with Glu251 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/ wild type (%) |
|---|---|---|---|
| | Wild type TSHR | Mutated TSHR | |
| Cyclic AMP assay buffer only | 1.78 ± 0.15 | 4.76 ± 0.73 | 267 |
| TSH[b] | 97.46 ± 6.92 | 76.06 ± 10.78 | 78 |
| 5B3 10 µg/mL + TSH[b] | 92.91 ± 4.18 | 68.71 ± 3.38 | 74 |
| 5B3 100 µg/mL + TSH[b] | 86.30 ± 10.26 | 76.69 ± 7.01 | 89 |
| K1-70 0.001 µg + TSH[b] | 90.50 ± 10.61 | 76.43 ± 13.91 | 84 |
| K1-70 0.01 µg + TSH[b] | 88.13 ± 2.76 | 60.62 ± 2.31 | 69 |
| K1-70 0.1 µg + TSH[b] | 4.06 ± 0.74 | 6.28 ± 2.22 | 155 |
| K1-70 1.0 µg + TSH[b] | 1.73 ± 0.11 | 2.17 ± 0.04 | 125 |

TABLE 15p-continued

TSH induced cyclic AMP production in CHO cells expressing wild type TSHR and TSHR with Glu251 mutated to Ala. Effect of different dilutions of human monoclonal antibody to the TSHR (K1-70) with TSH antagonist activity

| | | | |
|---|---|---|---|
| K1-70 10 µg + TSH[b] | 1.58 ± 0.15 | 3.18 ± 1.36 | 201 |
| K1-70 100 µg + TSH[b] | 1.66 ± 0.03 | 2.72 ± 0.52 | 164 |
| K1-70 100 µg | 1.54 ± 0.15 | 4.41 ± 1.24 | 286 |
| [b]TSH (2) | 104.06 ± 3.26 | 87.36 ± 14.82 | 84 |

| | % inhibition of TSH stimulation[c] | |
|---|---|---|
| Antibody concentration | Wild type TSHR | Mutated TSHR |
| 5B3 10 µg/mL | 5 | 10 |
| 5B3 100 µg/mL | 11 | 0 |
| K1-70 0.001 µg | 7 | 0 |
| K1-70 0.01 µg/mL | 10 | 20 |
| K1-70 0.1 µg/mL | 96 | 92 |
| K1-70 1 µg/mL | 98 | 97 |
| K1-70 10 µg/mL | 98 | 96 |
| K1-70 100 µg/mL | 98 | 96 |
| [b]TSH (2) | 0 | 0 |

See legend to Table 15a for details.

TABLE 15q

TSH induced cyclic AMP production in CHO cells expressing wild type TSHR and TSHR with Arg255 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 1.65 ± 0.42 | 2.04 ± 0.48 | 124 |
| TSH[b] | 62.43 ± 4.24 | 63.86 ± 4.18 | 102 |
| 5B3 10 µg/mL + TSH[b] | 75.59* | 56.36 ± 3.72 | 75 |
| 5B3 100 µg/mL + TSH[b] | 68.28 ± 4.90 | 62.53 ± 5.33 | 92 |
| K1-70 0.001 µg + TSH[b] | 89.67 ± 5.46 | 65.87 ± 8.49 | 73 |
| K1-70 0.01 µg + TSH[b] | 87.27 ± 9.27 | 55.02 ± 4.02 | 63 |
| K1-70 0.1 µg + TSH[b] | 33.63 ± 2.97 | 19.38 ± 3.27 | 58 |
| K1-70 1.0 µg + TSH[b] | 2.30 ± 0.34 | 3.96 ± 1.02 | 172 |
| K1-70 10 µg + TSH[b] | 1.28 ± 1.09 | 2.38 ± 0.52 | 186 |
| K1-70 100 µg + TSH[b] | 2.88 ± 1.98 | 1.94 ± 0.45 | 67 |
| K1-70 100 µg | 1.16 ± 0.45 | 1.34 ± 0.50 | 116 |
| [b]TSH (2) | 68.39 ± 1.88 | 59.58 ± 1.64 | 87 |

| | % inhibition of TSH stimulation[c] | |
|---|---|---|
| Antibody concentration | Wild type TSHR | Mutated TSHR |
| 5B3 10 µg/mL | 0 | 12 |
| 5B3 100 µg/mL | 0 | 2 |
| K1-70 0.001 µg | 0 | 0 |
| K1-70 0.01 µg/mL | 0 | 14 |
| K1-70 0.1 µg/mL | 46 | 70 |
| K1-70 1 µg/mL | 96 | 94 |
| K1-70 10 µg/mL | 98 | 96 |
| K1-70 100 µg/mL | 95 | 97 |
| [b]TSH (2) | 0 | 7 |

See legend to Table 15a for details.

TABLE 15r

TSH induced cyclic AMP production in CHO cells expressing wild type TSHR and TSHR with Thr257 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 0.67 ± 0.13 | 2.08 ± 0.22 | 310 |
| TSH[b] | 66.07 ± 7.95 | 93.16 ± 6.69 | 141 |
| 5B3 10 µg/mL + TSH[b] | 85.93 ± 3.35 | 94.23 ± 2.23 | 110 |
| 5B3 100 µg/mL + TSH[b] | 83.73 ± 9.86 | 86.78 ± 13.03 | 104 |
| K1-70 0.001 µg + TSH[b] | 88.71 ± 17.01 | 87.21 ± 14.51 | 98 |
| K1-70 0.01 µg + TSH[b] | 84.72 ± 18.03 | 97.91 ± 10.18 | 116 |
| K1-70 0.1 µg + TSH[b] | 55.12 ± 14.21 | 80.13 ± 9.78 | 145 |
| K1-70 1.0 µg + TSH[b] | 1.66 ± 0.44 | 3.97 ± 0.06 | 239 |
| K1-70 10 µg + TSH[b] | 0.91 ± 0.37 | 2.00 ± 0.28 | 220 |
| K1-70 100 µg + TSH[b] | 0.87 ± 0.31 | 2.25 ± 0.24 | 259 |
| K1-70 100 µg | 1.14 ± 0.11 | 1.44 ± 0.15 | 126 |
| [b]TSH (2) | 92.96 ± 1.88 | 85.41 ± 4.14 | 92 |

| | % inhibition of TSH stimulation[c] | |
|---|---|---|
| Antibody concentration | Wild type TSHR | Mutated TSHR |
| 5B3 10 µg/mL | 0 | 0 |
| 5B3 100 µg/mL | 0 | 7 |
| K1-70 0.001 µg | 0 | 6 |
| K1-70 0.01 µg/mL | 0 | 0 |
| K1-70 0.1 µg/mL | 17 | 14 |
| K1-70 1 µg/mL | 97 | 96 |
| K1-70 10 µg/mL | 99 | 98 |
| K1-70 100 µg/mL | 99 | 98 |
| [b]TSH (2) | 0 | 8 |

See legend to Table 15a for details.

TABLE 15s

TSH induced cyclic AMP production in CHO cells expressing wild type TSHR and TSHR with Trp258 mutated to Ala. Effect of different dilutions of human monoclonal antibody to the TSHR (K1-70) with TSH antagonist activity

| | Cyclic AMP produced (pmol/mL; mean ± SD, n = 3) | | Mutated/wild type (%) |
|---|---|---|---|
| Test sample[a] | Wild type TSHR | Mutated TSHR | |
| Cyclic AMP assay buffer only | 1.09 ± 0.13 | 1.93 ± 0.27 | 177 |
| TSH[b] | 58.81 ± 3.32 | 59.87 ± 5.65 | 102 |
| 5B3 10 µg/mL + TSH[b] | 67.66 ± 2.16 | 50.71 ± 1.58 | 75 |
| 5B3 100 µg/mL + TSH[b] | 72.85 ± 11.12 | 57.62 ± 12.06 | 79 |
| K1-70 0.001 µg + TSH[b] | 64.08 ± 4.50 | 51.10 ± 5.86 | 80 |
| K1-70 0.01 µg + TSH[b] | 68.76 ± 7.18 | 51.22 ± 2.22 | 74 |
| K1-70 0.1 µg + TSH[b] | 12.46 ± 3.44 | 11.56 ± 5.39 | 93 |
| K1-70 1.0 µg + TSH[b] | 0.99 ± 0.52 | 1.38 ± 0.12 | 139 |
| K1-70 10 µg + TSH[b] | 0.64 ± 0.08 | 1.06 ± 0.21 | 166 |
| K1-70 100 µg + TSH[b] | 0.77 ± 0.27 | 1.38 ± 0.65 | 179 |
| K1-70 100 µg | 0.52 ± 0.23 | 1.34 ± 0.29 | 258 |
| [b]TSH (2) | 69.57 ± 4.31 | 47.82 ± 3.23 | 69 |

| | % inhibition of TSH stimulation[c] | |
|---|---|---|
| Antibody concentration | Wild type TSHR | Mutated TSHR |
| 5B3 10 µg/mL | 0 | 15 |
| 5B3 100 µg/mL | 0 | 4 |
| K1-70 0.001 µg | 0 | 15 |
| K1-70 0.01 µg/mL | 0 | 14 |
| K1-70 0.1 µg/mL | 79 | 81 |
| K1-70 1 µg/mL | 98 | 98 |

TABLE 15s-continued

TSH induced cyclic AMP production in CHO cells expressing wild type TSHR and TSHR with Trp258 mutated to Ala. Effect of different dilutions of human monoclonal antibody to the TSHR (K1-70) with TSH antagonist activity

| | | |
|---|---|---|
| K1-70 10 μg/mL | 99 | 98 |
| K1-70 100 μg/mL | 99 | 98 |
| [b]TSH (2) | 0 | 20 |

See legend to Table 15a for details.

TABLE 15t

TSH induced cyclic AMP production in CHO cells expressing wild type TSHR and TSHR with Arg274 mutated to Ala. Effect of different dilutions of human monoclonal antibody to the TSHR (K1-70) with TSH antagonist activity

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.91 ± 0.23 | 2.61 ± 0.37 | 137 |
| TSH[b] | 97.06 ± 3.16 | 99.22 ± 9.24 | 102 |
| 5B3 10 μg/mL + TSH[b] | 115.56 ± 7.73 | 106.00 ± 9.5 | 92 |
| 5B3 100 μg/mL + TSH[b] | 120.83 ± 30.02 | 95.33 ± 4.48 | 79 |
| K1-70 0.001 μg + TSH[b] | 146.34 ± 0 | 117.54 ± 6.34 | 80 |
| K1-70 0.01 μg + TSH[b] | 133.74 ± 11.45 | 105.88 ± 9.33 | 79 |
| K1-70 0.1 μg + TSH[b] | 9.83 ± 1.02 | 4.09 ± 0.09 | 42 |
| K1-70 1.0 μg + TSH[b] | 1.99 ± 0.45 | 1.70 ± 0.34 | 85 |
| K1-70 10 μg + TSH[b] | 1.49 ± 0.15 | 1.90 ± 0.14 | 128 |
| K1-70 100 μg + TSH[b] | 1.54 ± 0.16 | 1.62 ± 0.21 | 105 |
| K1-70 100 μg | 1.30 ± 0.25 | 1.75 ± 0.34 | 135 |
| [b]TSH (2) | 109.43 ± 12.79 | 100.21 ± 9.82 | 92 |

| Antibody concentration | % inhibition of TSH stimulation[c] | |
|---|---|---|
| | Wild type TSHR | Mutated TSHR |
| 5B3 10 μg/mL | 0 | 0 |
| 5B3 100 μg/mL | 0 | 4 |
| K1-70 0.001 μg | 0 | 0 |
| K1-70 0.01 μg/mL | 0 | 0 |
| K1-70 0.1 μg/mL | 90 | 96 |
| K1-70 1 μg/mL | 98 | 98 |
| K1-70 10 μg/mL | 98 | 98 |
| K1-70 100 μg/mL | 98 | 98 |
| [b]TSH (2) | 0 | 0 |

See legend to Table 15a for details.

TABLE 15u

TSH induced cyclic AMP production in CHO cells expressing wild type TSHR and TSHR with Asp276 mutated to Ala. Effect of different dilutions of human monoclonal antibody to the TSHR (K1-70) with TSH antagonist activity Experiment 1

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 1.19 ± 0.45 | 7.20 ± 0.74 | 605 |
| TSH[b] | 78.01 ± 7.81 | 71.24 ± 4.72 | 91 |
| 5B3 10 μg/mL + TSH[b] | 79.58 ± 5.41 | 66.78 ± 3.68 | 84 |
| 5B3 100 μg/mL + TSH[b] | 72.68 ± 2.09 | 68.46 ± 7.03 | 94 |
| K1-70 0.001 μg + TSH[b] | 76.64 ± 4.38 | 68.87 ± 4.91 | 90 |
| K1-70 0.01 μg + TSH[b] | 71.64 ± 8.57 | 63.50 ± 3.61 | 89 |
| K1-70 0.1 μg + TSH[b] | 9.89 ± 3.19 | 67.79 ± 9.74 | 685 |
| K1-70 1.0 μg + TSH[b] | 1.02 ± 0.24 | 10.21 ± 0.58 | 1001 |
| K1-70 10 μg + TSH[b] | 0.36 ± 0.31 | 5.07 ± 1.35 | 1408 |
| K1-70 100 μg + TSH[b] | 0.70 ± 0.26 | 5.14 ± 3.18 | 734 |
| K1-70 100 μg | 0.21 ± 0.30 | 3.56 ± 0.74 | 1695 |
| [b]TSH (2) | 74.30 ± 8.20 | 67.04 ± 6.95 | 90 |

| Antibody concentration | % inhibition of TSH stimulation[c] | |
|---|---|---|
| | Wild type TSHR | Mutated TSHR |
| 5B3 10 μg/mL | 0 | 6 |
| 5B3 100 μg/mL | 7 | 4 |
| K1-70 0.001 μg | 2 | 3 |
| K1-70 0.01 μg/mL | 8 | 11 |
| K1-70 0.1 μg/mL | 87 | 5 |
| K1-70 1 μg/mL | 99 | 86 |
| K1-70 10 μg/mL | 99 | 93 |
| K1-70 100 μg/mL | 99 | 93 |
| [b]TSH (2) | 5 | 6 |

Experiment 2

| Test sample[a] | Cyclic AMP produced (pmol/mL; mean ± SD, n = 3) | | Mutated/wild type (%) |
|---|---|---|---|
| | Wild type TSHR | Mutated TSHR | |
| Cyclic AMP assay buffer only | 0.65 ± 0.27 | 12.17 ± 1.47 | 1872 |
| TSH[b] | 95.81 ± 9.24 | 74.82 ± 9.47 | 78 |
| 5B3 10 μg/mL + TSH[b] | 106.73 ± 8.52 | 71.56 ± 4.30 | 67 |
| 5B3 100 μg/mL + TSH[b] | 101.10 ± 2.58 | 75.93 ± 6.03 | 75 |
| K1-70 0.001 μg + TSH[b] | 104.99 ± 10.76 | 72.63 ± 9.99 | 69 |
| K1-70 0.01 μg + TSH[b] | 108.84 ± 12.41 | 78.47 ± 3.50 | 72 |
| K1-70 0.1 μg + TSH[b] | 18.40 ± 12.30 | 66.36 ± 5.38 | 361 |
| K1-70 1.0 μg + TSH[b] | 1.49 ± 0.67 | 9.63 ± 1.53 | 646 |
| K1-70 10 μg + TSH[b] | 0.85 ± 0.28 | 6.66 ± 0.81 | 784 |
| K1-70 100 μg + TSH[b] | 1.58 ± 0.41 | 6.53 ± 1.33 | 413 |
| K1-70 100 μg | 0.64 ± 0.04 | 5.88 ± 1.36 | 919 |
| [b]TSH (2) | 92.86 ± 4.90 | 61.21 ± 1.70 | 66 |

| Antibody concentration | % inhibition of TSH stimulation[c] | |
|---|---|---|
| | Wild type TSHR | Mutated TSHR |
| 5B3 10 μg/mL | 0 | 4 |
| 5B3 100 μg/mL | 0 | 0 |
| K1-70 0.001 μg | 0 | 3 |
| K1-70 0.01 μg/mL | 0 | 0 |
| K1-70 0.1 μg/mL | 81 | 11 |
| K1-70 1 μg/mL | 98 | 87 |
| K1-70 10 μg/mL | 99 | 91 |
| K1-70 100 μg/mL | 98 | 91 |
| [b]TSH (2) | 3 | 18 |

See legend to Table 15a for details.

TABLE 15v

TSH induced cyclic AMP production in CHO cells expressing wild type TSHR and TSHR with Ser281 mutated to Ala. Effect of different dilutions of human monoclonal antibody to the TSHR (K1-70) with TSH antagonist activity Experiment 1

| | Cyclic AMP produced (pmol/mL; mean ± SD, n = 3) | | |
|---|---|---|---|
| Test sample[a] | Wild type TSHR | Mutated TSHR | Mutated/wild type (%) |
| Cyclic AMP assay buffer only | 1.27 ± 0.10 | 1.47 ± 0.26 | 116 |
| TSH[b] | 87.93 ± 17.36 | 69.80 ± 10.34 | 79 |
| 5B3 10 μg/mL + TSH[b] | 84.72 ± 5.57 | 56.72 ± 2.69 | 67 |
| 5B3 100 μg/mL + TSH[b] | 87.99 ± 4.63 | 62.11 ± 5.75 | 71 |
| K1-70 0.001 μg + TSH[b] | 86.36* | 56.42 ± 8.88 | 65 |
| K1-70 0.01 μg + TSH[b] | 79.79 ± 8.53 | 50.66 ± 7.96 | 63 |
| K1-70 0.1 μg + TSH[b] | 25.52 ± 8.47 | 40.25 ± 1.49 | 158 |
| K1-70 1.0 μg + TSH[b] | 1.47 ± 0.12 | 2.19 ± 0.52 | 150 |
| K1-70 10 μg + TSH[b] | 1.51 ± 0.11 | 2.08 ± 0.95 | 138 |
| K1-70 100 μg + TSH[b] | 1.18 ± 0.32 | 1.52 ± 0.19 | 129 |
| K1-70 100 μg | 0.99 ± 0.29 | 1.22 ± 0.07 | 123 |
| [b]TSH (2) | 99.13 ± 16.11 | 56.62 ± 5.48 | 57 |

| | % inhibition of TSH stimulation[c] | |
|---|---|---|
| Antibody concentration | Wild type TSHR | Mutated TSHR |
| 5B3 10 μg/mL | 4 | 19 |
| 5B3 100 μg/mL | 0 | 11 |
| K1-70 0.001 μg | 2 | 19 |
| K1-70 0.01 μg/mL | 9 | 27 |
| K1-70 0.1 μg/mL | 71 | 42 |
| K1-70 1 μg/mL | 98 | 97 |
| K1-70 10 μg/mL | 98 | 97 |
| K1-70 100 μg/mL | 99 | 98 |
| [b]TSH (2) | 0 | 19 |

TABLE 15v-continued

TSH induced cyclic AMP production in CHO cells expressing wild type TSHR and TSHR with Ser281 mutated to Ala. Effect of different dilutions of human monoclonal antibody to the TSHR (K1-70) with TSH antagonist activity Experiment 2

| | Cyclic AMP produced (pmol/mL; mean ± SD, n = 3) | | |
|---|---|---|---|
| Test sample[a] | Wild type TSHR | Mutated TSHR | Mutated/wild type (%) |
| Cyclic AMP assay buffer only | 0.51 ± 0.27 | 2.70 ± 0.22 | 529 |
| TSH[b] | 75.33 ± 3.18 | 68.98 ± 3.03 | 92 |
| 5B3 10 μg/mL + TSH[b] | 82.84 ± 2.66 | 66.07 ± 3.09 | 80 |
| 5B3 100 μg/mL + TSH[b] | 82.89 ± 4.01 | 72.42 ± 3.12 | 87 |
| K1-70 0.001 μg + TSH[b] | 77.43 ± 3.86 | 53.94 ± 3.95 | 70 |
| K1-70 0.01 μg + TSH[b] | 87.16 ± 9.24 | 51.53 ± 6.84 | 59 |
| K1-70 0.1 μg + TSH[b] | 18.38 ± 2.79 | 40.45 ± 9.45 | 220 |
| K1-70 1.0 μg + TSH[b] | 0.60 ± 0.27 | 2.56 ± 0.63 | 427 |
| K1-70 10 μg + TSH[b] | 0.38 ± 0.07 | 2.17 ± 0.83 | 571 |
| K1-70 10 μg + TSH[b] | 0.42 ± 0.20 | 1.85 ± 0.40 | 440 |
| K1-70 100 μg | 0.22 ± 0.07 | 2.08 ± 1.29 | 945 |
| [b]TSH (2) | 83.91 ± 6.87 | 65.94 ± 6.27 | 79 |

| | % inhibition of TSH stimulation[c] | |
|---|---|---|
| Antibody concentration | Wild type TSHR | Mutated TSHR |
| 5B3 10 μg/mL | 0 | 4 |
| 5B3 100 μg/mL | 0 | 0 |
| K1-70 0.001 μg | 0 | 22 |
| K1-70 0.01 μg/mL | 0 | 25 |
| K1-70 0.1 μg/mL | 76 | 41 |
| K1-70 1 μg/mL | 99 | 96 |
| K1-70 10 μg/mL | 99 | 97 |
| K1-70 100 μg/mL | 99 | 97 |
| [b]TSH (2) | 0 | 4 |

See legend to Table 15a for details.

TABLE 16

Summary of effects of TSHR mutations (relative to wild type) on the ability of K1-18 IgG to stimulate cyclic AMP and K1-70 IgG to block TSH stimulation of cyclic AMP production in TSHR transfected CHO cells

| TSHR mutation | Stimulation (relative to wild type) of cyclic AMP production by TSH | Stimulation (relative to wild type) of cyclic AMP production by K1-18 IgG | Blocking (relative to wild type) of TSH stimulation of cyclic AMP production by K1-70 IgG |
|---|---|---|---|
| Wild type | +++++ | +++++ | +++++ |
| Asp43 Ala | +++++ | +++++ | +++++ |
| Ile60 Ala | +++++ | +++++ | ++ |
| Glu61 Ala | +++++ | +++++ | +++ |
| Thr104 Ala | +++++ | +++++ | +++++ |
| His105 Ala | +++++ | +++++ | +++++ |
| Asp151 Ala | ++++ | ++++ | +++++ |
| Glu157 Ala | +++++ | 0 | NT |
| Glu178 Ala | +++ | ++++ | ++++ |
| Tyr185 Ala | ++++ | 0 | +++++ |
| Tyr206 Ala | +++++ | ++ | +++++ |
| Lys209 Ala | ++++ | ++++ | +++++ |
| Asp232 Ala | ++++ | 0 | +++++ |
| Gln235 Ala | ++++ | ++++ | +++++ |
| Lys250 Ala | +++++ | +++++ | +++ |
| Glu251 Ala | ++++ | ++++ | +++++ |
| Arg255 Ala | +++++ | +++++ | +++++ |
| Thr257 Ala | +++++ | +++++ | +++++ |
| Trp258 Ala | +++++ | ++ | +++++ |
| Arg274 Ala | +++++ | ++ | +++++ |
| Asp276 Ala | +++++ | +++++ | +++ |

TABLE 16-continued

Summary of effects of TSHR mutations (relative to wild type) on the ability of K1-18 IgG to stimulate cyclic AMP and K1-70 IgG to block TSH stimulation of cyclic AMP production in TSHR transfected CHO cells

| TSHR mutation | Stimulation (relative to wild type) of cyclic AMP production by TSH | Stimulation (relative to wild type) of cyclic AMP production by K1-18 IgG | Blocking (relative to wild type) of TSH stimulation of cyclic AMP production by K1-70 IgG |
|---|---|---|---|
| Ser281 Ala | +++++ | +++++ | ++++ |
| Asp160 Lys | 0 | NT | +++++ |
| Lys183 Asp* | +++++ | 0 | +++++ |

Relative effects of TSHR mutations were expressed as a percentage of activity observed with wild type as follows:-
+++++ = 100% wild type activity; ++++ = <100-80% of wild type activity; +++ = <80-60% of wild type activity; ++ = <60-40% of wild type activity; + = <40-20% of wild type activity; 0 = <20% of wild type activity.
*Blocking of stimulation for this mutation was carried out using stimulation by M22 as the mutant did not respond to TSH stimulation. M22 Fab final concentration = 3 ng/mL.

TABLE 17a

Inhibition of $^{125}$I-TSH binding to TSHR coated tubes by recombinant K1-70 Fab expressed in *E coli* HB2151 cells

| Test sample | Dilution of culture supernatant (or concentration[1] of K1-70 Fab ng/mL) | % of $^{125}$I-TSH binding | % inhibition[2] |
|---|---|---|---|
| Assay buffer only | | 12.4 | 0 |
| K1-70 Fab transformed cells but non-induced | 1:2 | 11.4 | 8.0 |
| | 1:4 | 12.3 | 0.7 |
| | 1:8 | 10.9 | 12.4 |
| | 1:16 | 11.8 | 5.0 |
| | 1:32 | 12.6 | -1.4 |
| | 1:64 | 11.9 | 3.9 |
| | 1:128 | 11.5 | 7.6 |
| | 1:256 | 10.8 | 13.5 |
| | 1:512 | 10.4 | 16.3 |
| | 1:1024 | 10.7 | 14.2 |
| K1-70 Fab transformed cells and induced | 1:2 (700) | 1.0 | 91.9 |
| | 1:4 (350) | 1.3 | 89.4 |
| | 1:8 (175) | 1.5 | 87.8 |
| | 1:16 (87.5) | 1.3 | 89.6 |
| | 1:32 (44.8) | 1.5 | 88.0 |
| | 1:64 (22.4) | 3.4 | 72.9 |
| | 1:128 (11.2) | 6.1 | 51.3 |
| | 1:256 (5.6) | 9.0 | 27.9 |
| | 1:512 (2.8) | 10.8 | 13.1 |
| | 1:1024 (1.4) | 11.6 | 6.6 |
| K1-70 Fab (from hybridoma produced IgG) | (100) | 1.6 | 87.5 |
| | (50) | 1.7 | 86.1 |
| | (25) | 2.2 | 81.9 |
| | (10) | 6.6 | 47.0 |
| | (5) | 9.9 | 20.0 |
| | (2.5) | 11.0 | 11.5 |
| | (1) | 12.4 | 0.4 |

[1]Concentration of recombinant K1-70 Fab in culture supernatant measured using the Easy-Titer Human IgG (H = L) assay kit (Pierce Biotechnology) using different concentrations of hybridoma produced K1-70 Fab as a calibration curve
[2]inhibition of binding was calculated using the formula: % inhibition = 100 − [A/B × 100] where A = % of $^{125}$I-TSH binding in the presence of test sample; and B = % of $^{125}$I-TSH binding in the presence of assay buffer (50 mM NaCl, 10 mM Tris, pH 7.8, 1% Triton X-100 and 1 mg/mL BSA).

TABLE 17b

Inhibition of TSH mediated stimulation of cyclic AMP production in CHO cells expressing the TSHR by recombinant K1-70 Fab expressed in *E coli* HB2151 cells

| Test sample | Dilution[2] of culture supernatant (or concentration[3] of K1-70 Fab ng/mL) | Cyclic AMP (pmol/mL) mean ± SD (n = 3) | % inhibition of TSH stimulation of cyclic AMP[4] |
|---|---|---|---|
| Assay buffer[1] only | | 2.39 ± 0.20 | |
| TSH 3 ng/mL | | 61.87 ± 2.74 | 0 |
| K1-70 Fab transformed cells but non-induced | 1:10 | 5.67 ± 0.31 | |
| K1-70 Fab transformed cells but non-induced + 3 ng/mL TSH | 1:5 | 70.95 ± 6.32 | -14.7 |
| | 1:10 | 76.24 ± 6.55 | -23.2 |
| | 1:20 | 67.11 ± 3.51 | -8.5 |
| | 1:40 | 61.05 ± 8.44 | 1.3 |
| | 1:80 | 64.94 ± 5.20 | -5.0 |
| K1-70 Fab transformed and induced cells | 1:10 (140) | 2.74 ± 0.59 | |
| K1-70 Fab transformed and induced cells + 3 ng/mL TSH | 1:5 (280) | 6.64 ± 0.07 | 89.3 |
| | 1:10 (140) | 9.71 ± 1.50 | 84.3 |
| | 1:20 (70) | 18.55 ± 3.30 | 70.0 |
| | 1:40 (35) | 37.29 ± 6.47 | 39.7 |
| | 1:80 (17.5) | 51.68 ± 3.59 | 16.5 |
| K1-70 Fab (from hybridoma produced IgG) | (100,000) | 1.71 ± 0.36 | |

TABLE 17b-continued

Inhibition of TSH mediated stimulation of cyclic AMP production in CHO cells expressing the TSHR by recombinant K1-70 Fab expressed in *E coli* HB2151 cells

| Test sample | Dilution[2] of culture supernatant (or concentration[3] of K1-70 Fab ng/mL) | Cyclic AMP (pmol/mL) mean ± SD (n = 3) | % inhibition of TSH stimulation of cyclic AMP[4] |
|---|---|---|---|
| K1-70 Fab (from hybridoma produced IgG) + 3 ng/mL TSH | (100,000) | 1.66 ± 0.08 | 97.3 |
| | (10,000) | 2.20 ± 0.17 | 96.4 |
| | (1,000) | 3.11 ± 0.09 | 95.0 |
| | (100) | 6.52 ± 0.07 | 89.5 |
| | (10) | 55.13 ± 5.26 | 10.9 |

[1]Assay buffer: Hanks' buffered salt solution (NaCl free) containing 1 g/L glucose, 20 mmol/L HEPES, 222 mmol/L sucrose, 15 g/L BSA and 0.5 mmol/L 2-isobutyl-1-methylxanthine pH7.4
[2]Dilutions in assay buffer
[3]Concentration of recombinant K1-70 Fab in culture supernatant measured using the Easy-Titer Human IgG (H = L) assay kit (Pierce Biotechnology) using different concentrations of hybridoma produced K1-70 Fab as a calibration curve
[4]% inhibition of TSH stimulation of cyclic AMP: % inhibition = 100 − [A/B × 100] where A = stimulation of cyclic AMP by 3 ng/mL TSH in the presence of test sample; and B = stimulation of cyclic AMP by 3 ng/mL TSH.

The invention claimed is:

1. An isolated human monoclonal or recombinant antibody or fragment thereof that binds to the TSH receptor and stimulates the TSH receptor, wherein the antibody or fragment thereof comprises:
   an antibody VL domain having the amino acid sequence shown in residues 1-129 of SEQ ID NO:33; and
   an antibody VH domain having the amino acid sequence shown in residues 1-141 of SEQ ID NO:15.

2. The antibody or fragment thereof of claim 1, wherein the antibody or fragment thereof exhibits a binding affinity for the TSH receptor of at least $10^8$ L/mol.

3. The antibody or fragment thereof of claim 1, wherein the antibody or fragment thereof exhibits a binding affinity for the TSH receptor of about $10^9$ L/mol.

4. The antibody or fragment thereof of claim 1, wherein the antibody or fragment thereof, at 1 μg/ml, inhibited greater than 85% of $^{125}$I-TSH binding to TSHR.

5. The antibody or fragment thereof of claim 1, wherein the antibody or fragment thereof, at 1 μg/ml, inhibited about 90% of $^{125}$I-TSH binding to TSHR.

6. The antibody or fragment thereof of claim 1, wherein the antibody or fragment thereof, at 1 μg/ml, inhibited greater than 85% of TSH-biotin binding to TSHR.

7. The antibody or fragment thereof of claim 1, wherein the antibody or fragment thereof, at 1 μg/ml, inhibited about 90% of TSH-biotin binding to TSHR.

8. The antibody or fragment thereof of claim 1, wherein the antibody or fragment thereof stimulates cAMP production in CHO cells expressing TSHR in a dose dependent manner.

9. A pharmaceutical composition comprising the antibody or fragment thereof of claim 1 and a pharmaceutically acceptable carrier.

* * * * *

SEQUENCE LISTING

<160> NUMBER OF SEQ ID NOS: 85

<210> SEQ ID NO 1
<211> LENGTH: 687
<212> TYPE: DNA
<213> ORGANISM: Homo sapiens

<400> SEQUENCE: 1

```
gaagtgcagc tggtggagtc tggagcagag gtgaaaaagc ccggggagtc tctgaagatc      60
tcctgcaagg gttctggata cagctttacc aactactgga tcggctgggt gcgccagatg     120
cccgggaaag gcctggagtg gatggggatc atctatcctt atgactctga taccagatat     180
agcccgtcct tcgaaggcca ggtcaccatc tcagccgaca gtccatcag gaccgcctac      240 ctgcactgga gcagcctgaa ggcctcggac accgccatgt attactgtgt gagacccgc      300 gatgggagct atccttatga tgcttttgat atctggggcc aagggacaat ggtcaccgtc     360
tcttcagcct ccaccaaggg cccatcggtc ttccccctgg cacctcctc caagagcacc      420 tctggggca gcgcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagagagtt     660
gagcccaaat cttgtgacaa aactagt                                         687
```

<210> SEQ ID NO 2
<211> LENGTH: 15
<212> TYPE: DNA
<213> ORGANISM: Homo sapiens

<400> SEQUENCE: 2

```
aactactgga tcggc                                                       15
```

<210> SEQ ID NO 3
<211> LENGTH: 51
<212> TYPE: DNA
<213> ORGANISM: Homo sapiens

<400> SEQUENCE: 3

```
atcatctatc cttatgactc tgataccaga tatagcccgt ccttcgaagg c              51
```

<210> SEQ ID NO 4
<211> LENGTH: 39
<212> TYPE: DNA
<213> ORGANISM: Homo sapiens

<400> SEQUENCE: 4
ccccgcgatg ggagctatcc ttatgatgct tttgatatc                                    39

<210> SEQ ID NO 5
<211> LENGTH: 229
<212> TYPE: PRT
<213> ORGANISM: Homo sapiens

<400> SEQUENCE: 5

Glu Val Gln Leu Val Glu Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Tyr Asp Ser Asp Thr Arg Tyr Ser Pro Ser Phe
    50                  55                  60

Glu Gly Gln Val Thr Ile Ser Ala Asp Lys Ser Ile Arg Thr Ala Tyr
65                  70                  75                  80

Leu His Trp Ser Ser Leu Lys Ala Ser Asp Thr Ala Met Tyr Tyr Cys
                85                  90                  95

Val Arg Pro Arg Asp Gly Ser Tyr Pro Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Arg Val Glu Pro Lys Ser
    210                 215                 220

Cys Asp Lys Thr Ser
225

<210> SEQ ID NO 6
<211> LENGTH: 5
<212> TYPE: PRT
<213> ORGANISM: Homo sapiens

<400> SEQUENCE: 6

Asn Tyr Trp Ile Gly
1               5

<210> SEQ ID NO 7
<211> LENGTH: 17
<212> TYPE: PRT
<213> ORGANISM: Homo sapiens

<400> SEQUENCE: 7

Ile Ile Tyr Pro Tyr Asp Ser Asp Thr Arg Tyr Ser Pro Ser Phe Glu
1               5                   10                  15

Gly

<210> SEQ ID NO 8
<211> LENGTH: 13
<212> TYPE: PRT
<213> ORGANISM: Homo sapiens

<400> SEQUENCE: 8

Pro Arg Asp Gly Ser Tyr Pro Tyr Asp Ala Phe Asp Ile
1               5                   10

<210> SEQ ID NO 9
<211> LENGTH: 57
<212> TYPE: DNA
<213> ORGANISM: Homo sapiens

<400> SEQUENCE: 9
atggggtcaa ccgccatcct cgccctcctc ctgggtgttc tccaaggagt ctgtggc      57

<210> SEQ ID NO 10
<211> LENGTH: 672
<212> TYPE: DNA
<213> ORGANISM: Homo sapiens

<400> SEQUENCE: 10
gaggtgcagc tggtgcagtc tggagcagag gtgaaaaagc ccggggagtc tctgaagatc      60
tcctgcaagg gttctggata cagctttacc aactactgga tcggctgggt gcgccagatg     120
cccgggaaag gcctggagtg gatggggatc atctatcctt atgactctga taccagatat     180
agcccgtcct tcgaaggcca ggtcaccatc tcagccgaca gtccatcag accgcctac       240 ctgcactgga gcagcctgaa ggcctcggac accgccatgt attactgtgt gagaccccgc     300
gatgggagct atccttatga tgcttttgat atctggggcc aagggacaat ggtcaccgtc     360
tcttcagcct ccaccaaggg cccatcggtc ttccccctgg cacccctcctc caagagcacc    420 tctggggca cagcggccct gggctgcctg gtcaaggact acttccccga accggtgacg      480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagacagtt     660
gagcgcaaat ct                                                        672

<210> SEQ ID NO 11
<211> LENGTH: 15
<212> TYPE: DNA
<213> ORGANISM: Homo sapiens

<400> SEQUENCE: 11
aactactgga tcggc                                                      15

<210> SEQ ID NO 12
<211> LENGTH: 51
<212> TYPE: DNA
<213> ORGANISM: Homo sapiens

<400> SEQUENCE: 12

```
atcatctatc cttatgactc tgataccaga tatagcccgt ccttcgaagg c          51
```

```
<210> SEQ ID NO 13
<211> LENGTH: 39
<212> TYPE: DNA
<213> ORGANISM: Homo sapiens

<400> SEQUENCE: 13
ccccgcgatg ggagctatcc ttatgatgct tttgatatc                        39

<210> SEQ ID NO 14
<211> LENGTH: 19
<212> TYPE: PRT
<213> ORGANISM: Homo sapiens

<400> SEQUENCE: 14
```

Met Gly Ser Thr Ala Ile Leu Ala Leu Leu Leu Gly Val Leu Gln Gly
1               5                   10                  15

Val Cys Gly

```
<210> SEQ ID NO 15
<211> LENGTH: 224
<212> TYPE: PRT
<213> ORGANISM: Homo sapiens

<400> SEQUENCE: 15
```

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Gly Trp Val Arg Gln Met Pro Gly Lys Gly Leu Glu Trp Met
        35                  40                  45

Gly Ile Ile Tyr Pro Tyr Asp Ser Asp Thr Arg Tyr Ser Pro Ser Phe
    50                  55                  60

Glu Gly Gln Val Thr Ile Ser Ala Asp Lys Ser Ile Arg Thr Ala Tyr
65                  70                  75                  80

Leu His Trp Ser Ser Leu Lys Ala Ser Asp Thr Ala Met Tyr Tyr Cys
                85                  90                  95

Val Arg Pro Arg Asp Gly Ser Tyr Pro Tyr Asp Ala Phe Asp Ile Trp
            100                 105                 110

Gly Gln Gly Thr Met Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Thr Val Glu Arg Lys Ser
    210                 215                 220

```
<210> SEQ ID NO 16
<211> LENGTH: 5
<212> TYPE: PRT
```

<213> ORGANISM: Homo sapiens

<400> SEQUENCE: 16

Asn Tyr Trp Ile Gly
1               5

<210> SEQ ID NO 17
<211> LENGTH: 17
<212> TYPE: PRT
<213> ORGANISM: Homo sapiens

<400> SEQUENCE: 17

Ile Ile Tyr Pro Tyr Asp Ser Asp Thr Arg Tyr Ser Pro Ser Phe Glu
1               5                   10                  15

Gly

<210> SEQ ID NO 18
<211> LENGTH: 13
<212> TYPE: PRT
<213> ORGANISM: Homo sapiens

<400> SEQUENCE: 18

Pro Arg Asp Gly Ser Tyr Pro Tyr Asp Ala Phe Asp Ile
1               5                   10

<210> SEQ ID NO 19
<211> LENGTH: 618
<212> TYPE: DNA
<213> ORGANISM: Homo sapiens

<400> SEQUENCE: 19

```
gaaattgtgt tgacgcagtc tccaggcacc ctgtctttgt ctccagggga aagagccacc      60
ctctcctgca gggccagtca gagtgttagc aacaactact tagcctggta ccagcagaag     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattgtggta gctcactgag gcgttcggc      300
caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagacta cgagaaacac aaactctacg cctgcgaagt cacccatcag     600
ggcctgagct cgcccgtc                                                     618
```

<210> SEQ ID NO 20
<211> LENGTH: 36
<212> TYPE: DNA
<213> ORGANISM: Homo sapiens

<400> SEQUENCE: 20
agggccagtc agagtgttag caacaactac ttagcc                                 36

<210> SEQ ID NO 21
<211> LENGTH: 21
<212> TYPE: DNA
<213> ORGANISM: Homo sapiens

<400> SEQUENCE: 21

```
ggtgcatcca gcagggccac t                                              21
```

<210> SEQ ID NO 22
<211> LENGTH: 27
<212> TYPE: DNA
<213> ORGANISM: Homo sapiens

<400> SEQUENCE: 22

```
cagcattgtg gtagctcact gagggcg                                        27
```

<210> SEQ ID NO 23
<211> LENGTH: 206
<212> TYPE: PRT
<213> ORGANISM: Homo sapiens

<400> SEQUENCE: 23

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Cys Gly Ser Ser Leu
                85                  90                  95

Arg Ala Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val
        195                 200                 205
```

<210> SEQ ID NO 24
<211> LENGTH: 12
<212> TYPE: PRT
<213> ORGANISM: Homo sapiens

<400> SEQUENCE: 24

```
Arg Ala Ser Gln Ser Val Ser Asn Asn Tyr Leu Ala
1               5                   10
```

<210> SEQ ID NO 25
<211> LENGTH: 7
<212> TYPE: PRT
<213> ORGANISM: Homo sapiens

<400> SEQUENCE: 25

```
Gly Ala Ser Ser Arg Ala Thr
```

<210> SEQ ID NO 26
<211> LENGTH: 9
<212> TYPE: PRT
<213> ORGANISM: Homo sapiens

<400> SEQUENCE: 26

Gln His Cys Gly Ser Ser Leu Arg Ala
1               5

<210> SEQ ID NO 27
<211> LENGTH: 60
<212> TYPE: DNA
<213> ORGANISM: Homo sapiens

<400> SEQUENCE: 27
atggaaaccc cagcgcagct tctcttcctc ctgctactct ggctcccaga taccaccgga      60

<210> SEQ ID NO 28
<211> LENGTH: 621
<212> TYPE: DNA
<213> ORGANISM: Homo sapiens

<400> SEQUENCE: 28
gaaattgtgt tgacgcagtc tccaggcacc ctgtctttgt ctccagggga aagagccacc      60
ctctcctgca gggccagtca gagtgttagc aacaactact tagcctggta ccagcagaag     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cattgtggta gctcactgag gcgttcggc      300 caagggacca aggtggaaat caaacgaact gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaactctacg cctgcgaagt cacccatcag     600
ggcctgagct cgcccgtcac a                                               621

<210> SEQ ID NO 29
<211> LENGTH: 36
<212> TYPE: DNA
<213> ORGANISM: Homo sapiens

<400> SEQUENCE: 29
agggccagtc agagtgttag caacaactac ttagcc                                36

<210> SEQ ID NO 30
<211> LENGTH: 21
<212> TYPE: DNA
<213> ORGANISM: Homo sapiens

<400> SEQUENCE: 30
ggtgcatcca gcagggccac t                                                21

<210> SEQ ID NO 31
<211> LENGTH: 27
<212> TYPE: DNA
<213> ORGANISM: Homo sapiens

<400> SEQUENCE: 31
cagcattgtg gtagctcact gagggcg					27

<210> SEQ ID NO 32
<211> LENGTH: 20
<212> TYPE: PRT
<213> ORGANISM: Homo sapiens

<400> SEQUENCE: 32

Met Glu Thr Pro Ala Gln Leu Leu Phe Leu Leu Leu Leu Trp Leu Pro
1               5                   10                  15

Asp Thr Thr Gly
            20

<210> SEQ ID NO 33
<211> LENGTH: 207
<212> TYPE: PRT
<213> ORGANISM: Homo sapiens

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Asn Asn
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln His Cys Gly Ser Ser Leu
                85                  90                  95

Arg Ala Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Leu
            180                 185                 190

Tyr Ala Cys Glu Val Thr His Gln Gly Leu Ser Ser Pro Val Thr
        195                 200                 205

<210> SEQ ID NO 34
<211> LENGTH: 12
<212> TYPE: PRT
<213> ORGANISM: Homo sapiens

<400> SEQUENCE: 34

Arg Ala Ser Gln Ser Val Ser Asn Asn Tyr Leu Ala
1               5                   10

<210> SEQ ID NO 35
<211> LENGTH: 7

```
<212> TYPE: PRT
<213> ORGANISM: Homo sapiens

<400> SEQUENCE: 35

Gly Ala Ser Ser Arg Ala Thr
1               5

<210> SEQ ID NO 36
<211> LENGTH: 9
<212> TYPE: PRT
<213> ORGANISM: Homo sapiens

<400> SEQUENCE: 36

Gln His Cys Gly Ser Ser Leu Arg Ala
1               5

<210> SEQ ID NO 37
<211> LENGTH: 679
<212> TYPE: DNA
<213> ORGANISM: Homo sapiens

<400> SEQUENCE: 37
caggttcagc tggtgcagtc tggagcagag gtgaaaaagc ccgggcagtc tctgaagatc      60
tcctgtaagg cttctggata cagcttaacc gacaactgga tcggctgggt gcgccagaag     120
cccgggaaag gcctggagtg gatggggatc atctatcctg gtgactctga caccagatac     180
agtccgtcct tccaaggcca ggtcaccatc tcagccgaca gtccatcaa caccgcctac      240
ctgcagtgga gcagcctgaa ggcctcggac accgccatat attactgtgt gggactcgat     300
tggaactaca ccccctgcg atactggggc cgggaaccc tggtcaccgt ctcctcagcc       360
tccaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactagtg                                                  679

<210> SEQ ID NO 38
<211> LENGTH: 15
<212> TYPE: DNA
<213> ORGANISM: Homo sapiens

<400> SEQUENCE: 38
gacaactgga tcggc                                                       15

<210> SEQ ID NO 39
<211> LENGTH: 51
<212> TYPE: DNA
<213> ORGANISM: Homo sapiens

<400> SEQUENCE: 39
atcatctatc ctggtgactc tgacaccaga tacagtccgt ccttccaagg c                51

<210> SEQ ID NO 40
<211> LENGTH: 30
<212> TYPE: DNA
<213> ORGANISM: Homo sapiens

<400> SEQUENCE: 40
```

-continued ctcgattgga actacaaccc cctgcgatac                                      30

<210> SEQ ID NO 41
<211> LENGTH: 226
<212> TYPE: PRT
<213> ORGANISM: Homo sapiens

<400> SEQUENCE: 41

Gln Val Gln Leu Val Gln Ser Gly Ala Glu Val Lys Lys Pro Gly Gln
1               5                   10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr Ser
225

<210> SEQ ID NO 42
<211> LENGTH: 5
<212> TYPE: PRT
<213> ORGANISM: Homo sapiens

<400> SEQUENCE: 42

Asp Asn Trp Ile Gly
1               5

<210> SEQ ID NO 43
<211> LENGTH: 17
<212> TYPE: PRT
<213> ORGANISM: Homo sapiens

<400> SEQUENCE: 43

Ile Ile Tyr Pro Gly Asp Ser Asp Thr Arg Tyr Ser Pro Ser Phe Gln
1               5                   10                  15

Gly

<210> SEQ ID NO 44
<211> LENGTH: 10
<212> TYPE: PRT
<213> ORGANISM: Homo sapiens

<400> SEQUENCE: 44

Leu Asp Trp Asn Tyr Asn Pro Leu Arg Tyr
1               5                   10

<210> SEQ ID NO 45
<211> LENGTH: 57
<212> TYPE: DNA
<213> ORGANISM: Homo sapiens

<400> SEQUENCE: 45
atggggtcaa ccgccatcct cgccctcctc ctggctgttc tccagggagt ctgtgcc        57

<210> SEQ ID NO 46
<211> LENGTH: 663
<212> TYPE: DNA
<213> ORGANISM: Homo sapiens

<400> SEQUENCE: 46
gaggtgcagc tggtgcagtc tggagcagag gtgaaaaagc ccggcagtc tctgaagatc        60
tcctgtaagg cttctggata cagcttaacc gacaactgga tcggctgggt gcgccagaag      120
cccgggaaag gcctggagtg gatggggatc atctatcctg gtgactctga caccagatac      180
agtccgtcct tcaaggcca ggtcaccatc tcagccgaca gtccatcaa caccgcctac        240
ctgcagtgga gcagcctgaa ggcctcggac accgccatat attactgtgt gggactcgat      300
tggaactaca ccccctgcg atactggggc cgggaaccc tggtcaccgt ctcctcagcc        360
tccaccaagg gcccatcggt cttccccctg gcaccctcct ccaagagcac ctctgggggc      420
acagcggccc tgggctgcct ggtcaaggac tacttcccg aaccggtgac ggtgtcgtgg       480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac      600
atctgcaacg tgaatcacaa gcccagcaac accaaggtgg acaagacagt tgagcgcaaa      660
tct                                                                   663

<210> SEQ ID NO 47
<211> LENGTH: 15
<212> TYPE: DNA
<213> ORGANISM: Homo sapiens

<400> SEQUENCE: 47
gacaactgga tcggc                                                       15

<210> SEQ ID NO 48
<211> LENGTH: 51
<212> TYPE: DNA
<213> ORGANISM: Homo sapiens

<400> SEQUENCE: 48
atcatctatc ctggtgactc tgacaccaga tacagtccgt ccttccaagg c               51

<210> SEQ ID NO 49
<211> LENGTH: 30
<212> TYPE: DNA
<213> ORGANISM: Homo sapiens

```
<400> SEQUENCE: 49
ctcgattgga actacaaccc cctgcgatac                                              30

<210> SEQ ID NO 50
<211> LENGTH: 19
<212> TYPE: PRT
<213> ORGANISM: Homo sapiens

<400> SEQUENCE: 50

Met Gly Ser Thr Ala Ile Leu Ala Leu Leu Ala Val Leu Gln Gly
1               5                   10                  15

Val Cys Ala

<210> SEQ ID NO 51
<211> LENGTH: 221
<212> TYPE: PRT
<213> ORGANISM: Homo sapiens

<400> SEQUENCE: 51

Glu Val Gln Leu Val Gln Ser Gly Ala Glu Val Lys Lys Pro Gly Gln
1               5                   10                  15

Ser Leu Lys Ile Ser Cys Lys Ala Ser Gly Tyr Ser Leu Thr Asp Asn
            20                  25                  30

Trp Ile Gly Trp Val Arg Gln Lys Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Ile Tyr Tyr Cys
                85                  90                  95

Val Gly Leu Asp Trp Asn Tyr Asn Pro Leu Arg Tyr Trp Gly Pro Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Thr Val Glu Arg Lys Ser
    210                 215                 220

<210> SEQ ID NO 52
<211> LENGTH: 5
<212> TYPE: PRT
<213> ORGANISM: Homo sapiens

<400> SEQUENCE: 52

Asp Asn Trp Ile Gly
1               5
```

<210> SEQ ID NO 53
<211> LENGTH: 17
<212> TYPE: PRT
<213> ORGANISM: Homo sapiens

<400> SEQUENCE: 53

Ile Ile Tyr Pro Gly Asp Ser Asp Thr Arg Tyr Ser Pro Ser Phe Gln
1               5                   10                  15
Gly

<210> SEQ ID NO 54
<211> LENGTH: 10
<212> TYPE: PRT
<213> ORGANISM: Homo sapiens

<400> SEQUENCE: 54

Leu Asp Trp Asn Tyr Asn Pro Leu Arg Tyr
1               5                   10

<210> SEQ ID NO 55
<211> LENGTH: 639
<212> TYPE: DNA
<213> ORGANISM: Homo sapiens

<400> SEQUENCE: 55
ctgcctgtgc tgactcagcc accctcagtg tccgtgtccc caggacagac agccagcatc      60
acctgctctg gagataaaatt gggggataaa tatgcttgct ggtatcagca gaagccaggc    120
cagtcccctg tgctggtcat ctatcaagat agcaagcggc cctcagggat ccctgagcga    180
ttctctggct ccaactctgg gaacacagcc actctgacca tcagcgggac ccaggctatg    240
gatgaggctg actattactg tcaggcgtgg gacagcagca ctgccgtggt attcggcgga    300
gggaccaagc tgaccgtcct aggtcagccc aaggctgccc cctcggtcac tctgttcccg    360
ccctcctctg aggagcttca agccaacaag gccacactgg tgtgtctcat aagtgacttc    420
tacccgggag ccgtgacagt ggcctggaag gcagatagca gccccgtcaa ggcgggagtg    480
gagaccacca cacctccaa acaaagcaac aacaagtacg cggccagcag ctatctgagc    540
ctgacgcctg agcagtggaa gtcccacaga agctacagct gccaggtcac gcatgaaggg    600
agcaccgtgg agaagacagt ggcccctaca gaatgttca                           639

<210> SEQ ID NO 56
<211> LENGTH: 33
<212> TYPE: DNA
<213> ORGANISM: Homo sapiens

<400> SEQUENCE: 56
tctggagata aattggggga taaatatgct tgc                                   33

<210> SEQ ID NO 57
<211> LENGTH: 21
<212> TYPE: DNA
<213> ORGANISM: Homo sapiens

<400> SEQUENCE: 57
caagatagca agcggccctc a                                                21

<210> SEQ ID NO 58
<211> LENGTH: 30
<212> TYPE: DNA
<213> ORGANISM: Homo sapiens -continued

```
<400> SEQUENCE: 58
caggcgtggg acagcagcac tgccgtggta                                           30

<210> SEQ ID NO 59
<211> LENGTH: 213
<212> TYPE: PRT
<213> ORGANISM: Homo sapiens

<400> SEQUENCE: 59

Leu Pro Val Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 60
<211> LENGTH: 11
<212> TYPE: PRT
<213> ORGANISM: Homo sapiens

<400> SEQUENCE: 60

Ser Gly Asp Lys Leu Gly Asp Lys Tyr Ala Cys
1               5                   10

<210> SEQ ID NO 61
<211> LENGTH: 7
<212> TYPE: PRT
<213> ORGANISM: Homo sapiens

<400> SEQUENCE: 61

Gln Asp Ser Lys Arg Pro Ser
1               5

<210> SEQ ID NO 62
<211> LENGTH: 10
```

```
<212> TYPE: PRT
<213> ORGANISM: Homo sapiens

<400> SEQUENCE: 62

Gln Ala Trp Asp Ser Ser Thr Ala Val Val
1               5                   10

<210> SEQ ID NO 63
<211> LENGTH: 57
<212> TYPE: DNA
<213> ORGANISM: Homo sapiens

<400> SEQUENCE: 63
atggcctggt ctcctctcct cctcacccct ctcattcact gcacagggtc ctgggcc      57

<210> SEQ ID NO 64
<211> LENGTH: 648
<212> TYPE: DNA
<213> ORGANISM: Homo sapiens

<400> SEQUENCE: 64
cagtctgtgt tgacgcagcc gccctcagtg tctgcggccc caggacagaa ggtcaccatt    60
tcctgctccg gaagcagctc cgacattggg agtaattatg tatcctggta ccagcagttc   120
ccgggaacag cccccaaact cctcatttat gacaataata agcgaccctc agcgattcct   180
gaccgattct ctggctccaa gtctggcacg tcagccaccc tgggcatcac cggactccag   240
actggggacg aggccgatta ttactgcgga acatgggata gcagactggg tattgctgtg   300
ttcggaggag gcacccagct gaccgtcctc ggtcagccca aggctgcccc atcggtcact   360
ctgttcccac cctcctctga ggagcttcaa gccaacaagg ccacactggt gtgtctcgta   420
agtgacttct acccgggagc cgtgacagtg gcctggaagg cagatggcag ccccgtcaag   480
gtgggagtgg agaccaccaa accctccaaa caaagcaaca caagtatgc ggccagcagc    540 tacctgagcc tgacgcccga gcagtggaag tcccacagaa gctacagctg ccgggtcacg   600
catgaaggga gcaccgtgga aagacagtg gccccctacag aatgttca                648

<210> SEQ ID NO 65
<211> LENGTH: 39
<212> TYPE: DNA
<213> ORGANISM: Homo sapiens

<400> SEQUENCE: 65
tccggaagca gctccgacat tgggagtaat tatgtatcc                           39

<210> SEQ ID NO 66
<211> LENGTH: 21
<212> TYPE: DNA
<213> ORGANISM: Homo sapiens

<400> SEQUENCE: 66
gacaataata agcgaccctc a                                              21

<210> SEQ ID NO 67
<211> LENGTH: 33
<212> TYPE: DNA
<213> ORGANISM: Homo sapiens

<400> SEQUENCE: 67
ggaacatggg atagcagact gggtattgct gtg                                 33
```

```
<210> SEQ ID NO 68
<211> LENGTH: 19
<212> TYPE: PRT
<213> ORGANISM: Homo sapiens

<400> SEQUENCE: 68

Met Ala Trp Ser Pro Leu Leu Leu Thr Leu Leu Ile His Cys Thr Gly
1               5                   10                  15

Ser Trp Ala

<210> SEQ ID NO 69
<211> LENGTH: 216
<212> TYPE: PRT
<213> ORGANISM: Homo sapiens

<400> SEQUENCE: 69

Gln Ser Val Leu Thr Gln Pro Pro Ser Val Ser Ala Ala Pro Gly Gln
1               5                   10                  15

Lys Val Thr Ile Ser Cys Ser Gly Ser Ser Ser Asp Ile Gly Ser Asn
            20                  25                  30

Tyr Val Ser Trp Tyr Gln Gln Phe Pro Gly Thr Ala Pro Lys Leu Leu
        35                  40                  45

Ile Tyr Asp Asn Asn Lys Arg Pro Ser Ala Ile Pro Asp Arg Phe Ser
    50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Ser Arg Leu
                85                  90                  95

Gly Ile Ala Val Phe Gly Gly Gly Thr Gln Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Val Ser Asp Phe Tyr
    130                 135                 140

Pro Gly Ala Val Thr Val Ala Trp Lys Ala Asp Gly Ser Pro Val Lys
145                 150                 155                 160

Val Gly Val Glu Thr Thr Lys Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Arg Val Thr His Glu Gly Ser Thr Val Glu Lys
        195                 200                 205

Thr Val Ala Pro Thr Glu Cys Ser
    210                 215

<210> SEQ ID NO 70
<211> LENGTH: 13
<212> TYPE: PRT
<213> ORGANISM: Homo sapiens

<400> SEQUENCE: 70

Ser Gly Ser Ser Ser Asp Ile Gly Ser Asn Tyr Val Ser
1               5                   10

<210> SEQ ID NO 71
<211> LENGTH: 7
<212> TYPE: PRT
<213> ORGANISM: Homo sapiens
```

<400> SEQUENCE: 71

Asp Asn Asn Lys Arg Pro Ser
1               5

<210> SEQ ID NO 72
<211> LENGTH: 11
<212> TYPE: PRT
<213> ORGANISM: Homo sapiens

<400> SEQUENCE: 72

Gly Thr Trp Asp Ser Arg Leu Gly Ile Ala Val
1               5                   10

<210> SEQ ID NO 73
<211> LENGTH: 20
<212> TYPE: PRT
<213> ORGANISM: Homo sapiens
<220> FEATURE:
<221> NAME/KEY: MISC_FEATURE
<223> OTHER INFORMATION: K1-70 LC protein sequence of the 2-21
      consecutive N-terminal amino acids obtained by Edman reaction

<400> SEQUENCE: 73

Ser Val Leu Thr Gln Pro Pro Ser Val Ser Ala Ala Pro Gly Gln Lys
1               5                   10                  15

Val Thr Ile Ser
            20

<210> SEQ ID NO 74
<211> LENGTH: 764
<212> TYPE: PRT
<213> ORGANISM: Homo sapiens

<400> SEQUENCE: 74

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn

```
            195                 200                 205
Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
                260                 265                 270

Thr Arg Ala Asp Leu Ser Tyr Pro Ser His Cys Cys Ala Phe Lys Asn
            275                 280                 285

Gln Lys Lys Ile Arg Gly Ile Leu Glu Ser Leu Met Cys Asn Glu Ser
        290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
    450                 455                 460

Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Ile Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
        595                 600                 605

Arg Asn Pro Gln Tyr Asn Pro Gly Asp Lys Asp Thr Lys Ile Ala Lys
    610                 615                 620
```

```
Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
            645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Ala Phe Gln Arg Asp
            675                 680                 685

Val Phe Ile Leu Leu Ser Lys Phe Gly Ile Cys Lys Arg Gln Ala Gln
690                 695                 700

Ala Tyr Arg Gly Gln Arg Val Pro Pro Lys Asn Ser Thr Asp Ile Gln
705                 710                 715                 720

Val Gln Lys Val Thr His Asp Met Arg Gln Gly Leu His Asn Met Glu
                725                 730                 735

Asp Val Tyr Glu Leu Ile Glu Asn Ser His Leu Thr Pro Lys Lys Gln
                740                 745                 750

Gly Gln Ile Ser Glu Glu Tyr Met Gln Thr Val Leu
            755                 760
```

<210> SEQ ID NO 75
<211> LENGTH: 267
<212> TYPE: PRT
<213> ORGANISM: Homo sapiens

<400> SEQUENCE: 75

```
Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30

Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
            195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
```

```
225                 230                 235                 240
Leu Pro Ser Lys Gly Leu Glu His Leu Lys Glu Leu Ile Ala Arg Asn
                245                 250                 255

Thr Trp Thr Leu Asn His His His His His
            260                 265
```

<210> SEQ ID NO 76
<211> LENGTH: 336
<212> TYPE: PRT
<213> ORGANISM: Homo sapiens

<400> SEQUENCE: 76

```
Met Arg Pro Ala Asp Leu Leu Gln Leu Val Leu Leu Asp Leu Pro
1               5                   10                  15

Arg Asp Leu Gly Gly Met Gly Cys Ser Ser Pro Cys Glu Cys His
                20                  25                  30

Gln Glu Glu Asp Phe Arg Val Thr Cys Lys Asp Ile Gln Arg Ile Pro
                35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
                100                 105                 110

Asn Leu Thr Tyr Ile Asp Pro Asp Ala Leu Lys Glu Leu Pro Leu Leu
                115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
                180                 185                 190

Gln Gly Tyr Ala Phe Asn Gly Thr Lys Leu Asp Ala Val Tyr Leu Asn
                195                 200                 205

Lys Asn Lys Tyr Leu Thr Val Ile Asp Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
                260                 265                 270

Thr Arg Ala Asp Leu Ser Tyr Pro Ser His Cys Cys Ala Phe Lys Asn
    275                 280                 285

Gln Lys Lys Ile Arg Gly Ile Leu Glu Ser Leu Met Cys Asn Glu Ser
    290                 295                 300

Ser Tyr Asp Tyr Thr Ile Cys Gly Asp Ser Glu Asp Met Val Cys Thr
305                 310                 315                 320

Pro Lys Ser Asp Glu Phe Asn Pro Cys Glu His His His His His His
                325                 330                 335
```

<210> SEQ ID NO 77
<211> LENGTH: 36
<212> TYPE: DNA
<213> ORGANISM: Homo sapiens

<400> SEQUENCE: 77
cactgcgaat tcaaaatgag gccggcggac ttgctg                          36

<210> SEQ ID NO 78
<211> LENGTH: 48
<212> TYPE: DNA
<213> ORGANISM: Homo sapiens

<400> SEQUENCE: 78
gttctcctcc tcaactggga tgatgttaag agtccaggtg tttcttgc             48

<210> SEQ ID NO 79
<211> LENGTH: 48
<212> TYPE: DNA
<213> ORGANISM: Homo sapiens

<400> SEQUENCE: 79
gcaagaaaca cctggactct aacatcatc ccagttgagg aggagaac              48

<210> SEQ ID NO 80
<211> LENGTH: 54
<212> TYPE: DNA
<213> ORGANISM: Homo sapiens

<400> SEQUENCE: 80
gcagctctcg agtcagtggt ggtggtggtg gtgtgtctgc tcgaagcggc cggc      54

<210> SEQ ID NO 81
<211> LENGTH: 20
<212> TYPE: DNA
<213> ORGANISM: Homo sapiens

<400> SEQUENCE: 81
taatacgact cactataggg                                            20

<210> SEQ ID NO 82
<211> LENGTH: 50
<212> TYPE: DNA
<213> ORGANISM: Homo sapiens

<400> SEQUENCE: 82
tgtccccaca tatggtgtag tcataactgc tctcattaca catcaaggac           50

<210> SEQ ID NO 83
<211> LENGTH: 18
<212> TYPE: DNA
<213> ORGANISM: Homo sapiens

<400> SEQUENCE: 83
tagaaggcac agtcgagg                                              18

<210> SEQ ID NO 84
<211> LENGTH: 50
<212> TYPE: DNA
<213> ORGANISM: Homo sapiens

<400> SEQUENCE: 84
gtccttgatg tgtaatgaga gcagttatga ctacaccata tgtggggaca           50

```
<210> SEQ ID NO 85
<211> LENGTH: 59
<212> TYPE: DNA
<213> ORGANISM: Homo sapiens

<400> SEQUENCE: 85
gctactcgag ctagtggtgg tggtggtggt gttcacacgg gttgaactca tcggacttg      59
```